(12) United States Patent
Takahashi et al.

(10) Patent No.: US 7,935,688 B2
(45) Date of Patent: May 3, 2011

(54) VITAMIN D-LIKE COMPOUND

(75) Inventors: Tadakatsu Takahashi, Shizuoka (JP);
Yoshiyuki Ono, Shizuoka (JP);
Hirotaka Kashiwagi, Shizuoka (JP);
Tsuyoshi Haneishi, Tokyo (JP); Kazuki Shimizu, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 249 days.

(21) Appl. No.: 11/916,955

(22) PCT Filed: Jun. 9, 2006

(86) PCT No.: PCT/JP2006/312081
§ 371 (c)(1),
(2), (4) Date: Dec. 7, 2007

(87) PCT Pub. No.: WO2006/132442
PCT Pub. Date: Dec. 14, 2006

(65) Prior Publication Data
US 2009/0137609 A1 May 28, 2009

(30) Foreign Application Priority Data
Jun. 9, 2005 (JP) .................................. 2005-169568
Sep. 7, 2005 (JP) .................................. 2005-259634

(51) Int. Cl.
*A01N 31/00* (2006.01)
*A61K 31/655* (2006.01)
*A61K 31/192* (2006.01)
*A61K 31/341* (2006.01)
*A61K 31/382* (2006.01)
*A61K 31/426* (2006.01)
*A61K 31/4418* (2006.01)
*A61K 31/4433* (2006.01)
*A61K 31/4436* (2006.01)
*A61K 31/50* (2006.01)
*A61K 31/505* (2006.01)
*A61P 3/02* (2006.01)
*C07C 598/48* (2006.01)

(52) U.S. Cl. ........................................ 514/156; 546/340
(58) Field of Classification Search .................. 514/156; 546/340
See application file for complete search history.

(56) References Cited

U.S. PATENT DOCUMENTS

| 4,713,438 A | 12/1987 | Harris et al. |
| 5,141,948 A | 8/1992 | Miyamoto et al. |
| 5,578,625 A | 11/1996 | Suzuki et al. |
| 6,166,010 A | 12/2000 | Itoh et al. |
| 6,518,306 B1 | 2/2003 | Christensen, IV |
| 2006/0025474 A1 | 2/2006 | Wallace et al. |

FOREIGN PATENT DOCUMENTS

| JP | 3-232867 | 10/1991 |
| JP | 4-57812 | 2/1992 |
| JP | 7-97374 | 4/1995 |
| JP | 10-161332 | 6/1998 |
| JP | 2003-522129 | 7/2003 |
| JP | 2003-282270 | 10/2003 |
| JP | 2004-224766 | 8/2004 |
| WO | 93/25079 | 12/1993 |
| WO | 00/10958 | 3/2000 |
| WO | 01/10385 | 2/2001 |
| WO | 03/101978 | 12/2003 |
| WO | 2004/039864 | 5/2004 |
| WO | 2004/048309 | 6/2004 |
| WO | 2004/063345 | 7/2004 |
| WO | 2005/037755 | 4/2005 |
| WO | 2005/051893 | 6/2005 |
| WO | 2005/051898 | 6/2005 |
| WO | 2005/087700 | 9/2005 |
| WO | 2006/044602 | 4/2006 |

OTHER PUBLICATIONS

Kaji, et al. Synthesis of a bifunctional epoxy monomer containing biphenyl moiety and properties of its cured polymer with phenol novolac., Journal of Applied Polymer Science, vol. 74, No. 3, pp. 690-698, 1999.

Iijima, et al. Synthesis and curing of new epoxy resins containing rigid structure in the backbone, Netsu Kokasei Jushi, vol. 14 No. 4, pp. 202-212, 1993.

Fissekis, et al. Synthesis of 5-carboxymethyluridine. Nucleoside from transfer ribonucleic acid, Biochemistry, vol. 9, pp. 3136-3142, 1970.

Pan, et al. New and efficient method for esterification of carboxylic acids with simple primary and secondary alcohols using cerium(IV)ammonium nitrate (CAN), Tetrahedron Letters, vol. 44, pp. 331-334, 2003.

Brown, et al. Serum Bone Gla-Protein: A Specific Marker For Bone Formation In Postmenopausal Osteoporosis, The Lancet, vol. 323, No. 8386, pp. 1091-1093, 1984.

(Continued)

*Primary Examiner* — San-ming Hui
*Assistant Examiner* — Kathrien Cruz
(74) *Attorney, Agent, or Firm* — McDermott Will & Emery LLP

(57) ABSTRACT

The present invention provides a compound represented by the following general formula (I):

(I)

or a pharmaceutically acceptable salt thereof, a pharmaceutical composition containing such a compound, and the like. The compound or a pharmaceutically acceptable salt thereof, the pharmaceutical composition containing such a compound, or the like is useful as a medicine or the like for therapy of benign prostatic hyperplasia, cancer, osteoporosis, psoriasis, secondary hyperparathyroidism, chronic glomerulonephritis, lupus nephritis and/or diabetic nephropathy and the like.

21 Claims, No Drawings

OTHER PUBLICATIONS

Lian, et al. Contributions of nuclear architecture and chromatin to vitamin D-dependent transcriptional control of the rat osteocalcin gene, Steroids, vol. 66, No. 3-5, pp. 159-170, 2001.

Paredes, The Runx2 transcription factor plays a key role in the 1?,25-dihydroxy Vitamin D3-dependent upregulation of the rat osteocalcin (OC) gene expression in osteoblastic cells, The Journal of Steroid Biochemistry and Molecular Biology, vol. 89-90, pp. 269-271, 2004.

Peng, et al. Molecular Cloning and Characterization of a Channel-like Transporter Mediating Intestinal Calcium Absorption, The Journal of Biological Chemistry, vol. 274, No. 32, pp. 22739-22746, 1999.

Kurihara, et al. Design and synthesis of new ligand for VDR. The Pharmaceutical society of Japan, 114th I conference in Tokyo, 1994, 29 P2 I-405.

Boehm, et al. Novel nonsecosteroidal vitamin D mimics exert VDR-modulating activities with less calcium mobilization than 1,25-dihydroxyvitamin D3, Chemistry & Biology, vol. 6, No. 5, pp. 265-275, 1999.

Hosoda, et al. Ligands with dual vitamin D3-agonistic andandrogen-antagonistic activities, Bioorganic & Medicinal Chemistry Letters, vol. 15, pp. 4327-4331, 2005.

Yee, et al. Vitamin D Receptor Modulators for Inflammation and Cancer. Mini Reviews in Medicinal Chemistry, vol. 5, No. 8, 761-778, 2005.

Ma, et al. Identification and characterizationof noncalcemic, tissue-selective,nonsecosteroidal vitamin D receptor modulators, The Journal of Clinical Investigation, vol. 116, No. 4, pp. 892-904, 2006.

Takahashi, et al. Vitamin D receptor agonists: opportunities and challenges in drug discovery, Current Topics in Medicinal Chemistry, vol. 6, No. 12, pp. 1303-1316, 2006.

VITAMIN D-LIKE COMPOUND

CROSS REFERENCE TO PRIOR RELATED APPLICATIONS

This application is a U.S. national phase application under 35 U.S.C. §371 of International Patent Application No. PCT/JP2006/312081, filed Jun. 9, 2006, and claims the benefit of Japanese Patent Application No. 2005-169568, filed Jun. 9, 2005, and Japanese Patent Application No. 2005-259634, filed Sep. 7, 2005, all of which are incorporated by reference herein. The International Application was published in Japanese on Dec. 14, 2006 as International Publication No. WO 2006/132442 A1 under PCT Article 21(2).

FIELD OF THE INVENTION

The present invention relates to a novel vitamin D-like compound or a pharmaceutically acceptable salt thereof, a medicine containing such a compound (for example, a vitamin D3 receptor agonist), and the like.

BACKGROUND OF THE INVENTION

Active vitamin D3 (1α,25-dihydroxyvitamin D3) is a hormone having various physiological effects, and it is suggested that active vitamin D3 can be widely used as a medicine for various diseases. For example, Rocaltrol™ having active vitamin D3 as an active ingredient is actually used as a therapeutic agent for hyperparathyroidism, osteoporosis and the like. On the other hand, it is well known that active vitamin D3 increases the blood calcium level and may cause hypercalcemia as a side effect. The dose of active vitamin D3 or the patients suitable for active vitamin D3 is limited because of this side effect of active vitamin D3, and useful and various physiological effects of active vitamin D3 are not fully utilized for therapy of diseases, actually.

Various active vitamin D3 derivatives are synthesized to solve this problem. This is an attempt of modifying the structure of active vitamin D3 to provide vitamin D3-like agonists with a strong and desirable effect among various physiological effects of active vitamin D3 and, on the other hand, with a small effect of increasing the blood calcium level as a side effect. In such an attempt, there have been recently reported mimic compounds (VD3 mimic), specifically, compounds not having a secosteroid skeleton that is a characteristic structure of active vitamin D3 but having a vitamin D3-like effect (WO 00/10958, WO 2004/063345 and WO 2005/037755).

SUMMARY OF THE INVENTION

However, no such vitamin D3-like compounds have yet been commercially available or proceeded to clinical trials. Therefore, there is a need for a vitamin D3-like compound that has a stronger desirable effect as a vitamin D3 receptor agonist or a smaller effect of increasing the blood calcium level.

As a result of searching for a vitamin D-like compound having an improved effect in view of the above circumstances, the present inventors have found that a vitamin D-like compound having a bisphenyl structure with a specific substituent has an improved effect, specifically, a stronger desirable effect or a smaller effect of increasing the blood calcium level as a vitamin D3 receptor agonist. This finding has led to the completion of the present invention. That is, the present invention provides a vitamin D3-like compound, a pharmaceutical composition containing the compound, and the like as described below.

One aspect of the invention relates to a compound represented by the following general formula (I):

wherein $R_1$ and $R_2$ independently represent an optionally substituted $C_{1-6}$ alkyl group, a $C_{1-6}$ haloalkyl group, an optionally substituted $C_{2-6}$ alkenyl group, an optionally substituted $C_{2-6}$ alkynyl group or an optionally substituted $C_{1-6}$ alkoxy group, or $R_1$ and $R_2$ are taken together to form an optionally substituted $C_{3-8}$ cycloalkyl group;

$R_3$, $R_4$, $R_5$ and $R_6$ independently represent a hydrogen atom, a halogen atom, an optionally substituted $C_{1-6}$ alkyl group, a $C_{1-6}$ haloalkyl group, an optionally substituted $C_{2-6}$ alkenyl group, an optionally substituted $C_{2-6}$ alkynyl group or an optionally substituted $C_{1-6}$ alkoxy group;

$R_7$, $R_8$ and $R_9$ independently represent a hydrogen atom, an optionally protected hydroxyl group, an optionally substituted amino group, an optionally substituted carboxyl group, an optionally substituted $C_{1-10}$ alkyl group or a $C_{1-6}$ haloalkyl group, or any one pair of ($R_7$ and $R_8$), ($R_7$ and $R_9$) and ($R_8$ and $R_9$) are taken together to form an optionally substituted $C_{3-10}$ cycloalkyl group, a carbonyl group, an optionally substituted 3- to 12-membered heterocycle or a $C_{3-7}$ lactone;

X is a direct bond, methylene, ethylene, vinylene, ethynylene, —O—, —S—, —NH—, carbonyl, an optionally substituted $C_{6-12}$ aryl group or an optionally substituted 3- to 12-membered heterocycle;

Y represents an optionally substituted $C_{6-12}$ aryl group, an optionally substituted 3- to 12-membered heterocycle or an optionally substituted $C_{1-6}$ alkoxy group;

provided that X is selected from an optionally substituted $C_{6-12}$ aryl group and an optionally substituted 3- to 12-membered heterocycle when Y is an optionally substituted $C_{1-6}$ alkoxy group; and a represents an integer of 0 to 3, or a pharmaceutically acceptable salt thereof.

Another aspect of the invention relates to the compound described above, wherein $R_1$ and $R_2$ are independently an optionally substituted $C_{1-6}$ alkyl group or a $C_{1-6}$ haloalkyl group, or a pharmaceutically acceptable salt thereof.

Another aspect of the invention relates to the compound described immediately above, wherein $R_1$ and $R_2$ are independently a $C_{1-6}$ alkyl group, or a pharmaceutically acceptable salt thereof.

Another aspect of the invention relates to the compound described immediately above, wherein $R_1$ and $R_2$ are independently an ethyl group, or a pharmaceutically acceptable salt thereof.

Another aspect of the invention relates to the compound described above, wherein $R_3$, $R_4$, $R_5$ and $R_6$ are independently a hydrogen atom, a halogen atom, a $C_{1-6}$ alkyl group or a $C_{1-6}$ haloalkyl group, or a pharmaceutically acceptable salt thereof.

Another aspect of the invention relates to the compound described immediately above, wherein $R_3$, $R_4$, $R_5$ and $R_6$ are independently a hydrogen atom, a halogen atom or a $C_{1-6}$ alkyl group, or a pharmaceutically acceptable salt thereof.

Another aspect of the invention relates to the compound described immediately above, wherein $R_3$, $R_4$, $R_5$ and $R_6$ are independently a hydrogen atom, a halogen atom or a methyl group, or a pharmaceutically acceptable salt thereof.

Another aspect of the invention relates to the compound described immediately above,
wherein $R_3$ and $R_4$ are independently a hydrogen atom or a methyl group;
$R_5$ is a hydrogen atom; and
$R_6$ is a methyl group,
or a pharmaceutically acceptable salt thereof.

Another aspect of the invention relates to the compound described immediately above, wherein $R_3$ is a hydrogen atom, or a pharmaceutically acceptable salt thereof.

Another aspect of the invention relates to the compound described above, wherein $R_3$ is a methyl group, or a pharmaceutically acceptable salt thereof.

Another aspect of the invention relates to the compound described above, wherein $R_4$ is a hydrogen atom, or a pharmaceutically acceptable salt thereof.

Another aspect of the invention relates to the compound described above, wherein $R_4$ is a methyl group, or a pharmaceutically acceptable salt thereof.

Another aspect of the invention relates to the compound described above, wherein $R_7$, $R_8$ and $R_9$ independently represent a hydrogen atom, a hydroxyl group, a $C_{1-6}$ alkyl group or a $C_{1-6}$ haloalkyl group, or any one pair of ($R_7$ and $R_8$), ($R_7$ and $R_9$) and ($R_8$ and $R_9$) are taken together to form an optionally substituted $C_{3-10}$ cycloalkyl group, or a pharmaceutically acceptable salt thereof.

Another aspect of the invention relates to the compound described immediately above,
wherein any one of $R_7$, $R_8$ and $R_9$ is a hydroxyl group; and the remaining two are independently a hydrogen atom, a $C_{1-6}$ alkyl group or a $C_{1-6}$ haloalkyl group, or the remaining two are taken together to form a $C_{3-10}$ cycloalkyl group optionally substituted with one or two halogen atoms, hydroxyl groups and/or $C_{1-4}$ alkyl groups, or a pharmaceutically acceptable salt thereof.

Another aspect of the invention relates to the compound described immediately above, wherein any one of $R_7$, $R_8$ and $R_9$ is a hydroxyl group and the remaining two are the same and are each a $C_{1-6}$ alkyl group or a $C_{1-6}$ haloalkyl group, or a pharmaceutically acceptable salt thereof.

Another aspect of the invention relates to the compound described immediately above, wherein any one of $R_7$, $R_8$ and $R_9$ is a hydroxyl group and the remaining two are the same and are each an ethyl group or a trifluoromethyl group, or a pharmaceutically acceptable salt thereof.

Another aspect of the invention relates to the compound described above, wherein any one of $R_7$, $R_8$ and $R_9$ is a hydroxyl group and the remaining two are taken together to form a $C_{3-10}$ cycloalkyl group, or a pharmaceutically acceptable salt thereof.

Another aspect of the invention relates to the compound described above,
wherein X is a direct bond, methylene, ethylene, vinylene, ethynylene, —O—, —S—, —NH— or carbonyl; and
Y is an optionally substituted $C_{6-12}$ aryl group or an optionally substituted 3- to 12-membered heterocycle, or a pharmaceutically acceptable salt thereof.

Another aspect of the invention relates to the compound described immediately above, wherein X is a direct bond, methylene, ethylene, vinylene or ethynylene, or a pharmaceutically acceptable salt thereof.

Another aspect of the invention relates to the compound described immediately above, wherein X is ethylene, vinylene or ethynylene, or a pharmaceutically acceptable salt thereof.

Another aspect of the invention relates to the compound described above, wherein Y is a phenyl group having one or more substituents or a nitrogen-containing 3- to 12-membered heterocycle having one or more substituents; and the heterocycle is selected from pyrrole, oxazole, isoxazole, thiazole, isothiazole, furazan, imidazole, pyrazole, piperidine, piperazine, morpholine, thiomorpholine, pyridine, pyrazine, pyrimidine, pyridazine, indole, isoindole, indolizine, quinoline, isoquinoline, quinolizine, naphthyridine, benzimidazole, indazole, quinoxaline, quinazoline, cinnoline, phthalazine, purine, pteridine, benzoxazole and benzothiazole, or a pharmaceutically acceptable salt thereof.

Another aspect of the invention relates to the compound described immediately above, wherein Y is a phenyl group having one or more substituents or a nitrogen-containing 5- to 6-membered heterocycle having one or more substituents; and the heterocycle is selected from pyrrole, oxazole, isoxazole, thiazole, isothiazole, furazan, imidazole, pyrazole, piperidine, piperazine, morpholine, thiomorpholine, pyridine, pyrazine, pyrimidine and pyridazine, or a pharmaceutically acceptable salt thereof.

Another aspect of the invention relates to the compound described immediately above, wherein the nitrogen-containing 5- to 6-membered heterocycle having one or more substituents is pyridine having one or more substituents or thiazole having one or more substituents, or a pharmaceutically acceptable salt thereof.

Another aspect of the invention relates to the compound described above, wherein Y has one or two substituents each selected from a $C_{1-6}$ alkyl group optionally substituted with one or two hydroxyl groups, amino groups, $C_{1-6}$ alkoxycarbonyl groups and/or carboxyl groups; a $C_{1-6}$ haloalkyl group optionally substituted with one or two hydroxyl groups, amino groups, $C_{1-6}$ alkoxycarbonyl groups and/or carboxyl groups; a $C_{2-6}$ alkenyl group optionally substituted with one or two halogen atoms, amino groups, $C_{1-6}$ alkoxycarbonyl groups and/or carboxyl groups; a $C_{2-6}$ alkynyl group optionally substituted with one or two halogen atoms, amino groups, $C_{1-6}$ alkoxycarbonyl groups and/or carboxyl groups; a $C_{1-6}$ alkoxycarbonyl group; a carboxyl group; a $C_{1-6}$ alkoxy group; a cyano group; a halogen atom; a hydroxyl group; and/or a hydroxamic acid group, or a pharmaceutically acceptable salt thereof.

Another aspect of the invention relates to the compound described immediately above, wherein the substituents of Y are each selected from a $C_{1-6}$ alkyl group optionally substituted with a carboxyl group; a $C_{2-6}$ alkenyl group optionally substituted with a carboxyl group; a $C_{2-6}$ alkynyl group optionally substituted with a carboxyl group; a carboxyl group; and/or a halogen atom, or a pharmaceutically acceptable salt thereof.

Another aspect of the invention relates to the compound described immediately above, wherein the substituents of Y are each selected from a $C_{1-6}$ alkyl group optionally substituted with a carboxyl group; and/or a halogen atom, or a pharmaceutically acceptable salt thereof.

Another aspect of the invention relates to the compound described above, wherein at least one of the substituents of Y is a C$_{1-6}$ alkyl group substituted with a carboxyl group, or a pharmaceutically acceptable salt thereof.

Another aspect of the invention relates to the compound described above, which is selected from (4'-{1-ethyl-1-[4-(-3-hydroxy-4,4-dimethyl-pentyl)-3-methyl-phenyl]-propyl}-2'-methyl-biphenyl-4-yl)-acetic acid;

(4'-{1-ethyl-1-[4-(3-hydroxy-4,4-dimethyl-pentyl)-3-methyl-phenyl]-propyl}-2'-methyl-biphenyl-3-yl)-acetic acid;

(E)-(4'-{1-ethyl-1-[4-(3-ethyl-3-hydroxy-1-pentenyl)-3-methyl-phenyl]-propyl}-2'-methyl-biphenyl-4-yl)-acetic acid;

[6-(4-{1-ethyl-1-[4-(3-hydroxy-4,4-dimethyl-pentyl)-3-methyl-phenyl]-propyl}-2-methyl-phenyl)-pyridin-3-yl]-acetic acid;

[5-(4-{1-ethyl-1-[4-(3-hydroxy-4,4-dimethyl-pentyl)-3-methyl-phenyl]-propyl}-2-methyl-phenyl)-pyridin-3-yl]-acetic acid;

(4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)acetic acid;

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid;

sodium (4'-{1-ethyl-1-[4-((E)-3-ethyl-3-hydroxy-1-pentenyl)-3-methyl-phenyl]-propyl}-3-fluoro-2'-methyl-biphenyl-4-yl)acetate;

(4'-{1-ethyl-1-[4-(2-hydroxy-3,3-dimethyl-butoxy)-3-methyl-phenyl]-propyl}-2'-methyl-biphenyl-4-yl)acetic acid;

(E)-[4'-(1-ethyl-1-{4-[2-(1-hydroxy-cyclopentyl)-vinyl]-3-methyl-phenyl}-propyl)-2'-methyl-biphenyl-4-yl]-acetic acid;

(E)-[4'-(1-ethyl-1-{4-[2-(1-hydroxycyclohexyl)-vinyl]-3-methylphenyl}-propyl)-2'-methylbiphenyl-4-yl]-acetic acid;

(4'-{1-ethyl-1-[4-(3-hydroxy-4,4-dimethyl-pentyl)-3-methyl-phenyl]-propyl}-3-fluoro-2'-methyl-biphenyl-4-yl)acetic acid;

(4'-{1-ethyl-1-[4-(3-hydroxy-4,4-dimethyl-pentyl)-3-methyl-phenyl]-propyl}-3-chloro-2'-methyl-biphenyl-4-yl)acetic acid;

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid;

(4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)acetic acid;

(3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid;

[6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid;

[5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid;

[2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid;

(4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)acetic acid;

[5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid;

[6-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid;

sodium [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetate;

{6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic acid;

[4'-(1-ethyl-1-{4-[(E)-2-(1-hydroxycyclohexyl)-vinyl]-3-methylphenyl}-propyl)-3-fluoro-2'-methylbiphenyl-4-yl]-acetic acid;

[5-chloro-4'-(1-ethyl-1-{4-[(E)-2-(1-hydroxycyclohexyl)-vinyl]-3-methylphenyl}-propyl)-2'-methylbiphenyl-2-yl]-acetic acid;

[3-chloro-4'-(1-ethyl-1-{4-[(E)-2-(1-hydroxycyclohexyl)-vinyl]-3-methylphenyl}-propyl)-2'-methylbiphenyl-4-yl]-acetic acid;

{6-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic acid;

(4'-{1-ethyl-1-[4-(1-hydroxy-cyclopentylethynyl)-3-methyl-phenyl]-propyl}-3-fluoro-2'-methyl-biphenyl-4-yl) acetic acid;

(4'-{1-ethyl-1-[4-(1-hydroxy-cyclohexylethynyl)-3-methyl-phenyl]-propyl}-3-fluoro-2'-methyl-biphenyl-4-yl)acetic acid;

(4'-{1-ethyl-1-[4-(2-hydroxy-3,3-dimethyl-butoxy)-3-methyl-phenyl]-propyl}-3-fluoro-2'-methyl-biphenyl-4-yl) acetic acid;

[6-(4-{1-ethyl-1-[4-(2-hydroxy-3,3-dimethyl-butoxy)-3-methyl-phenyl]-propyl}-2-methyl-phenyl)-pyridin-3-yl]-acetic acid;

[5-(4-{1-ethyl-1-[4-(2-hydroxy-3,3-dimethyl-butoxy)-3-methyl-phenyl]-propyl}-phenyl)-pyridin-3-yl]-acetic acid;

[5-(4-{1-ethyl-1-[4-(1-hydroxy-cyclohexylethynyl)-3-methyl-phenyl]-propyl}-phenyl)-pyridin-3-yl]-acetic acid;

[5-(4-{1-ethyl-1-[4-(1-hydroxy-cyclopentylethynyl)-3-methyl-phenyl]-propyl}-phenyl)-pyridin-3-yl]-acetic acid;

{5-[4-(1-ethyl-1-{4-[2-(1-hydroxy-cyclohexyl)-ethyl]-3-methyl-phenyl}-propyl)-phenyl]-pyridin-3-yl}-acetic acid;

{5-[4-(1-ethyl-1-{4-[2-(1-hydroxy-cyclopentyl)-ethyl]-3-methyl-phenyl}-propyl)-phenyl]-pyridin-3-yl}-acetic acid; and pharmaceutically acceptable salts thereof.

Another aspect of the invention relates to the compound described above, which is selected from (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid;

[2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid;

[5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid;

[6-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid;

[5-chloro-4'-(1-ethyl-1-{4-[(E)-2-(1-hydroxycyclohexyl)-vinyl]-3-methylphenyl}-propyl)-2'-methylbiphenyl-2-yl]-acetic acid;

{5-[4-(1-ethyl-1-{4-[2-(1-hydroxy-cyclohexyl)-ethyl]-3-methyl-phenyl}-propyl)-phenyl]-pyridin-3-yl}-acetic acid; and pharmaceutically acceptable salts thereof.

Another aspect of the invention relates to a medicine containing the compound described above as an active ingredient.

Another aspect of the invention relates to a vitamin D3 receptor agonist containing the compound described above as an active ingredient.

Another aspect of the invention relates to a prophylactic or therapeutic agent containing the compound described above as an active ingredient for one or more conditions or diseases selected from abscess, acne, adhesion, alopecia, Alzheimer's disease, benign prostatic hyperplasia, fracture healing, cancer, autoimmune induced diabetes, host-graft rejection, insufficient sebum secretion, insufficient dermal firmness, humoral hypercalcemia, insufficient dermal hydration, leukemia, lupus, multiple sclerosis, osteomalacia, osteoporosis, psoriatic arthritis, psoriasis, renal failure, renal osteodystrophy, chronic rheumatoid arthritis, scleroderma, secondary hyperparathyroidism, systemic lupus erythematosus, wrinkle, corneal wound, corneal healing, retinopathy, sway, muscle weakness, fall, chronic glomerulonephritis, lupus nephritis, diabetic nephropathy, hypocalcemia, hypoparathyroidism, rachitis and osteoarthritis.

Another aspect of the invention relates to the prophylactic or therapeutic agent described immediately above, wherein the condition or disease to be prevented or cured is benign prostatic hyperplasia, cancer, osteoporosis, psoriasis, secondary hyperparathyroidism, chronic glomerulonephritis, lupus nephritis or diabetic nephropathy.

Another aspect of the invention relates to a pharmaceutical composition containing the compound described above and a pharmaceutically acceptable carrier.

Another aspect of the invention relates to a compound represented by the following general formula (II):

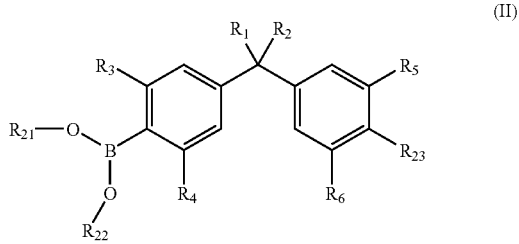

(II)

wherein $R_1$ and $R_2$ independently represent an optionally substituted $C_{1-6}$ alkyl group, a $C_{1-6}$ haloalkyl group, an optionally substituted $C_{2-6}$ alkenyl group, an optionally substituted $C_{2-6}$ alkynyl group or an optionally substituted $C_{1-6}$ alkoxy group, or $R_1$ and $R_2$ are taken together to form an optionally substituted $C_{3-8}$ cycloalkyl group;

$R_3$, $R_4$, $R_5$ and $R_6$ independently represent a hydrogen atom, a halogen atom, an optionally substituted $C_{1-6}$ alkyl group, a $C_{1-6}$ haloalkyl group, an optionally substituted $C_{2-6}$ alkenyl group, an optionally substituted $C_{2-6}$ alkynyl group or an optionally substituted $C_{1-6}$ alkoxy group;

$R_{21}$ and $R_{22}$ independently represent a hydrogen atom or an optionally substituted $C_{1-6}$ alkyl group, or $R_{21}$ and $R_{22}$ are taken together with oxygen atoms and a boron atom to which they belong to form a 4- to 12-membered dioxaborane ring optionally substituted with a $C_{1-6}$ alkyl group; and $R_{23}$ is a hydroxyl group, an optionally substituted $C_{6-12}$ aryl group, an optionally substituted 3- to 12-membered heterocycle, an optionally substituted $C_{1-6}$ alkoxy group or a group represented by the following general formula (III):

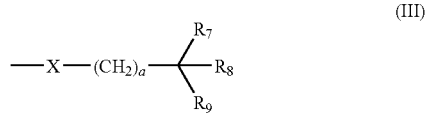

(III)

wherein $R_7$, $R_8$ and $R_9$ independently represent a hydrogen atom, an optionally protected hydroxyl group, an optionally substituted amino group, an optionally substituted carboxyl group, an optionally substituted $C_{1-10}$ alkyl group or a $C_{1-6}$ haloalkyl group, or any one pair of ($R_7$ and $R_8$), ($R_7$ and $R_9$) and ($R_8$ and $R_9$) are taken together to form an optionally substituted $C_{3-10}$ cycloalkyl group, a carbonyl group, an optionally substituted 3- to 12-membered heterocycle or a $C_{3-7}$ lactone;

X is a direct bond, methylene, ethylene, vinylene, ethynylene, —O—, —S—, —NH—, carbonyl, an optionally substituted $C_{6-12}$ aryl group or an optionally substituted 3- to 12-membered heterocycle; and a represents an integer of 0 to 3, or a chemically acceptable salt thereof.

Another aspect of the invention relates to the compound described immediately above, wherein $R_{23}$ is a group represented by the general formula (III), or a chemically acceptable salt thereof.

DETAILED DESCRIPTION OF THE INVENTION

The compound of the present invention, the method for producing the compound, and the medicine containing the compound will be described below.

Definition

The "$C_{1-6}$ alkyl group" herein refers to a linear or branched saturated monovalent $C_{1-6}$ hydrocarbon group. Examples of the $C_{1-6}$ alkyl group include a methyl group, ethyl group, propyl group, butyl group, pentyl group, hexyl group, i-propyl group, t-butyl group, sec-butyl group, 1-methylpropyl group, 1,1-dimethylpropyl group, 2,2-dimethylpropyl group, 1,2-dimethylpropyl group, 1,1,2-trimethylpropyl group, 1,2,2-trimethylpropyl group, 1,1,2,2-tetramethylpropyl group, 1-methylbutyl group, 2-methylbutyl group, 3-methylbutyl group, 1,1-dimethylbutyl group, 1,2-dimethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group and 2-ethylbutyl group.

The "$C_{2-6}$ alkenyl group" refers to a $C_{2-6}$ hydrocarbon group having at least one double bond. Examples of the $C_{2-6}$ alkenyl group include an ethenyl (vinyl) group, 1-propenyl group, 2-propenyl (allyl) group, isopropenyl group, 1-butenyl group, 2-butenyl group and 3-butenyl (homoallyl) group.

The "$C_{2-6}$ alkynyl group" refers to a $C_{2-6}$ hydrocarbon group having at least one triple bond. Examples of the $C_{2-6}$ alkynyl group include an ethynyl group, 1-propynyl group, 2-propynyl group, 1-butynyl group, 2-butynyl group, 3-butynyl group, pentynyl group and hexynyl group.

The "$C_{1-6}$ alkoxy group" refers to an O-alkyl group. Examples of the $C_{1-6}$ alkoxy group include a methoxy group, ethoxy group, propoxy group, i-propoxy group, butoxy group, t-butoxy group and sec-butoxy group.

The "halogen" refers to fluorine (F), chlorine (Cl), bromine (Br) or iodine (I) and is preferably fluorine or chlorine.

The "$C_{3-10}$ cycloalkyl group" refers to a saturated $C_{3-10}$ carbocyclic group. Examples of the $C_{3-10}$ cycloalkyl group include a cyclopropyl group, cyclobutyl group, cyclopentyl group, cyclohexyl group, cycloheptyl group, cyclooctyl group, cyclononyl group and cyclodecyl group.

The "$C_{1-6}$ haloalkyl group" refers to a "$C_{1-6}$ alkyl group" substituted with one or more halogen atoms. The $C_{1-6}$ haloalkyl group is preferably a $C_{1-2}$ alkyl group substituted with one or more fluorine or chlorine atoms. Examples of the $C_{1-6}$ haloalkyl group include a trifluoromethyl group, difluoromethyl group, fluoromethyl group, pentafluoroethyl group, tetrafluoroethyl group, trifluoroethyl group, difluoroethyl group, fluoroethyl group, trichloromethyl group, dichloromethyl group, chloromethyl group, pentachloroethyl group, tetrachloroethyl group, trichloroethyl group, dichloroethyl group and chloroethyl group.

The "$C_{1-6}$ haloalkoxy group" refers to a "$C_{1-6}$ alkoxy group" substituted with one or more halogen atoms. The $C_{1-6}$ haloalkoxy group is preferably a $C_{1-2}$ alkoxy group substituted with one or more fluorine or chlorine atoms. Examples of the $C_{1-6}$ haloalkoxy group include a trifluoromethoxy group, difluoromethoxy group, fluoromethoxy group, pentafluoroethoxy group, tetrafluoroethoxy group, trifluoroethoxy group, difluoroethoxy group, fluoroethoxy group, trichloromethoxy group, dichloromethoxy group, chloromethoxy group, pentachloroethoxy group, tetrachloroethoxy group, trichloroethoxy group, dichloroethoxy group and chloroethoxy group.

The "$C_{6-12}$ aryl group" refers to a monocyclic or bicyclic aromatic carbocyclic ring system having 6 to 12 ring carbon atoms. Examples of the $C_{6-12}$ aryl group include a phenyl group, naphthyl group, indanyl group, indenyl group and isoindenyl group. A phenyl group is preferable.

The "3- to 12-membered heterocycle" refers to an aromatic or non-aromatic heterocyclic group having 3 to 12 ring atoms including one or more (for example, one to four) hetero atoms each selected from O, S and N. The 3- to 12-membered heterocycle may be bonded at a desired position without specific limitations. Specific examples of the 3- to 12-membered heterocycle include furan, thiophene, pyrrole, oxazole, isoxazole, thiazole, isothiazole, furazan, imidazole, pyrazole, piperidine, piperazine, morpholine, thiomorpholine, tetrahydropyran, oxetane, oxepane, dioxane, tetrahydrothiopyran, pyran, thiopyran, pyridine, pyrazine, pyrimidine, pyridazine, benzofuran, isobenzofuran, benzothiophene, indole, isoindole, indolizine, chromene, benzopyran, quinoline, isoquinoline, quinolizine, naphthyridine, benzimidazole, indazole, quinoxaline, quinazoline, cinnoline, phthalazine, purine, pteridine, benzoxazole and benzothiazole.

The protecting group in the "optionally protected hydroxyl group" is not specifically limited insofar as it is useful as a protecting group for a hydroxyl group. Specific examples of the protecting group include a methoxymethyl group, methylthiomethyl group, (phenyldimethylsilyl)methoxymethyl group, benzoylmethyl group, p-methoxybenzyloxymethyl group, p-nitrobenzyloxymethyl group, o-nitrobenzyloxymethyl group, t-butoxymethyl group, (4-methoxyphenoxy)methyl group, 4-pentenyloxymethyl group, siloxymethyl group, 2-methoxyethoxymethyl group, 2,2,2-trichloroethoxymethyl group, bis(2-chloroethoxy)methyl group, 2-(trimethylsilyl)ethoxymethyl group, methoxymethyl group, tetrahydropyranyl group, 3-bromotetrahydropyranyl group, tetrahydrothiopyranyl group, 1-methoxycyclohexyl group, 4-methoxytetrahydrothiopyranyl group, tetrahydrofuranyl group, tetrahydrothiofuranyl group, 1-ethoxyethyl group, 1-(2-chloroethoxy)ethyl group, 1-[2-(trimethylsilyl)ethoxy] ethyl group, 1-methyl-1-methoxyethyl group, 1-methyl-benzyloxyethyl group, 1-methyl-1-benzyloxy-2-fluoroethyl group, 1-methyl-1-phenoxyethyl group, 2-trimethylsilylethyl group, 2-(benzylthio)ethyl group, t-butyl group, 2,2-trichloroethyl group, allyl group, propargyl group, p-chlorophenyl group, p-methoxyphenyl group, p-nitrobenzyl group, 2,4-dinitrophenyl group, benzyl group, p-methoxybenzyl group, 3,4-dimethoxybenzyl group, o-nitrophenyl group, p-nitrophenyl group, 2,6-dichlorobenzyl group, p-cyanobenzyl group, p-phenylbenzyl group, 2,6-difluorobenzyl group, p-acylaminobenzyl group, 2-trifluoromethylbenzyl group, 2-picolyl group, 4-picolyl group, triphenylmethyl group, trimethylsilyl group, triethylsilyl group, triisopropylsilyl group, dimethylisopropylsilyl group, diethylisopropylsilyl group, t-butyldimethylsilyl group, t-butyldiphenylsilyl group, methoxyacetyl group, pivaloyl group, benzoyl group, 2,4,6-trichlorobenzoyl group, methylcarbonyloxy group, methoxymethylcarbonyloxy group, ethylcarbonyloxy group, isobutylcarbonyloxy group, vinylcarbonyloxy group, benzylsulfonyl group, p-methoxybenzylcarbonyloxy group, dimethylisopropylsilyl group, diethylisopropylsilyl group, t-butyldimethylsilyl group, t-butyldiphenylsilyl group, tribenzylsilyl group, triphenylsilyl group, diphenylmethyl group, di-t-butylmethylsilyl group, tris(trimethylsilyl)silyl group, formyl group, benzoylformyl group, acetyl group, chloroacetyl group, dichloroacetyl group and trichloroacetyl group.

Examples of the substituent in the "optionally substituted carboxyl group" include a $C_{1-6}$ alkyl group optionally substituted with $C_{6-12}$ aryl; a $C_{6-12}$ aryl group; an amino group optionally substituted with a hydroxyl group or a $C_{1-6}$ alkyl group; and a hydrazinyl group optionally substituted with a $C_{1-6}$ alkyl group or $C_{6-12}$ aryl. Specific examples of the substituent include a methyl group, ethyl group, n-propyl group, i-propyl group, 1,1-dimethylpropyl group, 1-methyl-1-ethylpropyl group, 1,1-dimethylbutyl group, t-butyl group, allyl group, phenyl group, benzyl group, hydroxylamino group, 2,2,3,3-pentafluoropropylamino group, 2,2,2-trichloroethyl group, 2-chloroethyl group, N,N-dimethylamino group, pyrrolidinyl group, piperidinyl group, 5,6-dihydrophenanthridinyl group, 7-nitroindolyl group, 8-nitro-1,2,3,4-tetrahydroquinolyl group, hydrazinyl group, N-phenylhydrazinyl group and N,N'-diisopropylhydrazinyl group.

Examples of the substituent in the "optionally substituted $C_{1-10}$ alkyl group" include an acyl group (a formyl group, $C_{1-6}$ alkylcarbonyl group or $C_{6-12}$ arylcarbonyl group), acylamino group, acyloxy group, amino group, amino acid group, $C_{6-12}$ aryl group, $C_{6-12}$ aryloxy group, $C_{6-12}$ arylsulfonyl group, $C_{1-6}$ alkoxy group, $C_{1-6}$ alkylthio group, $C_{1-6}$ alkoxycarbonyl group, imino group, carboamide group, carboxyl group, carbothioamide group, cyanamide group, $C_{3-8}$ cycloalkyl group, hydroxyl group, thioacetal group, $C_{2-6}$ alkynyl group, $C_{2-6}$ alkenyl group, $C_{1-6}$ alkylsulfonyl group, $C_{1-6}$ haloalkylsulfonyl group, nitrile group, nitro group, $C_{1-6}$ haloalkoxy group, 3- to 12-membered heterocycle, mercapto group and hydroxamic acid group. A plurality of such substituents may be present. When a plurality of the substituents are present, they may be the same or different. The number of the substituents is preferably 1 or 2.

Examples of the substituent in the "optionally substituted $C_{3-10}$ cycloalkyl group" include an acyl group (a formyl group, $C_{1-6}$ alkylcarbonyl group or $C_{6-12}$ arylcarbonyl group), acylamino group, acyloxy group, amino group, amino acid group, $C_{6-12}$ arylsulfonyl group, $C_{1-6}$ alkoxy group, $C_{1-6}$ alkylthio group, $C_{1-6}$ alkoxycarbonyl group, imino group, carboamide group, carboxyl group, carbothioamide group, cyanamide group, hydroxyl group, thioacetal group, $C_{1-6}$ alkyl group, $C_{2-6}$ alkynyl group, $C_{2-6}$ alkenyl group, $C_{1-6}$ alkylsulfonyl group, $C_{1-6}$ alkyl group, $C_{1-6}$ haloalkyl group, $C_{1-6}$ haloalkylsulfonyl group, nitrile group, nitro group, $C_{1-6}$ haloalkoxy group, halogen atom, mercapto group and hydroxamic acid group. A plurality of such substituents may be present. When a plurality of the substituents are present, they may be the same or different. The number of the substituents is preferably 1 or 2.

Examples of the substituent in the "optionally substituted $C_{6-12}$ aryl group" include an acyl group (a formyl group, $C_{1-6}$ alkylcarbonyl group or $C_{6-12}$ arylcarbonyl group), acylamino group, acyloxy group, amino group, amino acid group, $C_{6-12}$ arylsulfonyl group, $C_{1-6}$ alkoxy group, $C_{1-6}$ alkylthio group, $C_{1-6}$ alkoxycarbonyl group, imino group, carboamide group, carboxyl group, carbothioamide group, cyanamide group, hydroxyl group, thioacetal group, $C_{1-6}$ alkyl group, $C_{2-6}$ alkynyl group, $C_{2-6}$ alkenyl group, $C_{1-6}$ alkylsulfonyl group, $C_{1-6}$ alkyl group, $C_{1-6}$ haloalkyl group, $C_{1-6}$ haloalkylsulfonyl group, nitrile group, nitro group, $C_{1-6}$ haloalkoxy group, halogen atom, mercapto group and hydroxamic acid group. A plurality of such substituents may be present. When a plurality of the substituents are present, they may be the same or different. The number of the substituents is preferably 1 or 2. The substituent may further have one or more hydroxyl groups, halogen atoms, amino groups, $C_{1-6}$ alkoxycarbonyl groups and/or carboxyl groups, if desired.

Examples of the substituent in the "optionally substituted 3- to 12-membered heterocycle" include an acyl group (a formyl group, $C_{1-6}$ alkylcarbonyl group or $C_{6-12}$ arylcarbonyl group), acylamino group, acyloxy group, amino group, amino acid group, $C_{6-12}$ arylsulfonyl group, $C_{1-6}$ alkoxy group, $C_{1-6}$ alkylthio group, $C_{1-6}$ alkoxycarbonyl group, imino group, carboamide group, carboxyl group, carbothioamide group, cyanamide group, hydroxyl group, thioacetal group, $C_{1-6}$ alkyl group, $C_{2-6}$ alkynyl group, $C_{2-6}$ alkenyl group, $C_{1-6}$ alkylsulfonyl group, $C_{1-6}$ alkyl group, $C_{1-6}$ haloalkyl group, $C_{1-6}$ haloalkylsulfonyl group, nitrile group, nitro group, $C_{1-6}$ haloalkoxy group, halogen atom, mercapto group and hydroxamic acid group. A plurality of such substituents may be present. When a plurality of the substituents are present, they may be the same or different. The number of the substituents is preferably 1 or 2. The substituent may further have one or more hydroxyl groups, halogen atoms, amino groups, $C_{1-6}$ alkoxycarbonyl groups and/or carboxyl groups, if desired.

Examples of the substituent in the "optionally substituted $C_{1-6}$ alkoxy group" include an acyl group (a formyl group, $C_{1-6}$ alkylcarbonyl group or $C_{6-12}$ arylcarbonyl group), acylamino group, acyloxy group, aralkyl group, amino group, amino acid group, $C_{6-12}$ aryl group, $C_{6-12}$ aryloxy group, $C_{6-12}$ arylsulfonyl group, $C_{1-6}$ alkylthio group, $C_{1-6}$ alkoxycarbonyl group, imino group, carboamide group, carboxyl group, carbothioamide group, cyanamide group, $C_{3-8}$ cycloalkyl group, hydroxyl group, thioacetal group, $C_{2-6}$ alkynyl group, $C_{2-6}$ alkenyl group, $C_{1-6}$ alkylsulfonyl group, $C_{1-6}$ haloalkylsulfonyl group, nitrile group, nitro group, 3- to 12-membered heterocycle, mercapto group and hydroxamic acid group. A plurality of such substituents may be present. When a plurality of the substituents are present, they may be the same or different. The number of the substituents is preferably 1 or 2.

PREFERRED EMBODIMENTS

In the formula (I), $R_1$ is preferably an unsubstituted $C_{1-6}$ alkyl group, and particularly preferably an ethyl group.

$R_2$ is preferably an unsubstituted $C_{1-6}$ alkyl group, and particularly preferably an ethyl group.

$R_3$ is preferably selected from a hydrogen atom, a halogen atom, an unsubstituted $C_{1-6}$ alkyl group and a $C_{1-6}$ haloalkyl group. More preferably, $R_3$ is a hydrogen atom or an unsubstituted $C_{1-6}$ alkyl group. Still more preferably, $R_3$ is a hydrogen atom or a methyl group. Most preferably, $R_3$ is a hydrogen atom.

$R_4$ is preferably selected from a hydrogen atom, a halogen atom, an unsubstituted $C_{1-6}$ alkyl group and a $C_{1-6}$ haloalkyl group. Particularly preferably, $R_4$ is a hydrogen atom or an unsubstituted $C_{1-6}$ alkyl group. Most preferably, $R_4$ is a hydrogen atom or a methyl group.

$R_5$ is preferably selected from a hydrogen atom, a halogen atom and an optionally substituted $C_{1-6}$ alkyl group. Here, the $C_{1-6}$ alkyl group is preferably such a group not having a substituent, and particularly preferably a methyl group. Most preferably, $R_5$ is a hydrogen atom.

$R_6$ is preferably selected from a hydrogen atom, a halogen atom, an unsubstituted $C_{1-6}$ alkyl group and a $C_{1-6}$ haloalkyl group. More preferably, $R_6$ is a hydrogen atom or an unsubstituted $C_{1-6}$ alkyl group. Still more preferably, $R_6$ is a hydrogen atom or a methyl group. Most preferably, $R_6$ is a methyl group.

Preferably, $R_7$, $R_8$ and $R_9$ are each a hydrogen atom, a hydroxyl group, an unsubstituted $C_{1-6}$ alkyl group or a $C_{1-6}$ haloalkyl group, or any one pair of ($R_7$ and $R_8$), ($R_7$ and $R_9$) and ($R_8$ and $R_9$) are taken together to form an optionally substituted $C_{3-10}$ cycloalkyl group. Here, the optionally substituted $C_{3-10}$ cycloalkyl group is preferably a $C_{3-10}$ cycloalkyl group optionally substituted with one or two halogen atoms, hydroxyl groups and/or $C_{1-4}$ alkyl groups. Further, any one of $R_7$, $R_8$ and $R_9$ is preferably a hydroxyl group. In a particularly preferred embodiment, i) any one of $R_7$, $R_8$ and $R_9$ is a hydroxyl group and the remaining two are independently a hydrogen atom, an unsubstituted $C_{1-6}$ alkyl group or a $C_{1-6}$ haloalkyl group, or ii) any one of $R_7$, $R_8$ and $R_9$ is a hydroxyl group and the remaining two are taken together to form an unsubstituted $C_{3-10}$ cycloalkyl group.

X is preferably selected from a direct bond, methylene, ethylene, vinylene, ethynylene, —O—, —S—, —NH— and carbonyl, more preferably selected from a direct bond, methylene, ethylene, vinylene and ethynylene, still more preferably selected from ethylene, vinylene and ethynylene, and most preferably selected from ethylene and vinylene.

When X is optionally substituted $C_{6-12}$ aryl, X is preferably an optionally substituted phenyl group. The substituent of X is preferably selected from a $C_{1-6}$ alkyl group optionally substituted with one or two hydroxyl groups; a $C_{1-6}$ haloalkyl group optionally substituted with one or two hydroxyl groups; a halogen atom; and/or a hydroxyl group. A plurality of such substituents may be present. When a plurality of the substituents are present, they may be the same or different. The number of the substituents is preferably 1 or 2.

When X is an optionally substituted 3- to 12-membered heterocycle, X is preferably an optionally substituted oxygen-containing or sulfur-containing 3- to 12-membered heterocycle. Specific examples of such a heterocycle include furan, thiophene, oxazole, isoxazole, thiazole, isothiazole, furazan, morpholine, thiomorpholine, tetrahydropyran, oxetane, oxepane, dioxane, tetrahydrothiopyran, pyran, thiopyran, benzofuran, isobenzofuran, benzothiophene, chromene, benzopyran, benzoxazole and benzothiazole. An optionally substituted oxygen-containing or sulfur-containing 5- to 6-membered heterocycle is more preferable. Specific examples of such a heterocycle include furan, thiophene, oxazole, isoxazole, thiazole, isothiazole, furazan, morpholine, thiomorpholine, tetrahydropyran, dioxane, tetrahydrothiopyran, pyran and thiopyran. The substituent of X is preferably selected from a $C_{1-6}$ alkyl group optionally substituted with one or two hydroxyl groups; a $C_{1-6}$ haloalkyl group optionally substituted with one or two hydroxyl groups; a halogen atom; and/or a hydroxyl group. A plurality of such substituents may be present. When a plurality of the substituents are present, they may be the same or different. The number of the substituents is preferably 1 or 2.

Y is preferably an optionally substituted $C_{6-12}$ aryl group or an optionally substituted 3- to 12-membered heterocycle. The optionally substituted $C_{6-12}$ aryl of Y is preferably such a group having one or more substituents, and particularly preferably a substituted phenyl group. The optionally substituted 3- to 12-membered heterocycle of Y is preferably a nitrogen-containing 3- to 12-membered heterocycle having one or more substituents. Specific examples of such a heterocycle include pyrrole, oxazole, isoxazole, thiazole, isothiazole, furazan, imidazole, pyrazole, piperidine, piperazine, morpholine, thiomorpholine, pyridine, pyrazine, pyrimidine, pyridazine, indole, isoindole, indolizine, quinoline, isoquinoline, quinolizine, naphthyridine, benzimidazole, indazole, quinoxaline, quinazoline, cinnoline, phthalazine, purine, pteridine, benzoxazole and benzothiazole. Y is more preferably a nitrogen-containing 5- to 6-membered heterocycle having one or more substituents. Specific examples of such a heterocycle include pyrrole, oxazole, isoxazole, thiazole, isothiazole, furazan, imidazole, pyrazole, piperidine, piperazine, morpholine, thiomorpholine, pyridine, pyrazine, pyrimidine and pyridazine. Particularly preferably, Y is pyridine having one or more substituents or thiazole having one or more substituents.

Here, the substituent of Y is preferably selected from a $C_{1-6}$ alkyl group optionally substituted with one or two amino groups, $C_{1-6}$ alkoxycarbonyl groups and/or carboxyl groups; a $C_{1-6}$ haloalkyl group optionally substituted with one or two amino groups, $C_{1-6}$ alkoxycarbonyl groups and/or carboxyl groups; a $C_{1-6}$ alkenyl group optionally substituted with one or two halogen atoms, amino groups, $C_{1-6}$ alkoxycarbonyl groups and/or carboxyl groups; a $C_{1-6}$ alkynyl group optionally substituted with one or two halogen atoms, amino groups, $C_{1-6}$ alkoxycarbonyl groups and/or carboxyl groups; a $C_{1-6}$ alkoxycarbonyl group; a carboxyl group; a $C_{1-6}$ alkoxy group; a cyano group; a halogen atom; a hydroxyl group; and/or a hydroxamic acid group. Among these, the substituent of Y is more preferably selected from a $C_{1-6}$ alkyl group optionally substituted with a carboxyl group; a $C_{1-6}$ alkenyl group optionally substituted with a carboxyl group; a $C_{1-6}$ alkynyl group optionally substituted with a carboxyl group; a carboxyl group; and/or a halogen atom. Further, the substituent of Y is particularly preferably selected from a $C_{1-6}$ alkyl group optionally substituted with a carboxyl group; and/or a halogen atom. A plurality of such substituents may be present. When a plurality of the substituents are present, they may be the same or different. The number of the substituents is preferably 1 or 2. At least one of the substituents is most preferably a $C_{1-6}$ alkyl group substituted with a carboxyl group.

In the formula (II), preferably, $R_{21}$ and $R_{22}$ are each a hydrogen atom, or $R_{21}$ and $R_{22}$ are taken together with oxygen atoms and a boron atom to which they belong to form a 4- to 12-membered dioxaborane ring optionally substituted with a $C_{1-6}$ alkyl group.

$R_{23}$ is preferably a group represented by the general formula (III).

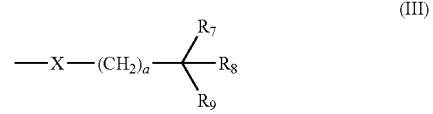

$R_7$, $R_8$, $R_9$, X and a are the same as defined for the formula (I), respectively, and preferable examples of $R_7$, $R_8$, $R_9$, X and a are also the same as in the formula (I), respectively.

(Specific Compounds)

Specific compounds include compounds shown in the examples below and salts thereof. Among these, preferable specific examples of the compound represented by the formula (I) include:

(4'-{1-ethyl-1-[4-(-3-hydroxy-4,4-dimethyl-pentyl)-3-methyl-phenyl]-propyl}-2'-methyl-biphenyl-4-yl)-acetic acid;

(4'-{1-ethyl-1-[4-(3-hydroxy-4,4-dimethyl-pentyl)-3-methyl-phenyl]-propyl}-2'-methyl-biphenyl-3-yl)-acetic acid;

(E)-(4'-{1-ethyl-1-[4-(3-ethyl-3-hydroxy-1-pentenyl)-3-methyl-phenyl]-propyl}-2'-methyl-biphenyl-4-yl)-acetic acid;

[6-(4-{1-ethyl-1-[4-(3-hydroxy-4,4-dimethyl-pentyl)-3-methyl-phenyl]-propyl}-2-methyl-phenyl)-pyridin-3-yl]-acetic acid;

[5-(4-{1-ethyl-1-[4-(3-hydroxy-4,4-dimethyl-pentyl)-3-methyl-phenyl]-propyl}-2-methyl-phenyl)-pyridin-3-yl]-acetic acid;

(4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)acetic acid;

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid;

sodium (4'-{1-ethyl-1-[4-((E)-3-ethyl-3-hydroxy-1-pentenyl)-3-methyl-phenyl]-propyl}-3-fluoro-2'-methyl-biphenyl-4-yl)acetate;

(4'-{1-ethyl-1-[4-(2-hydroxy-3,3-dimethyl-butoxy)-3-methyl-phenyl]-propyl}-2'-methyl-biphenyl-4-yl)acetic acid;

(E)-[4'-(1-ethyl-1-{4-[2-(1-hydroxy-cyclopentyl)-vinyl]-3-methyl-phenyl}-propyl)-2'-methyl-biphenyl-4-yl]-acetic acid;

(E)-[4'-(1-ethyl-1-{4-[2-(1-hydroxycyclohexyl)-vinyl]-3-methylphenyl}-propyl)-2'-methylbiphenyl-4-yl]-acetic acid;

(4'-{1-ethyl-1-[4-(3-hydroxy-4,4-dimethyl-pentyl)-3-methyl-phenyl]-propyl}-3-fluoro-2'-methyl-biphenyl-4-yl)acetic acid;

(4'-{1-ethyl-1-[4-(3-hydroxy-4,4-dimethyl-pentyl)-3-methyl-phenyl]-propyl}-3-chloro-2'-methyl-biphenyl-4-yl)acetic acid;

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid;

(4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)acetic acid;

(3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid;

[6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid;

[5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid;

[2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid;

(4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)acetic acid;

[5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid;

[6-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid;

sodium [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetate;

{6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic acid;

[4'-(1-ethyl-1-{4-[(E)-2-(1-hydroxycyclohexyl)-vinyl]-3-methylphenyl}-propyl)-3-fluoro-2'-methylbiphenyl-4-yl]-acetic acid;

[5-chloro-4'-(1-ethyl-1-{4-[(E)-2-(1-hydroxycyclohexyl)-vinyl]-3-methylphenyl}-propyl)-2'-methylbiphenyl-2-yl]-acetic acid;

[3-chloro-4'-(1-ethyl-1-{4-[(E)-2-(1-hydroxycyclohexyl)-vinyl]-3-methylphenyl}-propyl)-2'-methylbiphenyl-4-yl]-acetic acid;

{6-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic acid;

(4'-{1-ethyl-1-[4-(1-hydroxy-cyclopentylethynyl)-3-methyl-phenyl]-propyl}-3-fluoro-2'-methyl-biphenyl-4-yl) acetic acid;

(4'-{1-ethyl-1-[4-(1-hydroxy-cyclohexylethynyl)-3-methyl-phenyl]-propyl}-3-fluoro-2'-methyl-biphenyl-4-yl)acetic acid;

(4'-{1-ethyl-1-[4-(2-hydroxy-3,3-dimethyl-butoxy)-3-methyl-phenyl]-propyl}-3-fluoro-2'-methyl-biphenyl-4-yl) acetic acid;

[6-(4-{1-ethyl-1-[4-(2-hydroxy-3,3-dimethyl-butoxy)-3-methyl-phenyl]-propyl}-2-methyl-phenyl)-pyridin-3-yl]-acetic acid;

[5-(4-{1-ethyl-1-[4-(2-hydroxy-3,3-dimethyl-butoxy)-3-methyl-phenyl]-propyl}-phenyl)-pyridin-3-yl]-acetic acid;

[5-(4-{1-ethyl-1-[4-(1-hydroxy-cyclohexylethynyl)-3-methyl-phenyl]-propyl}-phenyl)-pyridin-3-yl]-acetic acid;

[5-(4-{1-ethyl-1-[4-(1-hydroxy-cyclopentylethynyl)-3-methyl-phenyl]-propyl}-phenyl)-pyridin-3-yl]-acetic acid;

{5-[4-(1-ethyl-1-{4-[2-(1-hydroxy-cyclohexyl)-ethyl]-3-methyl-phenyl}-propyl)-phenyl]-pyridin-3-yl}-acetic acid;

{5-[4-(1-ethyl-1-{4-[2-(1-hydroxy-cyclopentyl)-ethyl]-3-methyl-phenyl}-propyl)-phenyl]-pyridin-3-yl}-acetic acid; and pharmaceutically acceptable salts thereof.

Among the above compounds, most preferable specific examples of the compound represented by the formula (I) include:

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid;

[2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid;

[5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid;

[6-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid;

[5-chloro-4'-(1-ethyl-1-{4-[(E)-2-(1-hydroxycyclohexyl)-vinyl]-3-methylphenyl}-propyl)-2'-methylbiphenyl-2-yl]-acetic acid;

{5-[4-(1-ethyl-1-{4-[2-(1-hydroxy-cyclohexyl)-ethyl]-3-methyl-phenyl}-propyl)-phenyl]-pyridin-3-yl}-acetic acid; and pharmaceutically acceptable salts thereof.

General Synthesis Method

The compound of the present invention can be prepared by synthesis methods shown in the following reaction formulas 1 to 12. Each reaction formula will be described below.

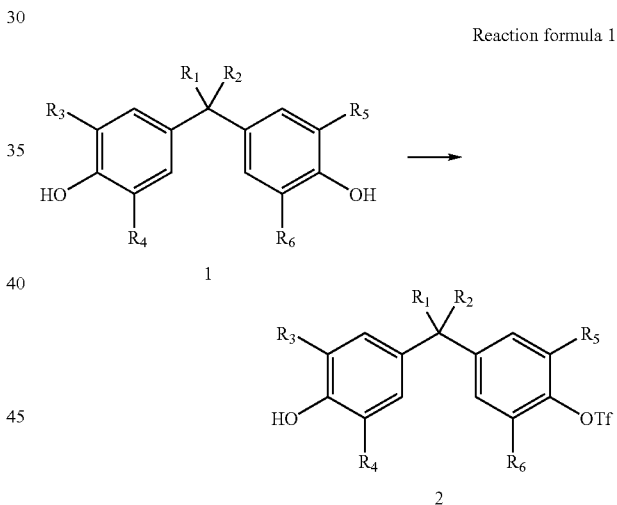

Reaction formula 1

In the reaction formula 1, a compound of the general formula (1) can be synthesized by the method described in WO 00/10958 (U.S. Pat. No. 6,218,430 B1). Specifically, a compound of the general formula (2) can be synthesized by reacting the compound (1) with trifluoromethanesulfonic anhydride or N-phenylbis(trifluoromethanesulfonimide) in the presence of a base.

The base used in the reaction formula 1 is preferably pyridine, 2,6-lutidine, 2,4,6-collidine, N,N-dimethylaminopyridine, imidazole or triethylamine, and more preferably pyridine or triethylamine. The solvent is preferably diethyl ether, tetrahydrofuran, dichloromethane, 1,2-dichloroethane, chloroform, benzene or toluene, and more preferably dichloromethane. The reaction temperature is preferably between −50° C. and 50° C., and more preferably between −20° C. and 30° C. However, the reaction temperature is not limited insofar as the reaction proceeds.

Reaction formula 2

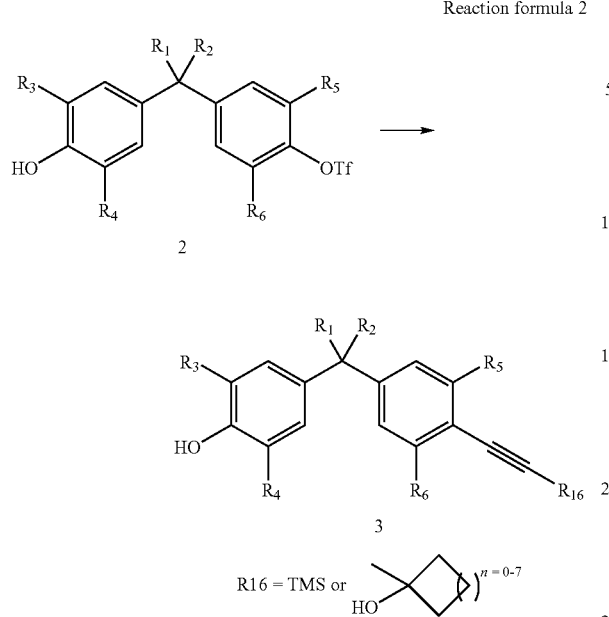

R16 = TMS or 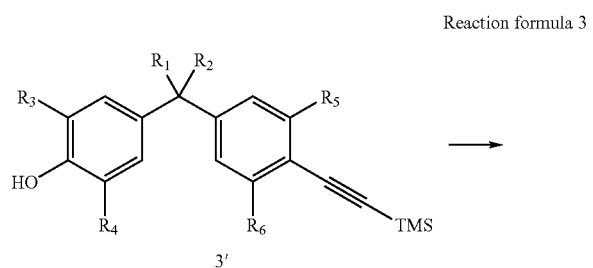

In the reaction formula 2, a compound of the general formula (3) can be synthesized by reacting the compound of the general formula (2) with acetylene substituted with $R_{16}$ (where $R_{16}$ is a trimethylsilyl group or a $C_{3-10}$ 1-hydroxycycloalkyl group) in the presence of a palladium catalyst, a ligand, copper (I) iodide and triethylamine.

The palladium catalyst used in the reaction formula 2 is preferably tetrakis(triphenylphosphine)palladium, bis(dibenzylideneacetone)palladium, a tris(dibenzylideneacetone)dipalladium chloroform complex, palladium acetate, palladium chloride or a [1,1'-bis(diphenylphosphino)-ferrocene]palladium dichloride dichloromethane complex. The ligand is preferably triphenylphosphine, tributylphosphine, tricyclohexylphosphine, 1,3-bis(diphenylphosphinopropane) or tri-t-butylphosphine. However, the ligand may or may not be used, since the ligand is used for improving activity of the palladium catalyst or reaction selectivity. The solvent used in the reaction formula 2 is preferably N,N-dimethylformamide, dimethyl sulfoxide, N,N-dimethylacetamide, 1,3-dimethyl-2-imidazolidinone, tetrahydrofuran, toluene or acetonitrile, and more preferably N,N-dimethylformamide or acetonitrile. The reaction temperature is preferably between 0° C. and 200° C., and more preferably between 20° C. and 150° C. However, the reaction temperature is not limited insofar as the reaction proceeds.

Reaction formula 3

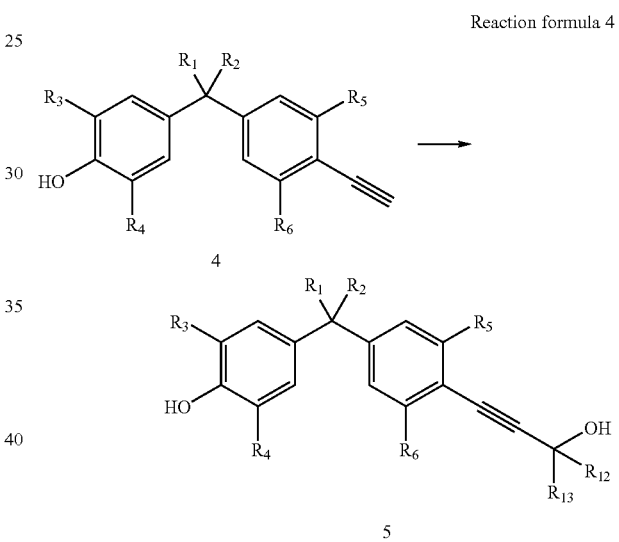

In the reaction formula 3, a compound of the general formula (4) can be synthesized by reacting the compound of the general formula (3') with tetra-n-butylammonium fluoride.

The solvent used in the reaction formula 3 is preferably N,N-dimethylformamide, dimethyl sulfoxide, N,N-dimethylacetamide, 1,3-dimethyl-2-imidazolidinone, tetrahydrofuran, toluene or acetonitrile, and more preferably tetrahydrofuran. The reaction temperature is preferably between 0° C. and 100° C., and more preferably between 0° C. and 50° C. However, the reaction temperature is not limited insofar as the reaction proceeds.

Reaction formula 4

In the reaction formula 4, a compound of the general formula (5) can be synthesized by reacting the compound of the general formula (4) with a ketone or aldehyde represented by the general formula $R_{12}(C=O)R_{13}$ in the presence of a base.

The base used in the reaction formula 4 is preferably n-butyllithium, sec-butyllithium, t-butyllithium, methyllithium, phenyllithium, methylmagnesium bromide, methylmagnesium chloride, methylmagnesium iodide, isopropylmagnesium bromide, diisopropylmagnesium, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride or potassium bis(trimethylsilyl)amide, and more preferably n-butyllithium. The solvent used in the reaction formula 4 is preferably a hydrocarbon or ether solvent, for example, hexane, benzene, toluene, diethyl ether, t-butyl methyl ether, tetrahydrofuran, 1,2-dimethoxyethane, 1,4-dioxane or anisole, and more preferably tetrahydrofuran.

The reaction temperature in the reaction formula 4 is preferably between −100° C. and 50° C., and more preferably between −80° C. and 30° C. However, the reaction temperature is not limited insofar as the reaction proceeds.

Reaction formula 5

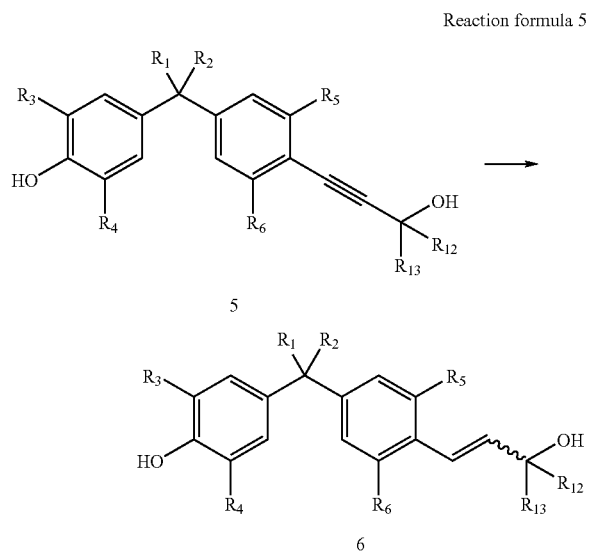

In the reaction formula 5, the compound of the general formula (5) can be converted into a compound of the general formula (6) by reduction.

In the reaction formula 5, $R_{12}$ and $R_{13}$ each represent any of $R_7$, $R_8$ and $R_9$ in the formula (I).

Preferable reduction in the reaction formula 5 is reduction using LiAlH$_4$ or Red-Al™ (sodium bis(2-methoxyethoxy) aluminum hydride) or catalytic reduction using a Lindlar catalyst. The solvent in the reduction using lithium aluminum hydride or Red-Al™ is preferably a hydrocarbon or ether solvent, for example, pentane, hexane, benzene, toluene, diethyl ether, t-butyl methyl ether, tetrahydrofuran, 1,2-dimethoxyethane, 1,4-dioxane or anisole, and more preferably tetrahydrofuran. The solvent in the catalytic reduction using a Lindlar catalyst is preferably methanol, ethanol or ethyl acetate, and more preferably methanol. The reaction temperature is preferably between −50° C. and 200° C., and more preferably between 0° C. and 100° C. However, the reaction temperature is not limited insofar as the reaction proceeds.

Reaction formula 6

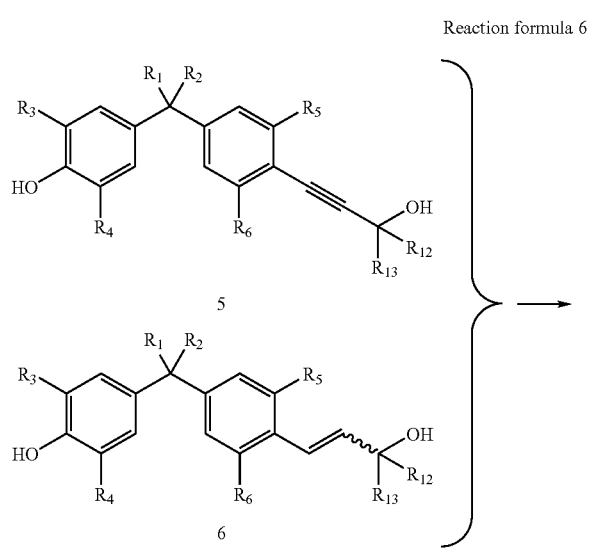

In the reaction formula 6, the compounds of the general formulas (5, 6) can be converted into a compound of the general formula (7) by catalytic reduction.

In the reaction formula 6, $R_{12}$ and $R_{13}$ are as defined for the reaction formula 5.

The catalyst used in the catalytic reduction in the reaction formula 6 is preferably a palladium, rhodium, ruthenium, nickel or platinum catalyst, for example, palladium on carbon, palladium hydroxide on carbon, platinum oxide, rhodium on alumina or a Wilkinson's catalyst, and more preferably palladium on carbon. The solvent is preferably methanol, ethanol, ethyl acetate or acetic acid, and more preferably methanol. The reaction temperature is preferably between −50° C. and 200° C., and more preferably between 0° C. and 100° C. However, the reaction temperature is not limited insofar as the reaction proceeds.

Reaction formula 7

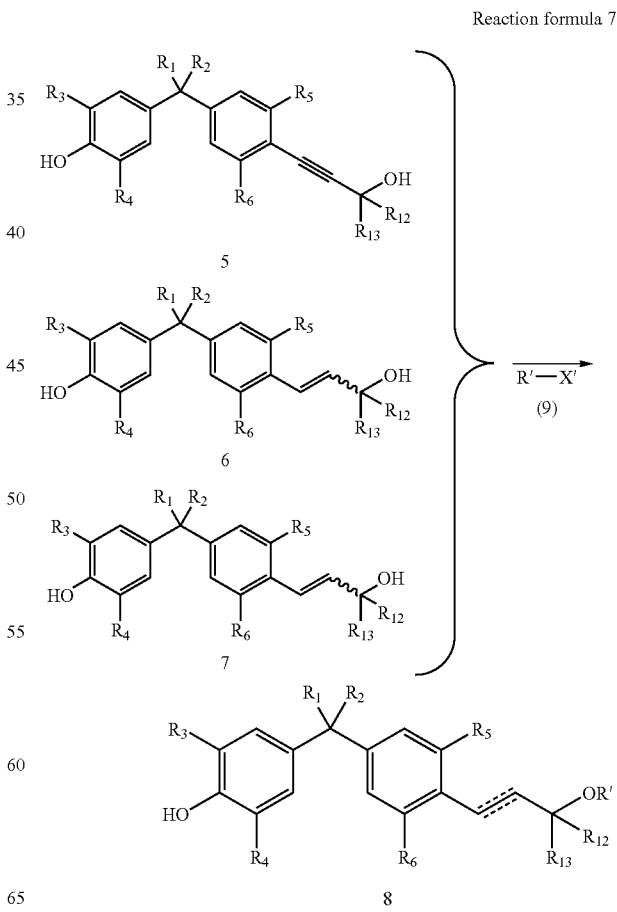

In the reaction formula 7, the compounds of the general formulas (5-7) can be converted into a compound of the general formula (8) by protecting a hydroxyl group in the presence of a base.

In the reaction formula 7, $R_{12}$ and $R_{13}$ are as defined for the reaction formula 5.

R' represents a protecting group for a hydroxyl group. Specific examples of the protecting group include a methoxymethyl group, 2-(trimethylsilyl)ethoxymethyl group, benzyl group, p-methoxybenzyl group, trimethylsilyl group, triethylsilyl group, t-butyldimethylsilyl group, t-butyldiphenylsilyl group and acetyl group.

X' represents a leaving group. Specific examples of the leaving group include a halogen atom, methanesulfonyloxy group, toluenesulfonyloxy group, trifluoromethanesulfonyloxy group and acetyloxy group.

The base used in the reaction formula 7 is preferably sodium t-butoxide, potassium t-butoxide, n-butyllithium, sec-butyllithium, t-butyllithium, lithium diisopropylamide, lithium dicyclohexylamide, lithium bis(trimethylsilyl)amide, potassium bis(trimethylsilyl)amide, sodium hydride, potassium hydride, potassium carbonate, sodium carbonate, sodium bicarbonate, cesium carbonate, pyridine, triethylamine, diisopropylethylamine, 2,6-lutidine, 2,4,6-collidine or N,N-dimethylaminopyridine, and more preferably sodium hydride, potassium hydride, potassium carbonate or pyridine. The solvent is preferably dichloromethane, 1,2-dichloroethane, chloroform, hexane, benzene, toluene, diethyl ether, t-butyl methyl ether, tetrahydrofuran, 1,2-dimethoxyethane, 1,4-dioxane, diisopropyl ether, N,N-dimethylformamide, dimethyl sulfoxide, N,N-dimethylacetamide, 1,3-dimethyl-2-imidazolidinone, 1,3-dimethyl-3,4,5,6-tetrahydro-2(1H)-pyrimidinone or acetonitrile, and more preferably N,N-dimethylformamide. The reaction temperature is preferably between −50° C. and 200° C., and more preferably between −20° C. and 100° C. However, the reaction temperature is not limited insofar as the reaction proceeds.

Reaction formula 8

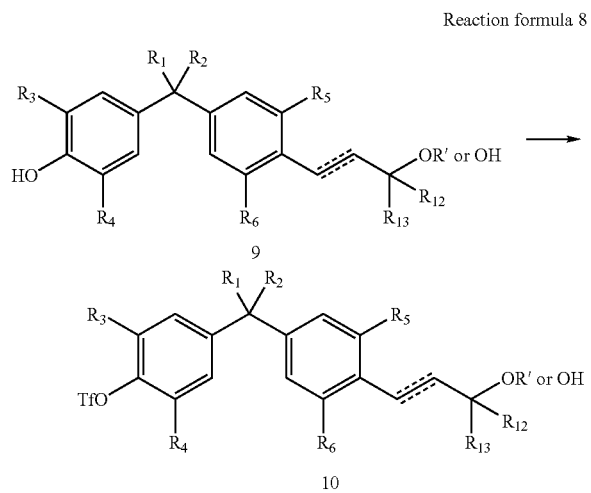

In the reaction formula 8, a compound of the general formula (10) can be synthesized by reacting the compound of the formula (9) with trifluoromethanesulfonic anhydride or N-phenylbis(trifluoromethanesulfonimide) in the presence of a base.

In the reaction formula 8, $R_{12}$ and $R_{13}$ are as defined for the reaction formula 5, and R' is as defined for the reaction formula 7.

The base used in the reaction formula 8 is preferably pyridine, 2,6-lutidine, 2,4,6-collidine, N,N-dimethylaminopyridine, imidazole or triethylamine, and more preferably pyridine or triethylamine. The solvent used in the reaction formula 8 is preferably diethyl ether, tetrahydrofuran, dichloromethane, 1,2-dichloroethane, chloroform, benzene or toluene, and more preferably dichloromethane. The reaction temperature is preferably between −50° C. and 50° C., and more preferably between −20° C. and 30° C. However, the reaction temperature is not limited insofar as the reaction proceeds.

Reaction formula 9

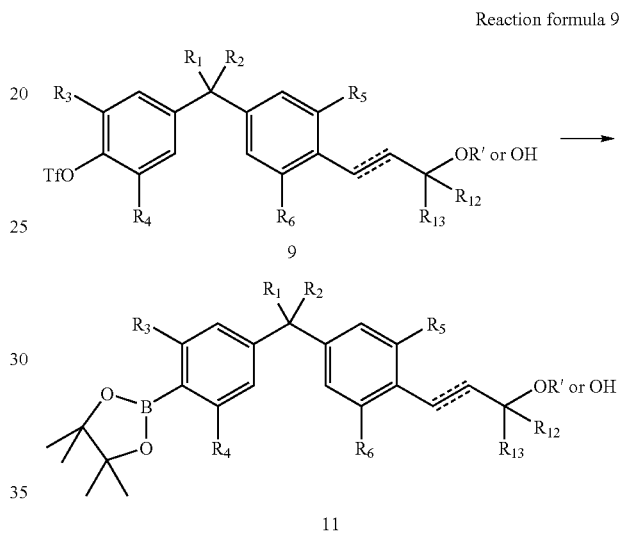

In the reaction formula 9, a compound of the general formula (11) can be synthesized by reacting the compound of the general formula (10) with bis(pinacolato)diboron in the presence of a palladium catalyst, a ligand and a base.

In the reaction formula 9, $R_{12}$ and $R_{13}$ are as defined for the reaction formula 5, and R' is as defined for the reaction formula 7.

The palladium catalyst used in the reaction formula 9 is preferably [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride or bis(dibenzylideneacetone)palladium (0). The ligand is preferably 1,1'-bis(diphenylphosphino)ferrocene, triphenylphosphine, 1,4-bis(diphenylphosphino)butane, 1,3-bis(diphenylphosphino)propane, 1,2-bis(diphenylphosphino)ethane or dibenzylideneacetone. However, the ligand may or may not be used. The base is preferably sodium acetate, potassium acetate or cesium fluoride. The solvent is preferably dimethyl sulfoxide, N,N-dimethylformamide, dioxane, toluene, dimethoxyethane, tetrahydrofuran or N-methylpyrrolidone. The reaction temperature is preferably between room temperature and 200° C., and more preferably between 50° C. and 120° C. However, the reaction temperature is not limited insofar as the reaction proceeds.

Reaction formula 10

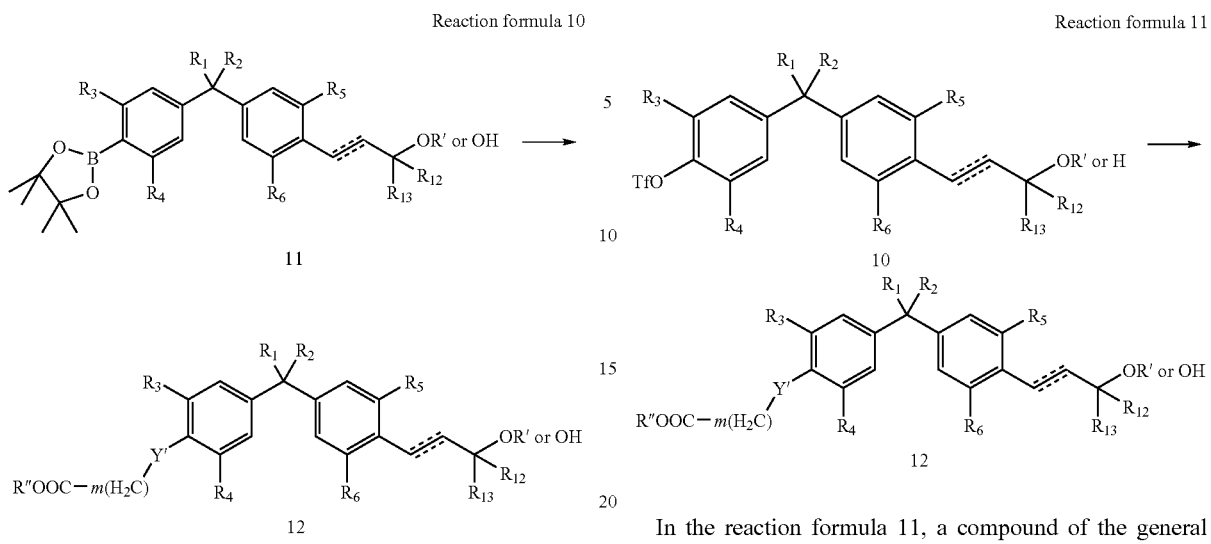

Reaction formula 11

In the reaction formula 10, a compound of the general formula (12) can be synthesized by reacting the compound of the general formula (11) with aryl halide in the presence of a palladium catalyst, a ligand and a base.

In the reaction formula 10, $R_{12}$ and $R_{13}$ are as defined for the reaction formula 5, and R' is as defined for the reaction formula 7. Y' represents an optionally substituted $C_{6-12}$ aryl group or an optionally substituted 3- to 12-membered heterocycle. m represents an integer of 0 to 4. R" represents a $C_{1-6}$ alkyl group.

The palladium catalyst used in the reaction formula 10 is preferably [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride, bis(dibenzylideneacetone)palladium (0), bis(tricyclohexylphosphine)palladium (II) dichloride, 2-cyclohexylphosphino-2',6'-dimethoxyphenylpalladium (II) acetate or palladium carbon. The ligand is preferably 2-(dimethylamino)-2'-dicyclohexylphosphinobiphenyl, o-(dicyclohexylphosphino)biphenyl, 2-(dimethylamino)-2'-di-t-butylphosphino)biphenyl, o-(di-t-butylphosphino)biphenyl, 1,3-bis(2,4,6-trimethylphenyl)imidazol-2-ylidene, tri-t-butylphosphine or tricyclohexylphosphine. However, the ligand may or may not be used. The base is preferably barium hydroxide, sodium hydroxide, potassium phosphate, potassium carbonate, sodium carbonate, sodium bicarbonate, potassium fluoride, cesium fluoride, sodium methoxide, cesium carbonate or tetrabutylammonium fluoride. The solvent is preferably dimethyl sulfoxide, N,N-dimethylformamide, dioxane, toluene, dimethoxyethane, tetrahydrofuran or N-methylpyrrolidone, or a combination of such a solvent with water. The reaction temperature is preferably between room temperature and 200° C., and more preferably between 50° C. and 120° C. However, the reaction temperature is not limited insofar as the reaction proceeds.

In the reaction formula 11, a compound of the general formula (12) can be synthesized from the compound of the general formula (10) by any of the following methods (I) to (V).

In the reaction formula 11, $R_{12}$ and $R_{13}$ are as defined for the reaction formula 5, R' is as defined for the reaction formula 7, and Y', m and R" are as defined for the reaction formula 10.

(I) A method of reacting with arylborane or aryl borate in the presence of a palladium catalyst, a ligand and a base.
(II) A method of reacting with an aryltin compound in the presence of a palladium catalyst, a ligand and a base.
(III) A method of reacting with arylzinc halide in the presence of a palladium catalyst, a ligand and a base.
(IV) A method of reacting with arylmagnesium halide in the presence of a nickel or palladium catalyst, a ligand and a base.
(V) A method of reacting with arylmanganese halide in the presence of a palladium catalyst, a ligand and a base.

Detailed conditions in each of the methods (I) to (V) will be shown below.

In the method (I), the palladium catalyst is preferably [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride, bis(dibenzylideneacetone)palladium (0), bis(tricyclohexylphosphine)palladium (II) dichloride, palladium (II) acetate, bis(dibenzylideneacetone)palladium (0) or palladium carbon.

The ligand is preferably 2-(dimethylamino)-2'-dicyclohexylphosphinobiphenyl, o-(dicyclohexylphosphino)biphenyl, 2-(dimethylamino)-2'-di-t-butylphosphino)biphenyl, o-(di-t-butylphosphino)biphenyl, 1,3-bis(2,4,6-trimethylphenyl)imidazol-2-ylidene, tri-t-butylphosphine, 2-dicyclohexylphosphino-2',6'-dimethoxy-1,1'-biphenyl or tricyclohexylphosphine. However, the ligand may or may not be used.

The base is preferably barium hydroxide, sodium hydroxide, potassium phosphate, potassium carbonate, sodium carbonate, sodium bicarbonate, potassium fluoride, cesium fluoride, sodium methoxide, cesium carbonate or tetrabutylammonium fluoride.

The solvent is preferably dimethyl sulfoxide, N,N-dimethylformamide, dioxane, toluene, dimethoxyethane, tetrahydrofuran or N-methylpyrrolidone, or a combination of such a solvent with water or ethanol.

The reaction temperature is preferably between room temperature and 200° C., and more preferably between 50° C. and 120° C. However, the reaction temperature is not limited insofar as the reaction proceeds.

In the method (II), the palladium catalyst is preferably [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride, bis(dibenzylideneacetone)palladium (0), bis(tricyclohexylphosphine)palladium (II) dichloride, palladium (II) acetate, bis(dibenzylideneacetone)palladium (0) or palladium carbon.

The ligand is preferably triphenylphosphine, tricyclohexylphosphine, tri(o-tolyl)phosphine or triphenylarsine. However, the ligand may or may not be used.

The base is preferably lithium chloride, tetrabutylammonium fluoride or copper (I) bromide.

The solvent is preferably N,N-dimethylformamide, dioxane, dimethoxyethane, tetrahydrofuran or N-methylpyrrolidone, or a combination of such a solvent with 2,6-di-t-butyl-4-methylphenol.

The reaction temperature is preferably between room temperature and 200° C., and more preferably between 50° C. and 120° C. However, the reaction temperature is not limited insofar as the reaction proceeds.

In the method (III), the palladium catalyst is preferably [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride, bis(dibenzylideneacetone)palladium (0), bis(tricyclohexylphosphine)palladium (II) dichloride, palladium (II) acetate, bis(dibenzylideneacetone)palladium (0) or palladium carbon.

The ligand is preferably triphenylphosphine, 1,3-bis(diphenylphosphino)propane or 1,1'-bis(diphenylphosphino)ferrocene. However, the ligand need not be used in some cases.

The solvent is preferably tetrahydrofuran, diethyl ether or a combination of such a solvent with hexane or cyclohexane. The reaction temperature is preferably between room temperature and 120° C., and more preferably between room temperature and 90° C. However, the reaction temperature is not limited insofar as the reaction proceeds.

In the method (IV), the nickel or palladium catalyst is preferably bis(triphenylphosphine)nickel (II) dichloride, bis(triphenylphosphine)nickel (II) dibromide, bis(acetylacetone)nickel (0), [1,3-bis(diphenylphosphino)propane]nickel (II) dichloride, [1,3-bis(diphenylphosphino)ethane]nickel (II) dichloride, [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride, bis(dibenzylideneacetone)palladium (0), bis(tricyclohexylphosphine)palladium (II) dichloride, palladium (II) acetate, bis(dibenzylideneacetone)palladium (0), [(2-dimethylamino)propyldiphenylphosphine]palladium (II) dichloride or palladium carbon.

The ligand is preferably triphenylphosphine, 1,3-bis(diphenylphosphino)propane or 1,1'-bis(diphenylphosphino)ferrocene. However, the ligand need not be used in some cases.

The solvent is preferably tetrahydrofuran, diethyl ether or a combination of such a solvent with N,N-dimethylformamide.

The reaction temperature is preferably between 0° C. and 120° C., and more preferably between 0° C. and 90° C. However, the reaction temperature is not limited insofar as the reaction proceeds.

In the method (V), the palladium catalyst is preferably [1,1'-bis(diphenylphosphino)ferrocene]palladium (II) dichloride, tetrakis(triphenylphosphine)palladium (0), bis(triphenylphosphine)palladium (II) dichloride, [1,4-bis(diphenylphosphino)butane]palladium (II) dichloride, [1,3-bis(diphenylphosphino)propane]palladium (II) dichloride, [1,2-bis(diphenylphosphino)ethane]palladium (II) dichloride, bis(dibenzylideneacetone)palladium (0), bis(tricyclohexylphosphine)palladium (II) dichloride, palladium (II) acetate, bis(dibenzylideneacetone)palladium (0), [(2-dimethylamino)propyldiphenylphosphine]palladium (II) dichloride or palladium carbon.

The ligand is preferably triphenylphosphine, 1,3-bis(diphenylphosphino)propane or 1,1'-bis(diphenylphosphino)ferrocene. However, the ligand need not be used in some cases.

The solvent is preferably tetrahydrofuran, dimethoxyethane or diethyl ether.

The reaction temperature is preferably between 0° C. and 100° C., and more preferably between 0° C. and 70° C. However, the reaction temperature is not limited insofar as the reaction proceeds.

Reaction formula 12

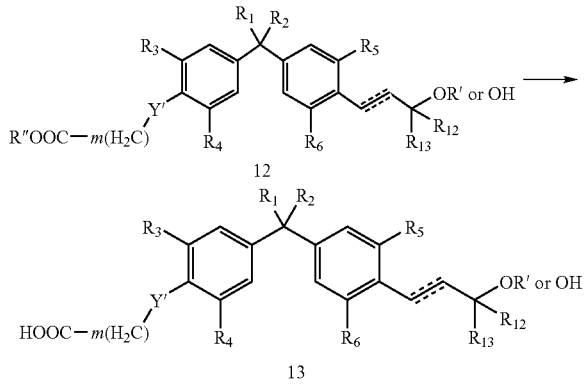

In the reaction formula 12, the compound of the general formula (12) can be converted into a compound of the general formula (13) by hydrolysis in the presence of a base.

In the reaction formula 12, $R_{12}$ and $R_{13}$ are as defined for the reaction formula 5, R' is as defined for the reaction formula 7, and Y', m and R" are as defined for the reaction formula 10.

The base used in the reaction formula 12 is preferably sodium hydroxide, potassium hydroxide, lithium hydroxide, potassium carbonate, sodium carbonate, sodium bicarbonate or cesium carbonate, and more preferably sodium hydroxide or potassium hydroxide. The solvent is preferably acetone, methanol, ethanol, propanol, isopropanol, tetrahydrofuran, 1,4-dioxane, 1,2-dimethoxyethane or water or a mixed solvent thereof, and more preferably a mixed solvent of methanol with water. The reaction temperature is preferably between −10° C. and 120° C., and more preferably between 0° C. and 100° C. However, the reaction temperature is not limited insofar as the reaction proceeds.

Reaction formula 13

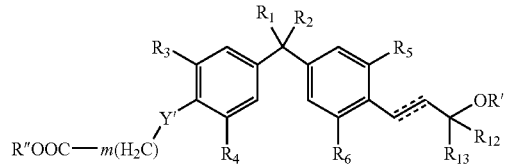

12

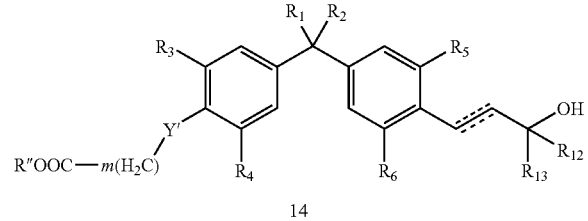

14

In the reaction formula 13, the compound of the general formula (12) can be converted into a compound of the general formula (14) by protecting a hydroxyl group according to a conventional technique.

In the reaction formula 13, $R_{12}$ and $R_{13}$ are as defined for the reaction formula 5, R' is as defined for the reaction formula 7, and Y', m and R" are as defined for the reaction formula 10.

In particular, when R' is a silyl protecting group, R' is deprotected with preferably hydrochloric acid, sulfuric acid, acetic acid, trifluoroacetic acid, p-toluenesulfonic acid, hydrogen fluoride, potassium fluoride, hydrogen fluoride-pyridine, hydrogen fluoride-triethylamine, cesium fluoride or tetrabutylammonium fluoride, and more preferably tetrabutylammonium fluoride. The solvent is preferably acetone, methanol, ethanol, propanol, isopropanol, tetrahydrofuran, 1,4-dioxane, 1,2-dimethoxyethane, acetonitrile, dichloromethane, chloroform, dimethyl sulfoxide or water or a mixed solvent thereof, and more preferably tetrahydrofuran. The reaction temperature is preferably between −10° C. and 120° C., and more preferably between 0° C. and 100° C. However, the reaction temperature is not limited insofar as the reaction proceeds. The reactions shown in the reaction formulas 12 and 13, respectively, may be carried out at the same time.

Reaction formula 14

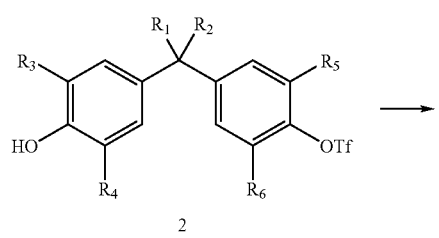

2

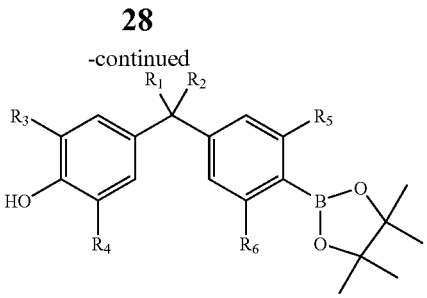

15

In the reaction formula 14, the compound of the general formula (2) can be converted into a compound of the general formula (15) by the same method as in the reaction formula 9.

Reaction formula 15

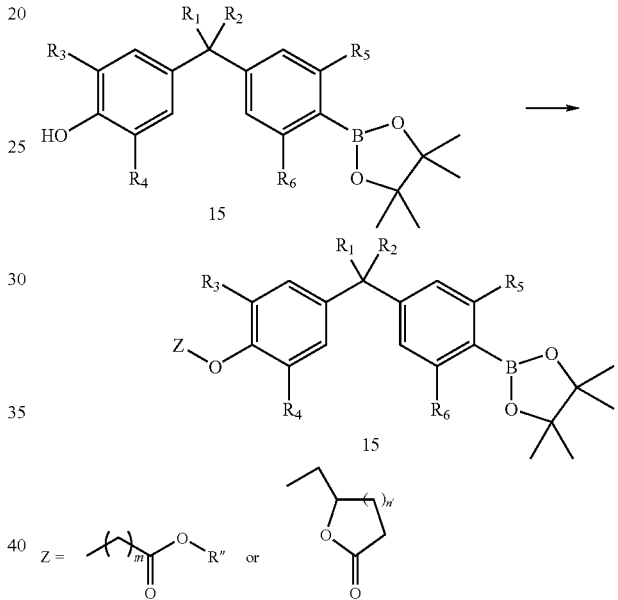

In the reaction formula 15, the compound of the general formula (15) can be converted into a compound of the general formula (16) by reacting with Z-X' (where Z is represented by the above formula) in the presence of a base.

In the reaction formula 15, m is as defined for the reaction formula 10. X' is as defined for the reaction formula 7. R" is as defined for the reaction formula 11. n' represents an integer of 0 to 3.

The base used in the reaction formula 15 is preferably sodium t-butoxide, potassium t-butoxide, n-butyllithium, sec-butyllithium, t-butyllithium, lithium diisopropylamide, lithium dicyclohexylamide, lithium bis(trimethylsilyl)amide, potassium bis(trimethylsilyl)amide, sodium hydride, potassium hydride, potassium carbonate, sodium carbonate, sodium bicarbonate, cesium carbonate, pyridine, triethylamine, diisopropylethylamine, 2,6-lutidine, 2,4,6-collidine or N,N-dimethylaminopyridine, and more preferably potassium carbonate. The solvent is preferably dichloromethane, 1,2-dichloroethane, chloroform, hexane, benzene, toluene, diethyl ether, t-butyl methyl ether, tetrahydrofuran, 1,2-dimethoxyethane, 1,4-dioxane, diisopropyl ether, N,N-dimethylformamide, dimethyl sulfoxide, N,N-dimethylacetamide, 1,3-dimethyl-2-imidazolidinone, 1,3-dimethyl-3,4,5, 6-tetrahydro-2(1H)-pyrimidinone or acetonitrile, and more preferably N,N-dimethylformamide. The reaction temperature is preferably between −50° C. and 200° C., and more preferably between 0° C. and 150° C. However, the reaction temperature is not limited insofar as the reaction proceeds.

Reaction formula 16

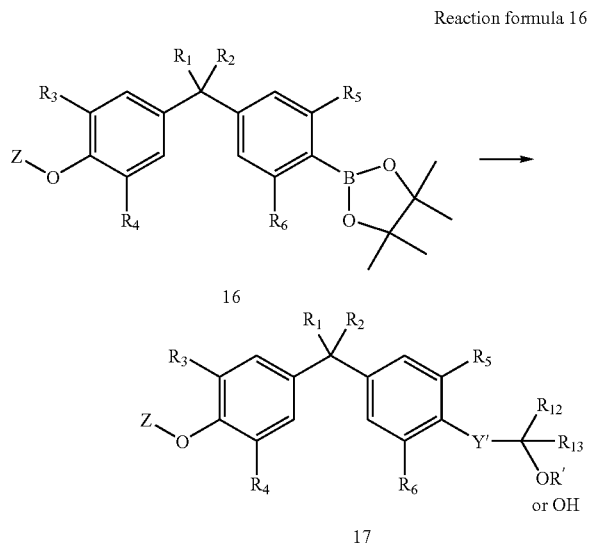

In the reaction formula 16, the compound of the general formula (16) can be converted into a compound of the general formula (17) by the same method as in the reaction formula 11. In the reaction formula 16, $R_{12}$ and $R_{13}$ are as defined for the reaction formula 5, R' is as defined for the reaction formula 7, and Y' is as defined for the reaction formula 10. Z is as defined for the reaction formula 15.

The ester or lactone of Z in the general formula (17) can be converted into a corresponding carboxylic acid by the same method as in the reaction formula 12. When the compound of the general formula (17) has a hydroxyl group with a protecting group as —OR', —OR' can be deprotected into a hydroxyl group.

The Medicine of the Present Invention

The compound obtained as described above has an effect as a vitamin D3 receptor agonist, for example. Accordingly, the present invention also provides a medicine containing the compound as an active ingredient. The phrase "containing the compound as an active ingredient" is herein used to include use of any of the compound of the present invention and pharmaceutically acceptable forms highly relevant to the compound (for example, salt, ester, amide, hydrate or solvate forms thereof; masked or protected forms (including prodrugs) thereof; and racemic mixtures or optical isomers (enantiomers, diastereomers or tautomers) thereof) as an active ingredient.

The present invention includes both free forms and pharmaceutically acceptable salts of the compound (I). Such "salts" are not specifically limited insofar as the salts are formed with the compound (I) of the present invention and are pharmaceutically acceptable. Examples of the salts include acid salts obtained by reacting the compound (I) with an acid and base salts obtained by reacting the compound (I) with a base.

The acid used for preparing a pharmaceutically acceptable acid salt of the compound (I) of the present invention preferably can be reacted with the compound (I) of the present invention to form a nontoxic acid salt. Examples of the acid salt include hydrochlorides, hydrobromides, hydroiodides, nitrates, sulfates, bisulfates, phosphates, acid phosphates, acetates, lactates, citrates, acid citrates, tartrates, bitartrates, succinates, maleates, fumarates, gluconates, saccharates, benzoates, methanesulfonates, ethanesulfonates, benzenesulfonates, p-toluenesulfonates and 1,1'-methylene-bis-(2-hydroxy-3-naphthoates).

The base used for preparing a pharmaceutically acceptable basic salt of the compound (I) of the present invention can preferably be reacted with the compound (I) of the present invention to form a nontoxic basic salt. Examples of the basic salt include alkaline metal salts such as sodium salts and potassium salts; alkaline earth metal salts such as calcium salts and magnesium salts; water-soluble amine addition salts such as ammonium salts and N-methylglucamine salts; lower alkanol ammonium salts; and pharmaceutically acceptable salts derived from other bases of organic amines.

Further, the compound (I) of the present invention may absorb another certain solvent to form a solvate, and the present invention includes such solvates. "Solvation" herein refers to a phenomenon in which a solute molecule or ion strongly attracts a solvent molecule adjacent to the solute molecule or ion to form one molecular assembly in a solution, and refers to hydration if the solvent is water.

The compound (I) of the present invention may be administered in the form of a prodrug. Here, the "prodrug" refers to a drug precursor compound that releases the active ingredient in vivo through a chemical or physical process after administration. For example, the prodrug is converted into a desired drug form at a specific pH or by the effect of an enzyme. The prodrug is typically a compound generating a free acid in vivo and having a hydrolyzable ester forming residue. Examples of such a hydrolyzable ester forming residue include, but are not limited to, residues having a carboxyl moiety in which free hydrogen (for example, free hydrogen in a carboxyl group when Y in the formula (I) has the carboxyl group) is substituted with a $C_{1-4}$ alkyl group, a $C_{2-7}$ alkanoyloxymethyl group, a 1-(alkanoyloxy)ethyl group having 4 to 9 carbon atoms, a 1-methyl-1-(alkanoyloxy)-ethyl group having 5 to 10 carbon atoms, an alkoxycarbonyloxymethyl group having 3 to 6 carbon atoms, a 1-(alkoxycarbonyloxy)ethyl group having 4 to 7 carbon atoms, a 1-methyl-1-(alkoxycarbonyloxy)ethyl group having 5 to 8 carbon atoms, N-(alkoxycarbonyl)aminomethyl having 3 to 9 carbon atoms, a 1-(N-(alkoxycarbonyl)amino)ethyl group having 4 to 10 carbon atoms, a 3-phthalidyl group, a 4-crotonolactonyl group, a γ-butyrolacton-4-yl group, a di-N,N-$(C_{1-2})$alkylamino$(C_{2-3})$ alkyl group (for example, a B-dimethylaminoethyl group), a carbamoyl-$(C_{1-2})$alkyl group, a N,N-di$(C_{1-2})$alkylcarbamoyl-$(C_{1-2})$alkyl group, a piperidino$(C_{2-3})$alkyl group, a pyrrolidino$(C_{2-3})$alkyl group or a morpholino$(C_{2-3})$alkyl group.

The term "pharmaceutical composition" defined herein refers to a composition containing an active ingredient useful in the method of the present invention and an additive such as a carrier used in preparation of a medicine. For example, the pharmaceutical composition of the present invention contains (a) a safe and therapeutically effective amount of the compound of the present invention or a corresponding enantiomer, diastereomer or tautomer thereof or a pharmaceutically acceptable salt thereof, or a prodrug thereof; and (b) a pharmaceutically acceptable carrier.

The compound useful in the present invention can be formulated into a pharmaceutical composition used for treatment of the above various diseases, specifically, prevention, treatment and therapy of such conditions. Such a standard formulation technique as described in Remington's Pharmaceutical Sciences, Mack Publishing Company, Easton, Pa. is used for formulation. A "safe and therapeutically effective amount" of the compound useful in the present invention refers to an amount of the compound which exhibits vitamin D receptor modulating activity (for example, agonist activity to a vitamin D3 receptor) in accordance with a reasonable benefit/risk ratio without showing inappropriate side effects (toxic, irritative or allergic reactions) in a subject, tissue or cell, preferably an animal, and more preferably a mammal, when the compound is used according to the method of the present invention. The specific "safe and therapeutically effective amount" may vary according to factors such as the specific condition to be treated, the physical condition of the patient, the duration of therapy, the character of concurrent therapy (if any), the specific dosage form used, the carrier used, solubility of the compound in the carrier, and the regimen designed for the compound. For example, the composition contains 0.001 to 99.999 wt % of the active ingredient.

The composition of the present invention contains a pharmaceutically acceptable carrier in addition to the selected compound useful for the present invention. The term "pharmaceutically acceptable carrier" herein refers to one or more compatible solid or liquid diluents or capsulating materials suitable for administration to a mammal. The term "acceptable" herein refers to the fact that a component in the composition can be mixed with the subject compound in such a manner that neither the component nor the compound causes reaction that substantially reduces pharmaceutical efficacy of the composition under normal use conditions. Obviously, the pharmaceutically acceptable carrier must have a sufficiently high purity and sufficiently low toxicity to make the composition suitable for administration to a subject to be treated, preferably an animal, and more preferably a mammal.

Examples of the material that may be used as a pharmaceutically acceptable carrier include saccharides such as lactose, glucose and sucrose; starches such as corn starch and potato starch; cellulose and its derivatives such as sodium carboxymethylcellulose, ethylcellulose and methylcellulose; tragacanth powder; malt; gelatin; talc; solid lubricants such as stearic acid and magnesium stearate; calcium sulfate; vegetable oils such as peanut oil, cottonseed oil, sesame oil, olive oil, corn oil, vegetable oil and cocoa butter; polyhydric alcohols such as propylene glycol, glycerol, sorbitol, mannitol and polyethylene glycol; alginic acid; emulsifiers such as TWEEN; wetting agents such as sodium lauryl sulfate; colorants; flavors; tableting agents; stabilizers; antioxidants; preservatives; pyrogen-free water; isotonic saline solutions; and phosphate buffers.

The compound and composition useful in the present invention can be topically or systemically administered. Systemic application includes any method of introducing the compound into a body tissue such as intraarticular administration, intrameningeal administration, epidural administration, intramuscular administration, dermal administration, intravenous administration, intraperitoneal administration, subcutaneous administration, sublingual administration, inhalation administration, rectal administration or oral administration. The compound useful in the present invention is preferably orally administered.

The medicine of the present invention may be in any of various dosage forms, and is formulated for oral administration, nasal administration, rectal administration, topical administration (including dermal administration), ocular administration, intracerebral administration, intravenous administration, intramuscular administration or dermal administration, for example. (The skilled artisan may prefer pulmonary and nasal compositions including compositions administered by inhalation and produced by a known method.) Various pharmaceutically acceptable carriers known in the art can be used according to the desired route of administration. Such carriers include solid or liquid additives, diluents, hydrotropy, surfactants and capsulating materials. Such carriers may include any pharmaceutically acceptable materials that do not substantially inhibit activity of the compound. The amount of the carrier used together with the compound is an amount sufficient to provide an amount of a material realistic for administration of a unit dose of the compound. Techniques and compositions for producing a dosage form useful in the method of the present invention are described in the following references: Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2nd Edition (1976), all of which are incorporated herein by reference.

The medicine of the present invention may be formulated as various oral dosage forms including tablets, capsules, granules and bulk powders. Such an oral dosage form contains a safe and effective amount of the compound of the present invention.

"Tablets" may be compressed tablets, triturated tablets, enteric-coated tablets, sugar-coated tablets, film-coated tablets or multilayer compressed tablets containing an appropriate binder, lubricant, diluent, disintegrant, colorant, flavor, fluidizer or solubilizer. A liquid oral dosage form contains an aqueous solution, an emulsion, a suspension, a solution and/or a suspension reconstituted from non-effervescent granules and also contains an effervescent preparation reconstituted from effervescent granules containing an appropriate solvent, preservative, emulsifier, suspending agent, diluent, sweetener, solubilizer, colorant or flavor.

"Tablets" typically contain a common pharmaceutically compatible adjuvant as an inert diluent such as calcium carbonate, sodium carbonate, mannitol, lactose or cellulose; a binder such as starch, gelatin or sucrose; a disintegrant such as starch, alginic acid or croscarmelose; or a lubricant such as magnesium stearate, stearic acid or talc. Fluidizers such as silicon dioxide may be used to improve flow characteristics of the powder mixture. Colorants such as FD and C dyes may be used for improving appearance. Sweeteners and flavors such as aspartame, saccharin, menthol, peppermint and fruit flavors are useful adjuvants for chewable tablets. Capsules typically contain one or more of the above solid diluents. The choice of carrier components depends on secondary factors such as taste, cost and storage stability which are not important for the purpose of the present invention, and such components may be easily chosen by the skilled artisan.

Tablets and granules may be coated by a common technique, and are typically coated so that the objective compound is released in a pH- or time-dependent manner near a site of the gastrointestinal tract where topical administration is desired, or at various time points to prolong the desired effect. Such dosage forms typically, but do not necessarily, contain one or more of cellulose acetate phthalate, polyvinyl acetate phthalate, hydroxypropylmethylcellulose phthalate, ethylcellulose, Eudragit coating, wax and shellac. The composition of the present invention may contain any other pharmaceutically active ingredient.

Compositions for oral administration include liquids such as solutions, emulsions and suspensions. Pharmaceutically acceptable carriers suitable for preparing such compositions are known in the art. Typical components of carriers for syrups, elixirs, emulsions and suspensions include ethanol, glycerol, propylene glycol, polyethylene glycol, liquid sucrose, sorbitol and water. Typical suspending agents for suspensions include methylcellulose, sodium carboxymethylcellulose, AVICEL RC-591, tragacanth and sodium alginate; typical wetting agents include lecithin and polysolvate 80; and typical preservatives include methylparaben and sodium benzoate. Oral solution compositions may contain one or more components such as the above sweeteners, flavors and colorants.

When the active ingredient is administered as an "injection", the pharmaceutically acceptable carrier is preferably sterile saline with a blood-compatible suspending agent adjusted to about pH 7.4. In particular, pharmaceutically acceptable carriers for systemic administration include saccharides, starches, cellulose and its derivatives, malt, gelatin, talc, calcium sulfate, vegetable oils, synthetic oils, polyhydric alcohols, alginic acid, phosphate buffers, emulsifiers, isotonic saline solutions and pyrogen-free water. Preferable carriers for parenteral administration include propylene glycol, ethyl oleate, pyrrolidone, ethanol and sesame oil.

Other compositions useful for systemic administration of the compound of the present invention include "sublingual, buccal and rectal dosage forms". Such compositions typically contain one or more of soluble excipient materials such as sucrose and sorbitol; and binders such as acacia, microcrystalline cellulose, carboxymethylcellulose and hydroxypropylcellulose. The compositions may contain the above fluidizers, lubricants, sweeteners, colorants, antioxidants and flavors.

The composition of the present invention can be topically administered to a patient by directly applying or spreading the compound of the present invention to the epidermal or epithelial tissue of the patient or by dermally applying the compound to the tissue through a patch, for example, in order to treat skin conditions such as psoriasis. Examples of such a composition include lotions, creams, solutions, gels and solids. Preferably, such a composition for topical administration contains a safe and effective amount of the compound of the present invention. For topical administration, the carrier preferably remains on the skin as a persistent thin film and is resistant to removal by sweating or water immersion. Generally, the carrier is an organic compound and can disperse or dissolve the compound of the present invention. The carrier may contain a pharmaceutically acceptable emollient, emulsifier, thickener or solvent.

The composition of the present invention is preferably provided in a unit dosage form. The "unit dosage form" is herein the composition of the present invention containing an amount of the compound suitable for administration to an animal subject, and preferably to a mammal subject in a single dose according to good medical practice. (However, preparation of a single or unit dosage form does not mean that the dosage form is administered once per day or once per course of therapy. This dosage form is intended to be administered once, twice, three times or more per day and is also planned to be administered once or more per course of therapy. However, single-time administration is not particularly excluded. The skilled artisan will recognize that the formulation is particularly not intended to be administered during one course of therapy and the skilled artisan should determine whether or not the formulation is administered during the course of therapy.)

The specific dose of the active ingredient to be administered, as well as the duration of therapy, should be individually determined by the physician responsible for therapy. Typically about 1 ng/kg to 50 mg/kg, preferably about 1 ng/kg to 1 mg/kg, and more preferably about 10 ng/kg to 100 µg/kg per day of the active ingredient is administered to the adult. It should be understood that the dose ranges are only for illustrative purposes and daily administration is controlled according to factors such as the type of the disease, the degree of the disease, the age of the patient, the sex of the patient and the route of administration.

In the whole description above, it is obvious that the compound useful in the present invention can be administered singly or in a mixture and the composition may further contain an additional drug or an additive suitable for an indication.

EXAMPLES

The present invention will be described below with reference to examples; however, the present invention is not limited thereto.

In the following examples, reaction was carried out at room temperature and in a nitrogen or argon atmosphere unless otherwise described. Reaction was carried out using an anhydrous solvent unless otherwise described. Purification by a silica gel column was carried out using a silica gel manufactured by Kanto Chemical Co., Inc. (silica gel 60N (spherical neutral), 40 to 50 µm) unless otherwise described. Purification by preparative TLC was carried out using Kiesel gel 60 F254 (0.5 mm) manufactured by Merck & Co., Inc. unless otherwise described. NMR analysis was carried out using EX-270 manufactured by JEOL Ltd. or Gemini 2000/300 manufactured by Varian, Inc. with deuterated chloroform as a solvent and tetramethylsilane as an internal standard unless otherwise described. Mass spectrometry was carried out using LCQ manufactured by Finnigan or Micromass ZQ manufactured by Waters Corporation (column: Chromoli tetrahydrofuran lash RP-18e 4.6×25 mm, methanol:10 mM ammonium acetate solution=50:50 to 100:0 (3-minute gradient), flow rate: 2 ml/min) unless otherwise described. Microwave irradiation experiments were carried out using Initiator manufactured by Biotage AB unless otherwise described.

Example 1

Synthesis of 4'-{1-ethyl-1-[4-((E)-3-ethyl-3-hydroxy-1-pentenyl)-3-methyl-phenyl]-propyl}-2'-methyl-biphenyl-3-carboxylic Acid

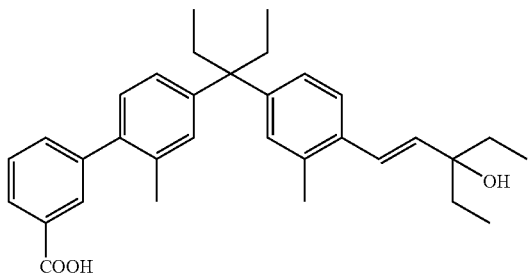

(1) Synthesis of Trifluoromethanesulfonic Acid 4-[1-ethyl-1-(4-hydroxy-3-methyl-phenyl)-propyl]-2-methyl-phenyl Ester

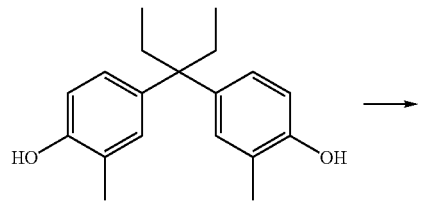

Pyridine (3 mL, 37.2 mmol) and trifluoromethanesulfonic anhydride (5.7 mL, 34.7 mmol) were added to a solution of 3,3-bis[4-hydroxy-3-methylphenyl]pentane (9.0 g, 31.6 mmol) in dichloromethane (300 mL) at 0° C., and then the mixture was stirred at the same temperature for one hour. Ethyl acetate was added to the reaction mixture. The organic layer was washed with a saturated aqueous sodium bicarbonate solution and brine, dried over anhydrous magnesium sulfate and concentrated under reduced pressure. The residue was purified by a silica gel column (hexane/ethyl acetate=10/1 to ethyl acetate only) to give the title compound (4.9 g, 37%).

$^1$H-NMR: 0.62 (t, 6H), 2.03 (q, 4H), 2.20 (s, 3H), 2.38 (s, 3H), 4.67 (s, 1H), 6.68 (d, 1H), 6.80-6.88 (m, 2H), 7.02-7.11 (m, 3H); MS (ESI+): 417 ([M+H]$^+$).

(2) Synthesis of 4-[1-ethyl-1-(3-methyl-4-trimethylsilanylethynyl-phenyl)-propyl]-2-methyl-phenol

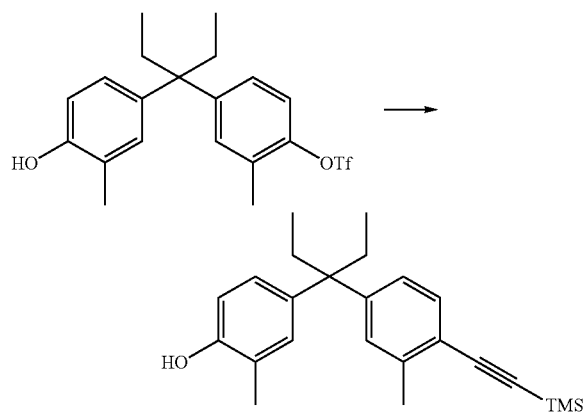

Triethylamine (25.1 mL, 180.09 mmol), ethynyltrimethylsilane (25.5 mL, 180.09 mmol), CuI (1.143 g, 6.00 mmol) and tetrakis(triphenylphosphine)palladium (0) (6.93 g, 6.00 mmol) were added to a solution of trifluoromethanesulfonic acid 4-[1-ethyl-1-(4-hydroxy-3-methyl-phenyl)-propyl]-2-methyl-phenyl ester (Example 1-(1); 25 g, 60.03 mmol) in acetonitrile (300 mL) at room temperature, and the mixture was stirred at 110° C. for 18 hours and concentrated under reduced pressure. Ethyl acetate and water were added to the residue, and a 1 N hydrochloric acid aqueous solution was added to adjust the pH to about 7. The organic layer was dried over anhydrous magnesium sulfate and concentrated under reduced pressure. The residue was purified by a silica gel column (hexane/ethyl acetate=15/1) to give the title compound (16 g, 74%).

$^1$H-NMR: 0.25 (s, 9H), 0.60 (t, 6H), 2.04 (q, 4H), 2.18 (s, 3H), 2.38 (s, 3H), 4.58 (s, 1H), 6.63 (d, 1H), 6.83-6.88 (m, 2H), 6.92 (d, 1H), 7.00 (s, 1H), 7.30 (d, 1H).

(3) Synthesis of 4-[1-ethyl-1-(4-ethynyl-3-methyl-phenyl)-propyl]-2-methyl-phenol

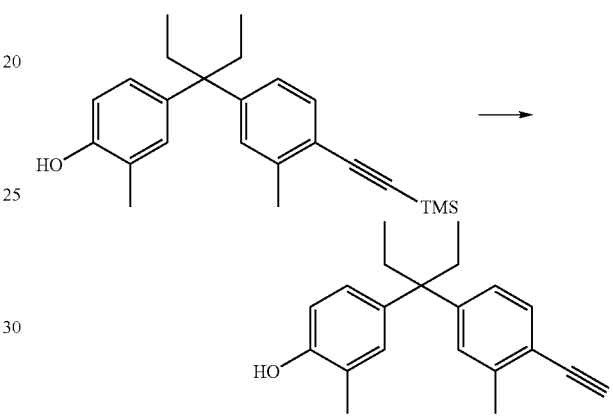

A 1 M solution of tetrabutylammonium fluoride in tetrahydrofuran (78.3 mL, 78.3 mmol) was added to a solution of 4-[1-ethyl-1-(3-methyl-4-trimethylsilanylethynyl-phenyl)-propyl]-2-methyl-phenol (Example 1-(2); 19.03 g, 52.19 mmol) in tetrahydrofuran (520 mL) at room temperature. The mixture was stirred at 0.5 hour and concentrated under reduced pressure. The residue was extracted with ethyl acetate, and the organic layer was washed with brine, dried over anhydrous magnesium sulfate and concentrated under reduced pressure. The residue was purified by a silica gel column (hexane/ethyl acetate=10/1) to give the title compound (15.6 g, 94%).

$^1$H-NMR: 0.60 (t, 6H), 2.04 (q, 4H), 2.20 (s, 3H), 2.41 (s, 3H), 3.23 (s, 1H), 4.51 (s, 1H), 6.64 (d, 1H), 6.82-6.86 (m, 2H), 6.90-6.95 (m, 1H), 7.00 (s, 1H), 7.29 (d, 1H); MS (ESI−): 291 ([M−H]$^-$).

(4) Synthesis of 4-{1-ethyl-1-[4-(3-ethyl-3-hydroxy-1-pentynyl)-3-methyl-phenyl]-propyl}-2-methyl-phenol

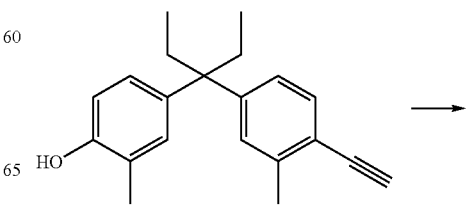

-continued

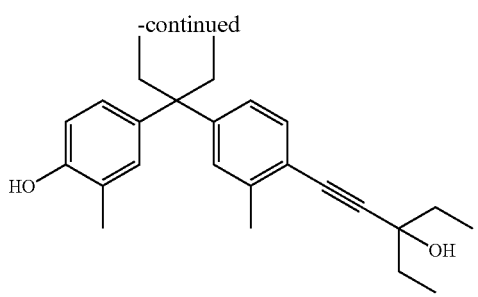

A 2.5 M solution of n-butyllithium in hexane (14.7 mL, 36.73 mmol) was added to a solution of 4-[1-ethyl-1-(4-ethynyl-3-methyl-phenyl)-propyl]-2-methyl-phenol (Example 1-(3); 4.28 g, 14.69 mmol) in tetrahydrofuran (92 mL) at −78° C. Pentan-3-one (4.85 mL, 44.07 mmol) was added to the mixture at −78° C., and the mixture was stirred at the same temperature for three hours and concentrated under reduced pressure. Ethyl acetate and water were added to the residue, and a 1 N hydrochloric acid aqueous solution was added to adjust the pH to about 7. The organic layer was dried over anhydrous magnesium sulfate and concentrated under reduced pressure. The residue was purified by a silica gel column (hexane/ethyl acetate=6/1) to give the title compound (3.66 g, 62%).

$^1$H-NMR: 0.61 (t, 6H), 1.11 (t, 6H), 1.72-1.78 (m, 4H), 2.02 (q, 4H), 2.19 (s, 3H), 2.38 (s, 3H), 4.50 (s, 1H), 6.65 (d, 1H), 6.82-6.86 (m, 2H), 6.90-6.95 (m, 1H), 7.00 (s, 1H), 7.29 (d, 1H); MS (ESI−): 377 ([M−H]−).

(5) Synthesis of 4-{1-ethyl-1-[4-(3-ethyl-3-hydroxy-1-pentenyl)-3-methyl-phenyl]-propyl}-2-methyl-phenol

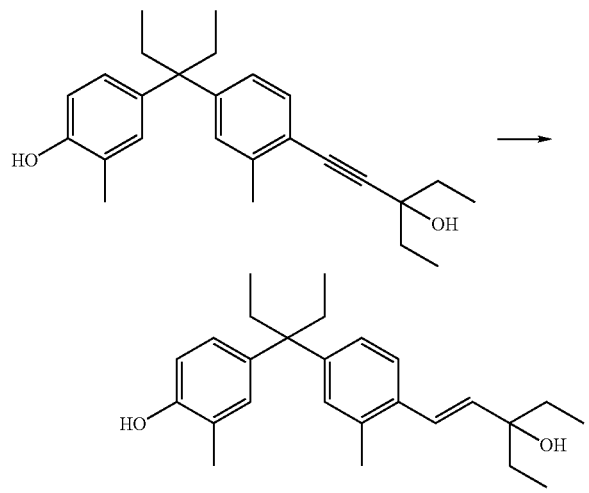

A 1 M solution of LiAlH$_4$ in tetrahydrofuran (5.28 mL, 5.28 mmol) was added to a solution of 4-{1-ethyl-1-(4-(3-ethyl-3-hydroxy-1-pentynyl)-3-methyl-phenyl)-propyl}-2-methyl-phenol (Example 1-(4); 800 mg, 2.11 mmol) in tetrahydrofuran (8 mL) at room temperature. The mixture was heated under reflux for 18 hours and cooled, and then water was added. The mixture was filtered, followed by extraction with ethyl acetate. The organic layer was washed with brine, dried over anhydrous magnesium sulfate and concentrated under reduced pressure. The residue was purified by a silica gel column (hexane/ethyl acetate=7/1) to give the title compound (500 mg, 62%).

$^1$H-NMR: 0.60 (t, 6H), 0.93 (t, 6H), 1.64 (q, 4H), 2.04 (q, 4H), 2.20 (s, 3H), 2.31 (s, 3H), 4.59 (s, 1H), 6.02 (d, 1H), 6.66 (d, 1H), 6.75 (d, 1H), 6.83-6.92 (m, 4H), 7.28 (d, 1H); MS (ESI−): 379 ([M−H]−).

(6) Synthesis of Trifluoromethanesulfonic Acid 4-{1-ethyl-1-[4-((E)-3-ethyl-3-hydroxy-1-pentenyl)-3-methyl-phenyl]-propyl}-2-methyl-phenyl Ester

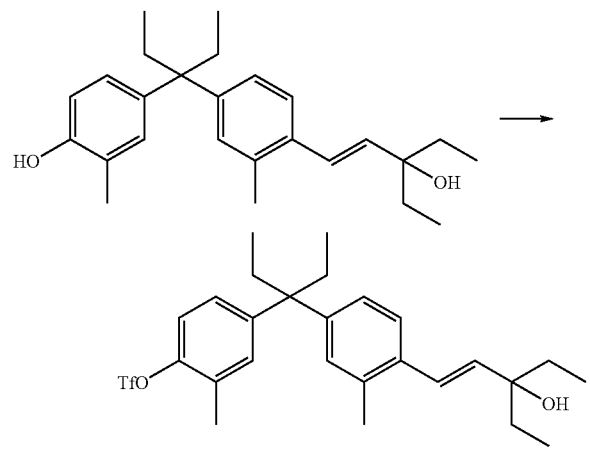

Pyridine (160 μl, 2.0 mmol) was added to a solution of 4-{1-ethyl-1-(4-(3-ethyl-3-hydroxy-1-pentenyl)-3-methyl-phenyl)-propyl}-2-methyl-phenol (Example 1-(5); 380 mg, 1.0 mmol) in dichloromethane (3 mL) at room temperature. The mixture was cooled to 0° C., trifluoromethanesulfonic anhydride (168 μl, 1 mmol) was added at the same temperature, and the mixture was stirred at the same temperature for one hour. Trifluoromethanesulfonic anhydride (84 μl, 0.5 mmol) was further added at 0° C., and the mixture was stirred at the same temperature for one hour. A saturated aqueous ammonium chloride solution was added to the reaction mixture, followed by extraction with ethyl acetate. The organic layer was washed with water, dried over anhydrous magnesium sulfate and concentrated under reduced pressure. The residue was purified by a silica gel column (hexane only to hexane/ethyl acetate=5/1) to give the title compound (324 mg, 63%).

$^1$H-NMR: 0.62 (t, 6H), 0.92 (t, 6H), 1.64 (q, 4H), 2.05 (q, 4H), 2.32 (s, 6H), 6.03 (d, 1H), 6.74 (d, 1H), 6.90-7.35 (m, 6H).

(7) Synthesis of 4'-{1-ethyl-1-[4-((E)-3-ethyl-3-hydroxy-1-pentenyl)-3-methyl-phenyl]-propyl}-2'-methyl-biphenyl-3-carboxylic Acid

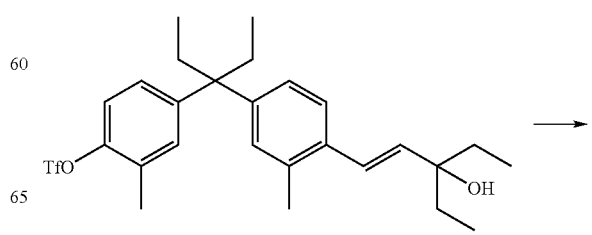

-continued

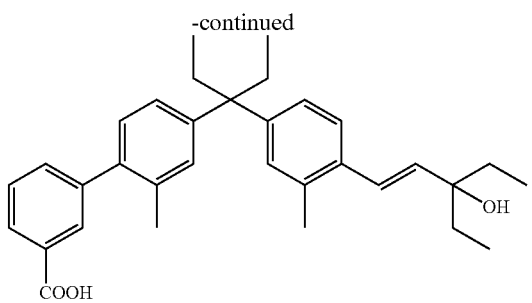

Tetrakis(triphenylphosphine)palladium (0) (6.8 mg, 0.0059 mmol), 3-carboxyphenylborane acid (6.8 mg, 0.0195 mmol) and potassium carbonate (13.4 mg, 97.5 μmol) were added to a solution of trifluoromethanesulfonic acid 4-{1-ethyl-1-[4-((E)-3-ethyl-3-hydroxy-1-pentenyl)-3-methyl-phenyl]-propyl}-2-methyl-phenyl ester (Example 1-(6); 10 mg, 0.0195 mmol) in N,N-dimethylformamide (0.5 mL) at room temperature, and then the mixture was stirred at 80° C. for five minutes. Water was added to the reaction mixture, followed by extraction with ethyl acetate. The organic layer was washed with water, dried over magnesium sulfate and concentrated under reduced pressure. The residue was purified by preparative TLC (chloroform/methanol=8/3, saturated with water) to give the title compound (5.6 mg, 60%).

$^1$H-NMR: 0.67 (t, 6H), 0.93 (t, 6H), 1.64 (q, 4H), 2.09 (q, 4H), 2.23 (s, 3H), 2.34 (s, 3H), 6.03 (d, 1H), 6.75 (d, 1H), 6.90-8.12 (m, 10H); MS (ESI+): 467 (M-OH)$^+$.

Example 2

Synthesis of 4'-{1-ethyl-1-[4-((E)-3-ethyl-3-hydroxy-1-pentenyl)-3-methyl-phenyl]-propyl}-2'-methyl-biphenyl-4-carboxylic Acid

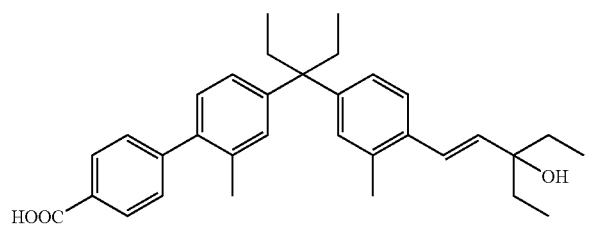

The title compound was synthesized by the same method as in Example 1-(7) using 4-carboxyphenylborane acid and the raw material 1-(6).

$^1$H-NMR: 0.66 (t, 6H), 0.92 (t, 6H), 1.64 (q, 4H), 2.08 (q, 4H), 2.24 (s, 3H), 2.39 (s, 3H), 6.03 (d, 1H), 6.76 (d, 1H), 7.00-7.46 (m, 6H), 7.43 (d, 2H), 8.12 (d, 2H); MS (ESI+): 467 (M-OH)$^+$.

Example 3

Synthesis of 5-(4-{1-ethyl-1-[4-(3-hydroxy-4,4-dimethyl-pentyl)-3-methyl-phenyl]-propyl}-2-methyl-phenyl)-furan-2-carboxylic Acid

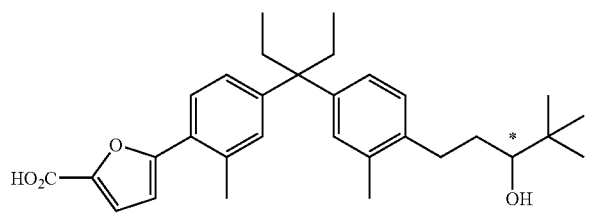

(1) Synthesis of 4-{1-ethyl-1-[4-(3-hydroxy-4,4-dimethyl-1-pentynyl)-3-methyl-phenyl]-propyl}-2-methyl-phenol (Racemic Mixture)

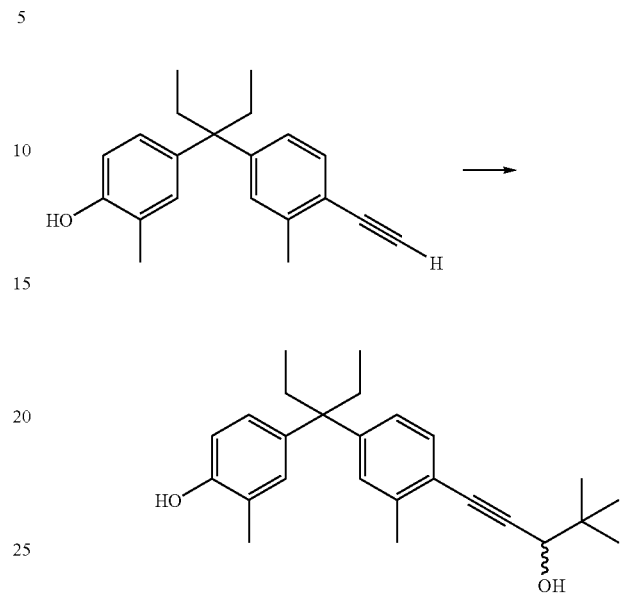

A 2.44 M solution of n-butyllithium in hexane (42.8 mL, 104.5 mmol) was added to a solution of 4-[1-ethyl-1-(4-ethynyl-3-methyl-phenyl)-propyl]-2-methyl-phenol (Example 1-(3); 12.22 g, 41.8 mmol) in tetrahydrofuran (300 mL) at 0° C., and the mixture was stirred at the same temperature for 30 minutes. Trimethylacetaldehyde (13.79 mL, 125.4 mmol) was added at 0° C., and the mixture was stirred at the same temperature for 30 minutes. A saturated aqueous ammonium chloride solution was added to the reaction mixture, followed by extraction with ethyl acetate. The organic layer was dried over anhydrous magnesium sulfate and concentrated under reduced pressure. The residue was purified by a silica gel column (hexane/ethyl acetate=9/1 to 3/1) to give the title compound (13.08 g, 83%).

$^1$H-NMR (chloroform-d): 0.59 (t, 6H), 1.07 (s, 9H), 1.86 (d, 1H), 2.03 (q, 4H), 2.19 (s, 3H), 2.38 (s, 3H), 4.26 (d, 1H), 4.59 (s, 1H), 6.65 (d, 1H), 6.82-6.85 (m, 2H), 6.92-6.95 (m, 1H), 7.00 (s, 1H), 7.28 (d, 1H).

(2) Chiral Resolution of 4-{1-ethyl-1-[4-(3-hydroxy-4,4-dimethyl-1-pentynyl)-3-methyl-phenyl]-propyl}-2-methyl-phenol

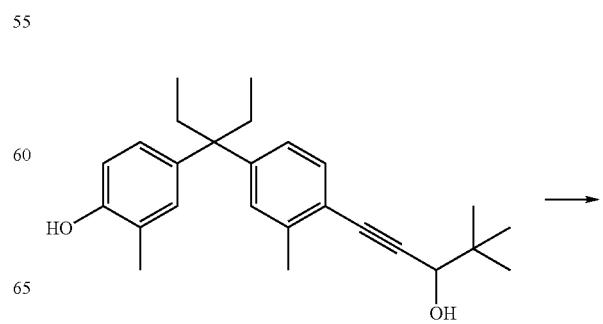

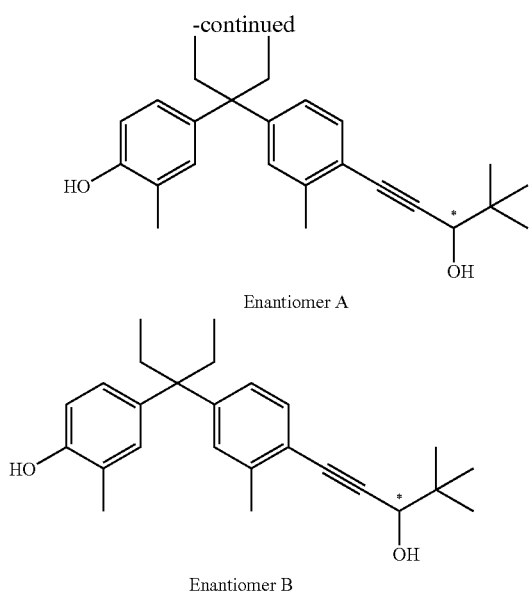

Enantiomer A

Enantiomer B

4-{1-Ethyl-1-[4-(3-hydroxy-4,4-dimethyl-1-pentynyl)-3-methyl-phenyl]-propyl}-2-methyl-phenol (Example 3-(1), racemic mixture; 13.08 g, 34.6 mmol) was resolved into two enantiomers (Enantiomer A: 99.9% ee, 5.58 g/Enantiomer B: 5.00 g, 99.4% ee) by HPLC (CHIRALPAK AD [DAICEL, 20 mm I.D., 250 mm], 2-propanol/hexane=15/85). HPLC analysis data of each enantiomer
Column: CHIRALPAK AD-H 4.6×150 mm (DAICEL)
Developing solvent: Hexane/2-propanol=85/15
Flow rate: 1.0 ml/min
Enantiomer A
Retention time: 5.1 min
Enantiomer B
Retention time: 7.2 min (3) Synthesis of 4-{1-ethyl-1-[4-(3-hydroxy-4,4-dimethyl-pentyl)-3-methyl-phenyl]-propyl}-2-methyl-phenol (Enantiomer 2)

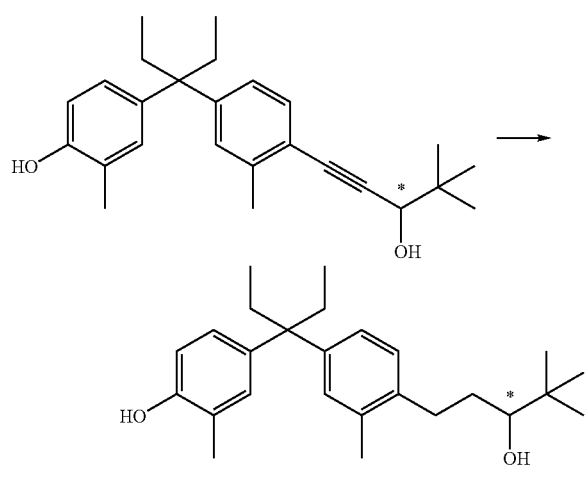

10% Pd—C (0.1 g) was added to a solution of 4-{1-ethyl-1-[4-(3-hydroxy-4,4-dimethyl-1-pentynyl)-3-methyl-phenyl]-propyl}-2-methyl-phenol (Example 3-(2), Enantiomer B; 725 mg, 1.92 mmol) in ethyl acetate (10 mL), and the mixture was stirred in a hydrogen atmosphere for 40 minutes. The reaction mixture was filtered and then concentrated under reduced pressure to give the title compound (720 mg, 98%).

$^1$H-NMR: 0.60 (t, 6H), 0.89 (s, 9H), 1.40 (d, 1H), 1.44-1.55 (m, 1H), 1.74-1.85 (m, 1H), 2.03 (q, 4H), 2.19 (s, 3H), 2.25 (s, 3H), 2.51-2.61 (m, 1H), 2.81-2.91 (m, 1H), 3.25 (dd, 1H), 4.59 (s, 1H), 6.64 (d, 1H), 6.85-7.00 (m, 4H), 7.03 (d, 1H).

(4) Synthesis of 4-(1-{4-[3-(t-butyl-dimethyl-silanyloxy)-4,4-dimethyl-pentyl]-3-methyl-phenyl}-1-ethyl-propyl)-2-methyl-phenol

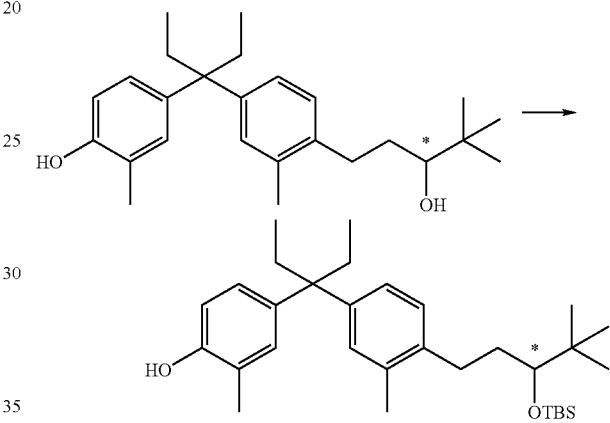

Trifluoromethanesulfonic acid t-butyldimethylsilyl ester (0.51 mL, 3.09 mmol) was added to a solution of 4-{1-ethyl-1-[4-(3-hydroxy-4,4-dimethyl-pentyl)-3-methyl-phenyl]-propyl}-2-methyl-phenol (Example 3-(3), Enantiomer B; 5.04 g, 13.2 mmol) in dichloromethane (40 mL) and lutidine (4.76 mL, 40.9 mmol) at 0° C., and the mixture was stirred at the same temperature for 0.5 hour. The reaction mixture was poured into water, followed by extraction with ethyl acetate and hexane. The organic layer was washed with a saturated aqueous ammonium chloride solution, dried over anhydrous magnesium sulfate and concentrated under reduced pressure. The residue was purified by a silica gel column (hexane only to hexane/ethyl acetate=9/1) to give a disilyl compound (7.32 g). The disilyl compound was dissolved in tetrahydrofuran (113 mL). A 1 M solution of tetrabutylammonium fluoride in tetrahydrofuran (12.6 mL, 12.6 mmol) was added to the solution at 0° C., and the mixture was stirred at the same temperature for five minutes. The reaction mixture was poured into brine, followed by extraction with ethyl acetate and hexane. The organic layer was washed with brine twice, dried over anhydrous magnesium sulfate and concentrated under reduced pressure. The residue was purified by a silica gel column (hexane/ethyl acetate=9/1 to 2/8) to give the title compound (5.66 g, 86%).

$^1$H-NMR: 0.07 (s, 3H), 0.10 (s, 3H), 0.60 (t, 6H), 0.88 (s, 9H), 0.93 (s, 9H), 1.51-1.63 (m, 1H), 1.73-1.84 (m, 1H), 2.03 (q, 4H), 2.20 (s, 3H), 2.23 (s, 3H), 2.36-2.46 (m, 1H), 2.71-2.81 (m, 1H), 3.34 (dd, 1H), 4.50 (s, 1H), 6.64 (d, 1H), 6.85-6.99 (m, 5H)

(5) Synthesis of Trifluoromethanesulfonic Acid 4-(1-{4-[3-(t-butyl-dimethyl-silanyloxy)-4,4-dimethyl-pentyl]-3-methyl-phenyl}-1-ethyl-propyl)-2-methyl-phenyl Ester

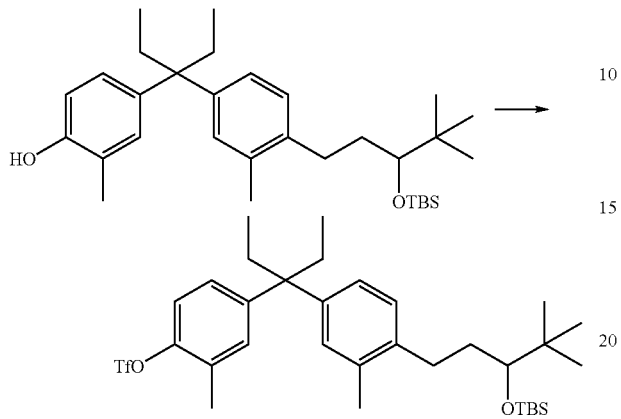

Trifluoromethanesulfonic anhydride (0.51 mL, 3.09 mmol) was added to a solution of 4-(1-{4-[3-(t-Butyl-dimethyl-silanyloxy)-4,4-dimethyl-pentyl]-3-methyl-phenyl}-1-ethyl-propyl)-2-methyl-phenol (Example 3-(4); 1.18 g, 2.38 mmol) in dichloromethane (40 mL) and pyridine (0.35 mL, 4.28 mmol) at room temperature, and the mixture was stirred at the same temperature for 20 minutes. A saturated aqueous ammonium chloride solution, ethyl acetate and hexane were added to the mixture. The organic layer was washed with water, dried over anhydrous magnesium sulfate and concentrated under reduced pressure. The residue was purified by silica gel column chromatography (hexane only to hexane/ethyl acetate=97/3) to give the title compound (11.31 g, 88%).

$^1$H-NMR: 0.07 (s, 3H), 0.10 (s, 3H), 0.60 (t, 6H), 0.88 (s, 9H), 0.94 (s, 9H), 1.51-1.64 (m, 1H), 1.72-1.84 (m, 1H), 2.05 (q, 4H), 2.24 (s, 3H), 2.32 (s, 3H), 2.42 (dq, 1H), 2.77 (dq, 1H), 3.35 (dd, 1H), 6.86-6.88 (m, 2H), 6.99-7.11 (m, 4H).

(6) Synthesis of 5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-carbaldehyde

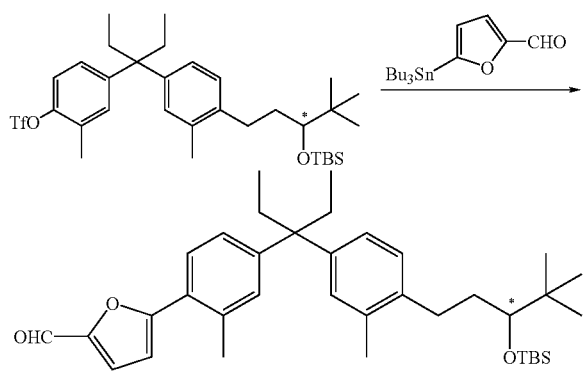

Lithium chloride (593 mg, 14 mmol), bis(triphenylphosphine)palladium (II) dichloride (123 mg, 0.175 mmol) and 5-tributylstannyl-1-furan-2-carbaldehyde (2.02 mg, 5.25 mmol) were added to a suspension of trifluoromethanesulfonic acid 4-(1-{4-[3-(t-butyl-dimethyl-silanyloxy)-4,4-dimethyl-pentyl]-3-methyl-phenyl}-1-ethyl-propyl)-2-methyl-phenyl ester (Example 3-(5); 1.10 g, 1.75 mmol) in dimethoxyethane (5.3 mL), and the mixture was stirred at 60° C. for 15 hours. Water and ethyl acetate were added to the mixture. The organic layer was washed with brine, dried over anhydrous magnesium sulfate and concentrated under reduced pressure. The residue was purified by silica gel chromatography (hexane only to hexane/ethyl acetate=90/1) to give the title compound (2404 mg, 24%).

$^1$H-NMR: 0.07 (s, 3H), 0.10 (s, 3H), 0.63 (t, 6H), 0.88 (s, 9H), 0.93 (s, 9H), 1.54-1.64 (m, 1H), 1.72-1.84 (m, 1H), 2.10 (q, 4H), 2.24 (s, 3H), 2.42 (dt, 1H), 2.50 (s, 3H), 2.76 (dt, 1H), 3.34 (dd, 1H), 6.70 (d, 1H), 6.90-7.11 (m, 5H), 7.32 (d, 1H), 7.67 (d, 1H), 9.65 (s, 1H)

(7) Synthesis of 5-(4-{1-ethyl-1-[4-(3-hydroxy-4,4-dimethyl-pentyl)-3-methyl-phenyl]-propyl}-2-methyl-phenyl)-furan-2-carboxylic Acid

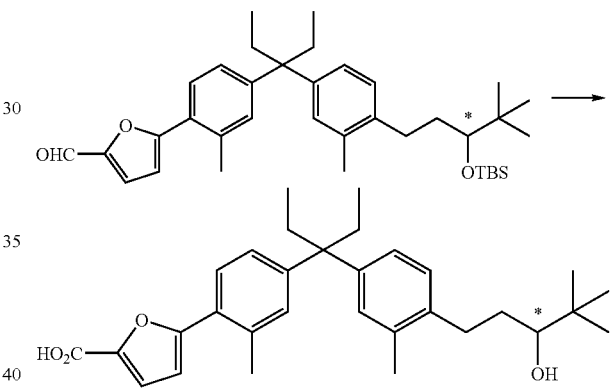

Sodium dihydrogenphosphate (9.6 mg, 0.062 mmol), sodium hypochlorite (11.1 mg, 0.123 mmol) and 2-methyl-2-butene (0.048 mL, 0.45 mmol) were added to a solution of 5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-carbaldehyde (Example 3-(6); 23.6 mg, 0.041 mmol) in water (0.2 mL) and t-butanol (1 mL) at room temperature, and the mixture was stirred at the same temperature for three days. A potassium bisulfate aqueous solution and ethyl acetate were added to the reaction mixture. The organic layer was washed with water twice, dried over anhydrous magnesium sulfate and concentrated under reduced pressure. The residue (25 mg) was dissolved in tetrahydrofuran (0.1 mL), and a 1 M solution of tetrabutylammonium fluoride in tetrahydrofuran (1 mL, 1 mmol) was added at room temperature. The reaction mixture was stirred at 65° C. for one hour. A potassium bisulfate aqueous solution and ethyl acetate were added to the reaction mixture. The organic layer was washed with water twice, dried over anhydrous magnesium sulfate and concentrated under reduced pressure. The residue was purified by preparative TLC (ethyl acetate/methanol=20/1) to give the title compound (12.4 mg, 63%).

$^1$H-NMR: 0.62 (t, 6H), 0.86 (s, 9H), 1.42-1.55 (m, 1H), 1.71-1.81 (m, 1H), 2.12 (q, 4H), 2.24 (s, 3H), 2.44 (s, 3H), 2.49-2.59 (m, 1H), 2.82-2.92 (m, 1H), 3.15 (d, 1H), 6.59 (d, 1H), 6.92-7.09 (m, 6H), 7.71 (d, 1H); MS (ESI–): 475 (M–H)⁻.

Example 4

Synthesis of [5-(4-{1-ethyl-1-[4-(3-hydroxy-4,4-dimethyl-pentyl)-3-methyl-phenyl]-propyl}-2-methyl-phenyl)-furan-2-yl]-acetic Acid

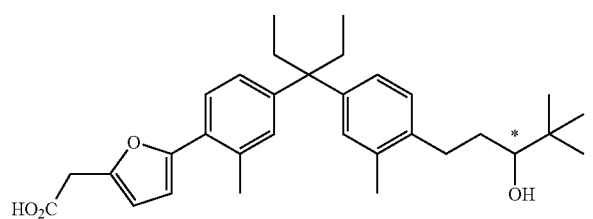

(1) Synthesis of t-butyl-(1-{2-[4-(1-ethyl-1-{4-[5-(2-methoxy-vinyl)-furan-2-yl]-3-methyl-phenyl}-propyl)-2-methyl-phenyl]-ethyl}-2,2-dimethyl-propoxy)-dimethyl-silane

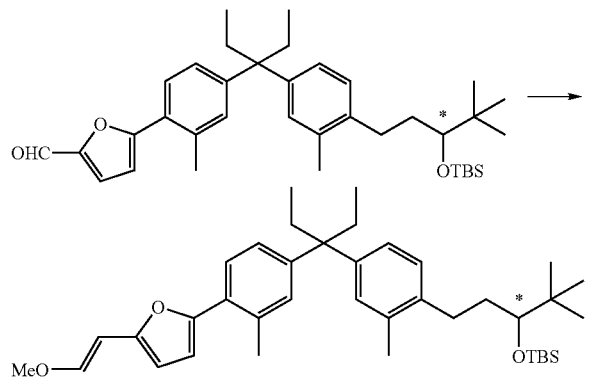

5-[4-(1-{4-[3-(t-Butyl-dimethyl-silanyloxy)-4,4-dimethyl-pentyl]-3-methyl-phenyl}-1-ethyl-propyl)-2-methyl-phenyl]-furan-2-carbaldehyde (Example 3-(6); 47.4 mg, 0.082 mmol) was added to a solution of potassium bis(trimethylsilyl)amide (0.5 M in toluene, 0.36 mL, 0.18 mmol) and (methoxymethyl)triphenylphosphonium chloride (56.2 mg, 0.164 mmol) in toluene (0.5 mL) at room temperature, and the mixture was stirred for 30 minutes. A saturated aqueous ammonium chloride solution and ethyl acetate were added to the reaction mixture. The organic layer was washed with brine, dried over anhydrous magnesium sulfate and concentrated under reduced pressure. The residue was purified by a silica gel column (hexane only to hexane/ethyl acetate=9/1) to give the title compound (42 mg, 85%).

¹H-NMR: 0.07 (s, 3H), 0.10 (s, 3H), 0.60-0.65 (m, 6H), 0.88 (s, 9H), 0.93 (s, 9H), 1.55-1.64 (m, 1H), 1.72-1.82 (m, 1H), 2.09 (q, 4H), 2.23 (s, 3H), 2.36-2.47 (m, 1H), 2.45 (s, 3H), 2.71-2.81 (m, 1H), 3.33-3.36 (m, 1H), 3.67 and 3.81 (s each, 3H) 5.41-7.58 (m, 10H).

(2) Synthesis of [5-(4-{1-ethyl-1-[4-(3-hydroxy-4,4-dimethyl-pentyl)-3-methyl-phenyl]-propyl}-2-methyl-phenyl)-furan-2-yl]-acetic Acid

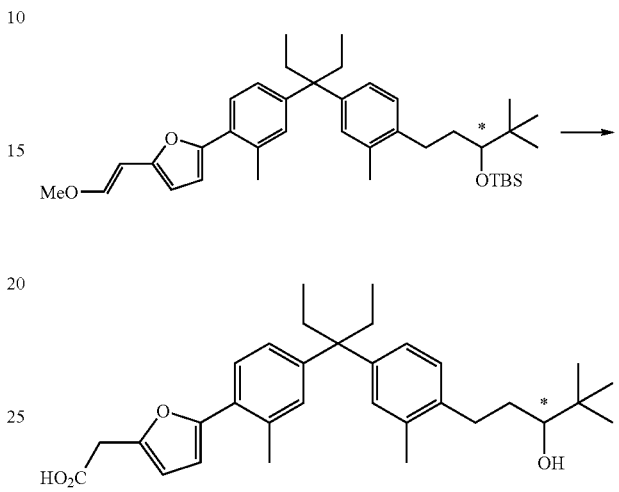

2 N Hydrochloric acid aqueous solution (0.2 mL) was added to a solution of t-butyl-(1-{2-[4-(1-ethyl-1-{4-[5-(2-methoxy-vinyl)-furan-2-yl]-3-methyl-phenyl}-propyl)-2-methyl-phenyl]-ethyl}-2,2-dimethyl-propoxy)-dimethyl-silane (Example 4-(1); 20 mg, 0.033 mmol) in tetrahydrofuran (0.5 mL) at room temperature, and the mixture was stirred at 65° C. for two hours. Tetrahydrofuran (0.3 mL) and 4 N hydrochloric acid aqueous solution (0.2 mL) were further added to the mixture at room temperature, and the mixture was stirred at 65° C. for two hours. A saturated aqueous sodium bicarbonate solution and ethyl acetate were added to the reaction mixture. The organic layer was washed with brine, dried over anhydrous magnesium sulfate and concentrated under reduced pressure. The residue was purified by preparative TLC (hexane/ethyl acetate=3/1). The resulting product (6 mg) was dissolved in water (0.1 mL) and t-butanol (0.4 mL). Sodium dihydrogenphosphate (2.9 mg, 0.019 mmol), sodium hypochlorite (3.4 mg, 0.038 mmol) and 2-methyl-2-butene (0.013 mL, 0.126 mmol) were added at room temperature, and the mixture was stirred at the same temperature for one hour. A saturated aqueous potassium bisulfate aqueous solution and ethyl acetate were added to the reaction mixture. The organic layer was washed with brine, dried over anhydrous magnesium sulfate and concentrated under reduced pressure. The residue was purified by preparative TLC (hexane/ethyl acetate=2/1) to give the title compound (1.2 mg, 7%).

¹H-NMR: 0.61 (t, 6H), 0.86 (s, 9H), 1.42-1.58 (m, 1H), 1.71-1.81 (m, 1H), 2.11 (q, 4H), 2.24 (s, 3H), 2.39 (s, 3H), 2.49-2.59 (m, 1H), 2.82-2.92 (m, 1H), 3.14-3.17 (m, 1H), 3.71 (s, 2H), 6.31 (d, 1H), 6.46 (d, 1H), 6.91-7.05 (m, 5H), 7.50 (d, 1H); MS (ESI+): 508 (M+NH₄)⁺.

Example 5

Synthesis of (E)-3-[5-(4-{1-ethyl-1-[4-(3-hydroxy-4,4-dimethyl-pentyl)-3-methyl-phenyl]-propyl}-2-methyl-phenyl)-furan-2-yl]-acrylic Acid

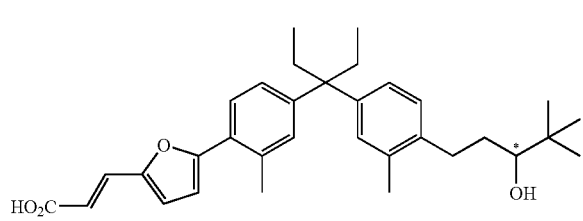

(1) Synthesis of (E)-3-{5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-yl}-acrylic Acid Ethyl Ester

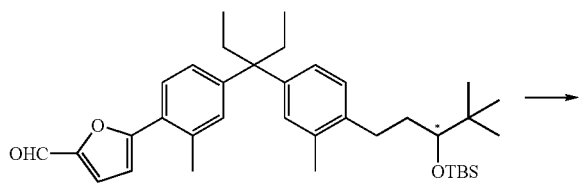

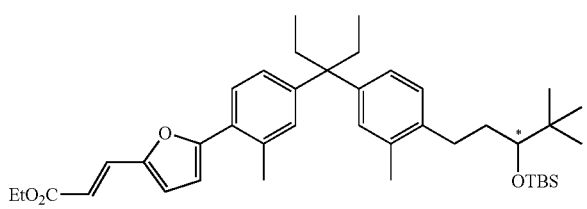

Sodium hydride (60% in oil, 8.4 mg, 0.209 mmol) was added to tetrahydrofuran (1 mL) at 0° C. Triethyl phosphonoacetate (0.049 mL, 0.244 mmol) and then a solution of 5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-carbaldehyde (Example 3-(6); 100 mg, 0.174 mmol) in tetrahydrofuran (0.6 mL) were added at the same temperature, and the mixture was stirred for 20 minutes. A saturated aqueous ammonium chloride solution and ethyl acetate were added to the reaction mixture. The organic layer was dried over anhydrous magnesium sulfate and concentrated under reduced pressure. The residue was purified by a silica gel column (hexane only to hexane/ethyl acetate=9/1) to give the title compound (112 mg, 100%).

$^1$H-NMR: 0.07 (s, 3H), 0.11 (s, 3H), 0.63 (t, 6H), 0.88 (s, 9H), 0.93 (s, 9H), 1.33 (t, 3H), 1.50-1.84 (m, 2H), 2.10 (q, 4H), 2.24 (s, 3H), 2.42 (dt, 1H), 2.49 (s, 3H), 2.77 (dt, 1H), 3.35 (dd, 1H), 4.25 (q, 2H), 6.34 (dd, 1H), 6.59 (d, 1H), 6.68 (d, 1H), 6.91-7.08 (m, 5H), 7.43 (d, 1H), 7.59-7.62 (m, 1H).

(2) Synthesis of (E)-3-[5-(4-{1-ethyl-1-[4-(3-hydroxy-4,4-dimethyl-pentyl)-3-methyl-phenyl]-propyl}-2-methyl-phenyl)-furan-2-yl]-acrylic Acid

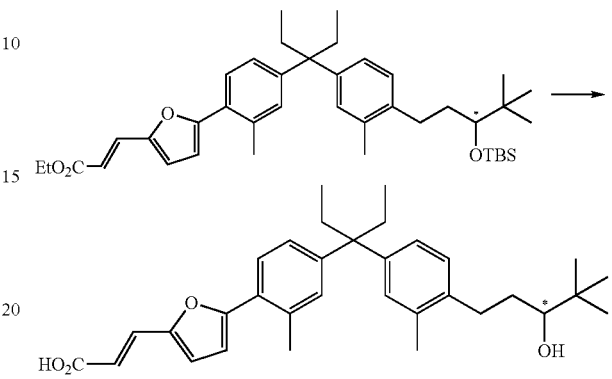

A 1 N potassium hydroxide aqueous solution (2 mL) was added to a solution of (E)-3-{5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-yl}-acrylic acid ethyl ester (Example 5-(1); 42 mg, 0.065 mmol) in methanol (2 mL) and tetrahydrofuran (2 mL) at room temperature, and the mixture was stirred at 60° C. for two hours. The reaction mixture was concentrated under reduced pressure, and ethyl acetate and a saturated aqueous potassium bisulfate solution were added to the residue. The organic layer was washed with water, dried over anhydrous magnesium sulfate and concentrated under reduced pressure. The residue was dissolved in tetrahydrofuran (0.2 mL). A 1 M solution of tetrabutylammonium fluoride in tetrahydrofuran (2 mL, 2 mmol) was added at room temperature, and the mixture was stirred at 65° C. for one hour. A potassium bisulfate aqueous solution and ethyl acetate were added to the reaction mixture to separate the layers. The organic layer was washed with water, dried over anhydrous magnesium sulfate and concentrated under reduced pressure. The residue was purified by preparative TLC (hexane/ethyl acetate=1/2) to give the title compound (21.2 mg, 65%).

$^1$H-NMR: 0.63 (t, 6H), 0.87 (s, 9H), 1.44-1.56 (m, 1H), 1.71-1.81 (m, 1H), 2.13 (q, 4H), 2.25 (s, 3H), 2.46 (s, 3H), 2.49-2.60 (m, 1H), 2.83-2.92 (m, 1H), 3.16 (d, 1H), 6.36 (d, 1H), 6.67 (d, 1H), 6.73 (d, 1H), 6.93-7.10 (m, 5H), 7.33 (d, 1H), 7.60 (d, 1H); MS (ESI–): 501 (M–H)$^-$.

Example 6

Synthesis of 3-[5-(4-{1-ethyl-1-[4-(3-hydroxy-4,4-dimethyl-pentyl)-3-methyl-phenyl]-propyl}-2-methyl-phenyl)-furan-2-yl]-propionic Acid

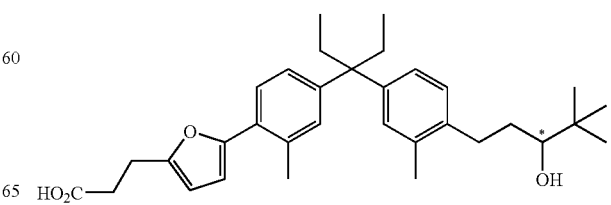

(1) Synthesis of 3-{5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-yl}-propionic Acid Methyl Ester

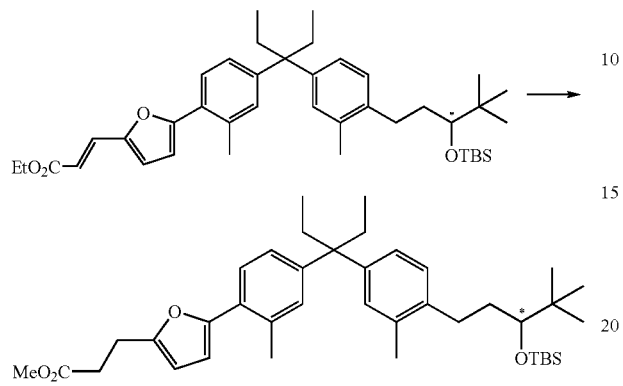

Magnesium (24.3 mg, 1.0 mmol) was added to a solution of (E)-3-{5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-yl}-acrylic acid ethyl ester (Example 5-(1); 64.5 mg, 0.10 mmol) in methanol (2 mL) and tetrahydrofuran (0.5 mL) at room temperature, and the mixture was stirred at the same temperature for two hours. Ethyl acetate and a potassium bisulfate aqueous solution were added to the reaction mixture to separate the layers. Then, the organic layer was washed with water, dried over anhydrous magnesium sulfate and concentrated under reduced pressure. The residue was purified by preparative TLC (hexane/ethyl acetate=10/1) to give the title compound (48 mg, 76%).

$^1$H-NMR: 0.07 (s, 3H), 0.10 (s, 3H), 0.62 (t, 6H), 0.88 (s, 9H), 0.93 (s, 9H), 1.51-1.64 (m, 1H), 1.72-1.84 (m, 1H), 2.08 (q, 4H), 2.23 (s, 3H), 2.36-2.47 (m, 1H), 2.42 (s, 3H), 2.68-2.81 (m, 3H), 3.02 (t, 2H), 3.34 (dd, 1H), 6.10 (d, 1H), 6.37 (d, 1H), 6.91-7.04 (m, 5H), 7.51 (d, 1H).

(2) Synthesis of 3-[5-(4-{1-ethyl-1-[4-(3-hydroxy-4,4-dimethyl-pentyl)-3-methyl-phenyl]-propyl}-2-methyl-phenyl)-furan-2-yl]-propionic Acid

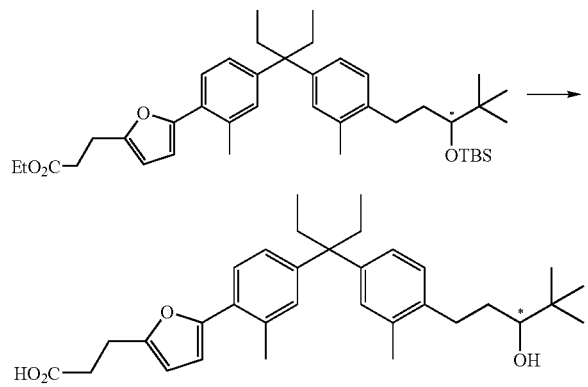

The title compound was obtained by the same method as in Example 5-(2) using 3-{5-[4-(1-{4-[3-(t-butyl-dimethyl-silanyloxy)-4,4-dimethyl-pentyl]-3-methyl-phenyl}-1-ethyl-propyl)-2-methyl-phenyl]-furan-2-yl}-propionic acid methyl ester (Example 6-(1)) as a starting material.

$^1$H-NMR: 0.61 (t, 6H), 0.86 (s, 9H), 1.42-1.55 (m, 1H), 1.70-1.81 (m, 1H), 2.10 (q, 4H), 2.24 (s, 3H), 2.37 (s, 3H), 2.48-2.59 (m, 1H), 2.63-2.68 (m, 2H), 2.82-2.92 (m, 1H), 2.98 (t, 2H), 3.15 (dd, 1H), 6.15 (dt, 1H), 6.41 (d, 1H) 6.91-7.04 (m, 5H), 7.48 (d, 2H); MS (ESI−): 503 (M−H)−.

Example 7

Synthesis of 5-(4-{1-ethyl-1-[4-(3-hydroxy-4,4-dimethyl-pentyl)-3-methyl-phenyl]-propyl}-2-methyl-phenyl)-furan-2-carboxylic Acid

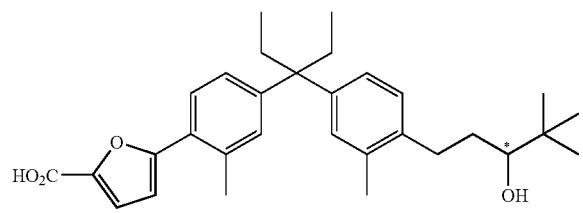

The title compound was obtained through the steps of Example 3-(3), Example 3-(4), Example 3-(5), Example 3-(6) and Example 3-(7) in this order using 4-{1-ethyl-1-[4-(3-hydroxy-4,4-dimethyl-1-pentynyl)-3-methyl-phenyl]-propyl}-2-methyl-phenol (Example 3-(2), Enantiomer A) as a starting material.

$^1$H-NMR (methanol-d4): 0.61 (t, 6H, J=8.1 Hz), 0.86 (s, 9H), 1.41-1.55 (m, 1H), 1.70-1.80 (m, 1H), 2.12 (q, 4H, J=8.1 Hz), 2.24 (s, 3H), 2.44 (s, 3H), 2.48-2.59 (m, 1H), 2.81-2.92 (m, 1H), 3.15 (dd, 1H, J=1.7, 11.5 Hz), 6.69 (d, 1H, J=3.8 Hz), 6.91-6.93 (m, 2H), 7.02-7.10 (m, 3H), 7.26 (d, 1H, J=3.9 Hz), 7.63 (brd, 1H, J=9.0 Hz); MS (ESI−): 475 ([M−H]+).

Example 8

Synthesis of [5-(4-{1-ethyl-1-[4-(3-hydroxy-4,4-dimethyl-pentyl)-3-methyl-phenyl]-propyl}-2-methyl-phenyl)-furan-2-yl]-acetic Acid

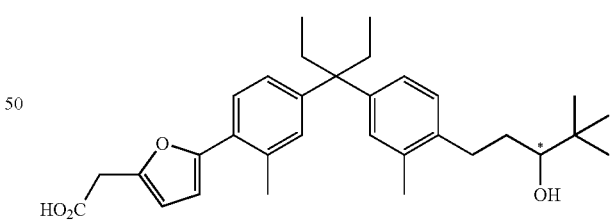

The title compound was obtained through the steps of Example 3-(3), Example 3-(4), Example 3-(5), Example 3-(6), Example 4-(1) and Example 4-(2) in this order using 4-{1-ethyl-1-[4-(3-hydroxy-4,4-dimethyl-1-pentynyl)-3-methyl-phenyl]-propyl}-2-methyl-phenol (Example 3-(2), Enantiomer A) as a starting material.

$^1$H-NMR: 0.61 (t, 6H), 0.86 (s, 9H), 1.42-1.58 (m, 1H), 1.71-1.81 (m, 1H), 2.11 (q, 4H), 2.24 (s, 3H), 2.39 (s, 3H), 2.49-2.59 (m, 1H), 2.82-2.92 (m, 1H), 3.14-3.17 (m, 1H), 3.71 (s, 2H), 6.31 (d, 1H), 6.46 (d, 1H), 6.91-7.05 (m, 5H), 7.50 (d, 1H);

MS (ESI+): 508 (M+NH4)+.

Example 9

Synthesis of (E)-3-[5-(4-{1-ethyl-1-[4-(3-hydroxy-4,4-dimethyl-pentyl)-3-methyl-phenyl]-propyl}-2-methyl-phenyl)-furan-2-yl]-acrylic Acid

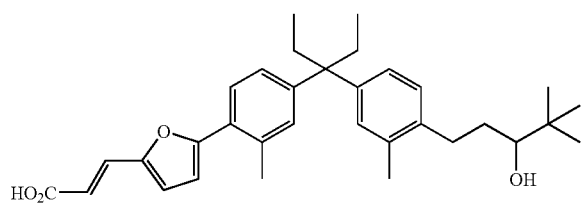

The title compound was obtained through the steps of Example 3-(3), Example 3-(4), Example 3-(5), Example 3-(6), Example 5-(1) and Example 5-(2) in this order using 4-{1-ethyl-1-[4-(3-hydroxy-4,4-dimethyl-1-pentynyl)-3-methyl-phenyl]-propyl}-2-methyl-phenol (Example 3-(2), Enantiomer A) as a starting material.

$^1$H-NMR (methanol-d4): 0.62 (t, 6H, J=7.3 Hz), 0.86 (s, 9H), 1.42-1.55 (m, 1H), 1.70-1.81 (m, 1H), 2.13 (q, 4H, J=7.2 Hz), 2.25 (s, 3H), 2.46 (s, 3H), 2.49-2.59 (m, 1H), 2.82-2.92 (m, 1H), 3.13 (dd, 1H, J=1.7, 10.5 Hz), 6.28 (d, 1H, J=15.7 Hz), 6.71 (d, 1H, J=3.7 Hz), 6.84 (d, 1H, J=3.7 Hz), 6.92-6.94 (m, 2H), 7.03-7.11 (m, 3H), 7.45 (d, 1H, J=15.7 Hz), 7.61 (brd, 1H, J=8.2 Hz); MS (ESI−): 501 (M−H)−.

Example 10

Synthesis of 3-[5-(4-{1-ethyl-1-[4-(3-hydroxy-4,4-dimethyl-pentyl)-3-methyl-phenyl]-propyl}-2-methyl-phenyl)-furan-2-yl]-propionic Acid

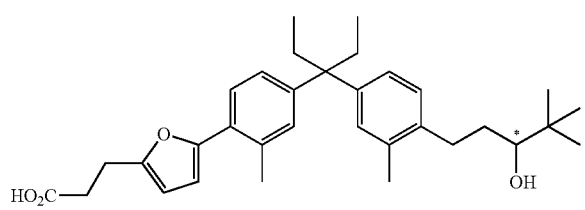

The title compound was obtained through the steps of Example 3-(3), Example 3-(4), Example 3-(5), Example 3-(6), Example 6-(1) and Example 6-(2) in this order using 4-{1-ethyl-1-[4-(3-hydroxy-4,4-dimethyl-1-pentynyl)-3-methyl-phenyl]-propyl}-2-methyl-phenol (Example 3-(2), Enantiomer A) as a starting material.

$^1$H-NMR (methanol-d4): 0.61 (t, 6H, J=7.3 Hz), 0.86 (s, 9H), 1.42-1.55 (m, 1H), 1.70-1.80 (m, 1H), 2.10 (q, 4H, J=7.3 Hz), 2.24 (s, 3H), 2.37 (s, 3H), 2.48-2.58 (m, 1H), 2.66 (t, 2H, J=7.4 Hz), 2.82-2.91 (m, 1H), 2.98 (t, 2H, J=7.5 Hz), 3.15 (dd, 1H, J=1.7, 10.5 Hz), 6.15 (d, 1H, J=3.5 Hz), 6.40 (d, 1H, J=3.2 Hz), 6.91-6.93 (m, 2H), 7.00-7.04 (m, 3H), 7.48 (d, 1H, J=8.4 Hz); MS (ESI−): 503 (M−H)−.

Example 11

Synthesis of 3-(4'-{1-ethyl-1-[4-(3-hydroxy-4,4-dimethyl-pentyl)-3-methyl-phenyl]-propyl}-2'-methyl-biphenyl-4-yl)-propionic Acid

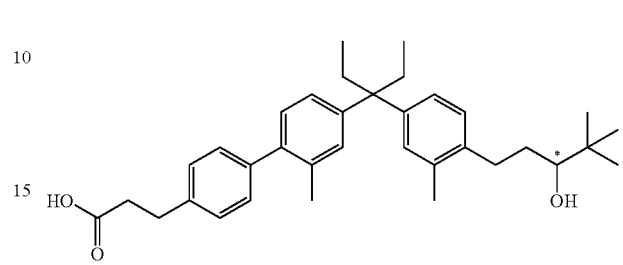

(1) Synthesis of Trifluoromethanesulfonic Acid 4-(1-{4-[3-(t-butyl-dimethyl-silanyloxy)-4,4-dimethyl-pentyl]-3-methyl-phenyl}-1-ethyl-propyl)-2-methyl-phenyl Ester

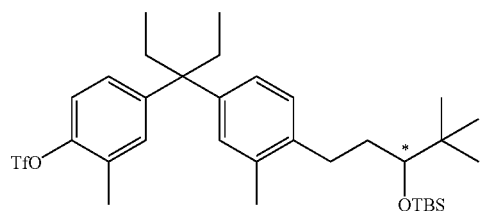

The title compound was obtained through the steps of Example 3-(3), Example 3-(4) and Example 3-(5) in this order using 4-{1-ethyl-1-[4-(3-hydroxy-4,4-dimethyl-1-pentynyl)-3-methyl-phenyl]-propyl}-2-methyl-phenol (Example 3-(2), Enantiomer A) as a starting material.

$^1$H-NMR: 0.07 (s, 3H), 0.10 (s, 3H), 0.60 (t, 6H), 0.88 (s, 9H), 0.94 (s, 9H), 1.51-1.64 (m, 1H), 1.72-1.84 (m, 1H), 2.05 (q, 4H), 2.24 (s, 3H), 2.32 (s, 3H), 2.42 (dq, 1H), 2.77 (dq, 1H), 3.35 (dd, 1H), 6.86-6.88 (m, 2H), 6.99-7.11 (m, 4H).

(2) Synthesis of 3-[4-(4,4,5,5-tetramethyl-[1,3,2]dioxaborolan-2-yl)-phenyl]-propionic Acid Methyl Ester

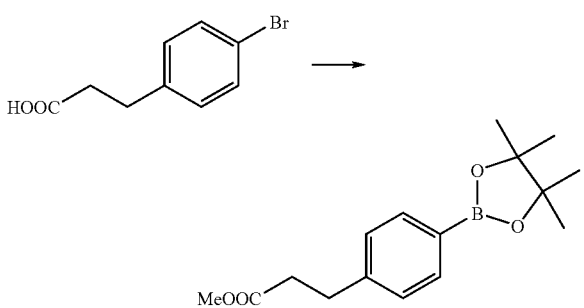

(Trimethylsilyl)diazomethane (2 M solution in diethyl ether, 0.5 mL, 1.0 mmol) was added to a mixture of 3-(4-bromo-phenyl)-propionic acid (0.1 g, 0.44 mmol), toluene (0.5 mL) and methanol (0.5 mL) while stirring at room temperature, and the mixture was stirred at the same temperature for 15 minutes. The reaction mixture was concentrated under reduced pressure. Potassium acetate (0.128 g, 1.3 mmol), bis(pinacolato)diboron (0.133 g, 0.52 mmol), a [1,1'-bis(diphenylphosphino)ferrocene]dichloropalladium (II), dichloromethane complex (1:1) (0.018 g, 0.02 mmol) and dimethyl sulfoxide (2 mL) were added to the resulting residue, and the mixture was stirred in a nitrogen atmosphere at 80° C. for two hours. Ethyl acetate was added to the reaction mixture. The organic layer was washed with a saturated aqueous ammonium chloride solution and water, dried over anhydrous magnesium sulfate and concentrated under reduced pressure. The residue was purified by preparative TLC (hexane/ethyl acetate=10/1) to give the title compound (0.06 g, 47%).

$^1$H-NMR (chloroform-d): 1.33 (s, 12H), 2.63 (t, 2H, J=7.7 Hz), 2.96 (t, 2H, J=7.7 Hz), 3.66 (s, 3H), 7.21 (d, 2H, J=7.7 Hz), 7.73 (d, 2H, J=7.7 Hz).

(3) Synthesis of 3-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-propionic Acid Methyl Ester

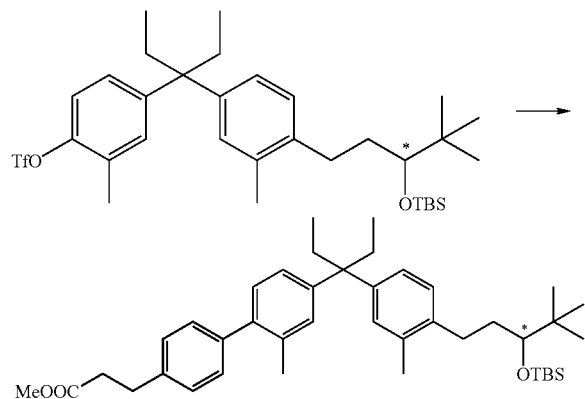

A mixture of trifluoromethanesulfonic acid 4-(1-{4-[3-(t-butyl-dimethyl-silanyloxy)-4,4-dimethyl-pentyl]-3-methyl-phenyl}-1-ethyl-propyl)-2-methyl-phenyl ester (Example 11-(1); 0.13 g, 0.2 mmol), 3-[4-(4,4,5,5-tetramethyl-[1,3,2]dioxaborolan-2-yl)-phenyl]-propionic acid methyl ester (Example 11-(2); 0.06 g, 0.2 mmol), a [1,1'-bis(diphenylphosphino)ferrocene]dichloropalladium (II), dichloromethane complex (1:1) (0.01 g, 0.01 mmol), a sodium carbonate solution (2 M, 0.3 ml, 0.6 mmol) and N,N-dimethylformamide (1 mL) was stirred in a nitrogen atmosphere at 80° C. for four hours. A saturated aqueous ammonium chloride solution was added to the reaction mixture, followed by extraction with ethyl acetate. The organic layer was then washed with brine, dried over anhydrous magnesium sulfate and concentrated under reduced pressure. The residue was purified by preparative TLC (hexane/ethyl acetate=10/1) to give the title compound (0.013 g, 10%).

$^1$H-NMR (chloroform-d): 0.07 (s, 3H), 0.11 (s, 3H), 0.65 (t, 6H, J=7.3 Hz), 0.88 (s, 9H), 0.93 (s, 9H), 1.20-1.50 (m, 1H), 1.70-1.90 (m, 1H), 2.10 (q, 4H, J=7.1 Hz), 2.23 (s, 3H), 2.26 (s, 3H), 2.42 (dt, 1H, J=4.8, 12.9 Hz), 2.67 (t, 2H, J=7.8 Hz), 2.77 (dt, 1H), 2.99 (t, 2H, J=7.9 Hz), 3.69 (s, 3H), 6.90-7.10 (m, 6H), 7.15-7.30 (m, 4H).

(4) Synthesis of 3-(4'-{1-ethyl-1-[4-(3-hydroxy-4,4-dimethyl-pentyl)-3-methyl-phenyl]-propyl}-2'-methyl-biphenyl-4-yl)-propionic Acid

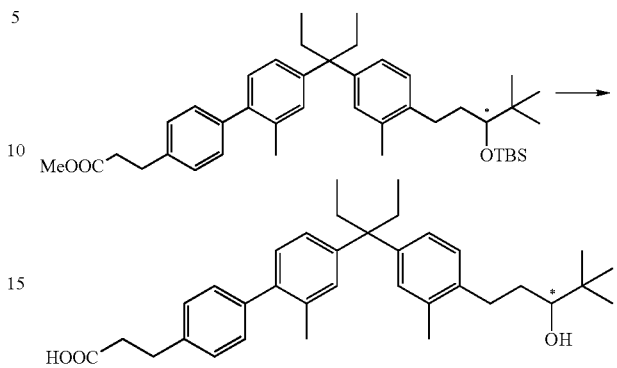

A sodium hydroxide aqueous solution (1 M, 0.5 mL, 0.5 mmol) was added to a mixture of 3-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-propionic acid methyl ester (Example 11-(3); 0.013 g, 0.02 mmol), tetrahydrofuran (0.5 mL) and methanol (1.0 mL) while stirring at room temperature, and the mixture was stirred at the same temperature for two hours. A 30% sodium dihydrogenphosphate aqueous solution was added to the reaction mixture, followed by extraction with ethyl acetate. The organic layer was dried over anhydrous magnesium sulfate and concentrated under reduced pressure. Tetra-n-butylammonium fluoride (1 M solution in tetrahydrofuran, 0.1 mL, 0.1 mmol) and tetrahydrofuran (1 mL) were added to the resulting residue, and the mixture was stirred at 60° C. for four hours. A 30% sodium dihydrogenphosphate aqueous solution was added to the reaction mixture, followed by extraction with ethyl acetate. The organic layer was washed with a 30% sodium dihydrogenphosphate aqueous solution and brine, dried over anhydrous magnesium sulfate and concentrated under reduced pressure. The residue was purified by preparative TLC (dichloromethane/methanol=10/1) to give the title compound (0.007 g, 67%).

$^1$H-NMR (chloroform-d): 0.69 (t, 6H, J=7.3 Hz), 0.89 (s, 9H), 1.40-1.60 (m, 1H), 1.70-1.90 (m, 1H), 2.10 (q, 4H, J=7.1 Hz), 2.22 (s, 3H), 2.28 (s, 3H), 2.50-2.65 (m, 1H), 2.73 (t, 2H, J=7.8 Hz), 2.80-2.95 (m, 1H), 3.00 (t, 2H, J=7.7 Hz), 3.26 (dd, 1H, J=1.5, 10.2 Hz), 6.90-7.10 (m, 6H), 7.19-7.30 (m, 4H); MS (ESI+): 532 ([M+NH$_4$]$^+$).

Example 12

Synthesis of 3-(4'-{1-ethyl-1-[4-(3-hydroxy-4,4-dimethyl-pentyl)-3-methyl-phenyl]-propyl}-2'-methyl-biphenyl-3-yl)-propionic Acid

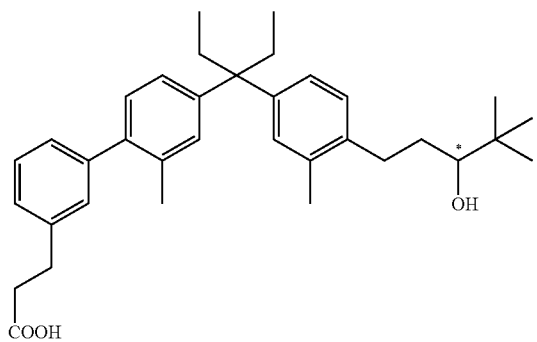

(1) Synthesis of 3-[3-(4,4,5,5-tetramethyl-[1,3,2]dioxaborolan-2-yl)-phenyl]-propionic Acid Methyl Ester

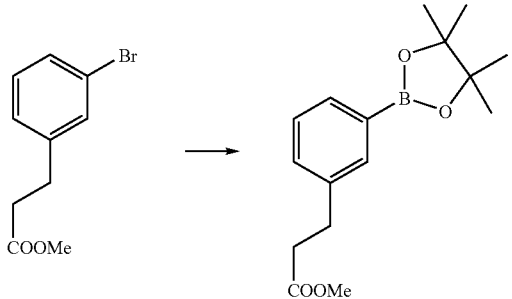

The title compound (95%) was obtained by the same method as in Example 11-(2) using 3-(3-bromo-phenyl)-propionic acid methyl ester as a starting material.
¹H-NMR (chloroform-d): 1.34 (s, 12H), 2.63 (t, 2H, J=7.9 Hz), 2.95 (t, 2H, J=7.9 Hz), 3.67 (s, 3H), 7.27-7.31 (m, 2H), 7.62-7.67 (m, 2H)

(2) Synthesis of 3-[4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-propionic Acid Methyl Ester

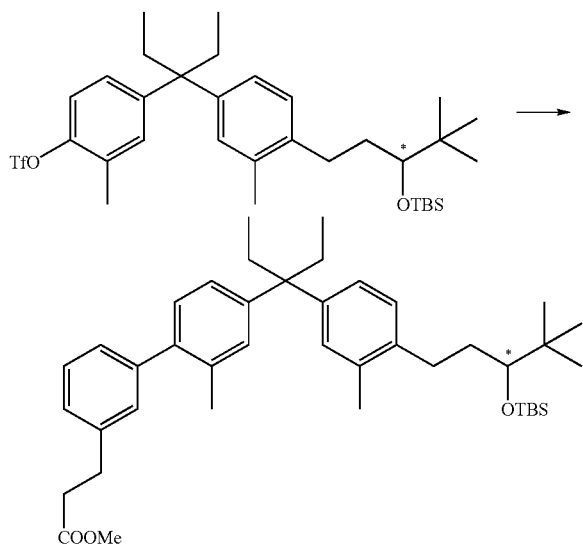

The title compound (12%) was obtained by the same method as in Example 11-(3) using, as a starting material, 3-[3-(4,4,5,5-tetramethyl-[1,3,2]dioxaborolan-2-yl)-phenyl]-propionic acid methyl ester (Example 12-(1)) in place of 3-[4-(4,4,5,5-tetramethyl-[1,3,2]dioxaborolan-2-yl)-phenyl]-propionic acid methyl ester.
¹H-NMR (chloroform-d): 0.07 (s, 3H), 0.11 (s, 3H), 0.65 (t, 6H, J=7.3 Hz), 0.88 (s, 9H), 0.94 (s, 9H), 1.50-1.66 (m, 1H), 1.70-1.87 (m, 1H), 2.11 (q, 4H, J=7.3 Hz), 2.22 (s, 3H), 2.26 (s, 3H), 2.43 (dt, 1H, J=4.5, 13.0 Hz), 2.66 (t, 2H, J=7.7 Hz), 2.78 (dt, 1H, J=5.5, 12.9 Hz), 2.98 (t, 2H, J=7.8 Hz), 3.35 (dd, 1H, J=3.2, 7.2 Hz), 3.67 (s, 3H), 6.92-7.34 (m, 10H).

(3) Synthesis of 3-(4'-{1-ethyl-1-[4-(3-hydroxy-4,4-dimethyl-pentyl)-3-methyl-phenyl]-propyl}-2'-methyl-biphenyl-3-yl)-propionic Acid

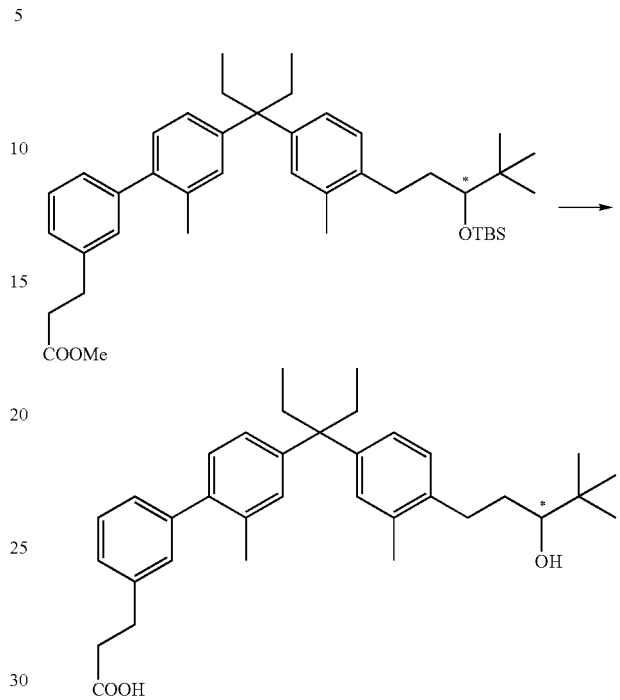

Tetra-n-butylammonium fluoride (1 M solution in tetrahydrofuran, 0.2 mL, 0.2 mmol) and tetrahydrofuran (1 mL) were added to 3-[4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-propionic acid methyl ester (Example 12-(2); 0.016 g, 0.025 mmol), and the mixture was stirred at 60° C. for four hours. A 30% sodium dihydrogenphosphate aqueous solution was added to the reaction mixture, followed by extraction with ethyl acetate. The organic layer was washed with water, dried over anhydrous magnesium sulfate and concentrated under reduced pressure. The residue was purified by preparative TLC (hexane/ethyl acetate=1/1) to give the title compound (0.012 g, 93%).
¹H-NMR (chloroform-d): 0.65 (t, 6H, J=7.3 Hz), 0.89 (s, 9H), 1.40-1.60 (m, 1H), 1.73-1.90 (m, 1H), 2.10 (q, 4H, J=7.3 Hz), 2.21 (s, 3H), 2.28 (s, 3H), 2.50-2.64 (m, 1H), 2.71 (t, 2H, J=7.6 Hz), 2.80-2.94 (m, 1H), 2.99 (t, 2H, J=7.6 Hz), 3.26 (dd, 1H, J=1.6, 10.4 Hz), 6.92-7.34 (m, 10H); MS (ESI+): 532 ([M+NH₄]⁺).

Example 13

Synthesis of (4'-{1-ethyl-1-[4-(3-hydroxy-4,4-dimethyl-pentyl)-3-methyl-phenyl]-propyl}-2'-methyl-biphenyl-4-yl)-acetic Acid

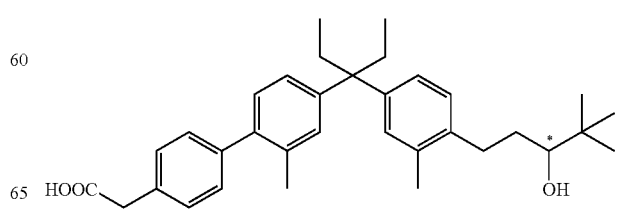

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic Acid Methyl Ester

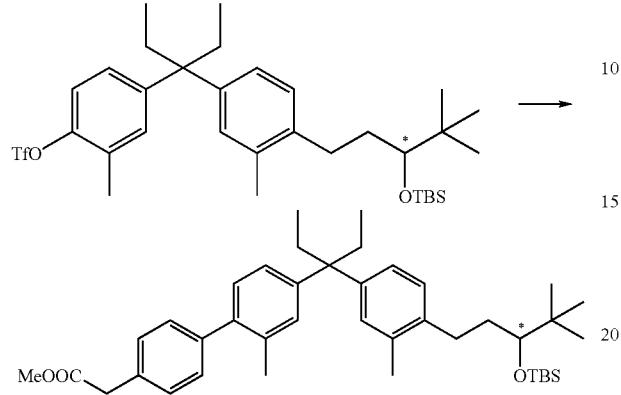

The title compound (35%) was obtained by the same method as in Example 11-(3) using, as a starting material, [4-(4,4,5,5-tetramethyl-[1,3,2]dioxaborolan-2-yl)-phenyl]-acetic acid methyl ester in place of 3-[4-(4,4,5,5-tetramethyl-[1,3,2]dioxaborolan-2-yl)-phenyl]-propionic acid methyl ester.

$^1$H-NMR (chloroform-d): 0.07 (s, 3H), 0.11 (s, 3H), 0.65 (t, 6H, J=7.3 Hz), 0.88 (s, 9H), 0.93 (s, 9H), 1.50-1.66 (m, 1H), 1.70-1.86 (m, 1H), 2.10 (q, 4H, J=7.3 Hz), 2.23 (s, 3H), 2.26 (s, 3H), 2.42 (dt, 1H, J=4.4, 12.9 Hz), 2.77 (dt, 1H, J=5.2, 12.9 Hz), 3.35 (dd, 1H, J=3.2, 7.2 Hz), 3.66 (s, 2H), 3.72 (s, 3H), 6.90-7.12 (m, 6H), 7.22-7.32 (m, 4H).

(2) Synthesis of (4'-{1-ethyl-1-[4-(3-hydroxy-4,4-dimethyl-pentyl)-3-methyl-phenyl]-propyl}-2'-methyl-biphenyl-4-yl)-acetic Acid

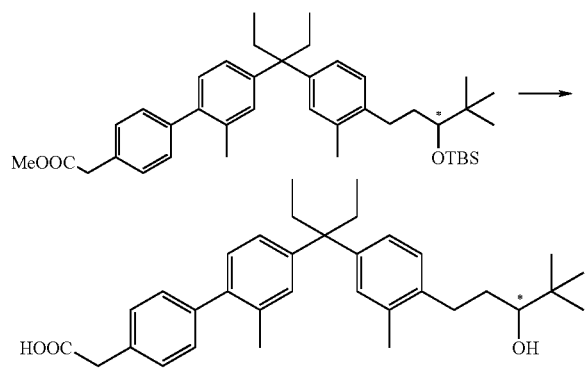

The title compound (35%) was obtained by the same method as in Example 12-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic acid methyl ester (Example 13-(1)) as a starting material.

$^1$H-NMR (chloroform-d): 0.64 (t, 6H, J=7.3 Hz), 0.89 (s, 9H), 1.48-1.52 (m, 1H), 1.54-1.58 (m, 1H), 2.10 (q, 4H, J=7.3 Hz), 2.22 (s, 3H), 2.28 (s, 3H), 2.50-2.65 (m, 1H), 2.60-2.90 (m, 1H), 3.26 (dd, 1H, J=1.6, 10.3 Hz), 3.69 (s, 2H), 6.92-7.10 (m, 6H), 7.30 (brs, 4H); MS (ESI+): 518 ([M+NH$_4$]$^+$).

Example 14

Synthesis of (4'-{1-ethyl-1-[4-(3-hydroxy-4,4-dimethyl-pentyl)-3-methyl-phenyl]-propyl}-2'-methyl-biphenyl-3-yl)-acetic Acid

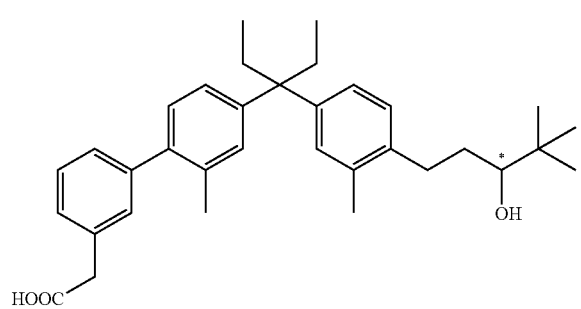

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-acetic Acid Methyl Ester

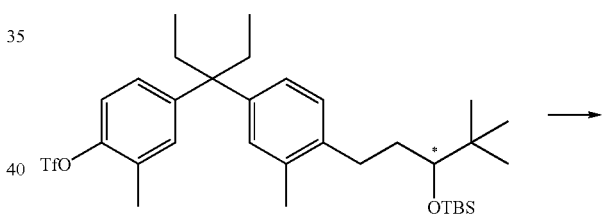

The title compound (50%) was obtained by the same method as in Example 11-(3) using, as a starting material, [3-(4,4,5,5-tetramethyl-[1,3,2]dioxaborolan-2-yl)-phenyl]-acetic acid methyl ester in place of 3-[4-(4,4,5,5-tetramethyl-[1,3,2]dioxaborolan-2-yl)-phenyl]-propionic acid methyl ester.

$^1$H-NMR (chloroform-d): 0.07 (s, 3H), 0.11 (s, 3H), 0.65 (t, 6H, J=7.3 Hz), 0.88 (s, 9H), 0.94 (s, 9H), 1.50-1.67 (m, 1H), 1.72-1.86 (m, 1H), 2.10 (q, 4H, J=7.3 Hz), 2.23 (s, 3H), 2.26 (s, 3H), 2.34-2.50 (m, 1H), 2.70-2.84 (m, 1H), 3.35 (dd, 1H, J=3.1, 7.1 Hz), 3.65 (s, 2H), 3.69 (s, 3H), 6.90-7.12 (m, 6H), 7.18-7.27 (m, 3H), 7.30-7.38 (m, 1H).

(2) Synthesis of (4'-{1-ethyl-1-[4-(3-hydroxy-4,4-dimethyl-pentyl)-3-methyl-phenyl]-propyl}-2'-methyl-biphenyl-3-yl)-acetic Acid

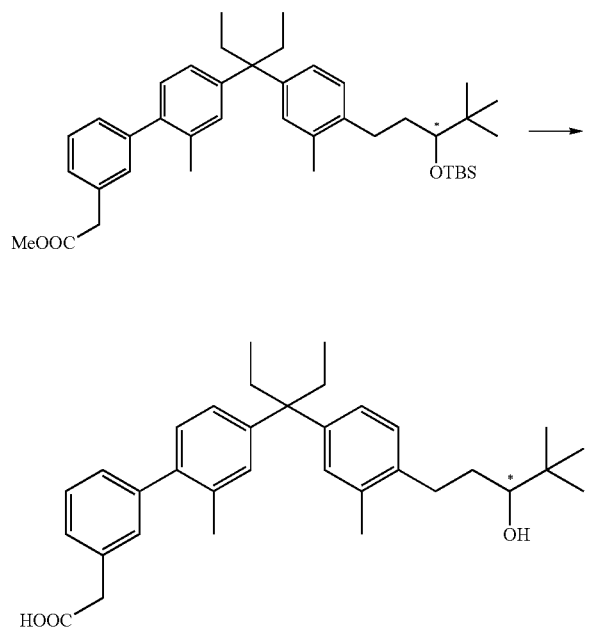

The title compound (16%) was obtained by the same method as in Example 12-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-acetic acid methyl ester (Example 14-(1)) as a starting material.

¹H-NMR (chloroform-d): 0.64 (t, 6H, J=7.2 Hz), 0.89 (s, 9H), 1.40-1.60 (m, 1H), 1.70-1.90 (m, 1H), 2.10 (q, 4H, J=7.2 Hz), 2.21 (s, 3H), 2.28 (s, 3H), 2.50-2.64 (m, 1H), 2.80-2.94 (m, 1H), 3.27 (dd, 1H, J=1.5, 10.4 Hz), 3.68 (s, 2H), 6.90-7.12 (m, 6H), 7.20-7.40 (m, 4H); MS (ESI+): 518 ([M+NH₄]⁺).

Example 15

Synthesis of (R)-5-(4-{1-ethyl-1-[4'-(1-hydroxy-1-methyl-ethyl)-2-methyl-biphenyl-4-yl]-propyl}-2-methyl-phenoxy)-4-hydroxy-pentanoic Acid (1) Synthesis of [1-(4-bromo-phenyl)-1-methyl-ethoxy]-trimethyl-silane

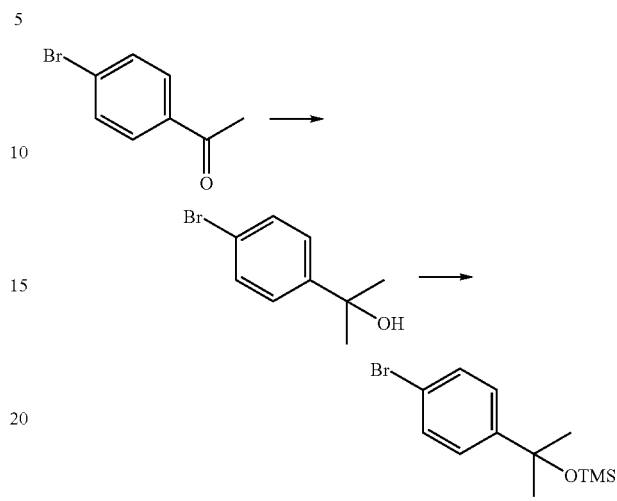

Methyllithium (1.10 mol/l solution in diethyl ether, 502 mL, 0.552 mol) was added to a solution of 4-bromoacetophenone (100 g, 0.502 mol) in tetrahydrofuran (500 mL) in a nitrogen atmosphere at −78° C., and the mixture was stirred at the same temperature for one hour. The reaction mixture was poured into a saturated aqueous ammonium chloride solution, followed by extraction with ethyl acetate. The extract was washed with brine and dried over anhydrous magnesium sulfate, and the solvent was distilled off under reduced pressure to give crude 2-(4-bromo-phenyl)-propan-2-ol.

N-trimethylsilylimidazole (80.6 mL, 0.552 mol) was added to a solution of the crude 2-(4-bromo-phenyl)-propan-2-ol in tetrahydrofuran (500 mL) in a nitrogen atmosphere at room temperature, and the mixture was stirred at the same temperature overnight. The reaction mixture was poured into a saturated aqueous sodium bicarbonate solution, followed by extraction with ethyl acetate. The extract was washed with brine, dried over anhydrous magnesium sulfate and filtered, and the solvent was distilled off under reduced pressure. The resulting residue was subjected to silica gel chromatography (n-hexane:ethyl acetate=40:1) to give the title compound as a colorless oil (125.6 g, 87% in two steps).

¹H-NMR (chloroform-d): 0.10 (9H, s), 1.55 (6H, s), 7.30 (2H, d, J=8.6 Hz), 7.42 (2H, d, J=8.6 Hz).

(2) Synthesis of 4-{1-ethyl-1-[3-methyl-4-(4,4,5,5-tetramethyl-[1,3,2]dioxaborolan-2-yl)-phenyl]-propyl}-2-methyl-phenol

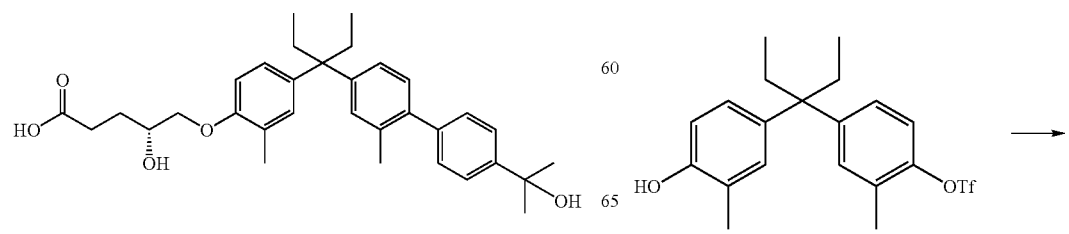

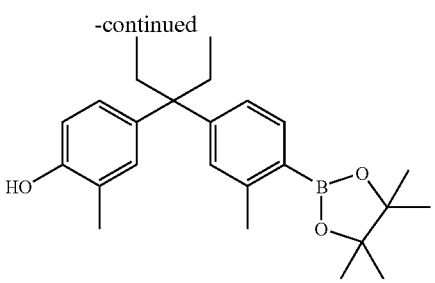

A [1,1'-bis(diphenylphosphino)ferrocene]palladium dichloride dichloromethane complex (0.39 g, 0.48 mmol), 4,4,5,5,4',4',5',5'-octamethyl-[2,2']bi[[1,3,2]dioxaborolanyl] (1.59 g, 6.243 mmol) and potassium acetate (2.59 g, 26.413 mmol) were added to a solution of trifluoromethanesulfonic acid 4-[1-ethyl-1-(4-hydroxy-3-methyl-phenyl)-propyl]-2-methyl-phenyl ester (Example 1-(1); 2 g, 4.082 mmol) in dimethyl sulfoxide (2.4 mL) at room temperature, and the mixture was stirred at 80° C. for 16 hours. Ethyl acetate was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=9/1 to ethyl acetate only) to give the title compound (1.57 g, 82.9%).

$^1$H-NMR (chloroform-d): 0.62 (t, 6H, J=7.2 Hz), 1.35 (s, 12H), 2.06 (q, 4H, J=7.2 Hz), 2.20 (s, 3H), 2.50 (s, 3H), 4.78 (brs, 1H), 6.64 (d, 1H, J=8.2 Hz), 6.84-6.90 (m, 3H), 7.00 (d, 1H, J=7.3 Hz), 7.66 (d, 1H, J=8.2 Hz).

(3) Synthesis of (R)-5-(4-{1-ethyl-1-[3-methyl-4-(4,4,5,5-tetramethyl-[1,3,2]dioxaborolan-2-yl)-phenyl]-propyl}-2-methyl-phenoxymethyl)-dihydro-furan-2-one

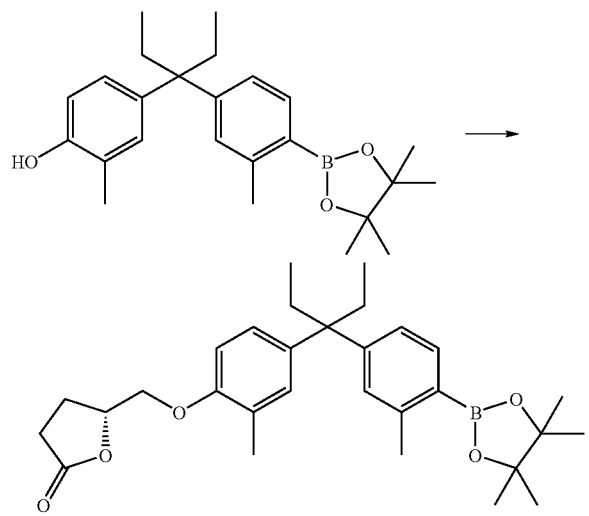

(R)-(−)-Dihydro-5-(p-tolyl-sulfonyloxymethyl)-2(3H)-furanone (293 mg, 1.084 mmol) and potassium carbonate (180 mg, 1.301 mmol) were added to a solution of 4-{1-ethyl-1-[3-methyl-4-(4,4,5,5-tetramethyl-[1,3,2]dioxaborolan-2-yl)-phenyl]-propyl}-2-methyl-phenol (Example 15-(2); 171 mg, 0.434 mmol) in N,N-dimethylformamide (1.5 mL) at room temperature, and the mixture was stirred at 110° C. for one hour. Ethyl acetate was added to the reaction solution. The organic layer was washed with brine and dried over anhydrous magnesium sulfate, and then the solvent was distilled off under reduced pressure. The residue was purified by silica gel chromatography (n-hexane/ethyl acetate=80/20 to ethyl acetate only) to give the title compound (164 mg, 76.8%).

$^1$H-NMR (chloroform-d): 0.60 (t, 6H, J=7.3 Hz), 1.33 (s, 12H), 2.06 (q, 4H, J=7.3 Hz), 2.15 (s, 3H), 2.23-2.61 (m, 3H), 2.48 (s, 3H), 2.71-2.83 (m, 1H), 4.06 (dd, 1H, J=3.5, 10.3 Hz), 4.16 (dd, 1H, J=3.5, 10.2 Hz), 4.84-4.91 (m, 1H), 6.65 (d, 1H, J=8.5 Hz), 6.90-6.99 (m, 4H), 7.64 (d, 1H, J=7.7 Hz); MS (ESI+): 510 ([M+NH$_4$]$^+$).

(4) Synthesis of (R)-5-(4-{1-ethyl-1-[2-methyl-4'-(1-methyl-1-trimethylsilanyloxy-ethyl)-biphenyl-4-yl]-propyl}-2-methyl-phenoxymethyl)-dihydro-furan-2-one

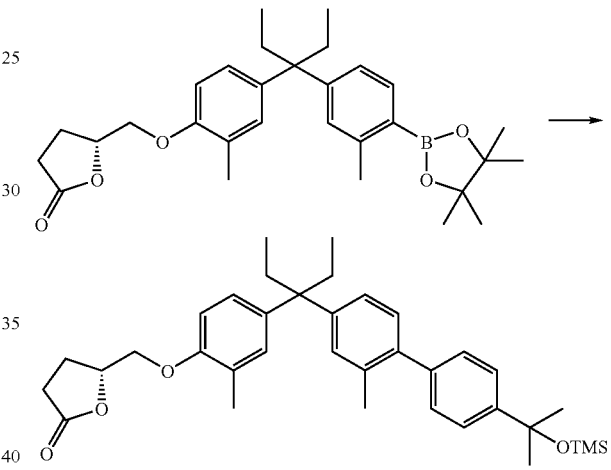

A [1,1'-bis(diphenylphosphino)ferrocene]palladium dichloride dichloromethane complex (1.49 mg, 0.002 mmol), a 2 M sodium carbonate solution (0.1 mL, 0.2 mmol) and [1-(4-bromo-phenyl)-1-methyl-ethoxy]-trimethylsilane (Example 15-(1); 26.25 mg, 0.091 mmol) were added to a solution of (R)-5-(4-{1-ethyl-1-[3-methyl-4-(4,4,5,5-tetramethyl-[1,3,2]dioxaborolan-2-yl)-phenyl]-propyl}-2-methyl-phenoxymethyl)-dihydro-furan-2-one (Example 15-(3); 30 mg, 0.061 mmol) in N,N-dimethylformamide (0.1 mL) at room temperature, and the mixture was stirred at 85° C. for 13.5 hours. Ethyl acetate was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=3/1, developed three times) to give the title compound (16.7 mg, 47.9%).

$^1$H-NMR (chloroform-d): 0.11 (s, 6H), 0.65 (t, 6H, J=7.2 Hz), 1.63 (s, 6H), 2.09 (q, 4H, J=7.2 Hz), 2.19 (s, 3H), 2.24 (s, 3H), 2.26-2.66 (m, 3H), 2.73-2.84 (m, 1H), 4.08 (dd, 1H, J=3.5, 10.2 Hz), 4.18 (dd, 1H, J=3.5, 10.3 Hz), 4.86-4.91 (m, 1H), 6.70 (d, 1H, J=8.2 Hz), 6.99-7.03 (m, 4H), 7.11 (d, 1H, J=7.9 Hz), 7.27 (brd, 2H, J=8.6 Hz), 7.45 (brd, 2H, J=8.5 Hz); MS (m/z): 590 ([M+NH$_4$]$^+$).

(5) Synthesis of (R)-5-(4-{1-ethyl-1-[4'-(1-hydroxy-1-methyl-ethyl)-2-methyl-biphenyl-4-yl]-propyl}-2-methyl-phenoxy)-4-hydroxy-pentanoic Acid

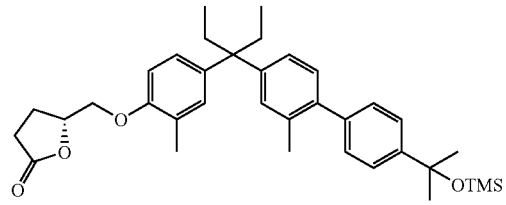

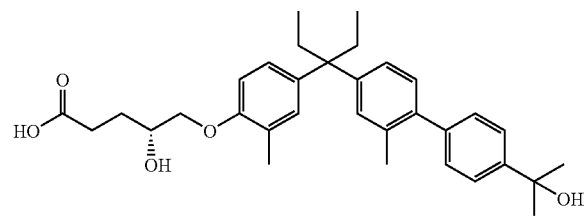

A 1.0 M solution of tetra-n-butylammonium fluoride in tetrahydrofuran (0.1 mL, 0.1 mmol) was added to a solution of (R)-5-(4-{1-ethyl-1-[2-methyl-4'-(1-methyl-1-trimethyl-silanyloxy-ethyl)-biphenyl-4-yl]-propyl}-2-methyl-phenoxymethyl)-dihydro-furan-2-one (Example 15-(4); 16 mg, 0.028 mmol) in tetrahydrofuran (0.1 mL) at room temperature, and the mixture was stirred at 75° C. for two hours. Ethyl acetate was added to the reaction solution. The organic layer was washed with a potassium bisulfate aqueous solution and brine and dried over anhydrous magnesium sulfate, and then the solvent was distilled off under reduced pressure. The residue was purified by silica gel chromatography (dichloromethane/methanol=10/1, developed three times) to give the title compound (11.3 mg, 78%).

$^1$H-NMR (chloroform-d): 0.63 (t, 6H, J=7.1 Hz), 1.56 (s, 6H), 1.73-1.87 (m, 1H), 1.73-1.87 (m, 1H), 2.00 (s, 1H), 2.10 (q, 4H, J=7.0 Hz), 2.17 (s, 6H), 2.39-2.55 (m, 2H), 3.89-4.00 (m, 3H), 6.77 (d, 1H, J=8.5 Hz), 6.91-7.06 (m, 5H), 7.24 (d, 2H, J=8.2 Hz), 7.50 (d, 2H); MS (ESI+): 536 ([M+NH$_4$]$^+$).

Example 16

Synthesis of (R)-5-(4-{1-ethyl-1-[3'-(1-hydroxy-1-methyl-ethyl)-2-methyl-biphenyl-4-yl]-propyl}-2-methyl-phenoxy)-4-hydroxy-pentanoic Acid

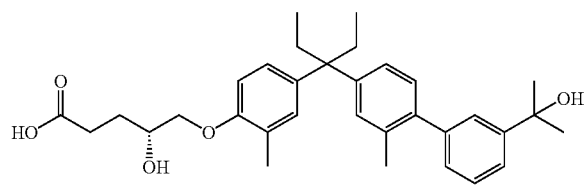

(1) Synthesis of [1-(3-bromo-phenyl)-1-methyl-ethoxy]-trimethyl-silane

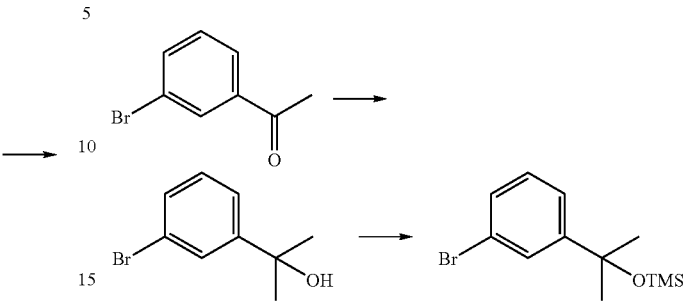

The title compound was obtained from 3-bromoacetophenone by the same method as in Example 15-(1). The yield was 78% in two steps.

$^1$H-NMR (chloroform-d): 0.11 (9H, s), 1.55 (6H, s), 7.17 (1H, m), 7.32-7.36 (2H, m), 7.58 (1H, t, J=1.48 Hz)

(2) Synthesis of (R)-5-(4-{1-ethyl-1-[2-methyl-3'-(1-methyl-1-trimethylsilanyloxy-ethyl)-biphenyl-4-yl]-propyl}-2-methyl-phenoxymethyl)-dihydro-furan-2-one

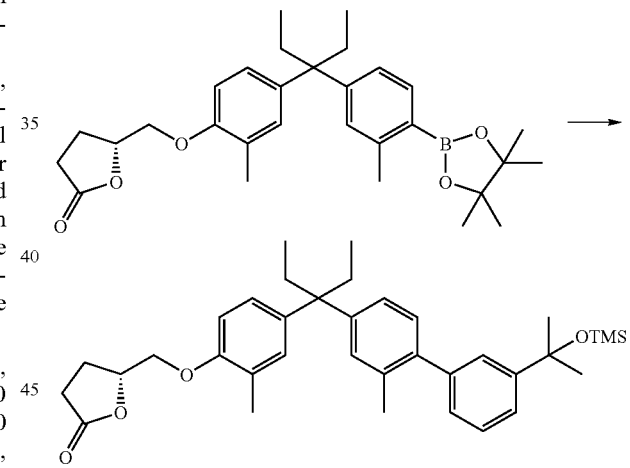

A [1,1'-bis(diphenylphosphino)ferrocene]palladium dichloride dichloromethane complex (1.49 mg, 0.002 mmol), a 2 M Na$_2$CO$_3$ solution (0.1 mL, 0.2 mmol) and [1-(3-bromo-phenyl)-1-methyl-ethoxy]-trimethylsilane (Example 16-(1); 26.3 mg, 0.091 mmol) were added to a solution of (R)-5-(4-{1-ethyl-1-[3-methyl-4-(4,4,5,5-tetramethyl-[1,3,2]dioxaborolan-2-yl)-phenyl]-propyl}-2-methyl-phenoxymethyl)-dihydro-furan-2-one (Example 15-(3); 30 mg, 0.061 mmol) in N,N-dimethylformamide (0.1 mL) at room temperature, and the mixture was stirred at 85° C. for 13.5 hours. Ethyl acetate was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=3/1, developed twice) to give the title compound (18 mg, 49.2%).

$^1$H-NMR (chloroform-d): 0.10 (s, 6H), 0.66 (t, 6H, J=7.3 Hz), 1.61 (s, 6H), 2.10 (q, 4H, J=7.3 Hz), 2.19 (s, 3H), 2.24 (s, 3H), 2.26-2.63 (m, 3H), 2.73-2.84 (m, 1H), 4.08 (dd, 1H, J=3.5, 10.4 Hz), 4.19 (dd, 1H, J=3.5, 10.3 Hz), 4.86-4.92 (m, 1H), 6.70 (d, 1H, J=8.0 Hz), 7.00-7.20 (m, 6H), 7.30-7.44 (m, 3H); MS (ESI+): 590 ([M+NH$_4$]$^+$).

(3) Synthesis of (R)-5-(4-{1-ethyl-1-[3'-(1-hydroxy-1-methyl-ethyl)-2-methyl-biphenyl-4-yl]-propyl}-2-methyl-phenoxy)-4-hydroxy-pentanoic Acid

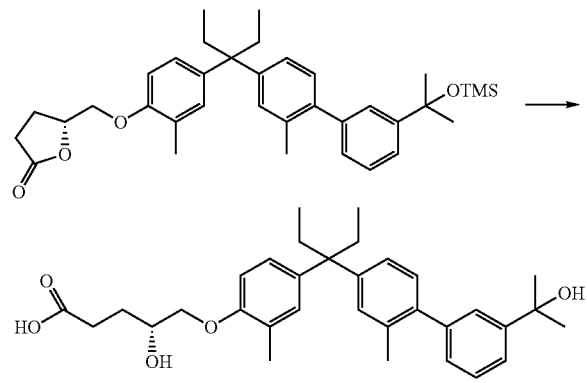

A 1.0 M solution of tetra-n-butylammonium fluoride in tetrahydrofuran (0.1 mL, 0.1 mmol) was added to a solution of (R)-5-(4-{1-ethyl-1-[2-methyl-3'-(1-methyl-1-trimethyl-silanyloxy-ethyl)-biphenyl-4-yl]-propyl}-2-methyl-phenoxymethyl)-dihydro-furan-2-one (Example 16-(2); 17 mg, 0.03 mmol) in tetrahydrofuran (0.1 mL) at room temperature, and the mixture was stirred at 75° C. for two hours. Ethyl acetate was added to the reaction solution. The organic layer was washed with a potassium bisulfate aqueous solution and brine and dried over anhydrous magnesium sulfate, and then the solvent was distilled off under reduced pressure. The residue was purified by silica gel chromatography (dichloromethane/methanol=10/1, developed three times) to give the title compound (9.6 mg, 62.4%).

$^1$H-NMR (chloroform-d): 0.63 (t, 6H, J=8.4 Hz), 1.54 (s, 6H), 1.74-1.87 (m, 1H), 1.93-2.05 (m, 1H), 2.11 (q, 4H, J=8.4 Hz), 2.17 (s, 3H), 2.18 (s, 3H), 2.38-2.56 (m, 2H), 3.87-3.99 (m, 3H), 6.77 (d, 1H, J=9.6 Hz), 6.90-7.08 (m, 5H), 7.14 (dt, 1H, J=8.4, 1.7 Hz), 7.33 (dt, 1H, J=1.3, 8.1 Hz), 7.41-7.45 (m, 2H); MS (ESI+): 530 ([M-OH]$^+$).

Example 17

Synthesis of (R)-5-(4-{1-ethyl-1-[3'-(1-ethyl-1-hydroxy-propyl)-2-methyl-biphenyl-4-yl]-propyl}-2-methyl-phenoxy)-4-hydroxy-pentanoic Acid

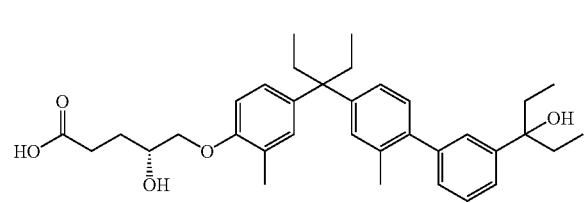

(1) Synthesis of [1-(3-bromo-phenyl)-1-ethyl-propoxy]-trimethyl-silane

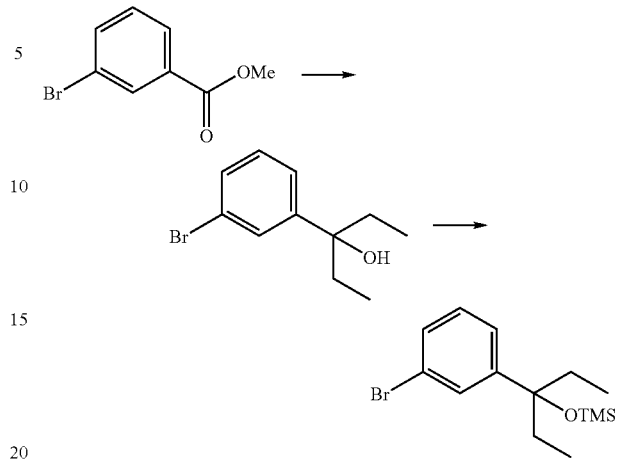

Ethylmagnesium bromide (3 mol/l solution in diethyl ether, 34.1 mL, 102.3 mmol) was added to a solution of 3-bromobenzoic acid methyl ester (10 g, 46.51 mmol) in tetrahydrofuran (100 mL) in a nitrogen atmosphere at −78° C. The mixture was stirred at the same temperature for one hour and then heated to room temperature. The reaction mixture was poured into a saturated aqueous ammonium chloride solution, followed by extraction with ethyl acetate. The extract was washed with brine, dried over anhydrous magnesium sulfate and filtered, and the solvent was distilled off under reduced pressure to give crude 3-(3-bromo-phenyl)-pentan-3-ol.

N-trimethylsilylimidazole (8.2 mL, 55.81 mol) was added to a solution of the crude 3-(3-bromo-phenyl)-pentan-3-ol in tetrahydrofuran (100 mL) in a nitrogen atmosphere at room temperature, and the mixture was stirred overnight. The reaction mixture was poured into distilled water, followed by extraction with dichloromethane. The extract was washed with brine, dried over anhydrous magnesium sulfate and filtered, and the solvent was distilled off under reduced pressure. The residue was subjected to silica gel chromatography (n-hexane:ethyl acetate=40:1) to give the title compound as a colorless oil (8.7 g, 59% in two steps).

$^1$H-NMR (chloroform-d): 0.13 (9H, s), 0.64 (6H, t, J=7.42 Hz), 1.82 (4H, q, J=7.58 Hz), 7.13-7.24 (2H, m), 7.31 (1H, dd, J=7.25, 1.65 Hz), 7.47 (1H, d, J=1.65 Hz).

(2) Synthesis of (R)-5-(4-{1-ethyl-1-[3'-(1-ethyl-1-trimethylsilanyloxy-propyl)-2-methyl-biphenyl-4-yl]-propyl}-2-methyl-phenoxymethyl)-dihydro-furan-2-one

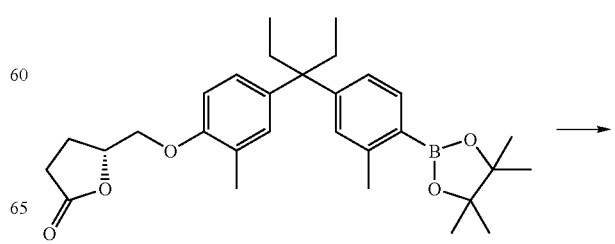

-continued

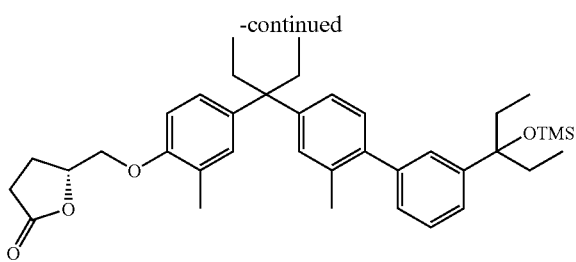

A [1,1'-bis(diphenylphosphino)ferrocene]palladium dichloride dichloromethane complex (1.49 mg, 0.002 mmol), a 2 M sodium carbonate solution (0.1 mL, 0.2 mmol) and [1-(3-bromo-phenyl)-1-ethyl-propoxy]-trimethyl-silane (Example 17-(1); 26.25 mg, 0.091 mmol) were added to a solution of (R)-5-(4-{1-ethyl-1-[3-methyl-4-(4,4,5,5-tetramethyl-[1,3,2]dioxaborolan-2-yl)-phenyl]-propyl}-2-methyl-phenoxymethyl)-dihydro-furan-2-one (Example 15-(3); 30 mg, 0.061 mmol) in N,N-dimethylformamide (0.1 mL) at room temperature, and the mixture was stirred at 85° C. for 13.5 hours. Ethyl acetate was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=3/1, developed twice) to give the title compound (18 mg, 49.2%).

$^1$H-NMR (chloroform-d): 0.05 (s, 9H), 0.66 (t, 6H, J=7.2 Hz), 0.69 (t, 6H, J=7.3 Hz), 1.80-1.95 (m, 4H), 2.10 (q, 4H, J=7.3 Hz), 2.19 (s, 3H), 2.22 (s, 3H), 2.27-2.63 (m, 3H), 2.73-2.84 (m, 1H), 4.08 (dd, 1H, J=3.5, 10.4 Hz), 4.18 (dd, 1H, J=3.5, 10.3 Hz), 4.86-4.92 (m, 1H), 6.70 (d, 1H, J=8.5 Hz), 7.00-7.33 (m, 9H); MS (ESI+): 618 ([M+NH$_4$]$^+$).

(3) Synthesis of (R)-5-(4-{1-ethyl-1-[3'-(1-ethyl-1-hydroxy-propyl)-2-methyl-biphenyl-4-yl]-propyl}-2-methyl-phenoxy)-4-hydroxy-pentanoic Acid

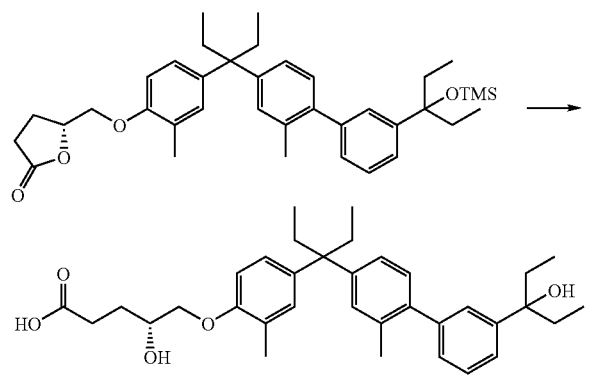

1.0 M tetra-n-butylammonium fluoride (0.1 mL, 0.1 mmol) was added to a solution of (R)-5-(4-{1-ethyl-1-[3'-(1-ethyl-1-trimethylsilanyloxy-propyl)-2-methyl-biphenyl-4-yl]-propyl}-2-methyl-phenoxymethyl)-dihydro-furan-2-one (Example 17-(2); 18 mg, 0.03 mmol) in tetrahydrofuran (0.1 mL) at room temperature, and the mixture was stirred at 75° C. for two hours. Ethyl acetate was added to the reaction solution. The organic layer was washed with a potassium bisulfate aqueous solution and brine and dried over anhydrous magnesium sulfate, and then the solvent was distilled off under reduced pressure. The residue was purified by silica gel chromatography (dichloromethane/methanol=10/1, developed three times) to give the title compound (13.1 mg, 80%).

$^1$H-NMR (chloroform-d): 0.63 (t, 6H, J=7.2 Hz), 0.76 (t, 6H, J=7.5 Hz), 1.76-1.90 (m, 4H), 1.93-2.05 (m, 2H), 2.11 (q, 4H, J=7.5 Hz), 2.16 (s, 6H), 2.39-2.56 (m, 2H), 3.89-3.99 (m, 3H), 6.77 (d, 1H, J=8.5 Hz), 6.92-7.14 (m, 6H), 7.30-7.34 (m, 3H); MS (ESI-): 545 ([M-H]$^-$).

Example 18

Synthesis of (R)-5-(4-{1-ethyl-1-[3'-(1-hydroxy-2,2-dimethyl-propyl)-2-methyl-biphenyl-4-yl]-propyl}-2-methyl-phenoxy)-4-hydroxy-pentanoic Acid

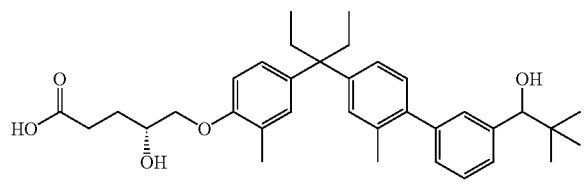

(1) Synthesis of [1-(3-bromo-phenyl)-2,2-dimethyl-propoxy]-trimethyl-silane

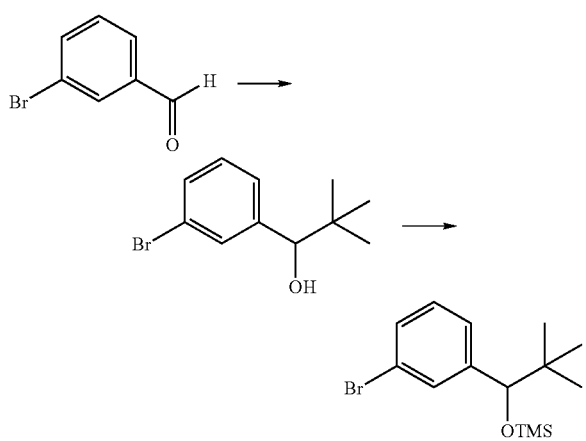

t-Butylmagnesium chloride (0.93 mol/l solution in tetrahydrofuran, 75.5 mL, 70.26 mmol) was added to a solution of 3-bromobenzaldehyde (10 g, 54.05 mmol) in tetrahydrofuran (100 mL) in a nitrogen atmosphere at −78° C. The mixture was stirred at the same temperature for one hour and then heated to room temperature. The reaction mixture was poured into a saturated aqueous ammonium chloride solution, followed by extraction with ethyl acetate. The extract was washed with brine and dried over anhydrous magnesium sulfate and filtered, and the solvent was distilled off under reduced pressure to give crude 1-(3-bromo-phenyl)-2,2-dimethyl-propan-1-ol.

N-trimethylsilylimidazole (9.5 mL, 64.86 mol) was added to a solution of the crude 1-(3-bromo-phenyl)-2,2-dimethyl-propan-1-ol in tetrahydrofuran (100 mL) in a nitrogen atmosphere at room temperature, and the mixture was stirred overnight. The reaction mixture was poured into distilled water, followed by extraction with dichloromethane. The extract was washed with brine and dried over anhydrous magnesium sulfate, and the solvent was distilled off under reduced pressure. The residue was subjected to silica gel chromatography (hexane:ethyl acetate=20:1) to give the title compound as a colorless oil (11.0 g, 64% in two steps).

$^1$H-NMR (chloroform-d): 0.10 (9H, s), 0.92 (9H, s), 4.29 (1H, s), 7.18-7.26 (2H, m), 7.34 (1H, d, J=7.25 Hz), 7.40 (1H, s).

(2) Synthesis of 5(R)-(4-{1-[3'-(2,2-dimethyl-1-trimethylsilanyloxy-propyl)-2-methyl-biphenyl-4-yl]-1-ethyl-propyl}-2-methyl-phenoxymethyl)-dihydro-furan-2-one

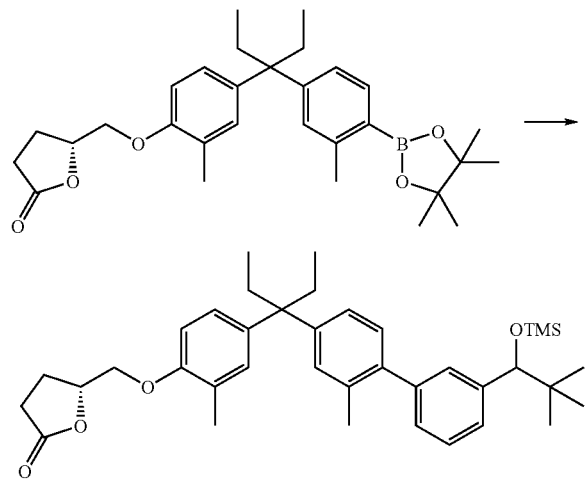

A [1,1'-bis(diphenylphosphino)ferrocene]palladium dichloride dichloromethane complex (1.68 mg, 0.002 mmol), a 2 M sodium carbonate aqueous solution (0.1 mL, 0.2 mmol) and [1-(3-bromo-phenyl)-2,2-dimethyl-propoxy]-trimethylsilane (Example 18-(1); 43.16 mg, 0.137 mmol) were added to a solution of (R)-5-(4-{1-ethyl-1-[3-methyl-4-(4,4,5,5-tetramethyl-[1,3,2]dioxaborolan-2-yl)-phenyl]-propyl}-2-methyl-phenoxymethyl)-dihydro-furan-2-one (Example 15-(3); 33.7 mg, 0.068 mmol) in N,N-dimethylformamide (0.1 mL) at room temperature, and the mixture was stirred at 85° C. for 13.5 hours. Ethyl acetate was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=3/1) to give the title compound (11.7 mg, 28.5%).

$^1$H-NMR (chloroform-d): −0.04 (s, 9H), 0.65 (t, 6H, J=7.3 Hz), 0.87 (s, 9H), 2.09 (q, 4H, J=7.3 Hz), 2.19 (s, 3H), 2.21 (s, 3H), 2.29-2.63 (m, 3H), 2.72-2.84 (m, 1H), 4.08 (dd, 1H, J=3.5, 10.2 Hz), 4.18 (dd, 1H, J=3.5, 10.3 Hz), 4.87-4.91 (m, 1H), 6.70 (d, 1H, J=8.6 Hz), 6.98-7.30 (m, 9H); MS (ESI+): 618 ([M+NH$_4$]$^+$).

(3) Synthesis of (R)-5-(4-{1-ethyl-1-[3'-(1-hydroxy-2,2-dimethyl-propyl)-2-methyl-biphenyl-4-yl]-propyl}-2-methyl-phenoxy)-4-hydroxy-pentanoic Acid

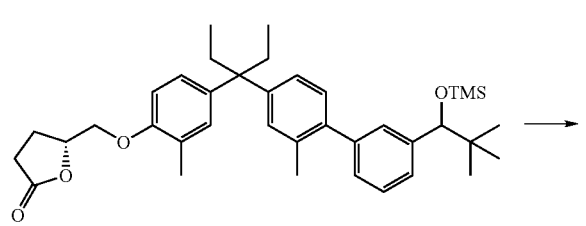

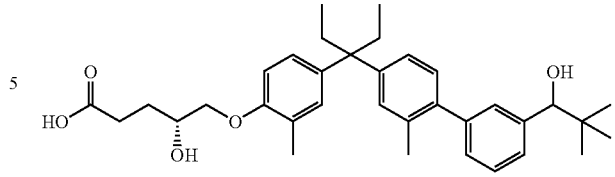

1.0 M tetra-n-butylammonium fluoride (0.097 mL, 0.097 mmol) was added to a solution of 5(R)-(4-{1-[3'-(2,2-dimethyl-1-trimethylsilanyloxy-propyl)-2-methyl-biphenyl-4-yl]-1-ethyl-propyl}-2-methyl-phenoxymethyl)-dihydro-furan-2-one (Example 18-(2); 11.7 mg, 0.019 mmol) in tetrahydrofuran (0.2 mL) at room temperature, and the mixture was stirred at 75° C. for two hours. Ethyl acetate was added to the reaction solution. The organic layer was washed with a potassium bisulfate aqueous solution and brine and dried over anhydrous magnesium sulfate, and then the solvent was distilled off under reduced pressure. The residue was purified by silica gel chromatography (dichloromethane/methanol=10/1, developed three times) to give the title compound (10.9 mg, 100%).

$^1$H-NMR (chloroform-d): 0.63 (t, 6H, J=7.2 Hz), 0.92 (s, 9H), 1.75-1.87 (m, 1H), 1.92-2.22 (m, 1H), 2.11 (q, 4H, J=7.3 Hz), 2.17 (s, 6H), 2.42-2.52 (m, 2H), 3.89-3.97 (m, 3H), 4.36 (s, 1H), 6.77 (d, 1H, J=8.3 Hz), 6.92-7.03 (m, 5H), 7.15-7.34 (m, 4H); MS (ESI−): 545 ([M−H]$^-$).

Example 19

Synthesis of 5-[4-(1-ethyl-1-{4-[5-(1-hydroxy-1-methyl-ethyl)-furan-2-yl]-3-methyl-phenyl}-propyl)-2-methyl-phenoxy]-4(R)-hydroxy-pentanoic Acid

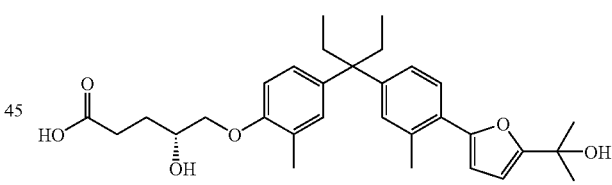

(1) Synthesis of 5-{4-[1-ethyl-1-(4-hydroxy-3-methyl-phenyl)-propyl]-2-methyl-phenyl}-furan-2-carboxylic Acid Methyl Ester

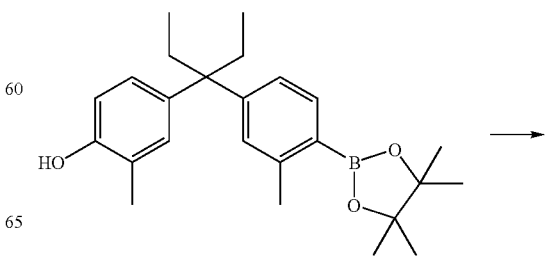

-continued

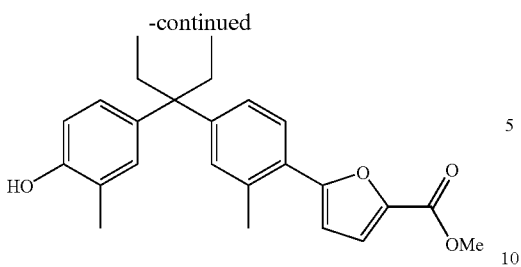

5-Bromo-furan-2-carboxylic acid methyl ester (J. Org. Chem., 1988, 53(9), 2099.; 156 mg, 0.761 mmol), tetrakistriphenylphosphine palladium (15 mg, 0.013 mmol) and a 2 M sodium carbonate aqueous solution (0.3 mL, 0.6 mmol) were added to a solution of 4-{1-ethyl-1-[3-methyl-4-(4,4,5,5-tetramethyl-[1,3,2]dioxaborolan-2-yl)-phenyl]-propyl}-2-methyl-phenol (Example 15-(2); 100 mg, 0.254 mmol) in toluene (0.5 mL) at room temperature, and the mixture was stirred at 85° C. for 17 hours. Ethyl acetate was added to the reaction solution. The organic layer was filtered through celite, and the solvent was distilled off under reduced pressure. The residue was purified by silica gel chromatography (n-hexane/ethyl acetate=3/1) to give the title compound (73.6 mg, 73.9%).

$^1$H-NMR (chloroform-d): 0.62 (t, H, J=7.2 Hz), 2.07 (q, H, J=7.2 Hz), 2.20 (s, H), 2.47 (s, H), 3.91 (s, H), 6.59 (d, H, J=3.7 Hz), 6.69 (d, H, J=8.1 Hz), 6.85-6.89 (m, H), 7.06-7.10 (m, H), 7.27 (d, H, J=3.7 Hz), 7.63 (d, H, J=8.2 Hz); MS (ESI+): 393 ([M+H]$^+$).

(2) Synthesis of 5-(4-{1-[4-(t-butyl-dimethyl-silanyloxy)-3-methyl-phenyl]-1-ethyl-propyl}-2-methyl-phenyl)-furan-2-carboxylic Acid Methyl Ester

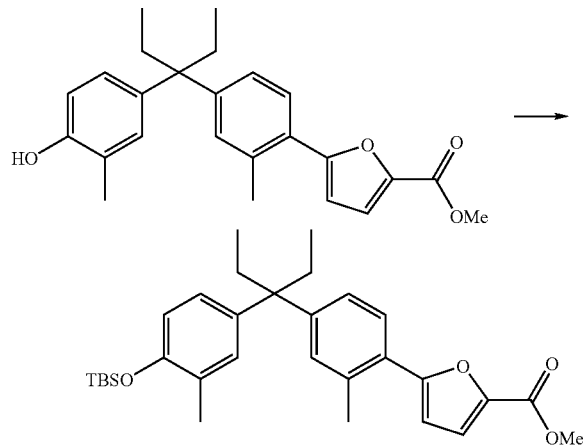

t-Butyldimethylsilyl chloride (42.24 mg, 0.28 mmol) and imidazole (47.7 mg, 0.701 mmol) were added to a solution of 5-{4-[1-ethyl-1-(4-hydroxy-3-methyl-phenyl)-propyl]-2-methyl-phenyl}-furan-2-carboxylic acid methyl ester (Example 19-(1); 55 mg, 0.14 mmol) in N,N-dimethylformamide (0.2 mL) at room temperature, and the mixture was stirred at room temperature for 0.2 hour. Diethyl ether was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=95/5 to ethyl acetate only) to give the title compound (61 mg, 86%).

$^1$H-NMR (chloroform-d): 0.21 (s, 6H), 0.62 (t, 6H, J=7.3 Hz), 1.01 (s, 9H), 2.07 (q, 4H, J=7.3 Hz), 2.16 (s, 3H), 2.47 (s, 3H), 3.91 (s, 3H), 6.59 (d, 1H, J=3.5 Hz), 6.65 (d, 1H, J=8.3 Hz), 6.82-6.90 (m, 2H), 7.06-7.10 (m, 2H), 7.26 (d, 1H, J=2.9 Hz), 7.63 (d, 1H, J=8.1 Hz); MS (ESI+): 524 ([M+NH$_4$]$^+$).

(3) Synthesis of 5(R)-[4-(1-ethyl-1-{4-[5-(1-hydroxy-1-methyl-ethyl)-furan-2-yl]-3-methyl-phenyl}-propyl)-2-methyl-phenoxymethyl]-dihydrofuran-2-one

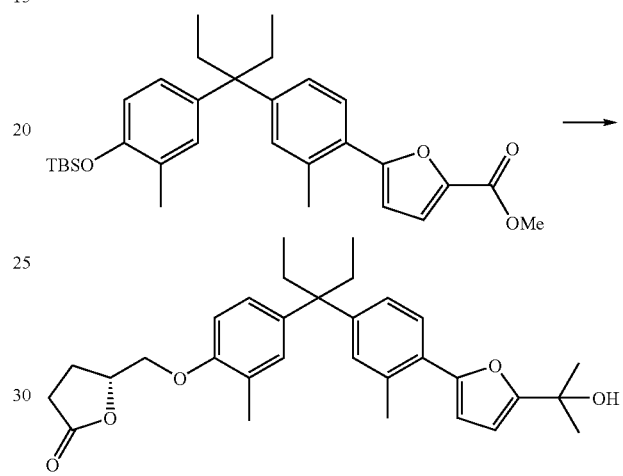

A 3 M solution of methylmagnesium bromide in tetrahydrofuran (0.08 mL, 0.24 mmol) was added to a solution of 5-(4-{1-[4-(t-butyl-dimethyl-silanyloxy)-3-methyl-phenyl]-1-ethyl-propyl}-2-methyl-phenyl)-furan-2-carboxylic acid methyl ester (Example 19-(2); 20 mg, 0.039 mmol) in tetrahydrofuran (0.2 mL) at 0° C., and the mixture was stirred at the same temperature for three hours. Ethyl acetate was added to the reaction solution. The organic layer was washed with a sodium bisulfate aqueous solution and brine and dried over anhydrous magnesium sulfate. Then, the solvent was distilled off under reduced pressure to give crude 2-[5-(4-{1-[4-(t-butyl-dimethyl-silanyloxy)-3-methyl-phenyl]-1-ethyl-propyl}-2-methyl-phenyl)-furan-2-yl]-propan-2-ol (8.5 mg). A 1 M solution of tetrabutylammonium fluoride in tetrahydrofuran (0.03 mL, 0.03 mmol) was added to a solution of the resulting compound in tetrahydrofuran (0.2 mL), and the mixture was stirred at room temperature for one minute. Ethyl acetate was added to the reaction mixture. The organic layer was washed with distilled water and brine and then dried over anhydrous magnesium sulfate, and the solvent was distilled off under reduced pressure. (R)-(−)-Dihydro-5-(p-tolyl-sulfonyloxymethyl)-2(3H)-furanone (11 mg, 0.041 mmol) and potassium carbonate (9 mg, 0.066 mmol) were added to a solution of the residue (6.5 mg) in N,N-dimethylformamide (0.2 mL) at room temperature, and the mixture was stirred at room temperature for 11 hours. Ethyl acetate was added to the reaction solution. The organic layer was washed with brine and dried over anhydrous magnesium sulfate, and then the solvent was distilled off under reduced pressure. The residue was purified by silica gel chromatography (n-hexane/ethyl acetate=1/1) to give the title compound (2.8 mg, 34.5%).

$^1$H-NMR (chloroform-d): 0.62 (t, 6H, J=8.0 Hz), 1.64 (s, 6H), 2.07 (q, 4H, J=8.0 Hz), 2.16 (s, 3H), 2.28-2.63 (m, 3H), 2.44 (s, 3H), 2.72-2.84 (m, 1H), 4.07 (dd, 1H, J=3.8, 11.5 Hz), 4.17 (dd, 1H, J=3.8, 11.5 Hz), 4.85-4.92 (m, 1H), 6.28 (d, 1H, J=3.7 Hz), 6.41 (d, 1H, J=3.8 Hz), 6.67 (d, 1H, J=9.3 Hz), 6.92-7.04 (m, 4H), 7.55 (d, 1H, J=9.2 Hz).

(4) Synthesis of 5-[4-(1-ethyl-1-{4-[5-(1-hydroxy-1-methyl-ethyl)-furan-2-yl]-3-methyl-phenyl}-propyl)-2-methyl-phenoxy]-4(R)-hydroxy-pentanoic Acid

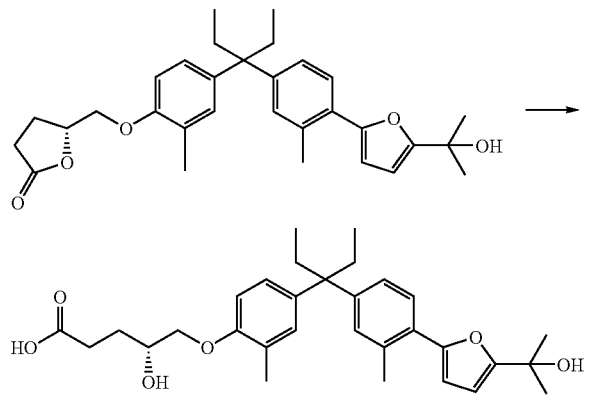

A 1 N potassium hydroxide aqueous solution (0.1 mL, 0.1 mmol) and water (0.1 mL) were added to a solution of 5(R)-[4-(1-ethyl-1-{4-[5-(1-hydroxy-1-methyl-ethyl)-furan-2-yl]-3-methyl-phenyl}-propyl)-2-methyl-phenoxymethyl]-dihydro-furan-2-one (Example 19-(3); 2.8 mg, 0.006 mmol) in methanol (1 mL) at room temperature, and the mixture was stirred at the same temperature for one hour. The reaction solution was directly purified by silica gel chromatography (dichloromethane/methanol=8/3, saturated with water) to give the title compound (0.9 mg, 31%).

$^1$H-NMR (chloroform-d): 0.62 (t, 6H, J=8.1 Hz), 1.64 (s, 6H), 1.89-1.98 (m, 2H), 2.07 (q, 4H, J=8.1 Hz), 2.17 (s, 3H), 2.44 (s, 3H), 2.62 (t, 2H, J=8.1 Hz), 3.85 (dd, 1H, J=7.9, 10.3 Hz), 3.98 (dd, 1H, J=3.9, 10.2 Hz), 4.06-4.14 (m, 1H), 6.28 (d, 1H, J=3.7 Hz), 6.41 (d, 1H, J=3.7 Hz), 6.68 (d, 1H, J=9.3 Hz), 6.87-7.05 (m, 4H), 7.55 (d, 1H, J=9.9 Hz); MS (ESI+): 491 ([M-OH]$^+$).

Example 20

Synthesis of 5-[4-(1-ethyl-1-{4-[5-(1-ethyl-1-hydroxy-propyl)-3-methyl-thiophen-2-yl]-3-methyl-phenyl}-propyl)-2-methyl-phenoxy]-4(R)-hydroxy-pentanoic Acid

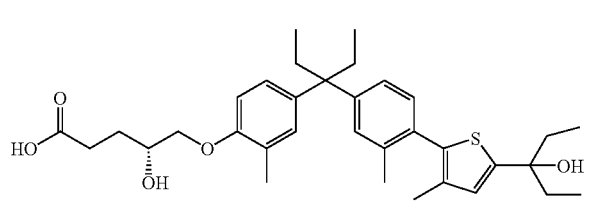

(1) Synthesis of 5-{4-[1-ethyl-1-(4-hydroxy-3-methyl-phenyl)-propyl]-2-methyl-phenyl}-4-methyl-thiophene-2-carboxylic Acid Methyl Ester Methyl 5-bromo-4-methyl-2-thiophenecarboxylate (178.85 mg, 0.761 mmol), tetrakistriphenylphosphine palladium (14.7 mg, 0.013 mmol) and a 2 M sodium carbonate aqueous solution (0.3 mL, 0.6 mmol) were added to a solution of 4-{1-ethyl-1-[3-methyl-4-(4,4,5,5-tetramethyl-[1,3,2]dioxaborolan-2-yl)-phenyl]-propyl}-2-methyl-phenol (Example 15-(2); 100 mg, 0.254 mmol) in toluene (0.5 mL) at room temperature, and the mixture was stirred at 85° C. for 17 hours. Ethyl acetate was added to the reaction solution. The organic layer was filtered through celite, and the solvent was distilled off under reduced pressure. The residue was purified by silica gel chromatography (n-hexane/ethyl acetate=3/1) to give the title compound (50.3 mg, 46.9%).

$^1$H-NMR (chloroform-d): 0.64 (t, 6H, J=7.3 Hz), 2.02 (s, 3H), 2.08 (q, 4H, J=7.3 Hz), 2.14 (s, 3H), 2.23 (s, 3H), 3.88 (s, 3H), 6.69 (d, 1H, J=8.2 Hz), 6.88-6.95 (m, 2H), 7.00-7.10 (m, 3H), 7.63 (d, 1H, J=0.5 Hz); MS (ESI+): 412 ([M+NH$_4$]$^+$).

(2) Synthesis of 5-(4-{1-[4-(t-butyl-dimethyl-silanyloxy)-3-methyl-phenyl]-1-ethyl-propyl}-2-methyl-phenyl)-4-methyl-thiophene-2-carboxylic Acid Methyl Ester -continued

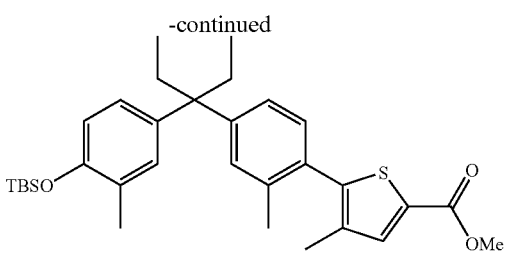

t-Butyldimethylsilyl chloride (36 mg, 0.238 mmol) and imidazole (40.5 mg, 0.595 mmol) were added to a solution of 5-{4-[1-ethyl-1-(4-hydroxy-3-methyl-phenyl)-propyl]-2-methyl-phenyl}-4-methyl-thiophene-2-carboxylic acid methyl ester (Example 20-(1); 50.3 mg, 0.119 mmol) in N,N-dimethylformamide (0.2 mL) at room temperature, and the mixture was stirred at the same temperature for 0.2 hour. Diethyl ether was added to the reaction solution. The organic layer was washed with distilled water and brine and dried over anhydrous magnesium sulfate, and then the solvent was distilled off under reduced pressure. The residue was purified by silica gel chromatography (n-hexane/ethyl acetate=95/5 to ethyl acetate only) to give the title compound (56.4 g, 88.3%).

1H-NMR (chloroform-d): 0.22 (s, 6H), 0.64 (t, 6H, J=7.3 Hz), 1.02 (s, 9H), 2.03 (s, 3H), 2.08 (q, 4H, J=7.3 Hz), 2.15 (s, 3H), 2.18 (s, 3H), 3.88 (s, 3H), 6.67 (d, 1H, J=8.4 Hz), 6.86 (dd, 1H, J=2.6, 8.4 Hz), 6.94 (d, 1H, J=2.3 Hz), 7.02 (dd, 1H, J=1.3, 8.1 Hz), 7.07-7.97 (m, 2H), 7.63 (d, 1H, J=0.5 Hz); MS (m/z): 537 ([M+H]$^+$).

(3) Synthesis of 5-[4-(1-ethyl-1-{4-[5-(1-ethyl-1-hydroxy-propyl)-3-methyl-thiophen-2-yl]-3-methyl-phenyl}-propyl)-2-methyl-phenoxy]-4(R)-hydroxy-pentanoic Acid

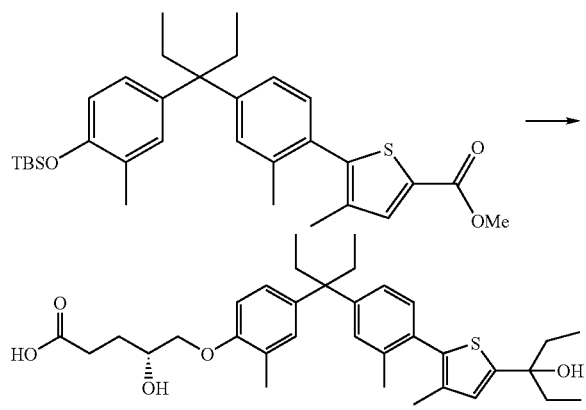

A 0.96 M solution of ethylmagnesium bromide in tetrahydrofuran (0.08 mL, 0.077 mmol) was added to a solution of 5-(4-{1-[4-(t-butyl-dimethyl-silanyloxy)-3-methyl-phenyl]-1-ethyl-propyl}-2-methyl-phenyl)-4-methyl-thiophene-2-carboxylic acid methyl ester (Example 20-(2); 20 mg, 0.039 mmol) in tetrahydrofuran (0.1 mL) at 0° C., and the mixture was stirred at the same temperature for three hours. Ethyl acetate was added to the reaction solution. The organic layer was washed with a saturated aqueous sodium bicarbonate solution and brine and dried over anhydrous magnesium sulfate, and then the solvent was distilled off under reduced pressure. A 1.0 M solution of tetra-n-butylammonium fluoride in tetrahydrofuran (0.02 mL, 0.02 mmol) was added to a solution of the residue (7.8 mg) in tetrahydrofuran (0.4 mL), and the mixture was stirred at room temperature for one minute. Ethyl acetate was added to the reaction solution. The organic layer was sequentially washed with distilled water and brine and dried over anhydrous magnesium sulfate, and then the solvent was distilled off under reduced pressure. (R)-(−)-Dihydro-5-(p-tolyl-sulfonyloxymethyl)-2(3H)-furanone (5.8 mg, 0.022 mmol) and potassium carbonate (5 mg, 0.036 mmol) were added to a solution of the residue in N,N-dimethylformamide (0.1 mL) at room temperature, and the mixture was stirred at 105° C. for 11 hours. Ethyl acetate was added to the reaction solution. The organic layer was washed with brine and dried over anhydrous magnesium sulfate, and then the solvent was distilled off under reduced pressure. The residue was purified by silica gel chromatography (dichloromethane/methanol/triethylamine=70/10/0.4, developed three times) to give the title compound (1.5 mg, 56% in four steps).

1H-NMR (methanol-d4): 0.62 (t, 6H, J=7.2 Hz), 0.88 (t, 6H, J=7.3 Hz), 1.32 (q, 4H, J=7.2 Hz), 1.83 (q, 4H, J=7.3 Hz), 1.94 (s, 3H), 2.06-2.15 (m, 2H), 2.11 (s, 3H), 2.18 (s, 3H), 2.47 (q, 2H, J=8.1 Hz), 3.90-3.93 (m, 2H), 3.92 (s, 3H), 3.90-3.99 (m, 1H), 6.68 (s, 1H), 6.79 (d, 1H, J=8.3 Hz), 6.91-7.09 (m, 5H); MS (ESI+): 549 ([M-OH]$^+$).

Example 21

Synthesis of 5-[4-(1-ethyl-1-{4-[5-(1-ethyl-1-hydroxy-propyl)-furan-2-yl]-3-methyl-phenyl}-propyl)-2-methyl-phenoxy]-4(R)-hydroxy-pentanoic Acid

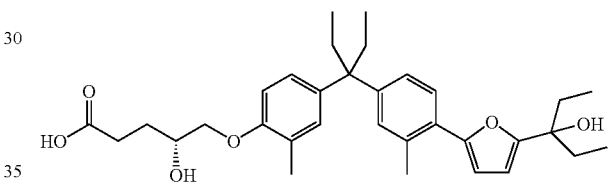

(1) Synthesis of 5(R)-[4-(1-ethyl-1-{4-[5-(1-ethyl-1-hydroxy-propyl)-furan-2-yl]-3-methyl-phenyl}-propyl)-2-methyl-phenoxymethyl]-dihydro-furan-2-one

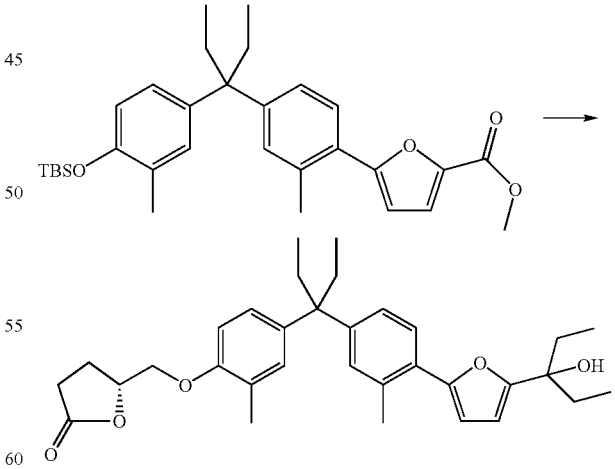

The title compound as a colorless oil (8.6 mg, 93%) was obtained by the same method as in Example 19-(3) using 2-[5-(4-{1-[4-(t-butyl-dimethyl-silanyloxy)-3-methyl-phenyl]-1-ethyl-propyl}-2-methyl-phenyl)-furan-2-yl]-propan-2-ol (Example 19-(2); 20 mg, 0.039 mmol) and a 0.96 M solution of EtMgBr in tetrahydrofuran.

¹H-NMR (chloroform-d) 0.62 (6H, t, J=7.09 Hz), 0.87 (6H, t, J=7.42 Hz), 1.90-1.98 (4H, m), 2.03-2.15 (4H, m), 2.15 (3H, s), 2.43 (3H, s), 2.24-2.63 (3H, m), 2.72-2.83 (1H, m), 4.04-4.20 (2H, m), 4.86-4.91 (1H, m), 6.30 (1H, d, J=3.29 Hz), 6.43 (1H, d, J=3.30 Hz), 6.67 (1H, d, J=8.58 Hz), 6.93-7.03 (4H, m), 7.53 (1H, d, J=8.91 Hz).

(2) Synthesis of 5-[4-(1-ethyl-1-{4-[5-(1-ethyl-1-hydroxy-propyl)-furan-2-yl]-3-methyl-phenyl}-propyl)-2-methyl-phenoxy]-4(R)-hydroxy-pentanoic Acid

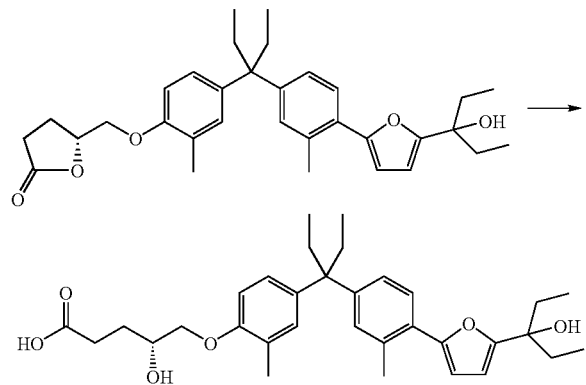

A 1 N potassium hydroxide aqueous solution (0.083 mL, 0.083 mmol) was added to a solution of 5(R)-[4-(1-ethyl-1-{4-[5-(1-ethyl-1-hydroxy-propyl)-furan-2-yl]-3-methyl-phenyl}-propyl)-2-methyl-phenoxymethyl]-dihydro-furan-2-one (Example 21-(1); 8.6 mg, 0.017 mmol) in tetrahydrofuran-methanol=10:1 (1.1 mL), and the mixture was stirred at 65° C. for one and half hours. The reaction solution was concentrated under reduced pressure, and the residue was purified by silica gel chromatography (chloroform/methanol=10/1, saturated with water) to give the title compound as a colorless oil (8.2 mg, 90%).

¹H-NMR (chloroform-d): 0.62 (6H, t, J=7.25 Hz), 0.86 (6H, t, J=7.42 Hz), 1.80-1.98 (6H, m), 2.07 (4H, q, J=7.26 Hz), 2.17 (3H, s), 2.43 (3H, s), 2.61 (2H, t, J=7.09 Hz), 3.85 (1H, dd, J=9.15, 6.84 Hz), 3.97 (1H, dd, J=9.15, 3.54 Hz), 4.02-4.12 (1H, m), 6.29 (1H, d, J=3.29 Hz), 6.43 (1H, d, J=3.14 Hz), 6.68 (1H, d, J=8.57 Hz), 6.92-7.04 (4H, m), 7.53 (1H, d, J=8.90 Hz); MS 519 (M+1-H₂O).

Example 22

Synthesis of (E)-(4'-{1-ethyl-1-[4-(3-ethyl-3-hydroxy-1-pentenyl)-3-methyl-phenyl]-propyl}-2'-methyl-biphenyl-4-yl)-acetic Acid

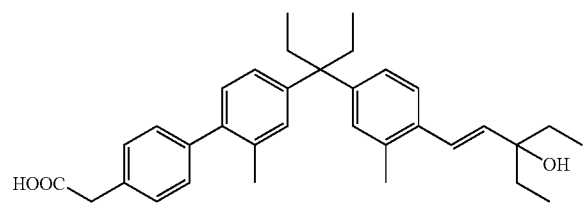

(1) Synthesis of (E)-(4'-{1-ethyl-1-[4-(3-ethyl-3-hydroxy-1-pentenyl)-3-methyl-phenyl]-propyl}-2'-methyl-biphenyl-4-yl)-acetic Acid Methyl Ester

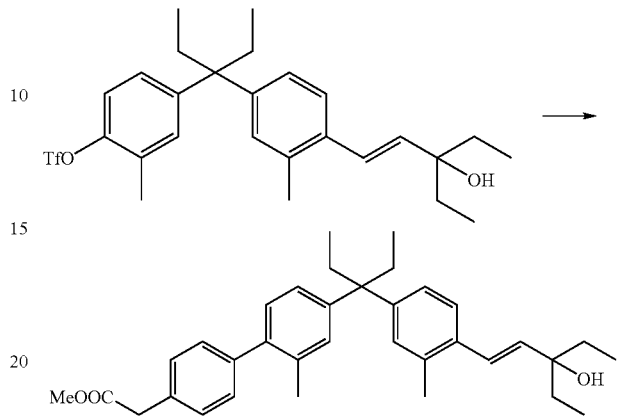

A mixture of (E)-trifluoromethanesulfonic acid 4-{1-ethyl-1-[4-(3-ethyl-3-hydroxy-1-pentenyl)-3-methyl-phenyl]-propyl}-2-methyl-phenyl ester (Example 1-(6); 0.045 g, 0.088 mmol), [4-(4,4,5,5-tetramethyl-[1,3,2]dioxaborolan-2-yl)-phenyl]-acetic acid methyl ester (0.048 g, 0.17 mmol), a [1,1'-bis(diphenylphosphino)ferrocene]dichloropalladium (II), dichloromethane complex (1:1) (0.007 g, 0.009 mmol), a sodium carbonate aqueous solution (2 M, 0.3 ml, 0.6 mmol) and N,N-dimethylformamide (1 mL) was stirred in a nitrogen atmosphere at 80° C. for three hours. Water was added to the reaction mixture, followed by extraction with ethyl acetate. The organic layer was then washed with brine, dried over anhydrous magnesium sulfate and concentrated under reduced pressure. The residue was purified by preparative TLC (hexane/ethyl acetate=5/1) to give the title compound (0.007 g, 16%).

¹H-NMR (chloroform-d): 0.66 (t, 6H, J=7.5 Hz), 0.92 (t, 6H, J=7.5 Hz), 1.64 (q, 4H, J=7.5 Hz), 2.11 (q, 4H, J=7.5 Hz), 2.23 (s, 3H), 2.33 (s, 3H), 3.67 (s, 2H), 3.18 (s, 2H), 3.72 (s, 3H), 6.02 (d, 1H, J=16.0 Hz), 6.76 (d, 1H, J=16.0 Hz), 6.94-7.10 (m, 5H), 7.26-7.38 (m, 4H), 7.50-7.56 (m, 1H).

(2) Synthesis of (E)-(4'-{1-ethyl-1-[4-(3-ethyl-3-hydroxy-1-pentenyl)-3-methyl-phenyl]-propyl}-2'-methyl-biphenyl-4-yl)-acetic Acid

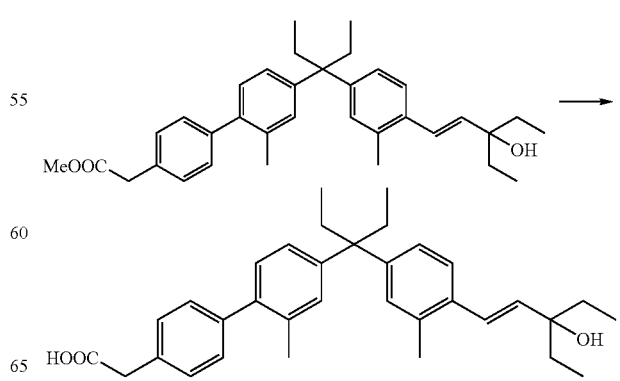

A sodium hydroxide aqueous solution (1 M, 0.1 mL, 0.1 mmol) was added to a mixture of (E)-(4'-{1-ethyl-1-[4-(3-ethyl-3-hydroxy-1-1-pentenyl)-3-methyl-phenyl]-propyl}-2'-methyl-biphenyl-4-yl)-acetic acid methyl ester (Example 22-(1); 0.007 g, 0.014 mmol) and methanol (0.5 mL) while stirring at room temperature, and the mixture was stirred at the same temperature for 14 hours. A 30% sodium dihydrogenphosphate aqueous solution was added to the reaction mixture, followed by extraction with ethyl acetate. The organic layer was dried over anhydrous magnesium sulfate and concentrated under reduced pressure. The resulting residue was purified by preparative TLC (hexane/ethyl acetate=1/3) to give the title compound (0.006 g, 88%).

$^1$H-NMR (chloroform-d): 0.66 (t, 6H, J=7.4 Hz), 0.92 (t, 6H, J=7.4 Hz), 1.64 (q, 4H, J=7.4 Hz), 2.11 (q, 4H, J=7.4 Hz), 2.22 (s, 3H), 2.33 (s, 3H), 3.70 (s, 2H), 6.02 (d, 1H, J=16.0 Hz), 6.75 (d, 1H, J=16.0 Hz), 6.96-7.10 (m, 5H), 7.28-7.34 (m, 5H); MS (ESI+): 480 ([M-OH]$^+$).

Example 23

Synthesis of [6-(4-{1-ethyl-1-[4-(3-hydroxy-4,4-dimethyl-pentyl)-3-methyl-phenyl]-propyl}-2-methyl-phenyl)-pyridin-3-yl]-acetic Acid A solution of trifluoro-methanesulfonic acid 4-(1-{4-[3-(t-butyl-dimethyl-silanyloxy)-4,4-dimethyl-pentyl]-3-methyl-phenyl}-1-ethyl-propyl)-2-methyl-phenyl ester (Example 11-(1); 145 mg, 0.231 mmol) in dioxane (1.5 mL) was added to a [1,1'-bis(diphenylphosphino)ferrocene]dichloropalladium (II), dichloromethane complex (1:1) (10.1 mg, 0.0124 mmol), 1,1'-bis(diphenylphosphino)ferrocene (7.4 mg, 0.013 mmol), potassium acetate (73 mg, 0.74 mmol) and bis(pinacolato)diboron (74 mg, 0.29 mmol). After replacement with nitrogen, the mixture was heated while stirring at an external temperature of 76 to 84° C. for eight hours and 30 minutes. Water was added to the reaction mixture, followed by extraction with ether. The extract was dried over anhydrous magnesium sulfate and then concentrated under reduced pressure. The residue was purified by silica gel chromatography (hexane/ethyl acetate=50/1) to give the title compound (130 mg, 93%).

$^1$H-NMR (chloroform-d): 0.08 (s, 3H), 0.11 (s, 3H), 0.61 (t, 6H), 0.89 (s, 9H), 0.94 (s, 9H), 1.34 (s, 12H), 1.56 (m, 1H), 1.78 (m, 1H), 2.08 (q, 4H), 2.23 (s, 3H), 2.42 (dt, 1H), 2.49 (s, 3H), 2.77 (dt, 1H), 3.34 (dd, 1H), 6.89-6.99 (m, 5H), 7.63 (d, 1H).

(2) Synthesis of {6-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic Acid Ethyl Ester

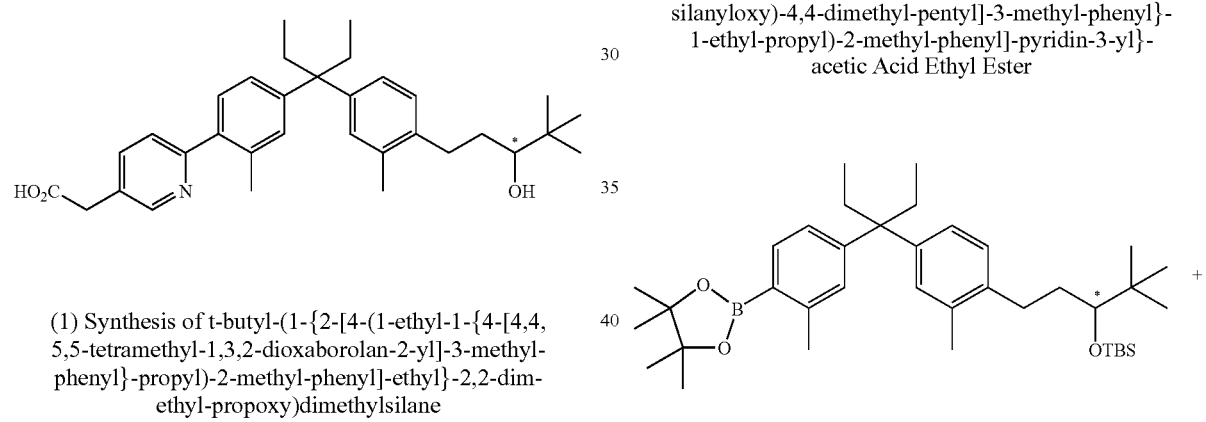

(1) Synthesis of t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane

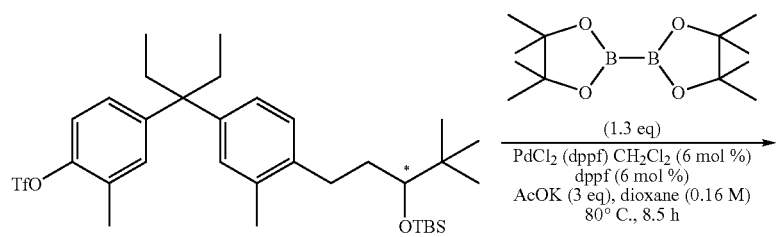

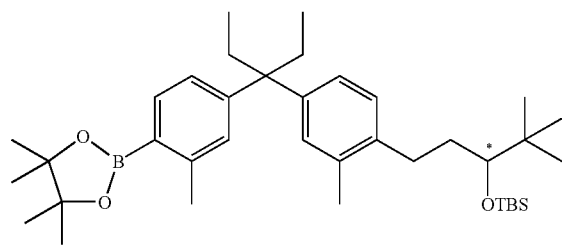

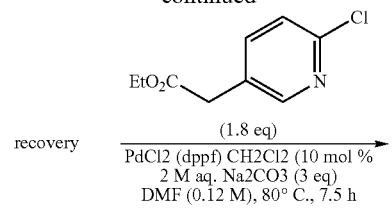

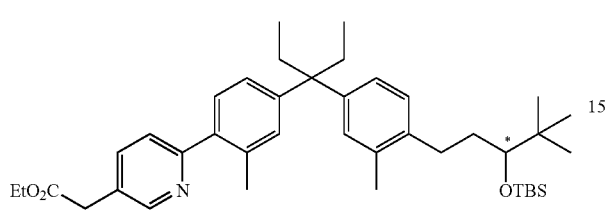

A solution of t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1); 13 mg, 0.021 mmol) in N,N-dimethylformamide (0.2 mL) was added to 2-chloropyridine-5-acetic acid ethyl ester (7.4 mg, 0.037 mmol) and a [1,1'-bis(diphenylphosphino)ferrocene]dichloropalladium (II), dichloromethane complex (1:1) (2.0 mg, 0.0024 mmol). After replacement with nitrogen, the mixture was heated while stirring at an external temperature of 76 to 84° C. for seven hours and 30 minutes. Water was added to the reaction mixture, followed by extraction with ether. The extract was dried over anhydrous magnesium sulfate and then concentrated under reduced pressure. The residue was purified by silica gel chromatography (hexane/ethyl acetate=10/1) to give the title compound (2.1 mg, 16%).

$^1$H-NMR (chloroform-d): 0.08 (s, 3H), 0.12 (s, 3H), 0.65 (t, 6H), 0.89 (s, 9H), 0.94 (s, 9H), 1.30 (t, 3H), 1.57 (m, 1H), 1.79 (m, 1H), 2.12 (q, 4H), 2.25 (s, 3H), 2.34 (s, 3H), 2.41 (m, 1H), 2.78 (m, 1H), 3.35 (dd, 1H), 3.67 (s, 2H), 4.20 (q, 2H), 6.93-7.09 (m, 5H), 7.28 (d, 1H), 7.39 (d, 1H), 7.69 (dd, 1H), 8.56 (d, 1H).

(3) Synthesis of [6-(4-{1-ethyl-1-[4-(3-hydroxy-4,4-dimethyl-pentyl)-3-methyl-phenyl]-propyl}-2-methyl-phenyl)-pyridin-3-yl]-acetic Acid Ethyl Ester

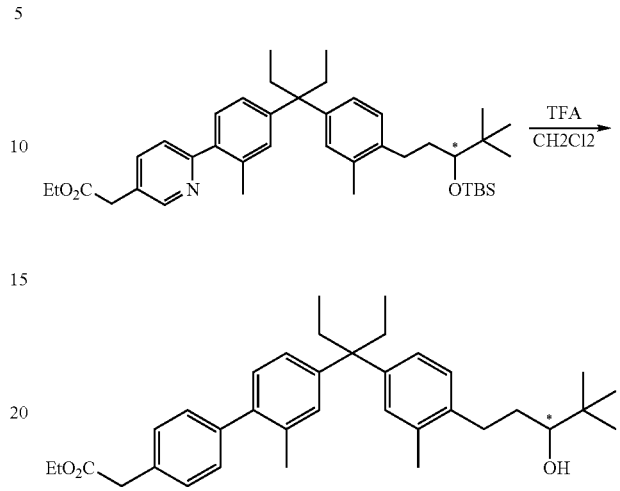

Trifluoroacetic acid (0.03 mL) was added to a solution of {6-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic acid ethyl ester (Example 23-(2); 2.1 mg, 0.0033 mmol) in dichloromethane (0.15 mL) at room temperature, and the mixture was stirred at room temperature for one hour and 15 minutes. The solvent in the reaction solution was distilled off under reduced pressure. The residue was purified by silica gel chromatography (hexane/ethyl acetate=3/1) to give the title compound (1.7 mg, 100%).

$^1$H-NMR (chloroform-d): 0.65 (t, 6H), 0.90 (s, 9H), 1.29 (t, 3H), 1.50 (m, 1H), 1.81 (m, 1H), 2.11 (q, 4H), 2.27 (s, 3H), 2.33 (s, 3H), 2.57 (m, 1H), 2.88 (m, 1H), 3.26 (dd, 1H), 3.67 (s, 2H), 4.20 (q, 2H), 6.94-7.08 (m, 5H), 7.28 (d, 1H), 7.39 (d, 1H), 7.69 (dd, 1H), 8.57 (d, 1H).

(4) Synthesis of [6-(4-{1-ethyl-1-[4-(3-hydroxy-4,4-dimethyl-pentyl)-3-methyl-phenyl]-propyl}-2-methyl-phenyl)-pyridin-3-yl]-acetic Acid

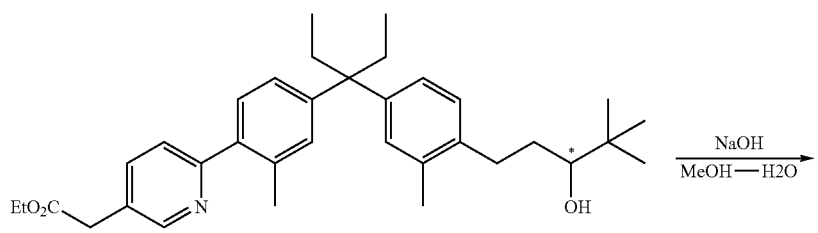

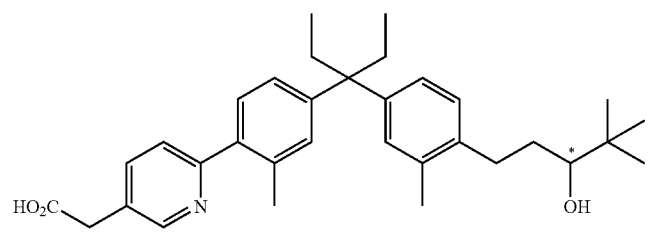

A mixed solution of a 6 N sodium hydroxide aqueous solution (0.003 mL) with water (0.01 mL) was added to a solution of [6-(4-{1-ethyl-1-[4-(3-hydroxy-4,4-dimethyl-pentyl)-3-methyl-phenyl]-propyl}-2-methyl-phenyl)-pyridin-3-yl]-acetic acid ethyl ester (Example 23-(3); 1.7 mg, 0.0032 mmol) in methanol (0.07 mL) at room temperature, and the mixture was stirred at room temperature for four hours. The mixture was acidified with a hydrochloric acid aqueous solution, followed by extraction with ethyl acetate. The extract was dried over anhydrous magnesium sulfate and then concentrated under reduced pressure to give the title compound (1.6 mg, 100%).

$^1$H-NMR (chloroform-d): 0.65 (t, 6H), 0.90 (s, 9H), 1.52 (m, 1H), 1.81 (m, 1H), 2.11 (q, 4H), 2.27 (s, 3H), 2.32 (s, 3H), 2.56 (m, 1H), 2.88 (m, 1H), 3.26 (dd, 1H), 3.71 (s, 2H), 6.94-7.09 (m, 5H), 7.25 (d, 1H), 7.40 (d, 1H), 7.71 (dd, 1H), 8.59 (d, 1H); MS (ESI+): 502 (M+1).

Example 24

Synthesis of [5-(4-{1-ethyl-1-[4-(3-hydroxy-4,4-dimethyl-pentyl)-3-methyl-phenyl]-propyl}-2-methyl-phenyl)-pyridin-3-yl]-acetic Acid

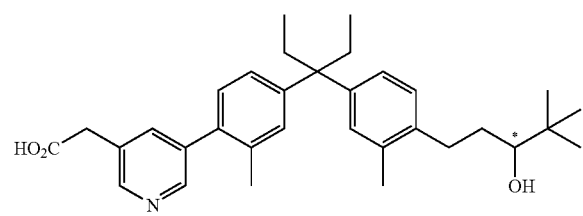

(1) Synthesis of t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane A solution of trifluoromethanesulfonic acid 4-(1-{4-[3-(t-butyl-dimethyl-silanyloxy)-4,4-dimethyl-pentyl]-3-methyl-phenyl}-1-ethyl-propyl)-2-methyl-phenyl ester (Example 3-(5); 30.4 mg, 0.0483 mmol) in dioxane (0.3 mL) was added to a [1,1'-bis(diphenylphosphino)ferrocene]dichloropalladium (II), dichloromethane complex (1:1) (1.5 mg, 0.018 mmol), 1,1'-bis(diphenylphosphino)ferrocene (1.0 mg, 0.0018 mmol), potassium acetate (14.5 mg, 0.148 mmol) and bis(pinacolato)diboron (14 mg, 0.055 mmol). After replacement with nitrogen, the mixture was heated while stirring at an external temperature of 76 to 84° C. for eight hours and 30 minutes. Water was added to the reaction mixture, followed by extraction with ether. The extract was dried over anhydrous magnesium sulfate and then concentrated under reduced pressure. The residue was purified by silica gel chromatography (hexane/ethyl acetate=50/1) to give the title compound (22.2 mg, 76%).

$^1$H-NMR (chloroform-d): 0.08 (s, 3H), 0.11 (s, 3H), 0.61 (t, 6H), 0.89 (s, 9H), 0.94 (s, 9H), 1.34 (s, 12H), 1.56 (m, 1H), 1.78 (m, 1H), 2.08 (q, 4H), 2.23 (s, 3H), 2.42 (dt, 1H), 2.49 (s, 3H), 2.77 (dt, 1H), 3.34 (dd, 1H), 6.89-6.99 (m, 5H), 7.63 (d, 1H).

(2) Synthesis of (5-bromo-pyridin-3-yl)-acetic Acid Methyl Ester

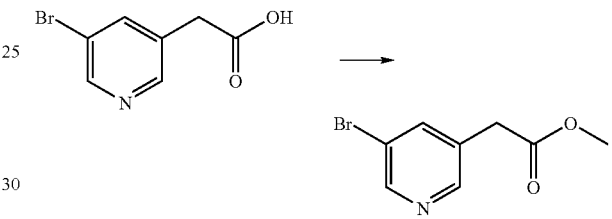

A 2.0 M solution of trimethylsilyldiazomethane in ether (10.3 mL, 20.5 mmol) was added dropwise to a mixed solution of (5-bromo-pyridin-3-yl)-acetic acid (4.04 g, 18.7 mmol) in toluene (17.3 mL) and methanol (11.5 mL), and the mixture was stirred at room temperature for 10 minutes. The reaction solution was concentrated under reduced pressure. The residue was purified by silica gel chromatography (hexane:ethyl acetate=1:3) to give the title compound (3.12 g, 72%).

$^1$H-NMR (chloroform-d): 3.63 (2H, s), 3.73 (3H, s), 7.81 (1H, s), 8.44 (1H, s), 8.60 (1H, s).

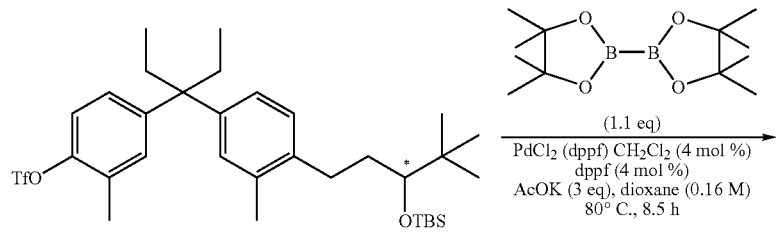

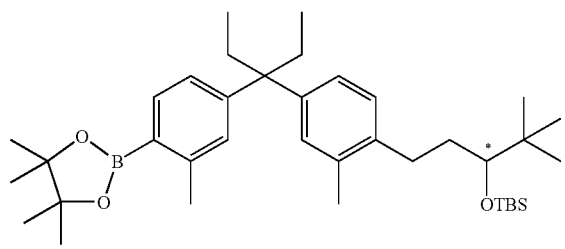

(3) Synthesis of {5-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic Acid Methyl Ester

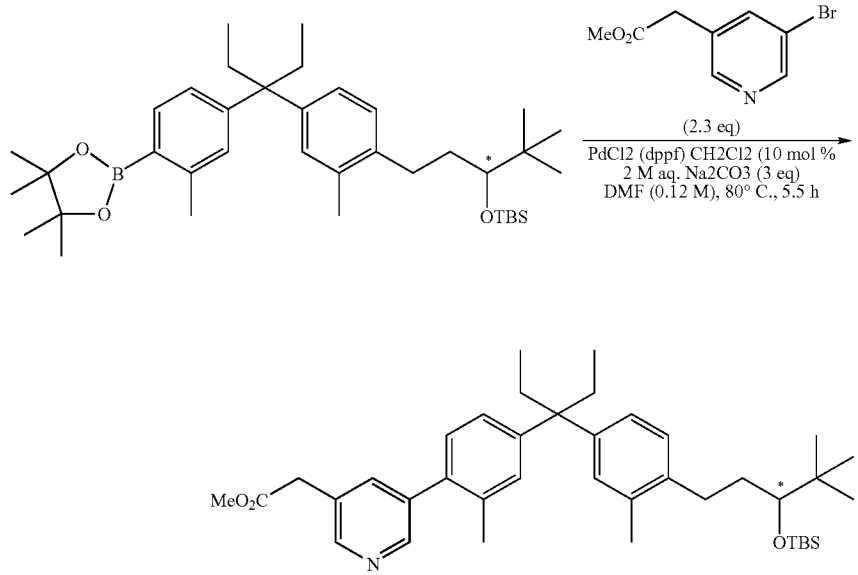

A solution of t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 24-(1); 22.0 mg, 0.036 mmol) in N,N-dimethylformamide (0.3 mL) was added to 5-bromopyridine-3-acetic acid methyl ester (Example 24-(2); 19.2 mg, 0.083 mmol) and a [1,1'-bis(diphenylphosphino)ferrocene]dichloropalladium (II), dichloromethane complex (1:1) (3.2 mg, 0.0039 mmol). After replacement with nitrogen, the mixture was heated while stirring at an external temperature of 76 to 84° C. for five hours and 30 minutes. Water was added to the reaction mixture, followed by extraction with ether. The extract was dried over anhydrous magnesium sulfate and then concentrated under reduced pressure. The residue was purified by silica gel chromatography (hexane/ethyl acetate=4/1) to give the title compound (17.2 mg, 76%).

$^1$H-NMR (chloroform-d): 0.08 (s, 3H), 0.12 (s, 3H), 0.66 (t, 6H), 0.89 (s, 9H), 0.94 (s, 9H), 1.57 (m, 1H), 1.79 (m, 1H), 2.12 (q, 4H), 2.15 (s, 3H), 2.25 (s, 3H), 2.43 (m, 1H), 2.78 (m, 1H), 3.35 (dd, 1H), 3.68 (s, 2H), 3.73 (s, 2H), 6.93-7.11 (m, 6H), 7.62 (t, 1H), 8.46 (d, 1H), 8.52 (d, 1H).

(4) Synthesis of [5-(4-{1-ethyl-1-[4-(3-hydroxy-4,4-dimethyl-pentyl)-3-methyl-phenyl]-propyl}-2-methyl-phenyl)-pyridin-3-yl]-acetic Acid Methyl Ester

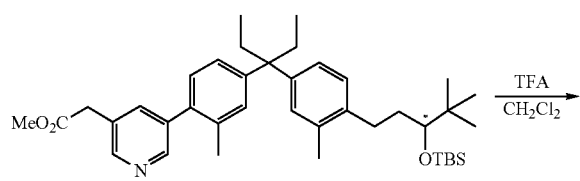

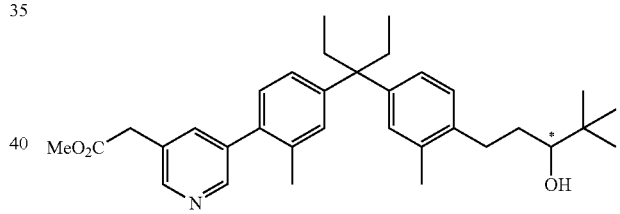

Trifluoroacetic acid (0.14 mL) was added to a solution of {5-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic acid methyl ester (Example 24-(3); 15.4 mg, 0.0244 mmol) in dichloromethane (0.7 mL) at room temperature, and the mixture was stirred at room temperature for one hour and 15 minutes. The solvent in the reaction solution was distilled off under reduced pressure. The residue was purified by silica gel chromatography (hexane/ethyl acetate=1/1 to 1/2) to give the title compound (11.6 mg, 92%).

$^1$H-NMR (chloroform-d): 0.66 (t, 6H), 0.91 (s, 9H), 1.54 (m, 1H), 1.81 (m, 1H), 2.12 (q, 4H), 2.25 (s, 3H), 2.29 (s, 3H), 2.58 (m, 1H), 2.89 (m, 1H), 3.26 (dull d, 1H), 3.68 (s, 2H), 3.73 (s, 3H), 6.94-7.10 (m, 6H), 7.63 (t, 1H), 7.46 (d, 1H), 8.52 (t, 1H).

(5) Synthesis of [5-(4-{1-ethyl-1-[4-(3-hydroxy-4,4-dimethyl-pentyl)-3-methyl-phenyl]-propyl}-2-methyl-phenyl)-pyridin-3-yl]-acetic Acid

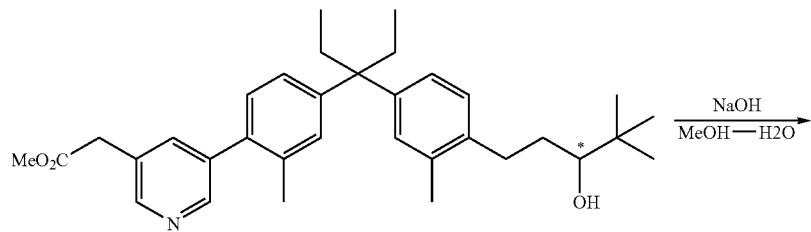

A mixed solution of a 6 N sodium hydroxide aqueous solution (0.003 mL) with water (0.008 mL) was added to a solution of [6-(4-{1-ethyl-1-[4-(3-hydroxy-4,4-dimethyl-pentyl)-3-methyl-phenyl]-propyl}-2-methyl-phenyl)-pyridin-3-yl]-acetic acid methyl ester (Example 24-(4); 2.2 mg, 0.0043 mmol) in methanol (0.04 mL) at room temperature, and the mixture was stirred at room temperature for four hours and 30 minutes. The mixture was acidified with a hydrochloric acid aqueous solution, followed by extraction with ethyl acetate. The extract was dried over anhydrous magnesium sulfate and then concentrated under reduced pressure to give the title compound (2.1 mg, 100%).

$^1$H-NMR (chloroform-d): 0.65 (t, 6H), 0.90 (s, 9H), 1.52 (m, 1H), 1.80 (m, 1H), 2.11 (q, 4H), 2.23 (s, 3H), 2.28 (s, 3H), 2.57 (m, 1H), 2.88 (m, 1H), 3.27 (dd, 1H), 3.73 (s, 2H), 6.9-7.1 (m, 6H), 7.71 (s, 1H), 8.52 (s, 2H); MS (ESI+): 502 (M+1).

Example 25

Synthesis of 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane

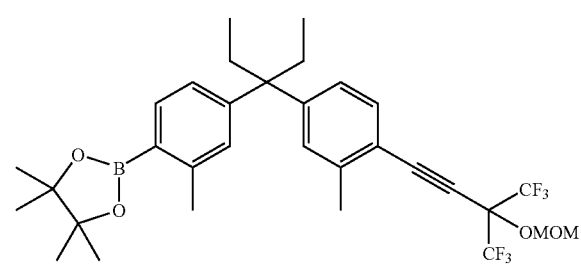

(1) Synthesis of 4-{1-ethyl-1-[3-methyl-4-(4,4,4-trifluoro-3-hydroxy-3-trifluoromethyl-1-butynyl)-phenyl]-propyl}-2-methyl-phenol

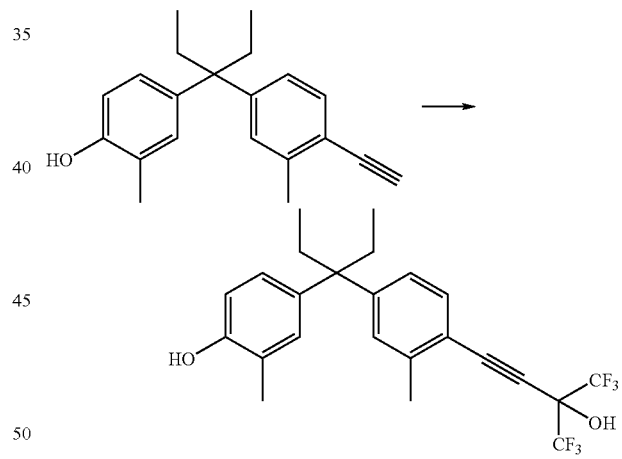

n-Butyllithium (2.5 M solution in hexane, 51.9 mL, 140.55 mmol) was added to a solution of 4-[1-ethyl-1-(4-ethynyl-3-methyl-phenyl)-propyl]-2-methyl-phenol (Example 1-(3); 16.44 g, 56.22 mmol) in tetrahydrofuran (250 mL) in a nitrogen atmosphere at 0° C., and the mixture was stirred for 30 minutes. Then, hexafluoroacetone gas was bubbled into the reaction mixture, which was further stirred at 0° C. for 30 minutes. The reaction mixture was then poured into a saturated aqueous ammonium chloride solution, followed by extraction with ethyl acetate. The organic layer was dried over anhydrous magnesium sulfate, filtered and concentrated under reduced pressure. The resulting residue was purified by silica gel chromatography (hexane:ethyl acetate=10:1 and 4:1) to give the target product as a colorless oil (17.62 g, 68%).

¹H-NMR (chloroform-d): 0.59 (6H, t, J=7.26 Hz), 2.04 (4H, q, J=7.26 Hz), 2.19 (3H, s), 2.38 (3H, s), 6.64-6.67 (1H, m), 6.81-6.84 (2H, m), 6.98-7.05 (2H, m), 7.35 (1H, d, J=7.91 Hz).

(2) Synthesis of 4-{1-ethyl-1-[3-methyl-4-(4,4,4-trifluoro-3-methoxymethoxy-3-trifluoromethyl-1-butynyl)-phenyl]-propyl}-2-methyl-phenol

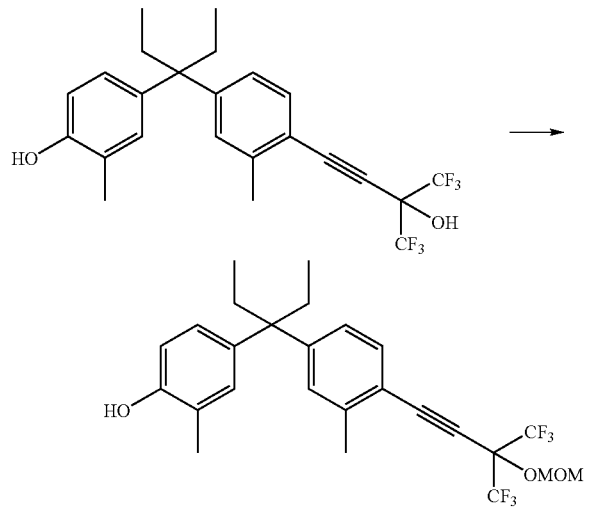

Potassium carbonate (1.8 g, 13.6 mmol) was added to a solution of 4-{1-ethyl-1-[3-methyl-4-(4,4,4-trifluoro-3-hydroxy-3-trifluoromethyl-1-butynyl)-phenyl]-propyl}-2-methyl-phenol (Example 25-(1); 2.50 g, 5.45 mmol) in N,N-dimethylformamide (36 mL), and the mixture was stirred for 20 minutes. Then, methoxymethyl chloride (0.50 mL, 6.54 mmol) was added, and the mixture was stirred for one hour. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by silica gel chromatography (10% ethyl acetate/hexane) to give the title compound (1.46 g, 66%).

¹H-NMR (chloroform-d): 0.59 (t, 6H, J=7.1 Hz), 2.04 (q, 4H, J=7.0 Hz), 2.19 (s, 3H), 2.39 (s, 3H), 3.47 (s, 3H), 4.69 (brs, 1H), 5.15 (s, 2H), 6.66 (d, 1H, J=8.1 Hz), 6.82 (d, 1H, J=7.7 Hz), 6.83 (s, 1H), 6.99 (d, 1H, J=7.7 Hz), 7.04 (s, 1H), 7.37 (d, 1H, J=8.1 Hz).

(3) Synthesis of Trifluoromethanesulfonic Acid 4-{1-ethyl-1-[3-methyl-4-(4,4,4-trifluoro-3-methoxymethoxy-3-trifluoromethyl-1-butynyl)-phenyl]-propyl}-2-methyl-phenyl Ester

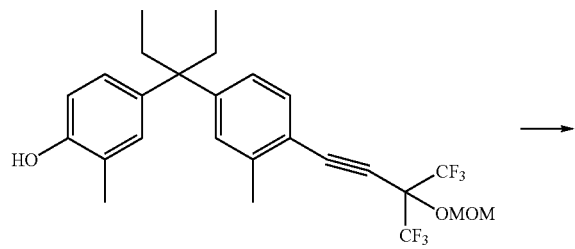

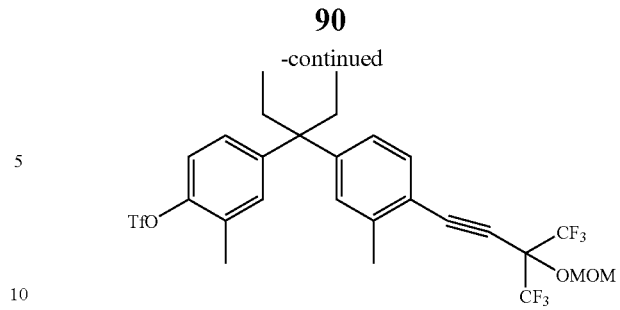

Pyridine (0.53 mL, 6.69 mmol) was added to a solution of 4-{1-ethyl-1-[3-methyl-4-(4,4,4-trifluoro-3-methoxymethoxy-3-trifluoromethyl-1-butynyl)-phenyl]-propyl}-2-methyl-phenol (Example 25-(2); 1.46 g, 2.91 mmol) in dichloromethane (15 mL), and the mixture was cooled to −10° C. Trifluoromethanesulfonic anhydride (0.58 mL, 6.11 mmol) was added dropwise, and the mixture was stirred at the same temperature for 30 minutes. Water was added to the reaction mixture, followed by extraction with ethyl acetate. The extract was dried over anhydrous sodium sulfate and concentrated under reduced pressure. The residue was purified by silica gel chromatography (3% ethyl acetate/hexane) to give the title compound (1.59 g, 86%).

¹H-NMR (chloroform-d): 0.60 (t, 6H, J=7.3 Hz), 2.07 (q, 4H, J=7.2 Hz), 2.32 (s, 3H), 2.41 (s, 3H), 3.48 (s, 3H), 5.15 (s, 2H), 6.95-7.02 (m, 4H), 7.12 (d, 1H, J=8.8 Hz), 7.40 (d, 1H, J=8.1 Hz).

(4) Synthesis of 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane

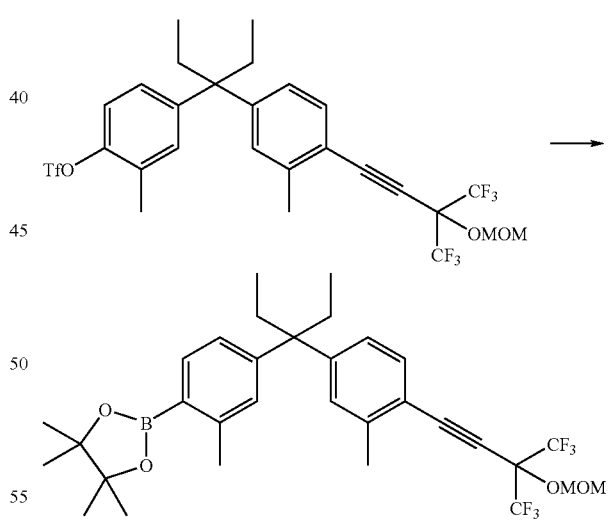

A [1,1'-bis(diphenylphosphino)ferrocene]dichloropalladium (II), dichloromethane complex (1:1) (205 mg, 0.251 mmol), 1,1'-bis(diphenylphosphino)ferrocene (139 mg, 0.251 mmol), potassium acetate (738 mg, 7.518 mmol) and bis(pinacolato)diboron (827 mg, 3.258 mmol) were added to a solution of trifluoromethanesulfonic acid 4-{1-ethyl-1-[3-methyl-4-(4,4,4-trifluoro-3-methoxymethoxy-3-trifluoromethyl-1-butynyl)-phenyl]-propyl}-2-methyl-phenyl ester (Example 25-(3); 1.59 g, 2.506 mmol) in anhydrous dioxane (30 mL). After replacement with nitrogen, the mixture was stirred at 80° C. overnight. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 30:70) to give the target product as a colorless oil (1.31 g, 85%).

$^1$H-NMR (chloroform-d): 0.59 (6H, t, J=7.26 Hz), 1.33 (12H, s), 2.07 (4H, q, J=7.26 Hz), 2.38 (3H, s), 2.47 (3H, s), 3.47 (3H, s), 5.15 (2H, s), 6.90-7.02 (4H, m), 7.36 (1H, d, J=7.91 Hz), 7.63 (1H, d, J=7.92 Hz).

Example 26

Synthesis of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (1) Synthesis of 4-{1-ethyl-1-[3-methyl-4-((E)-4,4,4-trifluoro-3-hydroxy-3-trifluoromethyl-1-butenyl)-phenyl]-propyl}-2-methyl-phenol

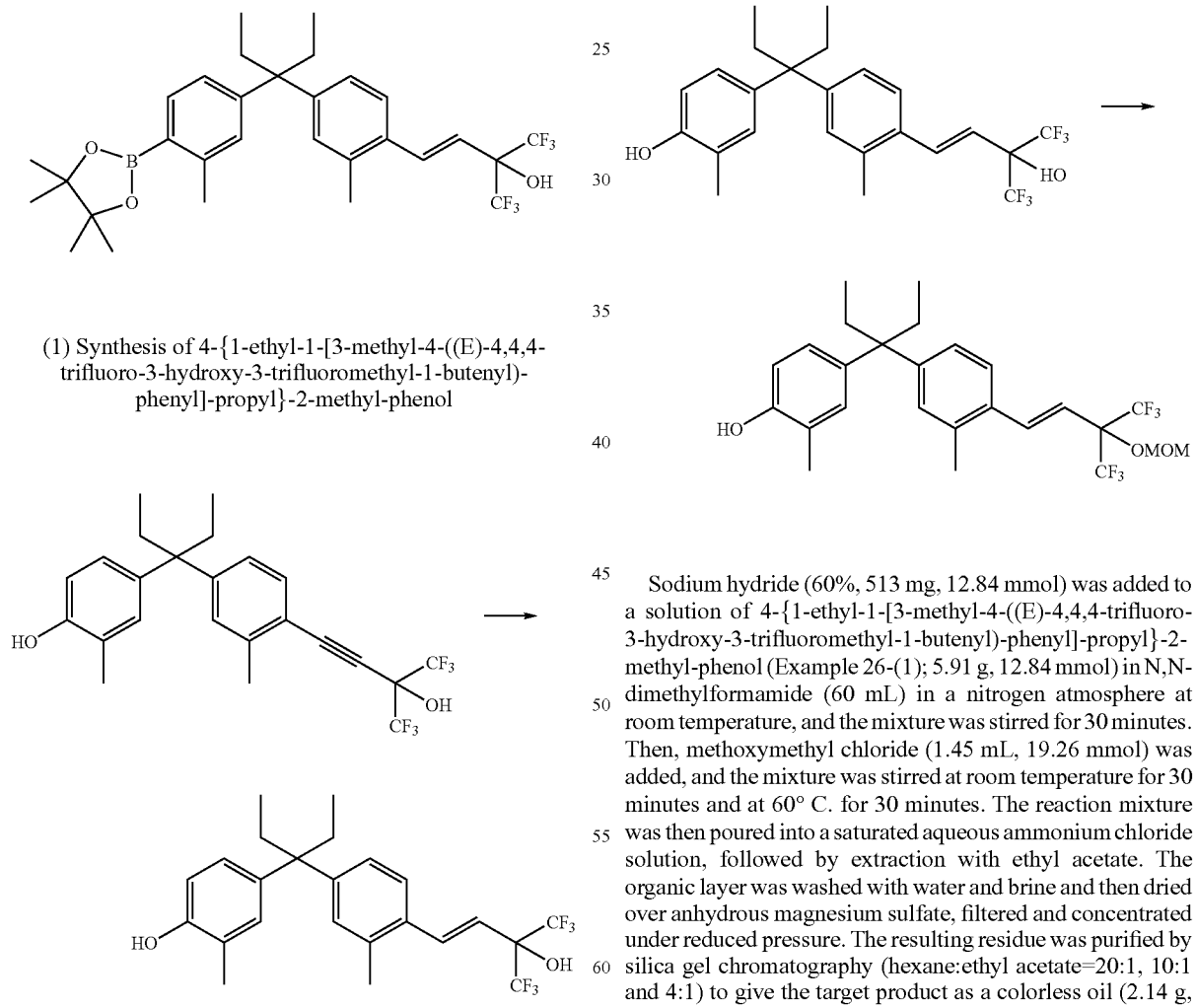

Sodium bis(2-methoxyethoxy)aluminum hydride (65 wt % solution in toluene, 17 mL, 56.74 mmol) was added to a solution of 4-{1-ethyl-1-[3-methyl-4-(4,4,4-trifluoro-3-hydroxy-3-trifluoromethyl-1-butynyl)-phenyl]-propyl}-2-methyl-phenol (Example 25-(1); 8.67 g, 18.91 mmol) in tetrahydrofuran (100 mL) in a nitrogen atmosphere at 0° C., and the mixture was stirred at 0° C. for one hour. The reaction mixture was then poured into 1 N hydrochloric acid aqueous solution, followed by extraction with dichloromethane. The organic layer was dried over anhydrous magnesium sulfate, filtered and concentrated under reduced pressure. The resulting residue was purified by silica gel chromatography (hexane:ethyl acetate=10:1 and 4:1) to give the target product as a colorless oil (6.11 g, 70%).

$^1$H-NMR (chloroform-d): 0.61 (6H, t, J=7.42 Hz), 2.05 (4H, q, J=7.42 Hz), 2.20 (3H, s), 2.34 (3H, s), 3.24 (1H, brs), 6.08 (1H, d, J=15.67 Hz), 6.65 (1H, d, J=8.08 Hz), 6.83-6.88 (2H, m), 6.99-7.02 (2H, m), 7.32-7.39 (2H, m).

(2) Synthesis of 4-{1-ethyl-1-[3-methyl-4-((E)-4,4,4-trifluoro-3-methoxymethoxy-3-trifluoromethyl-1-butenyl)-phenyl]-propyl}-2-methyl-phenol Sodium hydride (60%, 513 mg, 12.84 mmol) was added to a solution of 4-{1-ethyl-1-[3-methyl-4-((E)-4,4,4-trifluoro-3-hydroxy-3-trifluoromethyl-1-butenyl)-phenyl]-propyl}-2-methyl-phenol (Example 26-(1); 5.91 g, 12.84 mmol) in N,N-dimethylformamide (60 mL) in a nitrogen atmosphere at room temperature, and the mixture was stirred for 30 minutes. Then, methoxymethyl chloride (1.45 mL, 19.26 mmol) was added, and the mixture was stirred at room temperature for 30 minutes and at 60° C. for 30 minutes. The reaction mixture was then poured into a saturated aqueous ammonium chloride solution, followed by extraction with ethyl acetate. The organic layer was washed with water and brine and then dried over anhydrous magnesium sulfate, filtered and concentrated under reduced pressure. The resulting residue was purified by silica gel chromatography (hexane:ethyl acetate=20:1, 10:1 and 4:1) to give the target product as a colorless oil (2.14 g, 33%).

$^1$H-NMR (chloroform-d): 0.61 (6H, t, J=7.42 Hz), 2.05 (4H, q, J=7.42 Hz), 2.20 (3H, s), 2.32 (3H, s), 3.49 (3H, s), 4.55 (1H, brs), 4.96 (2H, s), 6.06 (1H, d, J=16.49 Hz), 6.65 (1H, d, J=8.07 Hz), 6.83-6.91 (2H, m), 6.99-7.03 (2H, m), 7.31-7.37 (2H, m).

(3) Synthesis of Trifluoromethanesulfonic Acid 4-{1-ethyl-1-[3-methyl-4-((E)-4,4,4-trifluoro-3-methoxymethoxy-3-trifluoromethyl-1-butenyl)-phenyl]-propyl}-2-methyl-phenyl Ester

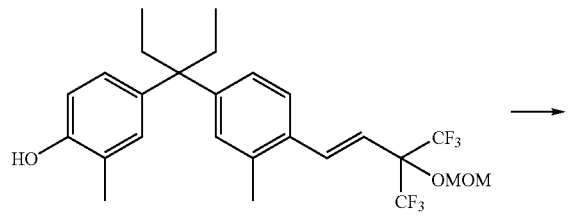

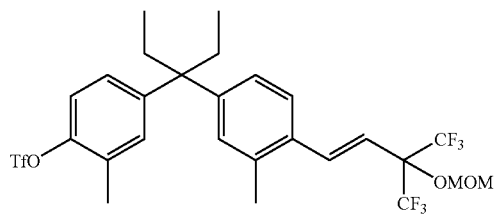

Pyridine (0.513 mL, 6.36 mmol) and trifluoromethanesulfonic anhydride (0.835 mL, 5.09 mmol) were added to a solution of 4-{1-ethyl-1-[3-methyl-4-((E)-4,4,4-trifluoro-3-methoxymethoxy-3-trifluoromethyl-1-butenyl)-phenyl]-propyl}-2-methyl-phenol (Example 26-(2); 2.14 g, 4.24 mmol) in dichloromethane (20 mL) in a nitrogen atmosphere at 0° C., and the mixture was stirred at 0° C. for 30 minutes. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 70:30) to give the target product as a colorless oil (2.41 g, 89%).

$^1$H-NMR (chloroform-d): 0.61 (6H, t, J=7.26 Hz), 2.08 (4H, q, J=7.42 Hz), 2.32 (6H, s), 3.50 (3H, m), 4.97 (2H, s), 6.08 (1H, d, J=16.65 Hz), 6.96-7.12 (5H, m), 7.31-7.39 (2H, m).

(4) Synthesis of Trifluoromethanesulfonic Acid 4-{1-ethyl-1-[3-methyl-4-((E)-4,4,4-trifluoro-3-hydroxy-3-trifluoromethyl-1-butenyl)-phenyl]-propyl}-2-methyl-phenyl Ester

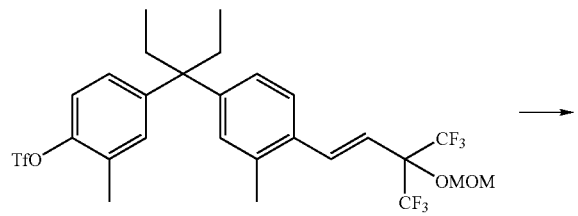

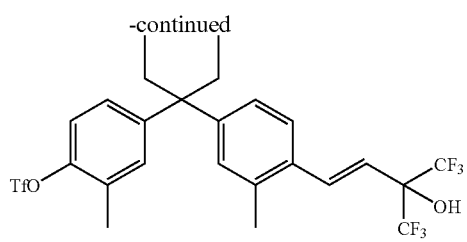

Trifluoroacetic acid (2 mL) was added to a solution of trifluoromethanesulfonic acid 4-{1-ethyl-1-[3-methyl-4-((E)-4,4,4-trifluoro-3-methoxymethoxy-3-trifluoromethyl-1-butenyl)-phenyl]-propyl}-2-methyl-phenyl ester (Example 26-(3); 2.41 g, 3.79 mmol) in dichloromethane (20 mL) at room temperature, and the mixture was stirred for 30 minutes. Then, the reaction mixture was concentrated under reduced pressure. The resulting residue was purified by silica gel chromatography (hexane:ethyl acetate=100:0 to 70:30) to give the target product as a colorless oil (2.24 g, 99%).

$^1$H-NMR (chloroform-d): 0.61 (6H, t, J=7.26 Hz), 2.08 (4H, q, J=7.26 Hz), 2.32 (3H, s), 2.35 (3H, s), 3.15 (1H, brs), 6.09 (1H, d, J=15.66 Hz), 6.96-7.12 (5H, m), 7.34-7.40 (2H, m).

(5) Synthesis of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol

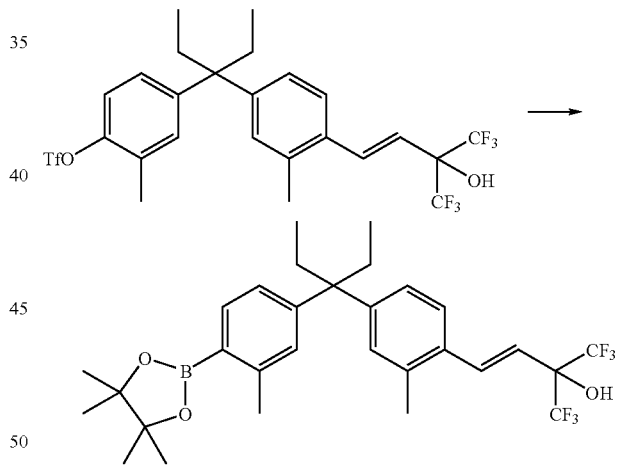

A [1,1'-bis(diphenylphosphino)ferrocene]dichloropalladium (II), dichloromethane complex (1:1) (338 mg, 0.414 mmol), 1,1'-bis(diphenylphosphino)ferrocene (229 mg, 0.414 mmol), potassium acetate (1.22 g, 12.41 mmol) and bis(pinacolato)diboron (1.37 g, 5.375 mmol) were added to a solution of trifluoromethanesulfonic acid 4-{1-ethyl-1-[3-methyl-4-((E)-4,4,4-trifluoro-3-hydroxy-3-trifluoromethyl-1-butenyl)-phenyl]-propyl}-2-methyl-phenyl ester (Example 26-(4); 2.45 g, 4.135 mmol) in anhydrous dioxane (50 mL). After replacement with nitrogen, the mixture was stirred at 80° C. overnight. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:dichloromethane=100:0 to 0:100) to give the target product as a colorless oil (2.12 g, 90%).

¹H-NMR (chloroform-d): 0.60 (6H, t, J=7.26 Hz), 1.33 (12H, s), 2.08 (4H, q, J=7.25 Hz), 2.32 (3H, s), 2.47 (3H, s), 3.20 (1H, brs), 6.07 (1H, d, J=15.83 Hz), 6.94-7.01 (4H, m), 7.31-7.39 (2H, m), 7.63 (1H, d, J=7.59 Hz).

Example 27

Synthesis of 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-butan-2-ol

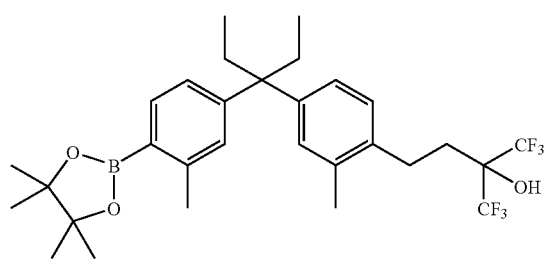

(1) Synthesis of 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-butyn-2-ol

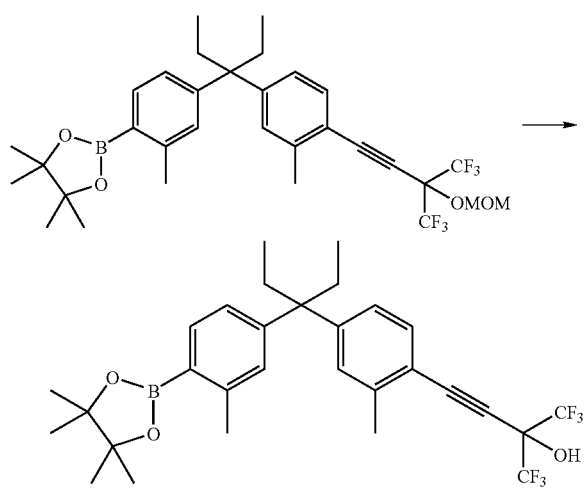

Trifluoroacetic acid (0.8 mL) was added to a solution of 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane (Example 25-(4); 284 mg, 0.464 mmol) in dichloromethane (4 mL) in a nitrogen atmosphere at room temperature, and the mixture was stirred at room temperature for six hours. Then, the reaction mixture was concentrated under reduced pressure. The resulting residue was purified by silica gel chromatography (hexane:ethyl acetate=100:0 to 70:30) to give the target product as a colorless oil (142 mg, 54%).

¹H-NMR (chloroform-d): 0.59 (6H, t, J=7.26 Hz), 1.33 (12H, s), 2.07 (4H, q, J=7.25 Hz), 2.37 (3H, s), 2.46 (3H, s), 3.62 (1H, brs), 6.90-7.03 (4H, m), 7.33 (1H, d, J=8.08 Hz), 7.63 (1H, d, J=7.92 Hz).

(2) Synthesis of 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-butan-2-ol

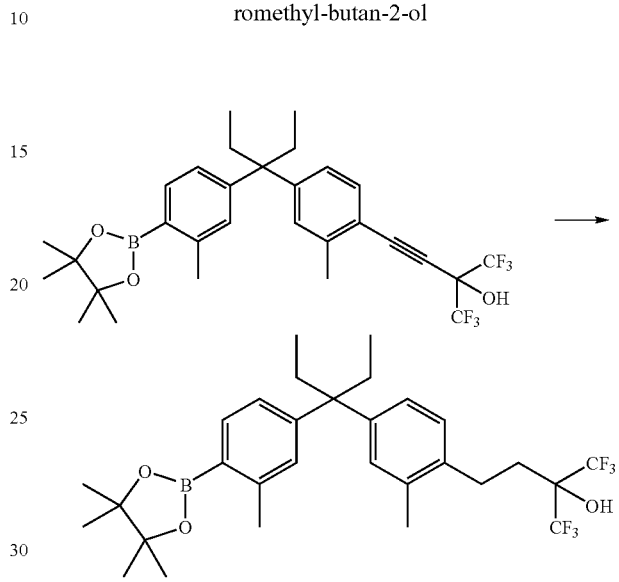

10% palladium-carbon (50 mg) was added to a solution of 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-butyn-2-ol (Example 27-(1); 142 mg, 0.249 mmol) in methanol (6 mL), and the mixture was stirred in a hydrogen atmosphere at room temperature for five hours. Then, the reaction mixture was filtered through celite, and the filtrate was concentrated under reduced pressure to give the target product as a colorless oil (134 mg, 94%).

¹H-NMR (chloroform-d): 0.59 (6H, t, J=7.26 Hz), 1.33 (12H, s), 2.07 (4H, q, J=7.26 Hz), 2.12-2.17 (2H, m), 2.24 (3H, s), 2.48 (3H, s), 2.76-2.82 (2H, m), 3.10 (1H, brs), 6.91-7.00 (5H, m), 7.63 (1H, d, J=8.24 Hz).

Example 28

Synthesis of (E)-3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-penten-3-ol

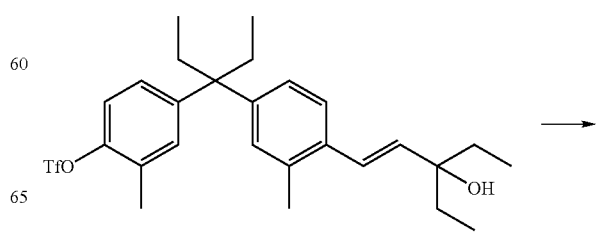

-continued

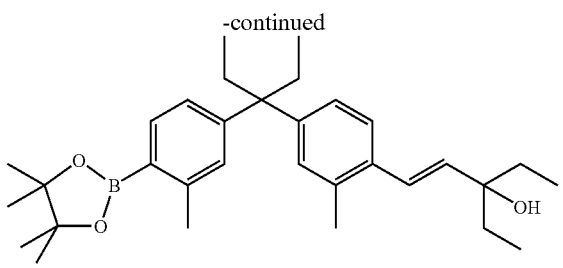

1,1'-Bis(diphenylphosphino)ferrocene (104 mg, 0.19 mmol), potassium acetate (0.919 g, 9.4 mmol), bis(pinacolato)diboron (1.03 g, 4.1 mmol), a [1,1'-bis(diphenylphosphino)ferrocene]dichloropalladium (II), dichloromethane complex (1:1) (0.15 g, 0.19 mmol) and dioxane (20 mL) were added to trifluoromethanesulfonic acid 4-{1-ethyl-1-[4-(3-ethyl-3-hydroxy-1-pentenyl)-3-methyl-phenyl]-propyl}-2-methyl-phenyl ester (Example 1-(6); 1.6 g, 3.1 mmol). The mixture was stirred in a nitrogen atmosphere at 80° C. for five hours. Diethyl ether was added to the reaction mixture. The organic layer was washed with water, dried over anhydrous magnesium sulfate and concentrated under reduced pressure. The residue was purified by silica gel column chromatography (hexane/ethyl acetate=10/1) to give the title compound (1.0 g, 65%).

$^1$H-NMR (chloroform-d): 0.60 (t, 6H, J=7.3 Hz), 0.92 (t, 6H, J=7.3 Hz), 1.32 (s, 12H), 1.64 (q, 4H, J=7.3 Hz), 2.07 (q, 4H, J=7.3 Hz), 2.29 (s, 3H), 2.48 (s, 3H), 6.00 (d, 1H, J=15.7 Hz), 6.74 (d, 1H, J=15.7 Hz), 6.9-7.00 (m, 4H), 7.25-7.30 (m, 1H), 7.63 (d, 1H, J=7.7 Hz).

Example 29

Synthesis of 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-pentan-3-ol

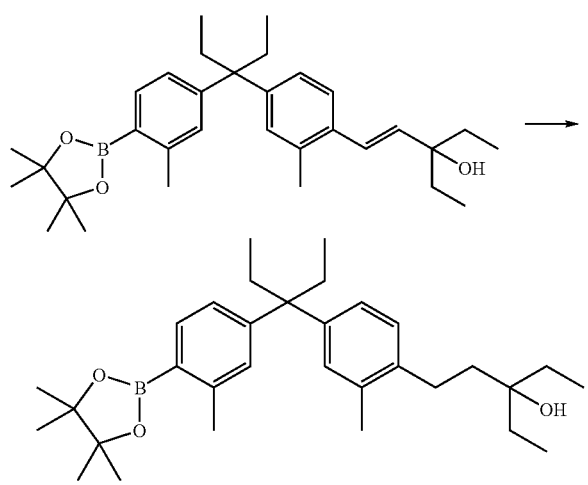

10% palladium carbon (50 mg) was added to a solution of (E)-3-ethyl-1-(4-{1-ethyl-1-[3-methyl-4-(4,4,5,5-tetramethyl-[1,3,2]dioxaborolan-2-yl)-phenyl]-propyl-2-methyl-phenyl)-1-penten-3-ol (Example 28; 150 mg, 0.306 mmol) in methanol (6 mL) and ethyl acetate (1.5 mL), and the mixture was stirred in a hydrogen atmosphere at room temperature for three hours. Then, the reaction mixture was filtered through celite, and the filtrate was concentrated under reduced pressure. The resulting residue was purified by silica gel chromatography (hexane:ethyl acetate=100:0 to 50:50, 40 minutes) to give the target product as a colorless oil (148 mg, 98%).

$^1$H-NMR (chloroform-d): 0.59 (6H, t, J=7.26 Hz), 0.90 (6H, t, J=7.42 Hz), 1.32 (12H, s), 1.55 (4H, q, J=7.42 Hz), 1.62-1.68 (2H, m), 2.06 (4H, q, J=7.42 Hz), 2.24 (3H, s), 2.48 (3H, s), 2.53-2.59 (2H, m), 6.88-6.91 (2H, m), 6.97-6.98 (3H, m), 7.62 (1H, d, J=8.41 Hz).

Example 30

Synthesis of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-one

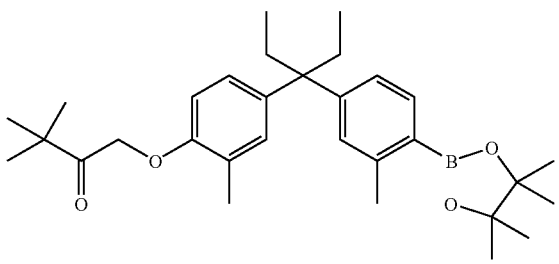

(1) Synthesis of Trifluoromethanesulfonic Acid 4-{1-[4-(3,3-dimethyl-2-oxo-butoxy)-3-methyl-phenyl]-1-ethyl-propyl}-2-methyl-phenyl Ester

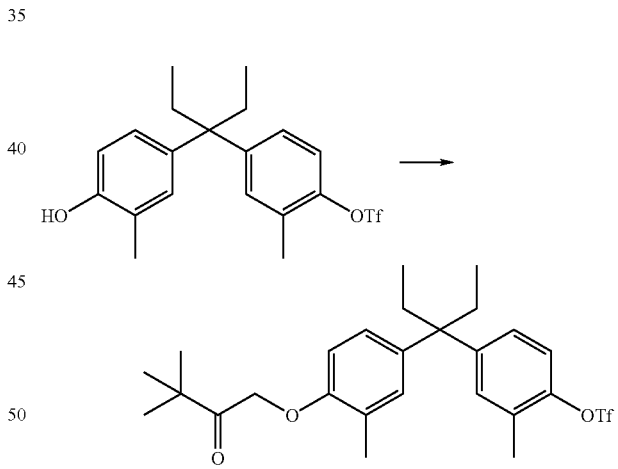

Potassium carbonate (59.7 mg, 0.43 mmol) and 1-chloropinacolin (42.0 mg, 0.31 mmol) were added to a solution of trifluoromethanesulfonic acid 4-[1-ethyl-1-(4-hydroxy-3-methyl-phenyl)-propyl]-2-methyl-phenyl ester (Example 1-(1); 0.1 g, 0.24 mmol) in acetone (1.2 mL), and the mixture was heated under reflux for 17 hours. The reaction mixture was filtered and the filtrate was concentrated under reduced pressure. The residue was purified by silica gel chromatography (6% ethyl acetate/hexane) to give the title compound (103.5 mg, 83%).

$^1$H-NMR (chloroform-d): 0.59 (t, 6H, J=7.1 Hz), 1.26 (s, 9H), 2.03 (q, 4H, J=7.3 Hz), 2.24 (s, 3H), 2.31 (s, 3H), 4.85 (s, 2H), 6.50 (d, 1H, J=8.4 Hz), 6.86-6.88 (m, 2H), 7.03-7.07 (m, 3H).

(2) Synthesis of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-one

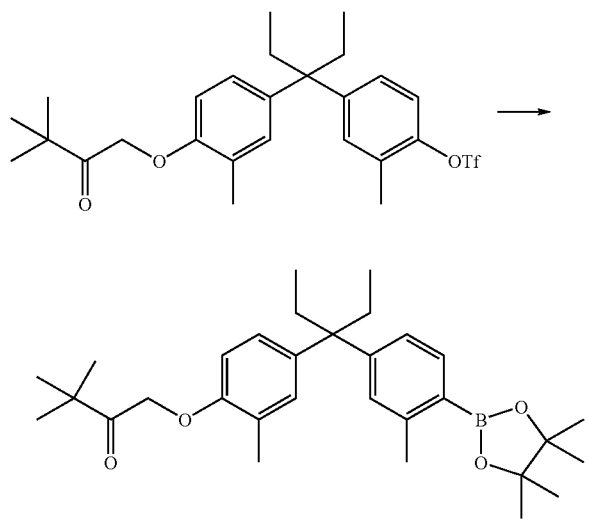

A solution of trifluoromethanesulfonic acid 4-{1-[4-(3,3-dimethyl-2-oxo-butoxy)-3-methyl-phenyl]-1-ethyl-propyl}-2-methyl-phenyl ester (Example 30-(1); 80.9 mg, 0.15 mmol), diphenylphosphinoferrocene (5.2 mg, 0.0094 mmol), a [1,1'-bis(diphenylphosphino)ferrocene]dichloropalladium (II), dichloromethane complex (1:1) (7.7 mg, 0.0094 mmol), potassium acetate (46.2 mg, 0.47 mmol) and bis(pinacolato) diboron (51.9 mg, 0.20 mmol) in dioxane (1.0 mL) was stirred at 85° C. for seven hours. The reaction mixture was extracted with diethyl ether. The organic layer was washed with water, dried over anhydrous sodium sulfate and concentrated under reduced pressure. The residue was purified by silica gel chromatography (5% ethyl acetate/hexane) to give the title compound (53.5 mg, 69%).

$^1$H-NMR (chloroform-d): 0.58 (t, 6H, J=7.1 Hz), 1.25 (s, 1H), 1.33 (s, 13H), 2.04 (q, 4H, J=7.1 Hz), 2.22 (s, 3H), 2.47 (s, 3H), 4.82 (s, 2H), 6.48 (d, 1H, J=8.8 Hz), 6.88-6.97 (m, 4H), 7.62 (d, 1H, J=7.7 Hz).

Example 31

Synthesis of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-ol

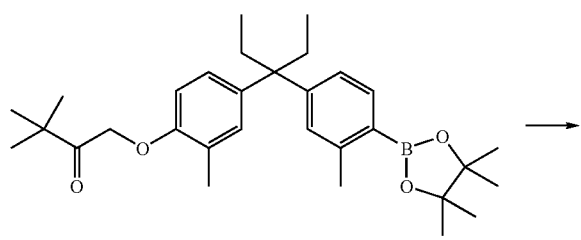

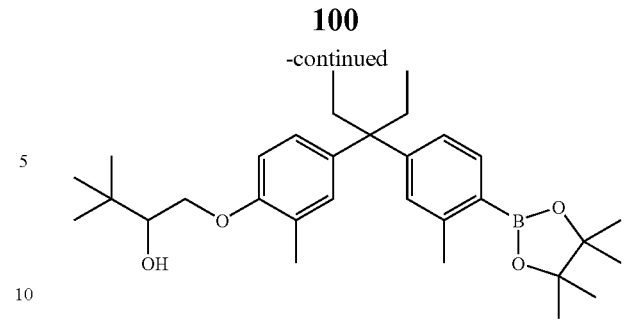

A solution of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-one (Example 30-(2); 0.50 g, 1.02 mmol) in tetrahydrofuran (10 mL) was cooled to −78° C. A 1 M solution of L-selectride (R) in tetrahydrofuran (1.0 mL) was added dropwise, and the mixture was stirred for 20 minutes. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by silica gel chromatography (5% ethyl acetate/hexane) to give the title compound (0.42 g, 83%).

$^1$H-NMR (chloroform-d): 0.59 (t, 6H, J=7.0 Hz), 1.01 (s, 9H), 1.33 (s, 12H), 2.05 (t, 4H, J=10.8 Hz), 2.16 (s, 3H), 2.47 (s, 3H), 3.70 (d, 1H, J=8.8 Hz), 3.85 (t, 1H, J=8.8 Hz), 4.07-4.15 (m, 2H), 6.68 (d, 1H, J=8.8 Hz), 6.88 (s, 1H), 6.96 (t, 3H, J=11.5 Hz), 7.63 (d, 1H, J=7.7 Hz).

Example 32

Synthesis of 1-(4-{1-ethyl-1-[3-methyl-4-(4,4,5,5-tetramethyl-[1,3,2]dioxaborolan-2-yl)-phenyl]-propyl}-2-methyl-phenylethynyl)-cyclopentanol

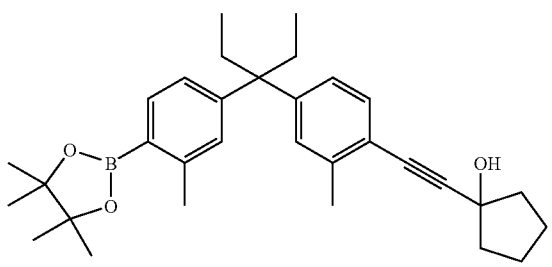

(1) Synthesis of 4-{1-ethyl-1-[4-(1-hydroxy-cyclopentylethynyl)-3-methyl-phenyl]-propyl}-2-methyl-phenol

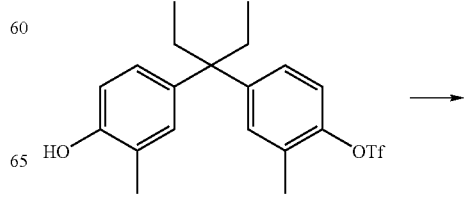

-continued

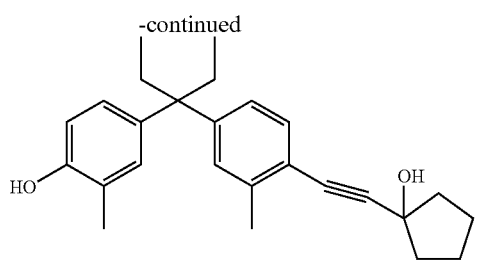

Triethylamine (5.2 mL, 37.3 mmol), 1-ethynylcyclopentanol (2 g, 18.2 mmol), cuprous iodide (0.24 g, 1.26 mmol) and tetrakis(triphenylphosphine)palladium (0) (1.44 g, 1.25 mmol) were added to a solution of trifluoromethanesulfonic acid 4-[1-ethyl-1-(4-hydroxy-3-methyl-phenyl)-propyl]-2-methyl-phenyl ester (Example 1-(1); 5.2 g, 12.5 mmol) in acetonitrile (52 mL) in a nitrogen atmosphere at room temperature, and the mixture was stirred at 110° C. for four hours. Ethyl acetate was added to the residue. The organic layer was washed with water and brine and then dried over anhydrous magnesium sulfate and concentrated under reduced pressure. The residue was purified by silica gel chromatography (hexane only to hexane/ethyl acetate=4/1) to give the title compound (3 g, 64%).

$^1$H-NMR (chloroform-d): 0.60 (t, 6H, J=7.3 Hz), 1.70-1.95 (m, 4H), 1.95-2.15 (m, 8H), 2.18 (s, 3H), 2.36 (s, 3H), 4.67 (s, 1H), 6.65 (d, 1H, J=8.8 Hz), 6.80-6.85 (m, 2H), 6.93 (d, 1H, J=8.1 Hz), 6.99 (s, 1H), 7.25-7.28 (m, 2H).

(2) Synthesis of Trifluoromethanesulfonic Acid 4-{1-ethyl-1-[4-(1-hydroxy-cyclopentylethynyl)-3-methyl-phenyl]-propyl}-2-methyl-phenyl Ester

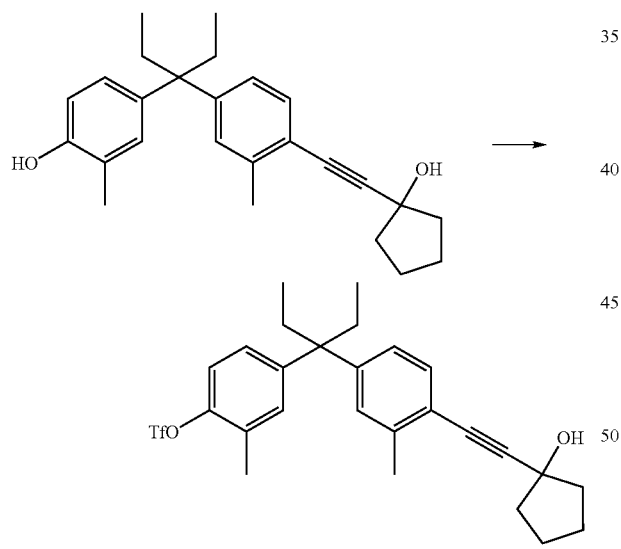

Pyridine (0.97 mL, 12 mmol) and trifluoromethanesulfonic anhydride (1.3 mL, 7.7 mmol) were added to a solution of 4-{1-ethyl-1-[4-(1-hydroxy-cyclopentylethynyl)-3-methyl-phenyl]-propyl}-2-methyl-phenol (Example 32-(1); 3 g, 8 mmol) in dichloromethane (30 mL) at −10° C., and the mixture was stirred at the same temperature for 10 minutes. A saturated aqueous sodium bicarbonate solution was added to the reaction mixture, followed by extraction with ethyl acetate. The organic layer was washed with brine, dried over anhydrous magnesium sulfate and concentrated under reduced pressure. The residue was purified by silica gel chromatography (hexane only to hexane/ethyl acetate=4/1) to give the title compound (2 g, 49%).

$^1$H-NMR (chloroform-d): 0.59 (t, 6H, J=7.3 Hz), 1.70-1.95 (m, 4H), 1.95-2.17 (m, 8H), 2.31 (s, 3H), 2.37 (s, 3H), 6.90 (d, 1H, J=8.1 Hz), 6.97 (s, 1H), 6.98-7.04 (m, 2H), 7.10 (d, 1H, J=8.1 Hz), 7.26-7.31 (m, 2H).

(3) Synthesis of 1-(4-{1-ethyl-1-[3-methyl-4-(4,4,5,5-tetramethyl-[1,3,2]dioxaborolan-2-yl)-phenyl]-propyl}-2-methyl-phenylethynyl)-cyclopentanol

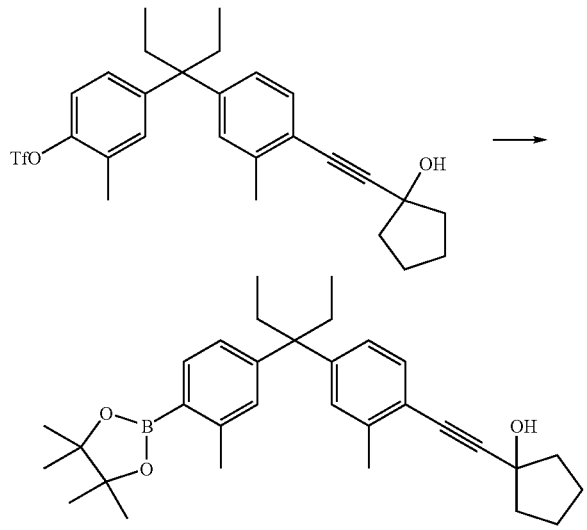

Potassium acetate (1.21 g, 12.3 mmol), bis(pinacolato)diboron (1.36 g, 5.36 mmol), a [1,1'-bis(diphenylphosphino)ferrocene]dichloropalladium (II), dichloromethane complex (1:1) (0.2 g, 0.25 mmol), 1,1'-bis(diphenylphosphino)ferrocene (0.14 g, 0.25 mmol) and dioxane (27 mL) were added to trifluoromethanesulfonic acid 4-{1-ethyl-1-[4-(1-hydroxy-cyclopentylethynyl)-3-methyl-phenyl]-propyl}-2-methyl-phenyl ester (Example 32-(2); 2 g, 3.9 mmol). The mixture was stirred in a nitrogen atmosphere at 85° C. for five hours. Diethyl ether was added to the reaction mixture. The organic layer was washed with water, dried over anhydrous magnesium sulfate and concentrated under reduced pressure. The residue was purified by silica gel column chromatography (hexane/ethyl acetate=10/1) to give the title compound (1.1 g, 57%).

$^1$H-NMR (chloroform-d): 0.58 (t, 6H, J=7.3 Hz), 1.33 (s, 12H), 1.7-2.2 (m, 12H), 2.35 (s, 3H), 2.46 (s, 3H), 6.80-7.00 (m, 4H), 7.25-7.30 (m, 1H), 7.63 (d, 1H, J=7.7 Hz).

(4) Synthesis of 2-(4-{1-ethyl-1-[3-methyl-4-(1-trimethylsilanyloxy-cyclopentylethynyl)-phenyl]-propyl}-2-methyl-phenyl)-4,4,5,5-tetramethyl-[1,3,2]dioxaborolane

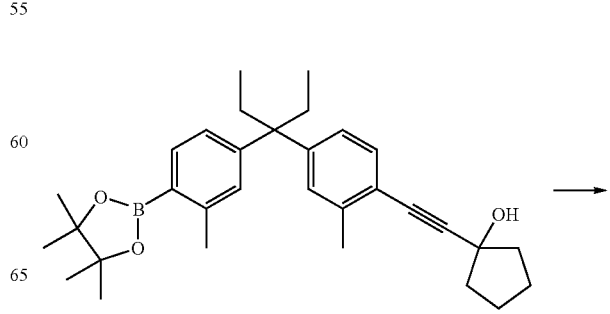

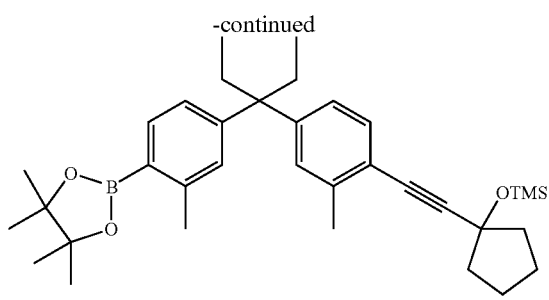

2,6-Lutidine (1.24 mL, 10.6 mmol) was added to a solution of 1-(4-{1-ethyl-1-[3-methyl-4-(4,4,5,5-tetramethyl-[1,3,2] dioxaborolan-2-yl)-phenyl]-propyl}-2-methyl-phenylethynyl)-cyclopentanol (Example 32-(3); 1.04 g, 2.13 mmol) in dichloromethane (10.7 mL). Trimethylsilyl triflate (0.92 mL, 5.13 mmol) was added at 0° C., and the mixture was directly stirred for one hour. A saturated aqueous sodium bicarbonate solution was added to the reaction mixture, followed by extraction with ethyl acetate. The organic layer was washed with water, dried over anhydrous sodium sulfate and concentrated under reduced pressure. The residue was purified by silica gel chromatography (3% ethyl acetate/hexane) to give the title compound (1.04 g, 87%).

$^1$H-NMR (chloroform-d): 0.23 (s, 9H), 0.61 (t, 6H, J=7.2 Hz), 1.34 (s, 12H), 1.73-1.83 (m, 4H), 1.97-2.11 (m, 8H), 2.36 (s, 3H), 2.48 (s, 3H), 6.90-6.97 (m, 4H), 7.25 (d, 1H, J=9.0 Hz), 7.63 (d, 1H, J=7.5 Hz).

Example 33

Synthesis of 1-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclopentanol

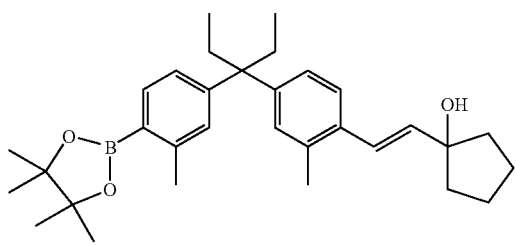

(1) Synthesis of 4-(1-ethyl-1-{4-[(E)-2-(1-hydroxy-cyclopentyl)-vinyl]-3-methyl-phenyl}-propyl)-2-methyl-phenol

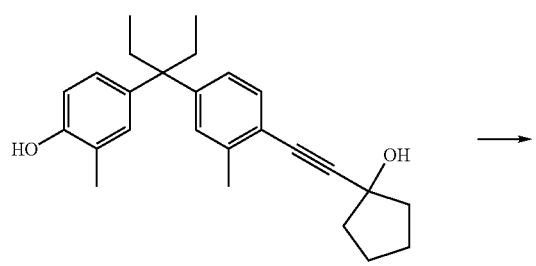

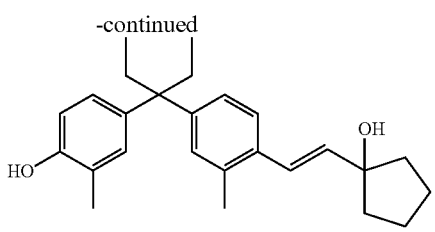

Sodium bis(2-methoxyethoxy)aluminum hydride (3.33 M solution in toluene, 6.7 mL, 22.3 mmol) was added to a solution of 4-{1-ethyl-1-[4-(1-hydroxy-cyclopentylethynyl)-3-methyl-phenyl]-propyl}-2-methyl-phenol (Example 32-(1); 2.8 g, 7.4 mmol) in tetrahydrofuran (37 mL) at 0° C., and the mixture was stirred at the same temperature for four hours. The reaction mixture was diluted with ethyl acetate. Brine and celite were added, and the mixture was stirred at room temperature for 30 minutes. The organic layer was dried over anhydrous magnesium sulfate and filtered, and then the filtrate was concentrated under reduced pressure. The residue was purified by silica gel chromatography (hexane only to hexane/ethyl acetate=3/1) to give the title compound (2.6 g, 92%).

$^1$H-NMR (chloroform-d): 0.60 (t, 6H, J=7.3 Hz), 1.65-1.95 (m, 8H), 2.03 (q, 4H, J=7.3 Hz), 2.19 (s, 3H), 2.31 (s, 3H), 4.50 (s, 1H), 6.26 (d, 1H, J=15.8 Hz), 6.65 (d, 1H, J=8.1 Hz), 6.80-6.97 (m, 5H), 7.33 (d, 1H, J=8.6 Hz).

(2) Synthesis of Trifluoromethanesulfonic Acid 4-(1-ethyl-1-{4-[(E)-2-(1-hydroxy-cyclopentyl)-vinyl]-3-methyl-phenyl}-propyl)-2-methyl-phenyl Ester

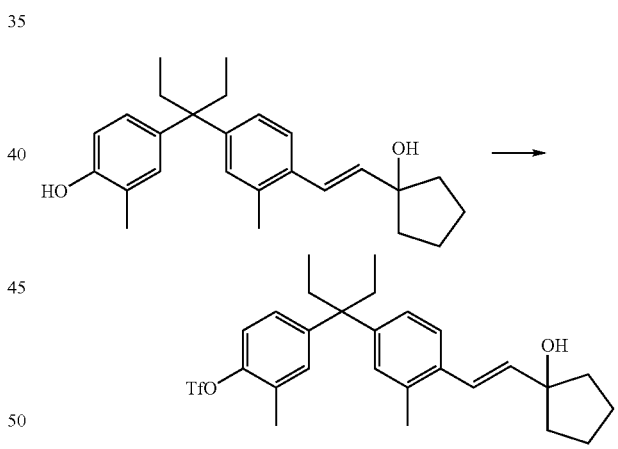

Pyridine (0.83 mL, 12 mmol) and trifluoromethanesulfonic anhydride (1.2 mL, 7.1 mmol) were added to a solution of 4-(1-ethyl-1-{4-[(E)-2-(1-hydroxy-cyclopentyl)-vinyl]-3-methyl-phenyl}-propyl)-2-methyl-phenol (Example 33-(1); 2.6 g, 6.9 mmol) in dichloromethane (26 mL) at −10° C., and the mixture was stirred at the same temperature for 10 minutes. A saturated aqueous sodium bicarbonate solution was added to the reaction mixture, followed by extraction with ethyl acetate. The organic layer was washed with brine, dried over anhydrous magnesium sulfate and concentrated under reduced pressure. The residue was purified by silica gel chromatography (hexane only to hexane/ethyl acetate=4/1) to give the title compound (1.8 g, 51%).

$^1$H-NMR (chloroform-d): 0.61 (t, 6H, J=7.3 Hz), 1.65-1.95 (m, 8H), 2.07 (q, 4H, J=7.3 Hz), 2.31 (s, 3H), 2.32 (s, 3H), 6.27 (d, 1H, J=15.7 Hz), 6.84 (d, 1H, J=15.7 Hz), 7.03 (brs, 2H), 7.04-7.12 (m, 3H), 7.35 (d, 1H, J=8.8 Hz).

(3) Synthesis of (E)-1-[2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclopentanol

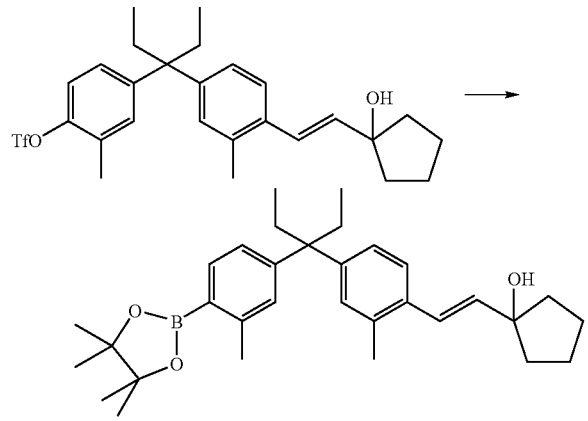

A solution of trifluoromethanesulfonic acid 4-(1-ethyl-1-{4-[(E)-2-(1-hydroxy-cyclopentyl)-vinyl]-3-methyl-phenyl}-propyl)-2-methyl-phenyl ester (Example 33-(2); 1.8 g, 3.52 mmol), diphenylphosphinoferrocene (117.2 mg, 0.211 mmol), a [1,1'-bis(diphenylphosphino)ferrocene]dichloropalladium (II), dichloromethane complex (1:1) (172.7 mg, 0.211 mmol), potassium acetate (1.03 g, 10.5 mmol) and bis(pinacolato)diboron (1.16 g, 4.58 mmol) in dioxane (23 mL) was stirred at 80° C. for seven hours. Water was added to the reaction mixture, followed by extraction with diethyl ether. The extract was dried over anhydrous sodium sulfate and concentrated under reduced pressure. The residue was purified by silica gel chromatography (8% ethyl acetate/hexane) to give the title compound (0.56 g, 32%).

¹H-NMR (chloroform-d): 0.60 (t, 6H, J=7.0 Hz), 1.33 (s, 15H), 1.71-1.92 (m, 8H), 2.03-2.10 (m, 5H), 2.30 (s, 3H), 2.47 (s, 3H), 6.26 (d, 1H, J=15.7 Hz), 6.83 (d, 1H, J=15.7 Hz), 6.94-6.98 (m, 4H), 7.32 (d, 1H, J=8.1 Hz), 7.63 (d, 1H, J=7.7 Hz).

Example 34

Synthesis of 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclopentanol

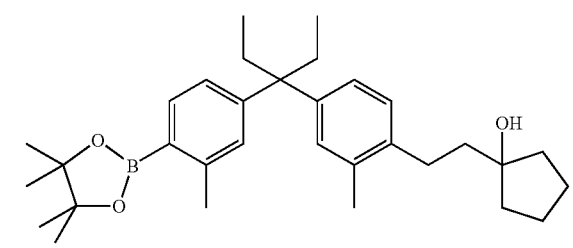

(1) Synthesis of 2-[4-(1-ethyl-1-{3-methyl-4-[2-(1-trimethylsilanyloxy-cyclopentyl)-ethyl]-phenyl}-propyl)-2-methyl-phenyl]-4,4,5,5-tetramethyl-[1,3,2]dioxaborolane

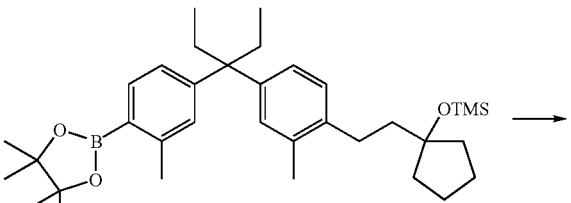

10% palladium carbon (40 mg) was added to a solution of 2-(4-{1-ethyl-1-[3-methyl-4-(1-trimethylsilanyloxy-cyclopentylethynyl)-phenyl]-propyl}-2-methyl-phenyl)-4,4,5,5-tetramethyl-[1,3,2]dioxaborolane (Example 32-(4); 0.26 g, 0.48 mmol) in ethyl acetate (2.5 mL), and the mixture was stirred under hydrogen charging for three hours. The reaction mixture was filtered and concentrated to give the title compound (0.26 g, 100%).

¹H-NMR (chloroform-d): 0.14 (s, 9H), 0.59 (t, 6H, J=7.3 Hz), 1.32 (s, 12H), 1.51-1.57 (m, 4H), 1.73-1.79 (m, 6H), 2.06 (q, 4H, J=7.3 Hz), 2.23 (s, 3H), 2.48 (s, 3H), 2.61-2.68 (m, 2H), 6.88-6.99 (m, 5H), 7.62 (d, 1H, J=8.3 Hz).

(2) Synthesis of 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclopentanol A 1 M solution of tetrabutylammonium fluoride in tetrahydrofuran (1.33 mL, 1.33 mmol) was added to 2-[4-(1-ethyl- 1-{3-methyl-4-[2-(1-trimethylsilanyloxy-cyclopentyl)-ethyl]-phenyl}-propyl)-2-methyl-phenyl]-4,4,5,5-tetramethyl-[1,3,2]dioxaborolane (Example 34-(1); 0.25 g, 0.48 mmol), and the mixture was stirred for three hours. The reaction mixture was purified by silica gel chromatography (14% ethyl acetate/hexane) to give the title compound (0.12 g, 53%).

$^1$H-NMR (chloroform-d): 0.59 (t, 6H, J=7.3 Hz), 1.33 (s, 12H), 1.64-1.75 (m, 6H), 1.78-1.88 (m, 4H), 2.06 (q, 4H, J=8.4 Hz), 2.24 (s, 3H), 2.39 (brs, 1H), 2.48 (s, 3H), 2.69 (t, 2H, J=8.2 Hz), 6.89-6.91 (m, 2H), 6.98-7.04 (m, 3H), 7.63 (d, 1H, J=8.1 Hz).

Example 35

Synthesis of 2-(4-{1-ethyl-1-[3-methyl-4-(1-trimethylsilanyloxy-cyclohexylethynyl)-phenyl]-propyl}-2-methyl-phenyl)-4,4,5,5-tetramethyl-[1,3,2]dioxaborolane

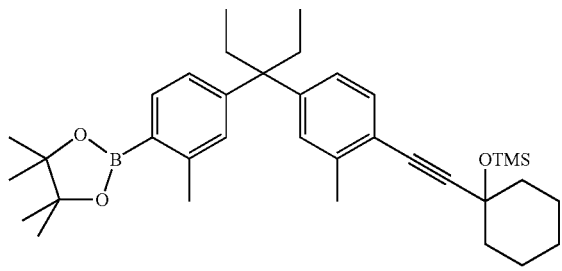

(1) Synthesis of 4-{1-ethyl-1-[4-(1-hydroxy-cyclohexylethynyl)-3-methyl-phenyl]-propyl}-2-methyl-phenol

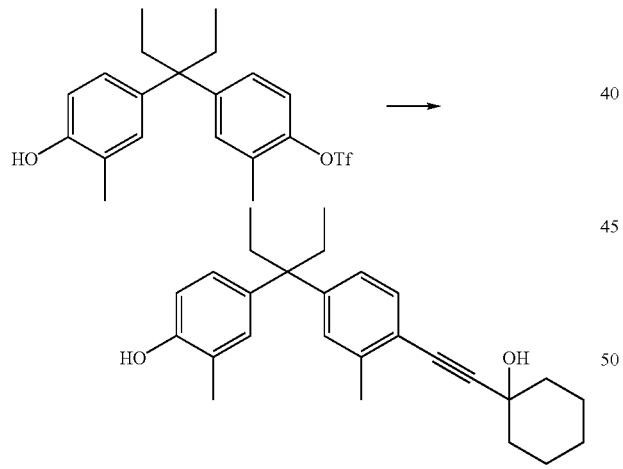

Triethylamine (8.0 mL, 57.6 mmol), tetrakistriphenylphosphine palladium (2.2 g, 1.92 mmol) and cuprous iodide (0.36 g, 1.92 mmol) were added to a solution of trifluoromethanesulfonic acid 4-[1-ethyl-1-(4-hydroxy-3-methyl-phenyl)-propyl]-2-methyl-phenyl ester (Example 1-(1); 8.0 g, 19.2 mmol) and 1-ethynyl-cyclohexanol (3.5 g, 28.8 mmol) in acetonitrile (96 mL), and the mixture was stirred at 110° C. for 1.5 hours. The reaction mixture was extracted with ethyl acetate. The organic layer was washed with water and then dried over anhydrous sodium sulfate and concentrated under reduced pressure. The residue was purified by silica gel chromatography (hexane/ethyl acetate=4/1) to give the title compound (4.75 g, 63%).

$^1$H-NMR (chloroform-d): 0.59 (t, 6H, J=7.3 Hz), 1.57-1.74 (m, 6H), 1.89-2.10 (m, 4H), 2.01 (q, 4H, J=7.3 Hz), 2.18 (s, 3H), 2.37 (s, 3H), 4.61 (s, 1H), 6.65 (d, 1H, J=8.1 Hz), 6.84 (d, 2H, J=7.7 Hz), 6.85 (s, 1H), 6.93 (d, 1H, J=8.1 Hz), 7.00 (s, 1H), 7.27 (d, 1H, J=7.7 Hz).

(2) Synthesis of Trifluoromethanesulfonic Acid 4-{1-ethyl-1-[4-(1-hydroxy-cyclohexylethynyl)-3-methyl-phenyl]-propyl}-2-methyl-phenyl Ester

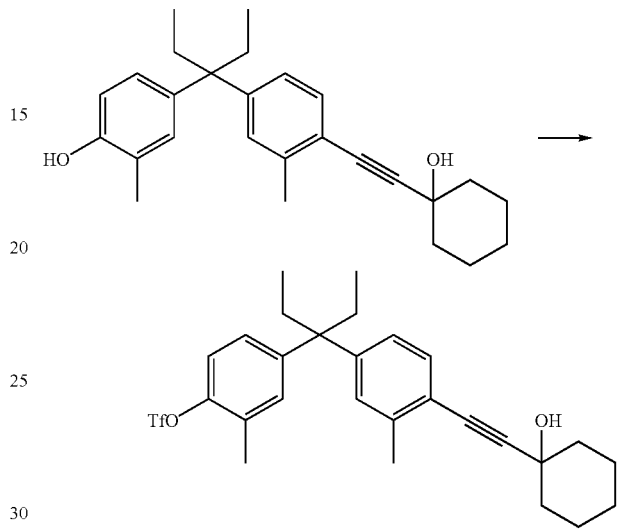

Pyridine (0.031 mL, 0.38 mmol) was added to a solution of 4-{1-ethyl-1-[4-(1-hydroxy-cyclohexylethynyl)-3-methyl-phenyl]-propyl}-2-methyl-phenol (Example 35-(1); 0.1 g, 0.25 mmol) in dichloromethane (1.0 mL). Trifluoromethanesulfonic anhydride (0.039 mL, 0.28 mmol) was added dropwise at −10° C., and the mixture was stirred at the same temperature for 10 minutes. The reaction mixture was extracted with ethyl acetate. The organic layer was washed with water, dried over anhydrous sodium sulfate and concentrated under reduced pressure. The residue was purified by silica gel chromatography (hexane/ethyl acetate=5/1) to give the title compound (84.6 mg, 63%).

$^1$H-NMR (chloroform-d): 0.59 (t, 6H, J=7.3 Hz), 1.61-1.75 (m, 6H), 2.00-2.06 (m, 4H), 2.05 (q, 4H, J=7.3 Hz), 2.31 (s, 3H), 2.39 (s, 3H), 6.91 (d, 1H, J=8.4 Hz), 6.97 (s, 1H), 6.98 (d, 1H, J=8.4 Hz), 7.03 (s, 1H), 7.06 (d, 1H, J=8.1 Hz), 7.30 (d, 1H, J=8.1 Hz).

(3) Synthesis of 1-(4-{1-ethyl-1-[3-methyl-4-(4,4,5,5-tetramethyl-[1,3,2]dioxaborolan-2-yl)-phenyl]-propyl}-2-methyl-phenylethynyl)-cyclohexanol

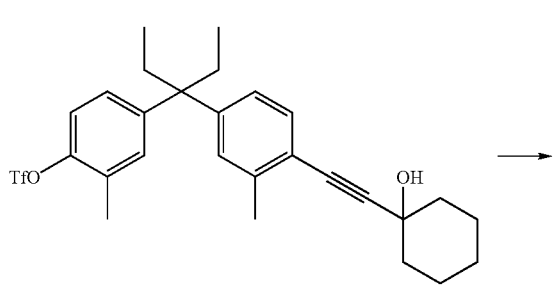

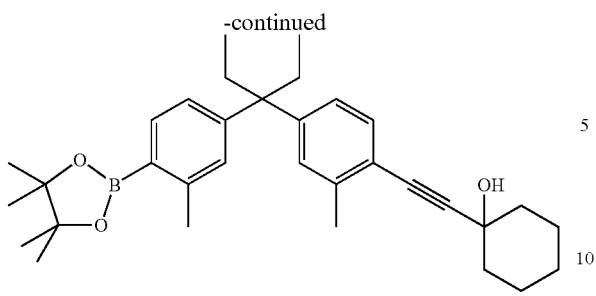

A solution of trifluoromethanesulfonic acid 4-{1-ethyl-1-[4-(1-hydroxy-cyclohexylethynyl)-3-methyl-phenyl]-propyl}-2-methyl-phenyl ester (Example 35-(2); 1.74 g, 3.33 mmol), diphenylphosphinoferrocene (0.11 g, 0.20 mmol), a [1,1'-bis(diphenylphosphino)ferrocene]dichloropalladium (II), dichloromethane complex (1:1) (0.16 g, 0.20 mmol), potassium acetate (0.98 g, 9.99 mmol) and bis(pinacolato) diboron (1.10 g, 4.33 mmol) in dioxane (22 mL) was stirred at 85° C. for five hours. A saturated aqueous ammonium chloride solution was added to the reaction mixture, followed by extraction with diethyl ether. The organic layer was washed with water, dried over anhydrous sodium sulfate and concentrated under reduced pressure. The residue was purified by silica gel chromatography (hexane/ethyl acetate=9/1) to give the title compound (1.43 g, 73%).

$^1$H-NMR (chloroform-d): 0.58 (t, 6H, J=7.3 Hz), 1.33 (s, 12H), 1.52-1.78 (m, 6H), 1.99-2.09 (m, 4H), 2.06 (q, 4H, J=7.3 Hz), 2.37 (s, 3H), 2.46 (s, 3H), 6.91-6.98 (m, 4H), 7.27 (d, 1H, J=6.6 Hz), 7.63 (d, 1H, J=8.1 Hz).

(4) Synthesis of 2-(4-{1-ethyl-1-[3-methyl-4-(1-trimethylsilanyloxy-cyclohexylethynyl)-phenyl]-propyl}-2-methyl-phenyl)-4,4,5,5-tetramethyl-[1,3,2]dioxaborolane

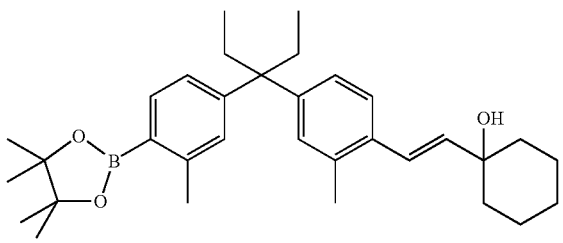

2,6-Lutidine (0.16 g, 1.49 mmol) was added to a solution of 1-(4-{1-ethyl-1-[3-methyl-4-(4,4,5,5-tetramethyl-[1,3,2]dioxaborolan-2-yl)-phenyl]-propyl}-2-methyl-phenylethynyl)-cyclohexanol (Example 35-(3); 0.15 g, 0.29 mmol) in dichloromethane (1.5 mL). Trimethylsilyl triflate (0.13 mL, 0.71 mmol) was added at 0° C., and the mixture was stirred at the same temperature for one hour. A saturated aqueous sodium bicarbonate solution was added to the reaction mixture, followed by extraction with ethyl acetate. The organic layer was washed with water, dried over anhydrous sodium sulfate and concentrated under reduced pressure. The residue was purified by silica gel chromatography (3% ethyl acetate/hexane) to give the title compound (0.16 g, 93%).

$^1$H-NMR (chloroform-d): 0.22 (s, 9H), 0.60 (t, 6H, J=7.0 Hz), 1.33 (s, 13H), 1.59-1.65 (m, 8H), 1.94-1.97 (m, 2H), 2.06-2.08 (m, 6H), 2.37 (s, 3H), 2.48 (s, 3H), 6.93-6.96 (m, 4H), 7.63 (d, 1H, J=7.7 Hz).

Example 36

Synthesis of (E)-1-[2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclohexanol (1) Synthesis of 4-(1-ethyl-1-{4-[(E)-2-(1-hydroxy-cyclohexyl)-vinyl]-3-methyl-phenyl}-propyl)-2-methyl-phenol

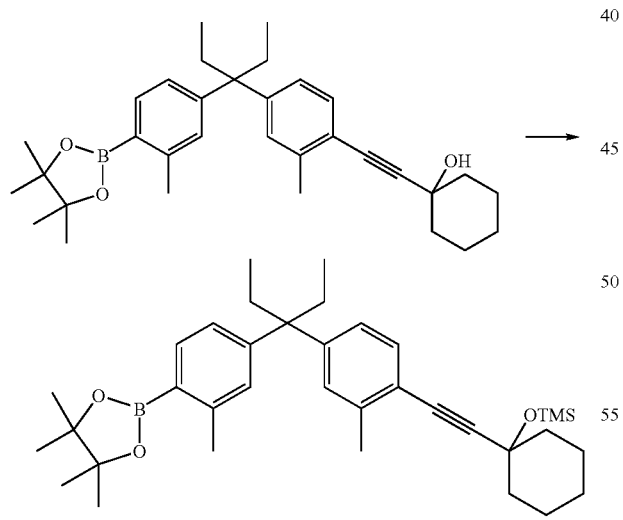

4-{1-Ethyl-1-[4-(1-hydroxy-cyclohexylethynyl)-3-methyl-phenyl]-propyl}-2-methyl-phenol (Example 35-(1); 0.2 g, 0.51 mmol) was added to a solution of lithium aluminum hydride (38.9 mg, 1.02 mmol) in tetrahydrofuran (2 mL), and the mixture was stirred for five hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by silica gel chromatography (20% ethyl acetate/hexane) to give the title compound (0.17 g, 88%).

¹H-NMR (chloroform-d): 0.60 (t, 6H, J=7.3 Hz), 1.51-1.75 (m, 8H), 2.00-2.08 (m, 2H), 2.03 (q, 4H, J=7.3 Hz), 2.19 (s, 3H), 2.30 (s, 3H), 4.70 (s, 1H), 6.21 (d, 1H, J=16.1 Hz), 6.64 (d, 1H, J=8.0 Hz), 6.81 (d, 1H, J=16.1 Hz), 6.85-7.00 (m, 4H), 7.32 (d, 1H, J=8.8 Hz).

(2) Synthesis of Trifluoromethanesulfonic Acid 4-(1-ethyl-1-{4-[(E)-2-(1-hydroxy-cyclohexyl)-vinyl]-3-methyl-phenyl}-propyl)-2-methyl-phenyl Ester

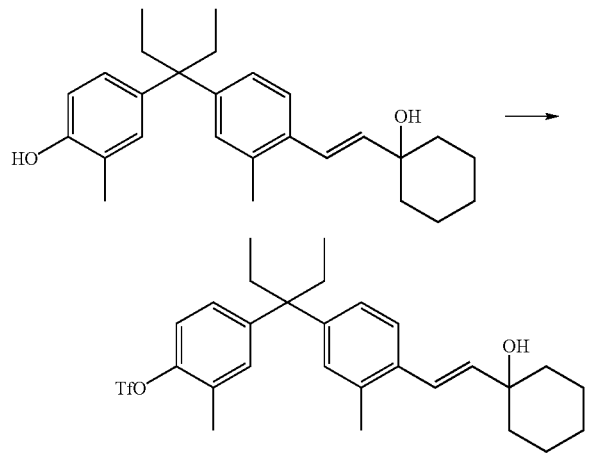

Pyridine (0.49 mL, 6.07 mmol) was added to a solution of 4-(1-ethyl-1-{4-[(E)-2-(1-hydroxy-cyclohexyl)-vinyl]-3-methyl-phenyl}-propyl)-2-methyl-phenol (Example 36-(1); 1.59 g, 4.05 mmol) in dichloromethane, and the mixture was cooled to −10° C. Trifluoromethanesulfonic anhydride (0.61 mL, 4.45 mmol) was added dropwise, and the mixture was stirred at the same temperature for 10 minutes. Water was added to the reaction mixture, followed by extraction with ethyl acetate. The extract was dried over anhydrous sodium sulfate and concentrated under reduced pressure. The residue was purified by silica gel chromatography (17% ethyl acetate/hexane) to give the title compound (1.55 g, 73%).

¹H-NMR (chloroform-d): 0.60 (t, 6H, J=7.3 Hz), 1.51-1.75 (m, 8H), 2.00-2.08 (m, 2H), 2.06 (q, 4H, J=7.3 Hz), 2.31 (s, 6H), 6.22 (d, 1H, J=16.1 Hz), 6.81 (d, 1H, J=16.1 Hz), 6.91 (s, 1H), 6.92 (s, 1H), 7.04 (d, 1H, J=8.6 Hz), 7.07-7.10 (m, 2H), 7.34 (d, 1H, J=8.6 Hz).

(3) Synthesis of (E)-1-[2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclohexanol

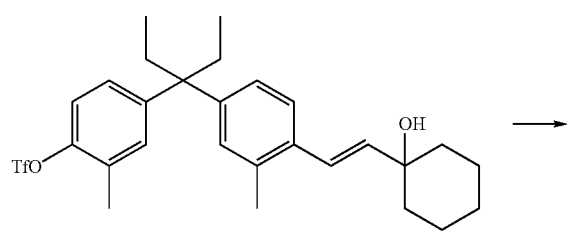

-continued

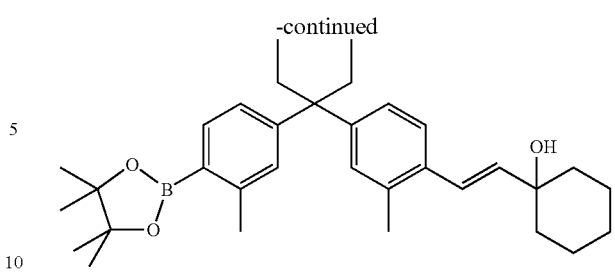

A solution of trifluoromethanesulfonic acid 4-(1-ethyl-1-{4-[(E)-2-(1-hydroxy-cyclohexyl)-vinyl]-3-methyl-phenyl}-propyl)-2-methyl-phenyl ester (Example 36-(2); 2.01 g, 3.84 mmol), diphenylphosphinoferrocene (118.6 mg, 0.214 mmol), a [1,1'-bis(diphenylphosphino)ferrocene]dichloropalladium (II), dichloromethane complex (1:1) (174.7 mg, 0.214 mmol), potassium acetate (1.04 g, 10.6 mmol) and bis(pinacolato)diboron (1.17 g, 4.63 mmol) in dioxane (23 mL) was stirred at 85° C. for five hours. Water was added to the reaction mixture, followed by extraction with diethyl ether. The extract was dried over anhydrous sodium sulfate and concentrated under reduced pressure. The residue was purified by silica gel chromatography (10% ethyl acetate/hexane) to give the title compound (1.36 g, 70%).

¹H-NMR (chloroform-d): 0.59 (t, 6H, J=7.3 Hz), 1.32 (s, 12H), 1.54-1.73 (m, 1H), 2.07 (q, 4H, J=7.3 Hz), 2.29 (s, 3H), 2.47 (s, 3H), 6.20 (d, 1H, J=16.1 Hz), 6.81 (d, 1H, J=16.1 Hz), 6.92-6.99 (m, 4H), 7.31 (d, 1H, J=8.0 Hz), 7.62 (d, 1H, J=7.7 Hz).

Example 37

Synthesis of 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclohexanol

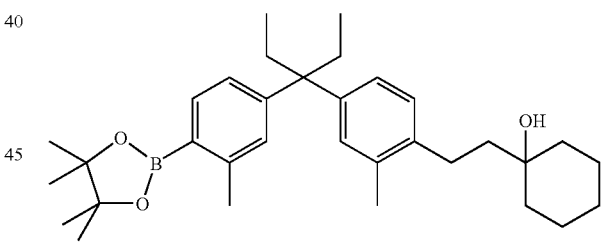

(1) Synthesis of 2-[4-(1-ethyl-1-{3-methyl-4-[2-(1-trimethylsilanyloxy-cyclohexyl)-ethyl]-phenyl}-propyl)-2-methyl-phenyl]-4,4,5,5-tetramethyl-[1,3,2]dioxaborolane

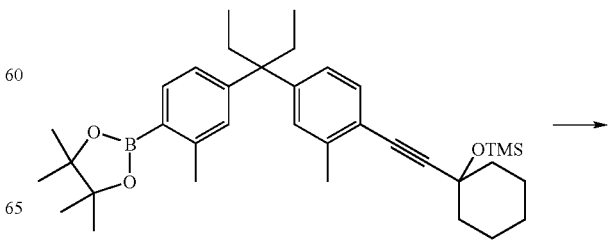

-continued

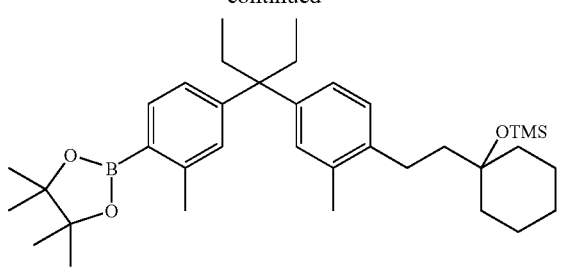

10% palladium carbon (11.3 mg) was added to a solution of 2-(4-{1-ethyl-1-[3-methyl-4-(1-trimethylsilanyloxy-cyclohexylethynyl)-phenyl]-propyl}-2-methyl-phenyl)-4,4,5,5-tetramethyl-[1,3,2]dioxaborolane (Example 35-(4); 49.7 mg, 0.0867 mmol) in ethyl acetate (0.5 mL), and the mixture was stirred under hydrogen charging for three hours. The reaction mixture was filtered and concentrated to give the title compound (43.3 mg, 86%).

$^1$H-NMR (chloroform-d): 0.15 (s, 9H), 0.60 (t, 6H, J=7.3 Hz), 1.24-1.38 (m, 2H), 1.32 (s, 10H), 1.39 (m, 4H), 1.55-1.73 (m, 8H), 2.06 (q, 4H, J=7.3 Hz), 2.23 (s, 3H), 2.48 (s, 3H), 2.54-2.61 (m, 2H), 6.88-6.99 (m, 5H), 7.62 (d, 1H, J=8.6 Hz).

(2) Synthesis of 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclohexanol

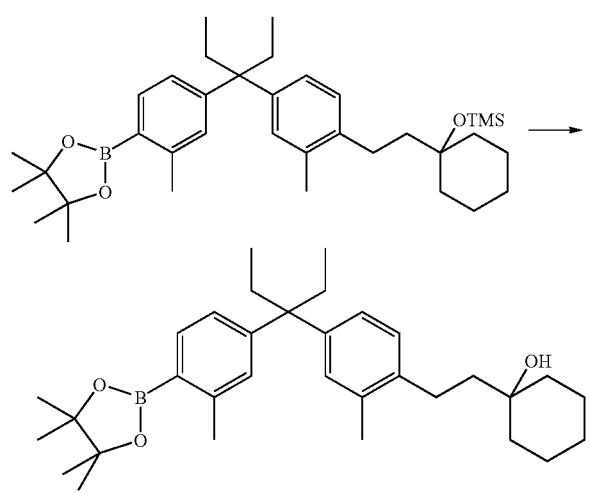

A 1 M solution of tetrabutylammonium fluoride in tetrahydrofuran (0.95 mL, 0.95 mmol) was added to 2-[4-(1-ethyl-1-{3-methyl-4-[2-(1-trimethylsilanyloxy-cyclohexyl)-ethyl]-phenyl}-propyl)-2-methyl-phenyl]-4,4,5,5-tetramethyl-[1,3,2]dioxaborolane (Example 37-(1); 0.23 g, 0.39 mmol), and the mixture was stirred for three hours. The reaction mixture was purified by silica gel chromatography (14% ethyl acetate/hexane) to give the title compound (0.15 g, 76%).

$^1$H-NMR (chloroform-d): 0.59 (t, 6H, J=6.8 Hz), 1.33 (s, 12H), 1.48-1.72 (m, 12H), 2.06 (q, 4H, J=7.6 Hz), 2.24 (s, 3H), 2.48 (s, 3H), 2.63 (t, 2H, J=8.2 Hz), 6.88-6.92 (m, 2H), 6.96-7.01 (m, 3H), 7.62 (d, 1H, J=8.4 Hz).

Example 38

Synthesis of (E)-1-(4-{1-[3,5-dimethyl-4-(4,4,5,5-tetramethyl-[1,3,2]dioxaborolan-2-yl)-phenyl]-1-ethyl-propyl}-2-methyl-phenyl)-3-ethyl-1-penten-3-ol

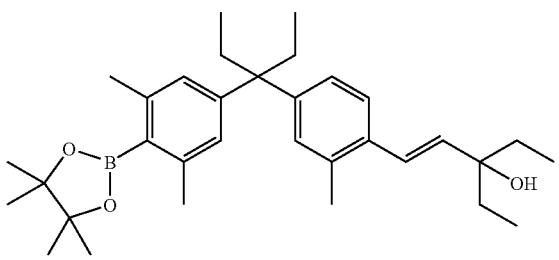

(1) Synthesis of 3-(4-bromo-3-methyl-phenyl)-pentan-3-ol

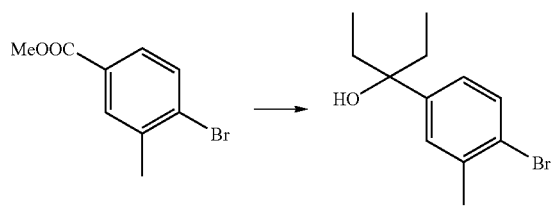

Ethylmagnesium bromide (3 M solution in diethyl ether, 73 mL, 218.3 mmol) was added to a solution of 4-bromo-3-methylbenzoic acid methyl ester (20 g, 87.31 mmol) in tetrahydrofuran (120 mL) in a nitrogen atmosphere at 0° C., and the mixture was stirred at 0° C. for one hour. The reaction mixture was then poured into a saturated aqueous ammonium chloride solution, followed by extraction with ethyl acetate. The organic layer was dried over anhydrous magnesium sulfate, filtered and concentrated under reduced pressure. The resulting residue was purified by silica gel chromatography (hexane:ethyl acetate=100:0 to 50:50) to give the target compound as a colorless oil (21.86 g, 97%).

$^1$H-NMR (chloroform-d): 0.75 (6H, t, J=7.25 Hz), 1.73-1.88 (4H, m), 2.40 (3H, s), 7.02 (1H, dd, J=8.41, 2.31 Hz), 7.25 (1H, d, J=2.30 Hz), 7.46 (1H, d, J=8.24 Hz).

(2) Synthesis of 4-[1-(4-bromo-3-methyl-phenyl)-1-ethyl-propyl]-2,6-dimethyl-phenol

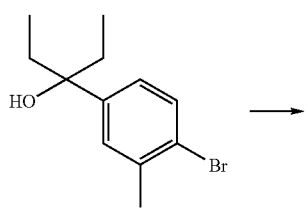

-continued

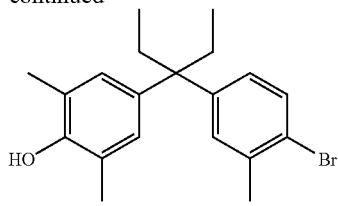

2,6-Dimethylphenol (950 mg, 7.78 mmol) was added to a solution of 3-(4-bromo-3-methyl-phenyl)-pentan-3-ol (Example 38-(1); 2.0 g, 7.78 mmol) in trifluoroacetic acid (20 mL), and the mixture was stirred at room temperature for two hours. Then, the reaction mixture was concentrated under reduced pressure. The resulting residue was purified by silica gel chromatography (hexane:ethyl acetate=100:0 to 50:50) to give the target compound as a colorless oil (2.62 g, 93%).

$^1$H-NMR (chloroform-d): 0.59 (6H, t, J=7.25 Hz), 2.01 (4H, q, J=7.26 Hz), 2.18 (6H, s), 2.34 (3H, s), 4.46 (1H, brs), 6.72 (2H, s), 6.84 (1H, dd, J=8.41, 1.98 Hz), 7.02 (1H, d, J=1.98 Hz), 7.36 (1H, d, J=8.41 Hz).

(3) Synthesis of 4-{1-ethyl-1-[4-(3-ethyl-3-hydroxy-1-pentynyl)-3-methyl-phenyl]-propyl}-2,6-dimethyl-phenol

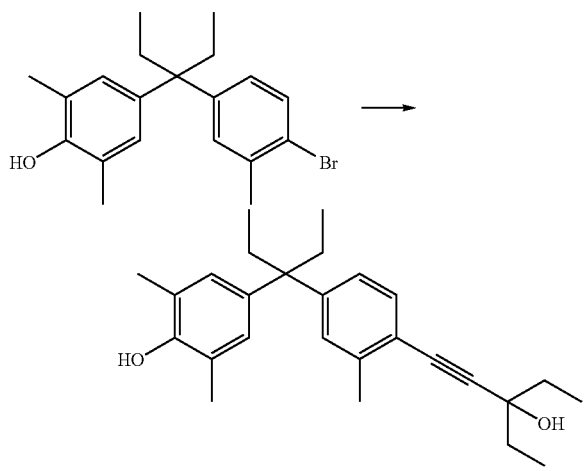

3-Ethyl-1-pentyn-3-ol (1.4 mL, 10.88 mmol), a [1,1'-bis(diphenylphosphino)ferrocene]dichloropalladium (II), dichloromethane complex (1:1) (592 mg, 0.725 mmol) and copper (I) iodide (138 mg, 0.725 mmol) were added to a solution of 4-[1-(4-bromo-3-methyl-phenyl)-1-ethyl-propyl]-2,6-dimethyl-phenol (Example 38-(2); 2.62 g, 7.25 mmol) in triethylamine (15 mL), and the mixture was stirred with microwave heating at 160° C. for three minutes. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50) to give the target compound as a colorless oil (2.77 g, 97%).

$^1$H-NMR (chloroform-d): 0.58 (6H, t, J=7.26 Hz), 1.11 (6H, q, J=7.25 Hz), 1.70-1.84 (4H, m), 2.02 (4H, q, J=7.26 Hz), 2.18 (6H, s), 2.38 (3H, s), 4.48 (1H, brs), 6.71 (2H, s), 6.93 (1H, d, J=8.24 Hz), 7.00 (1H, s), 7.27 (1H, d, J=7.91 Hz).

(4) Synthesis of 4-{1-ethyl-1-[(E)-4-(3-ethyl-3-hydroxy-1-pentenyl)-3-methyl-phenyl]-propyl}-2,6-dimethyl-phenol

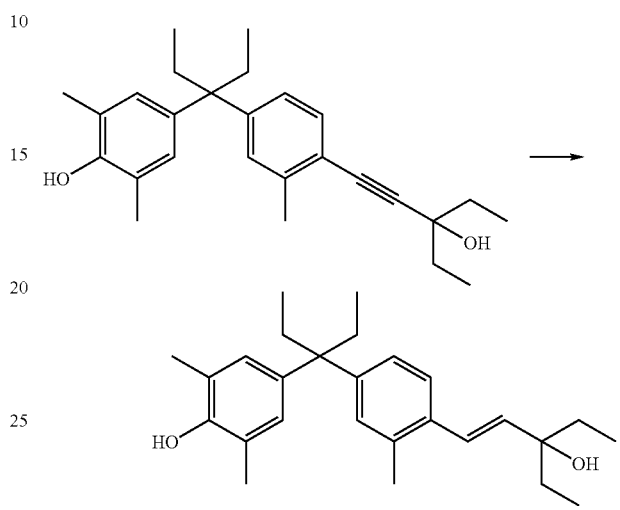

Sodium bis(2-methoxyethoxy)aluminum hydride (65 wt % solution in toluene, 4.2 mL, 13.98 mmol) was added to a solution of 4-{1-ethyl-1-[4-(3-ethyl-3-hydroxy-1-pentynyl)-3-methyl-phenyl]-propyl}-2,6-dimethyl-phenol (Example 38-(3); 1.83 g, 4.66 mmol) in tetrahydrofuran (20 mL) in a nitrogen atmosphere at 0° C., and the mixture was stirred at 0° C. for two hours. Then, ethyl acetate and brine were added to the reaction mixture, which was further diluted with ethyl acetate. Thereafter, celite was added and the mixture was stirred at room temperature for one hour. The reaction mixture was filtered through celite, and the filtrate was concentrated under reduced pressure. The resulting residue was purified by silica gel chromatography (hexane:ethyl acetate=100:0 to 30:70, 40 minutes) to give the target compound as a colorless oil (1.55 g, 84%).

$^1$H-NMR (chloroform-d): 0.60 (6H, t, J=7.25 Hz), 0.92 (6H, t, J=7.58 Hz), 1.64 (4H, q, J=7.58 Hz), 2.03 (4H, q, J=7.25 Hz), 2.19 (6H, s), 2.31 (3H, s), 4.49 (1H, brs), 6.01 (1H, d, J=16.16 Hz), 6.75 (1H, d, J=16.16 Hz), 6.76 (2H, s), 6.93-6.96 (2H, m), 7.29 (1H, d, J=8.74 Hz).

(5) Synthesis of Trifluoromethanesulfonic Acid 4-{1-ethyl-1-[(E)-4-(3-ethyl-3-hydroxy-1-pentenyl)-3-methyl-phenyl]-propyl}-2,6-dimethyl-phenyl Ester

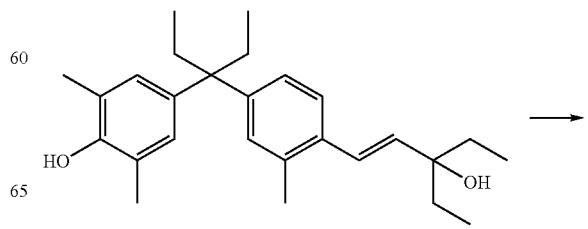

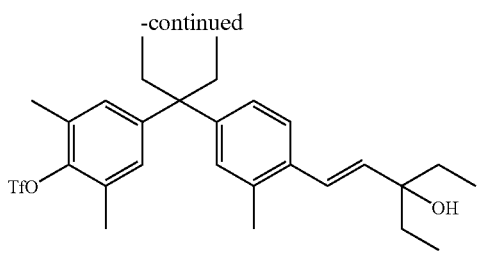

Diisopropylethylamine (2.2 mL, 12.92 mmol) and trifluoromethanesulfonic anhydride (1.3 mL, 7.75 mmol) were added to a solution of 4-{1-ethyl-1-[(E)-4-(3-ethyl-3-hydroxy-1-pentenyl)-3-methyl-phenyl]-propyl}-2,6-dimethyl-phenol (Example 38-(4); 2.55 g, 6.46 mmol) in dichloromethane (30 mL) at −40° C., and the mixture was stirred at −40° C. for 10 minutes. A saturated aqueous sodium bicarbonate solution was added to the reaction mixture, which was then heated to room temperature and extracted with dichloromethane. The organic layer was dried over anhydrous magnesium sulfate, filtered and concentrated under reduced pressure. The resulting residue was purified by silica gel chromatography (hexane:ethyl acetate=100:0 to 50:50, 40 minutes) to give the target compound as a colorless oil (2.92 g, 86%).

$^1$H-NMR (chloroform-d): 0.61 (6H, t, J=7.42 Hz), 0.92 (6H, t, J=7.41 Hz), 1.65 (4H, q, J=7.42 Hz), 2.05 (4H, q, J=7.42 Hz), 2.32 (9H, s), 6.02 (1H, d, J=15.99 Hz), 6.75 (1H, d, J=16.16 Hz), 6.90-6.92 (4H, m), 7.31 (1H, d, J=8.74 Hz).

(6) Synthesis of (E)-1-(4-{1-[3,5-dimethyl-4-(4,4,5,5-tetramethyl-[1,3,2]dioxaborolan-2-yl)-phenyl]-1-ethyl-propyl}-2-methyl-phenyl)-3-ethyl-1-penten-3-ol

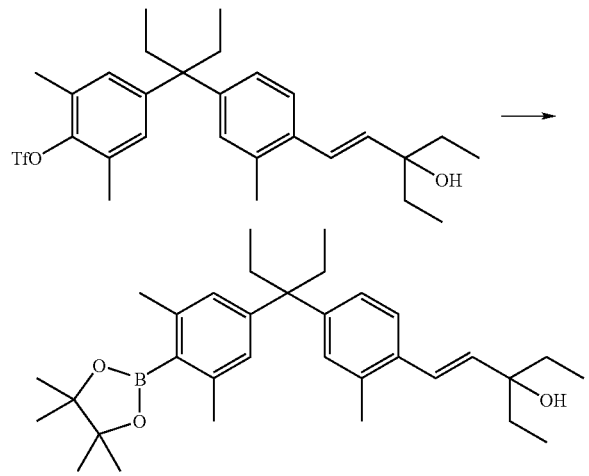

A [1,1'-bis(diphenylphosphino)ferrocene]dichloropalladium (II), dichloromethane complex (1:1) (261 mg, 0.32 mmol), 1,1'-bis(diphenylphosphino)ferrocene (177 mg, 0.32 mmol), potassium acetate (927 mg, 9.45 mmol) and bis(pinacolato)diboron (1.04 g, 4.10 mmol) were added to a solution of trifluoromethanesulfonic acid 4-{1-ethyl-1-[(E)-4-(3-ethyl-3-hydroxy-1-pentenyl)-3-methyl-phenyl]-propyl}-2,6-dimethyl-phenyl ester (Example 38-(5); 1.66 g, 3.15 mmol) in anhydrous dioxane (30 mL). After replacement with nitrogen, the mixture was stirred at 90° C. overnight. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 70:30, 40 minutes) to give the target compound as a colorless oil (0.87 g, 55%).

$^1$H-NMR (chloroform-d): 0.58 (6H, t, J=7.25 Hz), 0.92 (6H, t, J=7.42 Hz), 1.38 (12H, s), 1.64 (4H, q, J=7.42 Hz), 2.03 (4H, q, J=7.25 Hz), 2.28 (3H, s), 2.34 (6H, s), 6.01 (1H, d, J=16.00 Hz), 6.74 (1H, d, J=15.99 Hz), 6.75 (2H, s), 6.89-6.94 (2H, m), 7.26-7.28 (1H, m).

Example 39

Synthesis of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol

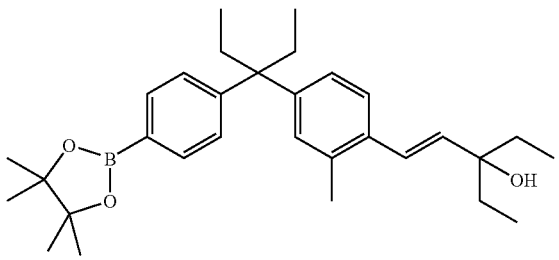

(1) Synthesis of 4-[1-(4-bromo-3-methyl-phenyl)-1-ethyl-propyl]-phenol

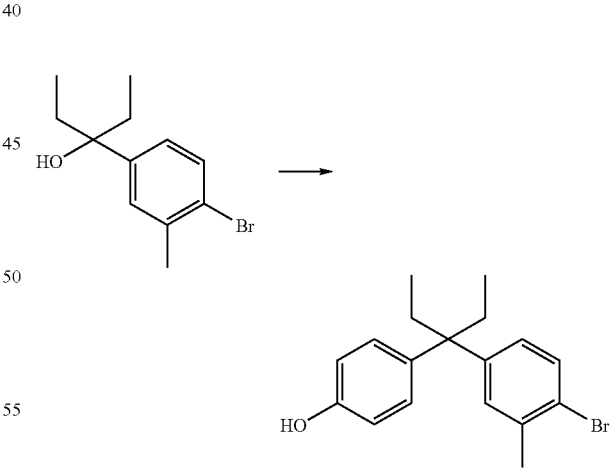

Phenol (732 mg, 7.78 mmol) was added to a solution of 3-(4-bromo-3-methyl-phenyl)-pentan-3-ol (Example 38-(1); 2.0 g, 7.78 mmol) in trifluoroacetic acid (20 mL), and the mixture was stirred at room temperature for five hours. Then, the reaction mixture was concentrated under reduced pressure. The resulting residue was purified by silica gel chromatography (hexane:ethyl acetate=100:0 to 30:70, 40 minutes) to give the target compound as a colorless oil (1.95 g, 75%).

¹H-NMR (chloroform-d): 0.60 (6H, t, J=7.25 Hz), 2.02 (4H, q, J=7.25 Hz), 2.33 (3H, s), 4.69 (1H, brs), 6.72 (2H, d, J=8.74 Hz), 6.83 (1H, d, J=8.57 Hz), 6.99-7.02 (3H, m), 7.37 (1H, d, J=8.41 Hz).

(2) Synthesis of 4-{1-ethyl-1-[4-(3-ethyl-3-hydroxy-1-pentynyl)-3-methyl-phenyl]-propyl}-phenol

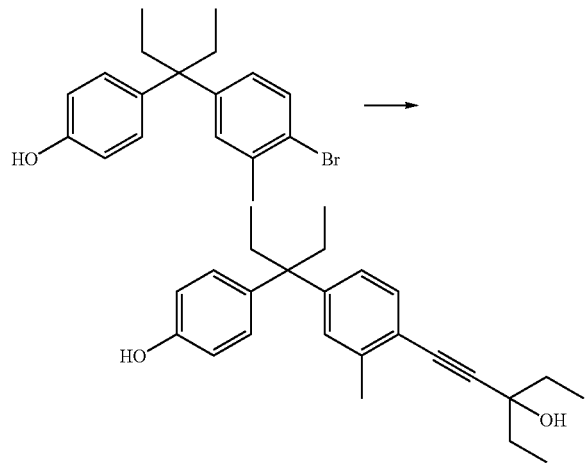

3-Ethyl-1-pentyn-3-ol (0.754 mL, 5.85 mmol), a [1,1'-bis (diphenylphosphino)ferrocene]dichloropalladium (II), dichloromethane complex (1:1) (482 mg, 0.59 mmol) and copper (I) iodide (112 mg, 0.59 mmol) were added to a solution of 4-[1-(4-bromo-3-methyl-phenyl)-1-ethyl-propyl]-phenol (Example 39-(1); 1.95 g, 5.85 mmol) in triethylamine (10 mL), and the mixture was stirred with microwave heating at 160° C. for three minutes. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 30:70, 40 minutes) to give the target compound as a colorless oil (0.79 g, 37%).

¹H-NMR (chloroform-d): 0.60 (6H, t, J=7.42 Hz), 1.11 (6H, t, J=7.42 Hz), 1.66-1.80 (4H, m), 2.03 (4H, m), 2.37 (3H, s), 4.70 (1H, brs), 6.71 (2H, d, J=8.74 Hz), 6.83 (1H, d, J=7.42 Hz), 6.97-7.01 (3H, m), 7.26-7.28 (1H, m).

(3) Synthesis of (E)-4-{1-ethyl-1-[(E)-4-(3-ethyl-3-hydroxy-1-pentenyl)-3-methyl-phenyl]-propyl}-phenol

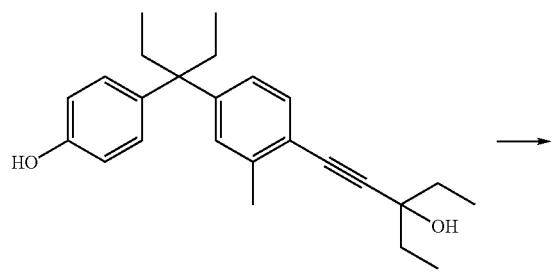

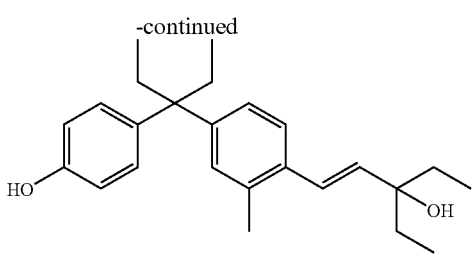

Sodium bis(2-methoxyethoxy)aluminum hydride (65 wt % solution in toluene, 2 mL, 6.50 mmol) was added to a solution of 4-{1-ethyl-1-[4-(3-ethyl-3-hydroxy-1-pentynyl)-3-methyl-phenyl]-propyl}-phenol (Example 39-(2); 0.79 g, 2.17 mmol) in tetrahydrofuran (10 mL) in a nitrogen atmosphere at 0° C., and the mixture was stirred at 0° C. for two hours. Then, ethyl acetate and brine were added to the reaction mixture, which was further diluted with ethyl acetate. Thereafter, celite was added and the mixture was stirred at room temperature for two hours. The reaction mixture was filtered through celite, and the filtrate was concentrated under reduced pressure. The resulting residue was purified by silica gel chromatography (hexane:ethyl acetate=100:0 to 50:50, 40 minutes) to give the target compound as a colorless oil (0.67 g, 84%).

¹H-NMR (chloroform-d): 0.61 (6H, t, J=7.26 Hz), 0.92 (6H, t, J=7.42 Hz), 1.64 (4H, q, J=7.58 Hz), 2.05 (4H, q, J=7.25 Hz), 2.30 (3H, s), 6.00 (1H, d, J=16.00 Hz), 6.70-6.77 (3H, m), 6.93-6.95 (2H, m), 7.02 (2H, d, J=8.57 Hz), 7.29 (1H, d, J=8.74 Hz).

(4) Synthesis of Trifluoromethanesulfonic Acid 4-{1-ethyl-1-[(E)-4-(3-ethyl-3-hydroxy-1-pentenyl)-3-methyl-phenyl]-propyl}-phenyl Ester

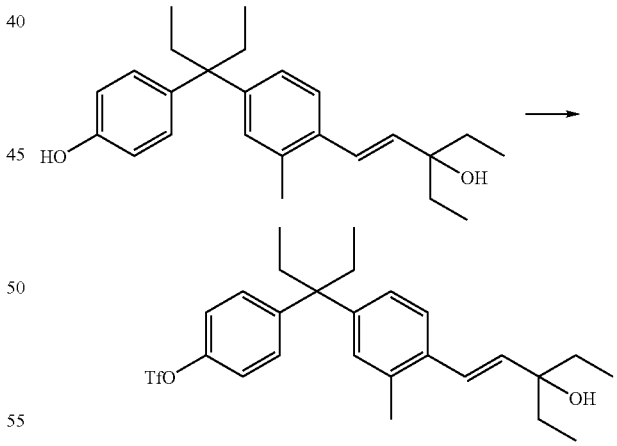

N,N-Diisopropylethylamine (0.83 mL, 2 mmol) and trifluoromethanesulfonic anhydride (0.26 mL, 1.6 mmol) were added to a solution of 4-{1-ethyl-1-[4-((E)-3-ethyl-3-hydroxy-1-pentenyl)-3-methyl-phenyl]-propyl}-phenol (Example 39-(3); 0.52 g, 1.4 mmol) in dichloromethane (7 mL) at −78° C., and the mixture was stirred at the same temperature for 10 minutes. A saturated aqueous sodium bicarbonate solution was added to the reaction mixture, followed by extraction with ethyl acetate. The organic layer was washed with brine, dried over anhydrous magnesium sulfate and concentrated under reduced pressure. The residue was purified by silica gel chromatography (hexane/ethyl acetate=3/1) to give the title compound (0.65 g, 92%).

¹H-NMR (chloroform-d): 0.62 (t, 6H, J=7.4 Hz), 0.92 (t, 6H, J=7.4 Hz), 1.64 (q, 4H, J=7.4 Hz), 2.08 (q, 4H, J=7.4 Hz), 2.31 (s, 3H), 6.01 (d, 1H, J=16.0 Hz), 6.74 (d, 1H, J=16.0 Hz), 6.85-6.92 (m, 2H), 7.13 (d, 2H, J=9.1 Hz), 7.22-7.26 (m, 2H), 7.31 (d, 1H, J=8.7 Hz).

(5) Synthesis of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol

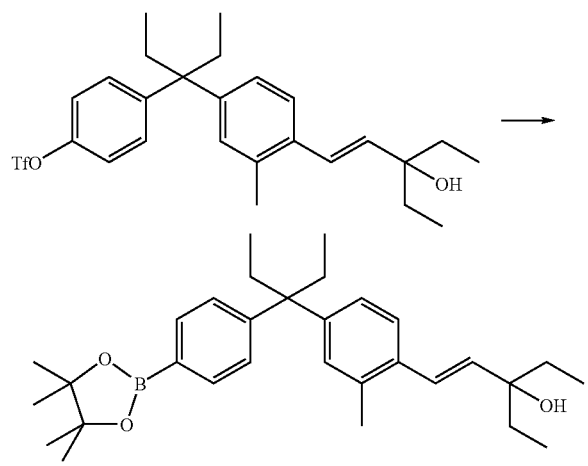

A solution of trifluoromethanesulfonic acid 4-{1-ethyl-1-[(E)-4-(3-ethyl-3-hydroxy-1-pentenyl)-3-methyl-phenyl]-propyl}-phenyl ester (Example 39-(4); 0.65 g, 1.30 mmol), diphenylphosphinoferrocene (43.3 mg, 0.078 mmol), a [1,1'-bis(diphenylphosphino)ferrocene]dichloropalladium (II), dichloromethane complex (1:1) (63.8 mg, 0.078 mmol), potassium acetate (0.38 g, 3.91 mmol) and bis(pinacolato)diboron (0.43 g, 1.69 mmol) in dioxane (8.7 mL) was stirred at 80° C. for four hours. Water was added to the reaction mixture, followed by extraction with diethyl ether. The extract was dried over anhydrous sodium sulfate and concentrated under reduced pressure. The residue was purified by silica gel chromatography (17% ethyl acetate/hexane) to give the title compound (0.40 g, 65%).

¹H-NMR (chloroform-d): 0.61 (t, 6H, J=7.3 Hz), 0.91 (t, 6H, J=7.5 Hz), 1.33 (s, 12H), 1.63 (q, 4H, J=7.5 Hz), 2.09 (q, 4H, J=7.3 Hz), 2.29 (s, 3H), 6.00 (d, 1H, J=15.7 Hz), 6.73 (d, 1H, J=15.7 Hz), 6.92-6.94 (m, 2H), 7.19 (d, 2H, J=8.1 Hz), 7.29 (d, 1H, J=8.8 Hz), 7.69 (d, 2H, J=8.1 Hz).

Example 40

Synthesis of (4-chloro-2-fluoro-phenyl)-acetic Acid Methyl Ester

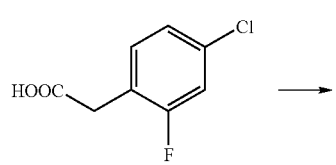

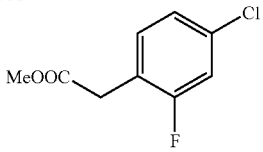

Thionyl chloride (0.94 mL, 0.0129 mol) was added dropwise to a solution of (4-chloro-2-fluoro-phenyl)acetic acid (2.03 g, 0.0108 mol) in methanol (100 mL) at 0° C., and the mixture was stirred at room temperature overnight. The solvent was distilled off under reduced pressure. The resulting residue was subjected to silica gel chromatography (n-hexane/ethyl acetate=1/0 to 3/1) to give the title compound (2.11 g, 96%).

¹H-NMR (chloroform-d): 3.65 (2H, s), 3.72 (3H, s), 7.09-7.12 (2H, m), 7.21 (1H, t, J=8.1 Hz); MS (ESI+): 203 ([M+H]⁺).

Example 41

Synthesis of (2,4-dichloro-phenyl)-acetic Acid Methyl Ester

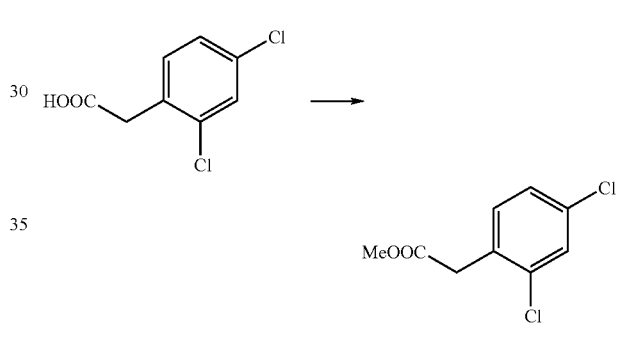

The title compound (2.33 g, 99%) was obtained from (2,4-dichloro-phenyl)acetic acid (2.20 g, 0.0107 mol) by the same method as in Example 40.

¹H-NMR (chloroform-d): 3.72 (3H, s), 3.75 (2H, s), 7.23 (2H, s), 7.41 (1H, s); MS (ESI+): 219 ([M+H]⁺).

Example 42

Synthesis of (2-bromo-thiazol-4-yl)-acetic Acid Ethyl Ester

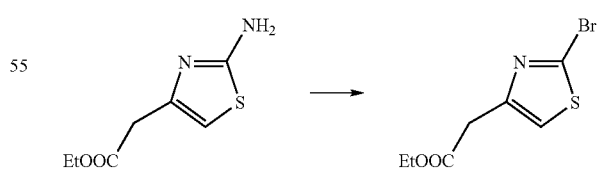

A solution of sodium nitrite (1.18 g, 0.0171 mol) in water (10 mL) was added dropwise to a mixture of (2-amino-thiazol-4-yl)acetic acid ethyl ester (2.60 g, 0.0140 mol), copper sulfate (6.84 g, 0.0429 mol), sodium bromide (5.89 g, 0.0573 mol) and 9 M hydrochloric acid aqueous solution (30 mL) at 0° C. over 10 minutes. After stirring at the same temperature for 20 minutes, the reaction solution was returned to room temperature over one hour and further stirred at room temperature for two hours. The reaction solution was diluted with water, filtered through celite and extracted with ethyl acetate. The organic layer was washed with brine, dried over anhydrous magnesium sulfate and concentrated under reduced pressure. The resulting residue was subjected to silica gel chromatography (n-hexane/ethyl acetate=1/0 to 9/1) to give the title compound (209.3 mg, 6%).

$^1$H-NMR (chloroform-d): 1.28 (3H, t, J=7.1 Hz), 3.81 (2H, d, J=0.7 Hz), 4.20 (2H, q, J=7.1 Hz), 7.18 (1H, t, J=0.8 Hz); MS (ESI+): 250 ([M+H]$^+$).

Example 43

Synthesis of (2-bromo-pyrimidin-5-yl)-acetic Acid Ethyl Ester

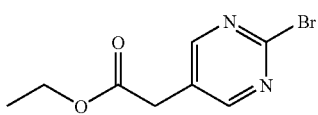

(1) Synthesis of (2,4-dichloro-pyrimidin-5-yl)-acetic Acid Ethyl Ester

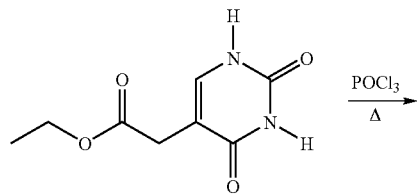

Phosphorus oxychloride (16 mL, 0.17 mmol) was added to (2,4-dioxo-1,2,3,4-tetrahydro-pyrimidin-5-yl)acetic acid ethyl ester (Biochemistry, 9, 3176-3142 (1970); 1.51 g, 7.64 mmol), and the mixture was heated while stirring at an external temperature of 114 to 121° C. The reaction mixture was concentrated under reduced pressure, and the residue was dissolved in carbon tetrachloride. Ice water (50 mL) was added, followed by extraction with carbon tetrachloride (3×80 mL). The extract was washed with a sodium bicarbonate aqueous solution. (Here, the aqueous layer was adjusted to pH 5 to 6.). The organic layer was dried over anhydrous magnesium sulfate and then concentrated under reduced pressure to give the title compound (1.57 g, 88%).

$^1$H-NMR (chloroform-d): 1.29 (t, 3H, J=7.2 Hz), 3.74 (s, 2H), 4.22 (q, 2H, J=7.2 Hz), 8.50 (s, 1H).

(2) Synthesis of (2-chloro-pyrimidin-5-yl)-acetic Acid Ethyl Ester

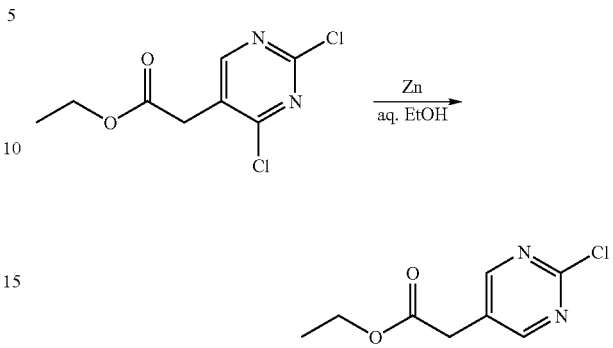

Zinc powder (3.55 g, 54.3 mmol) was added to a solution of (2,4-dichloro-pyrimidin-5-yl)acetic acid ethyl ester (Example 43-(1); 1.57 g, 6.70 mmol) in ethanol (10 mL)-water (8.5 mL), and the mixture was heated while stirring at an external temperature of 96 to 103° C. for 10 minutes. The reaction mixture was cooled to room temperature and then filtered, and the filtrate was concentrated under reduced pressure. Ethyl acetate and water were added to the residue, followed by extraction with ethyl acetate. The organic layer was dried over anhydrous magnesium sulfate and then concentrated under reduced pressure. The residue was purified by silica gel chromatography (hexane/ethyl acetate=2/1) to give the title compound (820 mg, 61%).

$^1$H-NMR (chloroform-d): 1.29 (t, 3H, J=7.2 Hz), 3.63 (s, 2H), 4.21 (q, 2H, J=7.2 Hz), 8.57 (s, 2H).

(3) Synthesis of (2-bromo-pyrimidin-5-yl)-acetic Acid Ethyl Ester

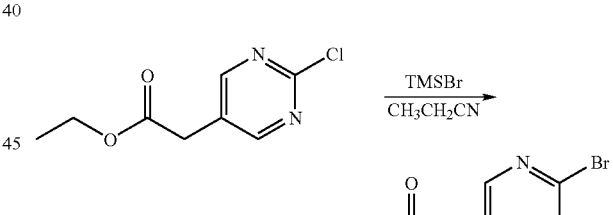

Bromotrimethylsilane (1.7 mL, 12 mmol) was added to a solution of (2-chloro-pyrimidin-5-yl)acetic acid ethyl ester (Example 43-(2); 810 mg, 4.04 mmol) in propionitrile (4 mL), and the mixture was heated under reflux at an external temperature of 98 to 105° C. for nine hours. After cooling the reaction mixture to room temperature, diethyl ether was added to the reaction mixture, which was neutralized with a 2 N sodium hydroxide aqueous solution (6.3 mL). The reaction mixture was extracted with diethyl ether. The organic layer was dried over anhydrous magnesium sulfate and then concentrated under reduced pressure. The residue was purified by silica gel chromatography (hexane/ethyl acetate=2/1) to give the title compound (897 mg, 91%).

$^1$H-NMR (chloroform-d): 1.29 (t, 3H, J=7.2 Hz), 3.60 (s, 2H), 4.21 (q, 2H, J=7.2 Hz), 8.51 (s, 2H); MS (ESI+): 245 ([M+H]$^+$).

Example 44

Synthesis of (5-bromo-2-pyridinyl)-acetic Acid Methyl Ester

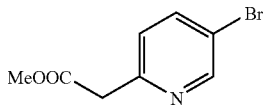

(1) Synthesis of 5-(5-bromo-1H-2-pyridinylidene)-2,2-dimethyl-[1,3]dioxane-4,6-dione

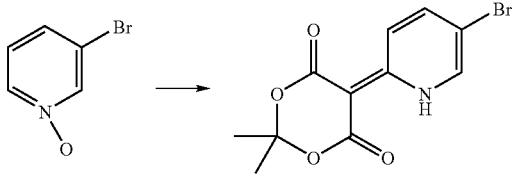

Meldrum's acid (6.63 g, 45.98 mmol) was added to a solution of 3-bromopyridine N-oxide (8 g, 45.98 mmol) in acetic anhydride (50 mL), and the mixture was stirred at room temperature overnight. Then, the reaction mixture was concentrated under reduced pressure. The resulting residue was purified by silica gel chromatography (hexane:ethyl acetate and ethyl acetate) to give the target compound (4.53 g, 33%).

$^1$H-NMR (DMSO-d6): 1.62 (6H, s), 8.23 (1H, dd, J=9.73, 2.31 Hz), 8.53 (1H, d, J=2.30 Hz), 8.64 (1H, d, J=9.56 Hz), 14.91 (1H, brs).

(2) Synthesis of (5-bromo-2-pyridinyl)-acetic Acid Methyl Ester

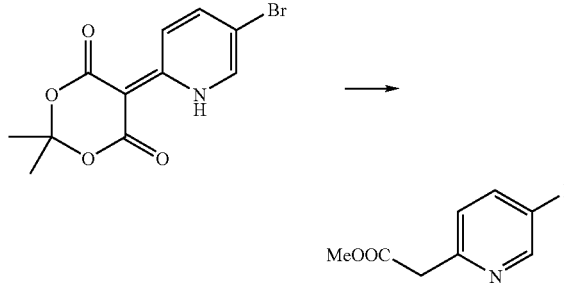

Concentrated hydrochloric acid (10 mL) was added to a solution of 5-(5-bromo-1H-2-pyridinylidene)-2,2-dimethyl-[1,3]dioxane-4,6-dione (Example 44-(1); 4.53 g, 15.09 mmol) in dioxane (20 mL), and the mixture was stirred at 100° C. for one hour. After cooling, the reaction mixture was concentrated. The residue was dissolved in methanol (20 mL) and toluene (20 mL). Trimethylsilyldiazomethane (2 M solution in diethyl ether, 25 mL) was added, and the mixture was stirred at room temperature for 30 minutes. Acetic acid was added to the reaction mixture to terminate the reaction. Then, the mixture was concentrated under reduced pressure. The resulting residue was purified by silica gel chromatography (hexane:ethyl acetate=100:0 to 30:70, 40 minutes) to give the target compound as a colorless oil (2.50 g, 72%).

$^1$H-NMR (chloroform-d): 3.73 (3H, s), 3.82 (2H, s), 7.21 (1H, d, J=8.24 Hz), 7.79 (1H, dd, J=8.25, 2.31 Hz), 8.62 (1H, d, J=2.31 Hz).

Example 45

Synthesis of (4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)-acetic Acid

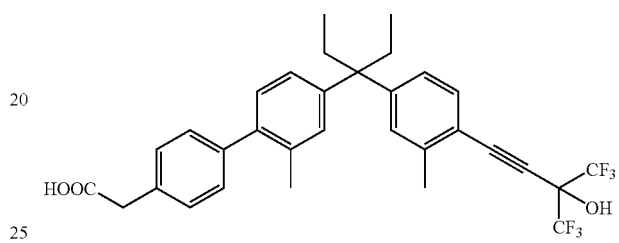

(1) Synthesis of (4'-{1-ethyl-1-[3-methyl-4-(4,4,4-trifluoro-3-methoxymethoxy-3-trifluoromethyl-1-butynyl)-phenyl]-propyl}-2'-methyl-biphenyl-4-yl)-acetic Acid Methyl Ester

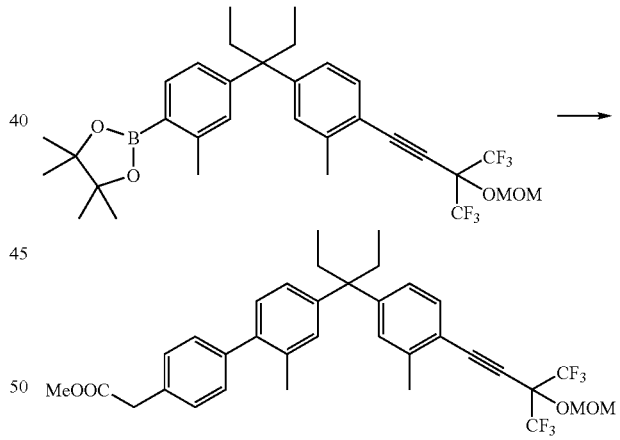

(4-Bromo-phenyl)acetic acid methyl ester (Tetrahedron Letters 44 (2003) 331-334; 28 mg, 0.122 mmol), palladium acetate (1.8 mg, 0.008 mmol), 2-dicyclohexylphosphino-2',6'-dimethoxy-1,1'-biphenyl (6.6 mg, 0.016 mmol), potassium phosphate (52 mg, 0.246 mmol) and water (0.1 mL) were added to a solution of 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane (Example 25-(4); 50 mg, 0.082 mmol) in toluene (1 mL). After replacement with nitrogen, the mixture was stirred at 100° C. for one hour. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (44.9 mg, 86%).

$^1$H-NMR (chloroform-d): 0.64 (6H, t, J=7.25 Hz), 2.11 (4H, q, J=7.09 Hz), 2.22 (3H, s), 2.42 (3H, s), 3.48 (3H, s), 3.67 (2H, s), 3.72 (3H, s), 5.16 (2H, s), 6.98-7.11 (5H, m), 7.26-7.30 (3H, m), 7.40 (2H, d, J=7.92 Hz).

(2) Synthesis of (4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)-acetic Acid Methyl Ester

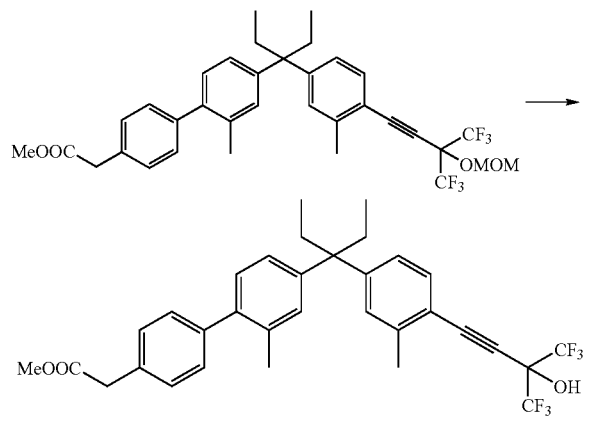

Trifluoroacetic acid (0.2 mL) was added to a solution of (4'-{1-ethyl-1-[3-methyl-4-(4,4,4-trifluoro-3-methoxymethoxy-3-trifluoromethyl-1-butynyl)-phenyl]-propyl}-2'-methyl-biphenyl-4-yl)acetic acid methyl ester (Example 45-(1); 44.9 mg, 0.071 mmol) in dichloromethane (2 mL), and the mixture was stirred at room temperature for one hour. The reaction mixture was concentrated under reduced pressure. The resulting residue was purified by silica gel chromatography (hexane:ethyl acetate=4:1) to give the target compound as a colorless oil (20 mg, 48%).

$^1$H-NMR (chloroform-d): 0.64 (6H, t, J=7.42 Hz), 2.11 (4H, q, J=7.42 Hz), 2.22 (3H, s), 2.41 (3H, s), 3.41 (1H, s), 3.67 (2H, s), 3.72 (3H, s), 6.95-7.12 (5H, m), 7.26-7.34 (3H, m), 7.38 (2H, d, J=8.08 Hz).

(3) Synthesis of (4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)-acetic Acid

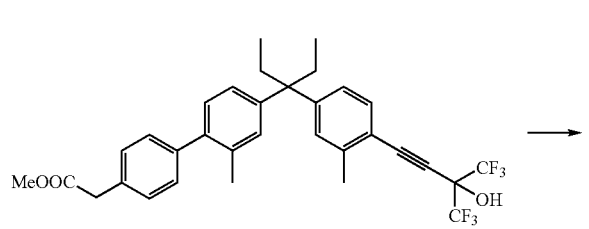

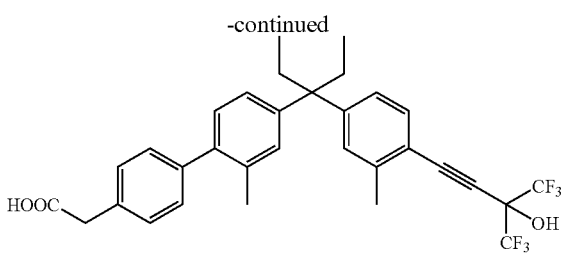

A 1 N sodium hydroxide aqueous solution (0.102 mL, 0.102 mmol) was added to a solution of (4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)acetic acid methyl ester (Example 45-(2); 20 mg, 0.034 mmol) in methanol-tetrahydrofuran (1:1, 2 mL), and the mixture was stirred at 60° C. for one hour. The reaction mixture was poured into 1 N hydrochloric acid aqueous solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (15 mg, 77%).

$^1$H-NMR (chloroform-d): 0.64 (6H, t, J=7.26 Hz), 2.11 (4H, q, J=7.25 Hz), 2.21 (3H, s), 2.41 (3H, s), 3.70 (2H, s), 6.95-7.11 (5H, m), 7.26-7.39 (5H, m); MS (ESI+): 594 ([M+NH$_4$]$^+$).

Example 46

Synthesis of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)-acetic Acid

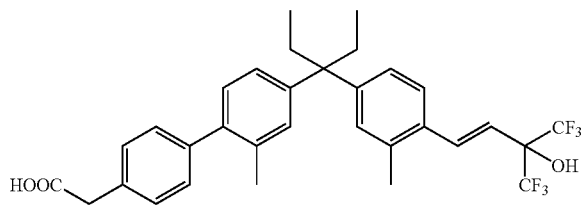

(1) Synthesis of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)-acetic Acid Methyl Ester

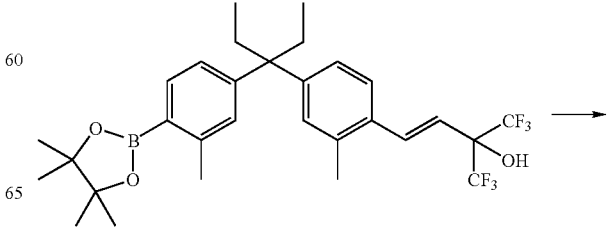

-continued

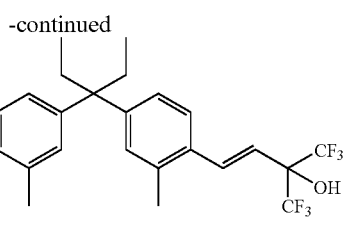

Palladium acetate (3.6 mg, 0.016 mmol), 2-dicyclohexylphosphino-2',6'-dimethoxy-1,1'-biphenyl (13.1 mg, 0.032 mmol), potassium phosphate (51 mg, 0.24 mmol) and water (0.04 mL) were added to a solution of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 40 mg, 0.070 mmol) and (4-bromo-phenyl)acetic acid methyl ester (Tetrahedron Letters 44 (2003) 331-334; 28 mg, 0.122 mmol) in toluene (0.4 mL). After replacement with nitrogen, the mixture was stirred at 100° C. for 30 minutes. Then, the reaction mixture was concentrated under reduced pressure, and the residue was dissolved in dichloromethane. Thereafter, the solution was filtered through amino silica gel, and the filtrate was concentrated under reduced pressure. The resulting residue was purified by silica gel chromatography (hexane:ethyl acetate=2:1) to give the target compound as a colorless oil (14.1 mg, 34%).

$^1$H-NMR (chloroform-d): 0.66 (6H, t, J=7.25 Hz), 2.12 (4H, q, J=7.25 Hz), 2.23 (3H, s), 2.37 (3H, s), 3.10 (1H, brs), 3.67 (2H, s), 3.72 (3H, s), 6.09 (1H, d, J=16.00 Hz), 6.98-7.10 (5H, m), 7.26-7.41 (6H, m).

(2) Synthesis of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)-acetic Acid

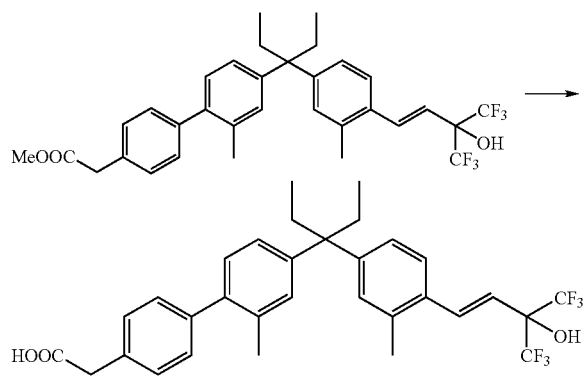

A 1 N sodium hydroxide aqueous solution (0.071 mL, 0.071 mmol) was added to a solution of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid methyl ester (Example 46-(1); 14.1 mg, 0.024 mmol) in methanol-tetrahydrofuran (1:1, 1 mL), and the mixture was stirred at 60° C. for one hour. Then, the reaction mixture was concentrated under reduced pressure. The resulting residue was purified by silica gel chromatography (chloroform:methanol=10:3, saturated with water) to give the target compound as a colorless oil (8.4 mg, 61%).

$^1$H-NMR (chloroform-d): 0.66 (6H, t, J=7.26 Hz), 2.12 (4H, q, J=7.03 Hz), 2.22 (3H, s), 2.37 (3H, s), 3.70 (2H, s), 6.09 (1H, d, J=16.15 Hz), 6.98-7.12 (5H, m), 7.26-7.41 (6H, m); MS (ESI+): 596 ([M+NH$_4$]$^+$).

Example 47

Synthesis of (4'-{1-ethyl-1-[3-methyl-4-(4,4,4-trifluoro-3-hydroxy-3-trifluoromethyl-butyl)-phenyl]-propyl}-2'-methyl-biphenyl-4-yl)-acetic Acid

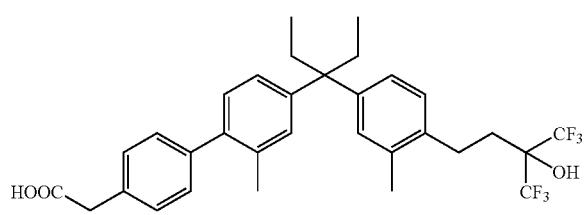

(1) Synthesis of (4'-{1-ethyl-1-[3-methyl-4-(4,4,4-trifluoro-3-hydroxy-3-trifluoromethyl-butyl)-phenyl]-propyl}-2'-methyl-biphenyl-4-yl)-acetic Acid Methyl Ester

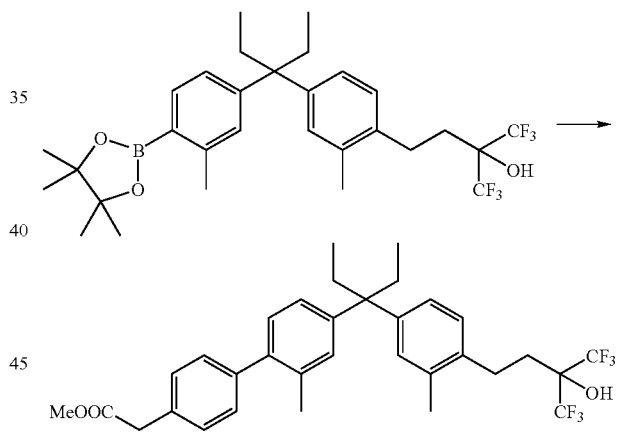

(4-Bromo-phenyl)acetic acid methyl ester (Tetrahedron Letters 44 (2003) 331-334; 25 mg, 0.109 mmol), palladium acetate (1.6 mg, 0.007 mmol), 2-dicyclohexylphosphino-2',6'-dimethoxy-1,1'-biphenyl (5.7 mg, 0.014 mmol), potassium phosphate (46 mg, 0.216 mmol) and water (0.2 mL) were added to a solution of 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-butan-2-ol (Example 27-(2); 41.5 mg, 0.072 mmol) in toluene (2 mL). After replacement with nitrogen, the mixture was stirred at 100° C. for one hour. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (25.9 mg, 61%).

¹H-NMR (chloroform-d): 0.64 (6H, t, J=7.26 Hz), 2.05-2.20 (6H, m), 2.23 (3H, m), 2.28 (3H, m), 2.78-2.84 (2H, m), 3.05 (1H, brs), 3.67 (2H, s), 3.72 (3H, s), 6.97-7.09 (6H, m), 7.29 (4H, s).

(2) Synthesis of (4'-{1-ethyl-1-[3-methyl-4-(4,4,4-trifluoro-3-hydroxy-3-trifluoromethyl-butyl)-phenyl]-propyl}-2'-methyl-biphenyl-4-yl)-acetic Acid

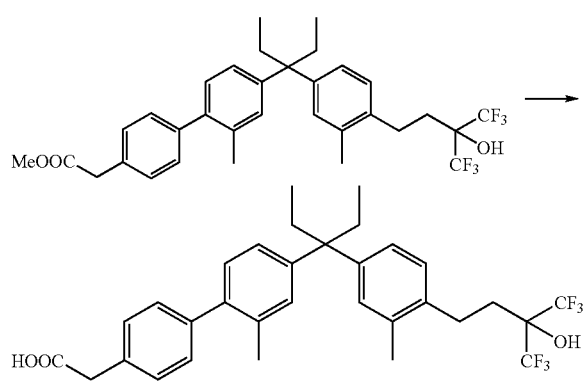

A 1 N sodium hydroxide aqueous solution (0.131 mL, 0.131 mmol) was added to a solution of (4'-{1-ethyl-1-[3-methyl-4-(4,4,4-trifluoro-3-hydroxy-3-trifluoromethyl-butyl)-phenyl]-propyl}-2'-methyl-biphenyl-4-yl)acetic acid methyl ester (Example 47-(1); 25.9 mg, 0.044 mmol) in methanol-tetrahydrofuran (1:1, 3 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (19.7 mg, 77%).

¹H-NMR (chloroform-d): 0.64 (6H, t, J=7.26 Hz), 2.06-2.23 (6H, m), 2.25 (3H, s), 2.28 (3H, s), 2.78-2.84 (2H, m), 3.70 (2H, s), 6.9-7.10 (6H, m), 7.31 (4H, s); MS (ESI+): 598 ([M+NH₄]⁺).

Example 48

Synthesis of Sodium (4'-{1-ethyl-1-[4-((E)-3-ethyl-3-hydroxy-1-pentenyl)-3-methyl-phenyl]-propyl}-3-fluoro-2'-methyl-biphenyl-4-yl)-acetate

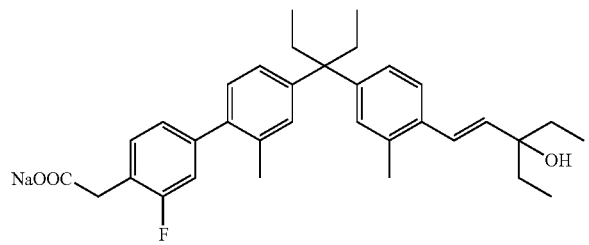

(1) Synthesis of Methyl (4'-{1-ethyl-1-[4-((E)-3-ethyl-3-hydroxy-1-pentenyl)-3-methyl-phenyl]-propyl}-3-fluoro-2'-methyl-biphenyl-4-yl)-acetate

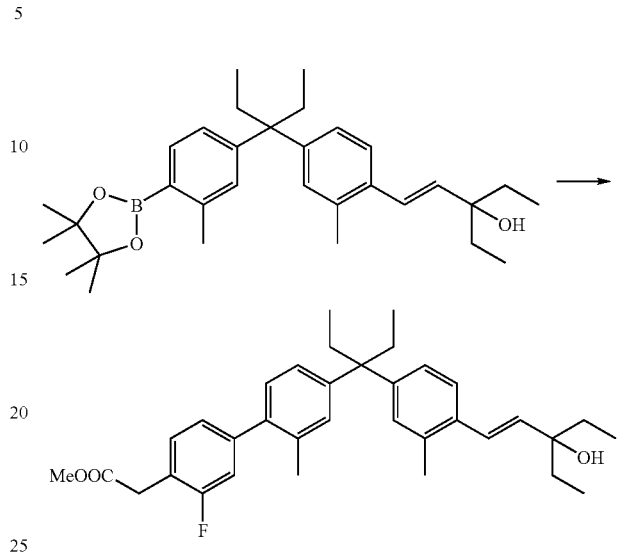

(4-Chloro-2-fluoro-phenyl)acetic acid methyl ester (Example 40; 52 mg, 0.256 mmol), toluene (2.8 mL), palladium acetate (3.8 mg, 0.017 mmol), 2-dicyclohexylphosphino-2',6'-dimethoxy-1,1'-biphenyl (14 mg, 0.034 mmol), potassium phosphate (108 mg, 0.510 mmol) and water (0.28 mL) were added to (E)-3-ethyl-1-(4-{1-ethyl-1-[3-methyl-4-(4,4,5,5-tetramethyl-[1,3,2]dioxaborolan-2-yl)-phenyl]-propyl-2-methyl-phenyl)-1-penten-3-ol (Example 28; 83.6 mg, 0.170 mmol), and the mixture was stirred in a nitrogen atmosphere at 100° C. for one hour. The reaction solution was poured into a saturated aqueous sodium bicarbonate solution, and then the aqueous layer was extracted with dichloromethane. The organic layer was dried over anhydrous sodium sulfate and concentrated under reduced pressure. The residue was purified by silica gel chromatography (17% ethyl acetate/hexane) to give the title compound (42 mg, 47%).

¹H-NMR (chloroform-d): 0.65 (t, 6H, J=7.3 Hz), 0.92 (t, 6H, J=7.6 Hz), 1.58 (s, 1H), 1.64 (q, 4H, J=7.2 Hz), 2.10 (q, 4H, J=7.2 Hz), 2.23 (s, 3H), 2.33 (s, 3H), 3.70 (s, 2H), 3.73 (s, 3H), 6.01 (d, 1H, J=15.9 Hz), 6.75 (d, 1H, J=16.2 Hz), 6.96-7.08 (m, 7H), 7.23-7.32 (m, 2H); MS (ESI+): 513 ([M+H—H₂O]+).

(2) Synthesis of Sodium (4'-{1-ethyl-1-[4-((E)-3-ethyl-3-hydroxy-1-pentenyl)-3-methyl-phenyl]-propyl}-3-fluoro-2'-methyl-biphenyl-4-yl)-acetate

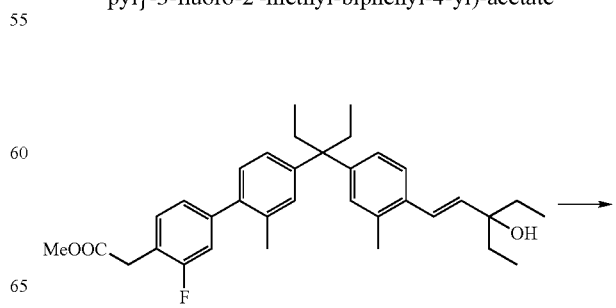

-continued

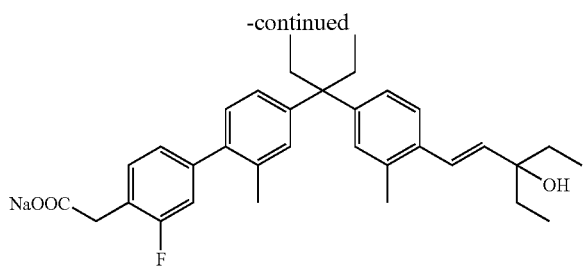

Methanol (1.3 mL), tetrahydrofuran (1.3 mL) and a 1 M sodium hydroxide aqueous solution (0.133 mL, 0.133 mmol) were added to methyl (4'-{1-ethyl-1-[4-((E)-3-ethyl-3-hydroxy-1-pentenyl)-3-methyl-phenyl]-propyl}-3-fluoro-2'-methyl-biphenyl-4-yl)acetate (23.5 mg, 0.044 mmol), and the mixture was stirred at room temperature for 18 hours. The reaction solution was poured into a saturated aqueous ammonium chloride solution, and then the aqueous layer was extracted with dichloromethane. The organic layer was dried over anhydrous sodium sulfate and concentrated under reduced pressure. The residue was purified by preparative TLC (chloroform/methanol=10/1). The purified product was diluted with methanol. After addition of sodium methoxide, the mixture was dried under reduced pressure to give the title compound (17.7 mg, 78%).

$^1$H-NMR (methanol-d4): 0.65 (t, 6H, J=7.3 Hz), 0.92 (t, 6H, J=7.4 Hz), 1.63 (q, 4H, J=7.4 Hz), 2.14 (q, 4H, J=7.3 Hz), 2.20 (s, 3H), 2.30 (s, 3H), 3.54 (s, 2H), 6.00 (d, 1H, J=15.9 Hz), 6.76 (d, 1H, J=16.1 Hz), 6.95-7.09 (m, 7H), 7.29-7.35 (m, 2H); MS (ESI+): 499 ([M-Na—H$_2$O+H]+).

Example 49

Synthesis of (4'-{1-ethyl-1-[4-(3-ethyl-3-hydroxy-pentyl)-3-methyl-phenyl]-propyl}-2'-methyl-biphenyl-4-yl)-acetic Acid

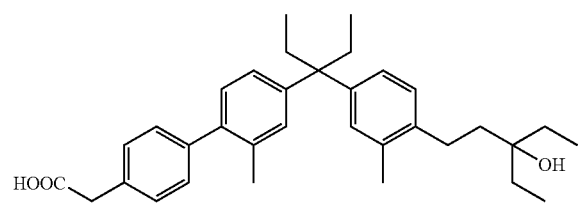

(1) Synthesis of (4'-{1-ethyl-1-[4-(3-ethyl-3-hydroxy-pentyl)-3-methyl-phenyl]-propyl}-2'-methyl-biphenyl-4-yl)-acetic Acid Methyl Ester

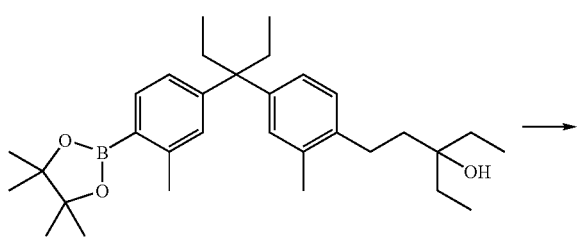

-continued

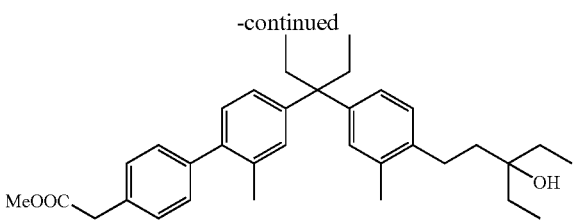

(4-Bromo-phenyl)acetic acid methyl ester (Tetrahedron Letters 44 (2003) 331-334; 38.5 mg, 0.168 mmol), palladium acetate (2.5 mg, 0.011 mmol), 2-dicyclohexylphosphino-2',6'-dimethoxy-1,1'-biphenyl (9.0 mg, 0.022 mmol), potassium phosphate (71 mg, 0.336 mmol) and water (0.2 mL) were added to a solution of 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-pentan-3-ol (Example 29; 55 mg, 0.112 mmol) in toluene (2 mL). After replacement with nitrogen, the mixture was stirred at 100° C. for 3.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (30.1 mg, 52%).

$^1$H-NMR (chloroform-d): 0.64 (6H, t, J=7.26 Hz), 0.91 (6H, t, J=7.42 Hz), 1.56 (4H, q, J=7.42 Hz), 1.64-1.70 (2H, m), 2.10 (4H, q, J=7.25 Hz), 2.23 (3H, s), 2.28 (3H, s), 2.55-2.61 (2H, m), 3.67 (2H, s), 3.72 (3H, s), 6.95-7.09 (6H, m), 7.29 (4H, s).

(2) Synthesis of (4'-{1-ethyl-1-[4-(3-ethyl-3-hydroxy-pentyl)-3-methyl-phenyl]-propyl}-2'-methyl-biphenyl-4-yl)-acetic Acid

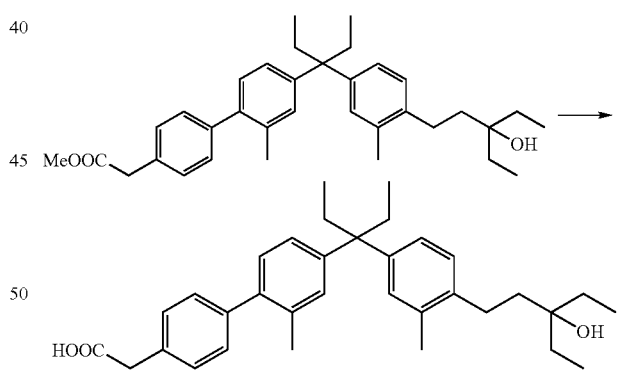

A 1 N sodium hydroxide aqueous solution (0.175 mL, 0.175 mmol) was added to a solution of (4'-{1-ethyl-1-[4-(3-ethyl-3-hydroxy-pentyl)-3-methyl-phenyl]-propyl}-2'-methyl-biphenyl-4-yl)acetic acid methyl ester (Example 49-(1); 30.1 mg, 0.058 mmol) in methanol-tetrahydrofuran (1:1, 3 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (25.2 mg, 87%).

¹H-NMR (chloroform-d): 0.64 (6H, t, J=7.26 Hz), 0.91 (6H, t, J=7.42 Hz), 1.56 (4H, q, J=7.42 Hz), 1.64-1.70 (2H, m), 2.10 (4H, q, J=7.26 Hz), 2.23 (3H, s), 2.28 (3H, s), 2.55-2.61 (2H, m), 3.70 (2H, s), 6.95-7.09 (6H, m), 7.30 (4H, s); MS (ESI+): 518 ([M+NH₄]⁺).

Example 50

Synthesis of (4'-{1-[4-(3,3-dimethyl-2-oxo-butoxy)-3-methyl-phenyl]-1-ethyl-propyl}-2'-methyl-biphenyl-4-yl)-acetic Acid

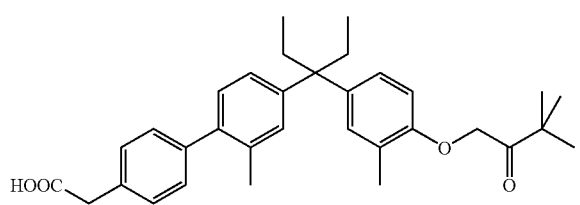

(1) Synthesis of (4'-{1-[4-(3,3-dimethyl-2-oxo-butoxy)-3-methyl-phenyl]-1-ethyl-propyl}-2'-methyl-biphenyl-4-yl)-acetic Acid Methyl Ester

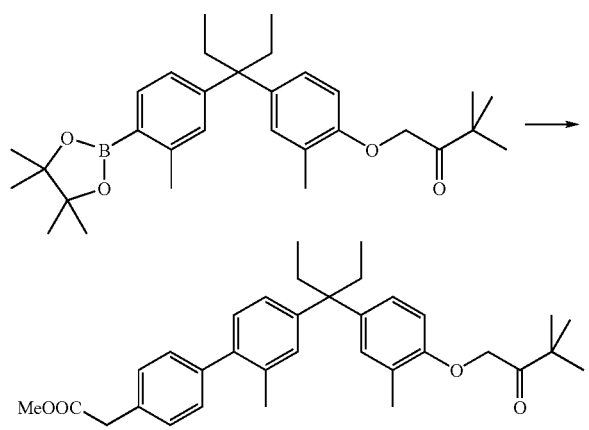

(4-Bromo-phenyl)acetic acid methyl ester (Tetrahedron Letters 44 (2003) 331-334; 35 mg, 0.153 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (62 mg, 0.306 mmol) and water (0.2 mL) were added to a solution of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-one (Example 30-(2); 50 mg, 0.102 mmol) in toluene (2 mL). After replacement with nitrogen, the mixture was stirred at 100° C. for 2.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (50.7 mg, 97%).

¹H-NMR (chloroform-d): 0.63 (6H, t, J=7.26 Hz), 1.25 (9H, s), 2.08 (4H, q, J=7.25 Hz), 2.22 (3H, s), 2.26 (3H, s), 3.67 (2H, s), 3.72 (3H, s), 4.84 (2H, s), 6.52 (1H, d, J=8.41 Hz), 6.93-7.09 (5H, m), 7.29 (4H, s).

(2) Synthesis of (4'-{1-[4-(3,3-dimethyl-2-oxo-butoxy)-3-methyl-phenyl]-1-ethyl-propyl}-2'-methyl-biphenyl-4-yl)-acetic Acid

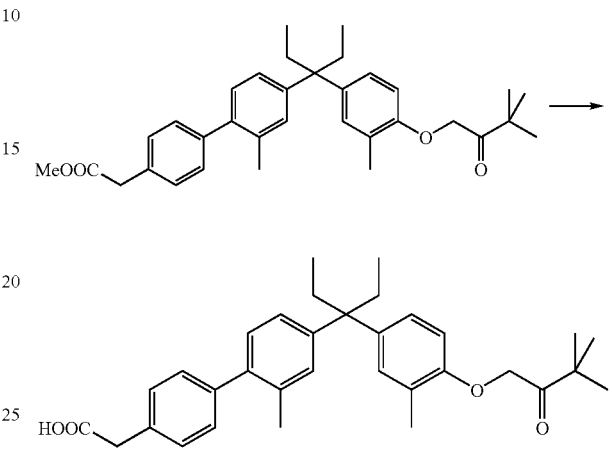

A 1 N sodium hydroxide aqueous solution (0.296 mL, 0.296 mmol) was added to a solution of (4'-{1-[4-(3,3-dimethyl-2-oxo-butoxy)-3-methyl-phenyl]-1-ethyl-propyl}-2'-methyl-biphenyl-4-yl)acetic acid methyl ester (Example 50-(1); 50.7 mg, 0.099 mmol) in methanol-tetrahydrofuran (1:1, 4 mL), and the mixture was stirred at 60° C. for two hours. The reaction mixture was then poured into 0.5 N hydrochloric acid aqueous solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (43.3 mg, 87%).

¹H-NMR (chloroform-d): 0.63 (6H, t, J=7.26 Hz), 1.25 (9H, s), 2.08 (4H, q, J=7.42 Hz), 2.22 (3H, s), 2.26 (3H, s), 3.70 (2H, s), 4.84 (2H, s), 6.52 (1H, d, J=8.41 Hz), 6.93-7.09 (5H, m), 7.30 (4H, s); MS (ESI+): 518 ([M+NH₄]⁺).

Example 51

Synthesis of (4'-{1-ethyl-1-[4-(2-hydroxy-3,3-dimethyl-butoxy)-3-methyl-phenyl]-propyl}-2'-methyl-biphenyl-4-yl)-acetic Acid

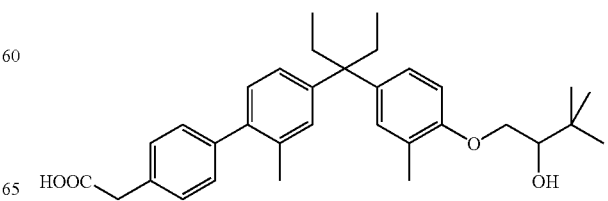

(1) Synthesis of (4'-{1-ethyl-1-[4-(2-hydroxy-3,3-dimethyl-butoxy)-3-methyl-phenyl]-propyl}-2'-methyl-biphenyl-4-yl)-acetic Acid Methyl Ester

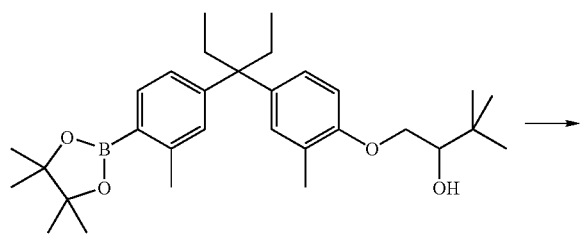

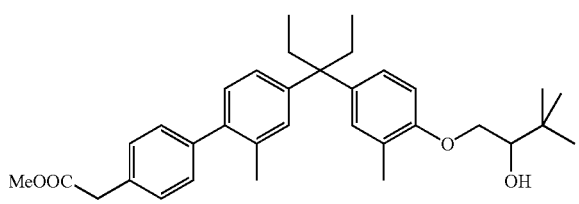

(4-Bromo-phenyl)acetic acid methyl ester (Tetrahedron Letters 44 (2003) 331-334; 35 mg, 0.152 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (64 mg, 0.303 mmol) and water (0.2 mL) were added to a solution of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-ol (Example 31; 50 mg, 0.101 mmol) in toluene (2 mL). After replacement with nitrogen, the mixture was stirred at 100° C. for 2.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (50.7 mg, 99%).

$^1$H-NMR (chloroform-d): 0.64 (6H, t, J=7.26 Hz), 1.01 (9H, s), 2.09 (4H, q, J=7.25 Hz), 2.20 (3H, s), 2.23 (3H, s), 2.46 (1H, brs), 3.66-3.72 (6H, m), 3.86 (1H, t, J=9.07 Hz), 4.10 (1H, dd, J=9.07, 2.47 Hz), 6.72 (1H, d, J=8.24 Hz), 6.98-7.09 (5H, m), 7.29 (4H, s).

(2) Synthesis of (4'-{1-ethyl-1-[4-(2-hydroxy-3,3-dimethyl-butoxy)-3-methyl-phenyl]-propyl}-2'-methyl-biphenyl-4-yl)-acetic Acid

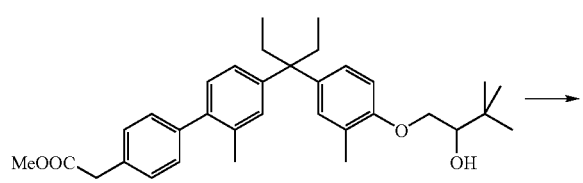

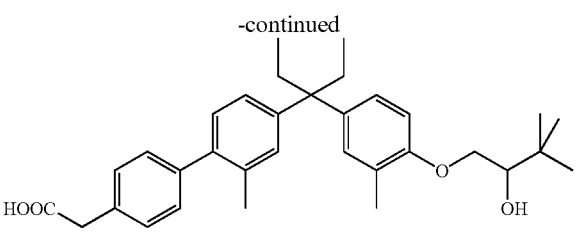

A 1 N sodium hydroxide aqueous solution (0.296 mL, 0.296 mmol) was added to a solution of (4'-{1-ethyl-1-[4-(2-hydroxy-3,3-dimethyl-butoxy)-3-methyl-phenyl]-propyl}-2'-methyl-biphenyl-4-yl)acetic acid methyl ester (Example 51-(1); 54.8 mg, 0.106 mmol) in methanol-tetrahydrofuran (1:1, 4 mL), and the mixture was stirred at 60° C. for two hours. The reaction mixture was then poured into 0.5 N hydrochloric acid aqueous solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (52 mg, 98%).

$^1$H-NMR (chloroform-d): 0.64 (6H, t, J=7.26 Hz), 1.01 (9H, s), 2.09 (4H, q, J=7.25 Hz), 2.19 (3H, s), 2.20 (3H, s), 3.69-3.73 (3H, m), 3.87 (1H, t, J=9.07 Hz), 4.10 (1H, dd, J=9.07, 2.64 Hz), 6.72 (1H, d, J=8.24 Hz), 6.98-7.09 (5H, m), 7.30 (4H, s); MS (ESI+): 520 ([M+NH$_4$]$^+$).

Example 52

Synthesis of (4'-{1-ethyl-1-[4-(1-hydroxy-cyclopentylethynyl)-3-methyl-phenyl]-propyl}-2'-methyl-biphenyl-4-yl)-acetic Acid

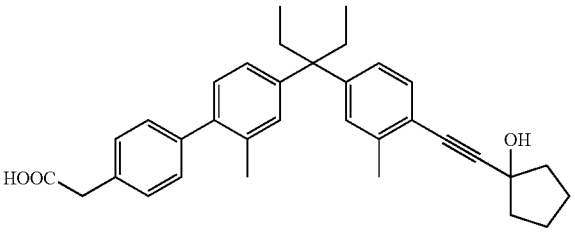

(1) Synthesis of (4'-{1-ethyl-1-[3-methyl-4-(1-trimethylsilanyloxy-cyclopentylethynyl)-phenyl]-propyl}-2'-methyl-biphenyl-4-yl)-acetic Acid Methyl Ester

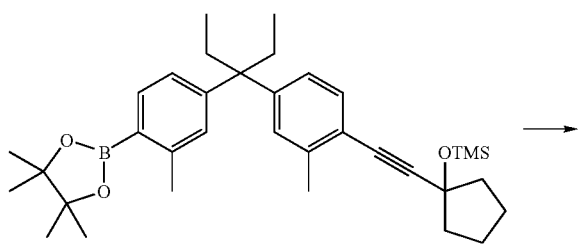

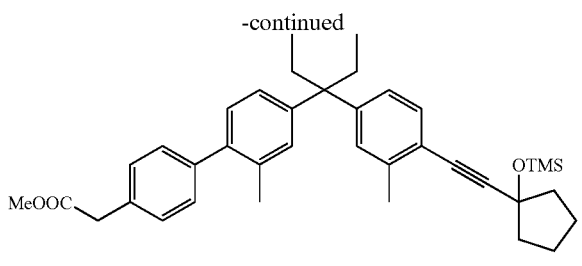

(4-Bromo-phenyl)acetic acid methyl ester (Tetrahedron Letters 44 (2003) 331-334; 34 mg, 0.147 mmol), palladium acetate (2.2 mg, 0.010 mmol), 2-dicyclohexylphosphino-2', 6'-dimethoxy-1,1'-biphenyl (8.2 mg, 0.020 mmol), potassium phosphate (62 mg, 0.294 mmol) and water (0.2 mL) were added to a solution of 2-(4-{1-ethyl-1-[3-methyl-4-(1-trimethylsilanyloxy-cyclopentylethynyl)-phenyl]-propyl}-2-methyl-phenyl)-4,4,5,5-tetramethyl-[1,3,2]dioxaborolane (Example 32-(4); 54.6 mg, 0.098 mmol) in toluene (2 mL). After replacement with nitrogen, the mixture was stirred at 100° C. for 2.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (36.5 mg, 64%).

¹H-NMR (chloroform-d): 0.23 (9H, s), 0.64 (6H, t, J=7.26 Hz), 1.67-1.1.92 (4H, m), 1.95-2.14 (8H, m), 2.22 (3H, s), 2.39 (3H, s), 3.67 (2H, s), 3.72 (3H, s), 6.96-7.09 (5H, m), 7.26-7.29 (5H, m).

(2) Synthesis of (4'-{1-ethyl-1-[4-(1-hydroxy-cyclopentylethynyl)-3-methyl-phenyl]-propyl}-2'-methyl-biphenyl-4-yl)-acetic Acid Methyl Ester

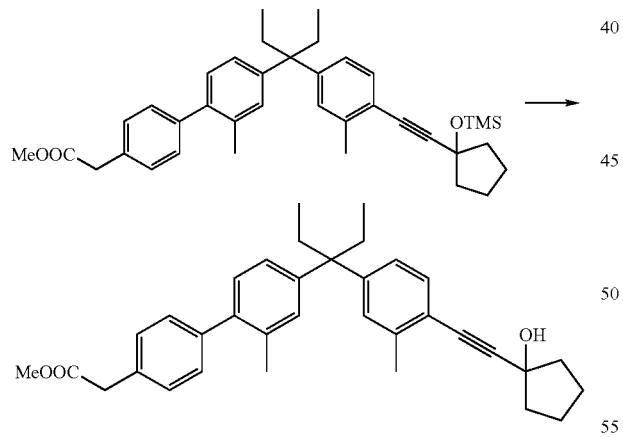

Tetrabutylammonium fluoride (1 M solution in tetrahydrofuran, 0.094 mL, 0.094 mmol) was added to a solution of (4'-{1-ethyl-1-[3-methyl-4-(1-trimethylsilanyloxy-cyclopentylethynyl)-phenyl]-propyl}-2'-methyl-biphenyl-4-yl) acetic acid methyl ester (Example 52-(1); 36.5 mg, 0.063 mmol) in tetrahydrofuran (3 mL), and the mixture was stirred at room temperature for two hours. The reaction mixture was then poured into water, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (25 mg, 78%).

¹H-NMR (chloroform-d): 0.64 (6H, t, J=7.25 Hz), 1.70-1.95 (4H, m), 2.02-2.14 (8H, m), 2.21 (3H, s), 2.39 (3H, s), 3.67 (2H, s), 3.72 (3H, s), 6.96-7.09 (5H, m), 7.29 (4H, s), 7.29 (1H, d, J=8.08 Hz).

(3) Synthesis of (4'-{1-ethyl-1-[4-(1-hydroxy-cyclopentylethynyl)-3-methyl-phenyl]-propyl}-2'-methyl-biphenyl-4-yl)-acetic Acid

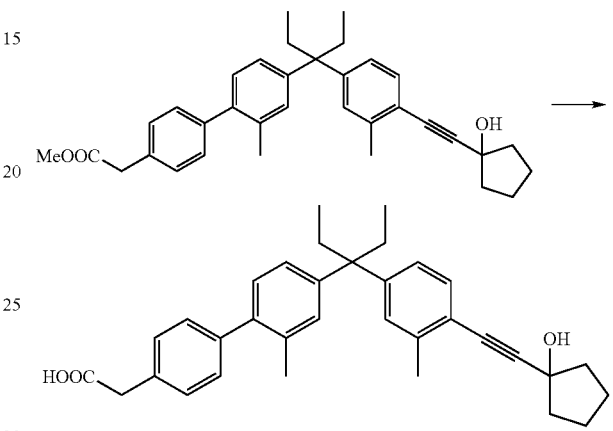

A 1 N sodium hydroxide aqueous solution (0.147 mL, 0.147 mmol) was added to a solution of (4'-{1-ethyl-1-[4-(1-hydroxy-cyclopentylethynyl)-3-methyl-phenyl]-propyl}-2'-methyl-biphenyl-4-yl)acetic acid methyl ester (Example 52-(2); 25 mg, 0.049 mmol) in methanol-tetrahydrofuran (1:1, 3 mL), and the mixture was stirred at room temperature for six hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (20.4 mg, 84%).

¹H-NMR (chloroform-d): 0.63 (6H, t, J=7.26 Hz), 1.70-1.95 (4H, m), 2.02-2.14 (8H, m), 2.21 (3H, s), 2.39 (3H, s), 3.69 (2H, s), 6.96-7.09 (5H, m), 7.26-7.30 (5H, m); MS (ESI+): 477 ([M−H₂O+H]⁺).

Example 53

Synthesis of (E)-[4'-(1-Ethyl-1-{4-[2-(1-hydroxy-cyclopentyl)-vinyl]-3-methyl-phenyl}-propyl)-2'-methyl-biphenyl-4-yl]-acetic Acid

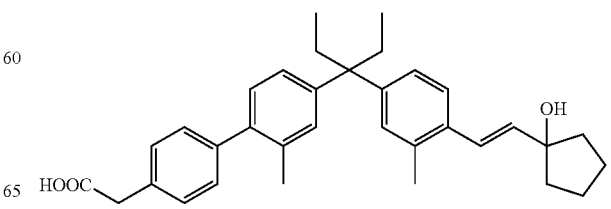

(1) Synthesis of (E)-[4'-(1-ethyl-1-{4-[2-(1-hydroxy-cyclopentyl)-vinyl]-3-methyl-phenyl}-propyl)-2'-methyl-biphenyl-4-yl]-acetic Acid Methyl Ester

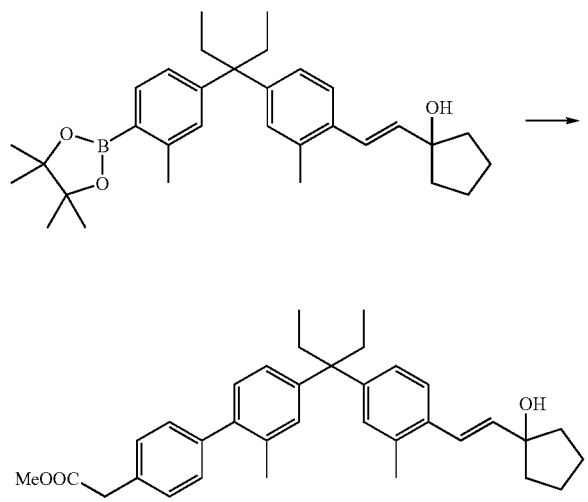

(4-Bromo-phenyl)acetic acid methyl ester (Tetrahedron Letters 44 (2003) 331-334; 35 mg, 0.153 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (65 mg, 0.306 mmol) and water (0.2 mL) were added to a solution of (E)-1-[2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclopentanol (Example 33-(3); 50 mg, 0.102 mmol) in toluene (2 mL). After replacement with nitrogen, the mixture was stirred at 100° C. for 2.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (15.3 mg, 29%).

¹H-NMR (chloroform-d): 0.65 (6H, t, J=7.25 Hz), 1.70-1.95 (8H, m), 2.11 (4H, q, J=6.98 Hz), 2.22 (3H, s), 2.34 (3H.s), 3.67 (2H, s), 3.72 (3H, s), 6.27 (1H, d, J=15.83 Hz), 6.85 (1H, d, J=15.83 Hz), 6.98-7.09 (5H, m), 7.29 (4H, s), 7.36 (1H, d, J=8.58 Hz).

(2) Synthesis of (E)-[4'-(1-ethyl-1-{4-[2-(1-hydroxy-cyclopentyl)-vinyl]-3-methyl-phenyl}-propyl)-2'-methyl-biphenyl-4-yl]-acetic Acid

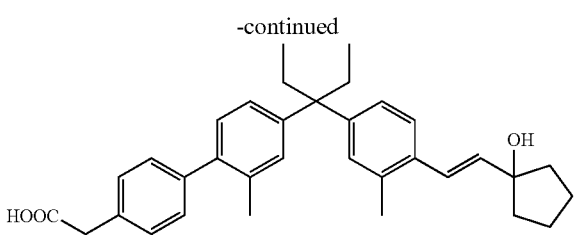

-continued

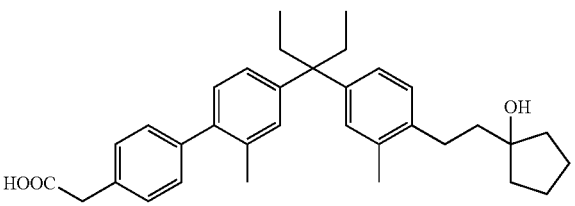

A 1 N sodium hydroxide aqueous solution (0.090 mL, 0.090 mmol) was added to a solution of (E)-[4'-(1-ethyl-1-{4-[2-(1-hydroxy-cyclopentyl)-vinyl]-3-methyl-phenyl}-propyl)-2'-methyl-biphenyl-4-yl]-acetic acid methyl ester (Example 53-(1); 15.3 mg, 0.030 mmol) in methanol-tetrahydrofuran (1:1, 2 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (7.0 mg, 47%).

¹H-NMR (methanol-d): 0.69 (6H, t, J=7.26 Hz), 1.75-2.00 (8H, m), 2.19 (4H, q, J=7.25 Hz), 2.24 (3H, s), 2.35 (3H, s), 3.68 (2H, s), 6.27 (1H, d, J=15.83 Hz), 6.89 (1H, d, J=15.99 Hz), 7.00-7.11 (5H, m), 7.29-7.40 (5H, m); MS (ESI−): 991 ([2M−H]−).

Example 54

Synthesis of [4'-(1-ethyl-1-{4-[2-(1-hydroxy-cyclopentyl)-ethyl]-3-methyl-phenyl}-propyl)-2'-methyl-biphenyl-4-yl]-acetic Acid (1) Synthesis of [4'-(1-ethyl-1-{4-[2-(1-hydroxy-cyclopentyl)-ethyl]-3-methyl-phenyl}-propyl)-2'-methyl-biphenyl-4-yl]-acetic Acid Methyl Ester

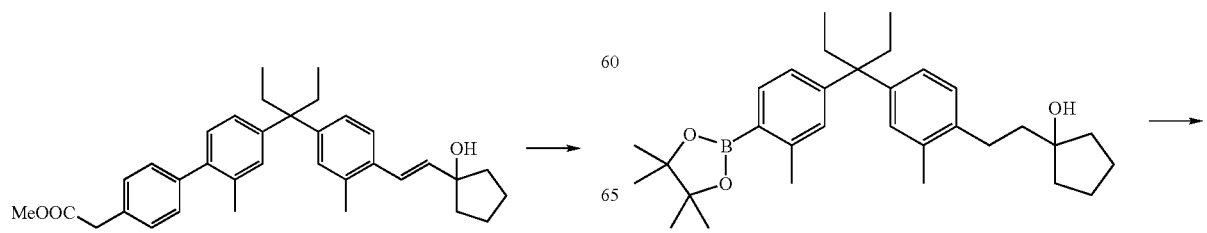

-continued

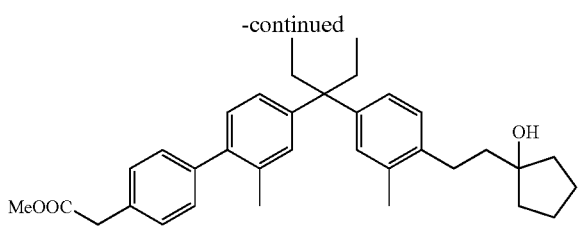

(4-Bromo-phenyl)acetic acid methyl ester (Tetrahedron Letters 44 (2003) 331-334; 30 mg, 0.129 mmol), palladium acetate (2.0 mg, 0.009 mmol), 2-dicyclohexylphosphino-2',6'-dimethoxy-1,1'-biphenyl (7.4 mg, 0.018 mmol), potassium phosphate (55 mg, 0.258 mmol) and water (0.2 mL) were added to a solution of 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclopentanol (Example 34-(2); 42.2 mg, 0.086 mmol) in toluene (2 mL). After replacement with nitrogen, the mixture was stirred at 100° C. for one hour. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (27.2 mg, 62%).

$^1$H-NMR (chloroform-d): 0.64 (6H, t, J=7.26 Hz), 1.60-1.75 (8H, m), 1.81-1.88 (2H, m), 2.10 (4H, q, J=7.25 Hz), 2.23 (3H, s), 2.28 (3H, s), 2.68-2.74 (2H, m), 3.67 (2H, s), 3.72 (3H, s), 6.95-7.09 (6H, m), 7.29 (4H, s).

(2) Synthesis of [4'-(1-ethyl-1-{4-[2-(1-hydroxy-cyclopentyl)-ethyl]-3-methyl-phenyl}-propyl)-2'-methyl-biphenyl-4-yl]-acetic Acid

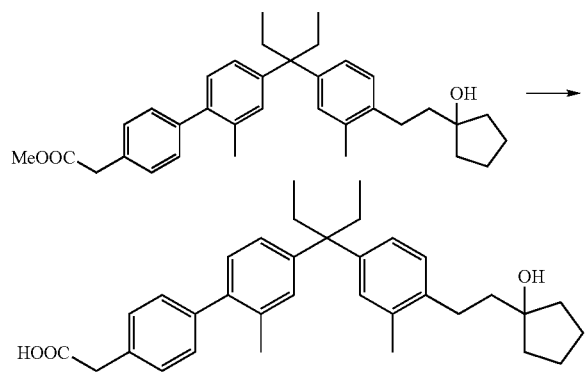

A 1 N sodium hydroxide aqueous solution (0.159 mL, 0.159 mmol) was added to a solution of [4'-(1-ethyl-1-{4-[2-(1-hydroxy-cyclopentyl)-ethyl]-3-methyl-phenyl}-propyl)-2'-methyl-biphenyl-4-yl]-acetic acid methyl ester (Example 54-(1); 27.2 mg, 0.053 mmol) in methanol-tetrahydrofuran (1:1, 3 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (20.2 mg, 76%).

$^1$H-NMR (chloroform-d): 0.64 (6H, t, J=7.25 Hz), 1.60-1.80 (8H, m), 1.81-1.88 (2H, m), 2.10 (4H, q, J=7.25 Hz), 2.22 (3H, s), 2.28 (3H, s), 2.68-2.74 (2H, m), 3.69 (2H, s), 6.95-7.09 (6H, m), 7.30 (4H, s).

Example 55

Synthesis of (4'-{1-ethyl-1-[4-(1-hydroxy-cyclohexylethynyl)-3-methyl-phenyl]-propyl}-2'-methyl-biphenyl-4-yl)-acetic Acid

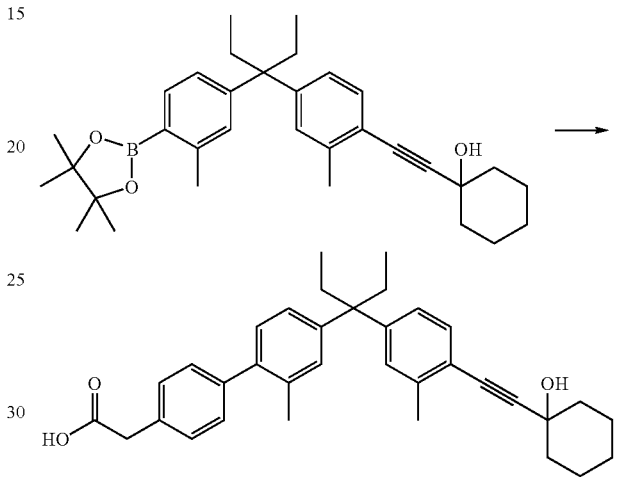

(4-Bromo-phenyl)acetic acid methyl ester (Tetrahedron Letters 44 (2003) 331-334; 28 mg, 0.12 mmol), palladium acetate (3.6 mg, 0.016 mmol), 2-dicyclohexylphosphino-2',6'-dimethoxy-1,1'-biphenyl (13.1 mg, 0.032 mmol), potassium phosphate (51 mg, 0.24 mmol) and water (0.04 mL) were added to a solution of 1-(4-{1-ethyl-1-[3-methyl-4-(4,4,5,5-tetramethyl-[1,3,2]dioxaborolan-2-yl)-phenyl]-propyl}-2-methyl-phenylethynyl)-cyclohexanol (Example 35-(3); 40 mg, 0.08 mmol) in tetrahydrofuran (0.4 mL). After replacement with nitrogen, the mixture was stirred at room temperature for 22 hours. The reaction mixture was purified by preparative thin layer silica gel chromatography (hexane/ethyl acetate=2/1) to give 20 mg of a mixture containing (4'-{1-ethyl-1-[4-(1-hydroxy-cyclohexylethynyl)-3-methyl-phenyl]-propyl}-2'-methyl-biphenyl-4-yl)acetic acid methyl ester.

A 1 N sodium hydroxide aqueous solution (0.1 mL, 0.1 mmol) was added to a solution of the resulting mixture (20 mg) in methanol (1 mL), and the mixture was stirred at 40° C. for one hour. A 30% sodium dihydrogenphosphate aqueous solution was added to the reaction mixture, followed by extraction with dichloromethane. The organic layer was dried over anhydrous magnesium sulfate, filtered and concentrated under reduced pressure. The resulting residue was purified by preparative thin layer silica gel chromatography (dichloromethane/methanol=10/1) to give the title compound (3 mg, 7%).

$^1$H-NMR (chloroform-d): 0.63 (t, 6H, J=7.3 Hz), 1.5-2.2 (m, 14H), 2.23 (s, 3H), 2.40 (s, 3H), 3.69 (s, 2H), 6.98 (d, 2H, J=7.6 Hz), 6.99 (s, 1H), 7.07 (d, 2H, J=7.6 Hz), 7.25-7.32 (m, 5H); MS (ESI-): 507 ([M–H]$^-$).

Example 56

Synthesis of (E)-[4'-(1-ethyl-1-{4-[2-(1-hydroxy-cyclohexyl)-vinyl]-3-methyl-phenyl}-propyl)-2'-methyl-biphenyl-4-yl]-acetic Acid

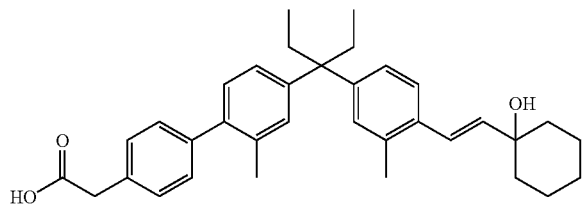

(1) Synthesis of (E)-[4'-(1-ethyl-1-{4-[2-(1-hydroxy-cyclohexyl)-vinyl]-3-methyl-phenyl}-propyl)-2'-methyl-biphenyl-4-yl]-acetic Acid Methyl Ester

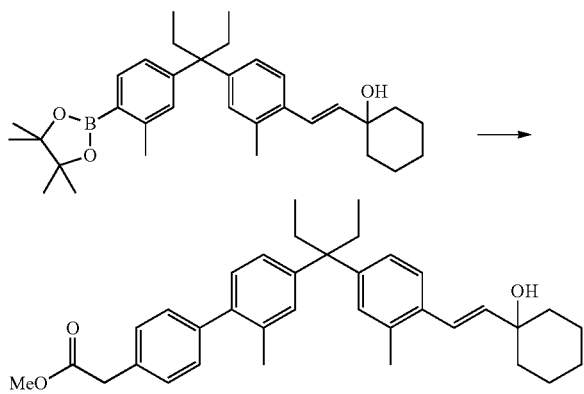

The title compound (54%) was obtained by the same method as in Example 46-(1) using, as starting materials, (E)-1-[2-(4-{1-ethyl-1-[3-methyl-4-(4,4,5,5-tetramethyl-[1,3,2]dioxaborolan-2-yl)-phenyl]-propyl}-2-methylphenyl)-vinyl]-cyclohexanol (Example 36-(3)) and 4-bromophenyl-acetic acid methyl ester (Tetrahedron Letters 44 (2003) 331-334).

$^1$H-NMR (chloroform-d): 0.67 (t, 6H, J=7.3 Hz), 1.27-1.80 (m, 10H), 2.12 (q, 4H, J=7.3 Hz), 2.23 (s, 3H), 2.34 (s, 3H), 3.68 (s, 2H), 3.73 (s, 3H), 6.23 (d, 1H, J=16.0 Hz), 6.84 (d, 1H, J=16.1 Hz), 6.96-7.10 (m, 5H), 7.23-7.37 (m, 5H);

MS (ESI+): 507 ([M–H$_2$O+H]$^+$).

(2) Synthesis of (E)-[4'-(1-ethyl-1-{4-[2-(1-hydroxy-cyclohexyl)-vinyl]-3-methyl-phenyl}-propyl)-2'-methyl-biphenyl-4-yl]-acetic Acid

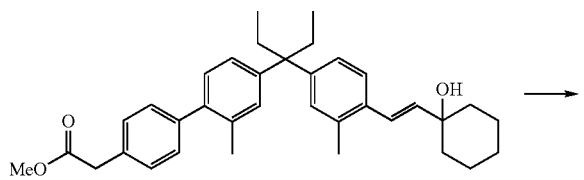

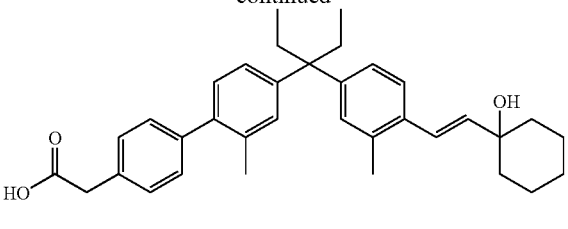

The title compound (39%) was obtained by the same method as in Example 46-(2) using (E)-[4'-(1-ethyl-1-{4-[2-(1-hydroxycyclohexyl)-vinyl]-3-methylphenyl}-propyl)-2'-methylbiphenyl-4-yl]-acetic acid methyl ester (Example 56-(1)) as a starting material.

$^1$H-NMR (chloroform-d): 0.66 (t, 6H, J=7.5 Hz), 1.25-1.72 (m, 10H), 2.12 (q, 4H, J=7.5 Hz), 2.23 (s, 3H), 2.34 (s, 3H), 3.70 (s, 2H), 6.23 (d, 1H, J=15.0 Hz), 6.84 (d, 1H, J=15.0 Hz), 6.99-7.09 (m, 5H), 7.26-7.37 (m, 5H); MS (ESI+): 493 ([M–H$_2$O+H]$^+$).

Example 57

Synthesis of [4'-(1-ethyl-1-{4-[2-(1-hydroxy-cyclohexyl)-ethyl]-3-methyl-phenyl}-propyl)-2'-methyl-biphenyl-4-yl]-acetic Acid

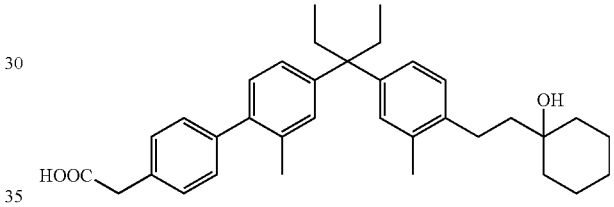

(1) Synthesis of [4'-(1-ethyl-1-{4-[2-(1-hydroxy-cyclohexyl)-ethyl]-3-methyl-phenyl}-propyl)-2'-methyl-biphenyl-4-yl]-acetic Acid Methyl Ester

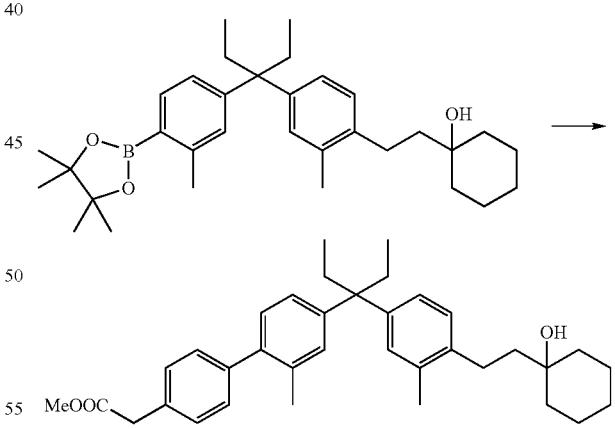

(4-Bromo-phenyl)acetic acid methyl ester (Tetrahedron Letters 44 (2003) 331-334; 32 mg, 0.139 mmol), palladium acetate (2.0 mg, 0.009 mmol), 2-dicyclohexylphosphino-2',6'-dimethoxy-1,1'-biphenyl (7.4 mg, 0.018 mmol), potassium phosphate (59 mg, 0.279 mmol) and water (0.2 mL) were added to a solution of 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclohexanol (Example 37-(2); 46.7 mg, 0.093 mmol) in toluene (2 mL). After replacement with nitrogen, the mixture was stirred at 100° C. for one hour. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (26.5 mg, 54%).

$^1$H-NMR (chloroform-d): 0.64 (6H, t, J=7.26 Hz), 1.45-1.73 (12H, m), 2.10 (4H, q, J=7.25 Hz), 2.23 (3H, s), 2.28 (3H, s), 2.61-2.68 (2H, m), 3.69 (2H, s), 3.72 (3H, s), 6.94-7.09 (6H, m), 7.29 (4H, s).

(2) Synthesis of [4'-(1-ethyl-1-{4-[2-(1-hydroxy-cyclohexyl)-ethyl]-3-methyl-phenyl}-propyl)-2'-methyl-biphenyl-4-yl]-acetic Acid

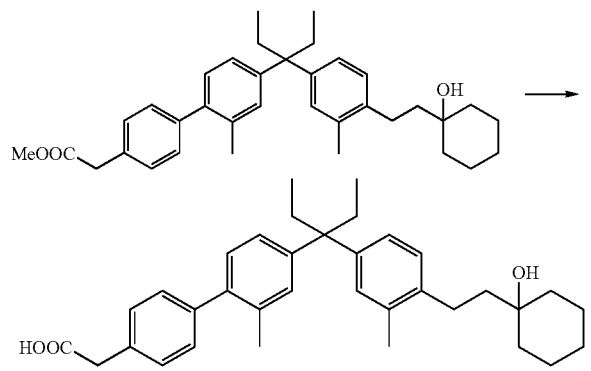

A 1 N sodium hydroxide aqueous solution (0.151 mL, 0.151 mmol) was added to a solution of [4'-(1-ethyl-1-{4-[2-(1-hydroxy-cyclohexyl)-ethyl]-3-methyl-phenyl}-propyl)-2'-methyl-biphenyl-4-yl]-acetic acid methyl ester (Example 57-(1); 26.5 mg, 0.050 mmol) in methanol-tetrahydrofuran (1:1, 3 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (24.6 mg, 96%).

$^1$H-NMR (chloroform-d): 0.64 (6H, t, J=7.26 Hz), 1.45-1.73 (12H, m), 2.10 (4H, q, J=7.25 Hz), 2.23 (3H, s), 2.28 (3H, s), 2.61-2.68 (2H, m), 3.70 (2H, s), 6.94-7.09 (6H, m), 7.34 (4H, s); MS (ESI+): 517 ([M–H$_2$O+Na]$^+$).

Example 58

Synthesis of (E)-(4'-{1-ethyl-1-[4-(3-ethyl-3-hydroxy-1-pentenyl)-3-methyl-phenyl]-propyl}-2',6'-dimethyl-biphenyl-4-yl)-acetic Acid

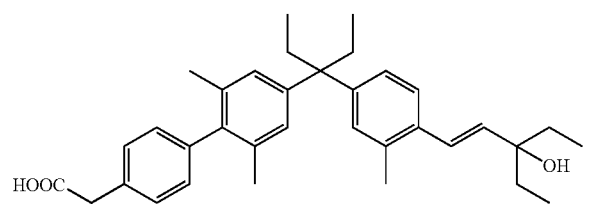

(1) Synthesis of (E)-(4'-{1-ethyl-1-[4-(3-ethyl-3-hydroxy-1-pentenyl)-3-methyl-phenyl]-propyl}-2',6'-dimethyl-biphenyl-4-yl)-acetic Acid Methyl Ester

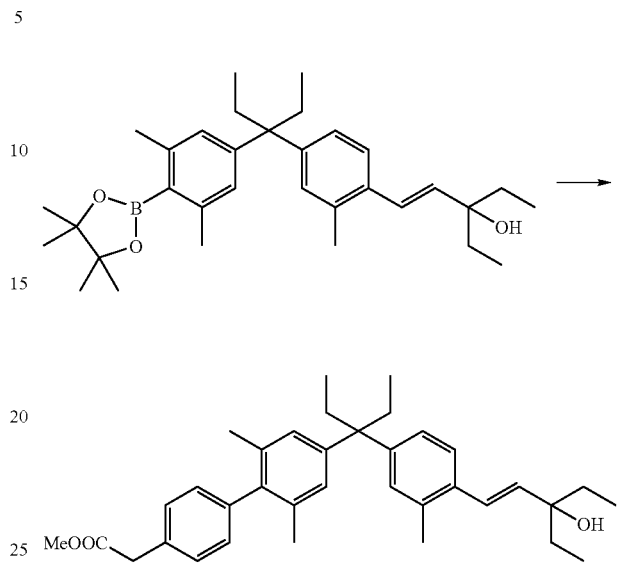

(4-Bromo-phenyl)acetic acid methyl ester (Tetrahedron Letters 44 (2003) 331-334; 34 mg, 0.149 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (63 mg, 0.297 mmol) and water (0.2 mL) were added to a solution of (E)-1-(4-{1-[3,5-dimethyl-4-(4,4,5,5-tetramethyl-[1,3,2]dioxaborolan-2-yl)-phenyl]-1-ethyl-propyl}-2-methyl-phenyl)-3-ethyl-1-penten-3-ol (Example 38-(6); 50 mg, 0.099 mmol) in toluene (2 mL). After replacement with nitrogen, the mixture was stirred at 100° C. for one hour. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (31.8 mg, 61%).

$^1$H-NMR (chloroform-d): 0.66 (6H, t, J=7.26 Hz), 0.92 (6H, t, J=7.42 Hz), 1.65 (4H, q, J=7.42 Hz), 1.96 (6H, s), 2.10 (4H, q, J=7.26 Hz), 2.34 (3H, s), 3.67 (2H, s), 3.73 (3H, s), 6.03 (1H, d, J=15.83 Hz), 6.76 (1H, d, J=16.16 Hz), 6.87 (2H, s), 6.99-7.02 (2H, m), 7.10 (2H, d, J=8.59 Hz), 7.29-7.34 (3H, m).

(2) Synthesis of (E)-(4'-{1-ethyl-1-[4-(3-ethyl-3-hydroxy-1-pentenyl)-3-methyl-phenyl]-propyl}-2',6'-dimethyl-biphenyl-4-yl)-acetic Acid

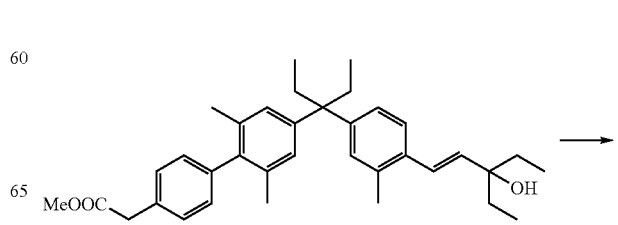

-continued

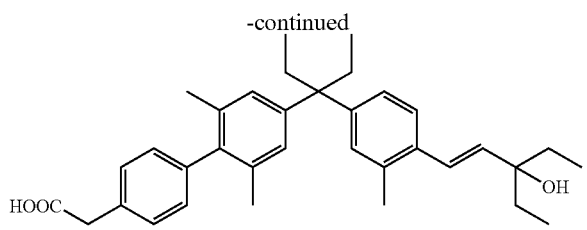

A 1 N sodium hydroxide aqueous solution (0.181 mL, 0.181 mmol) was added to a solution of (E)-(4'-{1-ethyl-1-[4-(3-ethyl-3-hydroxy-1-pentenyl)-3-methyl-phenyl]-propyl}-2',6'-dimethyl-biphenyl-4-yl)acetic acid methyl ester (Example 58-(1); 31.8 mg, 0.060 mmol) in methanol-tetrahydrofuran (1:1, 4 mL), and the mixture was stirred at room temperature for 10 hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (25.8 mg, 84%).

$^1$H-NMR (chloroform-d): 0.66 (6H, t, J=7.26 Hz), 0.92 (6H, t, J=7.59 Hz), 1.65 (4H, q, J=7.58 Hz), 1.96 (6H, s), 2.10 (4H, q, J=7.42 Hz), 2.34 (3H, s), 3.70 (2H, s), 6.02 (1H, d, J=16.00 Hz), 6.76 (1H, d, J=15.99 Hz), 6.87 (2H, s), 6.98-7.03 (2H, m), 7.12 (2H, d, J=7.91 Hz), 7.31-7.34 (3H, m); MS (ESI+): 495 ([M−H$_2$O+H]$^+$).

Example 59

Synthesis of (E)-(4'-{1-ethyl-1-[4-(3-ethyl-3-hydroxy-1-pentenyl)-3-methyl-phenyl]-propyl}-biphenyl-4-yl)-acetic Acid

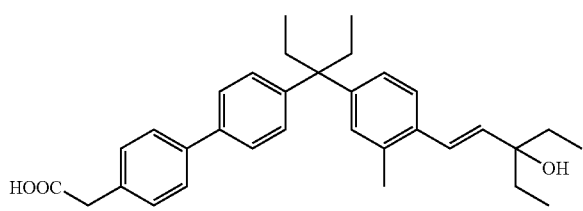

(1) Synthesis of (E)-(4'-{1-ethyl-1-[4-(3-ethyl-3-hydroxy-1-pentenyl)-3-methyl-phenyl]-propyl}-biphenyl-4-yl)-acetic Acid Methyl Ester

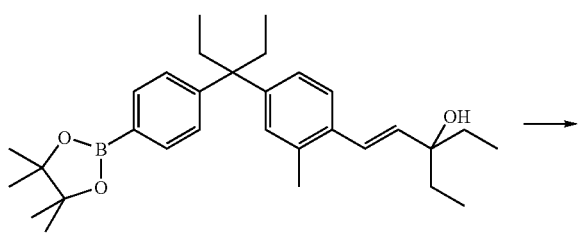

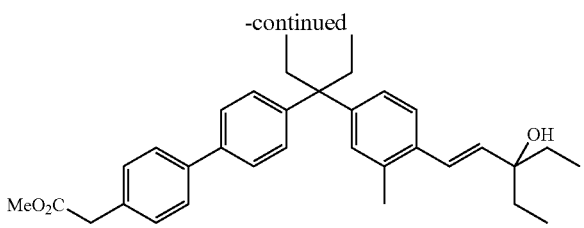

A solution of palladium acetate (3.3 mg, 0.0146 mmol), 2-dicyclohexylphosphino-2',6'-dimethoxybiphenyl (12.0 mg, 0.0293 mmol) and potassium phosphate (62.3 mg, 0.29 mmol) in water (0.05 mL) and toluene (0.20 mL) was stirred for three minutes. A solution of (4-bromo-phenyl)acetic acid methyl ester (Tetrahedron Letters 44 (2003) 331-334; 36.0 mg, 0.15 mmol) and (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 50.0 mg, 0.1049 mmol) in toluene (0.20 mL) was added, and the mixture was stirred in a nitrogen atmosphere at 100° C. for 1.5 hours. After filtration through cotton plug, the filtrate was concentrated under reduced pressure. The residue was purified by silica gel chromatography (17% ethyl acetate/hexane) to give the title compound (48.7 mg, 93%).

$^1$H-NMR (chloroform-d): 0.65 (t, 6H, J=7.1 Hz), 0.92 (t, 6H, J=7.3 Hz), 1.64 (q, 4H, J=7.5 Hz), 2.13 (q, 4H, J=7.2 Hz), 2.32 (s, 3H), 3.66 (s, 2H), 3.71 (s, 3H), 6.02 (d, 1H, J=16.1 Hz), 6.75 (d, 1H, J=16.1 Hz), 6.98-6.99 (m, 2H), 7.24-7.34 (m, 5H, J=7.3 Hz), 7.46 (d, 2H, J=8.1 Hz), 7.55 (d, 2H, J=8.1 Hz).

(2) Synthesis of (E)-(4'-{1-ethyl-1-[4-(3-ethyl-3-hydroxy-1-pentenyl)-3-methyl-phenyl]-propyl}-biphenyl-4-yl)-acetic Acid

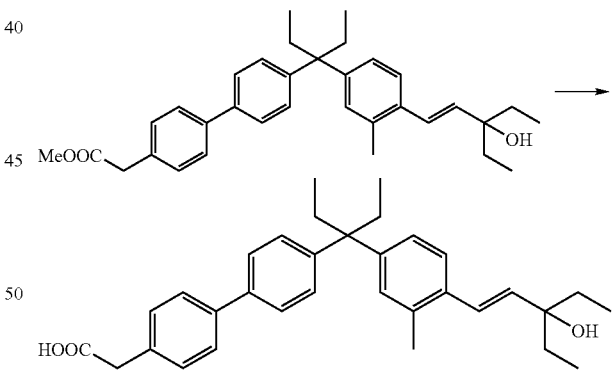

A 1 N sodium hydroxide aqueous solution (0.293 mL, 0.293 mmol) was added to a solution of (E)-(4'-{1-ethyl-1-[4-(3-ethyl-3-hydroxy-1-pentenyl)-3-methyl-phenyl]-propyl}-biphenyl-4-yl)acetic acid methyl ester (Example 59-(1); 48.7 mg, 0.098 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (38.8 mg, 82%).

<sup>1</sup>H-NMR (chloroform-d): 0.66 (6H, t, J=7.25 Hz), 0.92 (6H, t, J=7.42 Hz), 1.64 (4H, q, J=7.42 Hz), 2.13 (4H, q, J=7.26 Hz), 2.32 (3H, s), 3.69 (2H, s), 6.01 (1H, d, J=15.99 Hz), 6.75 (1H, d, J=15.99 Hz), 6.97-6.99 (2H, m), 7.22-7.35 (5H, m), 7.46 (2H, d, J=8.41 Hz), 7.55 (2H, d, J=8.08 Hz); MS (ESI+): 467 ([M−H$_2$O+H]$^+$).

Example 60

Synthesis of (4'-{1-ethyl-1-[4-(3-hydroxy-4,4-dimethyl-pentyl)-3-methyl-phenyl]-propyl}-3-fluoro-2'-methyl-biphenyl-4-yl)-acetic Acid

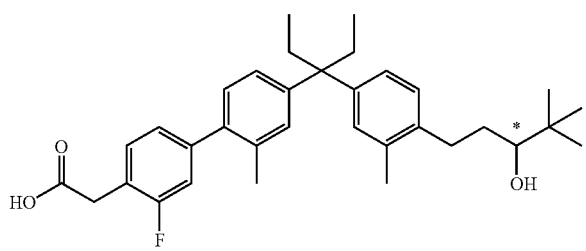

(1) Synthesis of [4'-(1-{4-[3-(t-butyl-dimethyl-silanyloxy)-4,4-dimethyl-pentyl]-3-methyl-phenyl}-1-ethyl-propyl)-3-fluoro-2'-methyl-biphenyl-4-yl]-acetic Acid Methyl Ester

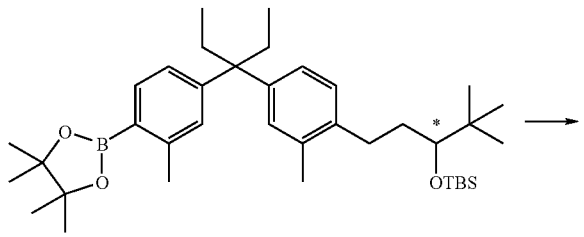

Degassed toluene (0.12 mL) and water (0.012 mL) were added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 16.5 mg, 0.0272 mmol), palladium (II) acetate (0.9 mg, 0.004 mmol), 2-dicyclohexylphosphino-2',6'-dimethoxy-1,1'-biphenyl (3.3 mg, 0.0080 mmol) and potassium phosphate (19.0 mg, 0.0895 mmol). After replacement with nitrogen, (4-chloro-2-fluoro-phenyl)acetic acid methyl ester (Example 40; 7.4 mg, 0.037 mmol) was added. After replacement with nitrogen, the mixture was heated while stirring at an external temperature of 96 to 104° C. for one hour. The reaction mixture was diluted with diethyl ether and filtered through cotton plug, and the filtrate was concentrated under reduced pressure. The residue was purified by silica gel chromatography (hexane/ethyl acetate=50/1) to give the title compound (13.5 mg, 77%).

<sup>1</sup>H-NMR (chloroform-d): 0.08 (s, 3H), 0.12 (s, 3H), 0.65 (t, 6H, J=7.5 Hz), 0.89 (s, 9H), 0.95 (s, 9H), 1.57 (m, 1H), 1.80 (m, 1H), 2.11 (q, 4H, J=7.5 Hz), 2.25 (s, 3H), 2.27 (s, 3H), 2.43 (m, 1H), 2.78 (m, 1H), 3.35 (dd, 1H, J=7.2, 3.3 Hz), 3.72 (s, 2H), 3.75 (s, 2H), 6.93-7.10 (m, 8H), 7.27 (t, 1H, J=8.3 Hz).

(2) Synthesis of (4'-{1-ethyl-1-[4-(3-hydroxy-4,4-dimethyl-pentyl)-3-methyl-phenyl]-propyl}-3-fluoro-2'-methyl-biphenyl-4-yl)-acetic Acid Methyl Ester

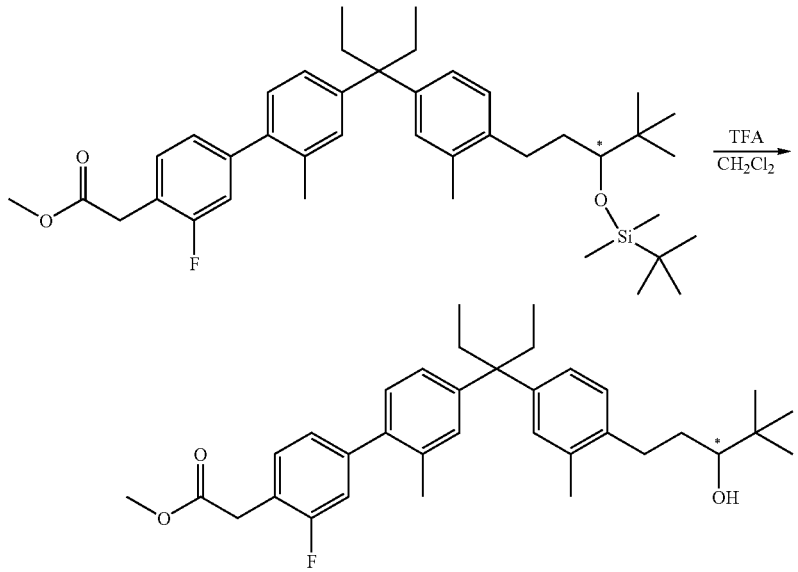

Trifluoroacetic acid (0.10 mL) was added to a solution of [4'-(1-{4-[3-(t-butyl-dimethyl-silanyloxy)-4,4-dimethyl-pentyl]-3-methyl-phenyl}-1-ethyl-propyl)-3-fluoro-2'-methyl-biphenyl-4-yl]-acetic acid methyl ester (Example 60-(1); 13.5 mg, 0.0209 mmol) in dichloromethane (0.50 mL) at room temperature, and the mixture was stirred at room temperature for two hours. The solvent in the reaction solution was distilled off under reduced pressure, and the residue was diluted with diethyl ether. The mixture was adjusted to pH 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=5/1) to give the title compound (8.5 mg, 76%).

$^1$H-NMR (chloroform-d): 0.65 (t, 6H, J=7.5 Hz), 0.91 (s, 9H), 1.54 (m, 1H), 1.81 (m, 1H), 2.11 (q, 4H, J=7.5 Hz), 2.24 (s, 3H), 2.29 (s, 3H), 2.58 (m, 1H), 2.90 (m, 1H), 3.26 (m, 1H), 3.72 (s, 2H), 3.75 (s, 3H), 6.94-7.10 (m, 8H), 7.26 (t, 1H, J=8.3 Hz).

(3) Synthesis of (4'-{1-ethyl-1-[4-(3-hydroxy-4,4-dimethyl-pentyl)-3-methyl-phenyl]-propyl}-3-fluoro-2'-methyl-biphenyl-4-yl)-acetic Acid

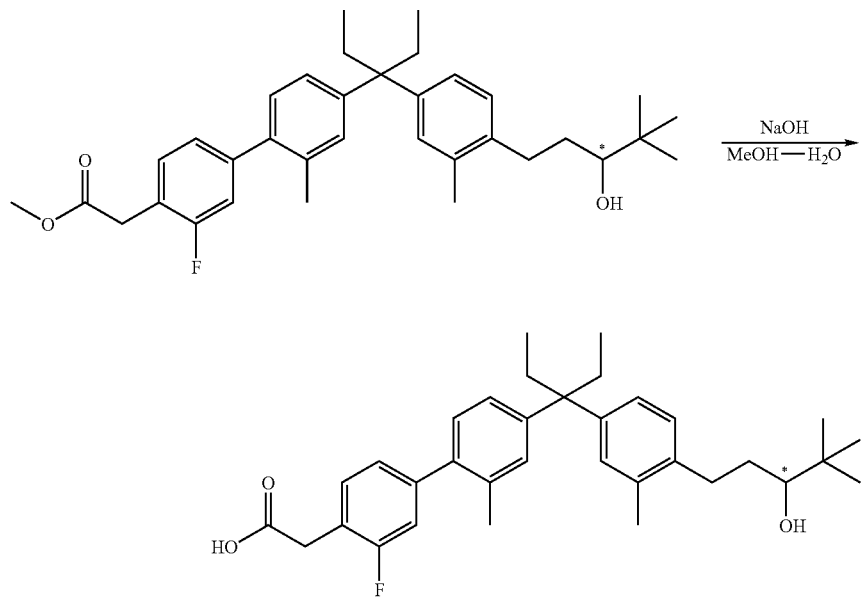

A mixed solution of a 6 N sodium hydroxide aqueous solution (0.011 mL) with water (0.032 mL) was added to a solution of (4'-{1-ethyl-1-[4-(3-hydroxy-4,4-dimethyl-pentyl)-3-methyl-phenyl]-propyl}-3-fluoro-2'-methyl-biphenyl-4-yl)acetic acid methyl ester (Example 60-(2); 8.5 mg, 0.016 mmol) in methanol (0.22 mL) at room temperature, and the mixture was stirred at room temperature for six hours. The mixture was acidified with dilute hydrochloric acid aqueous solution, followed by extraction with ethyl acetate. The extract was dried over anhydrous magnesium sulfate and then concentrated under reduced pressure to give the title compound (8 mg, 100%).

$^1$H-NMR (chloroform-d): 0.65 (t, 6H, J=7.5 Hz), 0.91 (s, 9H), 1.54 (m, 1H), 1.82 (m, 1H), 2.11 (q, 4H, J=7.5 Hz), 2.24 (s, 3H), 2.29 (s, 3H), 2.58 (m, 1H), 2.89 (m, 1H), 3.27 (dd, 1H, J=10.2 Hz, 1.5 Hz), 3.76 (s, 2H), 6.9-7.1 (m, 8H), 7.28 (t, 1H, J=8.1 Hz); MS (ESI–): 517 ([M–H]$^-$).

Example 61

Synthesis of (4'-{1-ethyl-1-[4-(3-hydroxy-4,4-dimethyl-pentyl)-3-methyl-phenyl]-propyl}-3-chloro-2'-methyl-biphenyl-4-yl)-acetic Acid

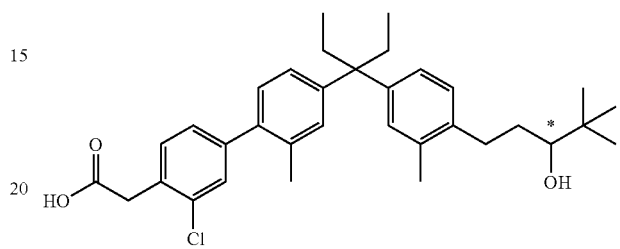

(1) Synthesis of [4'-(1-{4-[3-(t-butyl-dimethyl-silanyloxy)-4,4-dimethyl-pentyl]-3-methyl-phenyl}-1-ethyl-propyl)-3-chloro-2'-methyl-biphenyl-4-yl]-acetic Acid Methyl Ester

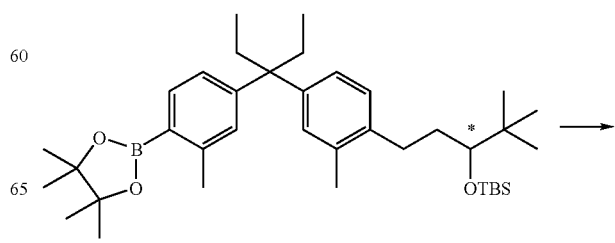

-continued

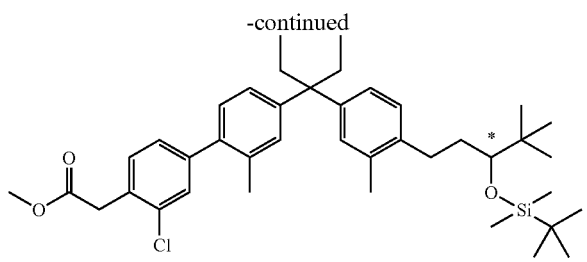

Degassed toluene (0.13 mL) and water (0.013 mL) were added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 15.7 mg, 0.0259 mmol), palladium (II) acetate (0.8 mg, 0.004 mmol), 2-dicyclohexylphosphino-2',6'-dimethoxy-1,1'-biphenyl (3 mg, 0.007 mmol) and potassium phosphate (20.0 mg, 0.0942 mmol). After replacement with nitrogen, (2,4-dichloro-phenyl)acetic acid methyl ester (Example 41; 17 mg, 0.078 mmol) was added. After replacement with nitrogen, the mixture was heated while stirring at an external temperature of 96 to 104° C. for 30 minutes. The reaction mixture was diluted with diethyl ether and filtered through cotton plug, and the filtrate was concentrated under reduced pressure. The residue was purified by silica gel chromatography (hexane/ethyl acetate=50/1) to give the title compound (3 mg, 17%).

$^1$H-NMR (chloroform-d): 0.08 (s, 3H), 0.12 (s, 3H), 0.65 (t, 6H, J=7.2 Hz), 0.89 (s, 9H), 0.94 (s, 9H), 1.61 (m, 1H), 1.80 (m, 1H), 2.11 (q, 4H, J=7.2 Hz), 2.24 (s, 3H), 2.27 (s, 3H), 2.43 (m, 1H), 2.78 (m, 1H), 3.35 (dd, 1H, J=7.2, 3.3 Hz), 3.75 (s, 3H), 3.82 (s, 2H), 6.93-7.09 (m, 6H), 7.20 (dd, 1H, J=8.0, 1.5 Hz), 7.30 (d, 1H, J=8.0 Hz), 7.37 (d, 1H, J=1.5 Hz).

(2) Synthesis of (4'-{1-ethyl-1-[4-(3-hydroxy-4,4-dimethyl-pentyl)-3-methyl-phenyl]-propyl}-3-chloro-2'-methyl-biphenyl-4-yl)-acetic Acid Methyl Ester

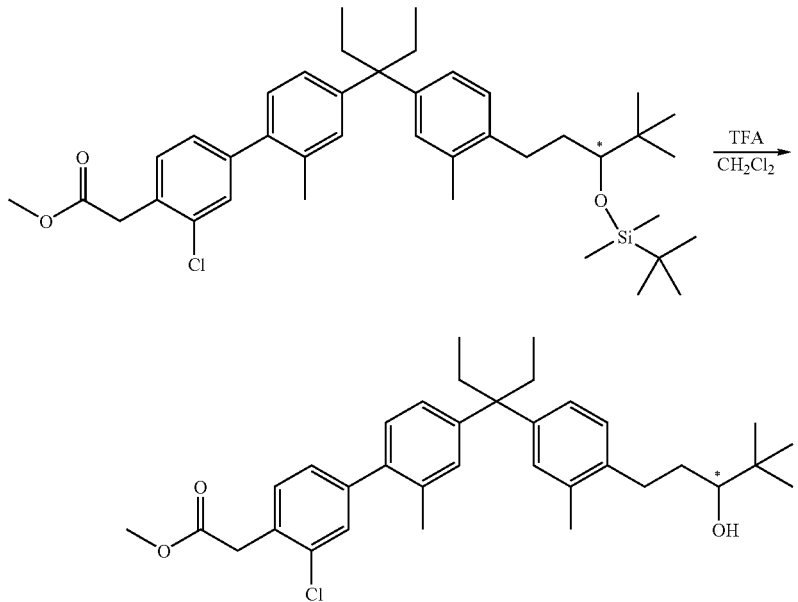

Trifluoroacetic acid (0.03 mL) was added to a solution of [4'-(1-{4-[3-(t-butyl-dimethyl-silanyloxy)-4,4-dimethyl-pentyl]-3-methyl-phenyl}-1-ethyl-propyl)-3-chloro-2'-methyl-biphenyl-4-yl]-acetic acid methyl ester (Example 61-(1); 3.0 mg, 0.045 mmol) in dichloromethane (0.15 mL) at room temperature, and the mixture was stirred at room temperature for one hour. The solvent in the reaction solution was distilled off under reduced pressure, and the residue was diluted with diethyl ether. The mixture was adjusted to pH 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=5/1) to give the title compound (2.3 mg, 93%).

$^1$H-NMR (chloroform-d): 0.65 (t, 6H, J=7.2 Hz), 0.91 (s, 9H), 1.53 (m, 1H), 1.81 (m, 1H), 2.11 (q, 4H, J=7.2 Hz), 2.24 (s, 3H), 2.29 (s, 3H), 2.58 (m, 1H), 2.89 (m, 1H), 3.26 (m, 1H), 3.75 (s, 3H), 3.82 (s, 2H), 6.94-7.10 (m, 6H), 7.21 (dd, 1H, J=8.0, 1.5 Hz), 7.34 (d, 1H, J=8.0 Hz), 7.37 (d, 1H, J=1.5 Hz).

(3) Synthesis of (4'-{1-ethyl-1-[4-(3-hydroxy-4,4-dimethyl-pentyl)-3-methyl-phenyl]-propyl}-3-chloro-2'-methyl-biphenyl-4-yl)-acetic Acid

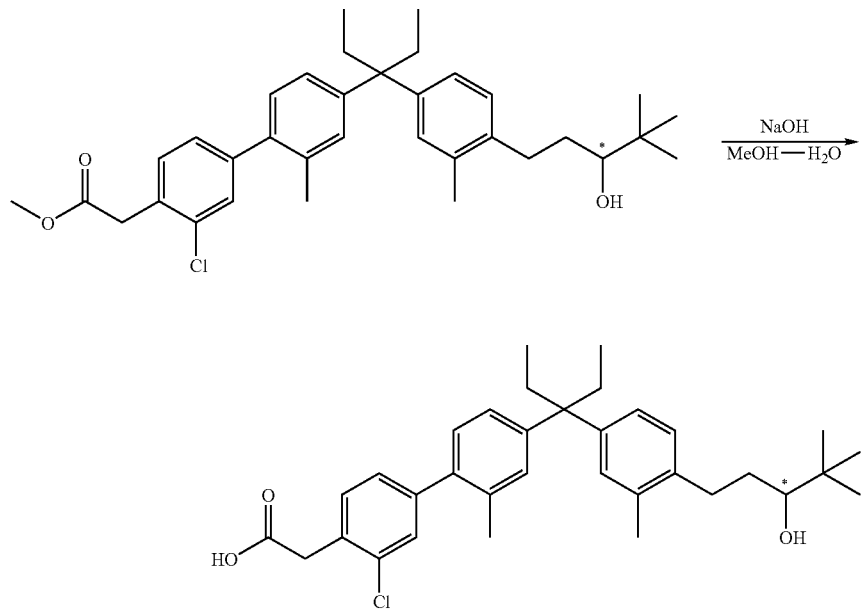

A mixed solution of a 6 N sodium hydroxide aqueous solution (0.009 mL) with water (0.027 mL) was added to a solution of (4'-{1-ethyl-1-[4-(3-hydroxy-4,4-dimethyl-pentyl)-3-methyl-phenyl]-propyl}-3-chloro-2'-methyl-biphenyl-4-yl)acetic acid methyl ester (Example 61-(2); 2.3 mg, 0.042 mmol) in methanol (0.08 mL) at room temperature, and the mixture was stirred at room temperature for six hours. The mixture was acidified with dilute hydrochloric acid aqueous solution, followed by extraction with ethyl acetate. The extract was dried over anhydrous magnesium sulfate and then concentrated under reduced pressure to give the title compound (2.2 mg, 100%).

$^1$H-NMR (chloroform-d): 0.65 (t, 6H, J=7.4 Hz), 0.91 (s, 9H), 1.53 (m, 1H), 1.82 (m, 1H), 2.11 (q, 4H, J=7.4 Hz), 2.24 (s, 3H), 2.29 (s, 3H), 2.58 (m, 1H), 2.88 (m, 1H), 3.27 (dd, 1H, J=10.5, 1.8 Hz), 3.87 (s, 2H), 6.9-7.1 (m, 6H), 7.21 (dd, 1H, J=8.0, 1.8 Hz), 7.32 (d, 1H), 7.39 (d, 1H, J=1.8 Hz).

MS (ESI+): 552 ([M+NH$_4$]$^+$).

Example 62

Synthesis of [5-(4-{1-ethyl-1-[4-(3-hydroxy-4,4-dimethyl-pentyl)-3-methyl-phenyl]-propyl}-2-methyl-phenyl)-pyridin-3-yl]-acetic Acid

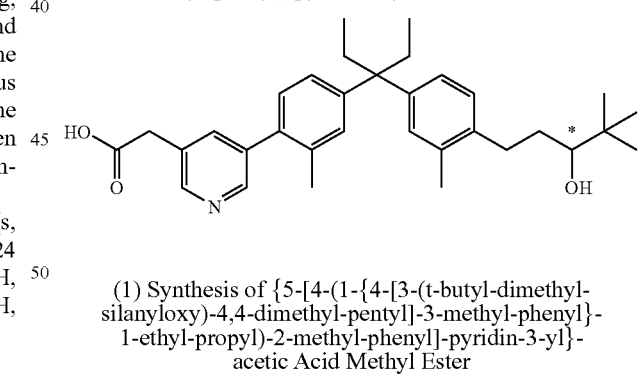

(1) Synthesis of {5-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic Acid Methyl Ester

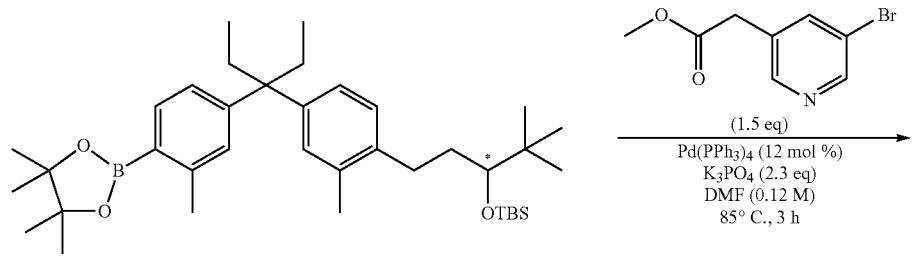

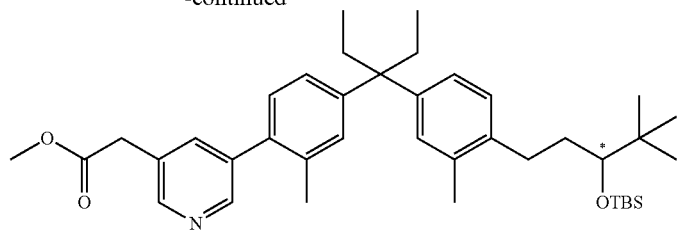

Degassed N,N-dimethylformamide (0.12 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 11.0 mg, 0.0181 mmol), (5-bromo-pyridin-3-yl)acetic acid methyl ester (Example 24-(2); 6.3 mg, 0.027 mmol), tetrakis(triphenylphosphine)palladium (0) (2.6 mg, 0.0022 mmol) and potassium phosphate (9.0 mg, 0.042 mmol). After replacement with nitrogen, the mixture was heated while stirring at an external temperature of 81 to 92° C. for three hours. Water was added to the reaction mixture, followed by extraction with diethyl ether. The extract was dried over anhydrous magnesium sulfate and then concentrated under reduced pressure. The residue was purified by silica gel chromatography (hexane/dichloromethane=3/1) to give the title compound (9.5 mg, 83%).

$^{1}$H-NMR (chloroform-d): 0.08 (s, 3H), 0.12 (s, 3H), 0.66 (t, 6H, J=7.4 Hz), 0.89 (s, 9H), 0.94 (s, 9H), 1.57 (m, 1H), 1.79 (m, 1H), 2.12 (q, 4H, J=7.4 Hz), 2.15 (s, 3H), 2.25 (s, 3H), 2.43 (m, 1H), 2.78 (m, 1H), 3.35 (dd, 1H, J=7.0, 3.0 Hz), 3.68 (s, 2H), 3.73 (s, 3H), 6.93-7.11 (m, 6H), 7.62 (t, 1H, J=2.0 Hz), 8.46 (d, 1H, J=2.0 Hz), 8.52 (d, 1H, J=2.0 Hz).

(2) Synthesis of [5-(4-{1-ethyl-1-[4-(3-hydroxy-4,4-dimethyl-pentyl)-3-methyl-phenyl]-propyl}-2-methyl-phenyl)-pyridin-3-yl]-acetic Acid Methyl Ester Trifluoroacetic acid (0.18 mL) was added to a solution of {5-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic acid methyl ester (Example 62-(1); 23.3 mg, 0.0370 mmol) in dichloromethane (0.9 mL) at room temperature, and the mixture was stirred at room temperature for one hour. The solvent in the reaction solution was distilled off under reduced pressure, and the residue was diluted with diethyl ether. The mixture was adjusted to pH 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=1/1 to 2/1) to give the title compound (17.0 mg, 89%).

$^{1}$H-NMR (chloroform-d): 0.66 (t, 6H, J=7.2 Hz), 0.91 (s, 9H), 1.54 (m, 1H), 1.81 (m, 1H), 2.12 (q, 4H, J=7.2 Hz), 2.25 (s, 3H), 2.29 (s, 3H), 2.58 (m, 1H), 2.89 (m, 1H), 3.26 (dd, 1H, J=10.5, 1.2 Hz), 3.68 (s, 2H), 3.73 (s, 3H), 6.94-7.10 (m, 6H), 7.63 (d, 1H, J=2.4, 1.8 Hz), 7.46 (d, 1H, J=2.4 Hz), 8.52 (t, 1H, J=1.8 Hz).

(3) Synthesis of [5-(4-{1-ethyl-1-[4-(3-hydroxy-4,4-dimethyl-pentyl)-3-methyl-phenyl]-propyl}-2-methyl-phenyl)-pyridin-3-yl]-acetic Acid

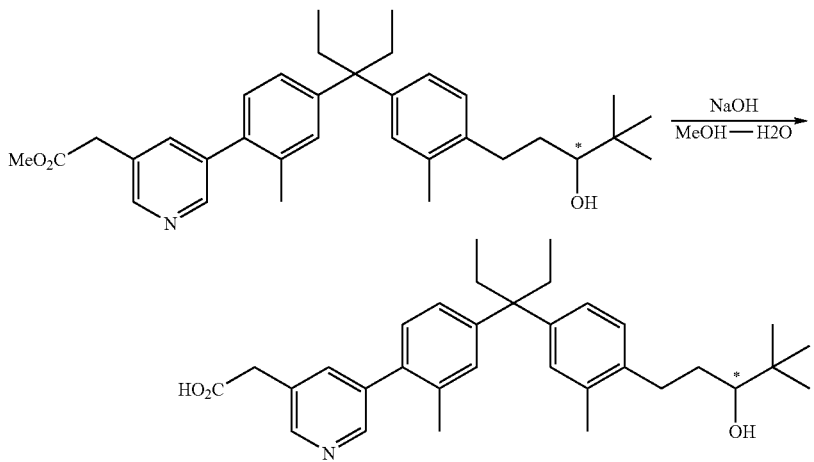

A mixed solution of a 6 N sodium hydroxide aqueous solution (0.022 mL) with water (0.066 mL) was added to a solution of [6-(4-{1-ethyl-1-[4-(3-hydroxy-4,4-dimethyl-pentyl)-3-methyl-phenyl]-propyl}-2-methyl-phenyl)-pyridin-3-yl]-acetic acid methyl ester (Example 62-(2); 17 mg, 0.033 mmol) in methanol (0.44 mL) at room temperature, and the mixture was stirred at room temperature for five hours and 30 minutes. The mixture was acidified with dilute hydrochloric acid aqueous solution, followed by extraction with ethyl acetate. The extract was dried over anhydrous magnesium sulfate and then concentrated under reduced pressure to give the title compound (16.6 mg, 100%).

$^1$H-NMR (chloroform-d): 0.65 (t, 6H, J=7.4 Hz), 0.90 (s, 9H), 1.52 (m, 1H), 1.80 (m, 1H), 2.11 (q, 4H, J=7.4 Hz), 2.23 (s, 3H), 2.28 (s, 3H), 2.57 (m, 1H), 2.88 (m, 1H), 3.27 (dd, 1H, J=10.2, 1.5 Hz), 3.73 (s, 2H), 6.9-7.1 (m, 6H), 7.71 (s, 1H), 8.52 (s, 2H).

MS (ESI+): 502 ([M+H]$^+$).

Example 63

Synthesis of [2-(4-{1-ethyl-1-[4-(3-hydroxy-4,4-dimethyl-pentyl)-3-methyl-phenyl]-propyl}-2-methyl-phenyl)-thiazol-4-yl]-acetic Acid

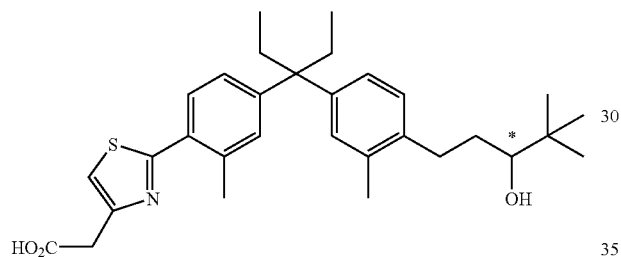

(1) Synthesis of {2-[4-(1-{4-[3-(t-butyl-dimethyl-silanyloxy)-4,4-dimethyl-pentyl]-3-methyl-phenyl}-1-ethyl-propyl)-2-methyl-phenyl]-thiazol-4-yl}-acetic Acid Ethyl Ester

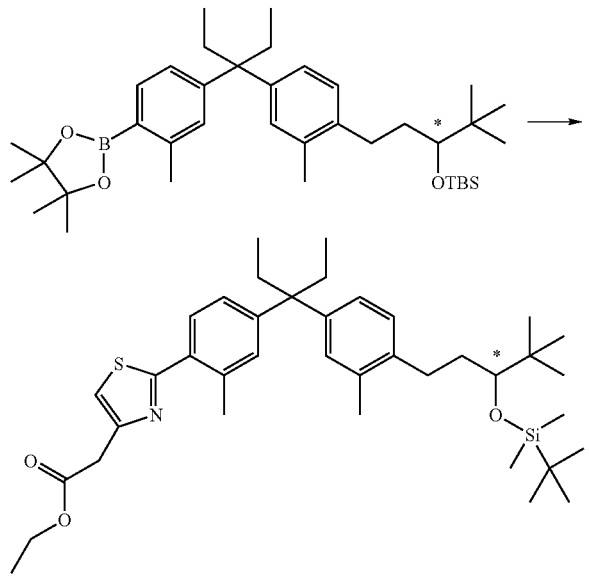

Degassed N,N-dimethylformamide (0.2 mL) was added to t-butyl-(1-{2-[4-(1-ethyl-1-{4-[4,4,5,5-tetramethyl-[1,3,2] dioxaborolan-2-yl]-3-methyl-phenyl}-propyl)-2-methyl-phenyl]-ethyl}-2,2-dimethyl-propoxy)dimethylsilane (Example 23-(1); 15.5 mg, 0.0249 mmol), (2-bromo-thiazol-4-yl)-acetic acid ethyl ester (Example 42; 6.4 mg, 0.026 mmol), tetrakis(triphenylphosphine)palladium (0) (4.7 mg, 0.0041 mmol) and potassium phosphate (9 mg, 0.04 mmol). After replacement with nitrogen, the mixture was heated while stirring at an external temperature of 96 to 104° C. for 11 hours. Water was added to the reaction mixture, followed by extraction with diethyl ether. The extract was dried over anhydrous magnesium sulfate and then concentrated under reduced pressure. The residue was purified by silica gel chromatography (hexane/dichloromethane=1/4) to give the title compound (9.7 mg, 60%).

$^1$H-NMR (chloroform-d): 0.08 (s, 3H), 0.12 (s, 3H), 0.64 (t, 6H, J=7.4 Hz), 0.89 (s, 9H), 0.95 (s, 9H), 1.29 (t, 3H, J=7.1 Hz), 1.59 (m, 1H), 1.79 (m, 1H), 2.10 (q, 4H, J=7.4 Hz), 2.24 (s, 3H), 2.41 (m, 1H), 2.52 (s, 3H), 2.77 (m, 1H), 3.35 (dd, 1H, J=6.9, 3 Hz), 3.89 (d, 2H, J=0.9 Hz), 4.21 (q, 2H, J=7.1 Hz), 6.86-7.13 (m, 5H), 7.21 (t, 1H, J=0.9 Hz), 7.56 (d, 1H, J=8.1 Hz).

(2) Synthesis of [2-(4-{1-ethyl-1-[4-(3-hydroxy-4,4-dimethyl-pentyl)-3-methyl-phenyl]-propyl}-2-methyl-phenyl)-thiazol-4-yl]-acetic Acid Methyl Ester

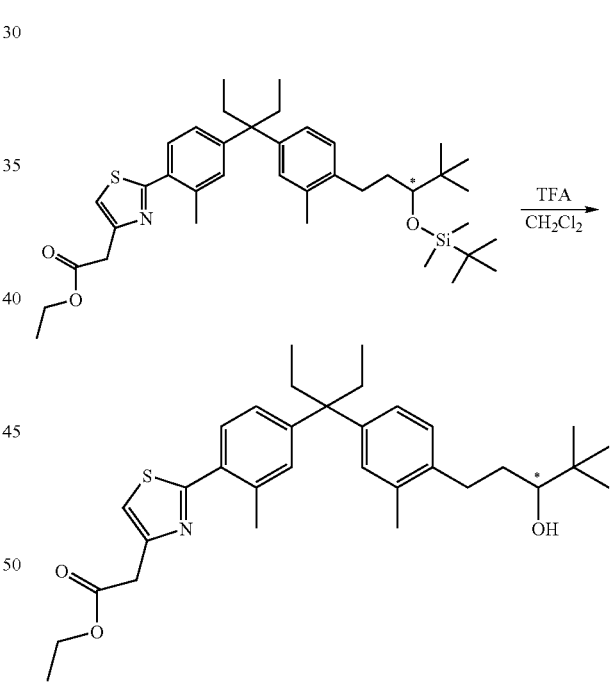

Trifluoroacetic acid (0.15 mL) was added to a solution of {2-[4-(1-{4-[3-(t-butyl-dimethyl-silanyloxy)-4,4-dimethyl-pentyl]-3-methyl-phenyl}-1-ethyl-propyl)-2-methyl-phenyl]-thiazol-4-yl}-acetic acid ethyl ester (Example 63-(1); 20.7 mg, 0.0318 mmol) in dichloromethane (0.75 mL) at room temperature, and the mixture was stirred at room temperature for one hour and 30 minutes. The solvent in the reaction solution was distilled off under reduced pressure. The residue was purified by silica gel chromatography (hexane/ethyl acetate=5/1) to give the title compound (15.9 mg, 93%).

¹H-NMR (chloroform-d): 0.63 (t, 6H, J=7.4 Hz), 0.90 (s, 9H), 1.29 (t, 3H, J=7.2 Hz), 1.52 (m, 1H), 1.81 (m, 1H), 2.10 (q, 4H, J=7.4 Hz), 2.26 (s, 3H), 2.51 (s, 3H), 2.58 (m, 1H), 2.88 (m, 1H), 3.26 (dd, 1H, J=10.5, 1.2 Hz), 3.90 (d, 2H, J=0.6 Hz), 4.21 (q, 2H, J=7.2 Hz), 6.91-7.12 (m, 5H), 7.21 (t, 1H, J=0.6 Hz), 7.54 (d, 1H, J=8.1 Hz).

(3) Synthesis of [2-(4-{1-ethyl-1-[4-(3-hydroxy-4,4-dimethyl-pentyl)-3-methyl-phenyl]-propyl}-2-methyl-phenyl)-thiazol-4-yl]-acetic Acid

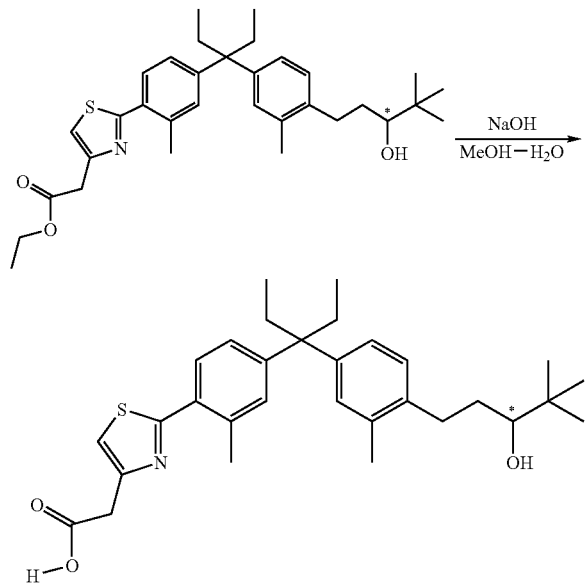

A mixed solution of a 6 N sodium hydroxide aqueous solution (0.02 mL) with water (0.06 mL) was added to a solution of [2-(4-{1-ethyl-1-[4-(3-hydroxy-4,4-dimethyl-pentyl)-3-methyl-phenyl]-propyl}-2-methyl-phenyl)-thiazol-4-yl]-acetic acid methyl ester (Example 63-(2); 15.9 mg, 0.0297 mmol) in methanol (0.4 mL) at room temperature, and the mixture was stirred at room temperature for 5.5 hours. The mixture was acidified with dilute hydrochloric acid aqueous solution, followed by extraction with ethyl acetate. The extract was dried over anhydrous magnesium sulfate and then concentrated under reduced pressure to give the title compound (15 mg, 100%).

¹H-NMR (chloroform-d): 0.65 (t, 6H, J=7.4 Hz), 0.90 (s, 9H), 1.54 (m, 1H), 1.80 (m, 1H), 2.12 (q, 4H, J=7.4 Hz), 2.28 (s, 3H), 2.55 (s, 3H), 2.57 (m, 1H), 2.89 (m, 1H), 3.26 (dd, 1H, J=10.5, 1.0 Hz), 3.93 (d, 2H, J=1 Hz), 6.92-7.12 (m, 5H), 7.15 (t, 1H, J=1 Hz), 7.58 (d, 1H, J=8.4 Hz).

MS (ESI+): 508 ([M+H]⁺).

Example 64

Synthesis of [2-(4-{1-ethyl-1-[4-(3-hydroxy-4,4-dimethyl-pentyl)-3-methyl-phenyl]-propyl}-2-methyl-phenyl)-pyrimidin-5-yl]-acetic Acid

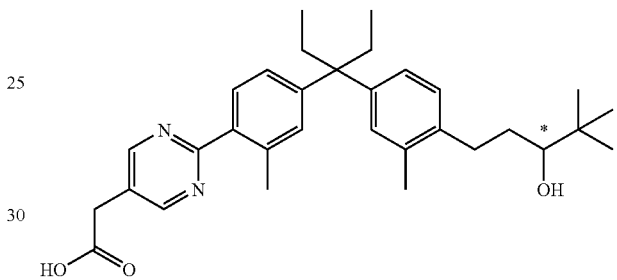

(1) Synthesis of {2-[4-(1-{4-[3-(t-butyl-dimethyl-silanyloxy)-4,4-dimethyl-pentyl]-3-methyl-phenyl}-1-ethyl-propyl)-2-methyl-phenyl]-pyrimidin-5-yl}-acetic Acid Ethyl Ester

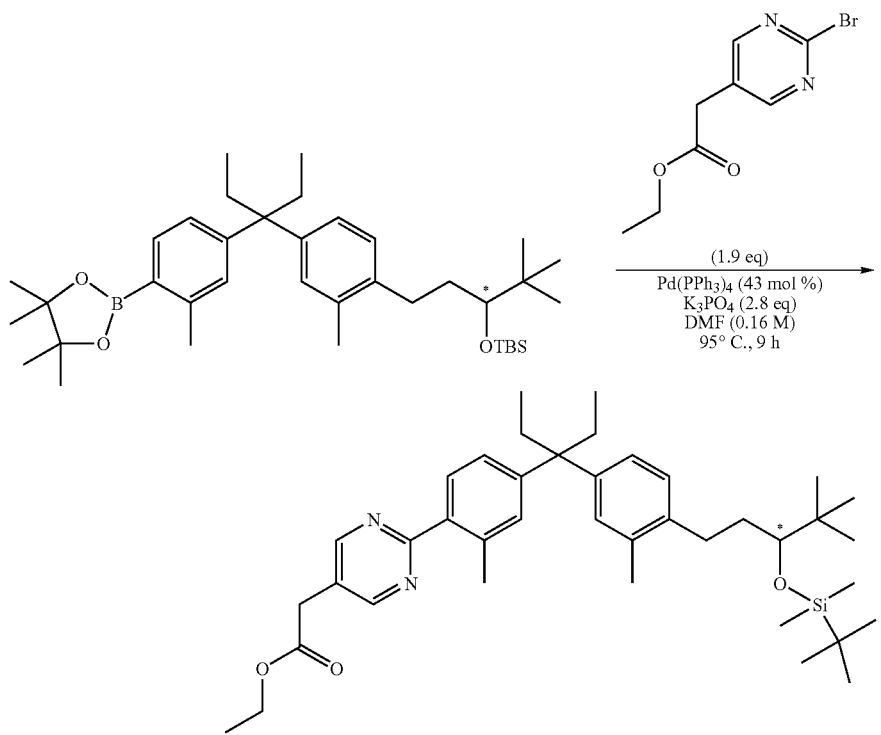

Degassed N,N-dimethylformamide (0.30 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 30.0 mg, 0.0494 mmol), 2-bromopyrimidine-5-acetic acid ethyl ester (Example 43-(3); 22.9 mg, 0.027 mmol), tetrakis(triphenylphosphine)palladium (0) (24.7 mg, 0.021 mmol) and potassium phosphate (29.3 mg, 0.138 mmol). After replacement with nitrogen, the mixture was heated while stirring at an external temperature of 91 to 100° C. for nine hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=10/1) to give the title compound (15 mg, 45%).

$^1$H-NMR (chloroform-d): 0.08 (s, 3H), 0.12 (s, 3H), 0.65 (t, 6H, J=7.4 Hz), 0.89 (s, 9H), 0.95 (s, 9H), 1.30 (t, 3H, J=7.2 Hz), 1.60 (m, 1H), 1.79 (m, 1H), 2.12 (q, 4H, J=7.4 Hz), 2.24 (s, 3H), 2.43 (m, 1H), 2.51 (s, 3H), 2.77 (m, 1H), 3.35 (dd, 1H, J=7.2, 3.6 Hz), 3.66 (s, 2H), 4.22 (q, 2H, J=7.2 Hz), 6.90-7.02 (m, 3H), 7.08-7.14 (m, 2H), 7.68 (d, 1H, J=8.4 Hz), 8.75 (s, 2H).

(2) Synthesis of [2-(4-{1-ethyl-1-[4-(3-hydroxy-4,4-dimethyl-pentyl)-3-methyl-phenyl]-propyl}-2-methyl-phenyl)-pyrimidin-5-yl]-acetic Acid Ethyl Ester

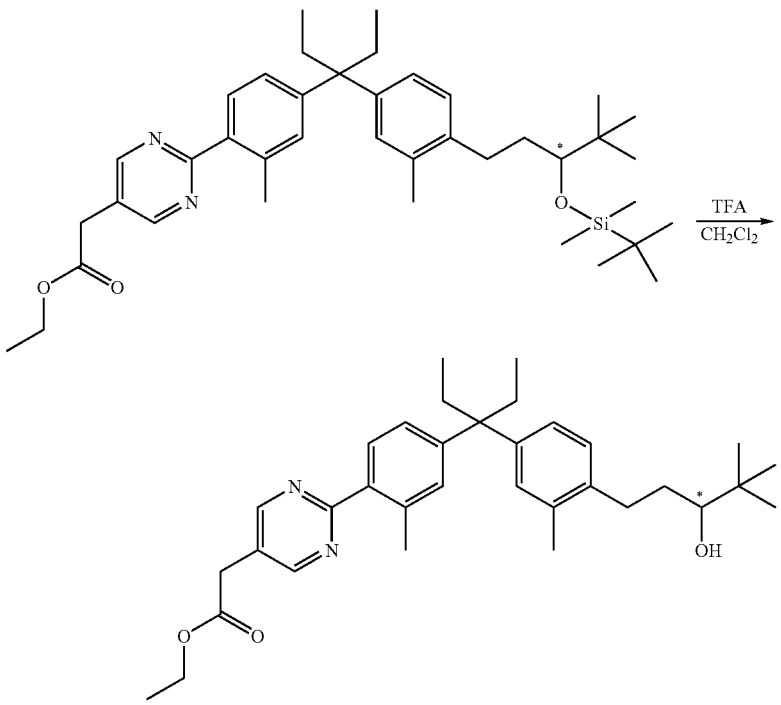

Trifluoroacetic acid (0.13 mL) was added to a solution of {2-[4-(1-{4-[3-(t-butyl-dimethyl-silanyloxy)-4,4-dimethyl-pentyl]-3-methyl-phenyl}-1-ethyl-propyl)-2-methyl-phenyl]-pyrimidin-5-yl}-acetic acid ethyl ester (Example 64-(1); 19.4 mg, 0.030 mmol) in dichloromethane (0.74 mL) at room temperature, and the mixture was stirred at room temperature for one hour. The solvent in the reaction solution was distilled off under reduced pressure, and the residue was diluted with diethyl ether. The mixture was adjusted to pH 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=2/1) to give the title compound (15.0 mg, 94%).

$^1$H-NMR (chloroform-d): 0.65 (t, 6H, J=7.4 Hz), 0.91 (s, 9H), 1.30 (t, 3H, J=7.2 Hz), 1.53 (m, 1H), 1.81 (m, 1H), 2.12 (q, 4H, J=7.4 Hz), 2.26 (s, 3H), 2.51 (s, 3H), 2.58 (m, 1H), 2.88 (m, 1H), 3.25 (dd, 1H, J=10.5, 1.5 Hz), 3.66 (s, 2H), 4.22 (q, 2H, J=7.2 Hz), 6.91-7.12 (m, 5H), 7.68 (d, 1H, J=8.4 Hz), 8.75 (s, 2H).

(3) Synthesis of [2-(4-{1-ethyl-1-[4-(3-hydroxy-4,4-dimethyl-pentyl)-3-methyl-phenyl]-propyl}-2-methyl-phenyl)-pyrimidin-5-yl]-acetic Acid

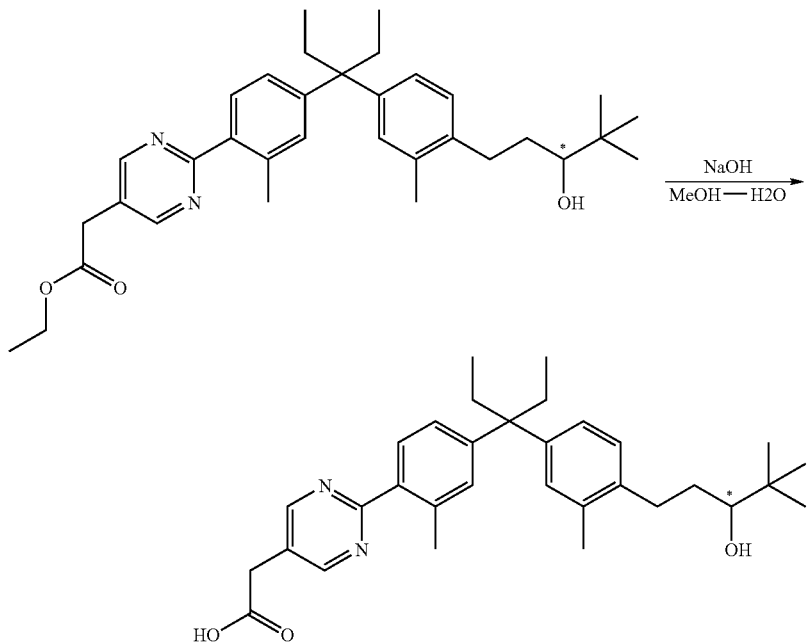

A 2 N sodium hydroxide aqueous solution (0.06 mL) was added to a solution of [2-(4-{1-ethyl-1-[4-(3-hydroxy-4,4-dimethyl-pentyl)-3-methyl-phenyl]-propyl}-2-methyl-phenyl)-pyrimidin-5-yl]-acetic acid ethyl ester (Example 64-(2); 15.0 mg, 0.0283 mmol) in methanol (0.38 mL) at room temperature, and the mixture was stirred at room temperature for three hours. The mixture was acidified with dilute hydrochloric acid aqueous solution, followed by extraction with ethyl acetate. The extract was dried over anhydrous magnesium sulfate and then concentrated under reduced pressure to give the title compound (14.5 mg, 100%).

$^1$H-NMR (chloroform-d): 0.65 (t, 6H, J=7.4 Hz), 0.90 (s, 9H), 1.52 (m, 1H), 1.81 (m, 1H), 2.12 (q, 4H, J=7.4 Hz), 2.26 (s, 3H), 2.50 (s, 3H), 2.57 (m, 1H), 2.87 (m, 1H), 3.26 (dd, 1H, J=10.2, 1.5 Hz), 3.71 (s, 2H), 6.9-7.15 (m, 5H), 7.66 (d, 1H, J=9.0 Hz), 8.77 (s, 2H).

MS (ESI+): 503 ([M+H]$^+$).

Example 65

Synthesis of (4'-{1-ethyl-1-[4-(3-hydroxy-4,4-dimethyl-pentyl)-3-methyl-phenyl]-propyl}-2'-methyl-biphenyl-4-yl)-acetic Acid

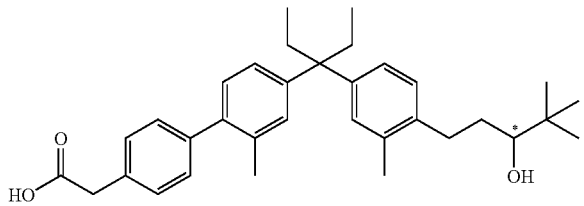

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic Acid Methyl Ester

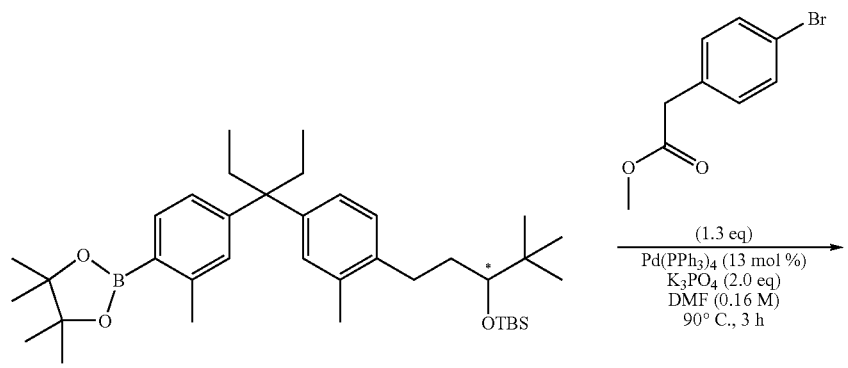

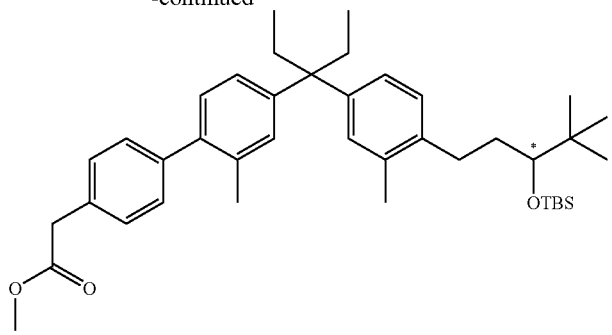

Degassed N,N-dimethylformamide (0.37 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 35.3 mg, 0.0582 mmol), 4-bromo-phenyl-acetic acid methyl ester (Tetrahedron Letters 44 (2003) 331-334; 18.6 mg, 0.812 mmol), tetrakis(triphenylphosphine)palladium (0) (9.1 mg, 0.0079 mmol) and potassium phosphate (26.9 mg, 0.127 mmol). After replacement with nitrogen, the mixture was heated while stirring at an external temperature of 87 to 94° C. for three hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=50/1) to give the title compound (31.5 mg, 86%).

$^1$H-NMR (chloroform-d): 0.09 (s, 3H), 0.13 (s, 3H), 0.67 (t, 6H, J=7.2 Hz), 0.90 (s, 9H), 0.95 (s, 9H), 1.60 (m, 1H), 1.81 (m, 1H), 2.12 (q, 4H, J=7.2 Hz), 2.24 (s, 3H), 2.28 (s, 3H), 2.44 (m, 1H), 2.79 (m, 1H), 3.36 (dd, 1H, J=7.0, 3.0 Hz), 3.68 (s, 2H), 3.73 (s, 3H), 6.94-7.10 (m, 6H), 7.30 (s, 4H).

(2) Synthesis of (4'-{1-ethyl-1-[4-(3-hydroxy-4,4-dimethyl-pentyl)-3-methyl-phenyl]-propyl}-2'-methyl-biphenyl-4-yl)-acetic Acid Methyl Ester

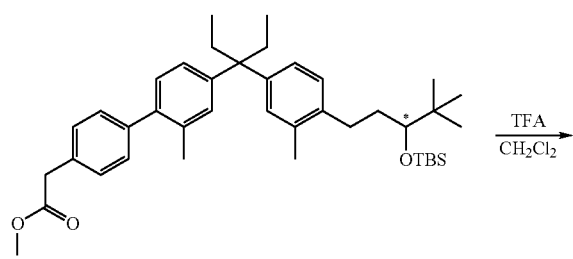

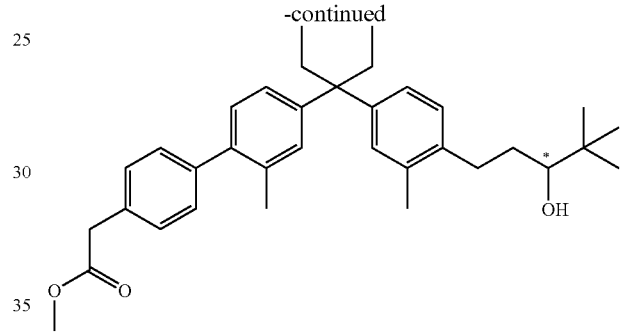

Trifluoroacetic acid (0.22 mL) was added to a solution of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic acid methyl ester (Example 65-(1); 31.5 mg, 0.050 mmol) in dichloromethane (1.2 mL) at room temperature, and the mixture was stirred at room temperature for one hour. The solvent in the reaction solution was distilled off under reduced pressure, and the residue was diluted with diethyl ether. The mixture was adjusted to pH 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=5/1) to give the title compound (21.5 mg, 84%).

$^1$H-NMR (chloroform-d): 0.66 (t, 6H, J=7.4 Hz), 0.91 (s, 9H), 1.54 (m, 1H), 1.82 (m, 1H), 2.12 (q, 4H, J=7.4 Hz), 2.24 (s, 3H), 2.29 (s, 3H), 2.58 (m, 1H), 2.89 (m, 1H), 3.26 (dd, 1H, J=10.2, 1.5 Hz), 3.67 (s, 2H), 3.73 (s, 3H), 6.95-7.10 (m, 6H), 7.30 (s, 4H).

(3) Synthesis of (4'-{1-ethyl-1-[4-(3-hydroxy-4,4-dimethyl-pentyl)-3-methyl-phenyl]-propyl}-2'-methyl-biphenyl-4-yl)-acetic Acid

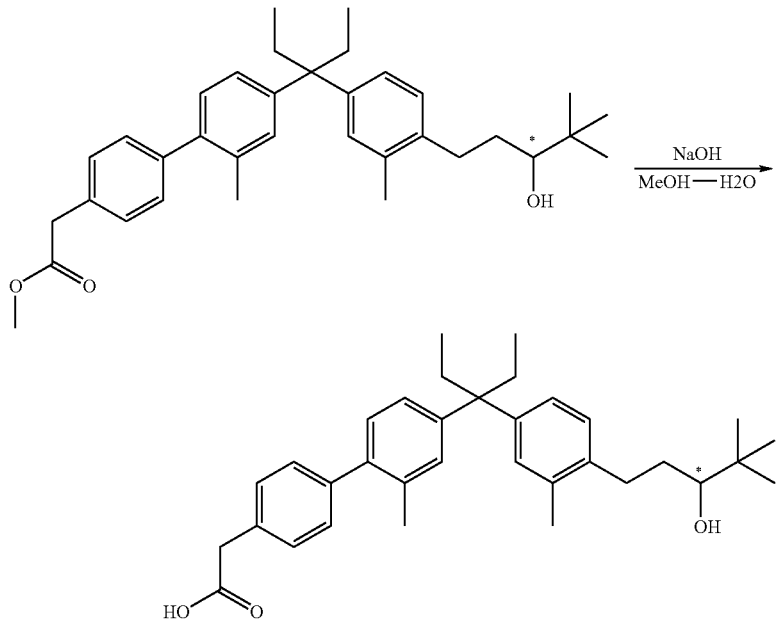

A 2 N sodium hydroxide aqueous solution (0.09 mL) was added to a solution of (4'-{1-ethyl-1-[4-(3-hydroxy-4,4-dimethyl-pentyl)-3-methyl-phenyl]-propyl}-2'-methyl-biphenyl-4-yl)acetic acid methyl ester (Example 65-(2); 21.5 mg, 0.0437 mmol) in methanol (0.6 mL) at room temperature, and the mixture was stirred at room temperature for three hours. The mixture was acidified with dilute hydrochloric acid aqueous solution, followed by extraction with ethyl acetate. The extract was dried over anhydrous magnesium sulfate and then concentrated under reduced pressure to give the title compound (20 mg, 91%).

$^1$H-NMR (chloroform-d): 0.66 (t, 6H, J=7.4 Hz), 0.91 (s, 9H), 1.54 (m, 1H), 1.82 (m, 1H), 2.12 (q, 4H, J=7.4 Hz), 2.23 (s, 3H), 2.29 (s, 3H), 2.58 (m, 1H), 2.88 (m, 1H), 3.27 (dd, 1H, J=10.2, 1.8 Hz), 3.71 (s, 2H), 6.95-7.10 (m, 6H), 7.31 (s, 4H); MS (ESI+): 518 ([M+NH$_4$]$^+$).

Example 66

Synthesis of (4'-{1-ethyl-1-[4-(3-hydroxy-4,4-dimethyl-pentyl)-3-methyl-phenyl]-propyl}-2'-methyl-biphenyl-3-yl)-acetic Acid

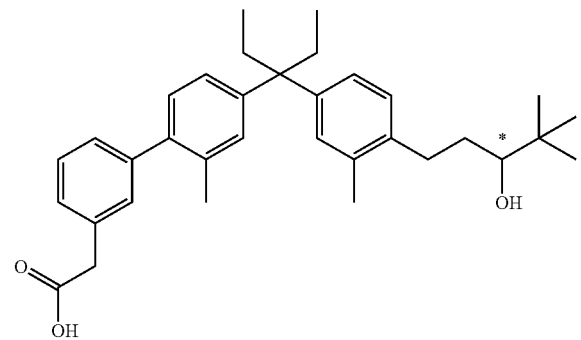

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-acetic Acid Methyl Ester

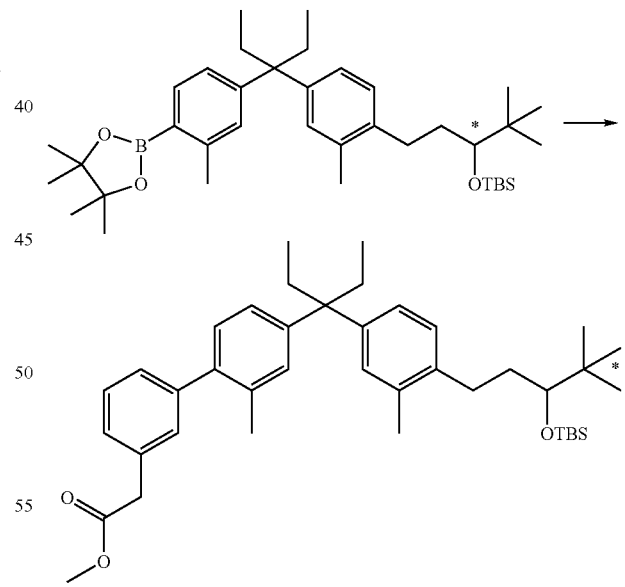

N,N-Dimethylformamide (0.7 mL) was added to 2-[4-(1-{4-[3-(t-butyl-dimethyl-silanyloxy)-4,4-dimethyl-pentyl]-3-methyl-phenyl}-1-ethyl-propyl)-2-methyl-phenyl]-4,4,5,5-tetramethyl-[1,3,2]dioxaborolane (Example 24-(1); 70 mg, 0.116 mmol), (3-bromo-phenyl)acetic acid methyl ester (Tetrahedron Letters 44 (2003) 331-334; 53 mg, 0.232 mmol), tetrakis(triphenylphosphine)palladium (0) (26.8 mg, 0.023 mmol) and potassium phosphate (63.9 mg, 0.30 mmol). The mixture was stirred with microwave heating at 140° C. for seven minutes in a nitrogen atmosphere. The reaction mixture was concentrated under reduced pressure. The residue was purified by preparative TLC (hexane/ethyl acetate=10/1) to give the title compound (36 mg, 50%).

$^1$H-NMR (chloroform-d): 0.07 (s, 3H), 0.11 (s, 3H), 0.65 (t, 6H, J=7.2 Hz), 0.88 (s, 9H), 0.94 (s, 3H), 1.56 (m, 1H), 1.80 (m, 1H), 2.10 (q, 4H, J=7.2 Hz), 2.23 (s, 3H), 2.26 (s, 3H), 2.42 (m, 1H), 2.76 (m, 1H), 3.35 (m, 1H), 3.65 (s, 2H), 3.69 (s, 3H), 6.92-7.34 (m, 10H).

(2) Synthesis of (4'-{1-ethyl-1-[4-(3-hydroxy-4,4-dimethyl-pentyl)-3-methyl-phenyl]-propyl}-2'-methyl-biphenyl-3-yl)-acetic Acid

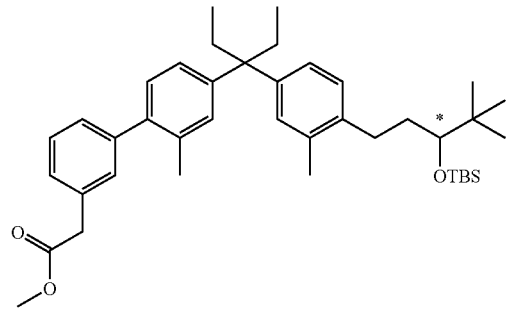

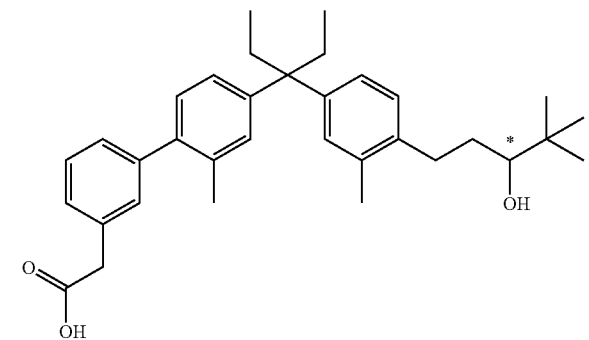

[4'-(1-{4-[3-(t-Butyl-dimethyl-silanyloxy)-4,4-dimethyl-pentyl]-3-methyl-phenyl}-1-ethyl-propyl)-2'-methyl-biphenyl-3-yl]-acetic acid methyl ester (Example 66-(1); 36 mg, 0.057 mmol) was dissolved in dichloromethane/trifluoroacetic acid=1/5 (1 mL), and the solution was stirred at room temperature for three hours. The reaction mixture was concentrated under reduced pressure, and then the residue was purified by silica gel chromatography (hexane only to hexane/ethyl acetate=1/1). The product was dissolved in methanol/tetrahydrofuran=1/1 (1 mL). A 1 N sodium hydroxide aqueous solution (0.1 mL) was added, and the mixture was stirred at room temperature for one hour. A 30% sodium dihydrogenphosphate aqueous solution (0.3 mL) was added to the reaction mixture, and then the reaction mixture was concentrated under reduced pressure. The residue was purified by preparative TLC (hexane/ethyl acetate=1/1) to give the title compound (23 mg, 80%).

$^1$H-NMR (chloroform-d): 0.64 (t, 6H, J=7.2 Hz), 0.89 (s, 9H), 1.52 (m, 1H), 1.80 (m, 1H), 2.09 (q, 4H, J=7.2 Hz), 2.20 (s, 3H), 2.27 (s, 3H), 2.55 (m, 1H), 2.85 (m, 1H), 3.25 (m, 1H), 3.65 (s, 2H), 6.92-7.32 (m, 10H); MS (ESI+): 518 ([M+NH$_4$]$^+$).

Example 67

Synthesis of (4'-{1-ethyl-1-[4-(3-hydroxy-4,4-dimethyl-pentyl)-3-methyl-phenyl]-propyl}-3-fluoro-2'-methyl-biphenyl-4-yl)-acetic Acid

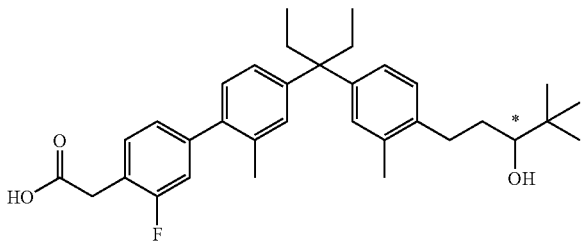

(1) Synthesis of [4'-(1-{4-[3-(t-butyl-dimethyl-silanyloxy)-4,4-dimethyl-pentyl]-3-methyl-phenyl}-1-ethyl-propyl)-3-fluoro-2'-methyl-biphenyl-4-yl]-acetic Acid Methyl Ester

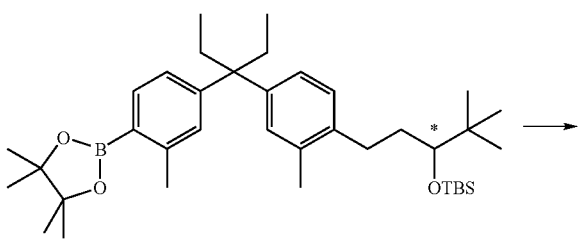

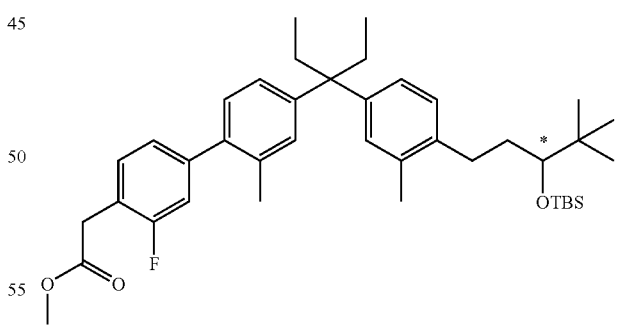

The title compound (39%) was obtained by the same method as in Example 66-(1) using (4-chloro-2-fluorophenyl)acetic acid methyl ester (Example 40) as a starting material.

$^1$H-NMR (chloroform-d): 0.08 (s, 3H), 0.11 (s, 3H), 0.64 (t, 6H, J=7.1 Hz), 0.88 (s, 9H), 0.94 (s, 9H), 1.56 (m, 1H), 1.80 (m, 1H), 2.09 (q, 4H, J=7.2 Hz), 2.24 (s, 3H), 2.26 (s, 3H), 2.42 (m, 1H), 2.78 (m, 1H), 3.34 (dd, 1H, J=1.5, 10.2 Hz), 3.71 (s, 2H), 3.73 (s, 3H), 6.93-7.29 (m, 9H).

(2) Synthesis of (4'-{1-ethyl-1-[4-(3-hydroxy-4,4-dimethyl-pentyl)-3-methyl-phenyl]-propyl}-3-fluoro-2'-methyl-biphenyl-4-yl)-acetic Acid

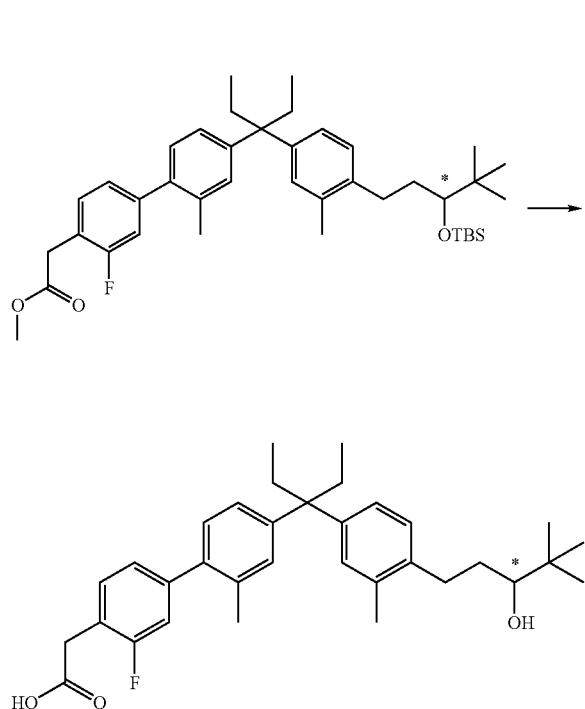

The title compound (71%) was obtained by the same method as in Example 66-(2) using [4'-(1-{4-[3-(t-butyl-dimethyl-silanyloxy)-4,4-dimethyl-pentyl]-3-methyl-phenyl}-1-ethyl-propyl)-3-fluoro-2'-methyl-biphenyl-4-yl]-acetic acid methyl ester (Example 67-(1)) as a starting material.

$^1$H-NMR (chloroform-d): 0.64 (t, 6H, J=7.1 Hz), 0.89 (s, 9H), 1.52 (m, 1H), 1.80 (m, 1H), 2.09 (q, 4H, J=7.1 Hz), 2.21 (s, 3H), 2.27 (s, 3H), 2.56 (m, 1H), 2.85 (m, 1H), 3.25 (dd, 1H, J=1.5, 10.2 Hz), 3.72 (s, 2H), 6.92-7.07 (m, 8H); MS (ESI+): 536 ([M+NH$_4$]$^+$).

Example 68

Synthesis of [6-(4-{1-ethyl-1-[4-(3-hydroxy-4,4-dimethyl-pentyl)-3-methyl-phenyl]-propyl}-2-methyl-phenyl)-pyridin-3-yl]-acetic Acid

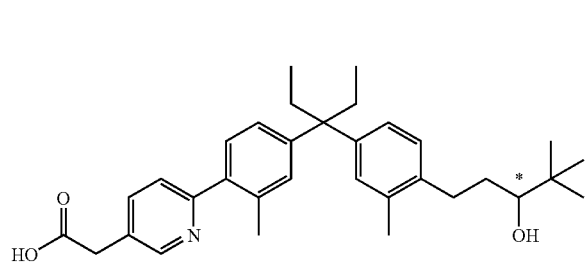

(1) Synthesis of {6-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic Acid Ethyl Ester

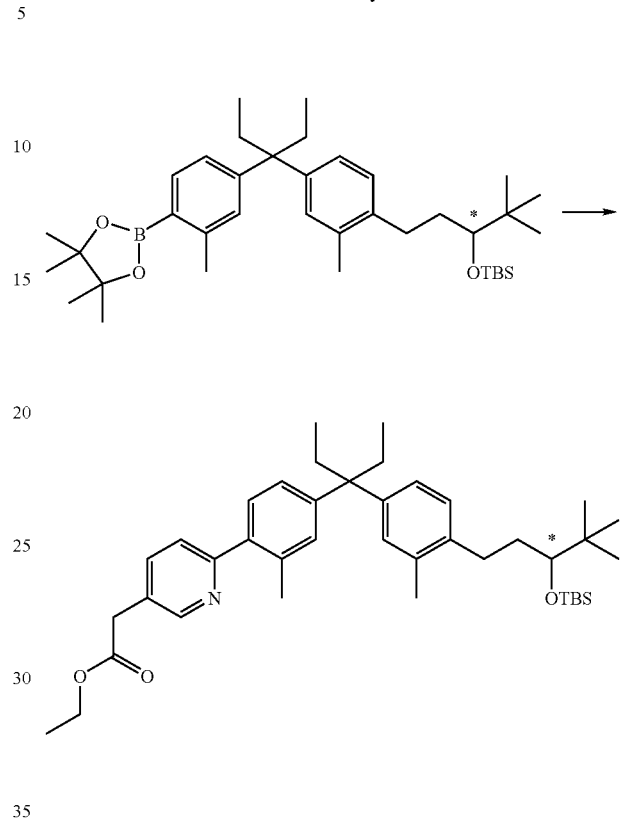

The title compound (51%) was obtained by the same method as in Example 66-(1) using (6-chloro-pyridin-3-yl) acetic acid ethyl ester as a starting material.

$^1$H-NMR (chloroform-d): 0.06 (s, 3H), 0.11 (s, 3H), 0.64 (t, 6H, J=7.1 Hz), 0.88 (s, 9H), 0.94 (s, 9H), 1.28 (t, 3H, J=7.1 Hz), 1.60 (m, 1H), 1.78 (m, 1H), 2.07 (q, 4H, J=7.1 Hz), 2.24 (s, 3H), 2.32 (s, 3H), 2.42 (m, 1H), 2.78 (m, 1H), 3.33 (m, 1H), 3.66 (s, 2H), 4.19 (q, 2H, J=7.1 Hz), 6.95-7.07 (m, 5H), 7.23 (d, 1H, J=7.9 Hz), 7.73 (d, 1H, J=8.1 Hz), 7.65 (m, 1H), 8.56 (d, 1H, J=1.8 Hz).

(2) Synthesis of [6-(4-{1-ethyl-1-[4-(3-hydroxy-4,4-dimethyl-pentyl)-3-methyl-phenyl]-propyl}-2-methyl-phenyl)-pyridin-3-yl]-acetic Acid

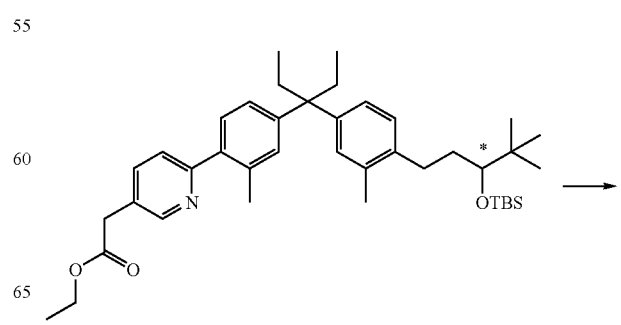

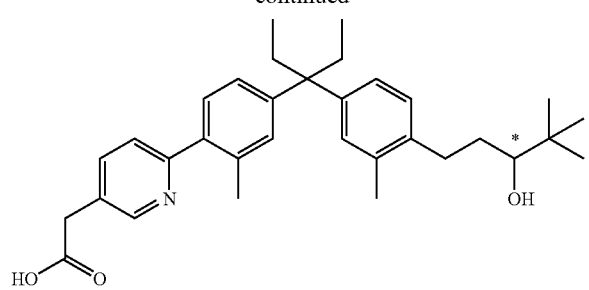

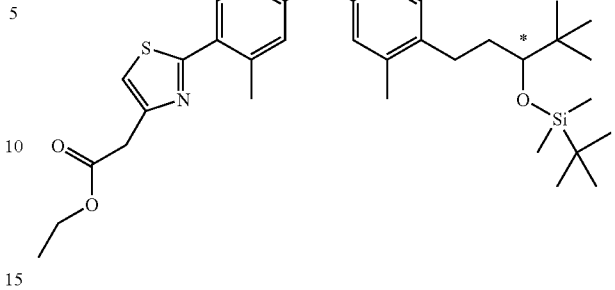

The title compound (83%) was obtained by the same method as in Example 66-(2) using {6-[4-(1-{4-[3-(t-butyl-dimethyl-silanyloxy)-4,4-dimethyl-pentyl]-3-methyl-phenyl}-1-ethyl-propyl)-2-methyl-phenyl]-pyridin-3-yl}-acetic acid ethyl ester (Example 68-(1)) as a starting material.

¹H-NMR (chloroform-d): 0.63 (t, 6H, J=7.1 Hz), 0.88 (s, 9H), 1.52 (m, 1H), 1.80 (m, 1H), 2.12 (q, 4H, J=7.1 Hz), 2.25 (s, 3H), 2.27 (s, 3H), 2.57 (m, 1H), 2.85 (m, 1H), 3.23 (m, 1H), 3.65 (s, 2H), 6.95-7.07 (m, 5H), 7.23 (d, 1H, J=7.9 Hz), 7.73 (d, 1H, J=8.1 Hz), 7.68 (m, 1H), 8.58 (d, 1H, J=1.8 Hz); MS (ESI+): 502 ([M+H]⁺).

Example 69

Synthesis of [2-(4-{1-ethyl-1-[4-(3-hydroxy-4,4-dimethyl-pentyl)-3-methyl-phenyl]-propyl}-2-methyl-phenyl)-thiazol-4-yl]-acetic Acid

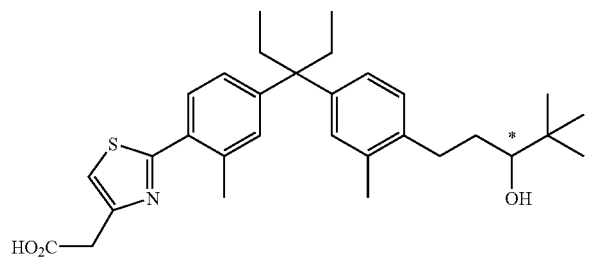

(1) Synthesis of {2-[4-(1-{4-[3-(t-butyl-dimethyl-silanyloxy)-4,4-dimethyl-pentyl]-3-methyl-phenyl}-1-ethyl-propyl)-2-methyl-phenyl]-thiazol-4-yl}-acetic Acid Ethyl Ester

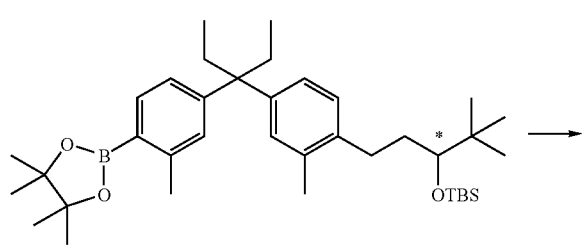

Degassed N,N-dimethylformamide (0.53 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 50.4 mg, 0.083 mmol), 2-bromothiazole-4-acetic acid ethyl ester (Example 42; 37.8 mg, 0.151 mmol), tetrakis(triphenylphosphine)palladium (0) (12.7 mg, 0.011 mmol) and potassium phosphate (50 mg, 0.24 mmol). After replacement with nitrogen, the mixture was heated while stirring at an external temperature of 96 to 104° C. for 12 hours. Water was added to the reaction mixture, followed by extraction with diethyl ether. The extract was dried over anhydrous magnesium sulfate and then concentrated under reduced pressure. The residue was purified by silica gel chromatography (hexane/dichloromethane=1/2) to give the title compound (44.4 mg, 82%).

¹H-NMR (chloroform-d): 0.08 (s, 3H), 0.12 (s, 3H), 0.64 (t, 6H, J=7.4 Hz), 0.89 (s, 9H), 0.95 (s, 9H), 1.29 (t, 3H, J=7.1 Hz), 1.59 (m, 1H), 1.79 (m, 1H), 2.10 (q, 4H, J=7.4 Hz), 2.24 (s, 3H), 2.41 (m, 1H), 2.52 (s, 3H), 2.77 (m, 1H), 3.35 (dd, 1H, J=6.9, 3.3 Hz), 3.89 (d, 2H, J=0.9 Hz), 4.21 (q, 2H, J=7.1 Hz), 6.86-7.13 (m, 5H), 7.21 (t, 1H, J=0.9 Hz), 7.56 (d, 1H, J=8.1 Hz).

(2) Synthesis of [2-(4-{1-ethyl-1-[4-(3-hydroxy-4,4-dimethyl-pentyl)-3-methyl-phenyl]-propyl}-2-methyl-phenyl)-thiazol-4-yl]-acetic Acid Methyl Ester

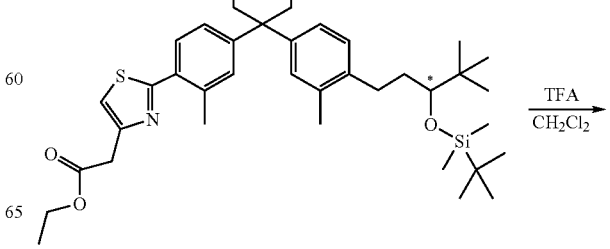

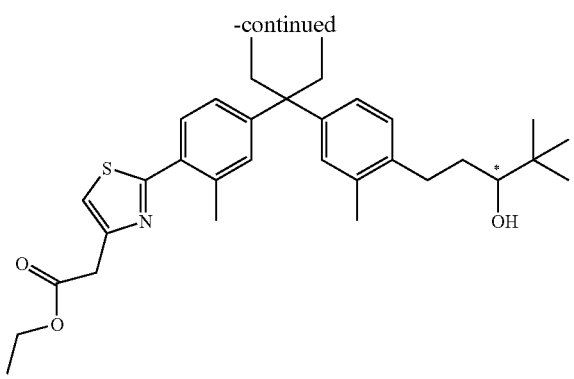

Trifluoroacetic acid (0.30 mL) was added to a solution of {2-[4-(1-{4-[3-(t-butyl-dimethyl-silanyloxy)-4,4-dimethyl-pentyl]-3-methyl-phenyl}-1-ethyl-propyl)-2-methyl-phenyl]-thiazol-4-yl}-acetic acid ethyl ester (Example 69-(1); 44.4 mg, 0.0683 mmol) in dichloromethane (1.7 mL) at room temperature, and the mixture was stirred at room temperature for one hour. The solvent in the reaction solution was distilled off under reduced pressure. The residue was purified by silica gel chromatography (hexane/ethyl acetate=4/1) to give the title compound (34.0 mg, 93%).

$^1$H-NMR (chloroform-d): 0.64 (t, 6H, J=7.4 Hz), 0.91 (s, 9H), 1.29 (t, 3H, J=7.2 Hz), 1.52 (m, 1H), 1.81 (m, 1H), 2.10 (q, 4H, J=7.4 Hz), 2.27 (s, 3H), 2.52 (s, 3H), 2.58 (m, 1H), 2.88 (m, 1H), 3.25 (dd, 1H, J=10.5, 1.2 Hz), 3.89 (d, 2H, J=0.6 Hz), 4.21 (q, 2H, J=7.2 Hz), 6.91-7.12 (m, 5H), 7.21 (t, 1H, J=0.6 Hz), 7.54 (d, 1H, J=8.1 Hz).

(3) Synthesis of [2-(4-{1-ethyl-1-[4-(3-hydroxy-4,4-dimethyl-pentyl)-3-methyl-phenyl]-propyl}-2-methyl-phenyl)-thiazol-4-yl]-acetic Acid

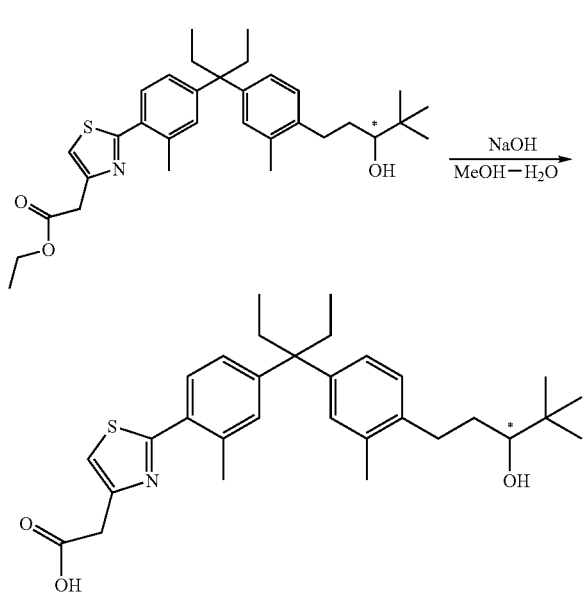

A 2 N sodium hydroxide aqueous solution (0.12 mL) was added to a solution of [2-(4-{1-ethyl-1-[4-(3-hydroxy-4,4-dimethyl-pentyl)-3-methyl-phenyl]-propyl}-2-methyl-phenyl)-thiazol-4-yl]-acetic acid ethyl ester (Example 69-(2); 34.0 mg, 0.0635 mmol) in methanol (0.85 mL) at room temperature, and the mixture was stirred at room temperature for 4.5 hours. The mixture was acidified with dilute hydrochloric acid aqueous solution, followed by extraction with ethyl acetate. The extract was dried over anhydrous magnesium sulfate and then concentrated under reduced pressure to give the title compound (32 mg, 100%).

$^1$H-NMR (chloroform-d): 0.65 (t, 6H, J=7.4 Hz), 0.91 (s, 9H), 1.54 (m, 1H), 1.80 (m, 1H), 2.12 (q, 4H, J=7.4 Hz), 2.28 (s, 3H), 2.55 (s, 3H), 2.58 (m, 1H), 2.89 (m, 1H), 3.26 (dd, 1H, J=10.5, 1.0 Hz), 3.93 (d, 2H, J=0.9 Hz), 6.92-7.12 (m, 5H), 7.15 (t, 1H, J=0.9 Hz), 7.58 (d, 1H, J=8.4 Hz).

MS (ESI+): 508 ([M+H]$^+$).

Example 70

Synthesis of [2-(4-{1-ethyl-1-[4-(3-hydroxy-4,4-dimethyl-pentyl)-3-methyl-phenyl]-propyl}-2-methyl-phenyl)-pyrimidin-5-yl]-acetic Acid

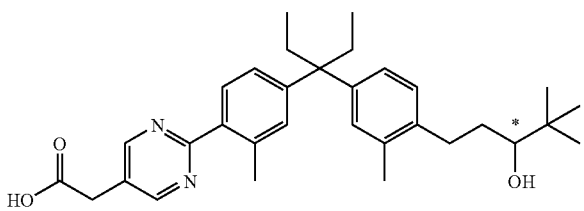

(1) Synthesis of {2-[4-(1-{4-[3-(t-butyl-dimethyl-silanyloxy)-4,4-dimethyl-pentyl]-3-methyl-phenyl}-1-ethyl-propyl)-2-methyl-phenyl]-pyrimidin-5-yl}-acetic Acid Ethyl Ester

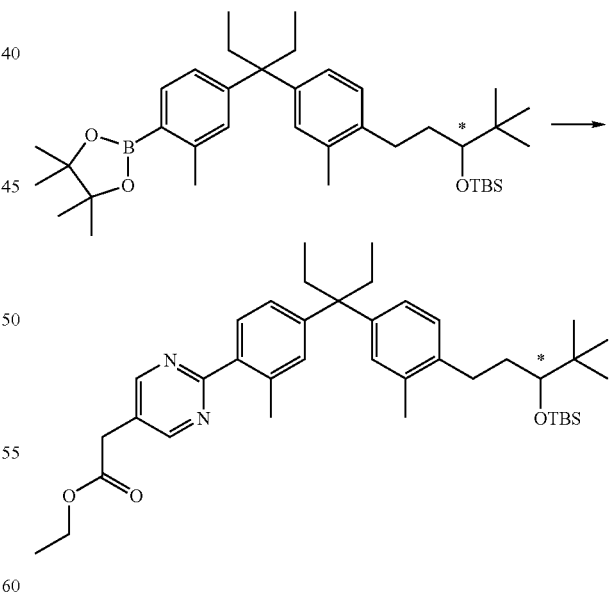

The title compound (39%) was obtained by the same method as in Example 66-(1) using (2-bromo-pyrimidin-5-yl)acetic acid ethyl ester (Example 43-(3)) as a starting material.

$^1$H-NMR (chloroform-d): 0.07 (s, 3H), 0.11 (s, 3H), 0.62 (t, 6H, J=7.1 Hz), 0.88 (s, 9H), 0.93 (s, 9H), 1.29 (t, 3H, J=7.0 Hz), 1.52 (m, 1H), 1.78 (m, 1H), 2.11 (q, 4H, J=7.1 Hz), 2.23

(s, 3H), 2.42 (m, 1H), 2.50 (s, 3H), 2.78 (m, 1H), 3.23 (m, 1H), 3.65 (s, 2H), 4.21 (q, 2H, J=7.0 Hz), 6.92-7.01 (m, 5H), 7.66 (d, 1H, J=8.8 Hz), 8.75 (s, 2H).

(2) Synthesis of [2-(4-{1-ethyl-1-[4-(3-hydroxy-4,4-dimethyl-pentyl)-3-methyl-phenyl]-propyl}-2-methyl-phenyl)-pyrimidin-5-yl]-acetic Acid

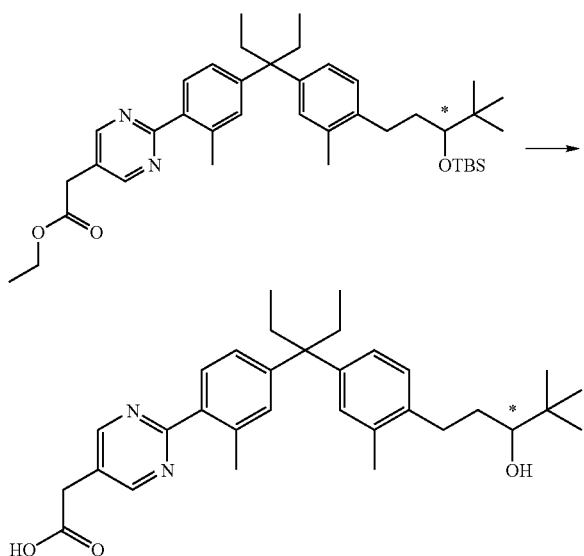

The title compound (64%) was obtained by the same method as in Example 66-(2) using {2-[4-(1-{4-[3-(t-butyl-dimethyl-silanyloxy)-4,4-dimethyl-pentyl]-3-methyl-phenyl}-1-ethyl-propyl)-2-methyl-phenyl]-pyrimidin-5-yl}-acetic acid ethyl ester (Example 70-(1)) as a starting material.

$^1$H-NMR (chloroform-d): 0.62 (t, 6H, J=7.1 Hz), 0.88 (s, 9H), 1.52 (m, 1H), 1.78 (m, 1H), 2.10 (q, 4H, J=7.1 Hz), 2.24 (s, 3H), 2.46 (s, 3H), 3.23 (m, 1H), 3.66 (s, 2H), 6.90-7.10 (m, 5H), 7.63 (d, 1H, J=8.4 Hz), 8.75 (s, 2H);

MS (ESI+): 503 ([M+H]$^+$).

Example 71

Synthesis of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)-acetic Acid

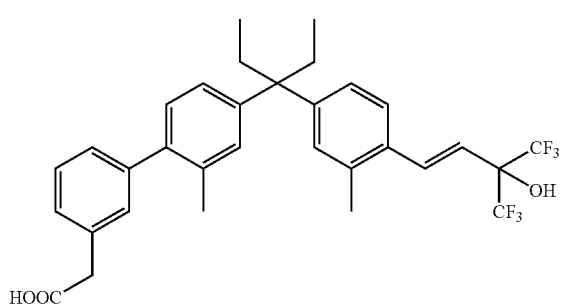

(1) Synthesis of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)-acetic Acid Methyl Ester

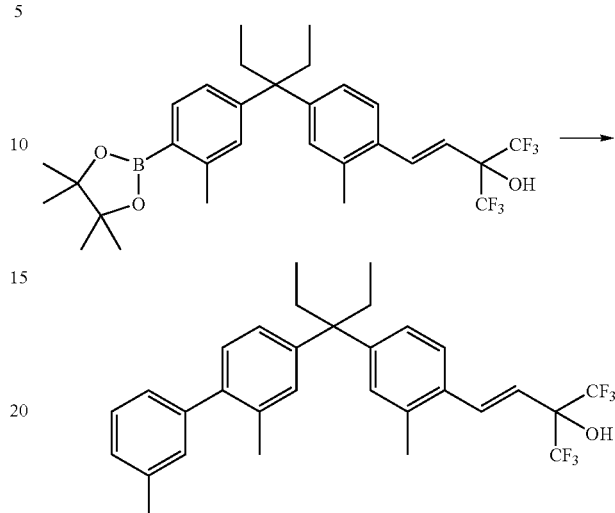

Palladium acetate (3.6 mg, 0.016 mmol), 2-dicyclohexylphosphino-2',6'-dimethoxy-1,1'-biphenyl (13.1 mg, 0.032 mmol), potassium phosphate (51 mg, 0.24 mmol) and water (0.04 mL) were added to a solution of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 40 mg, 0.070 mmol) and (3-bromo-phenyl)acetic acid methyl ester (Tetrahedron Letters 44 (2003) 331-334; 28 mg, 0.122 mmol) in toluene (0.4 mL). After replacement with nitrogen, the mixture was stirred at 100° C. for 30 minutes. Then, the reaction mixture was concentrated under reduced pressure, and the residue was dissolved in dichloromethane. Thereafter, the solution was filtered through amino silica gel, and the filtrate was concentrated under reduced pressure. The resulting residue was purified by silica gel chromatography (hexane:ethyl acetate=2:1) to give the target compound as a colorless oil (12.8 mg, 31%).

$^1$H-NMR (chloroform-d): 0.66 (6H, t, J=7.25 Hz), 2.12 (4H, q, J=7.25 Hz), 2.28 (3H, s), 2.36 (3H, s), 3.12 (1H, brs), 3.66 (2H, s), 3.70 (3H, s), 6.10 (1H, d, J=15.99 Hz), 6.98-7.11 (5H, m), 7.22-7.25 (3H, m), 7.32-7.41 (3H, m).

(2) Synthesis of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)-acetic Acid

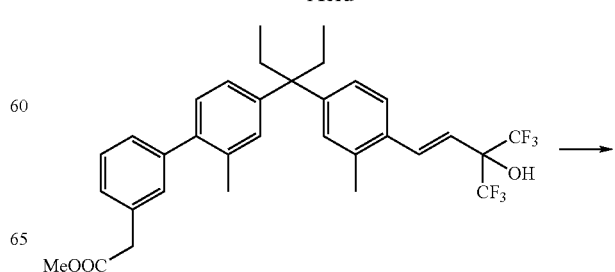

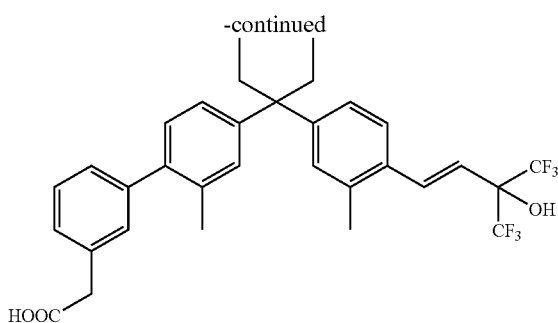

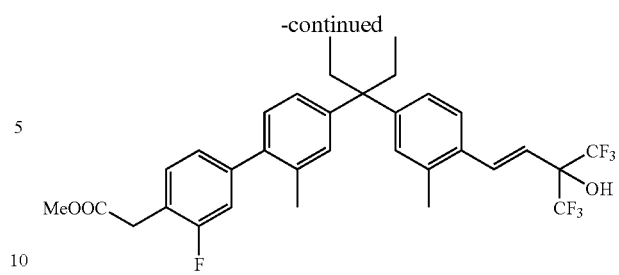

A 1 N sodium hydroxide aqueous solution (0.065 mL, 0.065 mmol) was added to a solution of (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid methyl ester (Example 71-(1); 12.8 mg, 0.022 mmol) in methanol-tetrahydrofuran (1:1, 1 mL), and the mixture was stirred at 60° C. for one hour. Then, the reaction mixture was concentrated under reduced pressure. The resulting residue was purified by silica gel chromatography (chloroform:methanol=8:3, saturated with water) to give the target compound as a colorless oil (12.1 mg, 97%).

$^1$H-NMR (chloroform-d): 0.65 (6H, t, J=7.25 Hz), 2.12 (4H, q, J=7.26 Hz), 2.21 (3H, s), 2.36 (3H, s), 3.68 (2H, s), 6.09 (1H, d, J=15.99 Hz), 6.98-7.10 (5H, m), 7.22-7.26 (3H, m), 7.33-7.41 (3H, m); MS (ESI+): 596 ([M+NH$_4$]$^+$).

Example 72

Synthesis of (4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)-acetic Acid (4-Chloro-2-fluoro-phenyl)acetic acid methyl ester (Example 40; 26.5 mg, 0.131 mmol), palladium acetate (2.0 mg, 0.009 mmol), 2-dicyclohexylphosphino-2',6'-dimethoxy-1,1'-biphenyl (7.2 mg, 0.018 mmol), potassium phosphate (56 mg, 0.263 mmol) and water (0.1 mL) were added to a solution of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 50 mg, 0.088 mmol) in toluene (1 mL). After replacement with nitrogen, the mixture was stirred at 100° C. overnight. Then, the reaction mixture was filtered through amino silica gel, and the filtrate was concentrated under reduced pressure. The resulting residue was purified by silica gel chromatography (hexane:ethyl acetate=2:1) to give the target compound as a colorless oil (26.6 mg, 50%).

$^1$H-NMR (chloroform-d): 0.65 (6H, t, J=7.26 Hz), 2.12 (4H, q, J=7.26 Hz), 2.23 (3H, s), 2.36 (3H, s), 3.71 (2H, s), 3.74 (3H, s), 6.09 (1H, d, J=15.99 Hz), 6.98-7.12 (7H, m), 7.24-7.30 (1H, m), 7.35-7.41 (2H, m).

(2) Synthesis of (4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)-acetic Acid

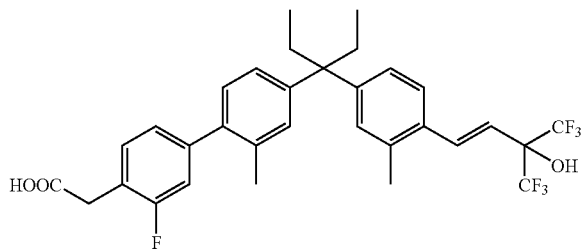

(1) Synthesis of (4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)-acetic Acid Methyl Ester

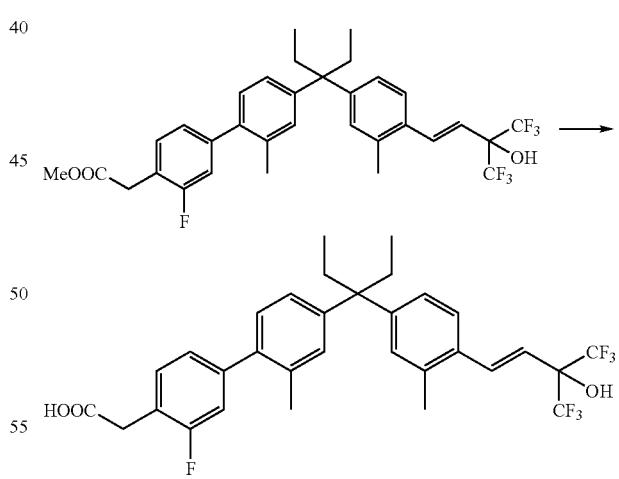

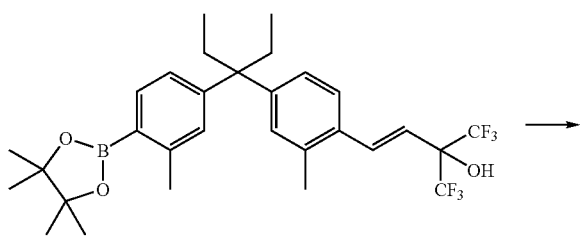

A 1 N sodium hydroxide aqueous solution (0.145 mL, 0.145 mmol) was added to a solution of (4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)acetic acid methyl ester (Example 72-(1); 29.6 mg, 0.049 mmol) in methanol-tetrahydrofuran (1:1, 1 mL), and the mixture was stirred at 60° C. for one hour. Then, the reaction mixture was concentrated under reduced pressure. The resulting residue was purified by silica gel chromatography (chloroform:methanol=8:3, saturated with water) to give the target compound as a colorless oil (27.5 mg, 95%).

$^1$H-NMR (chloroform-d): 0.65 (6H, t, J=7.26 Hz), 2.12 (4H, q, J=7.09 Hz), 2.23 (3H, s), 2.36 (3H, s), 3.75 (2H, s), 6.09 (1H, d, J=15.99 Hz), 6.99-7.09 (7H, m), 7.28-7.41 (3H, m); MS (ESI+): 614 ([M+NH$_4$]$^+$).

Example 73

Synthesis of (3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)-acetic Acid

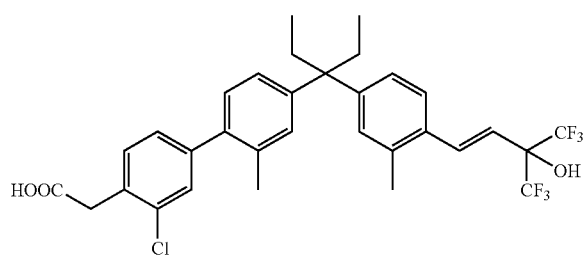

(1) Synthesis of (3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)-acetic Acid Methyl Ester

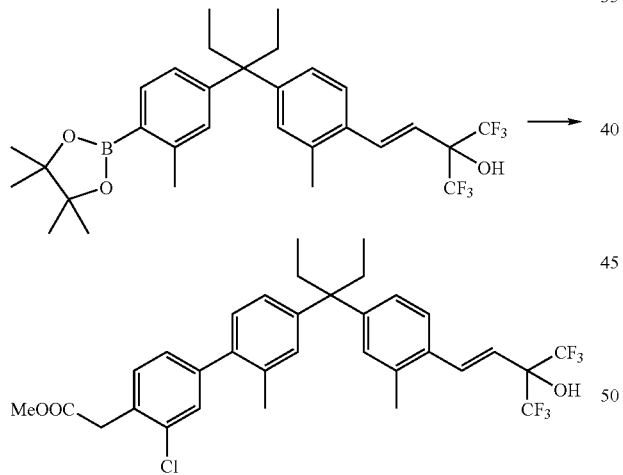

(2,4-Dichloro-phenyl)acetic acid methyl ester (Example 41; 28.7 mg, 0.131 mmol), palladium acetate (2.0 mg, 0.009 mmol), 2-dicyclohexylphosphino-2',6'-dimethoxy-1,1'-biphenyl (7.2 mg, 0.018 mmol), potassium phosphate (56 mg, 0.263 mmol) and water (0.1 mL) were added to a solution of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 50 mg, 0.088 mmol) in toluene (1 mL). After replacement with nitrogen, the mixture was stirred at 100° C. overnight. Then, the reaction mixture was filtered through amino silica gel, and the filtrate was concentrated under reduced pressure. The resulting residue was purified by silica gel chromatography (hexane:ethyl acetate=2:1) to give the target compound as a colorless oil (3.9 mg, 7%).

$^1$H-NMR (chloroform-d): 0.65 (6H, t, J=6.93 Hz), 2.12 (4H, q, J=7.25 Hz), 2.23 (3H, s), 2.37 (3H, s), 3.09 (1H, brs), 3.75 (3H, s), 3.82 (2H, s), 6.09 (1H, d, J=15.83 Hz), 6.96-7.11 (5H, m), 7.18-7.41 (5H, m).

(2) Synthesis of (3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)-acetic Acid

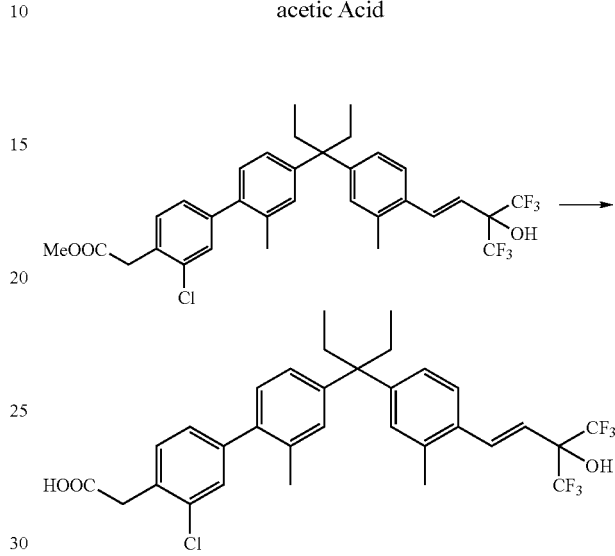

A 1 N sodium hydroxide aqueous solution (0.019 mL, 0.019 mmol) was added to a solution of (3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid methyl ester (Example 73-(1); 3.9 mg, 0.006 mmol) in methanol-tetrahydrofuran (1:1, 1 mL), and the mixture was stirred at 60° C. for one hour. Then, the reaction mixture was concentrated under reduced pressure. The resulting residue was purified by silica gel chromatography (chloroform:methanol=8:3, saturated with water) to give the target compound as a colorless oil (2.0 mg, 53%).

$^1$H-NMR (chloroform-d): 0.65 (6H, t, J=7.09 Hz), 2.12 (4H, q, J=6.92 Hz), 2.22 (3H, s), 2.36 (3H, s), 3.86 (2H, s), 6.09 (1H, d, J=16.16 Hz), 6.95-7.10 (5H, m), 7.22-7.41 (5H, m); MS (ESI+): 630 ([M+NH$_4$]$^+$).

Example 74

Synthesis of [6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic Acid

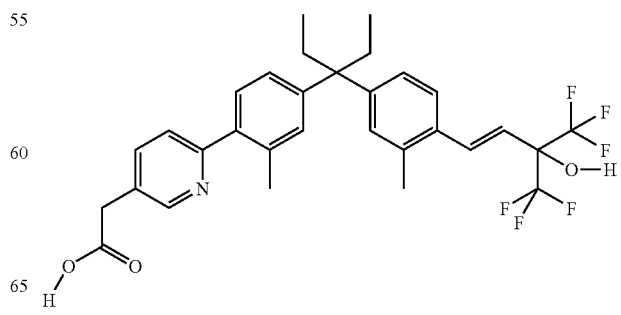

(1) Synthesis of (2-bromo-pyridin-5-yl)-acetic Acid Ethyl Ester

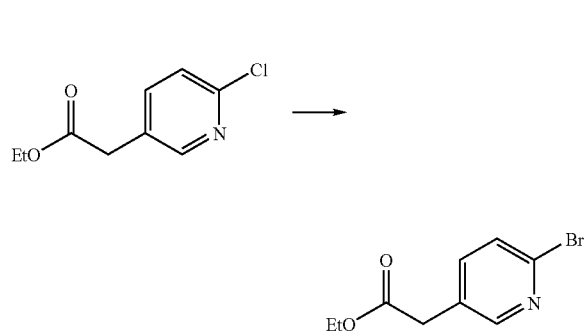

Lithium bromide (3.2 g, 37 mmol) and acetyl bromide (1.3 mL, 17 mmol) were added to a solution of (2-chloro-pyridin-5-yl)acetic acid ethyl ester (1.08 g, 5.42 mmol) in acetonitrile (7.2 mL), and the mixture was heated under reflux at an external temperature of 86 to 94° C. for 31 hours. The reaction mixture was dissolved in water. The solution was neutralized with a sodium hydroxide aqueous solution, followed by extraction with diethyl ether. The organic layer was dried over anhydrous magnesium sulfate and then concentrated under reduced pressure. The residue was purified by silica gel chromatography (hexane/ethyl acetate=4/1) to give the title compound (655 mg, 53%).

$^1$H-NMR (chloroform-d): 1.26 (t, 3H, J=7.2 Hz), 3.58 (s, 2H), 4.16 (q, 2H, J=7.2 Hz), 7.44 (d, 1H, J=8.4 Hz), 7.51 (dd, 1H, J=8.4, 2.4 Hz), 8.26 (d, 1H, J=2.4 Hz); MS (ESI+): 244 ([M+H]$^+$).

(2) Synthesis of [6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic Acid Ethyl Ester

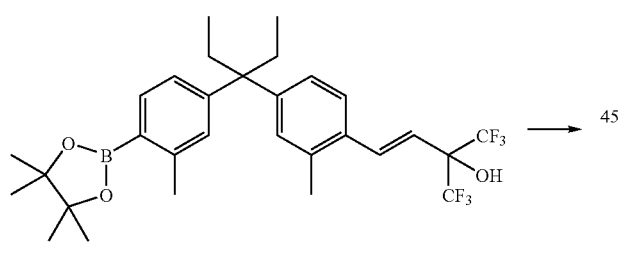

Degassed N,N-dimethylformamide (0.15 mL) was added to (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 14.0 mg, 0.0245 mmol), (2-bromo-pyridin-5-yl)acetic acid ethyl ester (Example 74-(1); 10.5 mg, 0.043 mmol), tetrakis(triphenylphosphine)palladium (0) (3.5 mg, 0.0030 mmol) and potassium phosphate (13.4 mg, 0.0631 mmol). After replacement with nitrogen, the mixture was heated while stirring at an external temperature of 85 to 95° C. for 10 hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=3/1) to give the title compound (12 mg, 80%).

$^1$H-NMR (chloroform-d): 0.62 (t, 6H, J=7.4 Hz), 1.30 (t, 3H, J=7.1 Hz), 2.12 (q, 4H, J=7.4 Hz), 2.31 (s, 3H), 2.33 (s, 3H), 3.67 (s, 2H), 3.74 (brs, 1H), 4.20 (q, 2H, J=7.1 Hz), 6.06 (d, 1H, J=15.9 Hz), 7.0-7.05 (m, 4H), 7.24-7.39 (m, 4H), 7.70 (dd, 1H, J=8.1, 2 Hz), 8.56 (d, 1H, J=2 Hz).

(3) Synthesis of [6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic Acid

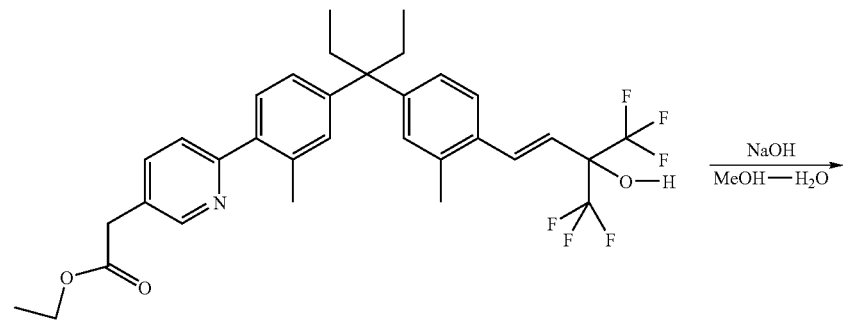

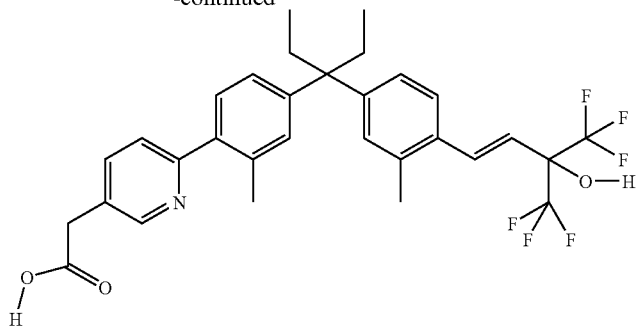

A 2 N sodium hydroxide aqueous solution (0.03 mL) was added to a solution of [6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid ethyl ester (Example 74-(2); 8.4 mg, 0.014 mmol) in methanol (0.2 mL) at room temperature, and the mixture was stirred at room temperature for three hours. The mixture was acidified with dilute hydrochloric acid aqueous solution, followed by extraction with ethyl acetate. The extract was dried over anhydrous magnesium sulfate and then concentrated under reduced pressure to give the title compound (8 mg, 100%).

$^{1}$H-NMR (chloroform-d): 0.66 (t, 6H, J=7.2 Hz), 2.13 (q, 4H, J=7.2 Hz), 2.31 (s, 3H), 2.34 (s, 3H), 3.71 (s, 2H), 6.09 (d, 1H, J=15.6 Hz), 7.00-7.10 (m, 4H), 7.24-7.41 (m, 4H), 7.72 (dd, 1H, J=8.1, 2 Hz), 8.57 (d, 1H, J=2 Hz).

MS (ESI+): 580 ([M+H]$^{+}$).

Example 75

Synthesis of [5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic Acid

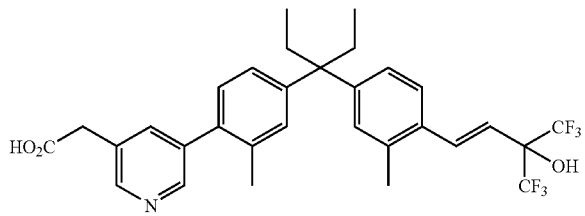

(1) Synthesis of [5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic Acid Methyl Ester

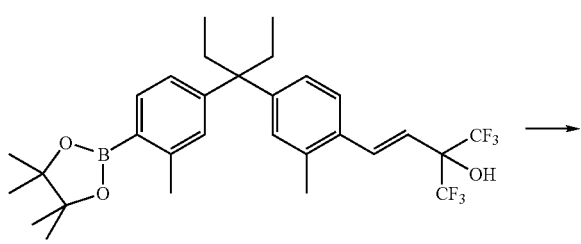

A solution of palladium acetate (1.4 mg, 0.00623 mmol), 2-dicyclohexylphosphino-2',6'-dimethoxybiphenyl (5.3 mg, 0.0124 mmol) and potassium phosphate (27.6 mg, 0.1246 mmol) in water (0.020 mL) and toluene (0.100 mL) was stirred for three minutes. Then, a solution of (5-bromo-pyridin-3-yl)acetic acid methyl ester (Example 24-(2); 15.2 mg, 0.0659 mmol) and (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 26.9 mg, 0.0471 mmol) in toluene (0.12 mL) was added, and the mixture was stirred in a nitrogen atmosphere at 100° C. for one hour. After filtration through cotton plug, the filtrate was concentrated under reduced pressure. The residue was purified by silica gel chromatography (hexane/ethyl acetate=3/2) to give the title compound (5.0 mg, 17%).

$^{1}$H-NMR (chloroform-d): 0.65 (t, 6H, J=7.2 Hz), 1.60 (brs, 1H), 2.12 (q, 4H, J=7.2 Hz), 2.24 (s, 6H), 3.69 (s, 2H), 3.73 (s, 3H), 6.16 (d, 1H, J=15.6 Hz), 6.97-7.05 (m, 5H), 7.36-7.43 (m, 2H), 7.66 (s, 1H), 8.43 (d, 1H, J=6.9 Hz).

(2) Synthesis of [5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic Acid

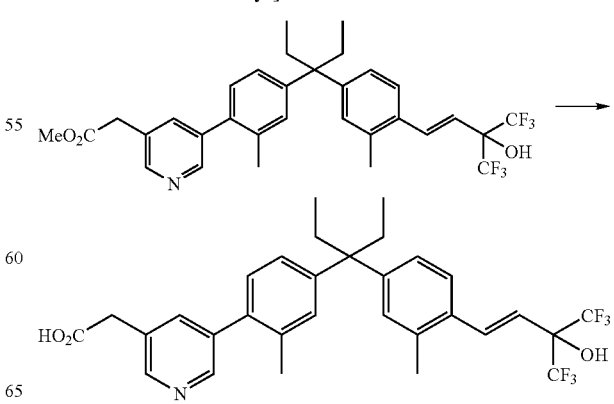

A 6 N sodium hydroxide aqueous solution (0.009 mL) was added to a solution of [5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid ethyl ester (Example 75-(1); 5.0 mg, 0.0084 mmol) in methanol (0.3 mL) and water (0.030 mL), and the mixture was stirred for two hours. 2 N hydrochloric acid aqueous solution and water were added to the reaction mixture, followed by extraction with diethyl ether and ethyl acetate. The organic layer was washed with water, dried over anhydrous sodium sulfate and concentrated under reduced pressure. The residue was purified by thin layer silica gel chromatography (dichloromethane/methanol=5/1) to give the title compound (3.0 mg, 60%).

$^1$H-NMR (chloroform-d): 0.65 (t, 6H, J=7.2 Hz), 2.04 (s, 3H), 2.11 (q, 4H, J=7.2 Hz), 2.22 (s, 3H), 2.80-3.80 (brs, 1H), 3.67 (s, 2H), 6.16 (d, 1H, J=15.9 Hz), 6.90 (s, 1H), 6.95-7.05 (m, 4H), 7.34-7.42 (m, 2H), 7.68 (s, 1H), 8.64 (d, 1H, J=16.9 Hz); MS (ESI+): 580 ([M+H]$^+$).

Example 76

Synthesis of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic Acid (1) Synthesis of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic Acid Ethyl Ester

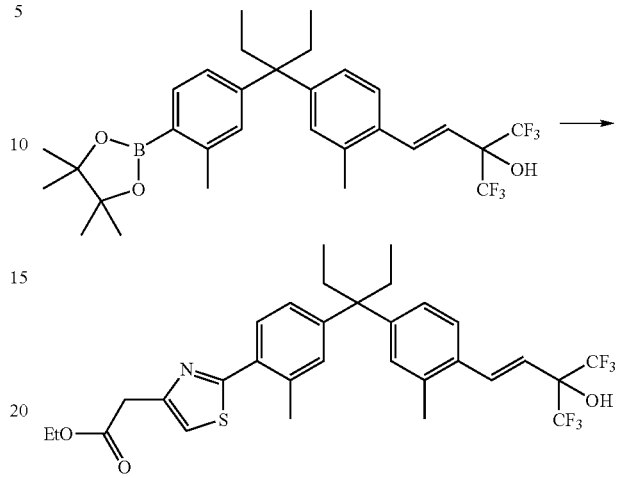

Degassed N,N-dimethylformamide (0.25 mL) was added to (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 22.9 mg, 0.0401 mmol), (2-bromo-thiazol-4-yl)-acetic acid ethyl ester (Example 42; 17.8 mg, 0.071 mmol), tetrakis(triphenylphosphine)palladium (0) (5.9 mg, 0.0051 mmol) and potassium phosphate (19.2 mg, 0.0904 mmol). After replacement with nitrogen, the mixture was heated while stirring at an external temperature of 95 to 105° C. for five hours. Water was added to the reaction mixture, followed by extraction with diethyl ether. The extract was dried over anhydrous magnesium sulfate and then concentrated under reduced pressure. The residue was purified by silica gel chromatography (hexane/dichloromethane=1/4) to give the title compound (9.7 mg, 39%).

$^1$H-NMR (chloroform-d): 0.64 (t, 6H, J=7.5 Hz), 1.29 (t, 3H, J=7.2 Hz), 2.12 (q, 4H, J=7.5 Hz), 2.35 (s, 3H), 2.51 (s, 3H), 3.17 (s, 1H), 3.90 (s, 2H), 4.21 (q, 2H, J=7.2 Hz), 6.09 (d, 1H, J=15.6 Hz), 6.97-7.10 (m, 4H), 7.22 (s, 1H), 7.34 (s, 1H), 7.38 (d, 1H, J=8 Hz), 7.55 (d, 1H, J=8 Hz).

(2) Synthesis of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic Acid

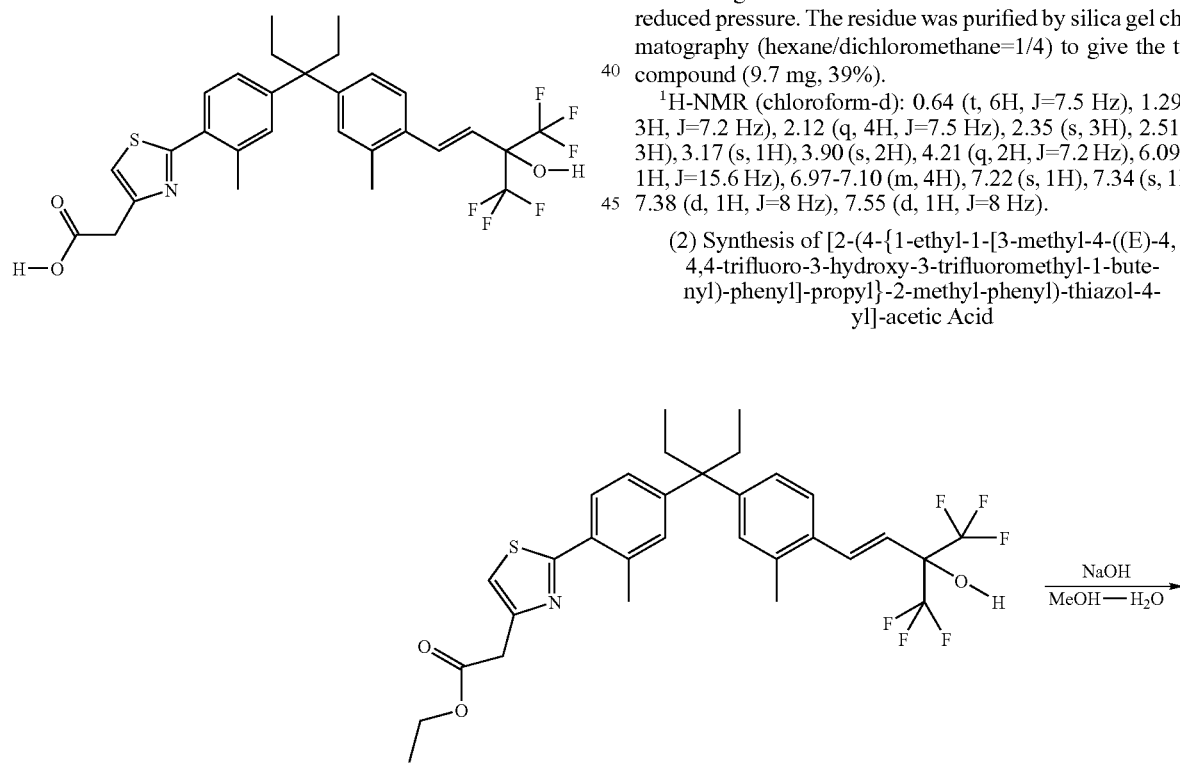

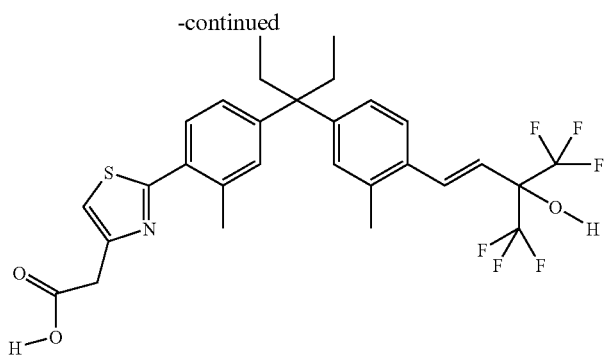

A mixed solution of a 6 N sodium hydroxide aqueous solution (0.11 mL) with water (0.033 mL) was added to a solution of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid ethyl ester (Example 76-(1); 9.7 mg, 0.016 mmol) in methanol (0.22 mL) at room temperature, and the mixture was stirred at room temperature for 6.5 hours. The mixture was acidified with dilute hydrochloric acid aqueous solution, followed by extraction with ethyl acetate. The extract was dried over anhydrous magnesium sulfate and then concentrated under reduced pressure. The residue was purified by preparative TLC (dichloromethane:methanol=10:1) to give the title compound (8.8 mg, 94%).

$^1$H-NMR (chloroform-d): 0.66 (t, 6H, J=7.4 Hz), 2.14 (q, 4H, J=7.4 Hz), 2.35 (s, 3H), 2.54 (s, 3H), 3.50 (s, 1H), 3.92 (s, 2H), 6.09 (d, 1H, J=15.9 Hz), 6.99-7.14 (m, 4H), 7.15 (s, 1H), 7.35 (s, 1H), 7.39 (d, 1H, J=6.9 Hz), 7.58 (d, 1H, J=8.1 Hz).

MS (ESI+): 586 ([M+H]$^+$).

Example 77

Synthesis of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyrimidin-5-yl]-acetic Acid

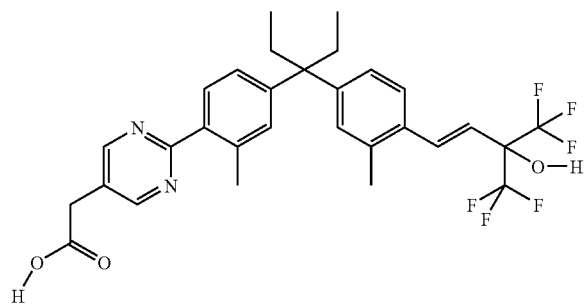

(1) Synthesis of 2-[4-(1-{4-[(E)-3-(t-butyl-dimethyl-silanyloxy)-4,4,4-trifluoro-3-trifluoromethyl-1-butenyl]-3-methyl-phenyl}-1-ethyl-propyl)-2-methyl-phenyl]-4,4,5,5-tetramethyl-[1,3,2]dioxaborolane

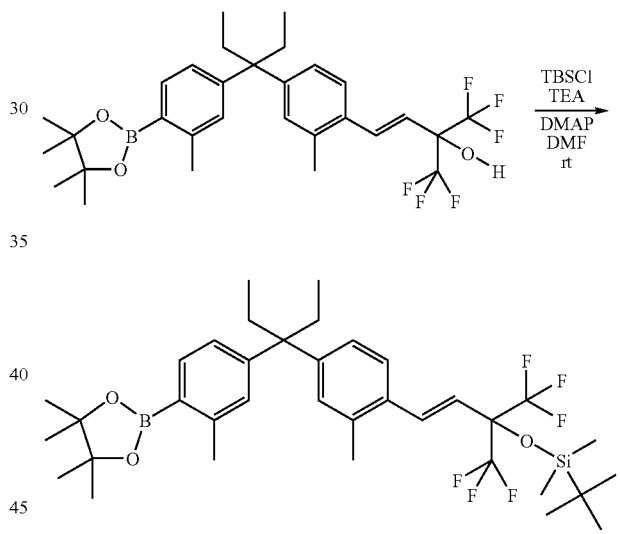

Triethylamine (0.10 mL, 0.72 mmol), t-butyldimethylsilyl chloride (48.5 mg, 0.322 mmol) and dimethylaminopyridine (1 mg, 0.008 mmol) were added to a solution of (E)-4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-3-buten-2-ol (Example 26-(5); 47.0 mg, 0.082 mmol) in N,N-dimethylformamide (0.10 mL), and the mixture was stirred at room temperature for 24 hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=50/1) to give the title compound (47 mg, 84%).

$^1$H-NMR (chloroform-d): 0.22 (s, 6H), 0.62 (t, 6H, J=7.4 Hz), 0.98 (s, 9H), 1.34 (s, 12H), 2.10 (q, 4H, J=7.4 Hz), 2.31 (s, 3H), 2.49 (s, 3H), 6.05 (d, 1H, J=15.6 Hz), 6.95-7.05 (m, 4H), 7.25-7.35 (m, 2H), 7.64 (d, 1H, J=8.4 Hz).

(2) Synthesis of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyrimidin-5-yl]-acetic Acid Ethyl Ester

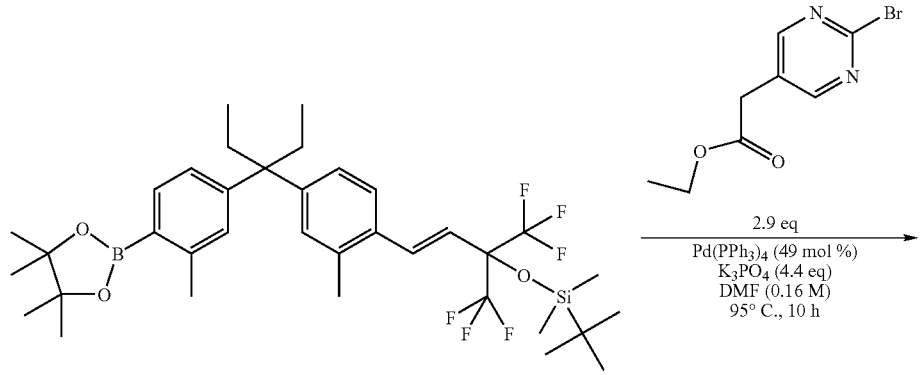

Degassed N,N-dimethylformamide (0.32 mL) was added to 2-[4-(1-{4-[(E)-3-(t-butyl-dimethyl-silanyloxy)-4,4,4-trifluoro-3-trifluoromethyl-1-butenyl]-3-methyl-phenyl}-1-ethyl-propyl)-2-methyl-phenyl]-4,4,5,5-tetramethyl-[1,3,2]dioxaborolane (Example 77-(1); 35.8 mg, 0.0523 mmol), 2-bromopyrimidine-5-acetic acid ethyl ester (Example 43-(3); 37.3 mg, 0.152 mmol), tetrakis(triphenylphosphine)palladium (0) (29.8 mg, 0.0258 mmol) and potassium phosphate (48.7 mg, 0.229 mmol). After replacement with nitrogen, the mixture was heated while stirring at an external temperature of 91 to 100° C. for 10 hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=4/1) to give the title compound (13 mg, 41%).

$^1$H-NMR (chloroform-d): 0.66 (t, 6H, J=7.2 Hz), 1.30 (t, 3H, J=7.2 Hz), 2.12 (q, 4H, J=7.2 Hz), 2.33 (s, 3H), 2.50 (s, 3H), 3.11 (s, 1H), 3.66 (s, 2H), 4.22 (q, 2H, J=7.2 Hz), 6.09 (d, 1H, J=16.2 Hz), 7.95-7.15 (m, 4H), 7.33-7.39 (m, 2H), 7.69 (d, 1H, J=8.1 Hz), 8.75 (s, 2H).

(3) Synthesis of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyrimidin-5-yl]-acetic Acid

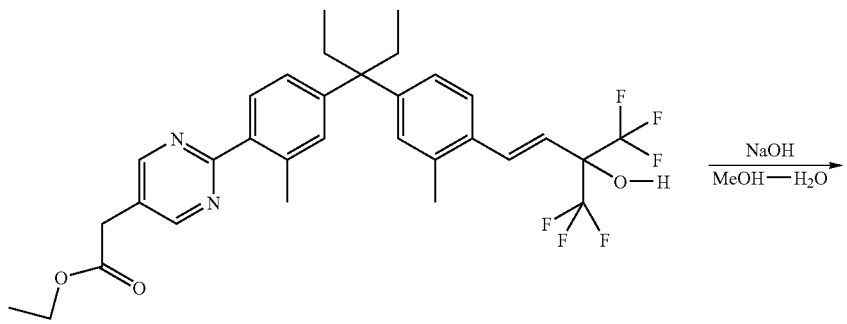

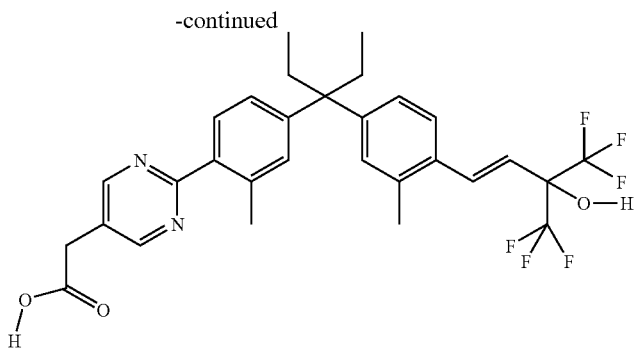

A 2 N sodium hydroxide aqueous solution (0.039 mL) was added to a solution of [2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyrimidin-5-yl]-acetic acid ethyl ester (Example 77-(2); 11.8 mg, 0.0194 mmol) in methanol (0.28 mL) at room temperature, and the mixture was stirred at room temperature for four hours. The mixture was acidified with dilute hydrochloric acid aqueous solution, followed by extraction with ethyl acetate. The extract was dried over anhydrous magnesium sulfate and then concentrated under reduced pressure to give the title compound (11.2 mg, 99%).

$^1$H-NMR (chloroform-d): 0.66 (t, 6H, J=7.4 Hz), 2.14 (q, 4H, J=7.4 Hz), 2.34 (s, 3H), 2.50 (s, 3H), 3.73 (s, 2H), 6.09 (d, 1H, J=15.6 Hz), 6.95-7.15 (m, 4H), 7.33-7.40 (m, 2H), 7.69 (d, 1H, J=8.1 Hz), 8.77 (s, 2H).

MS (ESI+): 581 ([M+H]$^+$).

Example 78

Synthesis of (4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)-acetic Acid

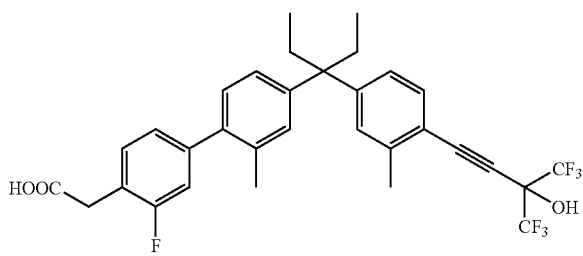

(1) Synthesis of (4'-{1-ethyl-1-[3-methyl-4-(4,4,4-trifluoro-3-methoxymethoxy-3-trifluoromethyl-1-butynyl)-phenyl]-propyl}-3-fluoro-2'-methyl-biphenyl-4-yl)-acetic Acid Methyl Ester

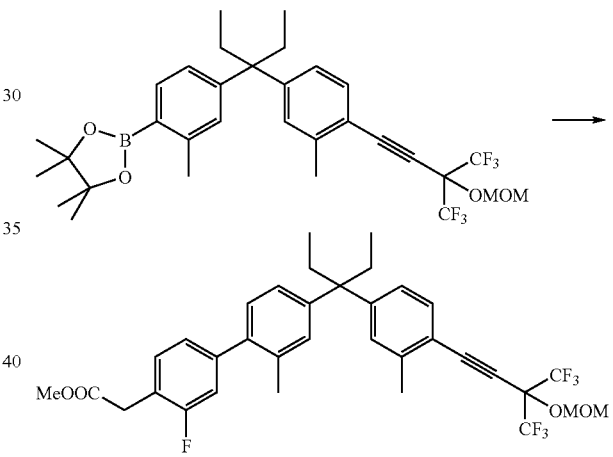

(4-Chloro-2-fluoro-phenyl)acetic acid methyl ester (Example 40; 37.2 mg, 0.183 mmol), toluene (2.0 mL), palladium acetate (2.7 mg, 0.012 mmol), 2-dicyclohexylphosphino-2',6'-dimethoxy-1,1'-biphenyl (10.0 mg, 0.0244 mmol), potassium phosphate (78 mg, 0.3666 mmol) and water (0.200 mL) were added to 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane (Example 25-(4); 75 mg, 0.122 mmol), and the mixture was stirred in a nitrogen atmosphere at 100° C. for 1.5 hours. The reaction solution was poured into a saturated aqueous sodium bicarbonate solution, and then the aqueous layer was extracted with dichloromethane. The organic layer was dried over anhydrous sodium sulfate and concentrated under reduced pressure. The residue was purified by silica gel chromatography (17% ethyl acetate/hexane) to give the title compound containing (4-chloro-2-fluorophenyl)acetic acid methyl ester (41 mg, 52%).

$^1$H-NMR (chloroform-d): 0.64 (t, 6H, J=7.3 Hz), 2.11 (q, 4H, J=7.2 Hz), 2.22 (s, 3H), 2.42 (s, 3H), 3.73 (s, 2H), 3.80 (s, 3H), 7.04-7.11 (m, 7H), 7.24-7.29 (m, 2H); MS (ESI+): 670 ([M+NH$_4$]$^+$).

(2) Synthesis of (4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)-acetic Acid Methyl Ester

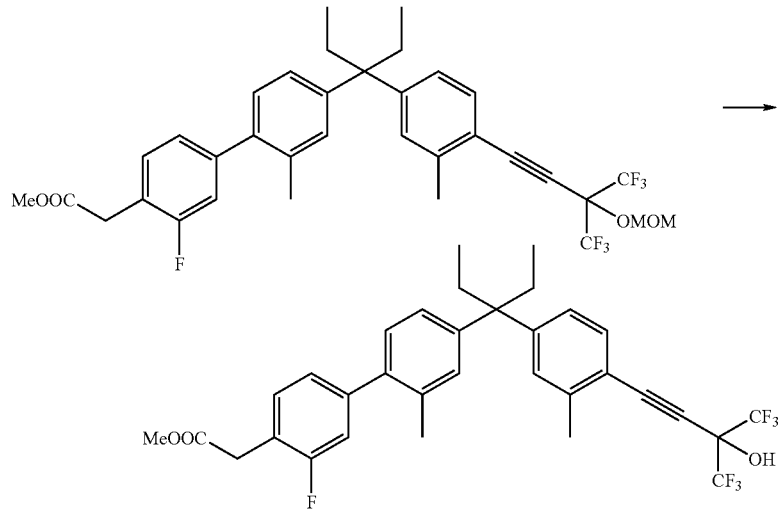

Dichloromethane (1.5 mL) and trifluoroacetic acid (0.153 mL) were added to (4'-{1-ethyl-1-[3-methyl-4-(4,4,4-trifluoro-3-methoxymethoxy-3-trifluoromethyl-1-butynyl)-phenyl]-propyl}-3-fluoro-2'-methyl-biphenyl-4-yl)acetic acid methyl ester (Example 78-(1); 41 mg, 0.063 mmol), and the mixture was stirred at room temperature for one day. The reaction solution was directly concentrated under reduced pressure and azeotropically distilled with toluene. The residue was purified by preparative TLC (hexane/ethyl acetate=5/1) to give the title compound (30.1 mg, 79%).

$^1$H-NMR (chloroform-d): 0.64 (t, 6H, J=7.3 Hz), 2.11 (q, 4H, J=7.2 Hz), 2.22 (s, 3H), 2.40 (s, 3H), 3.62 (s, 1H), 3.71 (s, 2H), 3.73 (s, 3H), 6.95-7.09 (m, 7H), 7.23-7.29 (m, 2H).

(3) Synthesis of (4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)-acetic Acid Methanol (1.5 mL) and a 1 N sodium hydroxide aqueous solution (0.200 mL, 0.200 mmol) were added to (4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)acetic acid methyl ester (Example 78-(2); 30.1 mg, 0.050 mmol), and the mixture was stirred at room temperature for five hours. The reaction solution was poured into a saturated aqueous ammonium chloride solution, and then the aqueous layer was extracted with ethyl acetate. The organic layer was dried over anhydrous sodium sulfate and concentrated under reduced pressure. The residue was purified by preparative TLC (chloroform/methanol=10/1) to give the title compound (15.6 mg, 52%).

$^1$H-NMR (methanol-d4): 0.65 (t, 6H, J=7.3 Hz), 2.16 (q, 4H, J=7.3 Hz), 2.21 (s, 3H), 2.38 (s, 3H), 3.68 (s, 2H), 7.00-7.14 (m, 7H), 7.29-7.37 (m, 2H); MS (ESI+): 595 ([M+H]$^+$).

Example 79

Synthesis of [6-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic Acid

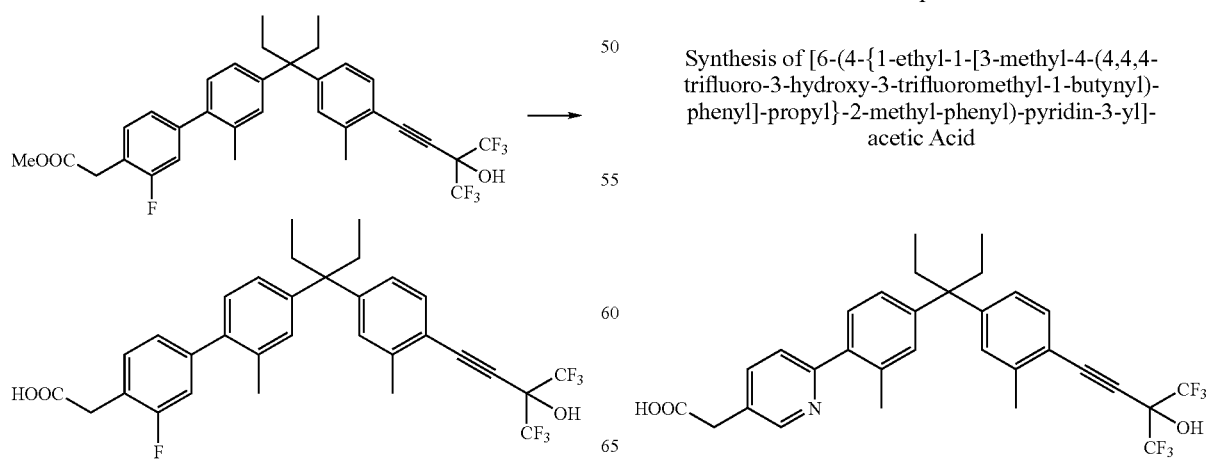

(1) Synthesis of [6-(4-{1-ethyl-1-[3-methyl-4-(4,4,4-trifluoro-3-methoxymethoxy-3-trifluoromethyl-1-butynyl)-phenyl]-propyl}-2-methyl-phenyl)-pyridin-3-yl]-acetic Acid Ethyl Ester

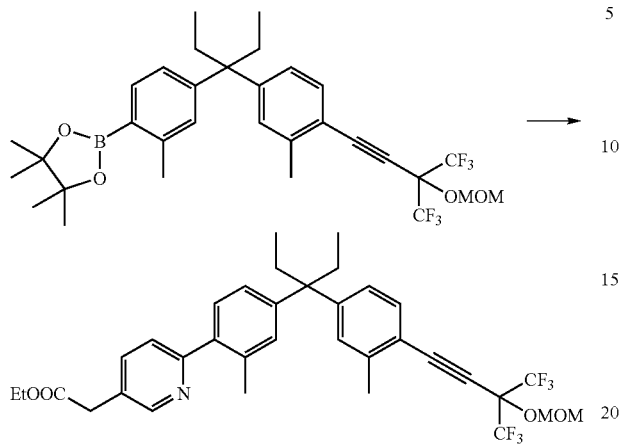

N,N-Dimethylformamide (0.7 mL) was added to 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane (Example 25-(4); 50 mg, 0.082 mmol), (6-bromo-pyridin-3-yl)acetic acid ethyl ester (Example 74-(1); 40 mg, 0.165 mmol), tetrakis(triphenylphosphine)palladium (0) (23 mg, 0.02 mmol) and potassium phosphate (63.9 mg, 0.30 mmol). The mixture was stirred with microwave heating at 140° C. for seven minutes in a nitrogen atmosphere. The reaction mixture was concentrated under reduced pressure. The residue was purified by preparative TLC (hexane/ethyl acetate=10/1, then dichloromethane/methanol=20/1) to give the title compound (31 mg, 58%).

¹H-NMR (chloroform-d): 0.64 (t, 6H, J=7.2 Hz), 1.27 (m, 3H), 2.11 (q, 4H, J=7.2 Hz), 2.32 (s, 3H), 2.40 (s, 3H), 3.48 (s, 3H), 3.66 (s, 2H), 4.19 (m, 2H), 5.15 (s, 2H), 7.00-7.70 (m, 6H), 8.27 (m, 2H), 8.57 (s, 1H).

(2) Synthesis of [6-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic Acid The title compound (45%) was obtained by the same method as in Example 66-(2) using [6-(4-{1-ethyl-1-[3-methyl-4-(4,4,4-trifluoro-3-methoxymethoxy-3-trifluoromethyl-1-butynyl)-phenyl]-propyl}-2-methyl-phenyl)-pyridin-3-yl]-acetic acid ethyl ester (Example 79-(1)) as a starting material.

¹H-NMR (methanol-d): 0.65 (t, 6H, J=7.1 Hz), 2.16 (q, 4H, J=7.1 Hz), 2.23 (s, 3H), 2.37 (s, 3H), 3.54 (s, 2H), 7.03-7.11 (m, 4H), 7.22-7.25 (m, 1H), 7.32-7.42 (m, 2H), 7.83 (dd, 1H, J=2.3, 8.1 Hz), 8.48 (d, 1H, J=1.5 Hz); MS (ESI+): 578 ([M+H]⁺).

Example 80

Synthesis of [5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic Acid

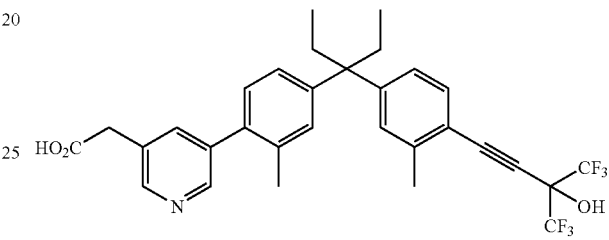

(1) Synthesis of [5-(4-{1-ethyl-1-[3-methyl-4-(4,4,4-trifluoro-3-methoxymethoxy-3-trifluoromethyl-1-butynyl)-phenyl]-propyl}-2-methyl-phenyl)-pyridin-3-yl]-acetic Acid Methyl Ester

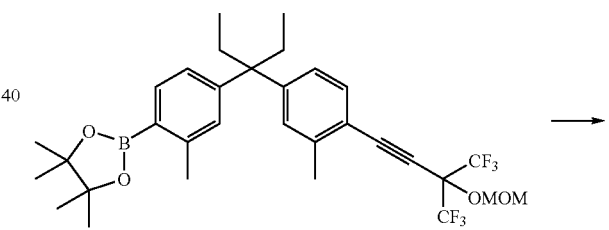

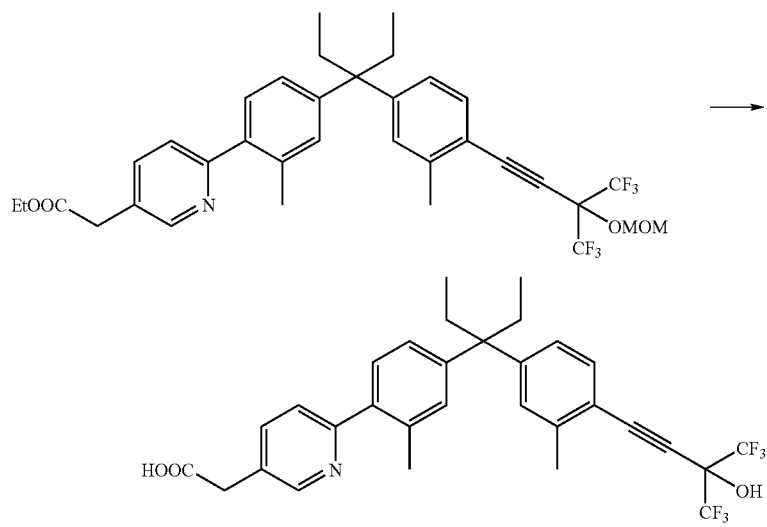

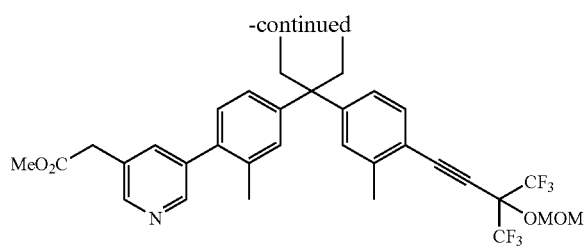

A solution of 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane (Example 25-(4); 47.7 mg, 0.1 mmol), (5-bromo-pyridin-3-yl)acetic acid methyl ester (Example 24-(2); 26.8 mg, 0.11 mmol), tetrakistriphenylphosphine palladium (12.5 mg, 0.0108 mmol) and potassium phosphate (24.7 mg, 0.11 mmol) in N,N-dimethylformamide (0.25 mL) was stirred with microwave heating at 140° C. for 10 minutes. The reaction mixture was filtered through cotton plug, and the mixture was purified by silica gel chromatography (40% ethyl acetate/hexane) to give the title compound (36.0 mg, 72%).

$^1$H-NMR (chloroform-d): 0.65 (t, 6H, J=7.3 Hz), 2.12 (q, 4H, J=7.4 Hz), 2.23 (s, 3H), 2.42 (s, 3H), 3.48 (s, 3H), 3.68 (s, 2H), 3.73 (d, 3H, J=2.9 Hz), 5.16 (s, 2H), 7.01-7.04 (m, 3H), 7.09-7.11 (m, 2H), 7.41 (d, 1H, J=8.1 Hz), 7.62 (t, 1H, J=2.0 Hz), 8.47 (d, 1H, J=1.8 Hz), 8.51 (d, 1H, J=1.8 Hz).

(2) Synthesis of [5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic Acid Methyl Ester

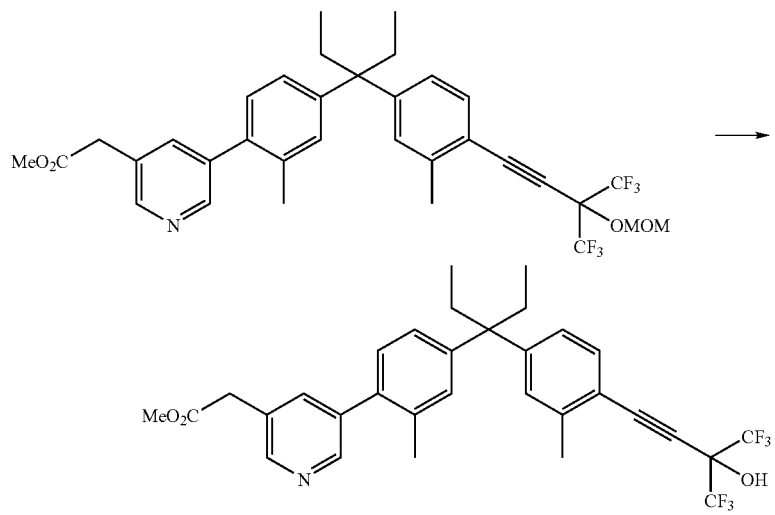

Trifluoroacetic acid (0.20 mL) was added to a solution of [5-(4-{1-ethyl-1-[3-methyl-4-(4,4,4-trifluoro-3-methoxymethoxy-3-trifluoromethyl-1-butynyl)-phenyl]-propyl}-2-methyl-phenyl)-pyridin-3-yl]-acetic acid methyl ester (Example 80-(1); 36.0 mg, 0.0566 mmol) in dichloromethane (1.0 mL) at 0° C., and the mixture was stirred at room temperature for three hours. A saturated aqueous sodium bicarbonate solution was added to the reaction mixture, followed by extraction with ethyl acetate. The organic layer was washed with water, dried over anhydrous sodium sulfate and concentrated under reduced pressure to give the title compound (34.3 mg, 99%).

$^1$H-NMR (chloroform-d): 0.63 (t, 6H, J=7.0 Hz), 2.04 (s, 3H), 2.11 (q, 4H, J=7.0 Hz), 2.32 (s, 3H), 3.69 (s, 2H), 3.72 (s, 3H), 6.89-7.05 (m, 5H), 7.21 (d, 1H, J=8.4 Hz), 7.66 (s, 1H), 8.45 (s, 1H), 8.50 (s, 1H).

(3) Synthesis of [5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic Acid

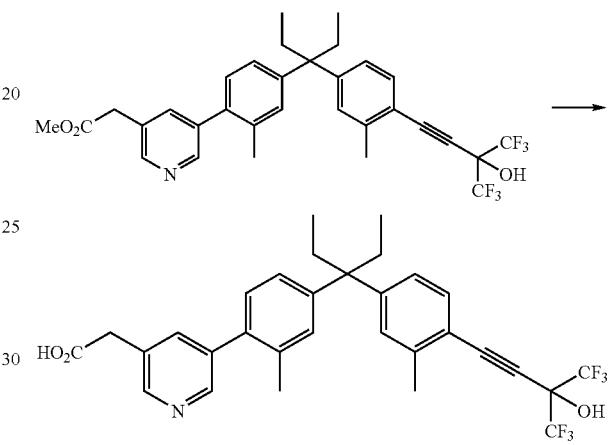

A 2 N sodium hydroxide aqueous solution (0.16 mL) was added to a solution of [5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid methyl ester (Example 80-(2); 31.9 mg, 0.0539 mmol) in methanol (1.0 mL), and the mixture was stirred for five hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (8% methanol/dichloromethane) to give the title compound (20.8 mg, 66%).

$^1$H-NMR (chloroform-d): 0.65 (t, 6H, J=7.1 Hz), 2.05 (s, 3H), 2.12 (q, 4H, J=7.1 Hz), 2.29 (s, 3H), 3.70 (s, 2H), 6.76 (d, 1H, J=8.4 Hz), 6.81 (d, 1H, J=8.4 Hz), 6.87 (s, 1H), 6.97 (d, 1H, J=8.1 Hz), 7.05 (s, 1H), 7.13 (d, 1H, J=8.1 Hz), 7.65 (s, 1H), 8.39 (s, 1H), 8.47 (d, 1H, J=1.8 Hz); MS (ESI+): 578 ([M+H]$^+$).

Example 81

Synthesis of [6-(4-{1-ethyl-1-[4-((E)-3-ethyl-3-hydroxy-1-pentenyl)-3-methyl-phenyl]-propyl}-2-methyl-phenyl)-pyridin-3-yl]-acetic Acid

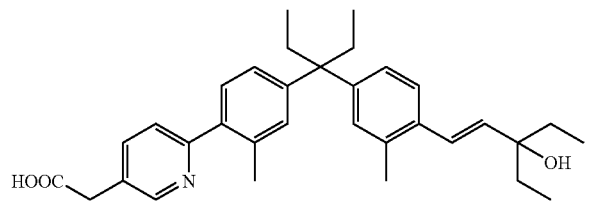

(1) Synthesis of [6-(4-{1-ethyl-1-[4-((E)-3-ethyl-3-hydroxy-1-pentenyl)-3-methyl-phenyl]-propyl}-2-methyl-phenyl)-pyridin-3-yl]-acetic Acid Ethyl Ester

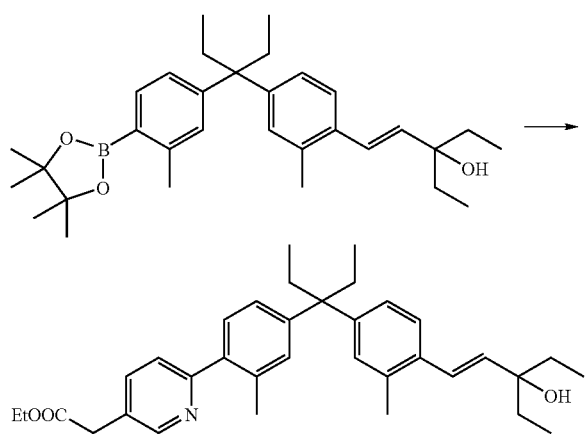

N,N-Dimethylformamide (0.7 mL) was added to 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-pentan-3-ol (Example 29; 50 mg, 0.102 mmol), (6-bromopyridin-3-yl)acetic acid ethyl ester (Example 74-(1); 40 mg, 0.165 mmol), tetrakis(triphenylphosphine)palladium (0) (23 mg, 0.02 mmol) and potassium phosphate (63.9 mg, 0.30 mmol). The mixture was stirred with microwave heating at 140° C. for seven minutes in a nitrogen atmosphere. The reaction mixture was concentrated under reduced pressure. The residue was purified by preparative TLC (hexane/ethyl acetate=10/1, then dichloromethane/methanol=20/1) to give the title compound (24.6 mg, 58%).

$^1$H-NMR (chloroform-d): 0.65 (t, 6H, J=7.1 Hz), 0.92 (t, 6H, J=7.3 Hz), 1.27 (m, 3H), 1.64 (m, 4H), 2.10 (q, 4H, J=7.1 Hz), 2.32 (m, 6H), 3.66 (s, 2H), 4.19 (m, 2H), 6.02 (d, 1H, J=15.8 Hz), 6.75 (d, 1H, J=15.8 Hz), 6.94-7.41 (m, 7H), 7.69 (m, 1H), 8.56 (s, 1H).

(2) Synthesis of [6-(4-{1-ethyl-1-[4-((E)-3-ethyl-3-hydroxy-1-pentenyl)-3-methyl-phenyl]-propyl}-2-methyl-phenyl)-pyridin-3-yl]-acetic Acid

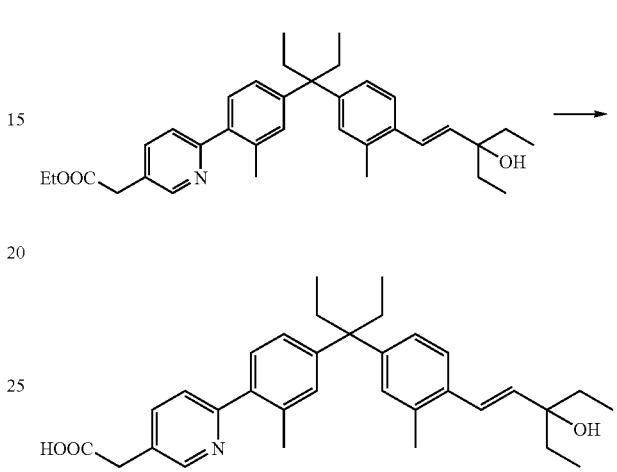

[6-(4-{1-Ethyl-1-[4-((E)-3-ethyl-3-hydroxy-1-pentenyl)-3-methyl-phenyl]-propyl}-2-methyl-phenyl)-pyridin-3-yl]-acetic acid ethyl ester (Example 81-(1); 24.6 mg, 0.047 mmol) was dissolved in methanol/tetrahydrofuran=1:1 (1 mL). A 1 N sodium hydroxide aqueous solution (0.1 mL) was added, and the mixture was stirred at room temperature for one hour. A 30% sodium dihydrogenphosphate aqueous solution (0.3 mL) was added to the reaction mixture, and then the reaction mixture was concentrated under reduced pressure. The residue was purified by preparative TLC (hexane/ethyl acetate=1/1) to give the title compound (15 mg, 65%).

$^1$H-NMR (methanol-d): 0.65 (t, 6H, J=7.1 Hz), 0.92 (t, 6H, J=7.3 Hz), 1.63 (q, 4H, J=7.3 Hz), 2.15 (q, 4H, J=7.1 Hz), 2.23 (s, 3H), 2.28 (s, 3H), 3.55 (s, 2H), 6.00 (d, 1H, J=16.0 Hz), 6.76 (d, 1H, J=16.0 Hz), 6.92-7.42 (m, 7H), 7.83 (m, 1H), 8.48 (s, 1H); MS (ESI+): 500 ([M+H]$^+$).

Example 82

Synthesis of [5-(4-{1-ethyl-1-[4-((E)-3-ethyl-3-hydroxy-1-pentenyl)-3-methyl-phenyl]-propyl}-2-methyl-phenyl)-pyridin-3-yl]-acetic Acid

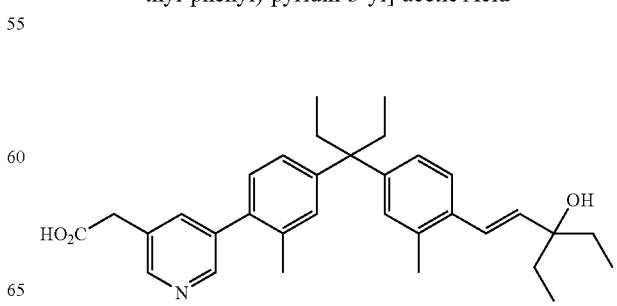

(1) Synthesis of [5-(4-{1-ethyl-1-[4-((E)-3-ethyl-3-hydroxy-1-pentenyl)-3-methyl-phenyl]-propyl}-2-methyl-phenyl)-pyridin-3-yl]-acetic Acid Methyl Ester

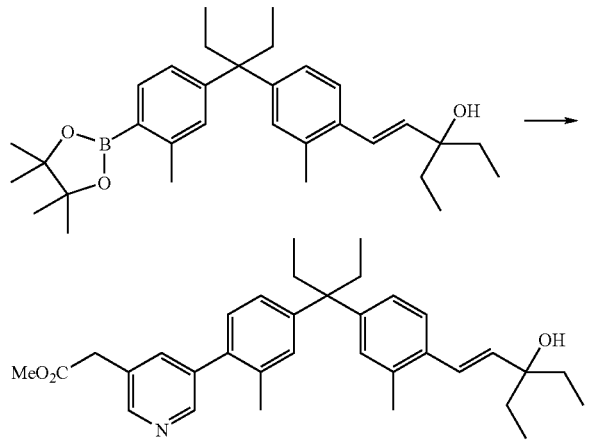

A solution of (E)-3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-penten-3-ol (Example 28; 49.3 mg, 0.1 mmol), (5-bromo-pyridin-3-yl)acetic acid methyl ester (Example 24-(2); 34.7 mg, 0.15 mmol), tetrakistriphenylphosphine palladium (16.2 mg, 0.014 mmol) and potassium phosphate (31.9 mg, 0.15 mmol) in N,N-dimethylformamide (0.27 mL) was stirred with microwave heating at 140° C. for 10 minutes. The reaction mixture was filtered through cotton plug, and the mixture was purified by silica gel chromatography (40% ethyl acetate/hexane) to give the title compound (37.1 mg, 71%).

$^1$H-NMR (chloroform-d): 0.66 (t, 6H, J=7.3 Hz), 0.92 (t, 6H, J=7.5 Hz), 1.65 (q, 4H, J=7.5 Hz), 2.12 (q, 4H, J=7.3 Hz), 2.24 (s, 3H), 2.34 (s, 3H), 3.68 (s, 2H), 3.72 (s, 3H), 6.03 (d, 1H, J=15.7 Hz), 6.76 (d, 1H, J=15.7 Hz), 6.97-6.99 (m, 2H), 7.05-7.10 (m, 3H), 7.33 (d, 1H, J=8.1 Hz), 7.62 (t, 1H, J=2.2 Hz), 8.46 (d, 1H, J=2.2 Hz), 8.52 (d, 1H, J=2.2 Hz).

(2) Synthesis of [5-(4-{1-ethyl-1-[4-((E)-3-ethyl-3-hydroxy-1-pentenyl)-3-methyl-phenyl]-propyl}-2-methyl-phenyl)-pyridin-3-yl]-acetic Acid

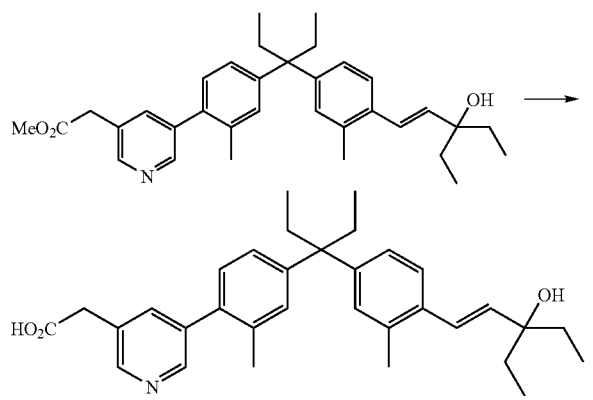

A 2 N sodium hydroxide aqueous solution (0.22 mL) was added to a solution of [5-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid methyl ester (Example 82-(1); 37.1 mg, 0.07 mmol) in methanol (1.2 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (33.2 mg, 91%).

$^1$H-NMR (chloroform-d): 0.65 (t, 6H, J=7.1 Hz), 0.91 (t, 6H, J=7.5 Hz), 1.64 (dq, 4H, J=1.4, 7.5 Hz), 2.11 (q, 4H, J=7.3 Hz), 2.22 (s, 3H), 2.32 (s, 3H), 3.71 (s, 2H), 6.02 (d, 1H, J=16.1 Hz), 6.75 (d, 1H, J=16.1 Hz), 6.97-6.98 (m, 2H), 7.04-7.08 (m, 3H), 7.32 (d, 1H, J=8.8 Hz), 7.71 (s, 1H), 8.51 (d, 1H, J=2.0 Hz), 8.52 (d, 1H, J=2.0 Hz); MS (ESI+): 500 ([M+H]$^+$).

Example 83

Synthesis of [2-(4-{1-ethyl-1-[4-((E)-3-ethyl-3-hydroxy-1-pentenyl)-3-methyl-phenyl]-propyl}-2-methyl-phenyl)-pyrimidin-5-yl]-acetic Acid

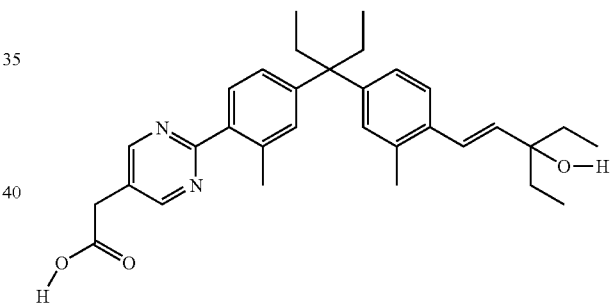

(1) Synthesis of [2-(4-{1-ethyl-1-[4-((E)-3-ethyl-3-hydroxy-1-pentenyl)-3-methyl-phenyl]-propyl}-2-methyl-phenyl)-pyrimidin-5-yl]-acetic Acid Ethyl Ester

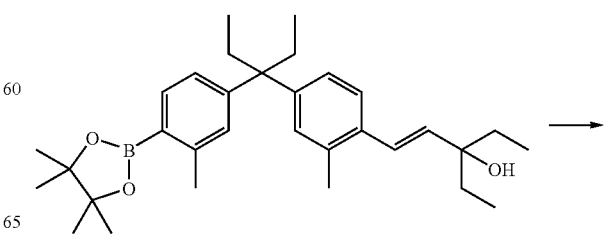

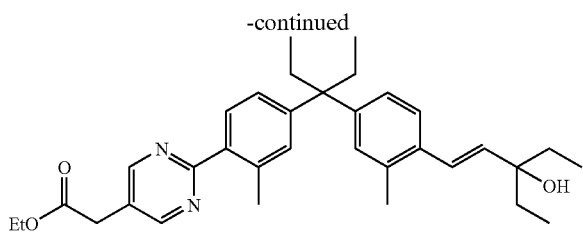

Degassed N,N-dimethylformamide (0.63 mL) was added to (E)-3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-penten-3-ol (Example 28; 52.6 mg, 0.107 mmol), 2-bromopyrimidine-5-acetic acid ethyl ester (Example 43-(3); 63 mg, 0.26 mmol), tetrakis(triphenylphosphine)palladium (0) (62.8 mg, 0.0543 mmol) and potassium phosphate (75 mg, 0.35 mmol). After replacement with nitrogen, the mixture was heated while stirring at an external temperature of 96 to 104° C. for 13 hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=3/1) to give the title compound (30 mg, 53%).

$^1$H-NMR (chloroform-d): 0.66 (t, 6H, J=7.4 Hz), 0.93 (t, 6H, J=7.4 Hz), 1.30 (t, 3H, J=7.2 Hz), 1.65 (q, 4H, J=7.4 Hz), 2.10 (q, 4H, J=7.4 Hz), 2.31 (s, 3H), 2.51 (s, 3H), 3.66 (s, 2H), 4.22 (q, 2H, J=7.2 Hz), 6.02 (d, 1H, J=15.9 Hz), 6.75 (d, 1H, J=15.9 Hz), 7.95-7.14 (m, 4H), 7.30 (d, 1H, J=8.4 Hz), 7.69 (d, 1H, J=8.4 Hz), 8.75 (s, 2H).

(2) Synthesis of [2-(4-{1-ethyl-1-[4-((E)-3-ethyl-3-hydroxy-1-pentenyl)-3-methyl-phenyl]-propyl}-2-methyl-phenyl)-pyrimidin-5-yl]-acetic Acid A 2 N sodium hydroxide aqueous solution (0.10 mL) was added to a solution of [2-(4-{1-ethyl-1-[4-((E)-3-ethyl-3-hydroxy-1-pentenyl)-3-methyl-phenyl]-propyl}-2-methyl-phenyl)-pyrimidin-5-yl]-acetic acid ethyl ester (Example 83-(1); 26.8 mg, 0.0507 mmol) in methanol (0.68 mL) at room temperature, and the mixture was stirred at room temperature for three hours. The solvent was distilled off and saturated aqueous ammonium chloride solution was added to the residue, followed by extraction with ethyl acetate. The extract was dried over anhydrous magnesium sulfate and then concentrated under reduced pressure to give the title compound (25 mg, 100%).

$^1$H-NMR (chloroform-d): 0.65 (t, 6H, J=7.4 Hz), 0.92 (t, 6H, J=7.5 Hz), 1.63 (q, 4H, J=7.5 Hz), 2.16 (q, 4H, J=7.4 Hz), 2.28 (s, 3H), 2.38 (s, 3H), 3.63 (s, 2H), 5.99 (d, 1H, J=15.9 Hz), 6.75 (d, 1H, J=15.9 Hz), 7.93-7.14 (m, 4H), 7.30 (d, 1H, J=8.1 Hz), 7.51 (d, 1H, J=8.7 Hz), 8.75 (s, 2H); MS (ESI+): 501 ([M+H]$^+$).

Example 84

Synthesis of Sodium [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetate

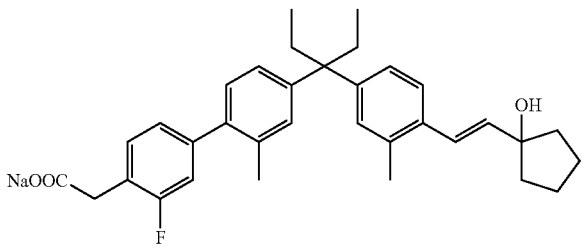

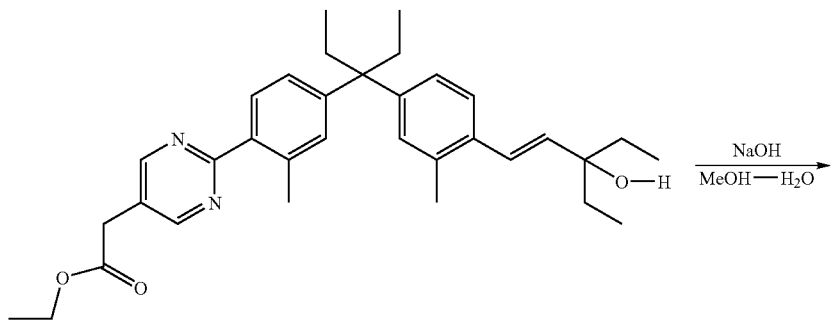

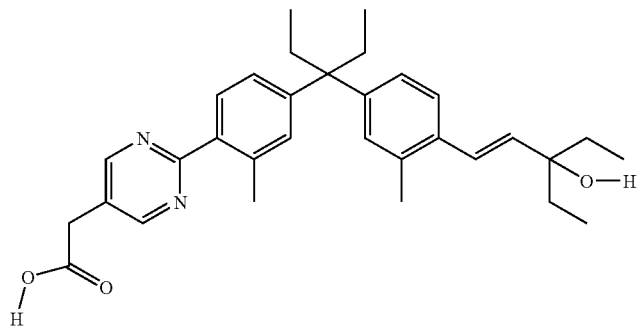

(1) Synthesis of [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetic Acid Methyl Ester

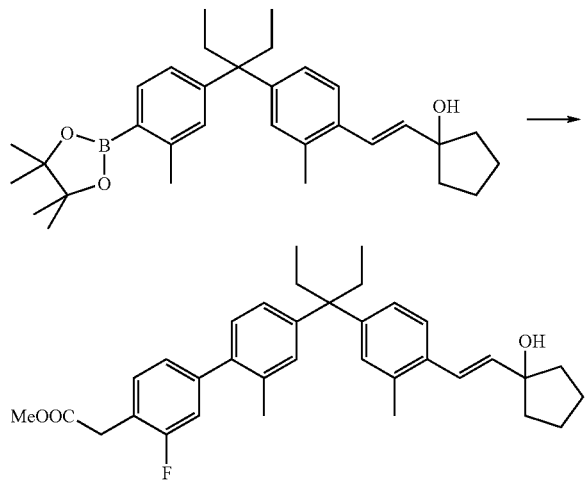

(4-Chloro-2-fluoro-phenyl)acetic acid methyl ester (Example 40; 47 mg, 0.230 mmol), toluene (2.5 mL), palladium acetate (3.4 mg, 0.015 mmol), 2-dicyclohexylphosphino-2',6'-dimethoxy-1,1'-biphenyl (12.6 mg, 0.031 mmol), potassium phosphate (97 mg, 0.459 mmol) and water (0.250 mL) were added to 1-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclopentanol (Example 33-(3); 75 mg, 0.153 mmol), and the mixture was stirred in a nitrogen atmosphere at 100° C. for two hours. The reaction solution was poured into a saturated aqueous sodium bicarbonate solution, and then the aqueous layer was extracted with dichloromethane. The organic layer was dried over anhydrous sodium sulfate and concentrated under reduced pressure. The residue was purified by silica gel chromatography (17% ethyl acetate/hexane) to give the title compound (24 mg, 30%).

$^1$H-NMR (chloroform-d): 0.65 (t, 6H, J=7.3 Hz), 1.72-1.96 (m, 8H), 2.11 (q, 4H, J=7.1 Hz), 2.22 (s, 3H), 2.33 (s, 3H), 3.70 (s, 2H), 3.73 (s, 3H), 6.26 (d, 1H, J=15.9 Hz), 6.83 (d, 1H, J=15.7 Hz), 6.97-7.07 (m, 7H), 7.24-7.28 (m, 2H); MS (ESI+): 511 ([M+H—H$_2$O]$^+$).

(2) Synthesis of Sodium [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetate

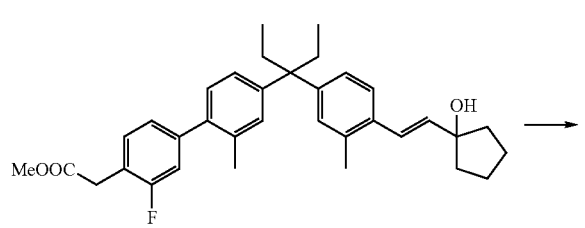

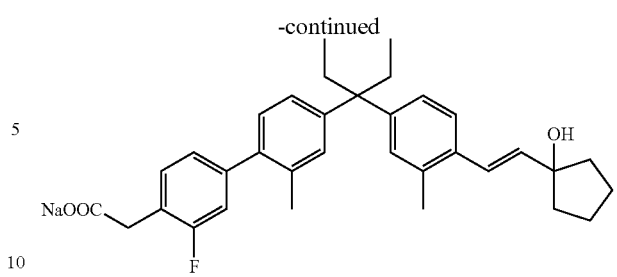

Methanol (1.3 mL), tetrahydrofuran (1.3 mL) and a 1 M sodium hydroxide aqueous solution (0.129 mL, 0.129 mmol) were added to [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetic acid methyl ester (Example 84-(1); 22.8 mg, 0.043 mmol), and the mixture was stirred at room temperature for 25 hours. The reaction solution was poured into a saturated aqueous ammonium chloride solution, and then the aqueous layer was extracted with dichloromethane. The organic layer was dried over anhydrous sodium sulfate and concentrated under reduced pressure. The residue was crudely purified by preparative TLC (chloroform/methanol=10/1). The crude purified product was diluted with methanol. After addition of sodium methoxide, the mixture was dried under reduced pressure. The residue was purified by preparative TLC (developer obtained by saturating chloroform/methanol=10/1 with water). The purified product was diluted with methanol. After addition of sodium methoxide, the mixture was dried under reduced pressure to give the title compound (12.6 mg, 57%).

$^1$H-NMR (methanol-d4): 0.64 (t, 6H, J=7.3 Hz), 1.76-1.90 (m, 8H), 2.13 (q, 4H, J=7.2 Hz), 2.20 (s, 3H), 2.29 (s, 3H), 3.65 (s, 2H), 6.22 (d, 1H, J=15.8 Hz), 6.84 (d, 1H, J=16.0 Hz), 6.97-7.09 (m, 7H), 7.29-7.34 (m, 2H); MS (ESI+): 497 ([M+H—H$_2$O]$^+$).

Example 85

Synthesis of {6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic Acid

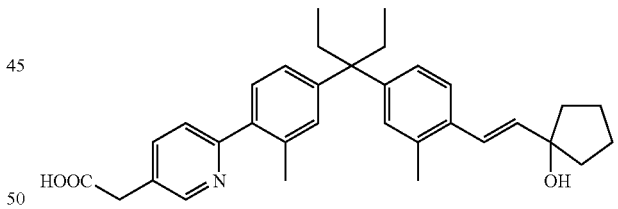

(1) Synthesis of {6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic Acid Ethyl Ester

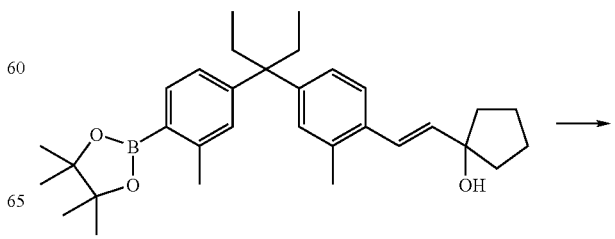

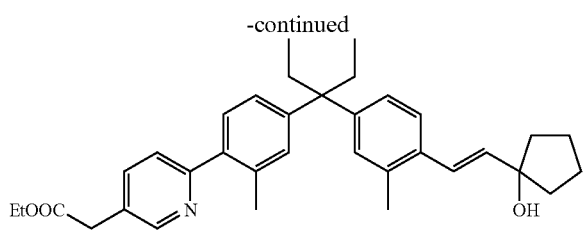

The title compound (38%) was obtained by the same method as in Example 79-(1) using (E)-1-[2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclopentanol (Example 33-(3)) as a starting material.

$^1$H-NMR (chloroform-d): 0.64 (t, 6H, J=7.1 Hz), 1.23 (m, 3H), 1.70-1.95 (m, 8H), 2.11 (q, 4H, J=7.1 Hz), 2.32 (s, 6H), 3.66 (s, 2H), 6.26 (d, 1H, J=15.8 Hz), 6.83 (d, 1H, J=15.8 Hz), 6.93-7.42 (m, 7H), 7.67 (m, 1H), 8.56 (s, 1H).

(2) Synthesis of {6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic Acid

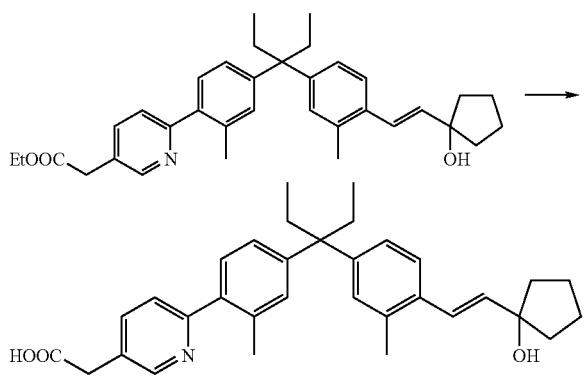

The title compound (55%) was obtained by the same method as in Example 81-(2) using {6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic acid ethyl ester (Example 85-(1)) as a starting material.

$^1$H-NMR (methanol-d): 0.65 (t, 6H, J=7.1 Hz), 1.70-1.95 (m, 8H), 2.15 (q, 4H, J=7.1 Hz), 2.23 (s, 3H), 2.28 (s, 3H), 3.57 (s, 2H), 6.23 (d, 1H, J=15.8 Hz), 6.82 (d, 1H, J=15.8 Hz), 6.93-7.42 (m, 7H), 7.83 (m, 1H), 8.48 (s, 1H);
MS (ESI+): 498 ([M+H]$^+$).

Example 86

Synthesis of {5-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic Acid

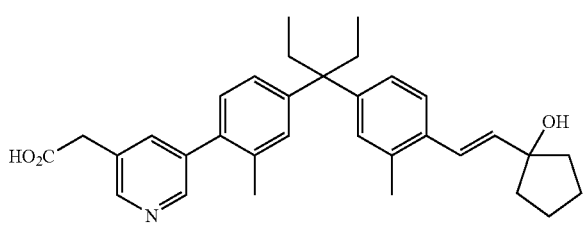

(1) Synthesis of {5-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic Acid Methyl Ester

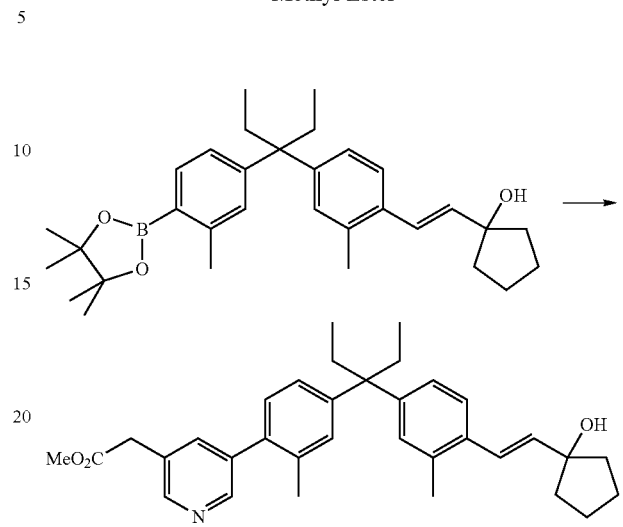

A solution of 1-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclopentanol (Example 33-(3); 0.05 g, 0.10 mmol), (5-bromo-pyridin-3-yl)acetic acid methyl ester (Example 24-(2); 35.3 mg, 0.15 mmol), tetrakistriphenylphosphine palladium (16.5 mg, 0.0143 mmol) and potassium phosphate (32.6 mg, 0.15 mmol) in N,N-dimethylformamide (0.3 mL) was stirred with microwave heating at 140° C. for 10 minutes. The reaction mixture was filtered through cotton plug, and the mixture was purified by silica gel chromatography (40% ethyl acetate/hexane) to give the title compound (41.0 mg, 78%).

$^1$H-NMR (chloroform-d): 0.65 (t, 6H, J=7.0 Hz), 1.72-1.86 (m, 6H), 1.91-1.99 (m, 2H), 2.12 (q, 4H, J=7.1 Hz), 2.23 (s, 3H), 2.34 (s, 3H), 3.68 (s, 2H), 3.72 (s, 3H), 6.28 (d, 1H, J=16.8 Hz), 6.85 (d, 1H, J=16.1 Hz), 6.98-7.02 (m, 2H), 7.05-7.10 (m, 3H), 7.36 (d, 1H, J=8.4 Hz), 7.62 (s, 1H), 8.46 (s, 1H), 8.52 (s, 1H).

(2) Synthesis of {5-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic Acid

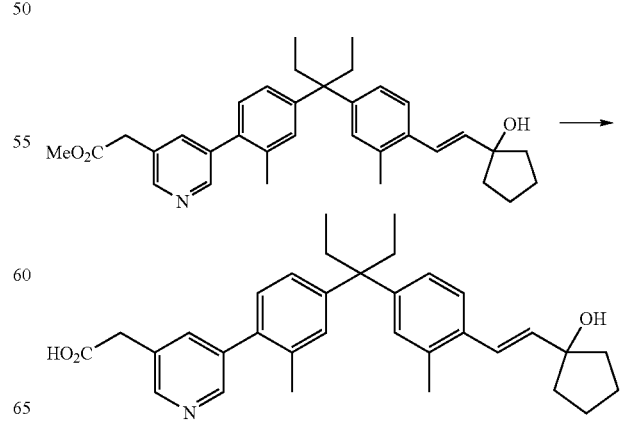

A 2 N sodium hydroxide aqueous solution (0.24 mL) was added to a solution of {5-[4-(1-ethyl-1-{4-[(E)-2-(1-hydroxy-cyclopentyl)-vinyl]-3-methyl-phenyl}-propyl]-2-methyl-phenyl]-pyridin-3-yl}-acetic acid methyl ester (Example 86-(1); 41.0 mg, 0.08 mmol) in methanol (1.3 mL), and the mixture was stirred for two hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (10% methanol/dichloromethane) to give the title compound (32.9 mg, 82%).

$^1$H-NMR (chloroform-d): 0.64 (t, 6H, J=7.1 Hz), 1.74-1.86 (m, 6H), 1.88-1.97 (m, 2H), 2.11 (q, 4H, J=7.3 Hz), 2.21 (s, 3H), 2.32 (s, 3H), 3.10-3.70 (brs, 1H), 3.71 (s, 2H), 6.27 (d, 1H, J=16.1 Hz), 6.84 (d, 1H, J=15.7 Hz), 6.97-7.01 (m, 2H), 7.03-7.08 (m, 3H), 7.35 (d, 1H, J=8.4 Hz), 7.70 (s, 1H), 8.51 (d, 1H, J=2.0 Hz), 8.52 (d, 1H, J=2.0 Hz);

MS (ESI+): 498 ([M+H]$^+$).

Example 87

Synthesis of [4'-(1-ethyl-1-{4-[(E)-2-(1-hydroxy-cyclohexyl)-vinyl]-3-methyl-phenyl}-propyl)-2'-methyl-biphenyl-3-yl]-acetic Acid

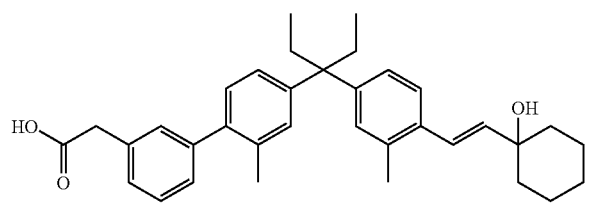

(1) Synthesis of [4'-(1-ethyl-1-{4-[(E)-2-(1-hydroxy-cyclohexyl)-vinyl]-3-methyl-phenyl}-propyl)-2'-methyl-biphenyl-3-yl]-acetic Acid Methyl Ester

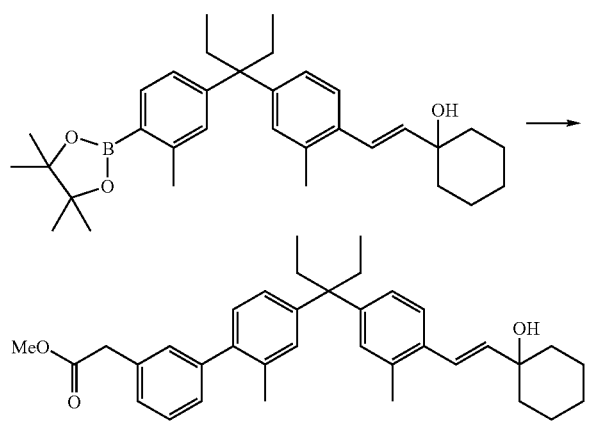

The title compound (58%) was obtained by the same method as in Example 56-(1) using, as starting materials, 1-[(E)-2-(4-{1-ethyl-1-[3-methyl-4-(4,4,5,5-tetramethyl-[1,3,2]dioxaborolan-2-yl)-phenyl]-propyl}-2-methylphenyl)-vinyl]-cyclohexanol (Example 36-(3)) and 3-bromophenyl-acetic acid methyl ester (Tetrahedron Letters 44 (2003) 331-334).

$^1$H-NMR (chloroform-d): 0.67 (t, 6H, J=7.3 Hz), 1.29-1.43 (m, 1H), 1.51-1.75 (m, 9H), 2.13 (q, 4H, J=7.3 Hz), 2.23 (s, 3H), 2.34 (s, 3H), 3.67 (s, 2H), 3.71 (s, 3H), 6.23 (d, 1H, J=16.0 Hz), 6.84 (d, 1H, J=16.1 Hz), 6.96-7.11 (m, 5H), 7.17-7.26 (m, 3H), 7.33-7.37 (m, 2H); MS (ESI+): 507 ([M−H$_2$O+H]$^+$).

(2) Synthesis of [4'-(1-ethyl-1-{4-[(E)-2-(1-hydroxy-cyclohexyl)-vinyl]-3-methyl-phenyl}-propyl)-2'-methyl-biphenyl-3-yl]-acetic Acid

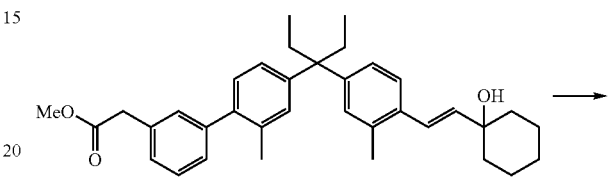

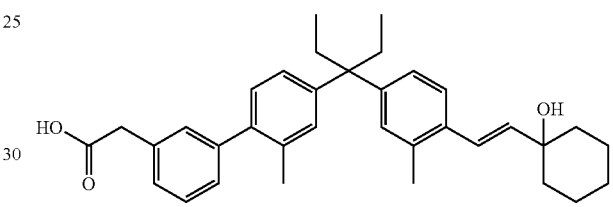

The title compound (41%) was obtained by the same method as in Example 56-(2) using [4'-(1-ethyl-1-{4-[(E)-2-(1-hydroxycyclohexyl)-vinyl]-3-methylphenyl}-propyl)-2'-methylbiphenyl-3-yl]-acetic acid methyl ester (Example 87-(1)) as a starting material.

$^1$H-NMR (chloroform-d): 0.66 (t, 6H, J=7.5 Hz), 1.25-1.84 (m, 10H), 2.12 (q, 4H, J=7.5 Hz), 2.22 (s, 3H), 2.33 (s, 3H), 3.68 (s, 2H), 6.23 (d, 1H, J=15.0 Hz), 6.84 (d, 1H, J=15.0 Hz), 6.96-6.81 (m, 5H), 7.21-7.29 (m, 3H), 7.33-7.38 (m, 2H); MS (ESI+): 493 ([M−H$_2$O+H]$^+$).

Example 88

Synthesis of [4'-(1-ethyl-1-{4-[(E)-2-(1-hydroxy-cyclohexyl)-vinyl]-3-methyl-phenyl}-propyl)-3-fluoro-2'-methyl-biphenyl-4-yl]-acetic Acid

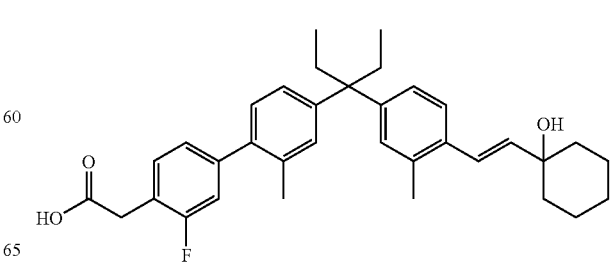

(1) Synthesis of [4'-(1-ethyl-1-{4-[(E)-2-(1-hydroxy-cyclohexyl)-vinyl]-3-methyl-phenyl}-propyl)-3-fluoro-2'-methyl-biphenyl-4-yl]-acetic Acid Methyl Ester

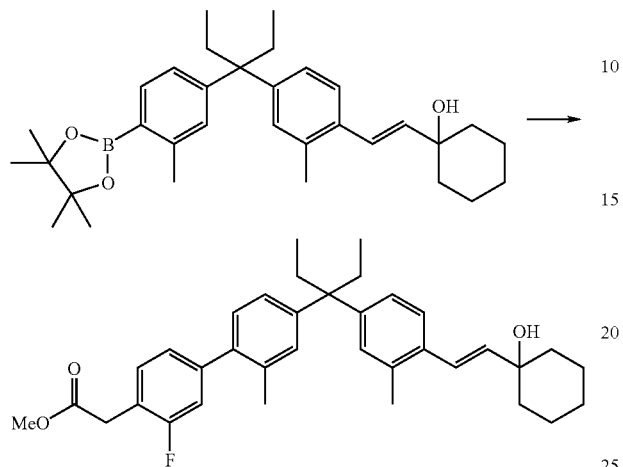

The title compound (56%) was obtained by the same method as in Example 56-(1) using, as starting materials, 1-[(E)-2-(4-{1-ethyl-1-[3-methyl-4-(4,4,5,5-tetramethyl-[1,3,2]dioxaborolan-2-yl)-phenyl]-propyl}-2-methylphenyl)-vinyl]-cyclohexanol (Example 36-(3)) and 4-chloro-2-phenyl-acetic acid methyl ester (Example 40).

$^1$H-NMR (chloroform-d): 0.66 (t, 6H, J=7.2 Hz), 1.29-1.42 (m, 1H), 1.53-1.75 (m, 9H), 2.12 (q, 4H, J=7.2 Hz), 2.24 (s, 3H), 2.34 (s, 3H), 3.72 (s, 2H), 3.75 (s, 3H), 6.22 (d, 1H, J=16.0 Hz), 6.83 (d, 1H, J=16.0 Hz), 6.97-7.12 (m, 7H), 7.22-7.37 (m, 2H); MS (ESI+): 525 ([M–H$_2$O+H]$^+$).

(2) Synthesis of [4'-(1-ethyl-1-{4-[(E)-2-(1-hydroxy-cyclohexyl)-vinyl]-3-methyl-phenyl}-propyl)-3-fluoro-2'-methyl-biphenyl-4-yl]-acetic Acid

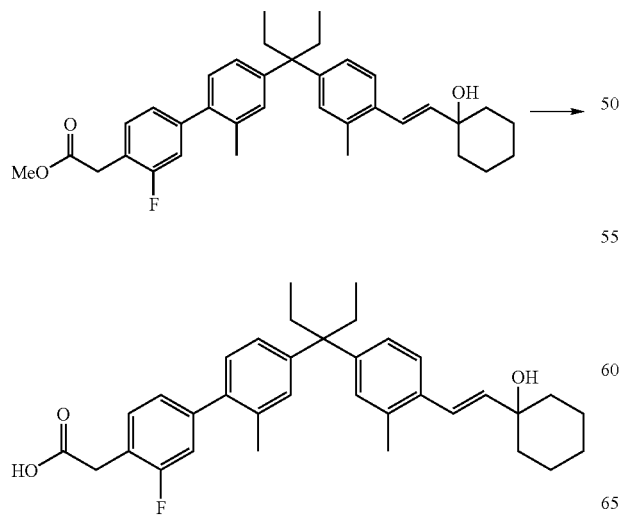

The title compound (55%) was obtained by the same method as in Example 56-(2) using [4'-(1-ethyl-1-{4-[(E)-2-(1-hydroxycyclohexyl)-vinyl]-3-methylphenyl}-propyl)-3-fluoro-2'-methylbiphenyl-4-yl]-acetic acid methyl ester (Example 88-(1)) as a starting material.

$^1$H-NMR (chloroform-d): 0.66 (t, 6H, J=7.5 Hz), 1.25-1.42 (m, 1H), 1.50-1.80 (m, 9H), 2.12 (q, 4H, J=7.5 Hz), 2.23 (s, 3H), 2.34 (s, 3H), 3.76 (s, 2H), 6.23 (d, 1H, J=15.0 Hz), 6.84 (d, 1H, J=15.0 Hz), 6.98-7.09 (m, 7H), 7.25-7.37 (m, 2H); MS (ESI+): 511 ([M–H$_2$O+H]$^+$).

Example 89

Synthesis of [5-chloro-4'-(1-ethyl-1-{4-[(E)-2-(1-hydroxy-cyclohexyl)-vinyl]-3-methyl-phenyl}-propyl)-2'-methyl-biphenyl-2-yl]-acetic Acid

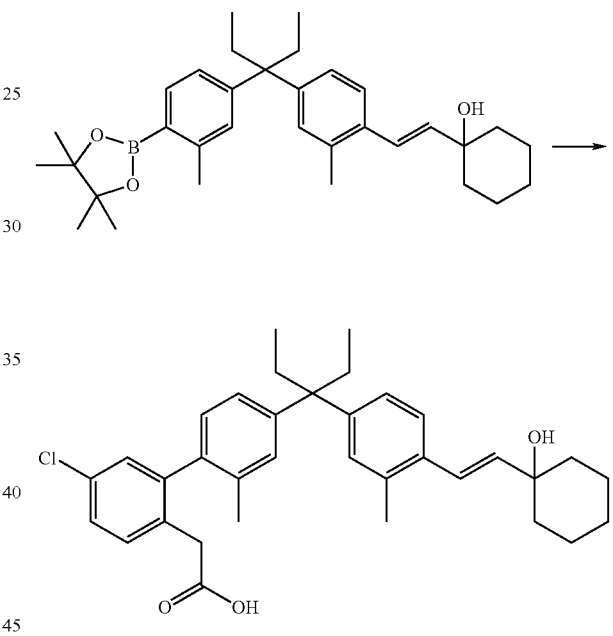

21 mg of a mixture of a methyl ester of the title compound with a methyl ester of the title compound of Example 90 was obtained by the same method as in Example 56-(1) using, as starting materials, 1-[(E)-2-(4-{1-ethyl-1-[3-methyl-4-(4,4,5,5-tetramethyl-[1,3,2]dioxaborolan-2-yl)-phenyl]-propyl}-2-methylphenyl)-vinyl]-cyclohexanol (Example 36-(3)) and 4-chloro-2-phenyl-acetic acid methyl ester (Example 41).

The mixture was hydrolyzed by the same method as in Example 56-(2) to give the title compound (12% in two steps).

$^1$H-NMR (chloroform-d): 0.64 (t, 6H, J=7.5 Hz), 1.24-1.37 (m, 1H), 1.57-1.71 (m, 9H), 1.98 (s, 3H), 2.10 (q, 4H, J=7.5 Hz), 2.32 (s, 3H), 3.33 (d, 1H, J=18.0 Hz), 3.45 (d, 1H, J=18.0 Hz), 6.22 (d, 1H, J=15.0 Hz), 6.83 (d, 1H, J=15.0 Hz), 6.91-7.04 (m, 5H), 7.20-7.36 (m, 4H); MS (ESI+): 527 ([M–H$_2$O+H]$^+$).

Example 90

Synthesis of [3-chloro-4'-(1-ethyl-1-{4-[(E)-2-(1-hydroxy-cyclohexyl)-vinyl]-3-methyl-phenyl}-propyl)-2'-methyl-biphenyl-4-yl]-acetic Acid

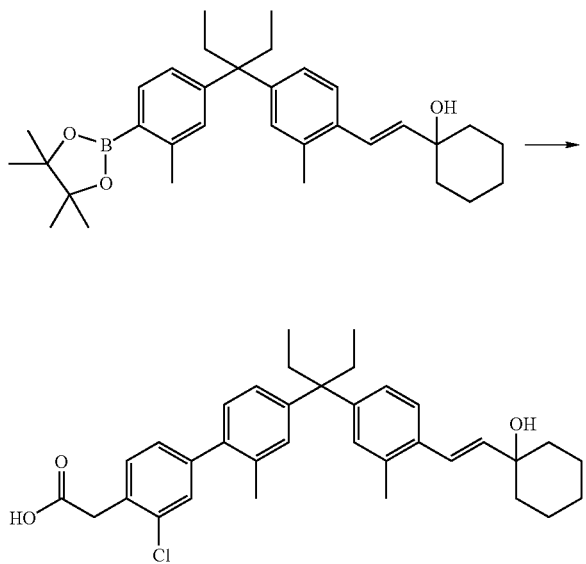

21 mg of a mixture of a methyl ester of the title compound with a methyl ester of the title compound of Example 89 was obtained by the same method as in Example 56-(1) using, as starting materials, 1-[(E)-2-(4-{1-ethyl-1-[3-methyl-4-(4,4,5,5-tetramethyl-[1,3,2]dioxaborolan-2-yl)-phenyl]-propyl}-2-methylphenyl)-vinyl]-cyclohexanol (Example 36-(3)) and (2,4-dichloro-phenyl)-acetic acid methyl ester (Example 41).

The mixture was hydrolyzed by the same method as in Example 56-(2) to give the title compound (6% in two steps).

$^1$H-NMR (chloroform-d): 0.65 (t, 6H, J=7.5 Hz), 1.24-1.42 (m, 1H), 1.53-1.77 (m, 9H), 2.12 (q, 4H, J=7.5 Hz), 2.23 (s, 3H), 2.33 (s, 3H), 3.87 (s, 2H), 6.22 (d, 1H, J=18.0 Hz), 6.83 (d, 1H), 6.97-7.08 (m, 5H), 7.19-7.22 (m, 1H), 7.30-7.38 (m, 3H); MS (ESI+): 527 ([M−H$_2$O+H]$^+$).

Example 91

Synthesis of {6-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic Acid

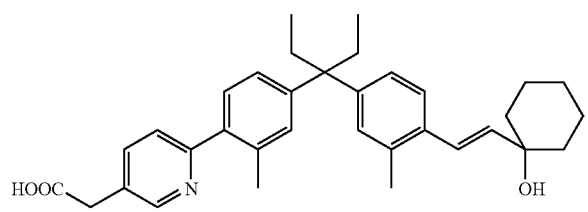

(1) Synthesis of (E)-{6-[4-(1-ethyl-1-{4-[2-(1-hydroxy-cyclohexyl)-vinyl]-3-methyl-phenyl}-propyl)-2-methyl-phenyl]-pyridin-3-yl}-acetic Acid Ethyl Ester

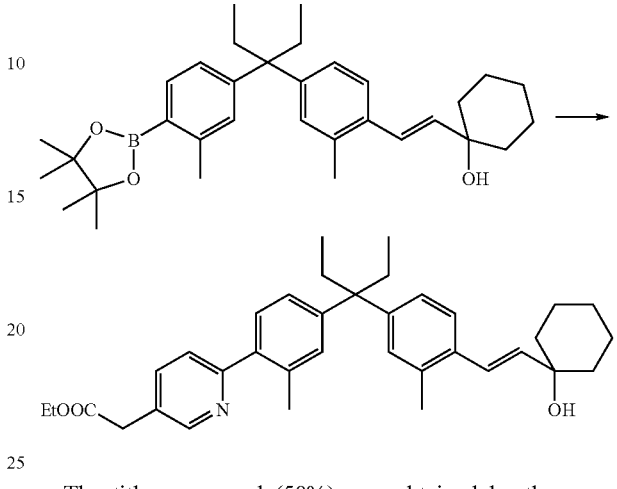

The title compound (50%) was obtained by the same method as in Example 79-(1) using (E)-1-[2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclohexanol (Example 36-(3)) as a starting material.

$^1$H-NMR (chloroform-d): 0.64 (t, 6H, J=7.2 Hz), 1.32 (t, 3H, J=7.0 Hz), 1.54-1.80 (m, 10H), 2.11 (q, 4H, J=7.2 Hz), 2.30 (s, 6H), 3.66 (s, 2H), 4.19 (q, 2H, J=7.0 Hz), 6.21 (d, 1H, J=14.0 Hz), 6.81 (d, 1H, J=14.0 Hz), 6.95-7.41 (m, 7H), 7.68 (m, 1H), 8.56 (d, 1H, J=2.2 Hz).

(2) Synthesis of {6-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic Acid

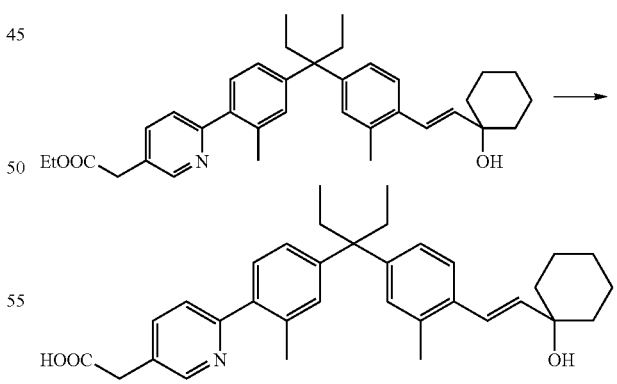

The title compound (40%) was obtained by the same method as in Example 81-(2) using (E)-{6-[4-(1-ethyl-1-{4-[2-(1-hydroxy-cyclohexyl)-vinyl]-3-methyl-phenyl}-propyl)-2-methyl-phenyl]-pyridin-3-yl}-acetic acid ethyl ester (Example 91-(1)) as a starting material.

$^1$H-NMR (methanol-d): 0.65 (t, 6H, J=7.1 Hz), 1.54-1.80 (m, 1H), 2.15 (q, 4H, J=7.1 Hz), 2.23 (s, 3H), 2.28 (s, 3H), 3.54 (s, 2H), 6.17 (d, 1H, J=15.9 Hz), 6.81 (d, 1H, J=15.9 Hz), 6.95-7.41 (m, 7H), 7.83 (d, 1H, J=7.8 Hz), 8.48 (s, 1H); MS (ESI+): 512 ([M+H]+).

Example 92

Synthesis of {5-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic Acid

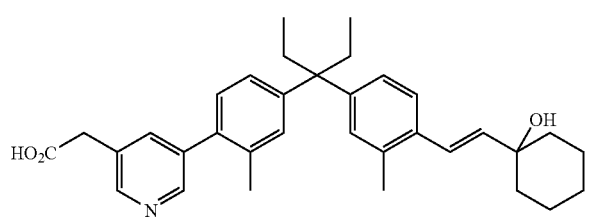

(1) Synthesis of {5-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic Acid Ethyl Ester

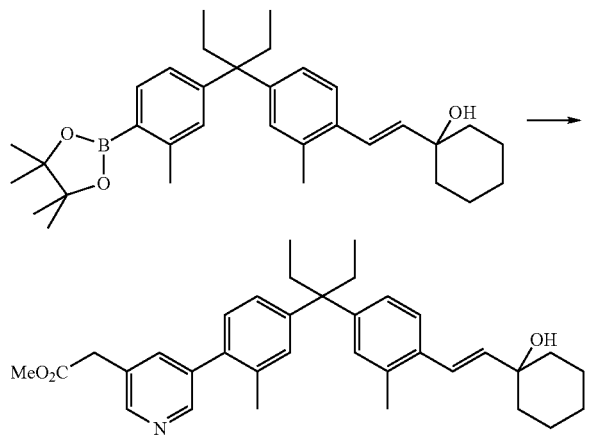

A solution of 1-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-cyclohexanol (Example 36-(3); 0.05 g, 0.0994 mmol), (5-bromo-pyridin-3-yl)acetic acid methyl ester (Example 24-(2); 34.3 mg, 0.14 mmol), tetrakistriphenylphosphine palladium (16.0 mg, 0.0139 mmol) and potassium phosphate (31.7 mg, 0.14 mmol) in N,N-dimethylformamide (0.27 mL) was stirred with microwave heating at 140° C. for 10 minutes. The reaction mixture was filtered through cotton plug, and the mixture was purified by silica gel chromatography (40% ethyl acetate/hexane) to give the title compound (47.8 mg, 91%).

1H-NMR (chloroform-d): 0.65 (t, 6H, J=7.0 Hz), 1.30-1.36 (m, 2H), 1.54-1.64 (m, 4H), 1.65-1.75 (m, 4H), 2.12 (q, 4H, J=7.3 Hz), 2.23 (s, 3H), 2.33 (s, 3H), 3.68 (s, 2H), 3.72 (s, 3H), 6.22 (d, 1H, J=16.1 Hz), 6.83 (d, 1H, J=16.1 Hz), 6.98-7.01 (m, 2H), 7.05-7.09 (m, 3H), 7.36 (d, 1H, J=8.1 Hz), 7.62 (s, 1H), 8.47 (s, 1H), 8.52 (s, 1H).

(2) Synthesis of {5-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic Acid

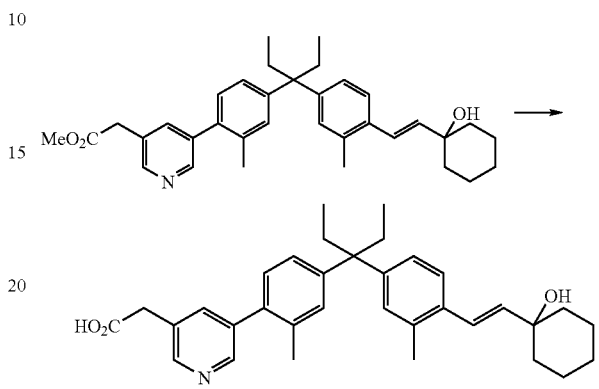

A 2 N sodium hydroxide aqueous solution (0.27 mL) was added to a solution of {5-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic acid methyl ester (Example 92-(1); 47.8 mg, 0.09 mmol) in methanol (1.5 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (10% methanol/dichloromethane) to give the title compound (39.8 mg, 85%).

1H-NMR (chloroform-d): 0.64 (t, 6H, J=7.1 Hz), 1.54-1.64 (m, 4H), 1.68-1.76 (m, 6H), 2.11 (q, 4H, J=7.2 Hz), 2.21 (s, 3H), 2.31 (s, 3H), 3.71 (s, 2H), 6.21 (d, 1H, J=16.1 Hz), 6.82 (d, 1H, J=16.1 Hz), 6.96-7.00 (m, 2H), 7.02-7.09 (m, 3H), 7.34 (d, 1H, J=8.8 Hz), 7.70 (s, 1H), 8.50 (d, 1H, J=1.8 Hz), 8.52 (d, 1H, J=1.8 Hz); MS (ESI+): 512 ([M+H]+).

Example 93

Synthesis of (4'-{1-ethyl-1-[4-(1-hydroxy-cyclopentylethynyl)-3-methyl-phenyl]-propyl}-3-fluoro-2'-methyl-biphenyl-4-yl)-acetic Acid

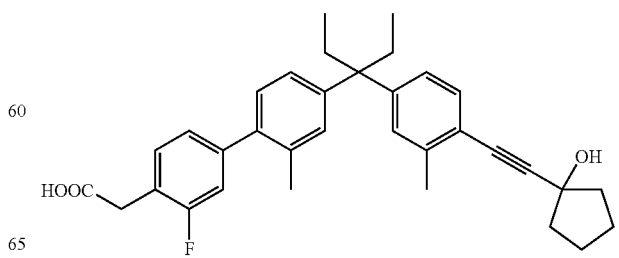

(1) Synthesis of (4'-{1-ethyl-1-[3-methyl-4-(1-trimethylsilanyloxy-cyclopentylethynyl)-phenyl]-propyl}-3-fluoro-2'-methyl-biphenyl-4-yl)-acetic Acid Methyl Ester

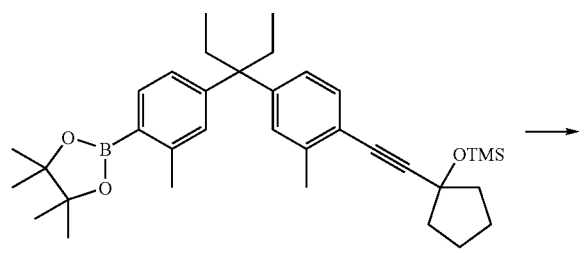

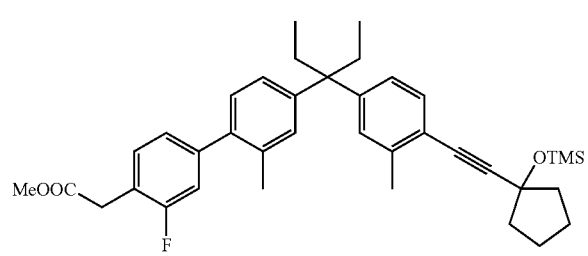

A solution of palladium acetate (3.4 mg, 0.015 mmol), 2-dicyclohexylphosphino-2',6'-dimethoxybiphenyl (12.3 mg, 0.03 mmol) and potassium phosphate (63.7 mg, 0.3 mmol) in water (0.045 mL) and toluene (0.200 mL) was stirred for three minutes. A solution of (4-chloro-2-fluorophenyl)acetic acid methyl ester (Example 40; 32.6 mg, 0.16 mmol) and 2-(4-{1-ethyl-1-[3-methyl-4-(1-trimethylsilanyloxy-cyclopentylethynyl)-phenyl]-propyl}-2-methyl-phenyl)-4,4,5,5-tetramethyl-[1,3,2]dioxaborolane (Example 32-(4); 60.0 mg, 0.10 mmol) in toluene (0.25 mL) was added, and the mixture was stirred in a nitrogen atmosphere at 100° C. for one hour. After filtration through cotton plug, the filtrate was concentrated under reduced pressure. The residue was purified by thin layer silica gel chromatography (3% ethyl acetate/hexane) to give the title compound (52.6 mg, 81%).

$^1$H-NMR (chloroform-d): 0.25 (s, 9H), 0.66 (t, 6H, J=7.2 Hz), 1.74-1.85 (m, 4H), 1.95-2.06 (m, 4H), 2.12 (q, 4H, J=7.2 Hz), 2.25 (s, 3H), 2.41 (s, 3H), 3.72 (s, 2H), 3.75 (s, 3H), 6.96-7.13 (m, 7H), 7.24-7.31 (m, 2H).

(2) Synthesis of (4'-{1-ethyl-1-[4-(1-hydroxy-cyclopentylethynyl)-3-methyl-phenyl]-propyl}-3-fluoro-2'-methyl-biphenyl-4-yl)-acetic Acid Methyl Ester

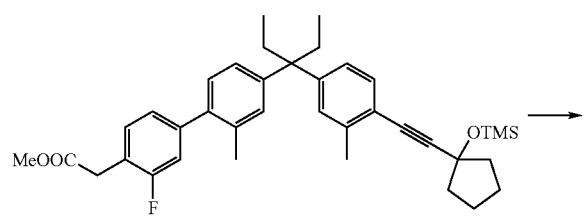

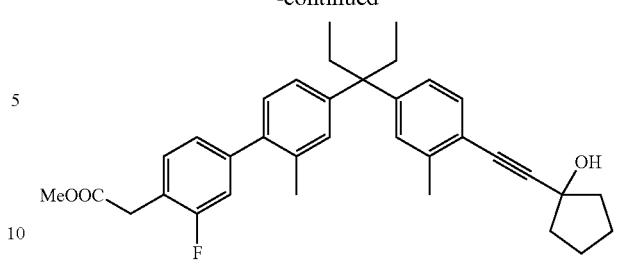

A 1 M solution of tetrabutylammonium fluoride in tetrahydrofuran (0.105 mL, 0.105 mmol) was added to (4'-{1-ethyl-1-[3-methyl-4-(1-trimethylsilanyloxy-cyclopentylethynyl)-phenyl]-propyl}-3-fluoro-2'-methyl-biphenyl-4-yl)acetic acid methyl ester (Example 93-(1); 52.6 mg, 0.0878 mmol), and the mixture was stirred for 40 minutes. A saturated aqueous ammonium chloride solution was added to the reaction mixture, followed by extraction with diethyl ether. The organic layer was washed with water, dried over anhydrous sodium sulfate and concentrated under reduced pressure. The residue was purified by silica gel chromatography (20% ethyl acetate/hexane) to give the title compound (41.1 mg, 88%).

$^1$H-NMR (chloroform-d): 0.65 (t, 6H, J=7.2 Hz), 1.77-1.99 (m, 4H), 2.01-2.15 (m, 8H), 2.23 (s, 3H), 2.40 (s, 3H), 3.72 (s, 2H), 3.75 (s, 3H), 6.97-7.09 (m, 7H), 7.25-7.31 (m, 2H).

(3) Synthesis of (4'-{1-ethyl-1-[4-(1-hydroxy-cyclopentylethynyl)-3-methyl-phenyl]-propyl}-3-fluoro-2'-methyl-biphenyl-4-yl)-acetic Acid

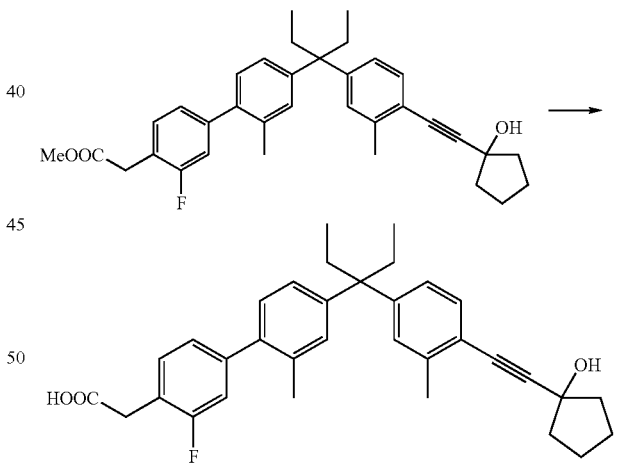

A 2 N sodium hydroxide aqueous solution (0.24 mL) was added to a solution of (4'-{1-ethyl-1-[4-(1-hydroxy-cyclopentylethynyl)-3-methyl-phenyl]-propyl}-3-fluoro-2'-methyl-biphenyl-4-yl)acetic acid methyl ester (Example 93-(2); 41.1 mg, 0.078 mmol) in methanol (1.3 mL), and the mixture was stirred for three hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (39.4 mg, 98%).

$^1$H-NMR (chloroform-d): 0.63 (t, 6H, J=7.2 Hz), 1.74-1.99 (m, 4H), 2.01-2.13 (m, 8H), 2.20 (s, 3H), 2.38 (s, 3H), 3.73 (s, 2H), 6.94-7.06 (m, 7H), 7.23-7.29 (m, 2H); MS (ESI+): 495 ([M–H$_2$O+H]$^+$).

Example 94

Synthesis of [5-(4-{1-ethyl-1-[4-(1-hydroxy-cyclopentylethynyl)-3-methyl-phenyl]-propyl}-2-methyl-phenyl)-pyridin-3-yl]-acetic Acid

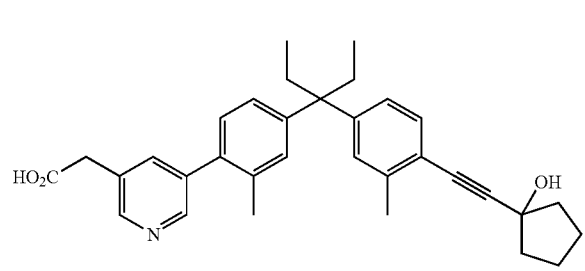

(1) Synthesis of [5-(4-{1-ethyl-1-[3-methyl-4-(1-trimethylsilanyloxy-cyclopentylethynyl)-phenyl]-propyl}-2-methyl-phenyl)-pyridin-3-yl]-acetic Acid Methyl Ester

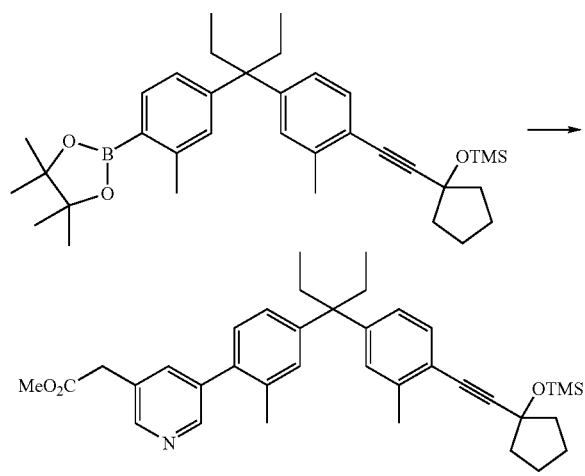

A solution of 2-(4-{1-ethyl-1-[3-methyl-4-(1-trimethylsilanyloxy-cyclopentylethynyl)-phenyl]-propyl}-2-methyl-phenyl)-4,4,5,5-tetramethyl-[1,3,2]dioxaborolane (Example 32-(4); 54.1 mg, 0.0968 mmol), (5-bromo-pyridin-3-yl)acetic acid methyl ester (Example 24-(2); 33.4 mg, 0.14 mmol), tetrakistriphenylphosphine palladium (15.6 mg, 0.0135 mmol) and potassium phosphate (30.8 mg, 0.14 mmol) in N,N-dimethylformamide (0.27 mL) was stirred with microwave heating at 140° C. for 10 minutes. The reaction mixture was filtered through cotton plug, and the mixture was purified by silica gel chromatography (45% ethyl acetate/hexane) to give the title compound (38.2 mg, 67%).

$^1$H-NMR (chloroform-d): 0.22 (s, 9H), 0.64 (t, 6H, J=7.3 Hz), 1.72-1.86 (m, 4H), 1.95-2.06 (m, 4H), 2.11 (q, 4H, J=7.3 Hz), 2.23 (s, 3H), 2.39 (s, 3H), 3.68 (s, 2H), 3.72 (s, 3H), 6.96-7.10 (m, 5H), 7.30 (d, 1H, J=8.1 Hz), 7.62 (s, 1H), 8.47 (s, 1H), 8.52 (s, 1H).

(2) Synthesis of [5-(4-{1-ethyl-1-[4-(1-hydroxy-cyclopentylethynyl)-3-methyl-phenyl]-propyl}-2-methyl-phenyl)-pyridin-3-yl]-acetic Acid Methyl Ester

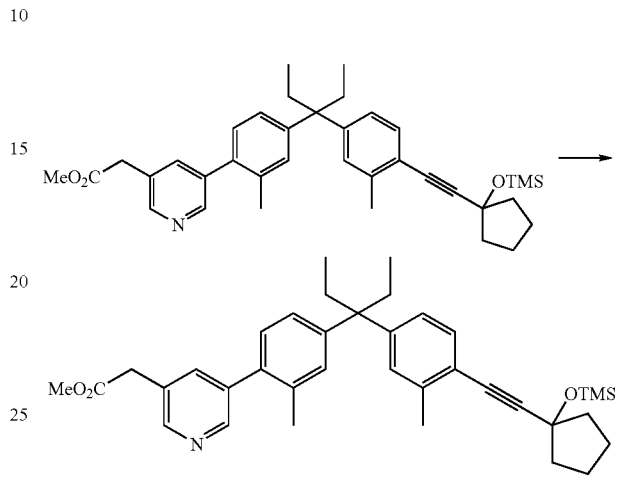

A 1.0 M solution of tetrabutylammonium fluoride in tetrahydrofuran (0.079 mL, 0.079 mmol) was added to [5-(4-{1-ethyl-1-[3-methyl-4-(1-trimethylsilanyloxy-cyclopentylethynyl)-phenyl]-propyl}-2-methyl-phenyl)-pyridin-3-yl]-acetic acid methyl ester (Example 94-(1); 38.2 mg, 0.0656 mmol), and the mixture was stirred for two hours. The reaction mixture was purified by silica gel chromatography (35 to 50% ethyl acetate/hexane) to give the title compound (13.1 mg, 39%).

$^1$H-NMR (chloroform-d): 0.64 (t, 6H, J=7.3 Hz), 1.75-1.93 (m, 4H), 2.02-2.13 (m, 4H), 2.11 (q, 4H, J=7.3 Hz), 2.22 (s, 3H), 2.39 (s, 3H), 3.67 (s, 2H), 3.72 (s, 3H), 6.96-7.10 (m, 5H), 7.30 (d, 1H, J=8.1 Hz), 7.62 (s, 1H), 8.47 (d, 1H, J=2.2 Hz), 8.51 (d, 1H, J=2.2 Hz).

(3) Synthesis of [5-(4-{1-ethyl-1-[4-(1-hydroxy-cyclopentylethynyl)-3-methyl-phenyl]-propyl}-2-methyl-phenyl)-pyridin-3-yl]-acetic Acid

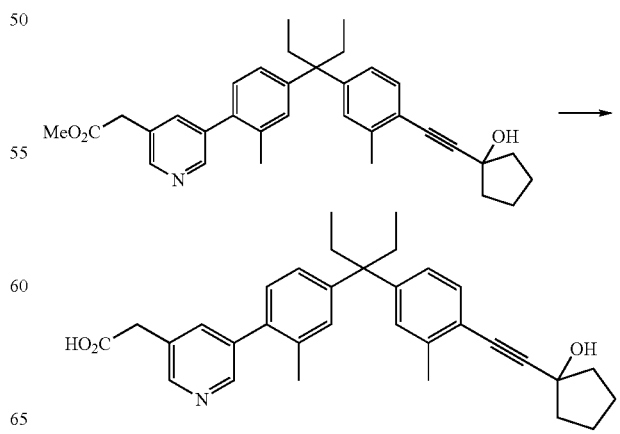

A 2 N sodium hydroxide aqueous solution (0.15 mL) was added to a solution of [5-(4-{1-ethyl-1-[4-(1-hydroxy-cyclopentylethynyl)-3-methyl-phenyl]-propyl}-2-methyl-phenyl)-pyridin-3-yl]-acetic acid methyl ester (Example 94-(2); 24.9 mg, 0.0488 mmol) in methanol (1.0 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (5% methanol/dichloromethane) to give the title compound (15.6 mg, 64%).

$^1$H-NMR (chloroform-d): 0.63 (t, 6H, J=7.3 Hz), 1.76-1.94 (m, 4H), 1.99-2.07 (m, 4H), 2.10 (q, 4H, J=6.2 Hz), 2.20 (s, 3H), 2.38 (s, 3H), 2.89 (brs, 1H), 3.69 (s, 2H), 6.96 (d, 1H, J=8.1 Hz), 7.01-7.02 (m, 3H), 7.07 (d, 1H, J=8.4 Hz), 7.28 (d, 1H, J=8.1 Hz), 7.69 (t, 1H, J=1.8 Hz), 8.50 (s, 2H); MS (ESI+): 496 ([M+H]$^+$).

Example 95

Synthesis of [5-(4-{1-ethyl-1-[4-(1-hydroxy-cyclopentylethynyl)-3-methyl-phenyl]-propyl}-2-methyl-phenyl)-pyridin-2-yl]-acetic Acid Methyl Ester (1) Synthesis of [5-(4-{1-ethyl-1-[3-methyl-4-(1-trimethylsilanyloxy-cyclopentylethynyl)-phenyl]-propyl}-2-methyl-phenyl)-pyridin-2-yl]-acetic Acid Methyl Ester A solution of 2-(4-{1-ethyl-1-[3-methyl-4-(1-trimethylsilanyloxy-cyclopentylethynyl)-phenyl]-propyl}-2-methyl-phenyl)-4,4,5,5-tetramethyl-[1,3,2]dioxaborolane (Example 32-(4); 60.8 mg, 0.10 mmol), (5-bromo-pyridin-2-yl)acetic acid methyl ester (Example 44-(2); 43.5 mg, 0.18 mmol), tetrakistriphenylphosphine palladium (17.3 mg, 0.015 mmol) and potassium phosphate (34.1 mg, 0.16 mmol) in N,N-dimethylformamide (0.6 mL) was stirred at 85° C. for four hours. A saturated aqueous ammonium chloride solution was added to the reaction mixture, followed by extraction with diethyl ether. The organic layer was washed with water, dried over anhydrous sodium sulfate and concentrated under reduced pressure. The residue was purified by silica gel chromatography (20% ethyl acetate/hexane to 60% ethyl acetate/hexane) to give the title compound (18.1 mg, 28%).

$^1$H-NMR (chloroform-d): 0.24 (s, 9H), 0.66 (t, 6H, J=7.2 Hz), 1.70-1.88 (m, 4H), 1.93-2.09 (m, 4H), 2.12 (q, 4H, J=7.2 Hz), 2.24 (s, 3H), 2.40 (s, 3H), 3.76 (s, 3H), 3.91 (s, 2H), 6.97 (d, 1H, J=8.1 Hz), 7.02-7.10 (m, 4H), 7.27-7.35 (m, 2H), 7.64 (d, 1H, J=8.1 Hz), 8.54 (s, 1H).

(2) Synthesis of [5-(4-{1-ethyl-1-[4-(1-hydroxy-cyclopentylethynyl)-3-methyl-phenyl]-propyl}-2-methyl-phenyl)-pyridin-2-yl]-acetic Acid Methyl Ester

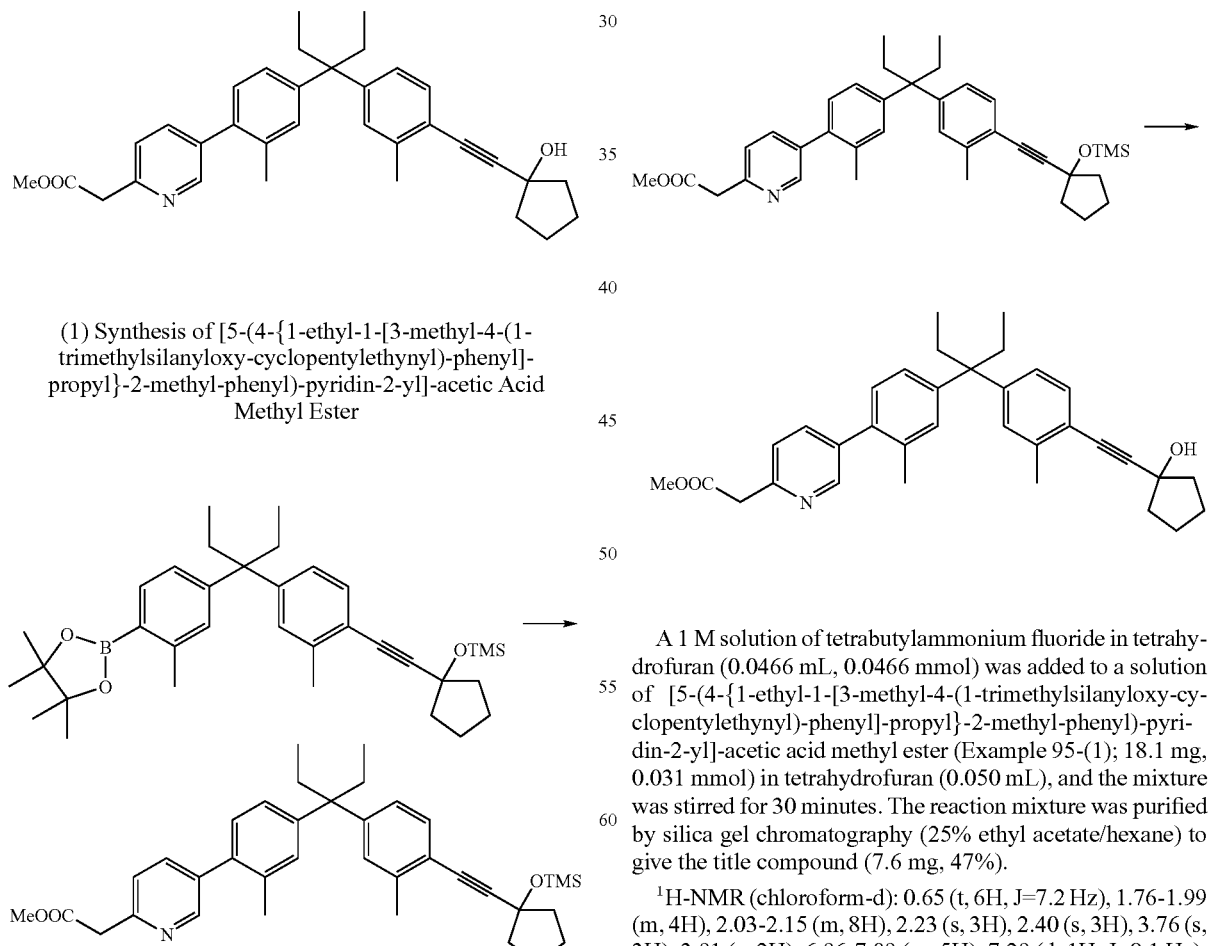

A 1 M solution of tetrabutylammonium fluoride in tetrahydrofuran (0.0466 mL, 0.0466 mmol) was added to a solution of [5-(4-{1-ethyl-1-[3-methyl-4-(1-trimethylsilanyloxy-cyclopentylethynyl)-phenyl]-propyl}-2-methyl-phenyl)-pyridin-2-yl]-acetic acid methyl ester (Example 95-(1); 18.1 mg, 0.031 mmol) in tetrahydrofuran (0.050 mL), and the mixture was stirred for 30 minutes. The reaction mixture was purified by silica gel chromatography (25% ethyl acetate/hexane) to give the title compound (7.6 mg, 47%).

$^1$H-NMR (chloroform-d): 0.65 (t, 6H, J=7.2 Hz), 1.76-1.99 (m, 4H), 2.03-2.15 (m, 8H), 2.23 (s, 3H), 2.40 (s, 3H), 3.76 (s, 3H), 3.91 (s, 2H), 6.96-7.09 (m, 5H), 7.29 (d, 1H, J=8.1 Hz), 7.33 (d, 1H, J=8.1 Hz), 7.63 (d, 1H, J=8.1 Hz), 8.54 (s, 1H); MS (ESI−): 508 ([M−H]$^−$).

Example 96

Synthesis of (4'-{1-ethyl-1-[4-(1-hydroxy-cyclohexylethynyl)-3-methyl-phenyl]-propyl}-2'-methyl-biphenyl-3-yl)-acetic Acid

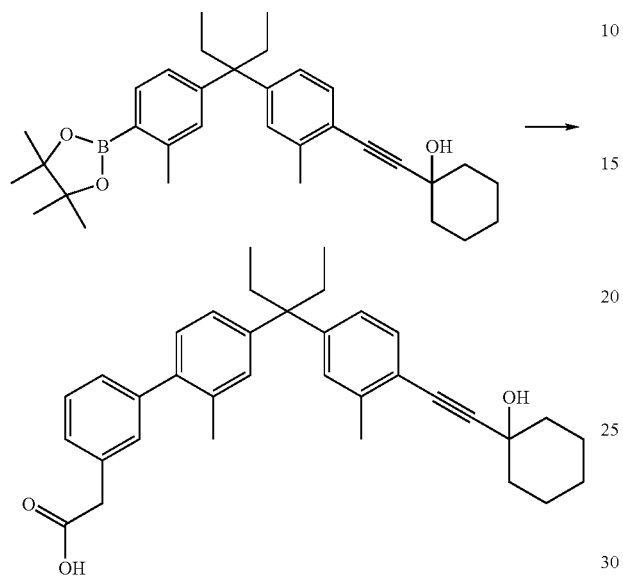

(3-Bromo-phenyl)acetic acid methyl ester (Tetrahedron Letters 44 (2003) 331-334; 28 mg, 0.12 mmol), palladium acetate (3.6 mg, 0.016 mmol), 2-dicyclohexylphosphino-2',6'-dimethoxy-1,1'-biphenyl (13.1 mg, 0.032 mmol), potassium phosphate (51 mg, 0.24 mmol) and water (0.04 mL) were added to a solution of 1-(4-{1-ethyl-1-[3-methyl-4-(4,4,5,5-tetramethyl-[1,3,2]dioxaborolan-2-yl)-phenyl]-propyl}-2-methyl-phenylethynyl)-cyclohexanol (Example 35-(3); 40 mg, 0.08 mmol) in tetrahydrofuran (0.4 mL). After replacement with nitrogen, the mixture was stirred at room temperature for 22 hours. The reaction mixture was purified by preparative thin layer silica gel chromatography (hexane/ethyl acetate=2/1) to give 28 mg of a mixture containing (4'-{1-ethyl-1-[4-(1-hydroxy-cyclohexylethynyl)-3-methyl-phenyl]-propyl}-2'-methyl-biphenyl-3-yl)acetic acid methyl ester.

A 1 N sodium hydroxide aqueous solution (0.1 mL, 0.1 mmol) was added to a solution of the resulting mixture (28 mg) in methanol (1 mL), and the mixture was stirred at 40° C. for one hour. A 30% sodium dihydrogenphosphate aqueous solution was added to the reaction mixture, followed by extraction with dichloromethane. The organic layer was dried over anhydrous magnesium sulfate, filtered and concentrated under reduced pressure. The resulting residue was purified by preparative thin layer silica gel chromatography (dichloromethane/methanol=10/1) to give the title compound (6 mg, 14%).

$^1$H-NMR (chloroform-d): 0.64 (t, 6H, J=7.2 Hz), 1.5-2.2 (m, 14H), 2.23 (s, 3H), 2.40 (s, 3H), 3.68 (s, 2H), 6.95-7.00 (m, 3H), 7.01-7.10 (m, 2H), 7.22-7.38 (m, 5H); MS (ESI-): 507 ([M-H]$^-$).

Example 97

Synthesis of (4'-{1-ethyl-1-[4-(1-hydroxy-cyclohexylethynyl)-3-methyl-phenyl]-propyl}-3-fluoro-2'-methyl-biphenyl-4-yl)-acetic Acid (1) Synthesis of (4'-{1-ethyl-1-[3-methyl-4-(1-trimethylsilanyloxy-cyclohexylethynyl)-phenyl]-propyl}-3-fluoro-2'-methyl-biphenyl-4-yl)-acetic Acid Methyl Ester

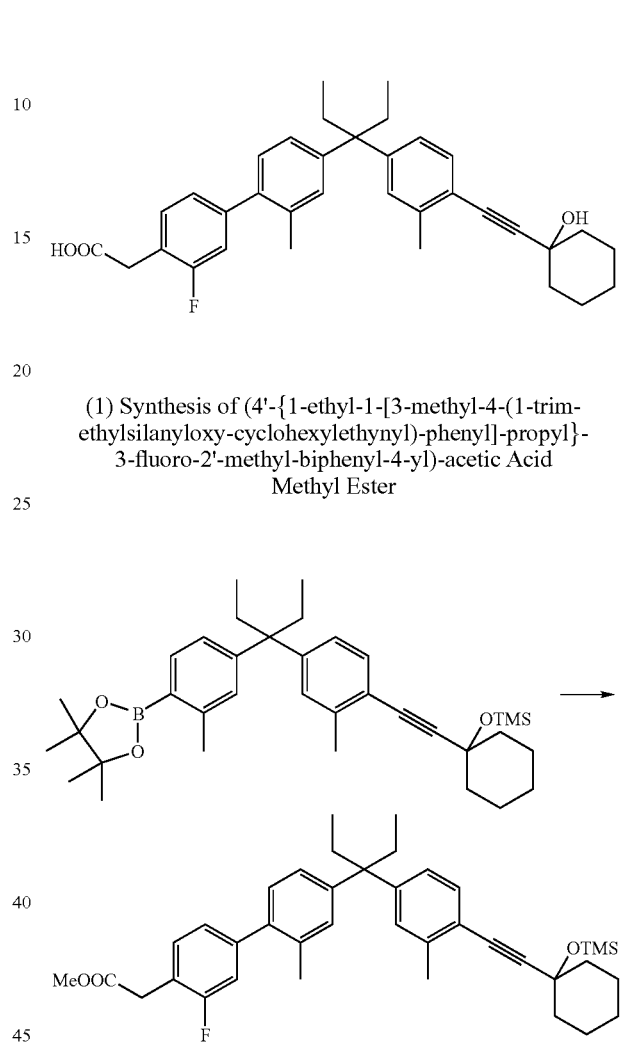

A solution of palladium acetate (2.0 mg, 0.009 mmol), 2-dicyclohexylphosphino-2',6'-dimethoxybiphenyl (7.4 mg, 0.018 mmol) and potassium phosphate (38.4 mg, 0.181 mmol) in water (0.032 mL) and toluene (0.150 mL) was stirred for three minutes. A solution of (4-chloro-2-fluorophenyl)acetic acid methyl ester (Example 40; 19.6 mg, 0.097 mmol) and 2-(4-{1-ethyl-1-[3-methyl-4-(1-trimethylsilanyloxy-cyclohexylethynyl)-phenyl]-propyl}-2-methyl-phenyl)-4,4,5,5-tetramethyl-[1,3,2]dioxaborolane (Example 35-(4); 37.1 mg, 0.0647 mmol) in toluene (0.18 mL) was added, and the mixture was stirred in a nitrogen atmosphere at 100° C. for one hour. After filtration through cotton plug, the filtrate was concentrated under reduced pressure. The residue was purified by thin layer silica gel chromatography (3% ethyl acetate/hexane) to give the title compound (30.9 mg, 77%).

$^1$H-NMR (chloroform-d): 0.23 (s, 9H), 0.65 (t, 6H, J=7.0 Hz), 1.60-1.65 (m, 8H), 1.96-1.98 (m, 2H), 2.11 (q, 4H, J=7.3 Hz), 2.24 (s, 3H), 2.42 (s, 3H), 3.72 (s, 2H), 3.74 (s, 3H), 6.97-7.12 (m, 7H), 7.19-7.31 (m, 2H).

(2) Synthesis of (4'-{1-ethyl-1-[4-(1-hydroxy-cyclohexylethynyl)-3-methyl-phenyl]-propyl}-3-fluoro-2'-methyl-biphenyl-4-yl)-acetic Acid Methyl Ester

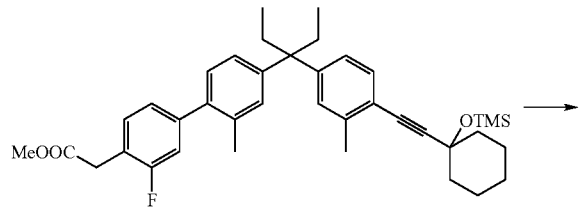

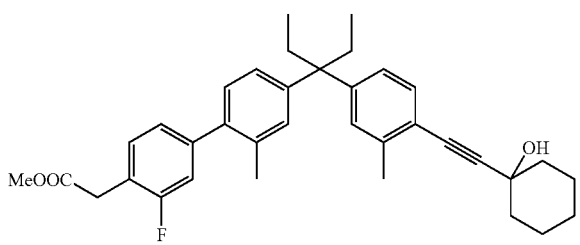

A 1 M solution of tetrabutylammonium fluoride in tetrahydrofuran (0.105 mL, 0.105 mmol) was added to (4'-{1-ethyl-1-[3-methyl-4-(1-trimethylsilanyloxy-cyclohexylethynyl)-phenyl]-propyl}-3-fluoro-2'-methyl-biphenyl-4-yl)acetic acid methyl ester (Example 97-(1); 54.0 mg, 0.0881 mmol), and the mixture was stirred for 40 minutes. A saturated aqueous ammonium chloride solution was added to the reaction mixture, followed by extraction with diethyl ether. The organic layer was washed with water, dried over anhydrous sodium sulfate and concentrated under reduced pressure. The residue was purified by silica gel chromatography (20% ethyl acetate/hexane) to give the title compound (44.2 mg, 92%).

$^1$H-NMR (chloroform-d): 0.65 (t, 6H, J=7.2 Hz), 1.57-1.77 (m, 8H), 2.01-2.05 (m, 2H), 2.11 (q, 4H, J=7.2 Hz), 2.24 (s, 3H), 2.42 (s, 3H), 3.72 (s, 2H), 3.75 (s, 3H), 6.96-7.09 (m, 7H), 7.25-7.32 (m, 2H).

(3) Synthesis of (4'-{1-ethyl-1-[4-(1-hydroxy-cyclohexylethynyl)-3-methyl-phenyl]-propyl}-3-fluoro-2'-methyl-biphenyl-4-yl)-acetic Acid

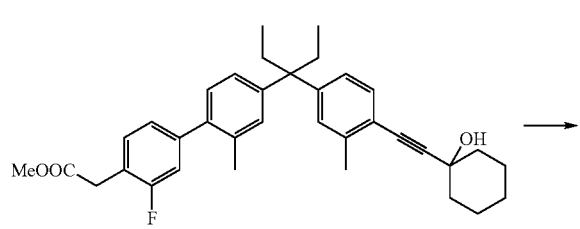

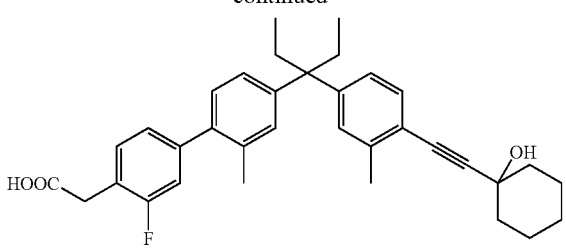

A 2 N sodium hydroxide aqueous solution (0.36 mL) was added to a solution of (4'-{1-ethyl-1-[4-(1-hydroxy-cyclopentylethynyl)-3-methyl-phenyl]-propyl}-3-fluoro-2'-methyl-biphenyl-4-yl)-acetic acid methyl ester (Example 97-(2); 44.2 mg, 0.0817 mmol) in methanol (1.3 mL), and the mixture was stirred for three hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (42.6 mg, 98%).

$^1$H-NMR (chloroform-d): 0.65 (t, 6H, J=7.2 Hz), 1.57-1.76 (m, 8H), 2.01-2.09 (m, 2H), 2.10 (q, 4H, J=7.2 Hz), 2.21 (s, 3H), 2.41 (s, 3H), 3.72 (s, 2H), 4.40-5.20 (brs, 1H), 6.96-7.07 (m, 7H), 7.23-7.31 (m, 2H); MS (ESI+): 509 ([M−H$_2$O+H]$^+$).

Example 98

Synthesis of [6-(4-{1-ethyl-1-[4-(1-hydroxy-cyclohexylethynyl)-3-methyl-phenyl]-propyl}-2-methyl-phenyl)-pyridin-3-yl]-acetic Acid

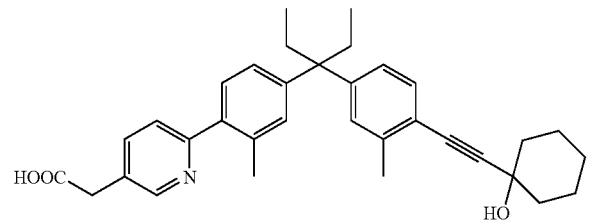

(1) Synthesis of [6-(4-{1-ethyl-1-[3-methyl-4-(1-trimethylsilanyloxy-cyclohexylethynyl)-phenyl]-propyl}-2-methyl-phenyl)-pyridin-3-yl]-acetic Acid Ethyl Ester

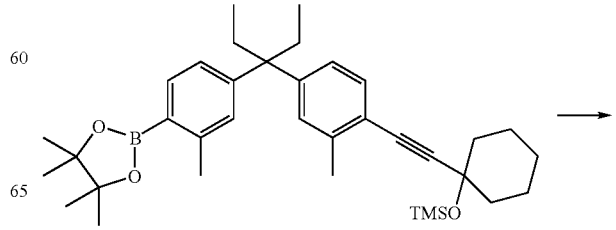

-continued

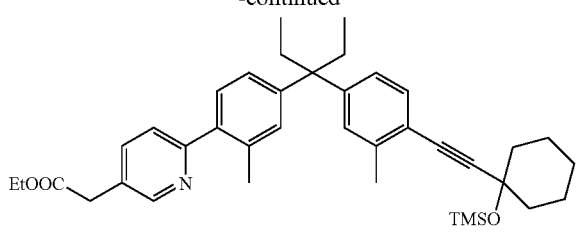

The title compound (23%) was obtained by the same method as in Example 79-(1) using 2-(4-{1-ethyl-1-[3-methyl-4-(1-trimethylsilanyloxy-cyclohexylethynyl)-phenyl]-propyl}-2-methyl-phenyl)-4,4,5,5-tetramethyl-[1,3,2]dioxaborolane (Example 35-(4)) as a starting material.

$^1$H-NMR (chloroform-d): 0.22 (s, 9H), 0.65 (t, 6H, J=7.1H), 1.24-1.81 (m, 10H), 2.16 (q, 4H, J=7.1 Hz), 2.23 (s, 3H), 2.36 (s, 3H), 3.66 (s, 2H), 6.90-7.05 (m, 6H), 7.39 (m, 1H), 7.67 (m, 1H), 8.57 (s, 1H).

(2) Synthesis of [6-(4-{1-ethyl-1-[4-(1-hydroxy-cyclohexylethynyl)-3-methyl-phenyl]-propyl}-2-methyl-phenyl)-pyridin-3-yl]-acetic Acid

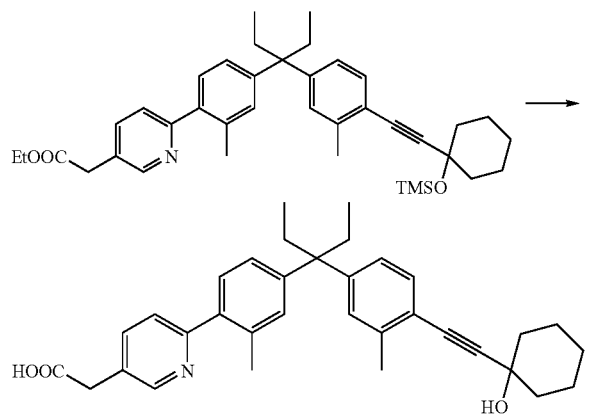

[6-(4-{1-Ethyl-1-[3-methyl-4-(1-trimethylsilanyloxy-cyclohexylethynyl)-phenyl]-propyl}-2-methyl-phenyl)-pyridin-3-yl]-acetic acid ethyl ester (Example 98-(1); 14 mg, 0.023 mmol) was dissolved in tetrahydrofuran (0.2 mL). Tetra-n-butylammonium fluoride (1 M solution in tetrahydrofuran; 0.1 mL) was added, and the mixture was stirred at room temperature for three hours. The reaction mixture was concentrated under reduced pressure, and then the residue was purified by silica gel chromatography (hexane only to hexane/ethyl acetate=1/1). The product was dissolved in methanol/tetrahydrofuran=1/1 (1 mL). A 1 N sodium hydroxide aqueous solution (0.1 mL) was added, and the mixture was stirred at room temperature for one hour. A 30% sodium dihydrogenphosphate aqueous solution (0.3 mL) was added to the reaction mixture, and then the reaction mixture was concentrated under reduced pressure. The residue was purified by preparative TLC (hexane/ethyl acetate=1/1) to give the title compound (3 mg, 25%).

$^1$H-NMR (methanol-d): 0.65 (t, 6H, J=7.1Hz), 1.24-1.81 (m, 10H), 2.16 (q, 4H, J=7.1 Hz), 2.23 (s, 3H), 2.36 (s, 3H), 3.54 (s, 2H), 6.98-7.18 (m, 6H), 7.40 (d, 1H, J=7.9 Hz), 7.84 (d, 1H, J=6.8 Hz), 8.48 (s, 1H); MS (ESI+): 510 ([M+H]$^+$).

Example 99

Synthesis of [5-(4-{1-ethyl-1-[4-(1-hydroxy-cyclohexylethynyl)-3-methyl-phenyl]-propyl}-2-methyl-phenyl)-pyridin-3-yl]-acetic Acid

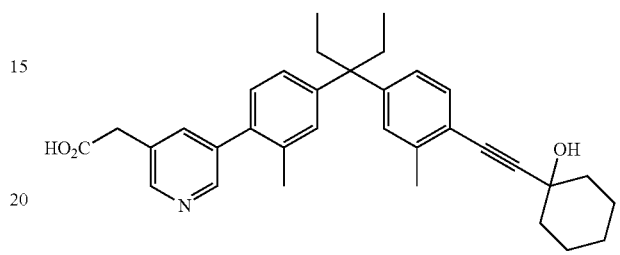

(1) Synthesis of [5-(4-{1-ethyl-1-[3-methyl-4-(1-trimethylsilanyloxy-cyclohexylethynyl)-phenyl]-propyl}-2-methyl-phenyl)-pyridin-3-yl]-acetic Acid Methyl Ester

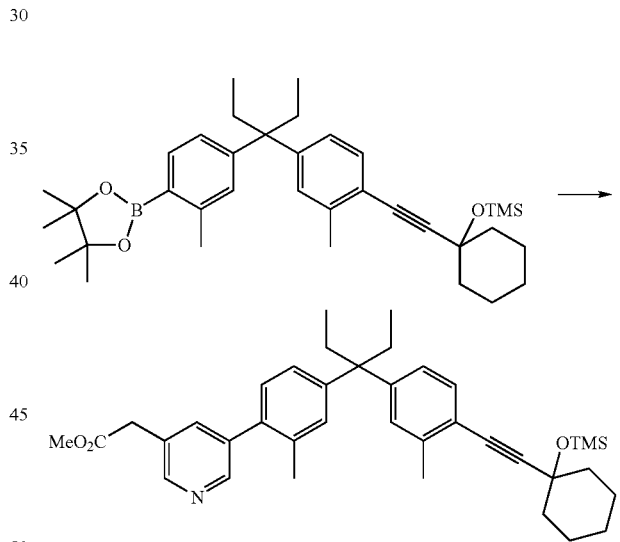

A solution of 2-(4-{1-ethyl-1-[3-methyl-4-(1-trimethylsilanyloxy-cyclohexylethynyl)-phenyl]-propyl}-2-methyl-phenyl)-4,4,5,5-tetramethyl-[1,3,2]dioxaborolane (Example 35-(4); 57.6 mg, 0.10 mmol), (5-bromo-pyridin-3-yl)acetic acid methyl ester (Example 24-(2); 30.1 mg, 0.13 mmol), tetrakistriphenylphosphine palladium (14.1 mg, 0.0122 mmol) and potassium phosphate (27.8 mg, 0.13 mmol) in N,N-dimethylformamide (0.27 mL) was stirred with microwave heating at 140° C. for 10 minutes. The reaction mixture was filtered through cotton plug, and the mixture was purified by silica gel chromatography (45% ethyl acetate/hexane) to give the title compound (37.3 mg, 62%).

$^1$H-NMR (chloroform-d): 0.23 (s, 9H), 0.65 (t, 6H, J=7.1 Hz), 1.54-1.69 (m, 8H), 1.93-2.02 (m, 2H), 2.11 (q, 4H, J=7.1 Hz), 2.24 (s, 3H), 2.41 (s, 3H), 3.68 (s, 2H), 3.72 (s, 3H), 6.96-7.11 (m, 5H), 7.30 (d, 1H, J=8.1 Hz), 7.62 (d, 1H, J=1.8 Hz), 8.47 (s, 1H), 8.52 (2, 1H).

(2) Synthesis of [5-(4-{1-ethyl-1-[4-(1-hydroxy-cyclohexylethynyl)-3-methyl-phenyl]-propyl}-2-methyl-phenyl)-pyridin-3-yl]-acetic Acid Methyl Ester

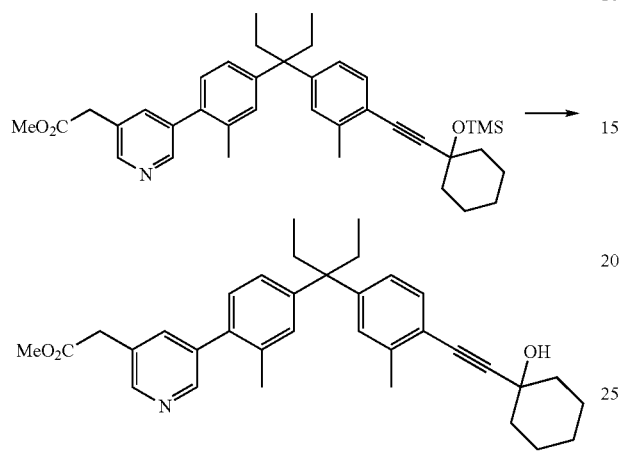

A 1.0 M solution of tetrabutylammonium fluoride in tetrahydrofuran (0.075 mL) was added to [5-(4-{1-ethyl-1-[3-methyl-4-(1-trimethylsilanyloxy-cyclohexylethynyl)-phenyl]-propyl}-2-methyl-phenyl)-pyridin-3-yl]-acetic acid methyl ester (Example 99-(1); 37.3 mg, 0.0625 mmol), and the mixture was stirred for two hours. The reaction mixture was purified by silica gel chromatography (45 to 50% ethyl acetate/hexane) to give the title compound (12.7 mg, 38%).

$^1$H-NMR (chloroform-d): 0.64 (t, 6H, J=7.3 Hz), 1.61-1.75 (m, 6H), 2.01-2.06 (m, 4H), 2.11 (q, 4H, J=7.3 Hz), 2.23 (s, 3H), 2.41 (s, 3H), 3.68 (s, 2H), 3.72 (s, 3H), 6.97-7.10 (m, 5H), 7.31 (d, 1H, J=8.1 Hz), 7.62 (t, 1H, J=2.2 Hz), 8.47 (d, 1H, J=2.2 Hz), 8.52 (d, 1H, J=1.8 Hz).

(3) Synthesis of [5-(4-{1-ethyl-1-[4-(1-hydroxy-cyclohexylethynyl)-3-methyl-phenyl]-propyl}-2-methyl-phenyl)-pyridin-3-yl]-acetic Acid

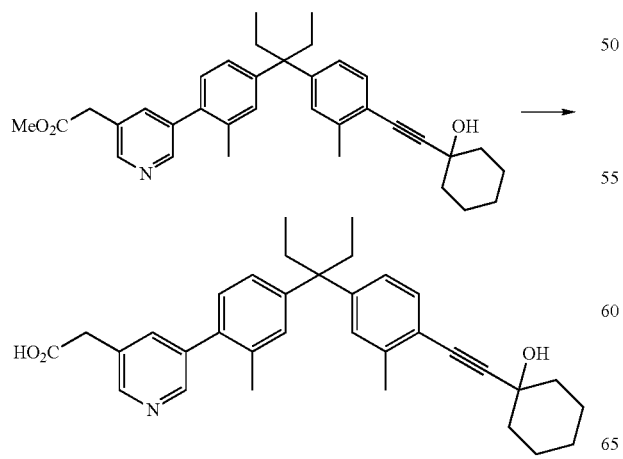

A 2 N sodium hydroxide aqueous solution (0.14 mL) was added to a solution of [5-(4-{1-ethyl-1-[4-(1-hydroxy-cyclohexylethynyl)-3-methyl-phenyl]-propyl}-2-methyl-phenyl)-pyridin-3-yl]-acetic acid methyl ester (Example 99-(2); 24.4 mg, 0.0465 mmol) in methanol (1.0 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (5% methanol/dichloromethane) to give the title compound (15.5 mg, 65%).

$^1$H-NMR (chloroform-d): 0.63 (t, 6H, J=7.1 Hz), 1.55-1.79 (m, 8H), 2.01-2.04 (m, 2H), 2.10 (q, 4H, J=7.2 Hz), 2.21 (s, 3H), 2.40 (s, 3H), 3.70 (s, 2H), 6.96 (d, 1H, J=8.4 Hz), 7.01-7.03 (m, 3H), 7.08 (d, 1H, J=8.4 Hz), 7.30 (d, 1H, J=8.4 Hz), 7.69 (s, 1H), 8.51 (s, 2H); MS (ESI+): 510 ([M+H]$^+$).

Example 100

Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid

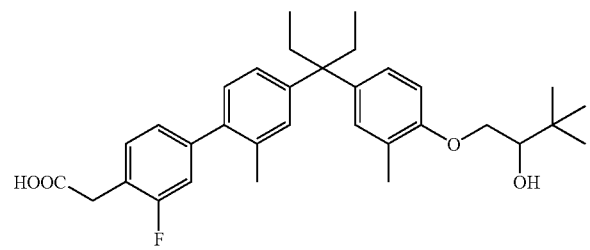

(1) Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid Methyl Ester

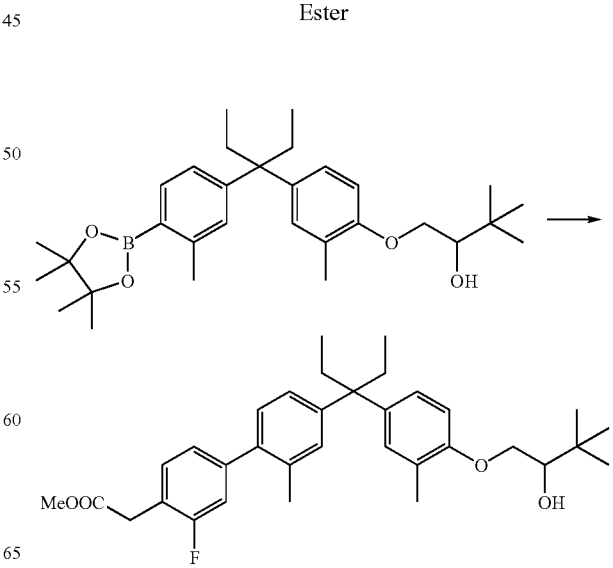

A solution of palladium acetate (3.8 mg, 0.0169 mmol), 2-dicyclohexylphosphino-2',6'-dimethoxybiphenyl (13.9 mg, 0.0339 mmol) and potassium phosphate (72.0 mg, 0.33 mmol) in water (0.050 mL) and toluene (0.200 mL) was stirred for three minutes. A solution of (4-chloro-2-fluorophenyl)acetic acid methyl ester (Example 40; 36.8 mg, 0.18 mmol) and 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-ol (Example 31; 60.0 mg, 0.12 mmol) in toluene (0.3 mL) was added, and the mixture was stirred in a nitrogen atmosphere at 100° C. for one hour. After filtration through cotton plug, the filtrate was concentrated under reduced pressure. The residue was purified by thin layer silica gel chromatography (8% ethyl acetate/hexane) to give the title compound (21.1 mg, 32%).

$^1$H-NMR (chloroform-d): 0.66 (t, 6H, J=7.2 Hz), 1.03 (s, 9H), 2.10 (q, 4H, J=7.2 Hz), 2.21 (s, 3H), 2.25 (s, 3H), 2.48 (brs, 1H), 3.72 (d, 1H, J=9.0 Hz), 3.72 (s, 2H), 3.75 (s, 3H), 3.88 (t, 1H, J=9.0 Hz), 4.11 (d, 1H, J=9.0 Hz), 6.73 (d, 1H, J=8.1 Hz), 6.97-7.09 (m, 7H), 7.28 (t, 1H, J=7.5 Hz).

(2) Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid

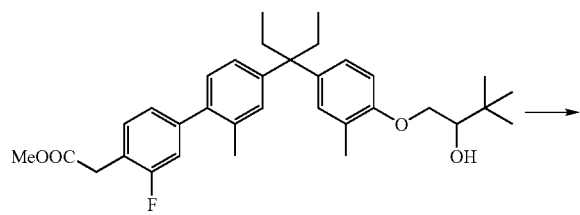

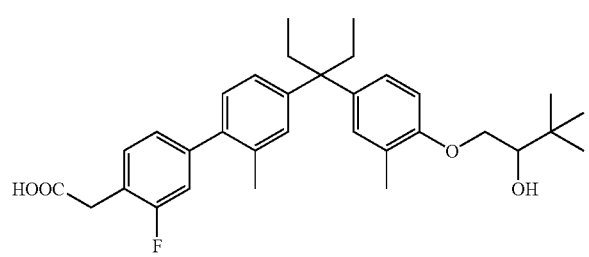

A 2 N sodium hydroxide aqueous solution (0.21 mL) was added to a solution of (4'-{1-ethyl-1-[4-(2-hydroxy-3,3-dimethyl-butoxy)-3-methyl-phenyl]-propyl}-3-fluoro-2'-methyl-biphenyl-4-yl)acetic acid methyl ester (Example 100-(1); 21.1 mg, 0.0394 mmol) in methanol (1.3 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (20.9 mg, 99%).

$^1$H-NMR (chloroform-d): 0.66 (t, 6H, J=7.2 Hz), 1.03 (s, 9H), 2.10 (q, 4H, J=7.2 Hz), 2.21 (s, 3H), 2.24 (s, 3H), 3.72 (d, 1H, J=9.0 Hz), 3.75 (s, 2H), 3.88 (t, 1H, J=9.0 Hz), 4.11 (d, 1H, J=9.0 Hz), 6.73 (d, 1H, J=8.1 Hz), 6.97-7.10 (m, 7H), 7.28 (t, 1H, J=7.5 Hz); MS (ESI+): 538 ([M+NH$_4$]$^+$).

Example 101

Synthesis of [6-(4-{1-ethyl-1-[4-(2-hydroxy-3,3-dimethyl-butoxy)-3-methyl-phenyl]-propyl}-2-methyl-phenyl)-pyridin-3-yl]-acetic Acid

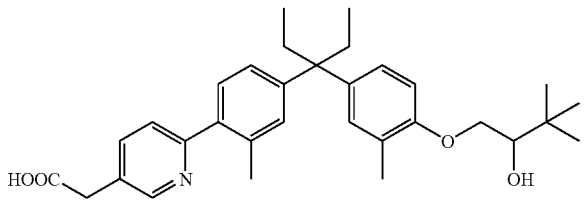

(1) Synthesis of [6-(4-{1-ethyl-1-[4-(2-hydroxy-3,3-dimethyl-butoxy)-3-methyl-phenyl]-propyl}-2-methyl-phenyl)-pyridin-3-yl]-acetic Acid Ethyl Ester

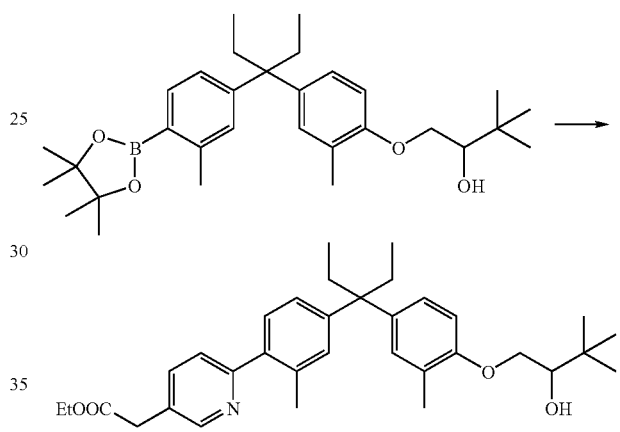

The title compound (41%) was obtained by the same method as in Example 79-(1) using 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-ol (Example 31) as a starting material.

$^1$H-NMR (chloroform-d): 0.63 (t, 6H, J=7.1 Hz), 1.01 (s, 9H), 2.08 (q, 4H, J=7.1 Hz), 2.18 (s, 3H), 2.31 (s, 3H), 3.66 (s, 2H), 3.68 (m, 1H), 3.86 (t, 1H, J=8.9 Hz), 6.69-7.70 (m, 8H), 8.56 (s, 1H).

(2) Synthesis of [6-(4-{1-ethyl-1-[4-(2-hydroxy-3,3-dimethyl-butoxy)-3-methyl-phenyl]-propyl}-2-methyl-phenyl)-pyridin-3-yl]-acetic Acid

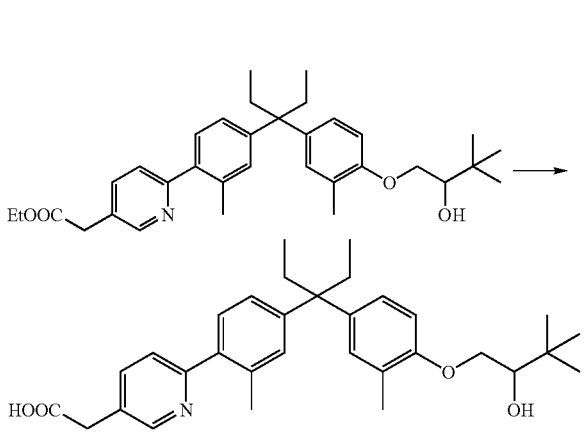

The title compound (41%) was obtained by the same method as in Example 81-(2) using [6-(4-{1-ethyl-1-[4-(2-hydroxy-3,3-dimethyl-butoxy)-3-methyl-phenyl]-propyl}-2-methyl-phenyl)-pyridin-3-yl]-acetic acid ethyl ester (Example 101-(1)) as a starting material.

1H-NMR (methanol-d): 0.63 (t, 6H, J=7.1 Hz), 1.00 (s, 9H), 2.12 (q, 4H, J=7.1 Hz), 2.16 (s, 3H), 2.22 (s, 3H), 3.61 (s, 2H), 3.61 (m, 1H), 3.87 (m, 1H), 4.12 (d, 1H), 6.78 (d, 1H, J=8.7 Hz), 6.88 (s, 1H), 7.01 (m, 1H), 7.12 (m, 1H), 7.20 (d, 1H, J=8.3 Hz), 7.39 (d, 1H, J=8.3 Hz), 7.82 (d, 1H, J=8.1 Hz), 8.48 (s, 1H); MS (ESI+): 504 ([M+H]$^+$).

Example 102

Synthesis of [5-(4-{1-ethyl-1-[4-(2-hydroxy-3,3-dimethyl-butoxy)-3-methyl-phenyl]-propyl}-2-methyl-phenyl)-pyridin-3-yl]-acetic Acid

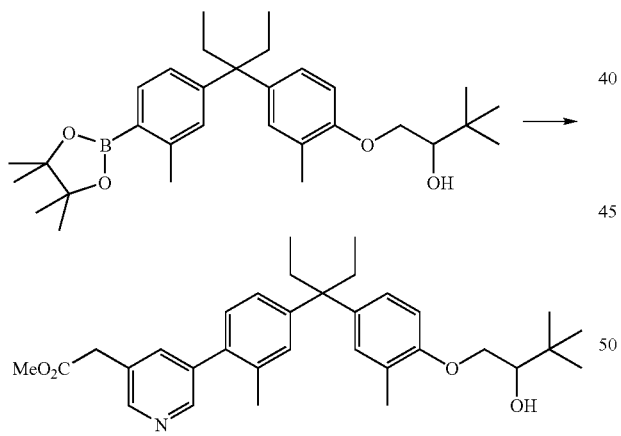

(1) Synthesis of [5-(4-{1-ethyl-1-[4-(2-hydroxy-3,3-dimethyl-butoxy)-3-methyl-phenyl]-propyl}-2-methyl-phenyl)-pyridin-3-yl]-acetic Acid Methyl Ester

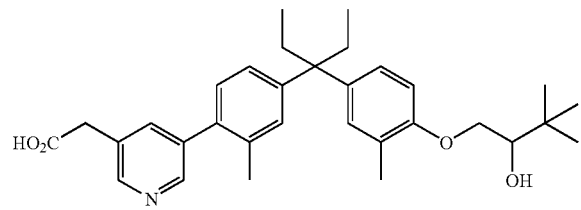

A solution of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-ol (Example 31; 0.06 g, 0.12 mmol), (5-bromo-pyridin-3-yl)acetic acid methyl ester (Example 24-(2); 41.8 mg, 0.18 mmol), tetrakistriphenylphosphine palladium (19.5 mg, 0.0169 mmol) and potassium phosphate (38.6 mg, 0.18 mmol) in N,N-dimethylformamide (0.3 mL) was stirred with microwave heating at 140° C. for 10 minutes. The reaction mixture was filtered through cotton plug, and the residue was purified by silica gel chromatography (50% ethyl acetate/hexane) to give the title compound (39.5 mg, 62%).

1H-NMR (chloroform-d): 0.64 (t, 6H, J=7.0 Hz), 1.01 (s, 9H), 2.09 (q, 4H, J=7.0 Hz), 2.20 (s, 3H), 2.24 (s, 3H), 3.68 (s, 2H), 3.70 (d, 1H, J=8.4 Hz), 3.72 (s, 3H), 3.87 (t, 1H, J=8.4 Hz), 4.10 (d, 1H, J=8.4 Hz), 6.73 (d, 1H, J=8.4 Hz), 6.95-7.00 (m, 2H), 7.04-7.10 (m, 3H) 7.63 (s, 1H), 8.46 (s, 1H), 8.52 (s, 1H).

(2) Synthesis of [5-(4-{1-ethyl-1-[4-(2-hydroxy-3,3-dimethyl-butoxy)-3-methyl-phenyl]-propyl}-2-methyl-phenyl)-pyridin-3-yl]-acetic Acid

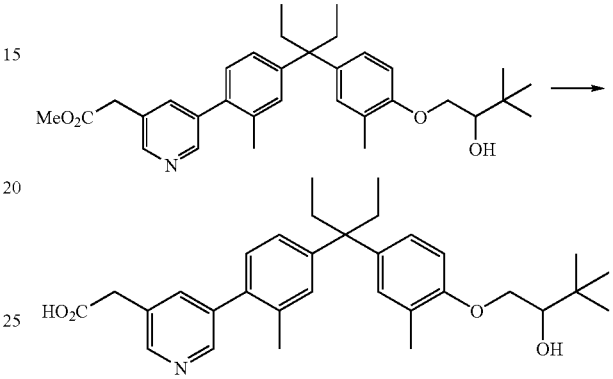

A 2 N sodium hydroxide aqueous solution (0.23 mL) was added to a solution of [5-(4-{1-ethyl-1-[4-(2-hydroxy-3,3-dimethyl-butoxy)-3-methyl-phenyl]-propyl}-2-methyl-phenyl)-pyridin-3-yl]-acetic acid methyl ester (Example 102-(1); 39.5 mg, 0.0762 mmol) in methanol (1.3 mL), and the mixture was stirred for two hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (8% methanol/dichloromethane) to give the title compound (21.6 mg, 56%).

1H-NMR (chloroform-d): 0.63 (t, 6H, J=7.3 Hz), 1.00 (s, 9H), 2.08 (q, 4H, J=7.8 Hz), 2.18 (s, 3H), 2.19 (s, 3H), 3.66 (s, 2H), 3.70 (dd, 1H, J=8.8, 2.6 Hz), 3.86 (t, 1H, J=9.0 Hz), 4.09 (dd, 1H, J=8.8, 2.9 Hz), 6.71 (d, 1H, J=8.8 Hz), 6.93 (s, 1H), 6.97 (d, 1H, J=8.4 Hz), 7.04-7.06 (m, 3H), 7.64 (s, 1H), 8.47 (s, 1H), 8.49 (s, 1H); MS (ESI+): 504 ([M+H]$^+$).

Example 103

Synthesis of (4'-{1-[4-(3,3-dimethyl-2-oxo-butoxy)-3-methyl-phenyl]-1-ethyl-propyl}-3-fluoro-2'-methyl-biphenyl-4-yl)-acetic Acid

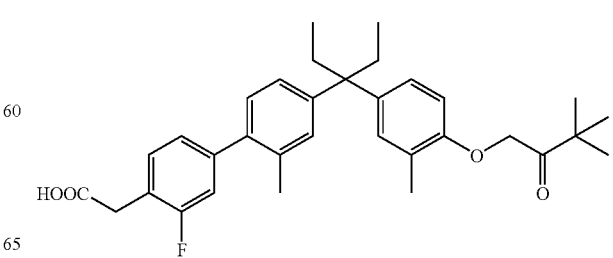

(1) Synthesis of (4'-{1-[4-(3,3-dimethyl-2-oxo-butoxy)-3-methyl-phenyl]-1-ethyl-propyl}-3-fluoro-2'-methyl-biphenyl-4-yl)-acetic Acid Methyl Ester

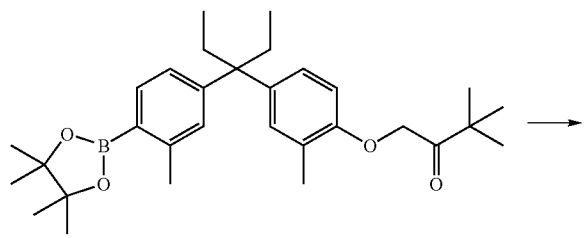

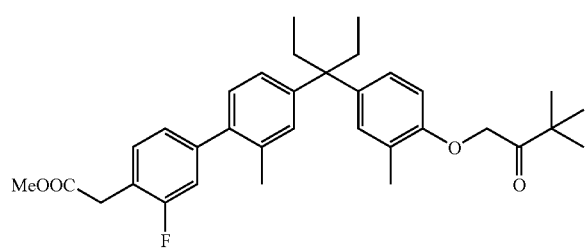

A solution of palladium acetate (3.8 mg, 0.017 mmol), 2-dicyclohexylphosphino-2',6'-dimethoxybiphenyl (14.0 mg, 0.034 mmol) and potassium phosphate (72.3 mg, 0.34 mmol) in water (0.050 mL) and toluene (0.200 mL) was stirred for three minutes. A solution of (4-chloro-2-fluorophenyl)acetic acid methyl ester (Example 40; 37.0 mg, 0.18 mmol) and 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-ol (Example 30-(2); 60.0 mg, 0.12 mmol) in toluene (0.3 mL) was added, and the mixture was stirred in a nitrogen atmosphere at 100° C. for one hour. After filtration through cotton plug, the filtrate was concentrated under reduced pressure. The residue was purified by thin layer silica gel chromatography (5% ethyl acetate/hexane) to give the title compound (38.6 mg, 59%).

$^1$H-NMR (chloroform-d): 0.64 (t, 6H, J=7.2 Hz), 1.27 (s, 9H), 2.09 (q, 4H, J=7.2 Hz), 2.24 (s, 3H), 2.27 (s, 3H), 3.72 (s, 2H), 3.75 (s, 3H), 4.85 (s, 2H), 6.53 (d, 1H, J=8.4 Hz), 6.92-7.09 (m, 7H), 7.27 (t, 1H, J=7.5 Hz).

(2) Synthesis of (4'-{1-[4-(3,3-dimethyl-2-oxo-butoxy)-3-methyl-phenyl]-1-ethyl-propyl}-3-fluoro-2'-methyl-biphenyl-4-yl)-acetic Acid

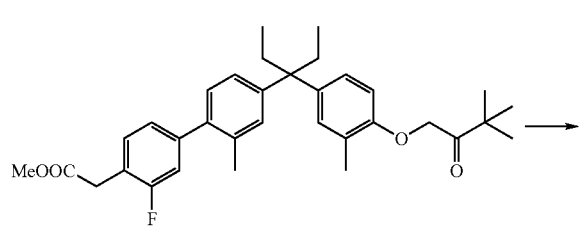

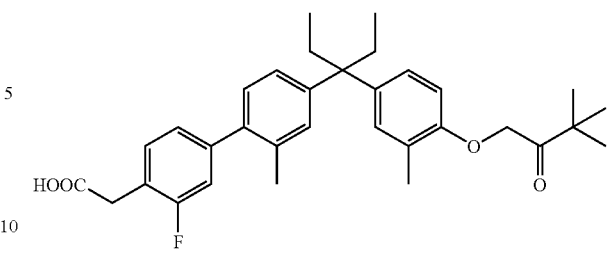

A 2 N sodium hydroxide aqueous solution (0.25 mL) was added to a solution of (4'-{1-[4-(3,3-dimethyl-2-oxo-butoxy)-3-methyl-phenyl]-1-ethyl-propyl}-3-fluoro-2'-methyl-biphenyl-4-yl)acetic acid methyl ester (Example 103-(1); 38.6 mg, 0.0724 mmol) in methanol (2.4 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (38.7 mg, 99%).

$^1$H-NMR (chloroform-d): 0.65 (t, 6H, J=7.2 Hz), 1.27 (s, 9H), 2.09 (q, 4H, J=7.2 Hz), 2.24 (s, 3H), 2.27 (s, 3H), 3.75 (s, 2H), 4.85 (s, 2H), 6.53 (d, 1H, J=8.4 Hz), 6.92-7.10 (m, 7H), 7.27 (t, 1H, J=7.5 Hz); MS (ESI+): 536 ([M+NH$_4$]$^+$).

Example 104

Synthesis of [6-(4-{1-[4-(3,3-dimethyl-2-oxo-butoxy)-3-methyl-phenyl]-1-ethyl-propyl}-2-methyl-phenyl)-pyridin-3-yl]-acetic Acid

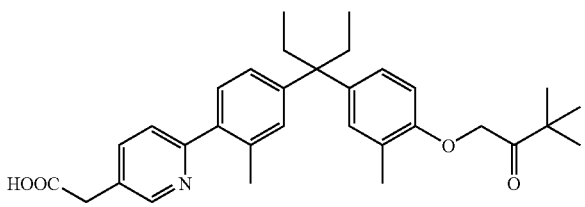

(1) Synthesis of [6-(4-{1-[4-(3,3-dimethyl-2-oxo-butoxy)-3-methyl-phenyl]-1-ethyl-propyl}-2-methyl-phenyl)-pyridin-3-yl]-acetic Acid Ethyl Ester

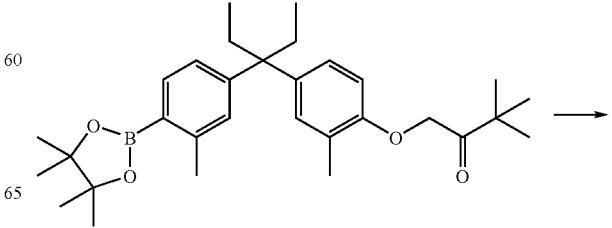

243

-continued

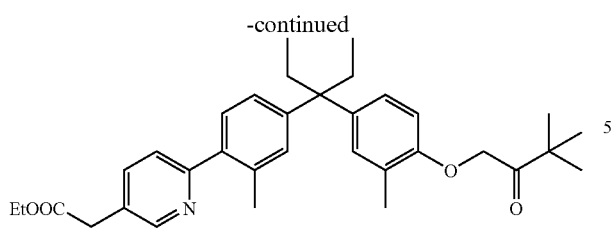

The title compound (64%) was obtained by the same method as in Example 79-(1) using 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-one (Example 30-(2)) as a starting material.

$^1$H-NMR (chloroform-d): 0.63 (t, 6H, J=6.9 Hz), 1.25 (s, 9H), 1.28 (t, 3H, J=7.1 Hz), 2.07 (q, 4H, J=6.9 Hz), 2.24 (s, 3H), 2.32 (s, 3H), 3.66 (s, 2H), 4.84 (s, 2H), 6.50 (d, 1H, J=7.6 Hz), 6.93 (m, 2H), 7.06 (m, 2H), 7.26 (m, 2H), 7.37 (d, 1H, J=7.9 Hz), 8.56 (s, 1H).

(2) Synthesis of [6-(4-{1-[4-(3,3-dimethyl-2-oxo-butoxy)-3-methyl-phenyl]-1-ethyl-propyl}-2-methyl-phenyl)-pyridin-3-yl]-acetic Acid

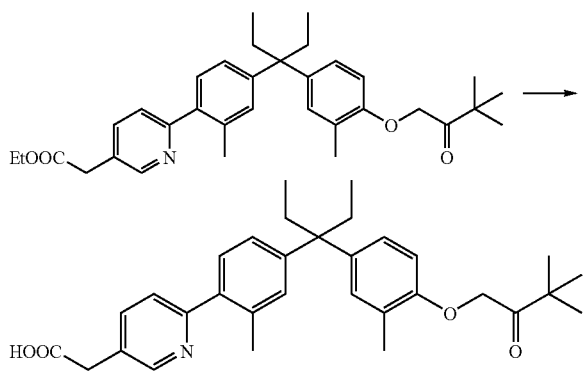

The title compound (69%) was obtained by the same method as in Example 81-(2) using [6-(4-{1-[4-(3,3-dimethyl-2-oxo-butoxy)-3-methyl-phenyl]-1-ethyl-propyl}-2-methyl-phenyl)-pyridin-3-yl]-acetic acid ethyl ester (Example 104-(1)) as a starting material.

$^1$H-NMR (methanol-d): 0.63 (t, 6H, J=7.0 Hz), 1.28 (s, 9H), 2.12 (q, 4H, J=7.0 Hz), 2.18 (s, 3H), 2.22 (s, 3H), 3.34 (s, 2H), 3.59 (s, 2H), 6.60 (d, 1H, J=8.4 Hz), 6.91 (s, 1H), 6.97 (d, 1H, J=8.4 Hz), 7.09 (m, 2H), 7.20 (d, 1H, J=8.4 Hz), 7.41 (d, 1H, J=8.1 Hz), 7.82 (d, 1H, 7.9 Hz), 8.48 (s, 1H); MS (ESI+): 502 ([M+H]$^+$).

Example 105

Synthesis of [5-(4-{1-[4-(3,3-dimethyl-2-oxo-butoxy)-3-methyl-phenyl]-1-ethyl-propyl}-2-methyl-phenyl)-pyridin-3-yl]-acetic Acid

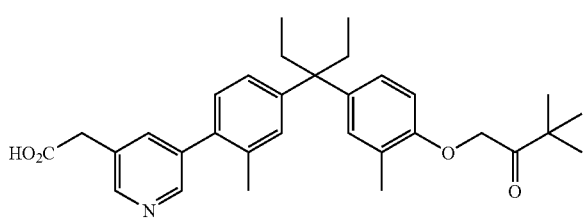

244

(1) Synthesis of [5-(4-{1-[4-(3,3-dimethyl-2-oxo-butoxy)-3-methyl-phenyl]-1-ethyl-propyl}-2-methyl-phenyl)-pyridin-3-yl]-acetic Acid Methyl Ester

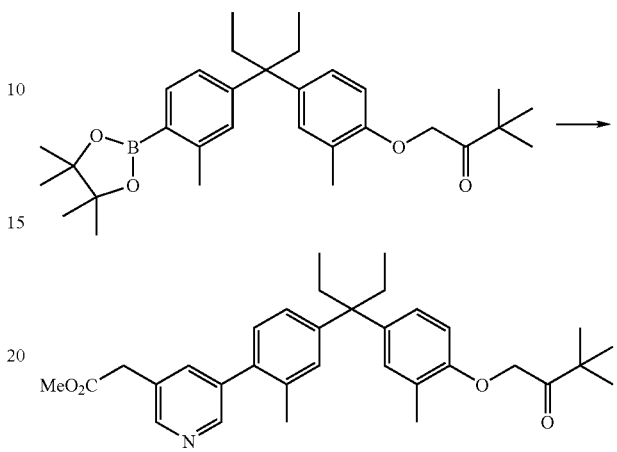

A solution of 1-(4-{1-ethyl-1-[3-methyl-4-(4,4,5,5-tetramethyl-[1,3,2]dioxaborolan-2-yl)-phenyl]-propyl}-2-methyl-phenoxy)-3,3-dimethyl-butan-2-one (Example 30-(2); 0.06 g, 0.12 mmol), (5-bromo-pyridin-3-yl)acetic acid methyl ester (Example 24-(2); 42.0 mg, 0.18 mmol), tetrakistriphenylphosphine palladium (19.6 mg, 0.017 mmol) and potassium phosphate (38.7 mg, 0.18 mmol) in N,N-dimethylformamide (0.3 mL) was stirred with microwave heating at 140° C. for 10 minutes. The reaction mixture was filtered through cotton plug, and the mixture was purified by silica gel chromatography (40% ethyl acetate/hexane) to give the title compound (52.8 mg, 83%).

$^1$H-NMR (chloroform-d): 0.64 (t, 6H, J=7.1 Hz), 1.25 (s, 9H), 2.08 (q, 4H, J=7.2 Hz), 2.23 (s, 3H), 2.26 (s, 3H), 3.68 (s, 2H), 3.72 (s, 3H), 4.85 (s, 2H), 6.52 (d, 1H, J=8.1 Hz), 6.92-6.96 (m, 2H), 7.04-7.10 (m, 3H), 7.62 (s, 1H), 8.47 (s, 1H), 8.52 (s, 1H).

(2) Synthesis of [5-(4-{1-[4-(3,3-dimethyl-2-oxo-butoxy)-3-methyl-phenyl]-1-ethyl-propyl}-2-methyl-phenyl)-pyridin-3-yl]-acetic Acid

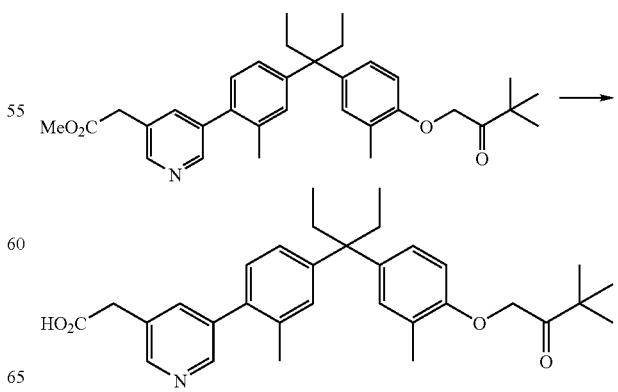

A 2 N sodium hydroxide aqueous solution (0.3 mL) was added to a solution of [5-(4-{1-[4-(3,3-dimethyl-2-oxo-butoxy)-3-methyl-phenyl]-1-ethyl-propyl}-2-methyl-phenyl)-pyridin-3-yl]-acetic acid methyl ester (Example 105-(1); 52.8 mg, 0.10 mmol) in methanol (1.7 mL), and the mixture was stirred for two hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (10% methanol/dichloromethane) to give the title compound (43.2 mg, 84%).

$^1$H-NMR (chloroform-d): 0.62 (t, 6H, J=7.1 Hz), 1.25 (s, 9H), 2.07 (q, 4H, J=7.0 Hz), 2.21 (s, 3H), 2.25 (s, 3H), 3.72 (s, 2H), 4.84 (s, 2H), 6.52 (d, 1H, J=8.1 Hz), 6.92-6.94 (m, 2H), 7.03-7.08 (m, 3H), 7.72 (t, 1H, J=1.8 Hz), 8.51 (d, 1H, J=1.8 Hz), 8.53 (d, 1H, J=1.8 Hz); MS (ESI+): 502 ([M+H]$^+$).

Example 106

Synthesis of (4'-{1-ethyl-1-[3-methyl-4-(4,4,4-trifluoro-3-hydroxy-3-trifluoromethyl-butyl)-phenyl]-propyl}-3-fluoro-2'-methyl-biphenyl-4-yl)-acetic Acid

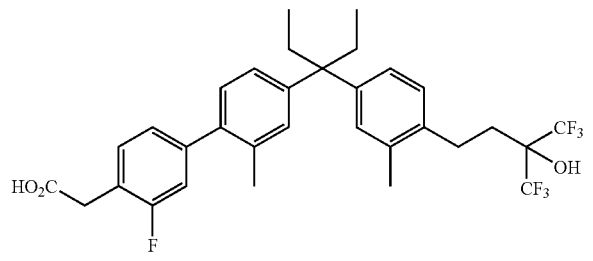

(1) Synthesis of (4'-{1-ethyl-1-[3-methyl-4-(4,4,4-trifluoro-3-hydroxy-3-trifluoromethyl-butyl)-phenyl]-propyl}-3-fluoro-2'-methyl-biphenyl-4-yl)-acetic Acid Methyl Ester

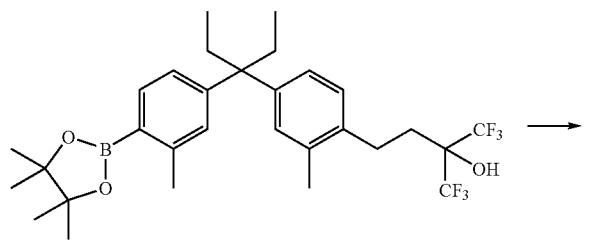

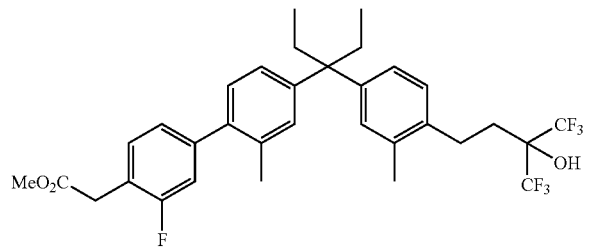

A solution of palladium acetate (2.3 mg, 0.0104 mmol), 2-dicyclohexylphosphino-2',6'-dimethoxybiphenyl (8.6 mg, 0.0209 mmol) and potassium phosphate (44.4 mg, 0.20 mmol) in water (0.040 mL) and toluene (0.150 mL) was stirred for three minutes. A solution of (4-chloro-2-fluorophenyl)acetic acid methyl ester (Example 40; 22.6 mg, 0.11 mmol) and 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-butan-2-ol (Example 27-(2); 42.8 mg, 0.0747 mmol) in toluene (0.230 mL) was added, and the mixture was stirred in a nitrogen atmosphere at 100° C. for three hours. After filtration through cotton plug, the filtrate was concentrated under reduced pressure. The residue was purified by silica gel chromatography (13% ethyl acetate/hexane) to give the title compound (21.9 mg, 47%).

$^1$H-NMR (chloroform-d): 0.66 (t, 6H, J=7.2 Hz), 2.12 (q, 4H, J=7.2 Hz), 2.15-2.21 (m, 2H), 2.25 (s, 3H), 2.29 (s, 3H), 2.80-2.86 (m, 2H), 3.07 (brs, 1H), 3.72 (s, 2H), 3.75 (s, 3H), 6.97-7.12 (m, 8H), 7.23 (t, 1H, J=8.1 Hz).

(2) Synthesis of (4'-{1-ethyl-1-[3-methyl-4-(4,4,4-trifluoro-3-hydroxy-3-trifluoromethyl-butyl)-phenyl]-propyl}-3-fluoro-2'-methyl-biphenyl-4-yl)-acetic Acid

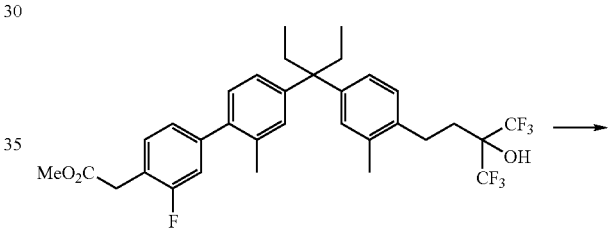

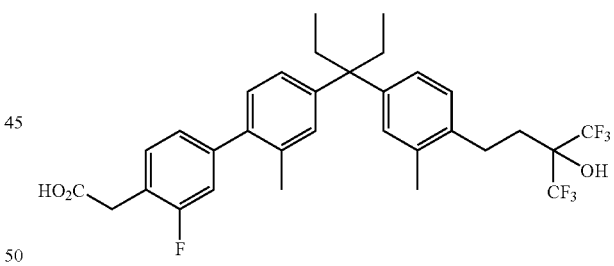

A 2 N sodium hydroxide aqueous solution (0.11 mL) was added to a solution of (4'-{1-ethyl-1-[3-methyl-4-(4,4,4-trifluoro-3-hydroxy-3-trifluoromethyl-butyl)-phenyl]-propyl}-3-fluoro-2'-methyl-biphenyl-4-yl)acetic acid methyl ester (Example 106-(1); 21.9 mg, 0.0357 mmol) in methanol (0.3 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (21.6 mg, 99%).

$^1$H-NMR (chloroform-d): 0.66 (t, 6H, J=7.2 Hz), 2.12 (q, 4H, J=7.2 Hz), 2.13-2.21 (m, 2H), 2.25 (s, 3H), 2.29 (s, 3H), 2.80-2.86 (m, 2H), 3.76 (s, 2H), 6.98-7.10 (m, 8H), 7.28 (t, 1H, J=8.1 Hz); MS (ESI+): 616 ([M+NH$_4$]$^+$).

Example 107

Synthesis of [6-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic Acid

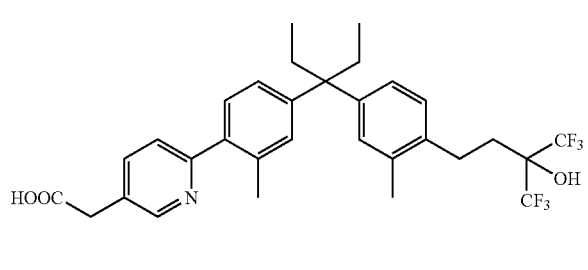

(1) Synthesis of [6-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic Acid Ethyl Ester

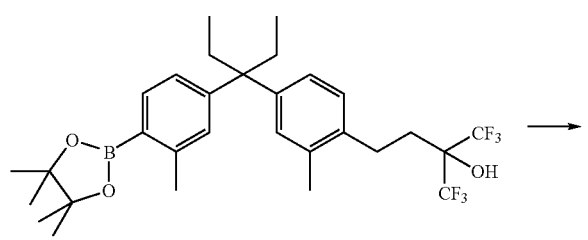

N,N-Dimethylformamide (0.7 mL) was added to 4-(4-{1-ethyl-1-[3-methyl-4-(4,4,5,5-tetramethyl-[1,3,2]dioxaborolan-2-yl)-phenyl]-propyl}-2-methyl-phenyl)-1,1,1-trifluoro-2-trifluoromethyl-butan-2-ol (Example 27-(2); 60 mg, 0.105 mmol), (6-chloro-pyridin-3-yl)acetic acid ethyl ester (40 mg, 0.201 mmol), tetrakis(triphenylphosphine)palladium (0) (23 mg, 0.02 mmol) and potassium phosphate (63.9 mg, 0.30 mmol). The mixture was stirred with microwave heating at 140° C. for seven minutes in a nitrogen atmosphere. The reaction mixture was concentrated under reduced pressure. The residue was purified by preparative TLC (hexane/ethyl acetate=5/1) to give the title compound (26 mg, 41%).

$^1$H-NMR (chloroform-d): 0.62 (t, 6H, J=7.0 Hz), 1.26 (t, 3H, J=6.9 Hz), 2.11 (q, 4H, J=7.0 Hz), 2.18 (m, 3H), 2.23 (m, 3H), 2.70 (m, 2H), 3.66 (s, 2H), 4.14 (q, 2H, J=6.9 Hz), 6.82-7.05 (m, 5H), 7.14 (d, 1H, J=8.1 Hz), 7.35 (d, 1H, J=7.9 Hz), 7.69 (d, 1H, J=8.1 Hz), 8.52 (s, 1H).

(2) Synthesis of [6-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic Acid

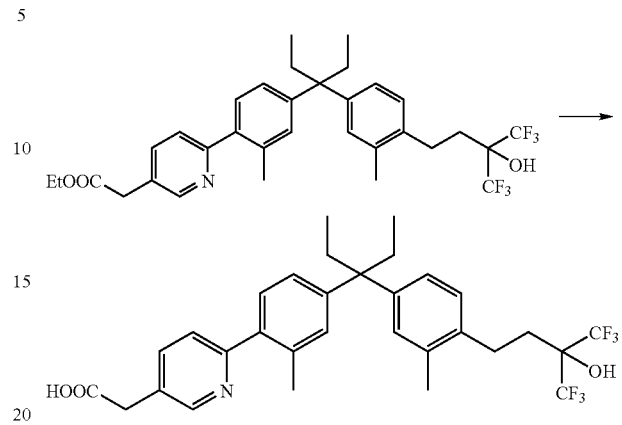

The title compound (41%) was obtained by the same method as in Example 81-(2) using [6-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic acid ethyl ester (Example 107-(1)) as a starting material.

$^1$H-NMR (chloroform-d): 0.63 (t, 6H, J=7.0 Hz), 2.09 (q, 4H, J=7.0 Hz), 2.75 (m, 2H), 3.65 (s, 2H), 6.89-7.08 (m, 5H), 7.18 (d, 1H, J=9.3 Hz), 7.36 (d, 1H, J=7.6 Hz), 7.71 (d, 1H, J=8.9 Hz), 8.54 (s, 1H); MS (ESI+): 582 ([M+H]$^+$).

Example 108

Synthesis of [5-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic Acid

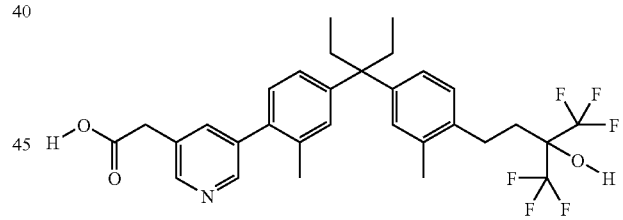

(1) Synthesis of 2-(4-{1-ethyl-1-[3-methyl-4-(4,4,4-trifluoro-3-methoxymethoxy-3-trifluoromethyl-butyl)-phenyl]-propyl}-2-methyl-phenyl)-4,4,5,5-tetramethyl-[1,3,2]dioxaborolane

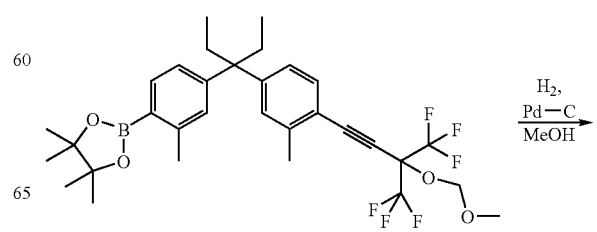

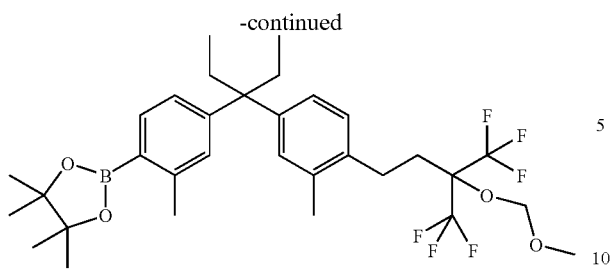

Palladium carbon (10%, 53 mg) was added to a solution of 2-(4-{1-ethyl-1-[3-methyl-4-(4,4,4-trifluoro-3-methoxymethoxy-3-trifluoromethyl-1-butynyl)-phenyl]-propyl}-2-methyl-phenyl)-4,4,5,5-tetramethyl-[1,3,2]dioxaborolane (Example 25-(4); 145.0 mg, 0.237 mmol) in methanol (6.5 mL) in a nitrogen atmosphere at room temperature, and the mixture was stirred in a hydrogen atmosphere at room temperature for four hours. The reaction mixture was filtered and the filtrate was concentrated under reduced pressure. The residue was purified by silica gel chromatography (hexane/ethyl acetate=30/1) to give the title compound (130 mg, 89%).

$^1$H-NMR (chloroform-d): 0.61 (t, 6H, J=7.2 Hz), 1.34 (s, 12H), 2.08 (q, 4H, J=7.2 Hz), 2.25 (s, 3H), 2.25 (m, 2H), 2.49 (s, 3H), 2.80 (m, 2H), 3.51 (2H, s), 4.99 (s, 3H), 6.91-7.00 (m, 5H), 7.63 (d, 1H, J=8.4 Hz).

(2) Synthesis of [5-(4-{1-ethyl-1-[3-methyl-4-(4,4,4-trifluoro-3-methoxymethoxy-3-trifluoromethyl-butyl)-phenyl]-propyl}-2-methyl-phenyl)-pyridin-3-yl]-acetic Acid Methyl Ester

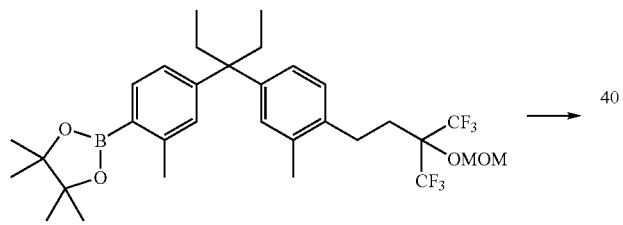

→

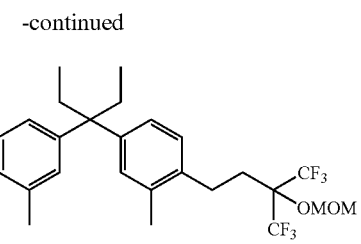

Degassed N,N-dimethylformamide (0.37 mL) was added to 2-(4-{1-ethyl-1-[3-methyl-4-(4,4,4-trifluoro-3-methoxymethoxy-3-trifluoromethyl-butyl)-phenyl]-propyl}-2-methyl-phenyl)-4,4,5,5-tetramethyl-[1,3,2]dioxaborolane (Example 108-(1); 38.4 mg, 0.0623 mmol), (5-bromo-pyridin-3-yl)acetic acid methyl ester (Example 24-(2); 19.9 mg, 0.0865 mmol), tetrakis(triphenylphosphine)palladium (0) (9.0 mg, 0.0078 mmol) and potassium phosphate (28.2 mg, 0.133 mmol). After replacement with nitrogen, the mixture was heated while stirring at an external temperature of 85 to 95° C. for three hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=2/1) to give the title compound (32 mg, 80%).

$^1$H-NMR (chloroform-d): 0.66 (t, 6H, J=7.4 Hz), 2.12 (q, 4H, J=7.4 Hz), 2.25 (m, 2H), 2.25 (s, 3H), 2.29 (s, 3H), 2.82 (m, 2H), 3.51 (s, 3H), 3.68 (s, 2H), 3.73 (s, 3H), 5.00 (s, 2H), 6.95-7.11 (m, 6H), 7.63 (dd, 1H, J=2.1, 1.8 Hz), 8.47 (d, 1H, J=2.1 Hz), 8.52 (d, 1H, J=1.8 Hz).

(3) Synthesis of [5-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic Acid Methyl Ester

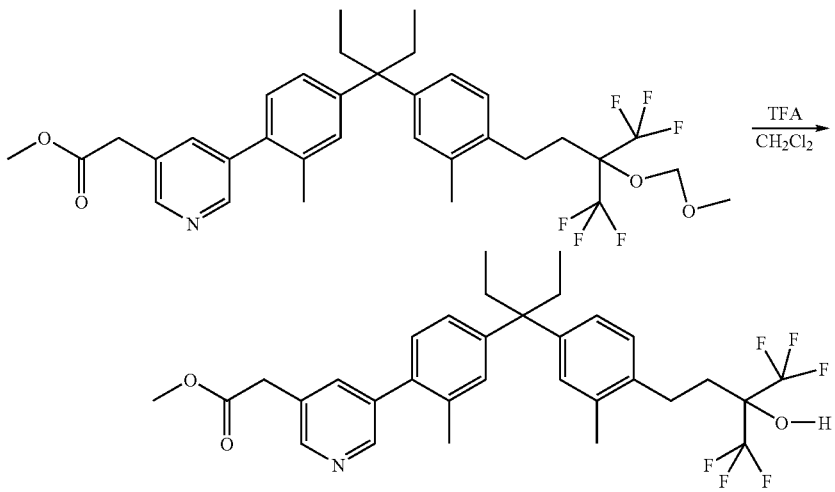

Trifluoroacetic acid (0.22 mL) was added to a solution of [5-(4-{1-ethyl-1-[3-methyl-4-(4,4,4-trifluoro-3-methoxymethoxy-3-trifluoromethyl-butyl)-phenyl]-propyl}-2-methyl-phenyl)-pyridin-3-yl]-acetic acid methyl ester (Example 108-(2); 32.0 mg, 0.0500 mmol) in dichloromethane (1.2 mL) at room temperature, and the mixture was stirred at room temperature for two hours. The solvent in the reaction solution was distilled off under reduced pressure, and the residue was diluted with diethyl ether. The mixture was adjusted to pH 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=1/1) to give the title compound (30.0 mg, 100%).

$^1$H-NMR (chloroform-d): 0.66 (t, 6H, J=7.4 Hz), 2.12 (q, 4H, J=7.4 Hz), 2.18 (m, 2H), 2.24 (s, 3H), 2.29 (s, 3H), 2.83 (m, 2H), 3.69 (s, 2H), 3.73 (s, 3H), 6.95-7.11 (m, 6H), 7.64 (dd, 1H, J=2.4, 2.1 Hz), 8.45 (d, 1H, J=2.1 Hz), 8.50 (d, 1H, J=2.4 Hz).

(4) Synthesis of [5-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic Acid

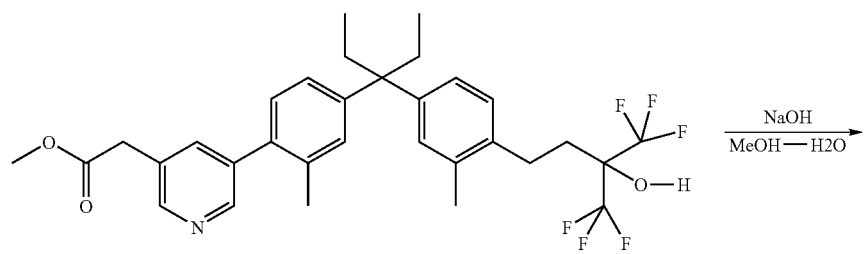

A 2 N sodium hydroxide aqueous solution (0.10 mL) was added to a solution of [5-(4-{1-ethyl-1-[3-methyl-4-(4,4,4-trifluoro-3-hydroxy-3-trifluoromethyl-butyl)-phenyl]-propyl}-2-methyl-phenyl)-pyridin-3-yl]-acetic acid methyl ester (Example 108-(3); 30 mg, 0.050 mmol) in methanol (0.7 mL) at room temperature, and the mixture was stirred at room temperature for four hours. The mixture was acidified with dilute hydrochloric acid aqueous solution, followed by extraction with ethyl acetate. The extract was dried over anhydrous magnesium sulfate and then concentrated under reduced pressure to give the title compound (28 mg, 96%).

$^1$H-NMR (methanol-d4): 0.64 (t, 6H, J=7.2 Hz), 2.06 (m, 2H), 2.15 (q, 4H, J=7.2 Hz), 2.21 (s, 3H), 2.25 (s, 3H), 2.79 (m, 2H), 3.74 (s, 2H), 6.95-7.15 (m, 6H), 7.76 (dd, 1H, J=2, 2 Hz), 8.38 (d, 1H, J=2 Hz), 8.42 (d, 1H, J=2 Hz); MS (ESI+): 582 ([M+H]+).

Example 109

Synthesis of (4'-{1-ethyl-1-[4-(3-ethyl-3-hydroxy-pentyl)-3-methyl-phenyl]-propyl}-3-fluoro-2'-methyl-biphenyl-4-yl)-acetic Acid

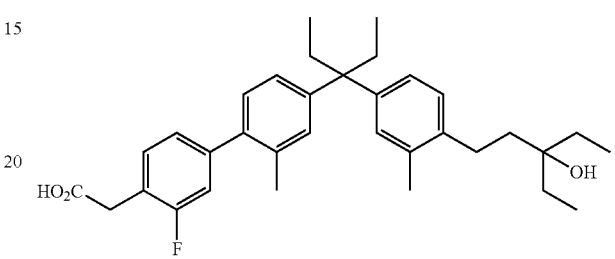

(1) Synthesis of (4'-{1-ethyl-1-[4-(3-ethyl-3-hydroxy-pentyl)-3-methyl-phenyl]-propyl}-3-fluoro-2'-methyl-biphenyl-4-yl)-acetic Acid Methyl Ester

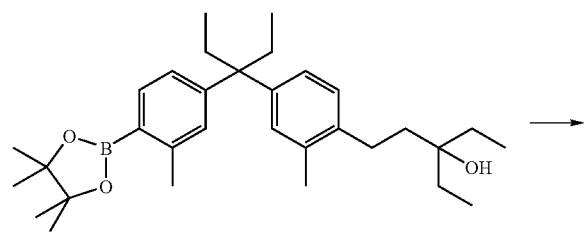

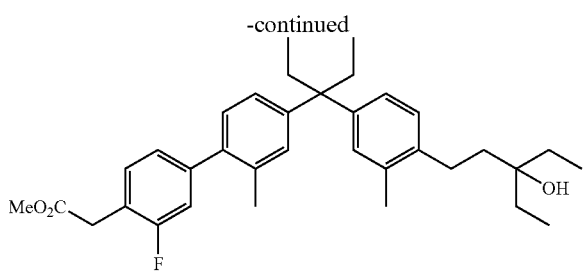

A solution of palladium acetate (3.1 mg, 0.0139 mmol), 2-dicyclohexylphosphino-2',6'-dimethoxybiphenyl (11.4 mg, 0.0279 mmol) and potassium phosphate (59.3 mg, 0.0279 mmol) in water (0.050 mL) and toluene (0.200 mL) was stirred for three minutes. A solution of (4-chloro-2-fluoro-phenyl)acetic acid methyl ester (Example 40; 30.3 mg, 0.14 mmol) and 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-pentan-3-ol (Example 29; 49.2 mg, 0.0998 mmol) in toluene (0.250 mL) was added, and the mixture was stirred in a nitrogen atmosphere at 100° C. for three hours. After filtration through cotton plug, the filtrate was concentrated under reduced pressure. The residue was purified by thin layer silica gel chromatography (15% ethyl acetate/hexane) to give the title compound (37.5 mg, 70%).

$^1$H-NMR (chloroform-d): 0.66 (t, 6H, J=7.2 Hz), 0.93 (t, 6H, J=7.5 Hz), 1.57 (q, 4H, J=7.5 Hz), 1.66-1.72 (m, 2H), 2.11 (q, 4H, J=7.2 Hz), 2.25 (s, 3H), 2.29 (s, 3H), 2.57-2.63 (m, 2H), 3.72 (s, 2H), 3.75 (s, 3H), 6.94-7.10 (m, 8H), 7.27 (t, 1H, J=7.8 Hz).

(2) Synthesis of (4'-{1-ethyl-1-[4-(3-ethyl-3-hydroxy-pentyl)-3-methyl-phenyl]-propyl}-3-fluoro-2'-methyl-biphenyl-4-yl)-acetic Acid

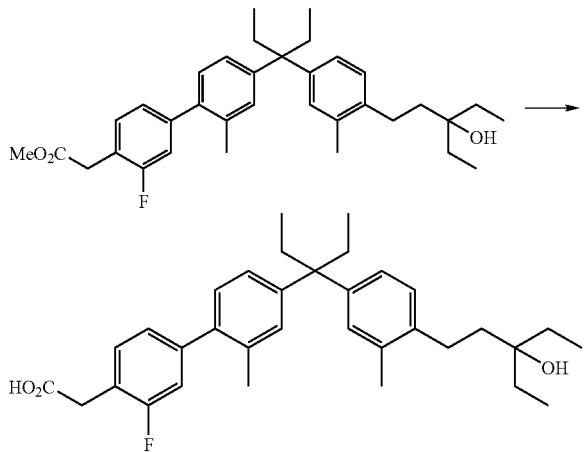

A 2 N sodium hydroxide aqueous solution (0.21 mL) was added to a solution of (4'-{1-ethyl-1-[4-(3-ethyl-3-hydroxy-pentyl)-3-methyl-phenyl]-propyl}-3-fluoro-2'-methyl-biphenyl-4-yl)acetic acid methyl ester (Example 109-(1); 37.5 mg, 0.0703 mmol) in methanol (0.7 mL), and the mixture was stirred for four hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (38.1 mg, 99%).

$^1$H-NMR (chloroform-d): 0.66 (t, 6H, J=7.2 Hz), 0.93 (t, 6H, J=7.5 Hz), 1.58 (q, 4H, J=7.5 Hz), 1.68-1.72 (m, 2H), 2.11 (q, 4H, J=7.2 Hz), 2.24 (s, 3H), 2.29 (s, 3H), 2.57-2.62 (m, 2H), 3.75 (s, 2H), 6.94-7.10 (m, 8H), 7.28 (t, 1H, J=8.1 Hz); MS (ESI+): 518 ([M+H]$^+$).

Example 110

Synthesis of [6-(4-{1-ethyl-1-[4-(3-ethyl-3-hydroxy-pentyl)-3-methyl-phenyl]-propyl}-2-methyl-phenyl)-pyridin-3-yl]-acetic Acid

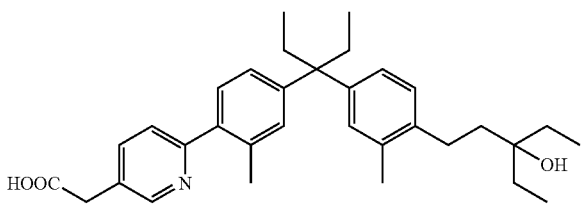

(1) Synthesis of [6-(4-{1-ethyl-1-[4-(3-ethyl-3-hydroxy-pentyl)-3-methyl-phenyl]-propyl}-2-methyl-phenyl)-pyridin-3-yl]-acetic Acid Ethyl Ester

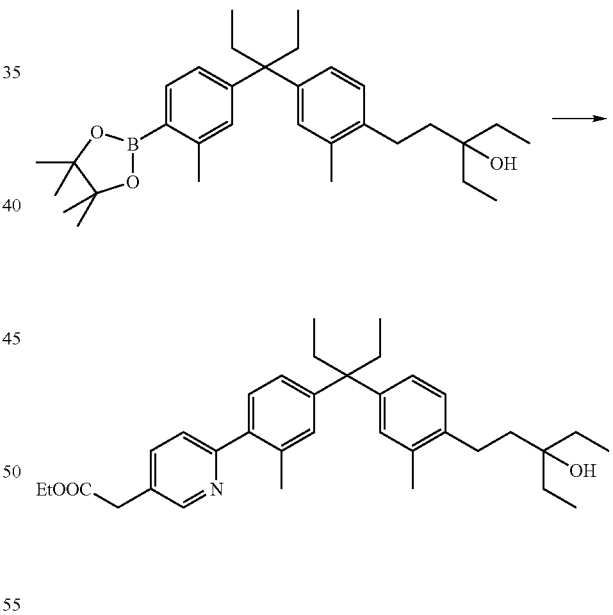

The title compound (57%) was obtained by the same method as in Example 107-(1) using 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-pentan-3-ol (Example 29) as a starting material.

$^1$H-NMR (chloroform-d): 0.64 (t, 6H, J=7.1 Hz), 0.90 (t, 6H, J=7.4 Hz), 1.27 (t, 3H, J=7.0 Hz), 1.54 (q, 4H, J=9.4 Hz), 1.64 (q, 1H), 2.08 (q, 4H, J=7.1 Hz), 2.25 (s, 3H), 2.28 (s, 3H), 2.58 (m, 2H), 3.66 (s, 2H), 4.21 (q, 2H, J=7.4 Hz), 6.91-7.10 (m, 5H), 7.26 (d, 1H, J=7.8 Hz), 7.37 (d, 1H, J=7.8 Hz), 7.68 (m, 1H), 8.57 (s, 1H).

(2) Synthesis of [6-(4-{1-ethyl-1-[4-(3-ethyl-3-hydroxy-pentyl)-3-methyl-phenyl]-propyl}-2-methyl-phenyl)-pyridin-3-yl]-acetic Acid

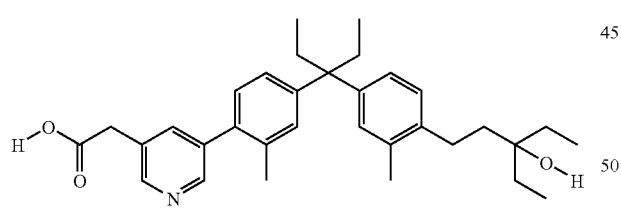

The title compound (55%) was obtained by the same method as in Example 81-(2) using [6-(4-{1-ethyl-1-[4-(3-ethyl-3-hydroxy-pentyl)-3-methyl-phenyl]-propyl}-2-methyl-phenyl)-pyridin-3-yl]-acetic acid ethyl ester (Example 110-(1)) as a starting material.

$^1$H-NMR (chloroform-d): 0.63 (t, 6H, J=7.0 Hz), 0.90 (t, 6H, J=7.6 Hz), 1.55 (q, 4H, J=7.6 Hz), 1.62 (m, 2H), 2.09 (q, 4H, J=7.0 Hz), 2.25 (s, 3H), 2.27 (s, 3H), 2.57 (m, 2H), 3.63 (s, 2H), 6.91-7.10 (m, 5H), 7.21 (d, 1H, J=7.9 Hz), 7.35 (d, 1H, J=7.9 Hz), 7.66 (m, 1H), 8.58 (s, 1H); MS (ESI+): 502 ([M+H]$^+$).

Example 111

Synthesis of [5-(4-{1-ethyl-1-[4-(3-ethyl-3-hydroxy-pentyl)-3-methyl-phenyl]-propyl}-2-methyl-phenyl)-pyridin-3-yl]-acetic Acid

(1) Synthesis of [5-(4-{1-ethyl-1-[4-(3-ethyl-3-hydroxy-pentyl)-3-methyl-phenyl]-propyl}-2-methyl-phenyl)-pyridin-3-yl]-acetic Acid Methyl Ester

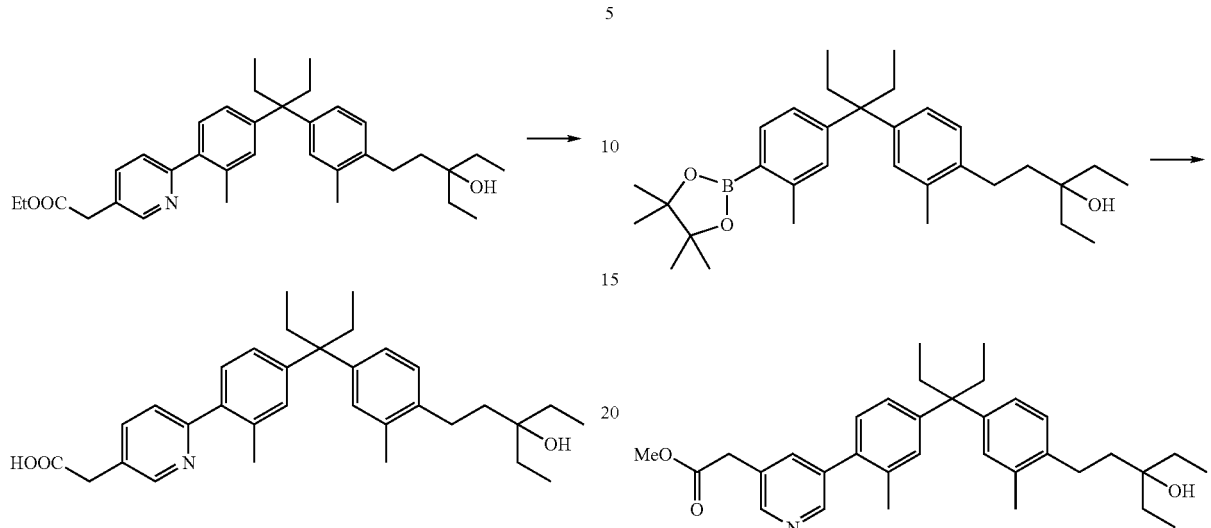

Degassed N,N-dimethylformamide (0.37 mL) was added to 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-pentan-3-ol (Example 29; 30.6 mg, 0.0621 mmol), (5-bromo-pyridin-3-yl)acetic acid methyl ester (Example 24-(2); 21.1 mg, 0.0917 mmol), tetrakis(triphenylphosphine) palladium (0) (9.0 mg, 0.0078 mmol) and potassium phosphate (29.4 mg, 0.138 mmol). After replacement with nitrogen, the mixture was heated while stirring at an external temperature of 85 to 94° C. for three hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=1/1) to give the title compound (29.5 mg, 92%).

$^1$H-NMR (chloroform-d): 0.66 (t, 6H, J=7.4 Hz), 0.93 (t, 6H, J=7.5 Hz), 1.57 (q, 4H, J=7.5 Hz), 1.68 (m, 2H), 2.12 (q, 4H, J=7.4 Hz), 2.25 (s, 3H), 2.30 (s, 3H), 2.59 (m, 2H), 3.68 (s, 2H), 3.73 (s, 3H), 6.93-7.11 (m, 6H), 7.62 (dd, 1H, J=2.1, 1.8 Hz), 8.46 (d, 1H, J=2.1 Hz), 8.52 (d, 1H, J=1.8 Hz).

(2) Synthesis of [5-(4-{1-ethyl-1-[4-(3-ethyl-3-hydroxy-pentyl)-3-methyl-phenyl]-propyl}-2-methyl-phenyl)-pyridin-3-yl]-acetic Acid

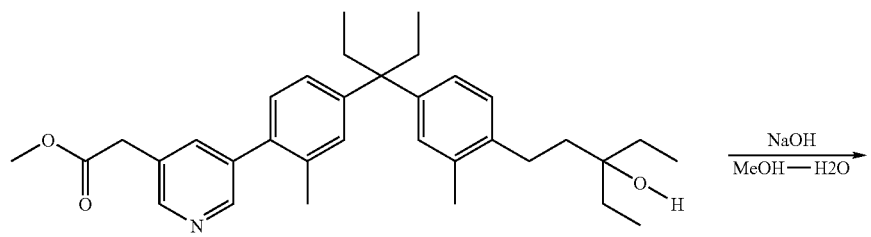

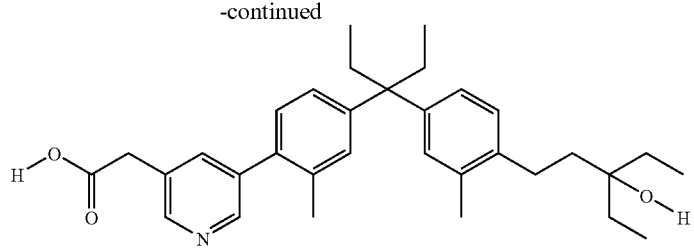

A 2 N sodium hydroxide aqueous solution (0.12 mL) was added to a solution of [5-(4-{1-ethyl-1-[4-(3-ethyl-3-hydroxy-pentyl)-3-methyl-phenyl]-propyl}-2-methyl-phenyl)-pyridin-3-yl]-acetic acid methyl ester (Example 111-(1); 29.5 mg, 0.0572 mmol) in methanol (0.77 mL) at room temperature, and the mixture was stirred at room temperature for three hours. The mixture was acidified with dilute hydrochloric acid aqueous solution, followed by extraction with ethyl acetate. The extract was dried over anhydrous magnesium sulfate and then concentrated under reduced pressure to give the title compound (29 mg, 100%).

$^1$H-NMR (chloroform-d): 0.65 (t, 6H, J=7.4 Hz), 0.92 (t, 6H, J=7.5 Hz), 1.57 (q, 4H, J=7.5 Hz), 1.68 (m, 2H), 2.11 (q, 4H, J=7.4 Hz), 2.23 (s, 3H), 2.28 (s, 3H), 2.58 (m, 2H), 3.72 (s, 2H), 6.92-7.10 (m, 6H), 7.71 (dd, 1H, J=2.1, 2.1 Hz), 8.508 (d, 1H, J=2.1 Hz), 8.514 (d, 1H, J=2.1 Hz);

MS (ESI+): 502 ([M+H]$^+$).

Example 112

Synthesis of [4'-(1-ethyl-1-{4-[2-(1-hydroxy-cyclopentyl)-ethyl]-3-methyl-phenyl}-propyl)-3-fluoro-2'-methyl-biphenyl-4-yl]-acetic Acid

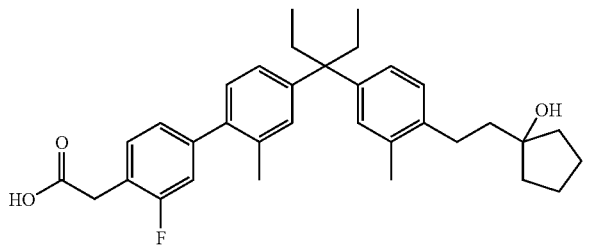

(1) Synthesis of [4'-(1-ethyl-1-{4-[2-(1-hydroxy-cyclopentyl)-ethyl]-3-methyl-phenyl}-propyl)-3-fluoro-2'-methyl-biphenyl-4-yl]-acetic Acid Methyl Ester

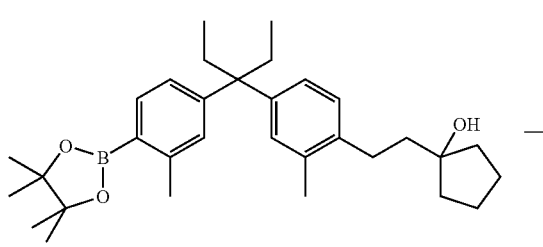

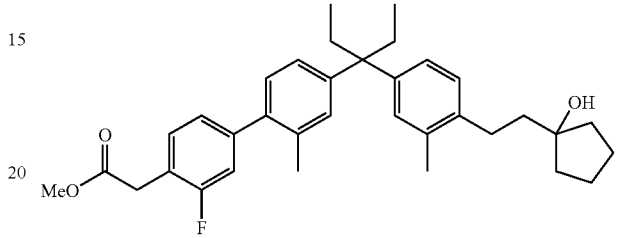

A solution of palladium acetate (2.6 mg, 0.0114 mmol), 2-dicyclohexylphosphino-2',6'-dimethoxybiphenyl (9.4 mg, 0.0228 mmol) and potassium phosphate (48.4 mg, 0.22 mmol) in water (0.040 mL) and toluene (0.200 mL) was stirred for three minutes. A solution of (4-chloro-2-fluoro-phenyl)acetic acid methyl ester (Example 40; 24.7 mg, 0.12 mmol) and 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclopentanol (Example 40; 40.0 mg, 0.0815 mmol) in toluene (0.200 mL) was added, and the mixture was stirred in a nitrogen atmosphere at 100° C. for three hours. After filtration through cotton plug, the filtrate was concentrated under reduced pressure. The residue was purified by silica gel chromatography (17% ethyl acetate/hexane) to give the title compound (30.9 mg, 77%).

$^1$H-NMR (chloroform-d): 0.66 (t, 6H, J=7.2 Hz), 1.61-1.75 (m, 6H), 1.81-1.89 (m, 4H), 2.11 (q, 4H, J=7.2 Hz), 2.25 (s, 3H), 2.29 (s, 3H), 2.70-2.75 (m, 2H), 3.72 (s, 2H), 3.75 (s, 3H), 6.95-7.09 (m, 8H), 7.27 (t, 1H, J=8.1 Hz).

(2) Synthesis of [4'-(1-ethyl-1-{4-[2-(1-hydroxy-cyclopentyl)-ethyl]-3-methyl-phenyl}-propyl)-3-fluoro-2'-methyl-biphenyl-4-yl]-acetic Acid

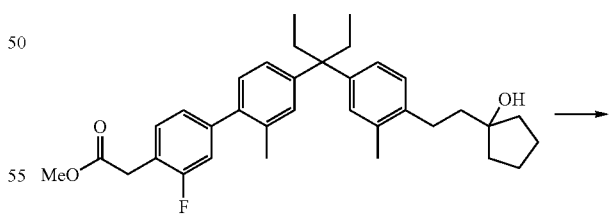

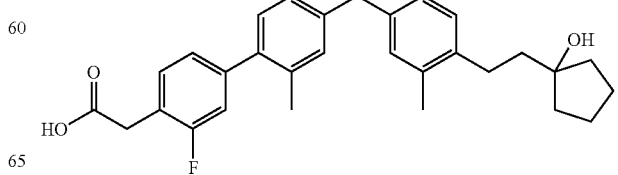

A 2 N sodium hydroxide aqueous solution (0.07 mL) was added to a solution of [4'-(1-ethyl-1-{4-[2-(1-hydroxy-cyclopentyl)-ethyl]-3-methyl-phenyl}-propyl)-3-fluoro-2'-methyl-biphenyl-4-yl]-acetic acid methyl ester (Example 112-(1); 25.8 mg, 0.0486 mmol) in methanol (1.6 mL), and the mixture was stirred for five hours. A saturated aqueous ammonium chloride solution was added to the reaction mixture, followed by extraction with ethyl acetate. The organic layer was washed with water, dried over anhydrous sodium sulfate and concentrated under reduced pressure to give the title compound (29.0 mg, 99%).

$^1$H-NMR (chloroform-d): 0.65 (t, 6H, J=7.2 Hz), 1.62-1.72 (m, 6H), 1.81-1.89 (m, 4H), 2.11 (q, 4H, J=7.2 Hz), 2.24 (s, 3H), 2.29 (s, 3H), 2.69-2.75 (m, 2H), 3.76 (s, 2H), 6.94-7.10 (m, 8H), 7.28 (t, 1H, J=7.8 Hz); MS (ESI+): 516 ([M+H]$^+$).

Example 113

Synthesis of {6-[4-(1-ethyl-1-{4-[2-(1-hydroxy-cyclopentyl)-ethyl]-3-methyl-phenyl}-propyl)-2-methyl-phenyl]-pyridin-3-yl}-acetic Acid

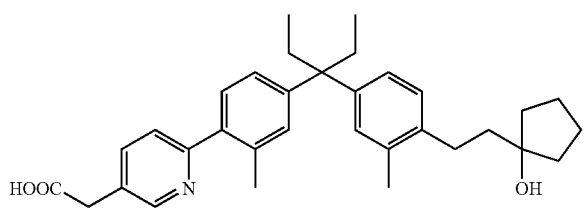

(1) Synthesis of {6-[4-(1-ethyl-1-{4-[2-(1-hydroxy-cyclopentyl)-ethyl]-3-methyl-phenyl}-propyl)-2-methyl-phenyl]-pyridin-3-yl}-acetic Acid Ethyl Ester

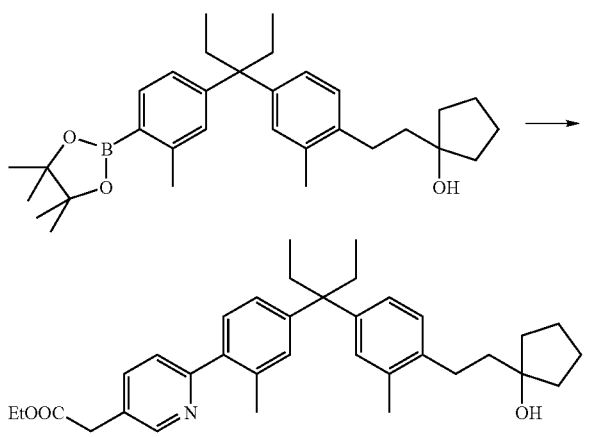

The title compound (48%) was obtained by the same method as in Example 107-(1) using 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclopentanol (Example 34-(2)) as a starting material.

$^1$H-NMR (chloroform-d): 0.63 (t, 6H, J=7.1 Hz), 1.31 (t, 3H, J=7.0 Hz), 1.58-1.90 (m, 1H), 2.10 (q, 4H, J=7.1 Hz), 2.26 (s, 3H), 2.32 (s, 3H), 2.70 (m, 2H), 3.66 (s, 2H), 4.18 (q, 2H, J=7.0 Hz), 6.89-7.12 (m, 5H), 7.25 (m, 1H), 7.37 (d, 1H, J=7.9 Hz), 7.68 (d, 1H, J=8.0 Hz), 8.56 (s, 1H).

(2) Synthesis of {6-[4-(1-ethyl-1-{4-[2-(1-hydroxy-cyclopentyl)-ethyl]-3-methyl-phenyl}-propyl)-2-methyl-phenyl]-pyridin-3-yl}-acetic Acid

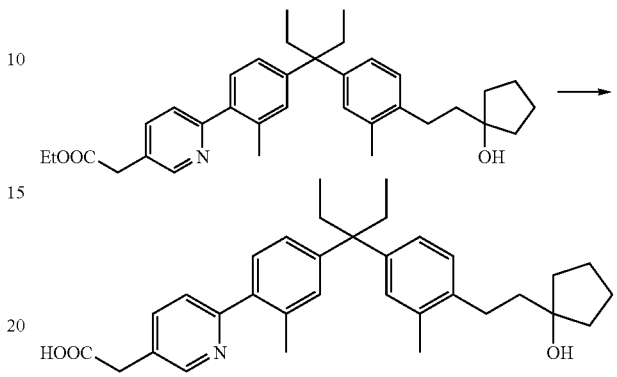

The title compound (48%) was obtained by the same method as in Example 81-(2) using {6-[4-(1-ethyl-1-{4-[2-(1-hydroxy-cyclopentyl)-ethyl]-3-methyl-phenyl}-propyl)-2-methyl-phenyl]-pyridin-3-yl}-acetic acid ethyl ester (Example 113-(1)) as a starting material.

$^1$H-NMR (chloroform-d): 0.63 (t, 6H, J=7.0 Hz), 1.62 (m, 8H), 1.80 (m, 2H), 2.25 (s, 3H), 2.27 (s, 3H), 2.70 (m, 2H), 3.63 (s, 2H), 6.93-7.20 (m, 5H), 7.21 (d, 1H, J=7.9 Hz), 7.34 (d, 1H, J=7.9 Hz), 7.66 (dd, 1H, J=2.0, 8.1 Hz), 8.58 (d, 1H, J=2.0 Hz); MS (ESI+): 500 ([M+H]$^+$).

Example 114

Synthesis of {5-[4-(1-ethyl-1-{4-[2-(1-hydroxy-cyclopentyl)-ethyl]-3-methyl-phenyl}-propyl)-2-methyl-phenyl]-pyridin-3-yl}-acetic Acid

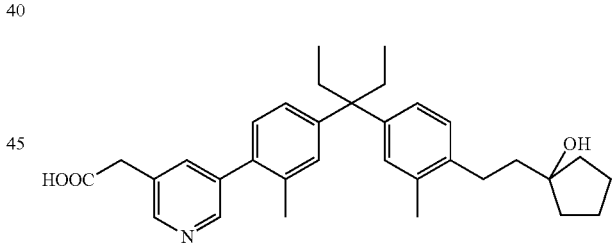

(1) Synthesis of {5-[4-(1-ethyl-1-{3-methyl-4-[2-(1-trimethylsilanyloxy-cyclopentyl)-ethyl]-phenyl}-propyl)-2-methyl-phenyl]-pyridin-3-yl}-acetic Acid Methyl Ester

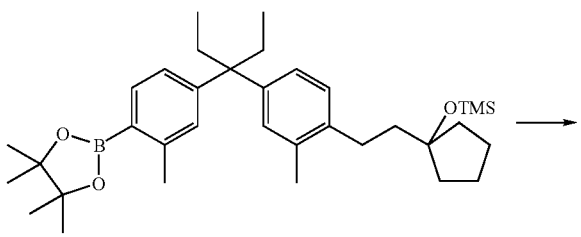

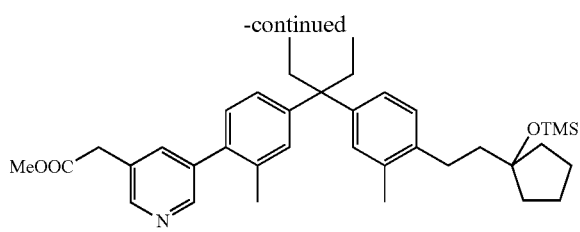

2-[4-(1-ethyl-1-{3-methyl-4-[2-(1-trimethylsilanyloxy-cyclopentyl)-ethyl]-phenyl}-propyl)-2-methyl-phenyl]-4,4,5,5-tetramethyl-[1,3,2]dioxaborolane (Example 34-(1); 35.7 mg, 0.063 mmol), (5-bromo-pyridin-3-yl)acetic acid methyl ester (Example 24-(2); 19.0 mg, 0.082 mmol), tetrakis(triphenylphosphine)palladium (0) (9.2 mg, 0.080 mmol), potassium phosphate (26.3 mg, 0.124 mmol) and N,N-dimethylformamide (0.38 mL) were placed in a reaction vessel and stirred in a nitrogen atmosphere at 95° C. for three hours. A saturated aqueous ammonium chloride solution (0.1 mL) and water (0.1 mL) were added to the reaction mixture, followed by extraction with diethyl ether. The organic layer was dried over anhydrous magnesium sulfate and concentrated under reduced pressure. The residue was purified by silica gel chromatography (hexane only to hexane/ethyl acetate=3/1) to give the title compound (26.8 mg, 72%).

$^1$H-NMR (chloroform-d): 0.15 (s, 9H), 0.65 (t, 6H, J=7.3 Hz), 1.58 (m, 4H), 1.75-1.81 (m, 6H), 2.11 (q, 4H, J=7.3 Hz), 2.24 (s, 3H), 2.28 (s, 3H), 2.64-2.70 (m, 2H), 3.68 (s, 2H), 3.72 (s, 3H), 6.93-7.10 (m, 6H), 7.62 (dd, 1H, J=2.0, 2.1 Hz), 8.46 (d, 1H, J=2.1 Hz), 8.52 (d, 1H, J=2.0 Hz).

(2) Synthesis of {5-[4-(1-ethyl-1-{4-[2-(1-hydroxy-cyclopentyl)-ethyl]-3-methyl-phenyl}-propyl)-2-methyl-phenyl]-pyridin-3-yl}-acetic Acid Methyl Ester

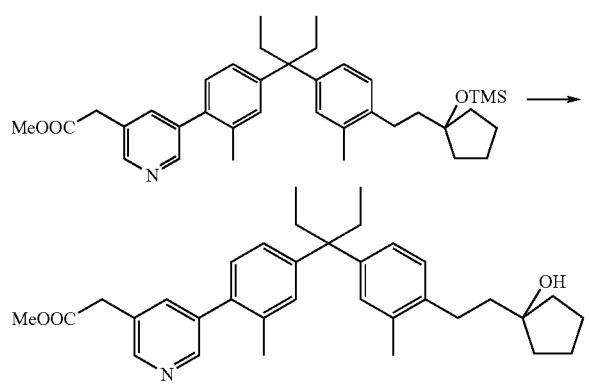

{5-[4-(1-Ethyl-1-{3-methyl-4-[2-(1-trimethylsilanyloxy-cyclopentyl)-ethyl]-phenyl}-propyl)-2-methyl-phenyl]-pyridin-3-yl}-acetic acid methyl ester (Example 114-(1); 26.8 mg, 0.046 mmol) was dissolved in tetrahydrofuran (0.4 mL). Tetra-n-butylammonium fluoride (1 M solution in tetrahydrofuran; 0.05 mL, 0.05 mmol) was added at room temperature, and the mixture was stirred for two hours. A saturated aqueous ammonium chloride solution and water were added to the reaction mixture, followed by extraction with ethyl acetate. The organic layer was dried over anhydrous magnesium sulfate and concentrated under reduced pressure. Then, the resulting residue was purified by silica gel chromatography (hexane only to hexane/ethyl acetate=3/1) to give the title compound (16.4 mg, 70%).

$^1$H-NMR (chloroform-d): 0.64 (t, 6H, J=7.3 Hz), 1.66 (m, 4H), 1.81-1.88 (m, 6H), 2.11 (q, 4H, J=7.3 Hz), 2.24 (s, 3H), 2.29 (s, 3H), 2.68-2.74 (m, 2H), 3.68 (s, 2H), 3.72 (s, 3H), 6.94-7.10 (m, 6H), 7.63 (dd, 1H, J=2.0, 2.1 Hz), 8.46 (d, 1H, J=2.1 Hz), 8.51 (d, 1H, J=2.0 Hz).

(3) Synthesis of {5-[4-(1-ethyl-1-{4-[2-(1-hydroxy-cyclopentyl)-ethyl]-3-methyl-phenyl}-propyl)-2-methyl-phenyl]-pyridin-3-yl}-acetic Acid

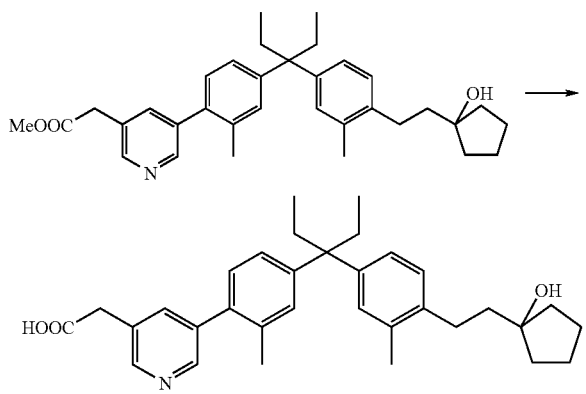

The title compound (10.1 mg, 64%) was obtained by the same method as in Example 64-(3) using {5-[4-(1-ethyl-1-{4-[2-(1-hydroxy-cyclopentyl)-ethyl]-3-methyl-phenyl}-propyl)-2-methyl-phenyl]-pyridin-3-yl}-acetic acid methyl ester (Example 114-(2); 16.4 mg, 0.032 mmol) as a starting material.

$^1$H-NMR (methanol-d): 0.68 (t, 6H, J=7.3 Hz), 1.67-1.86 (m, 10H), 2.18 (q, 4H, J=7.3 Hz), 2.25 (s, 3H), 2.30 (s, 3H), 2.71-2.77 (m, 2H), 3.77 (s, 2H), 6.98-7.16 (m, 6H), 7.79 (dd, 1H, J=2.0, 2.1 Hz), 8.42 (d, 1H, J=2.1 Hz), 8.46 (d, 1H, J=2.0 Hz); MS (ESI+): 500 ([M+H]$^+$).

Example 115

Synthesis of [4'-(1-ethyl-1-{4-[2-(1-hydroxy-cyclohexyl)-ethyl]-3-methyl-phenyl}-propyl)-3-fluoro-2'-methyl-biphenyl-4-yl]-acetic Acid

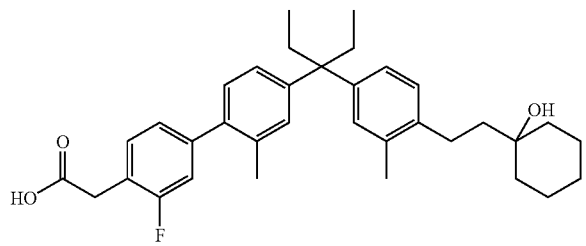

(1) Synthesis of [4'-(1-ethyl-1-{4-[2-(1-hydroxy-cyclohexyl)-ethyl]-3-methyl-phenyl}-propyl)-3-fluoro-2'-methyl-biphenyl-4-yl]-acetic Acid Methyl Ester

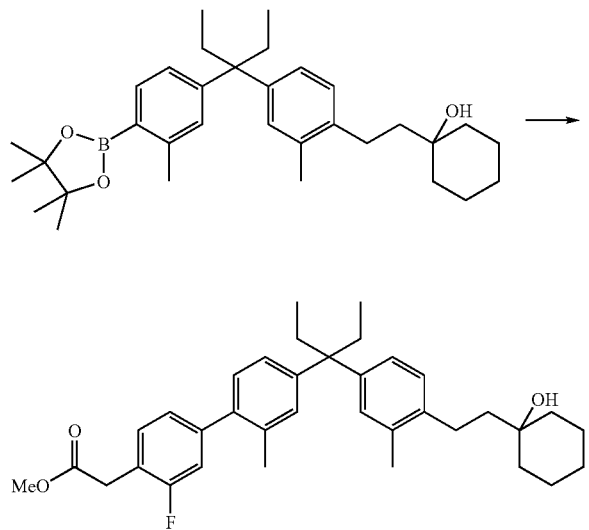

A solution of palladium acetate (3.4 mg, 0.0153 mmol), 2-dicyclohexylphosphino-2',6'-dimethoxybiphenyl (12.6 mg, 0.0307 mmol) and potassium phosphate (65.3 mg, 0.30 mmol) in water (0.050 mL) and toluene (0.250 mL) was stirred for three minutes. A solution of (4-chloro-2-fluoro-phenyl)acetic acid methyl ester (Example 40; 33.2 mg, 0.16 mmol) and 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclohexanol (Example 37-(2); 55.4 mg, 0.109 mmol) in toluene (0.150 mL) was added, and the mixture was stirred in a nitrogen atmosphere at 100° C. for three hours. After filtration through cotton plug, the filtrate was concentrated under reduced pressure. The residue was purified by thin layer silica gel chromatography (20% ethyl acetate/hexane) to give the title compound (45.6 mg, 76%).

$^1$H-NMR (chloroform-d): 0.66 (t, 6H, J=7.2 Hz), 1.25-1.38 (m, 2H), 1.48-1.74 (m, 1H), 2.11 (q, 4H, J=7.2 Hz), 2.25 (s, 3H), 2.29 (s, 3H), 2.63-2.68 (m, 2H), 3.72 (s, 2H), 3.75 (s, 3H), 6.95-7.10 (m, 8H), 7.27 (t, 1H, J=7.8 Hz).

(2) Synthesis of [4'-(1-ethyl-1-{4-[2-(1-hydroxy-cyclohexyl)-ethyl]-3-methyl-phenyl}-propyl)-3-fluoro-2'-methyl-biphenyl-4-yl]-acetic Acid

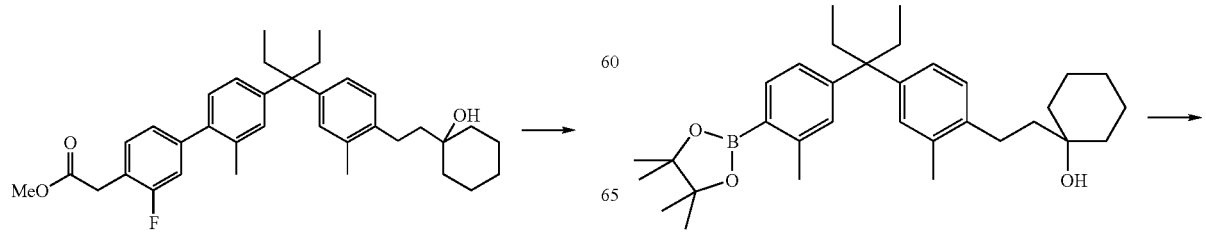

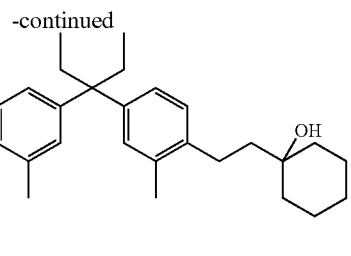

A 2 N sodium hydroxide aqueous solution (0.3 mL) was added to a solution of [4'-(1-ethyl-1-{4-[2-(1-hydroxy-cyclohexyl)-ethyl]-3-methyl-phenyl}-propyl)-3-fluoro-2'-methyl-biphenyl-4-yl]-acetic acid methyl ester (Example 115-(1); 45.6 mg, 0.0837 mmol) in methanol (0.8 mL), and the mixture was stirred for five hours. A saturated aqueous ammonium chloride solution was added to the reaction mixture, followed by extraction with ethyl acetate. The organic layer was washed with water, dried over anhydrous sodium sulfate and concentrated under reduced pressure. The residue was purified by thin layer silica gel chromatography (3% methanol/dichloromethane) to give the title compound (34.1 mg, 76%).

$^1$H-NMR (chloroform-d): 0.66 (t, 6H, J=7.2 Hz), 1.27-1.38 (m, 2H), 1.48-1.65 (m, 8H), 1.69-1.75 (m, 2H), 2.11 (q, 4H, J=7.2 Hz), 2.24 (s, 3H), 2.29 (s, 3H), 2.63-2.69 (m, 2H), 3.75 (s, 2H), 6.94-7.09 (m, 8H), 7.28 (t, 1H, J=8.4 Hz); MS (ESI+): 530 ([M+H]$^+$).

Example 116

Synthesis of {6-[4-(1-ethyl-1-{4-[2-(1-hydroxy-cyclohexyl)-ethyl]-3-methyl-phenyl}-propyl)-2-methyl-phenyl]-pyridin-3-yl}-acetic Acid

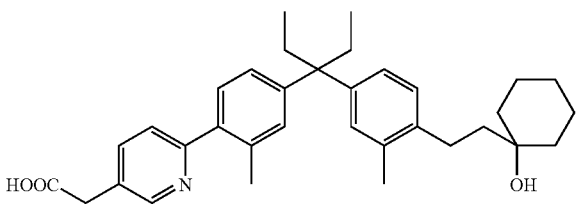

(1) Synthesis of {6-[4-(1-ethyl-1-{4-[2-(1-hydroxy-cyclohexyl)-ethyl]-3-methyl-phenyl}-propyl)-2-methyl-phenyl]-pyridin-3-yl}-acetic Acid Ethyl Ester -continued

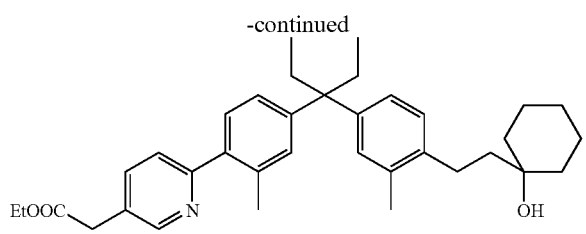

The title compound (56%) was obtained by the same method as in Example 107-(1) using 1-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-cyclohexanol (Example 37-(2)) as a starting material.

$^1$H-NMR (chloroform-d): 0.63 (t, 6H, J=7.0 Hz), 1.29 (m, 3H), 1.42-1.73 (m, 10H), 2.08 (q, 4H, J=7.0 Hz), 2.25 (s, 3H), 2.32 (s, 3H), 2.62 (m, 2H), 3.65 (s, 2H), 4.09 (m, 2H), 6.92-7.10 (m, 5H), 7.26 (m, 1H), 7.38 (d, 1H, J=8.0 Hz), 7.67 (d, 1H, J=7.7 Hz), 8.56 (s, 1H).

(2) Synthesis of {6-[4-(1-ethyl-1-{4-[2-(1-hydroxy-cyclohexyl)-ethyl]-3-methyl-phenyl}-propyl)-2-methyl-phenyl]-pyridin-3-yl}-acetic Acid

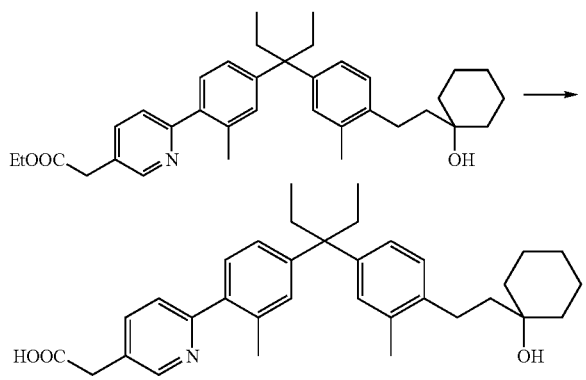

The title compound (55%) was obtained by the same method as in Example 81-(2) using {6-[4-(1-ethyl-1-{4-[2-(1-hydroxy-cyclohexyl)-ethyl]-3-methyl-phenyl}-propyl)-2-methyl-phenyl]-pyridin-3-yl}-acetic acid ethyl ester (Example 116-(1)) as a starting material.

$^1$H-NMR (chloroform-d): 0.63 (t, 6H, J=7.0 Hz), 1.21-1.75 (m, 12H), 2.09 (q, 4H, J=7.0 Hz), 2.25 (s, 3H), 2.27 (s, 3H), 2.62 (m, 2H), 3.63 (s, 2H), 6.90-7.11 (m, 5H), 7.21 (d, 1H, J=8.1 Hz), 7.34 (d, 1H, J=8.1 Hz), 7.66 (d, 1H, J=8.0 Hz), 8.58 (s, 1H); MS (ESI+): 514 ([M+H]$^+$).

Example 117

Synthesis of {5-[4-(1-ethyl-1-{4-[2-(1-hydroxy-cyclohexyl)-ethyl]-3-methyl-phenyl}-propyl)-2-methyl-phenyl]-pyridin-3-yl}-acetic Acid

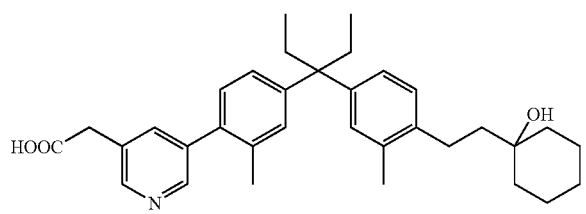

(1) Synthesis of {5-[4-(1-ethyl-1-{3-methyl-4-[2-(1-trimethylsilanyloxy-cyclohexyl)-ethyl]-phenyl}-propyl)-2-methyl-phenyl]-pyridin-3-yl}-acetic Acid Methyl Ester

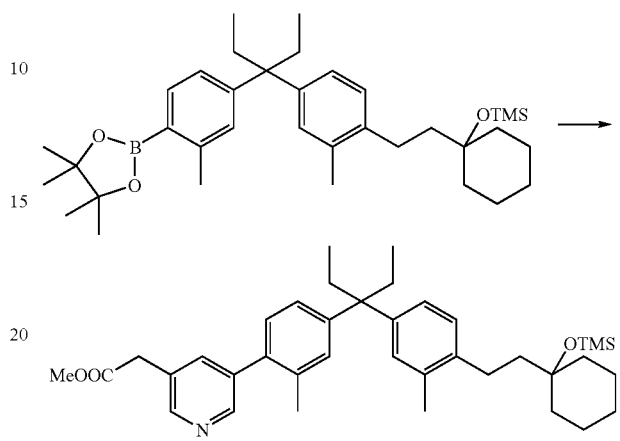

The title compound (44.5 mg, 75%) was obtained by the same method as in Example 114-(1) using 2-[4-(1-ethyl-1-{3-methyl-4-[2-(1-trimethylsilanyloxy-cyclohexyl)-ethyl]-phenyl}-propyl)-2-methyl-phenyl]-4,4,5,5-tetramethyl-[1,3,2]dioxaborolane (Example 37-(1); 57.1 mg, 0.099 mmol) as a starting material.

$^1$H-NMR (chloroform-d): 0.15 (s, 9H), 0.65 (t, 6H, J=7.3 Hz), 1.40 (m, 4H), 1.60-1.76 (m, 8H), 2.11 (q, 4H, J=7.3 Hz), 2.24 (s, 3H), 2.27 (s, 3H), 2.57-2.63 (m, 2H), 3.68 (s, 2H), 3.72 (s, 3H), 6.93-7.11 (m, 6H), 7.62 (dd, 1H, J=2.0, 2.1 Hz), 8.46 (d, 1H, J=2.1 Hz), 8.52 (d, 1H, J=2.0 Hz)

(2) Synthesis of {5-[4-(1-ethyl-1-{4-[2-(1-hydroxy-cyclohexyl)-ethyl]-3-methyl-phenyl}-propyl)-2-methyl-phenyl]-pyridin-3-yl}-acetic Acid Methyl Ester

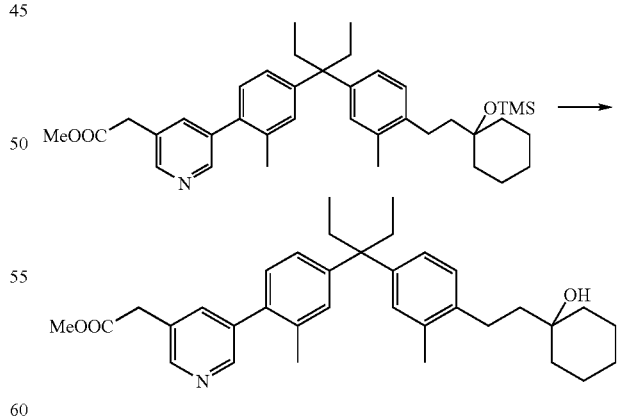

The title compound (20.3 mg, 52%) was obtained by the same method as in Example 114-(2) using {5-[4-(1-ethyl-1-{3-methyl-4-[2-(1-trimethylsilanyloxy-cyclohexyl)-ethyl]-phenyl}-propyl)-2-methyl-phenyl]-pyridin-3-yl}-acetic acid methyl ester (Example 117-(1); 44.5 mg, 0.074 mmol) as a starting material.

¹H-NMR (chloroform-d): 0.64 (t, 6H, J=7.3 Hz), 1.31 (m, 2H), 1.49-1.73 (m, 10H), 2.11 (q, 4H, J=7.3 Hz), 2.24 (s, 3H), 2.28 (s, 3H), 2.62-2.68 (m, 2H), 3.68 (s, 2H), 3.72 (s, 3H), 6.93-7.10 (m, 6H), 7.62 (dd, 1H, J=2.1, 2.2 Hz), 8.46 (d, 1H, J=2.2 Hz), 8.52 (d, 1H, J=2.1 Hz).

(3) Synthesis of {5-[4-(1-ethyl-1-{4-[2-(1-hydroxy-cyclohexyl)-ethyl]-3-methyl-phenyl}-propyl)-2-methyl-phenyl]-pyridin-3-yl}-acetic Acid

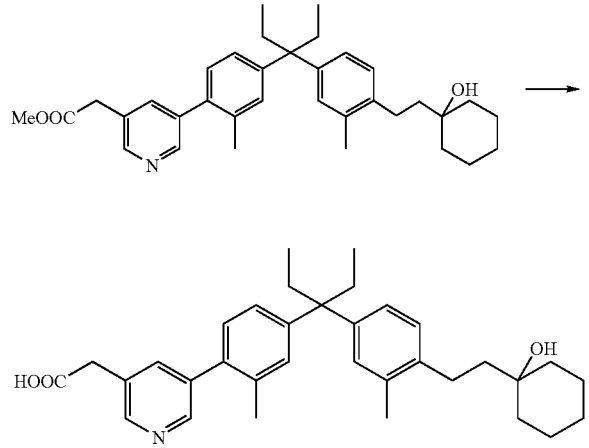

The title compound (17.6 mg, 89%) was obtained by the same method as in Example 64-(3) using {5-[4-(1-ethyl-1-{4-[2-(1-hydroxy-cyclohexyl)-ethyl]-3-methyl-phenyl}-propyl)-2-methyl-phenyl]-pyridin-3-yl}-acetic acid methyl ester (Example 117-(2); 20.3 mg, 0.039 mmol) as a starting material.

¹H-NMR (chloroform-d): 0.63 (t, 6H, J=7.1 Hz), 1.29 (m, 2H), 1.53-1.72 (m, 10H), 2.09 (q, 4H, J=7.1 Hz), 2.21 (s, 3H), 2.26 (s, 3H), 2.60-2.67 (m, 2H), 3.69 (s, 2H), 6.93-7.08 (m, 6H), 7.69 (m, 1H), 8.50-8.51 (m, 2H); MS (ESI+): 514 ([M+H]⁺).

Example 118

Synthesis of (E)-(4'-{1-ethyl-1-[4-(3-ethyl-3-hydroxy-1-pentenyl)-3-methyl-phenyl]-propyl}-3-fluoro-2',6'-dimethyl-biphenyl-4-yl)-acetic Acid

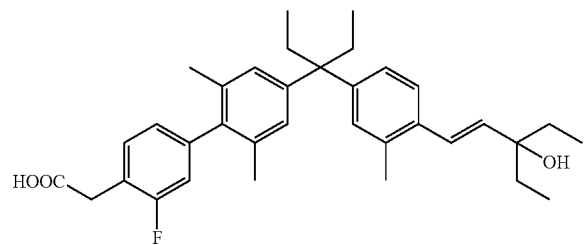

(1) Synthesis of (E)-(4'-{1-ethyl-1-[4-(3-ethyl-3-hydroxy-1-pentenyl)-3-methyl-phenyl]-propyl}-3-fluoro-2',6'-dimethyl-biphenyl-4-yl)-acetic Acid Methyl Ester

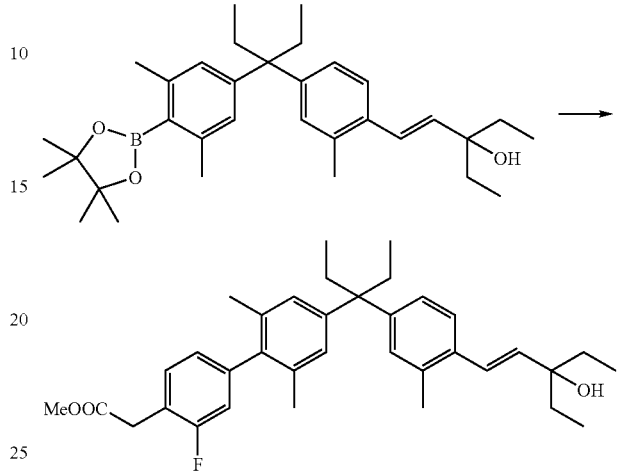

(4-Chloro-2-fluoro-phenyl)acetic acid methyl ester (Example 40; 30 mg, 0.149 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (63 mg, 0.297 mmol) and water (0.2 mL) were added to a solution of (E)-1-(4-{1-[3,5-dimethyl-4-(4,4,5,5-tetramethyl-[1,3,2]dioxaborolan-2-yl)-phenyl]-1-ethyl-propyl}-2-methyl-phenyl)-3-ethyl-1-penten-3-ol (Example 38-(6); 50 mg, 0.099 mmol) in toluene (2 mL). After replacement with nitrogen, the mixture was stirred at 100° C. for one hour. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (32.5 mg, 60%).

¹H-NMR (chloroform-d): 0.65 (6H, t, J=7.26 Hz), 0.92 (6H, t, J=7.58 Hz), 1.65 (4H, q, J=7.59 Hz), 1.97 (6H, s), 2.10 (4H, q, J=7.25 Hz), 2.34 (3H, s), 3.72 (2H, s), 3.75 (3H, s), 6.03 (1H, d, J=15.99 Hz), 6.76 (1H, d, J=15.99 Hz), 6.85-6.92 (4H, m), 6.95-7.02 (2H, m), 7.28-7.34 (2H, m).

(2) Synthesis of (E)-(4'-{1-ethyl-1-[4-(3-ethyl-3-hydroxy-1-pentenyl)-3-methyl-phenyl]-propyl}-3-fluoro-2',6'-dimethyl-biphenyl-4-yl)-acetic Acid

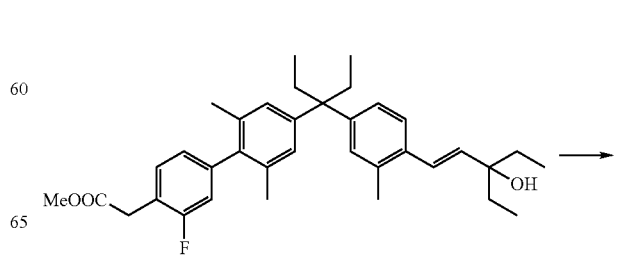

-continued

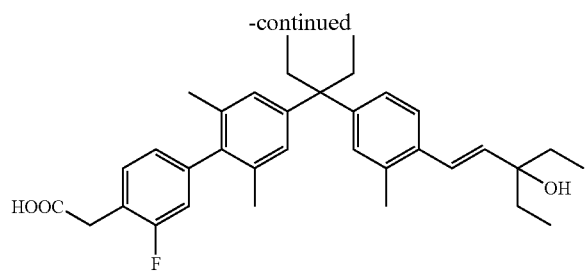

A 1 N sodium hydroxide aqueous solution (0.180 mL, 0.180 mmol) was added to a solution of (E)-(4'-{1-ethyl-1-[4-(3-ethyl-3-hydroxy-1-pentenyl)-3-methyl-phenyl]-propyl}-3-fluoro-2',6'-dimethyl-biphenyl-4-yl)acetic acid methyl ester (Example 118-(1); 32.5 mg, 0.060 mmol) in methanol-tetrahydrofuran (1:1, 4 mL), and the mixture was stirred at room temperature for 10 hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (23.8 mg, 75%).

$^1$H-NMR (chloroform-d): 0.65 (6H, t, J=7.25 Hz), 0.92 (6H, t, J=7.42 Hz), 1.65 (4H, q, J=7.42 Hz), 1.97 (6H, s), 2.10 (4H, q, J=7.25 Hz), 2.34 (3H, s), 3.76 (2H, s), 6.03 (1H, d, J=15.99 Hz), 6.76 (1H, d, J=15.99 Hz), 6.86-6.93 (4H, m), 6.96-7.02 (2H, m), 7.26-7.33 (2H, m); MS (ESI+): 513 ([M−H$_2$O+H]$^+$).

Example 119

Synthesis of (E)-[6-(4-{1-ethyl-1-[4-(3-ethyl-3-hydroxy-1-pentenyl)-3-methyl-phenyl]-propyl}-2,6-dimethyl-phenyl)-3-pyridinyl]-acetic Acid

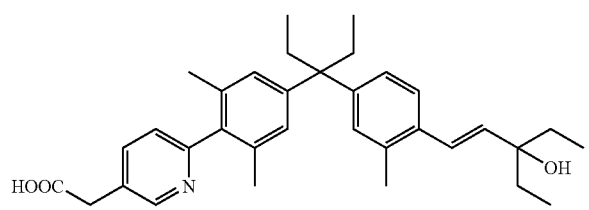

(1) Synthesis of (E)-[6-(4-{1-ethyl-1-[4-(3-ethyl-3-hydroxy-1-pentenyl)-3-methyl-phenyl]-propyl}-2,6-dimethyl-phenyl)-3-pyridinyl]-acetic Acid Ethyl Ester

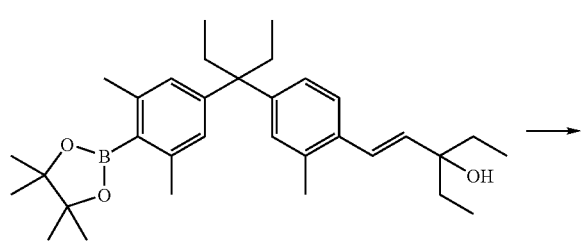

-continued

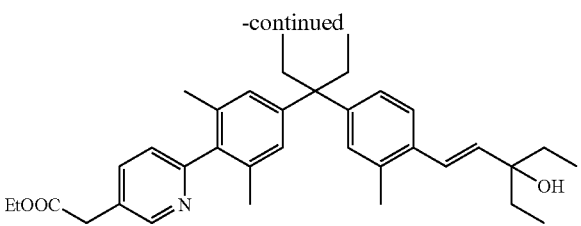

(6-Chloro-pyridin-3-yl)-acetic acid ethyl ester (30 mg, 0.149 mmol), tetrakis(triphenylphosphine)palladium (0) (16 mg, 0.014 mmol) and potassium phosphate (32 mg, 0.149 mmol) were added to a solution of (E)-1-(4-{1-[3,5-dimethyl-4-(4,4,5,5-tetramethyl-[1,3,2]dioxaborolan-2-yl)-phenyl]-1-ethyl-propyl}-2-methyl-phenyl)-3-ethyl-1-penten-3-ol (Example 38-(6); 50 mg, 0.099 mmol) in N,N-dimethylformamide (0.5 mL). After replacement with nitrogen, the mixture was stirred with microwave heating at 140° C. for 10 minutes. Then, ethyl acetate was added to the reaction mixture, which was washed with water and brine. The organic layer was dried over anhydrous magnesium sulfate, filtered and concentrated under reduced pressure. The resulting residue was purified by silica gel chromatography (hexane:ethyl acetate=4:1) to give the target compound as a colorless oil (11.6 mg, 22%).

$^1$H-NMR (chloroform-d): 0.65 (6H, t, J=7.25 Hz), 0.93 (6H, t, J=7.25 Hz), 1.29 (3H, t, J=7.26 Hz), 1.65 (4H, q, J=7.26 Hz), 1.99 (6H, s), 2.09 (4H, q, J=7.26 Hz), 2.33 (3H, s), 3.67 (2H, s), 4.21 (2H, q, J=7.25 Hz), 6.02 (1H, d, J=15.99 Hz), 6.75 (1H, d, J=15.82 Hz), 6.89 (2H, s), 6.98-7.01 (2H, m), 7.22 (1H, d, J=8.08 Hz), 7.31 (1H, d, J=8.90 Hz), 7.71 (1H, dd, J=8.08, 2.31 Hz), 8.59 (1H, d, J=1.82 Hz).

(2) Synthesis of (E)-[6-(4-{1-ethyl-1-[4-(3-ethyl-3-hydroxy-1-pentenyl)-3-methyl-phenyl]-propyl}-2,6-dimethyl-phenyl)-3-pyridinyl]-acetic Acid A 1 N sodium hydroxide aqueous solution (0.063 mL, 0.063 mmol) was added to a solution of (E)-[6-(4-{1-ethyl-1-[4-(3-ethyl-3-hydroxy-1-pentenyl)-3-methyl-phenyl]-propyl}-2,6-dimethyl-phenyl)-3-pyridinyl]-acetic acid ethyl ester (Example 119-(1); 11.6 mg, 0.021 mmol) in methanol-tetrahydrofuran (1:1, 2 mL), and the mixture was stirred at room temperature for six hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (6.4 mg, 59%).

$^1$H-NMR (chloroform-d): 0.65 (6H, t, J=7.42 Hz), 0.92 (6H, t, J=7.26 Hz), 1.64 (4H, q, J=7.26 Hz), 1.97 (6H, s), 2.09 (4H, q, J=6.92 Hz), 2.32 (3H, s), 3.66 (2H, s), 6.02 (1H, d, J=15.82 Hz), 6.75 (1H, d, J=16.16 Hz), 6.89 (2H, s), 6.95-7.02 (2H, m), 7.21-7.32 (2H, m), 7.72 (1H, d, J=6.92 Hz), 8.62 (1H, s); MS (ESI+): 514 ([M+H]$^+$).

Example 120

Synthesis of (E)-[5-(4-{1-ethyl-1-[4-(3-ethyl-3-hydroxy-1-pentenyl)-3-methyl-phenyl]-propyl}-2,6-dimethyl-phenyl)-3-pyridinyl]-acetic Acid

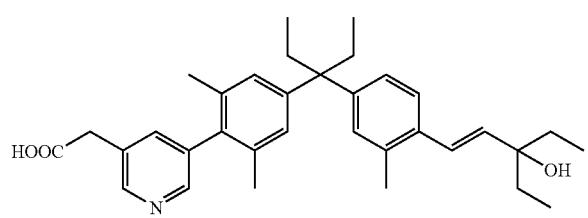

(1) Synthesis of (E)-[5-(4-{1-ethyl-1-[4-(3-ethyl-3-hydroxy-1-pentenyl)-3-methyl-phenyl]-propyl}-2,6-dimethyl-phenyl)-3-pyridinyl]-acetic Acid Methyl Ester

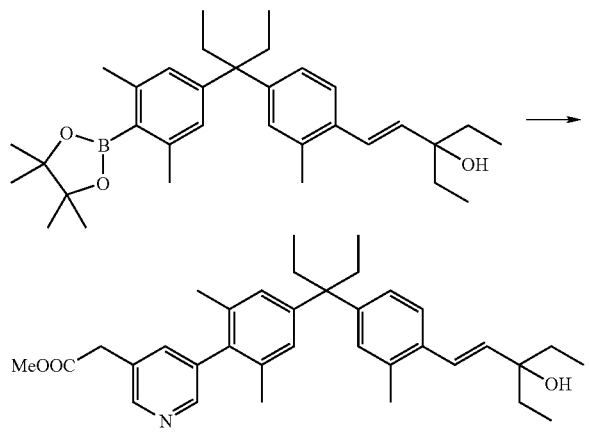

(5-Bromo-pyridin-3-yl)acetic acid methyl ester (Example 24-(2); 30 mg, 0.149 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (63 mg, 0.297 mmol) and water (0.2 mL) were added to a solution of (E)-1-(4-{1-[3,5-dimethyl-4-(4,4,5,5-tetramethyl-[1,3,2]dioxaborolan-2-yl)-phenyl]-1-ethyl-propyl}-2-methyl-phenyl)-3-ethyl-1-penten-3-ol (Example 38-(6); 50 mg, 0.099 mmol) in toluene (2 mL). After replacement with nitrogen, the mixture was stirred at 100° C. for 2.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (12.5 mg, 24%).

$^1$H-NMR (chloroform-d): 0.66 (6H, t, J=7.26 Hz), 0.93 (6H, t, J=7.25 Hz), 1.65 (4H, q, J=7.34 Hz), 1.98 (6H, s), 2.11 (4H, q, J=7.42 Hz), 2.35 (3H, s), 3.68 (2H, s), 3.72 (3H, s), 6.03 (1H, d, J=15.99 Hz), 6.76 (1H, d, J=16.00 Hz), 6.91 (2H, s), 6.97-7.01 (2H, m), 7.33 (1H, d, J=7.91 Hz), 7.49 (1H, s), 8.35 (1H, d, J=2.14 Hz), 8.47 (1H, d, J=2.14 Hz).

(2) Synthesis of (E)-[5-(4-{1-ethyl-1-[4-(3-ethyl-3-hydroxy-1-pentenyl)-3-methyl-phenyl]-propyl}-2,6-dimethyl-phenyl)-3-pyridinyl]-acetic Acid

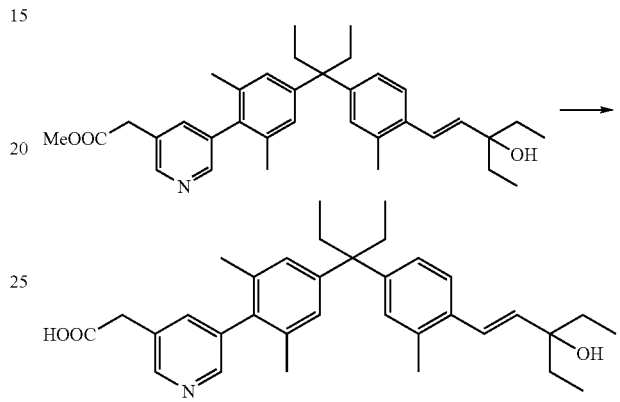

A 1 N sodium hydroxide aqueous solution (0.150 mL, 0.150 mmol) was added to a solution of (E)-[5-(4-{1-ethyl-1-[4-(3-ethyl-3-hydroxy-1-pentenyl)-3-methyl-phenyl]-propyl}-2,6-dimethyl-phenyl)-3-pyridinyl]-acetic acid methyl ester (Example 120-(1); 26.2 mg, 0.050 mmol) in methanol-tetrahydrofuran (1:1, 2 mL), and the mixture was stirred at room temperature for six hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (11.8 mg, 46%).

$^1$H-NMR (chloroform-d): 0.64 (6H, t, J=7.25 Hz), 0.92 (6H, t, J=7.25 Hz), 1.65 (4H, q, J=7.42 Hz), 1.96 (6H, s), 2.10 (4H, q, J=7.42 Hz), 2.34 (3H, s), 3.71 (2H, s), 6.02 (1H, d, J=15.99 Hz), 6.76 (1H, d, J=16.15 Hz), 6.90 (2H, s), 6.96-6.99 (2H, m), 7.32 (1H, d, J=8.58 Hz), 7.54 (1H, s), 8.35 (1H, d, J=1.65 Hz), 8.52 (1H, d, J=1.81 Hz); MS (ESI+): 514 ([M+H]$^+$).

Example 121

Synthesis of (E)-(4'-{1-ethyl-1-[4-(3-ethyl-3-hydroxy-1-pentenyl)-3-methyl-phenyl]-propyl}-3-fluoro-biphenyl-4-yl)-acetic Acid

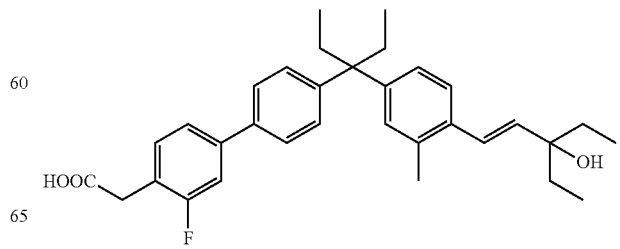

(1) Synthesis of (E)-(4'-{1-ethyl-1-[4-(3-ethyl-3-hydroxy-1-pentenyl)-3-methyl-phenyl]-propyl}-3-fluoro-biphenyl-4-yl)-acetic Acid Methyl Ester

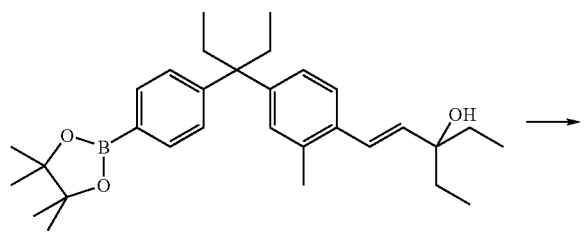

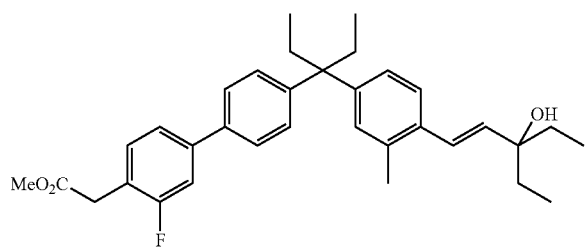

A solution of palladium acetate (3.3 mg, 0.0146 mmol), 2-dicyclohexylphosphino-2',6'-dimethoxybiphenyl (12.0 mg, 0.0293 mmol) and potassium phosphate (62.3 mg, 0.29 mmol) in water (0.050 mL) and toluene (0.200 mL) was stirred for three minutes. A solution of (4-chloro-2-fluorophenyl)acetic acid methyl ester (Example 40; 31.8 mg, 0.15 mmol) and (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 50.0 mg, 0.1049 mmol) in toluene (0.250 mL) was added, and the mixture was stirred in a nitrogen atmosphere at 100° C. for 1.5 hours. After filtration through cotton plug, the filtrate was concentrated under reduced pressure. The residue was purified by silica gel chromatography (17% ethyl acetate/hexane) to give the title compound (40.1 mg, 73%).

$^{1}$H-NMR (chloroform-d): 0.65 (t, 6H, J=7.3 Hz), 0.92 (t, 6H, J=7.5 Hz), 1.64 (q, 4H, J=7.6, Hz), 2.13 (q, 4H, J=7.3 Hz), 2.32 (s, 3H), 3.70 (s, 2H), 3.73 (s, 3H), 6.02 (d, 1H, J=16.1 Hz), 6.75 (d, 1H, J=16.1 Hz), 6.97-6.99 (m, 2H), 7.21-7.35 (m, 6H), 7.45 (d, 2H, J=8.4 Hz).

(2) Synthesis of (E)-(4'-{1-ethyl-1-[4-(3-ethyl-3-hydroxy-1-pentenyl)-3-methyl-phenyl]-propyl}-3-fluoro-biphenyl-4-yl)-acetic Acid

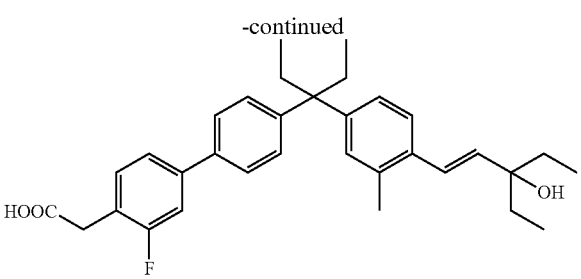

A 1 N sodium hydroxide aqueous solution (0.233 mL, 0.233 mmol) was added to a solution of (E)-(4'-{1-ethyl-1-[4-(3-ethyl-3-hydroxy-1-pentenyl)-3-methyl-phenyl-propyl}-3-fluoro-biphenyl-4-yl)acetic acid methyl ester (Example 121-(1); 40.1 mg, 0.078 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (24.3 mg, 62%).

$^{1}$H-NMR (chloroform-d): 0.65 (6H, t, J=7.26 Hz), 0.92 (6H, t, J=7.42 Hz), 1.64 (4H, q, J=7.75 Hz), 2.13 (4H, q, J=7.09 Hz), 2.32 (3H, s), 3.74 (2H, s), 6.01 (1H, d, J=15.99 Hz), 6.75 (1H, d, J=15.99 Hz), 6.96-7.00 (2H, m), 7.22-7.33 (6H, m), 7.44 (2H, d, J=8.41 Hz); MS (ESI+): 485 ([M−H$_2$O+H]$^+$).

Example 122

Synthesis of (E)-[6-(4-{1-ethyl-1-[4-(3-ethyl-3-hydroxy-1-pentenyl)-3-methyl-phenyl]-propyl}-phenyl)-3-pyridinyl]-acetic Acid

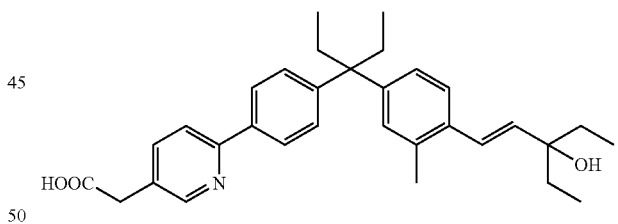

(1) Synthesis of (E)-[6-(4-{1-ethyl-1-[4-(3-ethyl-3-hydroxy-1-pentenyl)-3-methyl-phenyl]-propyl}-phenyl)-pyridin-3-yl]-acetic Acid Ethyl Ester

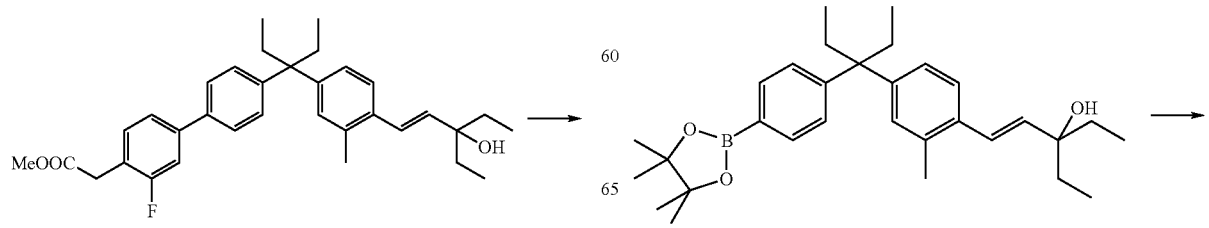

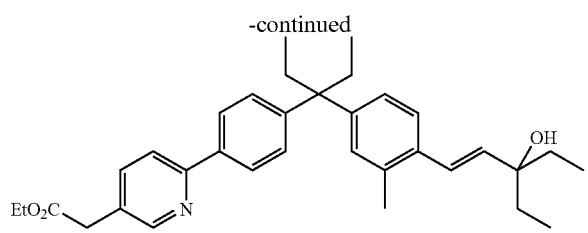

A solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 50.0 mg, 0.10 mmol), (6-chloro-pyridin-3-yl)acetic acid ethyl ester (31.4 mg, 0.15 mmol), tetrakistriphenylphosphine palladium (16.9 mg, 0.0146 mmol) and potassium phosphate (33.4 mg, 0.15 mmol) in N,N-dimethylformamide (0.30 mL) was stirred with microwave heating at 140° C. for 10 minutes. The reaction mixture was filtered through cotton plug, and the residue was purified by silica gel chromatography (30 to 40% ethyl acetate/hexane) to give the title compound (37.6 mg, 69%).

$^1$H-NMR (chloroform-d): 0.65 (t, 6H, J=7.3 Hz), 0.92 (t, 6H, J=7.3 Hz), 1.26 (t, 3H, J=7.1 Hz), 1.64 (q, 4H, J=7.5 Hz), 2.13 (q, 4H, J=7.2 Hz), 2.30 (s, 3H), 3.64 (s, 2H), 4.18 (q, 2H, J=7.1 Hz), 6.01 (d, 1H, J=16.1 Hz), 6.75 (d, 1H, J=16.1 Hz), 6.96-6.99 (m, 2H), 7.26-7.32 (m, 3H), 7.68 (s, 2H), 7.85 (d, 2H, J=8.4 Hz), 8.56 (s, 1H).

(2) Synthesis of (E)-[6-(4-{1-ethyl-1-[4-(3-ethyl-3-hydroxy-1-pentenyl)-3-methyl-phenyl]-propyl}-phenyl)-3-pyridinyl]-acetic Acid

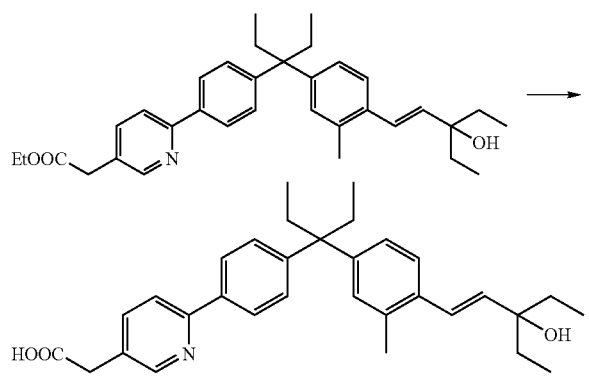

A 1 N sodium hydroxide aqueous solution (0.220 mL, 0.220 mmol) was added to a solution of (E)-[6-(4-{1-ethyl-1-[4-(3-ethyl-3-hydroxy-1-pentenyl)-3-methyl-phenyl]-propyl}-phenyl)-pyridin-3-yl]-acetic acid ethyl ester (Example 122-(1); 37.6 mg, 0.073 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (18.5 mg, 52%).

$^1$H-NMR (chloroform-d): 0.65 (6H, t, J=7.26 Hz), 0.91 (6H, t, J=7.42 Hz), 1.64 (4H, q, J=7.42 Hz), 2.13 (4H, q, J=7.42 Hz), 2.30 (3H, s), 3.69 (2H, s), 6.01 (1H, d, J=16.00 Hz), 6.74 (1H, d, J=16.15 Hz), 6.96-6.99 (2H, m), 7.26-7.32 (3H, m), 7.64-7.72 (2H, m), 7.82 (2H, d, J=8.08 Hz), 8.58 (1H, s); MS (ESI+): 486 ([M+H]$^+$).

Example 123

Synthesis of (E)-[5-(4-{1-ethyl-1-[4-(3-ethyl-3-hydroxy-1-pentenyl)-3-methyl-phenyl]-propyl}-phenyl)-3-pyridinyl]-acetic Acid

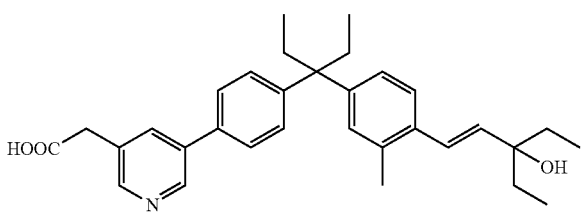

(1) Synthesis of (E)-[5-(4-{1-ethyl-1-[4-(3-ethyl-3-hydroxy-1-pentenyl)-3-methyl-phenyl]-propyl}-phenyl)-pyridin-3-yl]-acetic Acid Methyl Ester

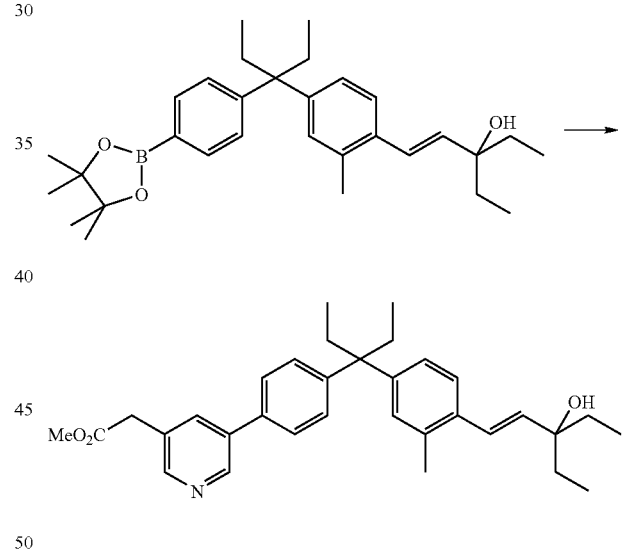

A solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 50.0 mg, 0.10 mmol), (5-bromo-pyridin-3-yl)acetic acid methyl ester (Example 24-(2); 36.2 mg, 0.15 mmol), tetrakistriphenylphosphine palladium (16.8 mg, 0.0146 mmol) and potassium phosphate (33.4 mg, 0.15 mmol) in N,N-dimethylformamide (0.30 mL) was stirred with microwave heating at 140° C. for 10 minutes. The reaction mixture was filtered through cotton plug, and the residue was purified by silica gel chromatography (40 to 50% ethyl acetate/hexane) to give the title compound (46.5 mg, 88%).

$^1$H-NMR (chloroform-d): 0.66 (t, 6H, J=7.1 Hz), 0.92 (t, 6H, J=7.5 Hz), 1.64 (q, 4H, J=7.6 Hz), 2.13 (q, 4H, J=7.3 Hz), 2.32 (s, 3H), 3.69 (s, 2H), 3.72 (s, 3H), 6.02 (d, 1H, J=16.1

Hz), 6.75 (d, 1H, J=15.7 Hz), 6.98 (brs, 2H), 7.26-7.34 (m, 3H), 7.47 (d, 2H, J=8.4 Hz), 7.81 (s, 1H), 8.46 (d, 1H, J=1.8 Hz), 8.76 (d, 1H, J=1.8 Hz).

(2) Synthesis of (E)-[5-(4-{1-ethyl-1-[4-(3-ethyl-3-hydroxy-1-pentenyl)-3-methyl-phenyl]-propyl}-phenyl)-3-pyridinyl]-acetic Acid

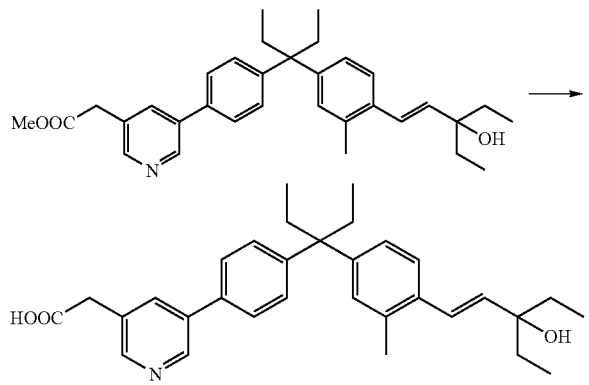

A 1 N sodium hydroxide aqueous solution (0.279 mL, 0.279 mmol) was added to a solution of (E)-[5-(4-{1-ethyl-1-[4-(3-ethyl-3-hydroxy-1-pentenyl)-3-methyl-phenyl]-propyl}-phenyl)-pyridin-3-yl]-acetic acid methyl ester (Example 123-(1); 46.5 mg, 0.093 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (29.7 mg, 66%).

$^1$H-NMR (chloroform-d): 0.65 (6H, t, J=7.25 Hz), 0.91 (6H, t, J=7.42 Hz), 1.64 (4H, q, J=7.42 Hz), 2.12 (4H, q, J=7.25 Hz), 2.30 (3H, s), 3.72 (2H, s), 6.01 (1H, d, J=16.00 Hz), 6.74 (1H, d, J=16.16 Hz), 6.94-6.97 (2H, m), 7.26-7.33 (3H, m), 7.45 (2H, d, J=8.25 Hz), 7.89 (1H, s), 8.50 (1H, s), 8.73 (1H, s); MS (ESI+): 486 ([M+H]$^+$).

Example 124

Synthesis of (4'-{1-ethyl-1-[4-((E)-3-ethyl-3-hydroxy-1-pentenyl)-3-methyl-phenyl]-propyl}-biphenyl-3-yl)-acetic Acid

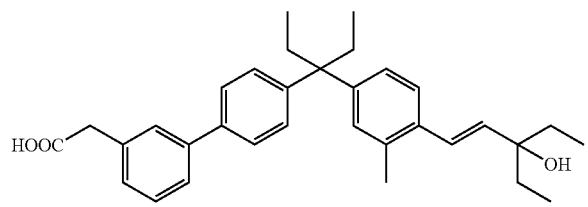

(1) Synthesis of (4'-{1-ethyl-1-[4-((E)-3-ethyl-3-hydroxy-1-pentenyl)-3-methyl-phenyl]-propyl}-biphenyl-3-yl)-acetic Acid Methyl Ester

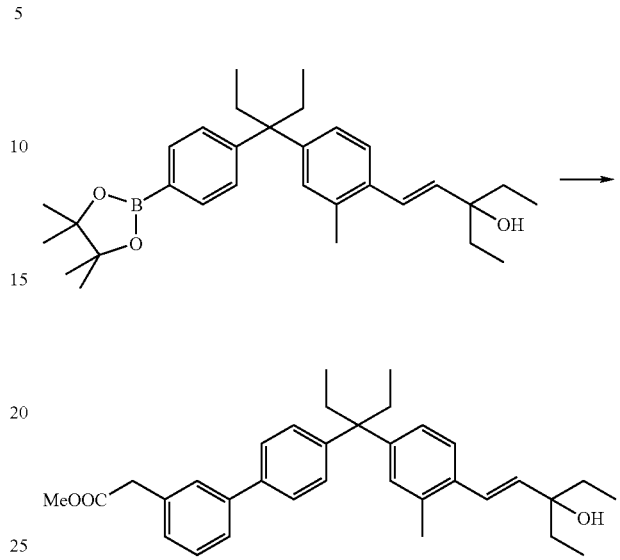

(3-Bromo-phenyl)acetic acid methyl ester (Tetrahedron Letters 44 (2003) 331-334; 26 mg, 0.114 mmol), palladium acetate (1.8 mg, 0.008 mmol), 2-dicyclohexylphosphino-2',6'-dimethoxy-1,1'-biphenyl (6.2 mg, 0.015 mmol), potassium phosphate (48 mg, 0.228 mmol) and water (0.2 mL) were added to a solution of 3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 36.3 mg, 0.076 mmol) in toluene (2 mL). After replacement with nitrogen, the mixture was stirred at 100° C. for 2.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (30.8 mg, 81%).

$^1$H-NMR (chloroform-d): 0.66 (6H, t, J=7.26 Hz), 0.92 (6H, t, J=7.42 Hz), 1.64 (4H, q, J=7.43 Hz), 2.13 (4H, q, J=7.26 Hz), 2.32 (3H, s), 3.68 (2H, s), 3.70 (3H, s), 6.02 (1H, d, J=16.00 Hz), 6.75 (1H, d, J=16.00 Hz), 6.95-7.02 (2H, m), 7.22-7.26 (3H, m), 7.30-7.40 (2H, m), 7.46-7.50 (4H, m).

(2) Synthesis of (4'-{1-ethyl-1-[4-((E)-3-ethyl-3-hydroxy-1-pentenyl)-3-methyl-phenyl]-propyl}-biphenyl-3-yl)-acetic Acid

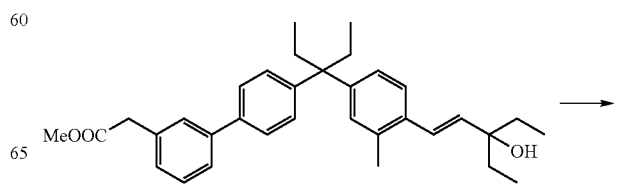

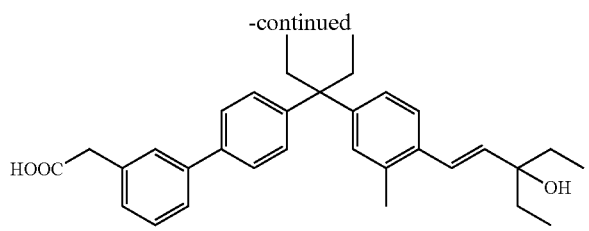

A 1 N sodium hydroxide aqueous solution (0.185 mL, 0.185 mmol) was added to a solution of (4'-{1-ethyl-1-[4-((E)-3-ethyl-3-hydroxy-1-pentenyl)-3-methyl-phenyl]-propyl}-biphenyl-3-yl)-acetic acid methyl ester (Example 124-(1); 30.8 mg, 0.062 mmol) in methanol-tetrahydrofuran (1:1, 3 mL), and the mixture was stirred at room temperature for three days. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (23.8 mg, 79%).

$^1$H-NMR (chloroform-d): 0.65 (6H, t, J=7.25 Hz), 0.92 (6H, t, J=7.42 Hz), 1.64 (4H, q, J=7.42 Hz), 2.12 (4H, q, J=7.26 Hz), 2.31 (3H, s), 3.70 (2H, s), 6.01 (1H, d, J=16.00 Hz), 6.75 (1H, d, J=16.00 Hz), 6.95-7.02 (2H, m), 7.22-7.25 (3H, m), 7.30-7.40 (2H, m), 7.44-7.50 (4H, m);

MS (ESI+): 467 ([M−H$_2$O+H]$^+$).

Example 125

Synthesis of (4'-{1-ethyl-1-[4-(3-ethyl-3-hydroxy-1-pentynyl)-3-methyl-phenyl]-propyl}-2'-methyl-biphenyl-4-yl)-acetic Acid

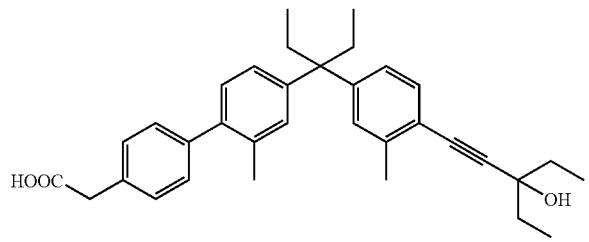

(1) Synthesis of Trifluoromethanesulfonic Acid 4-{1-ethyl-1-[4-(3-ethyl-3-hydroxy-1-pentynyl)-3-methyl-phenyl]-propyl}-2-methyl-phenyl Ester

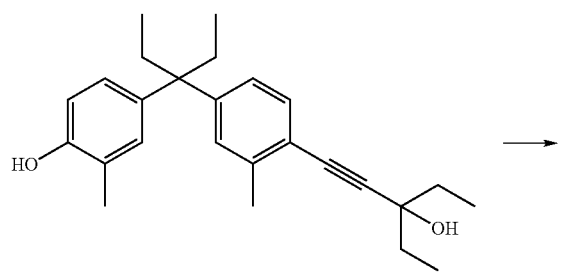

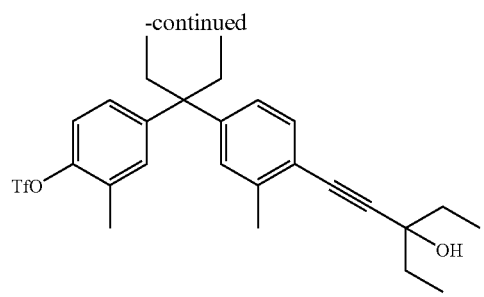

N,N-Diisopropylethylamine (0.19 mL, 1.09 mmol) was added to a solution of 4-{1-ethyl-1-[4-(3-ethyl-3-hydroxy-1-pentynyl)-3-methyl-phenyl]-propyl}-2-methyl-phenol (Example 1-(4); 165 mg, 0.436 mmol) and N-phenylbis(trifluoromethanesulfonimide) (202 mg, 0.565 mmol) in dichloromethane (2.0 mL), and the mixture was stirred at room temperature for one hour. Further, sodium bis(trimethylsilyl)amide (1 M solution in tetrahydrofuran, 0.44 mL, 0.44 mmol) was added to the reaction mixture in a nitrogen atmosphere at 0° C., and the mixture was stirred at room temperature for one hour. An ammonium chloride solution was added to the reaction mixture, followed by extraction with ethyl acetate. The extract was concentrated under reduced pressure. The residue was purified by silica gel chromatography (hexane:ethyl acetate=100:0 to 70:30) to give the target compound as a colorless oil (212 mg, 95%).

$^1$H-NMR (chloroform-d): 0.60 (t, 6H, J=7.3 Hz), 1.11 (t, 6H, J=7.5 Hz), 1.72-1.82 (m, 4H), 2.06 (q, 4H, J=7.3 Hz), 2.31 (s, 3H), 2.38 (s, 3H), 6.87-6.93 (m, 1H), 6.96 (brs, 1H), 7.03 (brs, 2H), 7.10 (d, 1H, J=8.4 Hz), 7.30 (d, 1H, J=8.1 Hz);
MS (ESI+): 493.1 ([M−H$_2$O+H]$^+$).

(2) Synthesis of 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-pentyn-3-ol

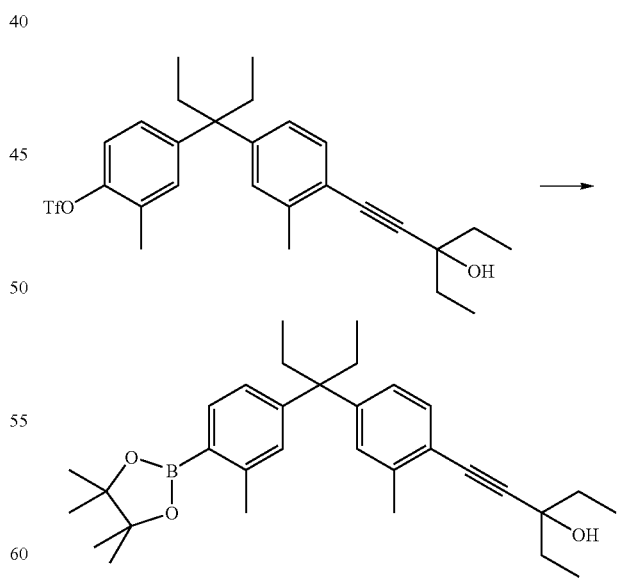

A solution of trifluoromethanesulfonic acid 4-{1-ethyl-1-[4-(3-ethyl-3-hydroxy-1-pentynyl)-3-methyl-phenyl]-propyl}-2-methyl-phenyl ester (Example 125-(1); 212 mg, 0.415 mmol), diphenylphosphinoferrocene (23.3 mg, 0.042 mmol), a [1,1'-bis(diphenylphosphino)ferrocene]dichloropalladium (II), dichloromethane complex (1:1) (33.9 mg, 0.042 mmol), potassium acetate (122 mg, 1.245 mmol) and bis(pinacolato) diboron (158 mg, 0.623 mmol) in dioxane (6 mL) was stirred at 90° C. for four hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (dichloromethane) to give the target compound as a colorless oil (175 mg, 86%).

$^1$H-NMR (chloroform-d): 0.59 (6H, t, J=7.42 Hz), 1.11 (6H, t, J=7.42 Hz), 1.33 (12H, s), 1.72-1.78 (4H, m), 2.06 (4H, q, J=7.26 Hz), 2.36 (3H, s), 2.46 (3H, s), 6.90-6.98 (4H, m), 7.26 (1H, d, J=7.75 Hz), 7.62 (1H, d, J=7.91 Hz).

(3) Synthesis of 2-(4-{1-ethyl-1-[4-(3-ethyl-3-trimethylsilanyloxy-1-pentynyl)-3-methyl-phenyl]-propyl}-2-methyl-phenyl)-4,4,5,5-tetramethyl-[1,3,2]dioxaborolane

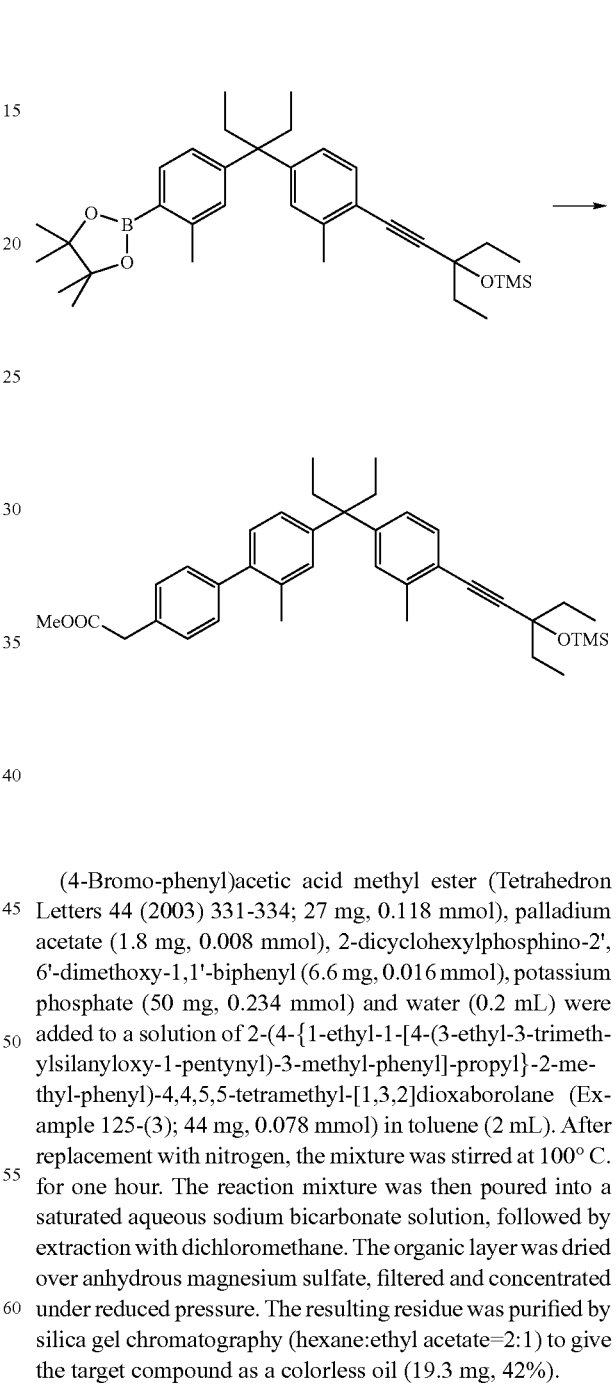

Pyridine (0.116 mL, 1.432 mmol) and trimethylsilyl triflate (0.129 mL, 0.716 mmol) were added to a solution of 3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-pentyn-3-ol (Example 125-(2); 175 mg, 0.358 mmol) in dichloromethane (5 mL) at 0° C., and the mixture was stirred for one hour. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 70:30) to give the target compound as a colorless oil (158 mg, 79%).

$^1$H-NMR (chloroform-d): 0.21 (9H, s), 0.60 (6H, t, J=7.26 Hz), 1.02 (6H, t, J=7.42 Hz), 1.33 (12H, s), 1.72 (4H, q, J=7.58 Hz), 2.07 (4H, q, J=7.42 Hz), 2.36 (3H, s), 2.48 (3H, s), 6.90-6.98 (4H, m), 7.25 (1H, d, J=8.08 Hz), 7.63 (1H, d, J=7.92 Hz).

(4) Synthesis of (4'-{1-ethyl-1-[4-(3-ethyl-3-trimethylsilanyloxy-1-pentynyl)-3-methyl-phenyl]-propyl}-2'-methyl-biphenyl-4-yl)-acetic Acid Methyl Ester (4-Bromo-phenyl)acetic acid methyl ester (Tetrahedron Letters 44 (2003) 331-334; 27 mg, 0.118 mmol), palladium acetate (1.8 mg, 0.008 mmol), 2-dicyclohexylphosphino-2',6'-dimethoxy-1,1'-biphenyl (6.6 mg, 0.016 mmol), potassium phosphate (50 mg, 0.234 mmol) and water (0.2 mL) were added to a solution of 2-(4-{1-ethyl-1-[4-(3-ethyl-3-trimethylsilanyloxy-1-pentynyl)-3-methyl-phenyl]-propyl}-2-methyl-phenyl)-4,4,5,5-tetramethyl-[1,3,2]dioxaborolane (Example 125-(3); 44 mg, 0.078 mmol) in toluene (2 mL). After replacement with nitrogen, the mixture was stirred at 100° C. for one hour. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (19.3 mg, 42%).

$^1$H-NMR (chloroform-d): 0.21 (9H, s), 0.65 (6H, t, J=7.26 Hz), 1.03 (6H, t, J=7.42 Hz), 1.73 (4H, q, J=7.42 Hz), 2.11 (4H, q, J=7.42 Hz), 2.23 (3H, s), 2.40 (3H, s), 3.67 (2H, s), 3.72 (3H, s), 6.97-7.10 (5H, m), 7.28-7.31 (5H, m).

(5) Synthesis of (4'-{1-ethyl-1-[4-(3-ethyl-3-hydroxy-1-pentynyl)-3-methyl-phenyl]-propyl}-2'-methyl-biphenyl-4-yl)-acetic Acid Methyl Ester

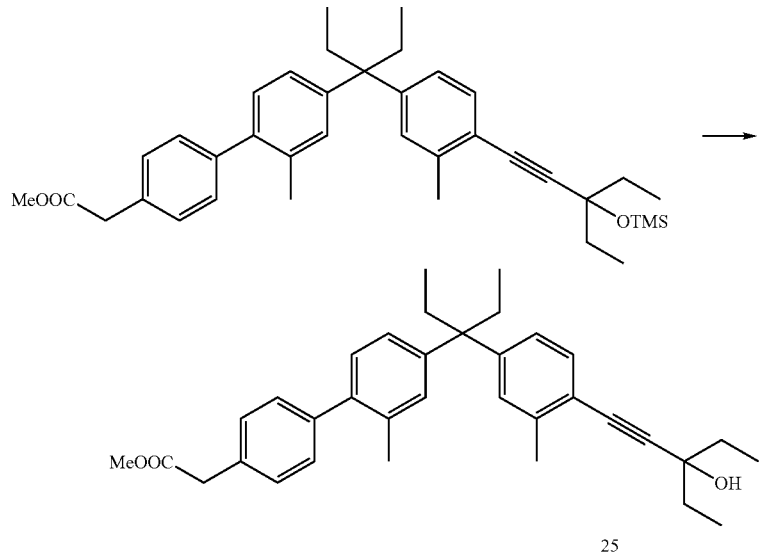

Tetrabutylammonium fluoride (1 M solution in tetrahydrofuran, 0.166 mL, 0.166 mmol) was added to a solution of (4'-{1-ethyl-1-[4-(3-ethyl-3-trimethylsilanyloxy-1-pentynyl)-3-methyl-phenyl]-propyl}-2'-methyl-biphenyl-4-yl)-acetic acid methyl ester (Example 125-(4); 19.3 mg, 0.033 mmol) in tetrahydrofuran (2 mL), and the mixture was stirred at room temperature for 30 minutes. Then, the reaction mixture was diluted with ethyl acetate and was washed with brine. The organic layer was dried over anhydrous magnesium sulfate, filtered and concentrated under reduced pressure. The resulting residue was purified by silica gel chromatography (hexane:ethyl acetate=4:1) to give the target compound as a colorless oil (11.6 mg, 69%).

$^1$H-NMR (chloroform-d): 0.64 (6H, t, J=7.26 Hz), 1.11 (6H, t, J=7.58 Hz), 1.70-1.84 (4H, m), 2.11 (4H, q, J=7.59 Hz), 2.23 (3H, s), 2.40 (3H, s), 3.67 (2H, s), 3.72 (3H, s), 6.96-7.09 (5H, m), 7.26-7.32 (5H, m).

(6) Synthesis of (4'-{1-ethyl-1-[4-(3-ethyl-3-hydroxy-1-pentynyl)-3-methyl-phenyl]-propyl}-2'-methyl-biphenyl-4-yl)-acetic Acid A 1 N sodium hydroxide aqueous solution (0.068 mL, 0.068 mmol) was added to a solution of (4'-{1-ethyl-1-[4-(3-ethyl-3-hydroxy-1-pentynyl)-3-methyl-phenyl]-propyl}-2'-methyl-biphenyl-4-yl)-acetic acid methyl ester (Example 125-(5); 11.6 mg, 0.023 mmol) in methanol-tetrahydrofuran (1:1, 2 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (8.1 mg, 71%).

$^1$H-NMR (chloroform-d): 0.64 (6H, t, J=7.25 Hz), 1.11 (6H, t, J=7.42 Hz), 1.70-1.84 (4H, m), 2.10 (4H, q, J=7.42 Hz), 2.21 (3H, s), 2.40 (3H, s), 3.70 (2H, s), 6.97-7.09 (5H, m), 7.28-7.34 (5H, m); MS (ESI+): 479 ([M–H$_2$O+H]$^+$).

Example 126

Synthesis of (4'-{1-ethyl-1-[4-((E)-3-ethyl-3-hydroxy-1-pentenyl)-3-methyl-phenyl]-propyl}-biphenyl-2-yl)-acetic Acid

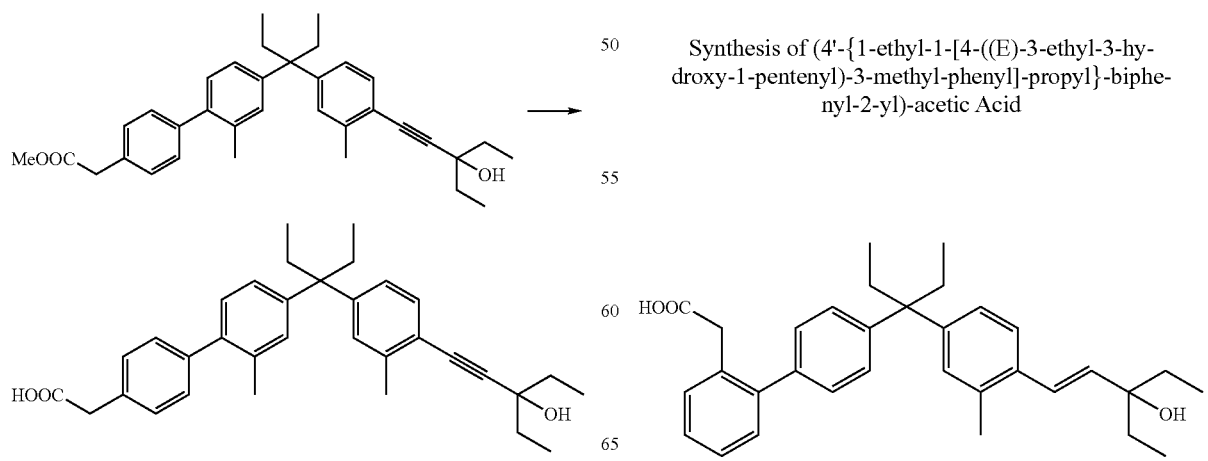

(1) Synthesis of (2-bromo-phenyl)-acetic Acid Methyl Ester

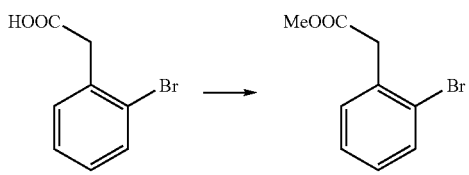

Trimethylsilyldiazomethane (2 M solution in diethyl ether, 0.349 mL, 0.698 mmol) was added to a solution of (2-bromophenyl)acetic acid (50 mg, 0.233 mmol) in methanol (0.4 mL) and toluene (2 mL), and the mixture was stirred at room temperature for five minutes. Acetic acid was added to the reaction mixture to terminate the reaction, and then the mixture was concentrated under reduced pressure to give the target compound as a colorless oil (53 mg, 99%).

$^1$H-NMR (chloroform-d): 3.72 (3H, s), 3.80 (2H, s), 7.11-7.18 (1H, m), 7.26-7.29 (2H, m), 7.57 (1H, d, J=8.05 Hz).

(2) Synthesis of (4'-{1-ethyl-1-[4-((E)-3-ethyl-3-hydroxy-1-pentenyl)-3-methyl-phenyl]-propyl}-biphenyl-2-yl)-acetic Acid Methyl Ester

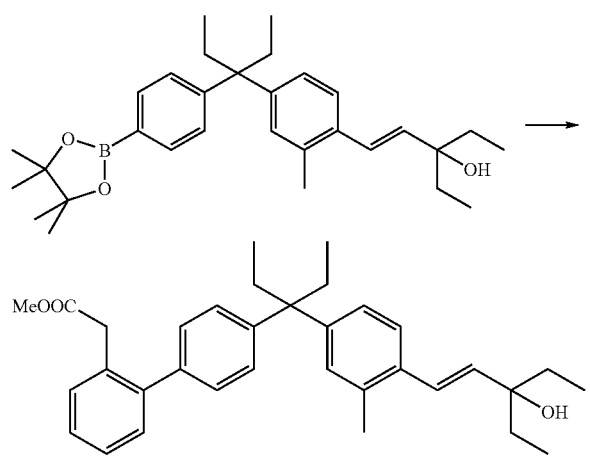

(2-Bromo-phenyl)acetic acid methyl ester (Example 126-(1); 35 mg, 0.152 mmol), palladium acetate (2.2 mg, 0.010 mmol), 2-dicyclohexylphosphino-2',6'-dimethoxy-1,1'-biphenyl (8.2 mg, 0.016 mmol), potassium phosphate (64 mg, 0.303 mmol) and water (0.2 mL) were added to a solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 48.3 mg, 0.101 mmol) in toluene (3 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (26.6 mg, 53%).

$^1$H-NMR (chloroform-d): 0.66 (6H, t, J=7.09 Hz), 0.92 (6H, t, J=7.42 Hz), 1.64 (4H, q, J=7.59 Hz), 2.13 (4H, q, J=7.58 Hz), 2.33 (3H, s), 3.58 (3H, s), 3.63 (2H, s), 6.02 (1H, d, J=15.83 Hz), 6.75 (1H, d, J=16.15 Hz), 6.95-7.00 (2H, m), 7.18-7.34 (9H, m).

(3) Synthesis of (4'-{1-ethyl-1-[4-((E)-3-ethyl-3-hydroxy-1-pentenyl)-3-methyl-phenyl]-propyl}-biphenyl-2-yl)-acetic Acid

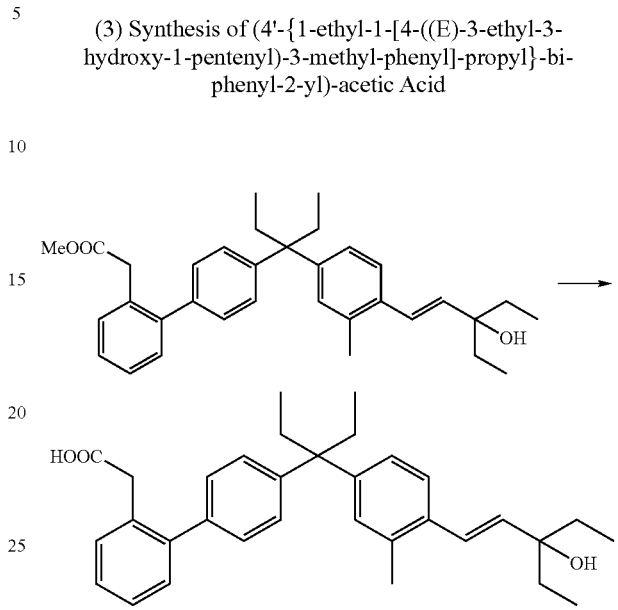

A 1 N sodium hydroxide aqueous solution (0.160 mL, 0.160 mmol) was added to a solution of (4'-{1-ethyl-1-[4-((E)-3-ethyl-3-hydroxy-1-pentenyl)-3-methyl-phenyl]-propyl}-biphenyl-2-yl)-acetic acid methyl ester (Example 126-(2); 26.6 mg, 0.053 mmol) in methanol-tetrahydrofuran (1:1, 3 mL), and the mixture was stirred at 60° C. for 2.5 hours. Then, the reaction mixture was concentrated under reduced pressure. The resulting residue was purified by silica gel chromatography (ethyl acetate:methanol:water=4:1:0.3) to give the target compound as a colorless oil (19.2 mg, 75%).

$^1$H-NMR (chloroform-d): 0.65 (6H, t, J=7.25 Hz), 0.91 (6H, t, J=7.58 Hz), 1.64 (4H, q, J=7.58 Hz), 2.12 (4H, q, J=7.25 Hz), 2.32 (3H, s), 3.64 (2H, s), 6.01 (1H, d, J=15.99 Hz), 6.75 (1H, d, J=16.16 Hz), 6.96-6.99 (2H, m), 7.13-7.23 (4H, m), 7.28-7.33 (5H, m); MS (ESI+): 467 ([M−H$_2$O+H]$^+$).

Example 127

Synthesis of (4'-{1-ethyl-1-[4-((E)-3-ethyl-3-hydroxy-1-pentenyl)-3-methyl-phenyl]-propyl}-5-fluoro-biphenyl-3-yl)-acetic Acid

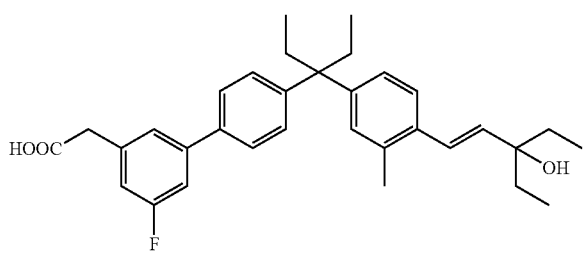

(1) Synthesis of (3-chloro-5-fluoro-phenyl)-acetic Acid Methyl Ester

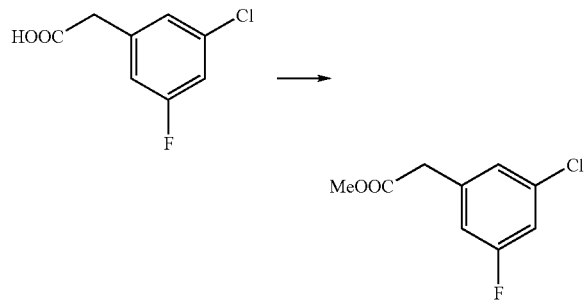

Trimethylsilyldiazomethane (2 M solution in diethyl ether, 0.199 mL, 0.398 mmol) was added to a solution of (3-chloro-5-fluoro-phenyl)acetic acid (50 mg, 0.265 mmol) in methanol (0.5 mL) and toluene (2 mL), and the mixture was stirred at room temperature for 10 minutes. Acetic acid was added to the reaction mixture to terminate the reaction, and then the mixture was concentrated under reduced pressure to give the target compound as a colorless oil (53 mg, 99%).

$^1$H-NMR (chloroform-d): 3.59 (2H, s), 3.72 (3H, s), 6.90-6.94 (1H, m), 6.99-7.02 (1H, m), 7.08 (1H, s).

(2) Synthesis of (4'-{1-ethyl-1-[4-((E)-3-ethyl-3-hydroxy-1-pentenyl)-3-methyl-phenyl]-propyl}-5-fluoro-biphenyl-3-yl)-acetic Acid Methyl Ester

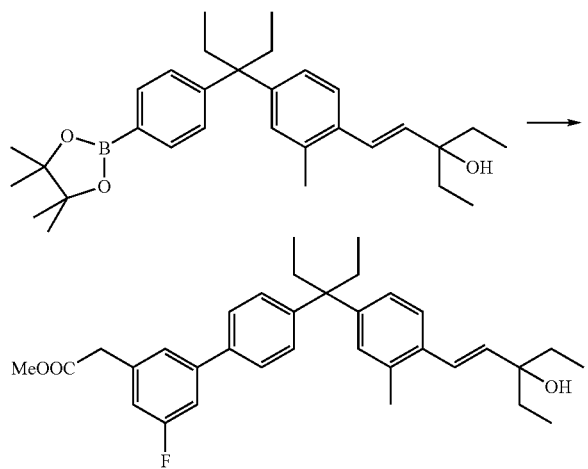

(3-Chloro-5-fluoro-phenyl)acetic acid methyl ester (Example 127-(1); 35 mg, 0.173 mmol), palladium acetate (2.7 mg, 0.012 mmol), 2-dicyclohexylphosphino-2',6'-dimethoxy-1,1'-biphenyl (9.4 mg, 0.023 mmol), potassium phosphate (73 mg, 0.345 mmol) and water (0.2 mL) were added to a solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 55 mg, 0.115 mmol) in toluene (2 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (57.7 mg, 97%).

$^1$H-NMR (chloroform-d): 0.65 (6H, t, J=7.42 Hz), 0.92 (6H, t, J=7.42 Hz), 1.64 (4H, q, J=7.58 Hz), 2.13 (4H, q, J=7.42 Hz), 2.32 (3H, s), 3.66 (2H, s), 3.71 (3H, s), 6.01 (1H, d, J=15.99 Hz), 6.75 (1H, d, J=15.99 Hz), 6.91-7.00 (3H, m), 7.17-7.33 (5H, m), 7.44 (2H, d, J=8.41 Hz).

(3) Synthesis of (4'-{1-ethyl-1-[4-((E)-3-ethyl-3-hydroxy-1-pentenyl)-3-methyl-phenyl]-propyl}-5-fluoro-biphenyl-3-yl)-acetic Acid

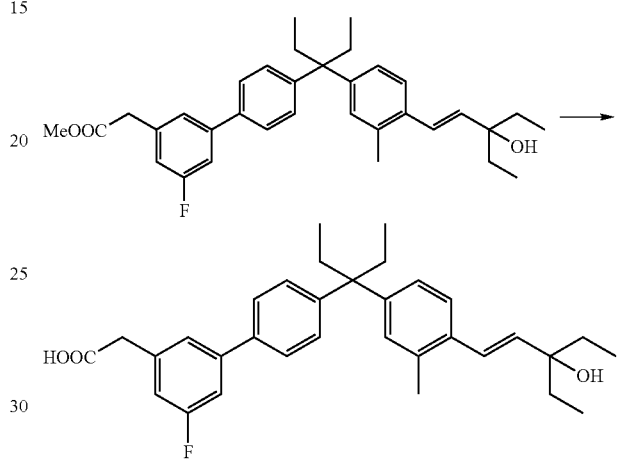

A 1 N sodium hydroxide aqueous solution (0.335 mL, 0.335 mmol) was added to a solution of (4'-{1-ethyl-1-[4-((E)-3-ethyl-3-hydroxy-1-pentenyl)-3-methyl-phenyl]-propyl}-5-fluoro-biphenyl-3-yl)-acetic acid methyl ester (Example 127-(2); 57.7 mg, 0.112 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (38.5 mg, 68%).

$^1$H-NMR (chloroform-d): 0.65 (6H, t, J=7.26 Hz), 0.92 (6H, t, J=7.42 Hz), 1.64 (4H, q, J=7.75 Hz), 2.12 (4H, q, J=7.25 Hz), 2.31 (3H, s), 3.69 (2H, s), 6.01 (1H, d, J=15.99 Hz), 6.75 (1H, d, J=16.00 Hz), 6.95-6.99 (3H, m), 7.17-7.34 (5H, m), 7.44 (2H, d, J=8.25 Hz); MS (ESI+): 485 ([M−H$_2$O+H]$^+$).

Example 128

Synthesis of (4'-{1-ethyl-1-[4-(1-hydroxy-cycloheptylethynyl)-3-methyl-phenyl]-propyl}-2'-methyl-biphenyl-4-yl)-acetic Acid

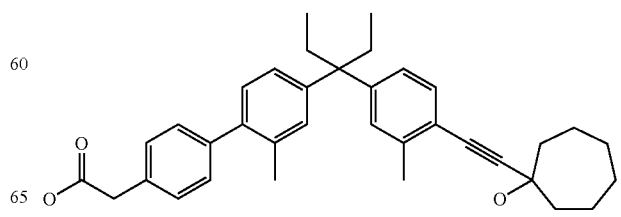

(1) Synthesis of 1-{4-[1-ethyl-1-(4-hydroxy-3-methyl-phenyl)-propyl]-2-methyl-phenylethynyl}-cycloheptanol

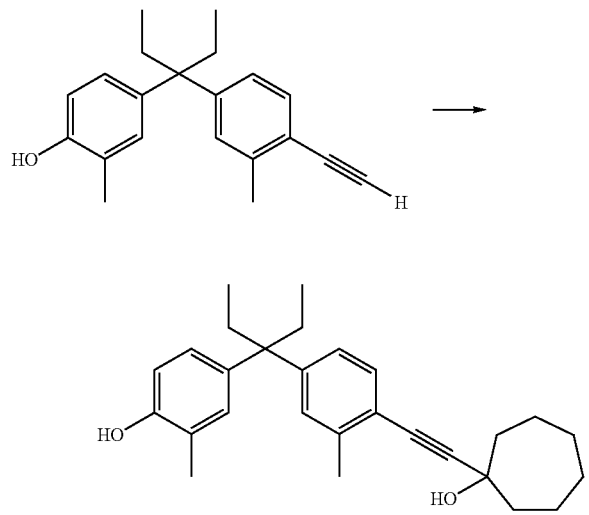

n-Butyllithium (1.59 M solution in hexane, 5.4 mL, 8.59 mmol) was added to a solution of 4-[1-ethyl-1-(4-ethynyl-3-methyl-phenyl)-propyl]-2-methyl-phenol (Example 1-(3); 1.00 g, 3.42 mmol) in tetrahydrofuran (15 mL) in a nitrogen atmosphere at 0° C., and the mixture was stirred for 15 minutes. Then, cycloheptanone (0.81 mL, 6.87 mmol) was added to the reaction mixture, which was stirred at 0° C. for one hour, heated to room temperature and further stirred for one hour. The reaction mixture was then poured into a saturated aqueous ammonium chloride solution, followed by extraction with ethyl acetate. The organic layer was concentrated under reduced pressure. The resulting residue was purified by silica gel chromatography (hexane:ethyl acetate=90:10 to 50:50) to give the target compound as a colorless oil (829 mg, 60%).

$^1$H-NMR (chloroform-d): 0.59 (t, 6H, J=7.3 Hz), 1.59-1.74 (m, 7H), 1.87-1.96 (m, 3H), 2.03 (dt, 5H, J=14.6, 3.6 Hz), 2.08-2.16 (m, 2H), 2.18 (s, 3H), 2.38 (s, 3H), 4.54 (s, 1H), 6.65 (d, 1H, J=8.4 Hz), 6.82-6.86 (m, 2H), 6.94 (dd, 1H, J=8.4, 4.2 Hz), 7.00 (brs, 1H), 7.28 (brs, 1H); MS (ESI+): 387.2 ([M–H$_2$O+H]$^+$); MS (ESI–): 403.4 ([M–H]$^-$).

(2) Synthesis of 2-(4-{1-ethyl-1-[3-methyl-4-(1-trimethylsilanyloxy-cycloheptylethynyl)-phenyl]-propyl}-2-methyl-phenyl)-4,4,5,5-tetramethyl-[1,3,2]dioxaborolane

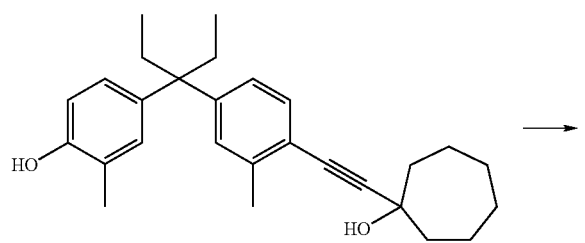

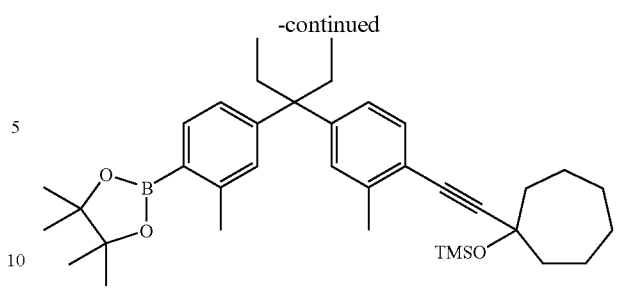

Sodium bis(trimethylsilyl)amide (1 M solution in tetrahydrofuran, 2.5 mL, 2.5 mmol) was added to a solution of 1-{4-[1-ethyl-1-(4-hydroxy-3-methyl-phenyl)-propyl]-2-methyl-phenylethynyl}-cycloheptanol (Example 128-(1); 421 mg, 1.11 mmol) and N-phenylbis(trifluoromethanesulfonimide) (516 mg, 1.44 mmol) in dichloromethane (5.0 mL) in a nitrogen atmosphere at 0° C., and the mixture was stirred at the same temperature for 10 minutes. An ammonium chloride solution was added to the reaction mixture, followed by extraction with ethyl acetate. The extract was concentrated under reduced pressure. The residue was crudely purified by silica gel chromatography (hexane:ethyl acetate=98:2 to 70:30) to give a mixture containing trifluoromethanesulfonic acid 4-{1-ethyl-1-[3-methyl-4-(1-trimethylsilanyloxy-cycloheptylethynyl)-phenyl]-propyl}-2-methyl-phenyl ester (592 mg). The mixture was used in the following reaction without further purification.

A solution of the mixture containing trifluoromethanesulfonic acid 4-{1-ethyl-1-[3-methyl-4-(1-trimethylsilanyloxy-cycloheptylethynyl)-phenyl]-propyl}-2-methyl-phenyl ester (592 mg), a [1,1'-bis(diphenylphosphino)ferrocene]dichloropalladium (II), dichloromethane complex (1:1) (45.0 mg, 0.0551 mmol), potassium acetate (324 mg, 3.30 mmol) and bis(pinacolato)diboron (335 mg, 1.32 mmol) in dimethyl sulfoxide (5.0 mL) was stirred in a nitrogen atmosphere at an external temperature of 100° C. for four hours and 10 minutes. Water was added to the reaction mixture, followed by extraction with ethyl acetate. The extract was concentrated under reduced pressure. The residue was crudely purified by silica gel chromatography (hexane:ethyl acetate=95:5 to 70:30). However, since the reaction was not completed, heating (80 minutes), extraction and silica gel chromatography were carried out similarly again to give a mixture containing 1-(4-{1-ethyl-1-[3-methyl-4-(4,4,5,5-tetramethyl-[1,3,2]dioxaborolan-2-yl)-phenyl]-propyl}-2-methyl-phenylethynyl)-cycloheptanol (529 mg). The mixture was used in the following reaction without further purification.

Trifluoromethanesulfonic acid trimethylsilyl ester (0.37 mL, 2.04 mmol) was added to a solution of the mixture containing 1-(4-{1-ethyl-1-[3-methyl-4-(4,4,5,5-tetramethyl-[1,3,2]dioxaborolan-2-yl)-phenyl]-propyl}-2-methyl-phenylethynyl)-cycloheptanol (529 mg) and pyridine (0.42 mL, 5.19 mmol) in dichloromethane (4.0 mL) at 0° C., and the mixture was stirred at the same temperature for 90 minutes. An ammonium chloride solution was added to the reaction mixture, followed by extraction with ethyl acetate. The extract was concentrated under reduced pressure. The residue was purified by silica gel chromatography (hexane:ethyl acetate=100:0 to 80:20) to give the target compound as a colorless oil (183 mg, 28% in three steps).

$^1$H-NMR (chloroform-d): 0.21 (s, 9H), 0.59 (t, 6H, J=7.3 Hz), 1.33 (s, 12H), 2.06 (q, 4H, J=7.3 Hz), 2.37 (s, 3H), 2.47 (s, 3H), 6.90-7.00 (m, 4H), 7.23-7.25 (m, 1H), 7.63 (d, 1H, J=8.1 Hz); MS (ESI+): 497.2 ([M–TMSOH+H]$^+$).

(3) Synthesis of [5-(4-{1-ethyl-1-[3-methyl-4-(1-trimethylsilanyloxy-cycloheptylethynyl)-phenyl]-propyl}-2-methyl-phenyl)-pyridin-3-yl]-acetic Acid Methyl Ester

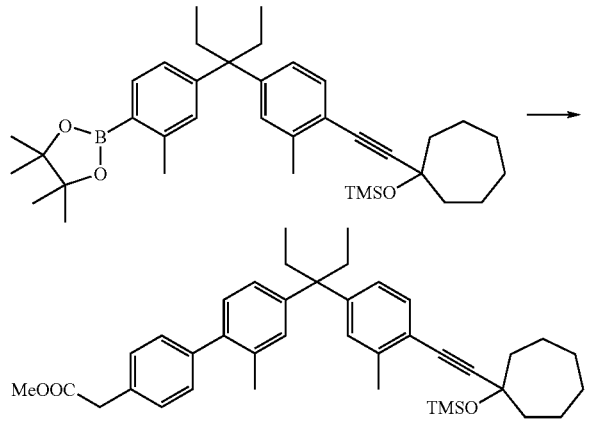

N,N-Dimethylformamide (2.0 mL) was added to 2-(4-{1-ethyl-1-[3-methyl-4-(1-trimethylsilanyloxy-cycloheptylethynyl)-phenyl]-propyl}-2-methyl-phenyl)-4,4,5,5-tetramethyl-[1,3,2]dioxaborolane (Example 128-(2); 64.4 mg, 0.110 mmol), (4-bromo-phenyl)-acetic acid methyl ester (30.2 mg, 0.132 mmol), tetrakis(triphenylphosphine)palladium (0) (12.7 mg, 0.0110 mmol) and potassium phosphate (35.0 mg, 0.165 mmol), and the mixture was stirred with microwave heating at 140° C. for seven minutes in a nitrogen atmosphere. An ammonium chloride solution was added to the reaction mixture, followed by extraction with ethyl acetate. The organic layer was concentrated under reduced pressure. The residue was purified by silica gel chromatography (hexane:ethyl acetate=100:0 to 85:15) to give the target compound as a colorless oil (27.0 mg, 46%).

$^1$H-NMR (chloroform-d): 0.22 (s, 9H), 0.65 (t, 6H, J=7.3 Hz), 2.10 (q, 4H, J=7.3 Hz), 2.23 (s, 3H), 2.41 (s, 3H), 3.68 (d, 2H, J=10.6 Hz), 3.72 (s, 3H), 6.95-7.18 (m, 6H), 7.28-7.29 (m, 4H); MS (ESI+): 519.3 ([M-TMSOH+H]$^+$).

(4) Synthesis of (4'-{1-ethyl-1-[4-(1-hydroxy-cycloheptylethynyl)-3-methyl-phenyl]-propyl}-2'-methyl-biphenyl-4-yl)-acetic Acid

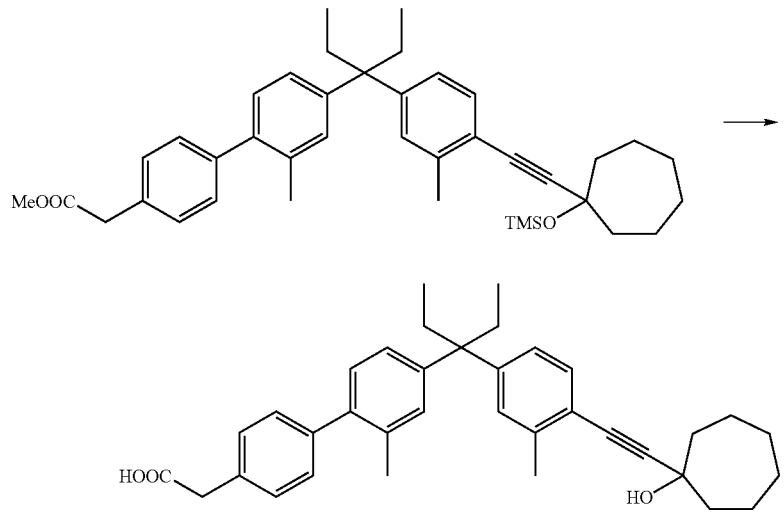

A 1 M solution of tetrabutylammonium fluoride in tetrahydrofuran (1.0 mL, 1.0 mmol) was added to [5-(4-{1-ethyl-1-[3-methyl-4-(1-trimethylsilanyloxy-cycloheptylethynyl)-phenyl]-propyl}-2-methyl-phenyl)-pyridin-3-yl]-acetic acid methyl ester (Example 128-(3); 27.0 mg, 0.0503 mmol), and the mixture was stirred with microwave heating at 100° C. for five minutes. An ammonium chloride solution was added to the reaction mixture, followed by extraction with ethyl acetate. The organic layer was concentrated under reduced pressure. The residue was purified by high performance liquid chromatography (Shiseido CAPCELL PAK C$_{18}$ MGII, 20 mm I.D.×50 mm, methanol:20 mM ammonium acetate solution=55:45 to 100:0, 20 mL/min). A sodium bicarbonate solution was added to the eluate, followed by extraction with ethyl acetate. The organic layer was concentrated under reduced pressure to give the target compound as a colorless oil (11.4 mg, 20% in two steps).

$^1$H-NMR (methanol-d$_4$): 0.64 (t, 6H, J=7.3 Hz), 1.59-1.75 (m, 8H), 1.82-1.94 (m, 2H), 2.05-2.20 (m, 6H), 2.07 (s, 3H), 2.38 (s, 3H), 3.62 (s, 2H), 6.96-7.09 (m, 5H), 7.22-7.27 (m, 3H), 7.28-7.33 (m, 2H); MS (ESI+): 505.2 ([M−H$_2$O+H]$^+$); MS (ESI−): 521.4 ([M−H]$^−$).

Example 129

Synthesis of [4'-(1-ethyl-1-{4-[2-(1-hydroxy-cycloheptyl)-(E)-vinyl]-3-methyl-phenyl}-propyl)-2'-methyl-biphenyl-4-yl]-acetic Acid

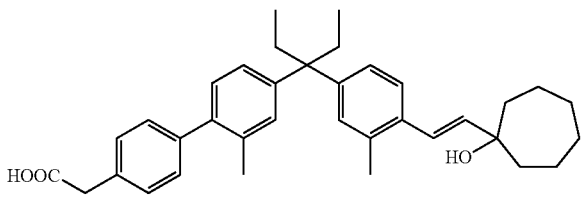

(1) Synthesis of 1-(2-{4-[1-ethyl-1-(4-hydroxy-3-methyl-phenyl)-propyl]-2-methyl-phenyl}-(E)-vinyl)-cycloheptanol

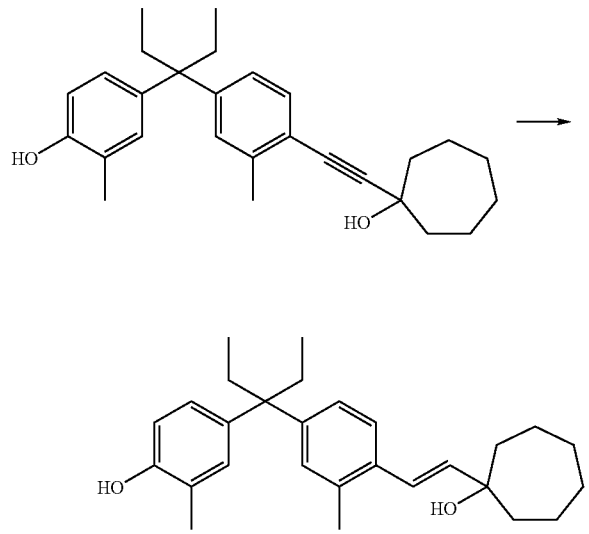

Sodium bis(2-methoxyethoxy)aluminum hydride (65 wt % solution in toluene, 1.4 mL, 4.66 mmol) was added to a solution of 1-{4-[1-ethyl-1-(4-hydroxy-3-methyl-phenyl)-propyl]-2-methyl-phenylethynyl}-cycloheptanol (Example 128-(1); 624 mg, 1.54 mmol) in tetrahydrofuran (7.5 mL) in a nitrogen atmosphere at 0° C., and the mixture was stirred at 0° C. for two hours. Brine and ethyl acetate were added to the reaction mixture, which was stirred for 20 minutes. Then, celite was added and the mixture was further stirred for 30 minutes. The mixture was dried over anhydrous magnesium sulfate, filtered and concentrated under reduced pressure. The resulting residue was purified by silica gel chromatography (hexane:ethyl acetate=90:10 to 50:50) to give the target compound as a colorless oil (629 mg, 100%).

$^1$H-NMR (chloroform-d): 0.60 (t, 6H, J=7.3 Hz), 1.45-1.90 (m, 7H), 2.00-2.11 (m, 3H), 2.04 (q, 4H, J=7.3 Hz), 2.19 (s, 3H), 2.30 (s, 3H), 3.40 (s, 1H), 3.60 (t, 1H, J=4.8 Hz), 4.23 (t, 1H, J=4.8 Hz), 4.53-4.58 (m, 1H), 6.25 (d, 1H, J=16.1 Hz), 6.65 (d, 1H, J=8.4 Hz), 6.78 (d, 1H, J=16.1 Hz), 6.86-6.96 (m, 4H), 7.32 (d, 1H, J=8.8 Hz); MS (ESI+): 389.2 ([M−H$_2$O+H]$^+$); MS (ESI−): 405.3 ([M−H]$^−$).

(2) Synthesis of Trifluoromethanesulfonic Acid 4-(1-ethyl-1-{4-[2-(1-hydroxy-cycloheptyl)-(E)-vinyl]-3-methyl-phenyl}-propyl)-2-methyl-phenyl Ester

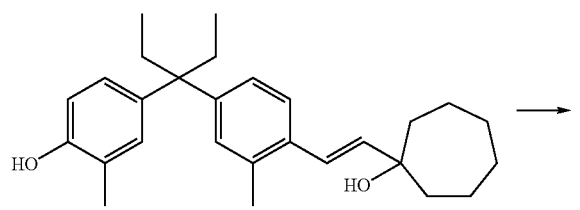

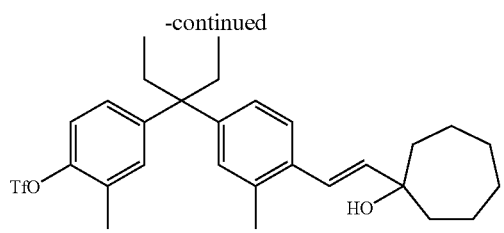

Sodium bis(trimethylsilyl)amide (1 M solution in tetrahydrofuran, 2.4 mL, 2.4 mmol) was added to a solution of 1-(2-{4-[1-ethyl-1-(4-hydroxy-3-methyl-phenyl)-propyl]-2-methyl-phenyl}-(E)-vinyl)-cycloheptanol (Example 129-(1); 434 mg, 1.07 mmol) and N-phenylbis(trifluoromethanesulfonimide) (497 mg, 1.39 mmol) in dichloromethane (5.0 mL) in a nitrogen atmosphere at 0° C., and the mixture was stirred at the same temperature for two hours and 30 minutes. An ammonium chloride solution was added to the reaction mixture, followed by extraction with ethyl acetate. The extract was concentrated under reduced pressure. The residue was purified by silica gel chromatography (hexane:ethyl acetate=100:0 to 80:20) to give the target compound as a brown oil (258 mg, 45%).

$^1$H-NMR (chloroform-d): 0.61 (t, 6H, J=7.3 Hz), 1.62-1.90 (m, 4H), 2.06 (q, 3H, J=7.3 Hz), 2.31 (s, 6H), 6.26 (d, 1H, J=15.7 Hz), 6.78 (d, 1H, J=15.7 Hz), 6.91 (brs, 1H), 6.98-7.45 (m, 5H); MS (ESI+): 512.1 ([M−H$_2$O+H]$^+$).

(3) Synthesis of 1-[2-(4-{1-ethyl-1-[3-methyl-4-(4,4,5,5-tetramethyl-[1,3,2]dioxaborolan-2-yl)-phenyl]-propyl}-2-methyl-phenyl)-(E)-vinyl]-cycloheptanol

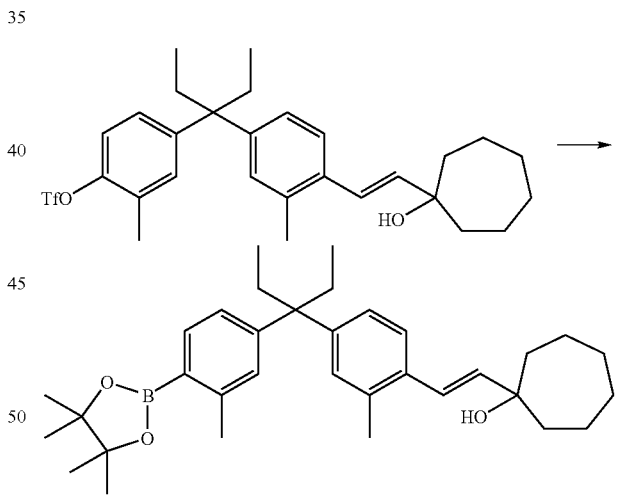

A solution of trifluoromethanesulfonic acid 4-(1-ethyl-1-{4-[2-(1-hydroxy-cycloheptyl)-(E)-vinyl]-3-methyl-phenyl}-propyl)-2-methyl-phenyl ester (Example 129-(2); 258 mg, 0.479 mmol), a [1,1'-bis(diphenylphosphino)ferrocene]dichloropalladium (II), dichloromethane complex (1:1) (20.0 mg, 0.0245 mmol), potassium acetate (141 mg, 1.44 mmol), and bis(pinacolato)diboron (146 mg, 0.575 mmol) in dimethyl sulfoxide (4.0 mL) was stirred in a nitrogen atmosphere at an external temperature of 100° C. for two hours and 15 minutes. An ammonium chloride solution was added to the reaction mixture, followed by extraction with ethyl acetate. The extract was concentrated under reduced pressure. The residue was crudely purified by silica gel chromatography (hexane:ethyl acetate=100:0 to 75:25). However, since the reaction was not completed, heating was carried out similarly again for two hours and 30 minutes and extraction and silica gel chromatography were carried out similarly to give the target compound as a colorless oil (104 mg, 42%).

$^1$H-NMR (chloroform-d): 0.60 (t, 6H, J=7.3 Hz), 1.33 (s, 12H), 1.51-1.89 (m, 12H), 2.07 (q, 4H, J=7.3 Hz), 2.29 (s, 3H), 2.47 (s, 3H), 6.24 (d, 1H, J=16.0 Hz), 6.77 (d, 1H, J=16.0 Hz), 6.90-7.03 (m, 4H), 7.37-7.43 (m, 1H), 7.63 (d, 1H, J=8.1 Hz); MS (ESI+): 499.3 ([M−H$_2$O+H]$^+$).

(4) Synthesis of [4'-(1-ethyl-1-{4-[2-(1-hydroxy-cycloheptyl)-(E)-vinyl]-3-methyl-phenyl}-propyl)-2'-methyl-biphenyl-4-yl]-acetic Acid

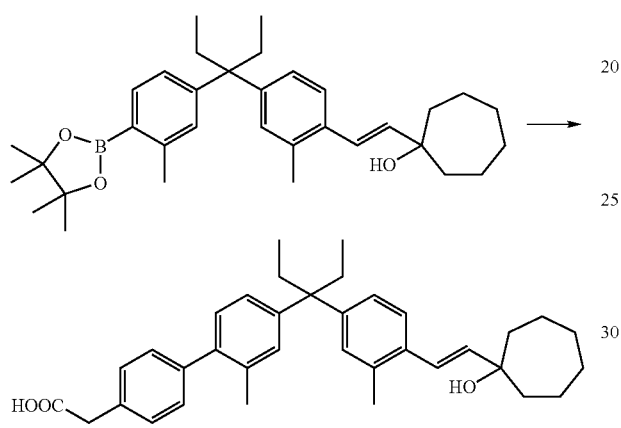

N,N-Dimethylformamide (0.60 mL) was added to 1-[2-(4-{1-ethyl-1-[3-methyl-4-(4,4,5,5-tetramethyl-[1,3,2]dioxaborolan-2-yl)-phenyl]-propyl}-2-methyl-phenyl)-(E)-vinyl]-cycloheptanol (Example 129-(3); 40.6 mg, 0.0786 mmol), (4-bromo-phenyl)-acetic acid methyl ester (23.4 mg, 0.102 mmol), tetrakis(triphenylphosphine)palladium (0) (9.1 mg, 0.00787 mmol) and potassium phosphate (41.7 mg, 0.196 mmol), and the mixture was stirred with microwave heating at 150° C. for five minutes in a nitrogen atmosphere. Water was added to the reaction mixture, followed by extraction with ethyl acetate and washing with brine. The organic layer was dried over anhydrous magnesium sulfate, filtered and concentrated under reduced pressure. However, since the reaction was not completed, microwave heating was carried out similarly again at 140° C. for 10 minutes and extraction and silica gel chromatography were carried out similarly. The residue was purified by silica gel chromatography (hexane:ethyl acetate=90:10 to 60:40) to give a mixture containing [4'-(1-ethyl-1-{4-[2-(1-hydroxy-cycloheptyl)-(E)-vinyl]-3-methyl-phenyl}-propyl)-2'-methyl-biphenyl-4-yl]-acetic acid methyl ester as a colorless oil (14.0 mg).

A 2 N sodium hydroxide aqueous solution (0.50 mL, 1.0 mmol) was added to a solution of the mixture containing [4'-(1-ethyl-1-{4-[2-(1-hydroxy-cycloheptyl)-(E)-vinyl]-3-methyl-phenyl}-propyl)-2'-methyl-biphenyl-4-yl]-acetic acid methyl ester (14.0 mg) in methanol (1.0 mL), and the mixture was stirred with microwave heating at 100° C. for five minutes. An ammonium chloride solution was added to the reaction mixture, followed by extraction with ethyl acetate and washing with brine. The organic layer was dried over anhydrous magnesium sulfate, filtered and concentrated under reduced pressure. The residue was purified by silica gel chromatography (ethyl acetate:methanol=100:0 to 90:10) to give the target compound as a colorless oil (8.0 mg, 19% in two steps).

$^1$H-NMR (methanol-d$_4$): 0.64 (t, 6H, J=7.3 Hz), 1.45-1.90 (m, 12H), 2.14 (q, 4H, J=7.3 Hz), 2.19 (s, 3H), 2.29 (s, 3H), 3.61 (s, 2H), 6.21 (d, 1H, J=15.9 Hz), 6.78 (d, 1H, J=15.9 Hz), 6.94-7.09 (m, 5H), 7.24 (d, 2H, J=8.2 Hz), 7.28-7.33 (m, 1H), 7.31 (d, 2H, J=8.2 Hz); MS (ESI+): 507.2 ([M−H$_2$O+H]$^+$); MS (ESI−): 523.4 ([M−H]$^−$).

Example 130

Synthesis of (4'-{1-ethyl-1-[4-(4-hydroxy-tetrahydro-pyran-4-ylethynyl)-3-methyl-phenyl]-propyl}-2'-methyl-biphenyl-4-yl)-acetic Acid

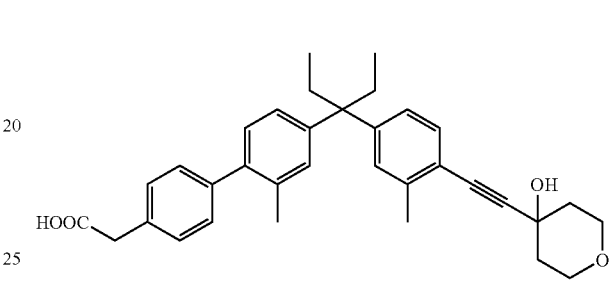

(1) Synthesis of 4-{4-[1-ethyl-1-(4-hydroxy-3-methyl-phenyl)-propyl]-2-methyl-phenylethynyl}-tetrahydro-pyran-4-ol

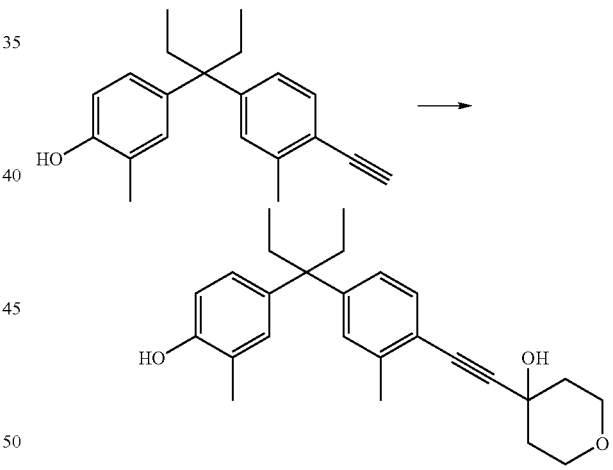

n-Butyllithium (2.71 M solution in hexane, 3.15 mL, 8.55 mmol) was added to a solution of 4-[1-ethyl-1-(4-ethynyl-3-methyl-phenyl)-propyl]-2-methyl-phenol (Example 1-(3); 1.0 g, 3.42 mmol) in tetrahydrofuran (30 mL) in a nitrogen atmosphere at 0° C., and the mixture was stirred for 15 minutes. Then, tetrahydropyran-4-one (685 mg, 6.84 mmol) was added to the reaction mixture, which was further stirred at 0° C. for 30 minutes. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 30:70) to give the target compound as a colorless oil (0.97 g, 72%).

¹H-NMR (chloroform-d): 0.59 (6H, t, J=7.26 Hz), 1.91-1.95 (2H, m), 1.99-2.07 (6H, m), 2.18 (3H, s), 2.37 (3H, s), 3.70-3.79 (2H, m), 3.93-3.99 (2H, m), 5.40 (1H, brs), 6.65 (1H, d, J=8.25 Hz), 6.80-6.85 (2H, m), 6.95 (1H, d, J=8.08 Hz), 7.01 (1H, s), 7.27 (1H, d, J=8.08 Hz).

(2) Synthesis of Trifluoromethanesulfonic Acid 4-{1-ethyl-1-[4-(4-hydroxy-tetrahydro-pyran-4-ylethynyl)-3-methyl-phenyl]-propyl}-2-methyl-phenyl Ester

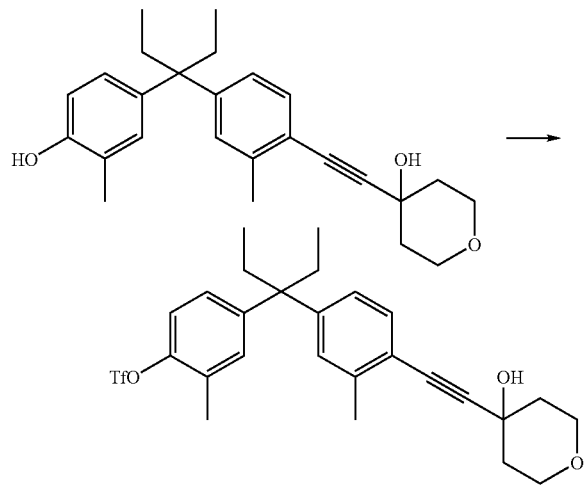

N-Phenylbis(trifluoromethanesulfonimide) (532 mg, 1.490 mmol) and triethylamine (0.318 mL, 2.292 mmol) were added to a solution of 4-{4-[1-ethyl-1-(4-hydroxy-3-methyl-phenyl)-propyl]-2-methyl-phenylethynyl}-tetrahydro-pyran-4-ol (Example 130-(1); 0.45 g, 1.146 mmol) in dichloromethane (10 mL) at room temperature, and the mixture was stirred overnight. Then, the reaction mixture was concentrated under reduced pressure. The resulting residue was purified by silica gel chromatography (hexane:ethyl acetate=100:0 to 50:50) to give the target compound as a colorless oil (0.58 g, 96%).

¹H-NMR (chloroform-d): 0.60 (6H, t, J=7.42 Hz), 1.86-1.95 (2H, m), 2.01-2.11 (6H, m), 2.31 (3H, s), 2.39 (3H, s), 3.69-3.78 (2H, m), 3.92-4.00 (2H, m), 6.92 (1H, d, J=7.92 Hz), 6.98-7.03 (3H, m), 7.10 (1H, d, J=8.41 Hz), 7.30 (1H, d, J=8.08 Hz).

(3) Synthesis of 4-(4-{1-ethyl-1-[3-methyl-4-(4,4,5,5-tetramethyl-[1,3,2]dioxaborolan-2-yl)-phenyl]-propyl}-2-methyl-phenylethynyl)-tetrahydro-pyran-4-ol

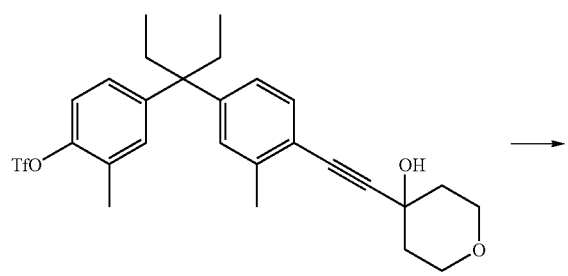

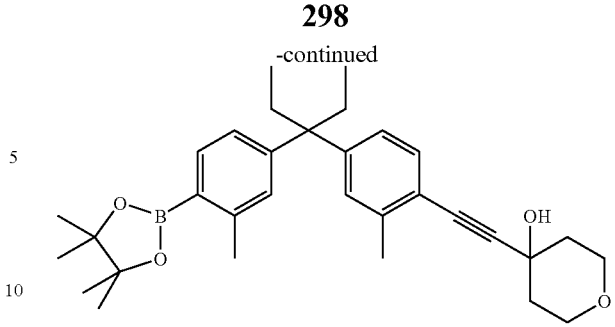

A [1,1'-bis(diphenylphosphino)ferrocene]dichloropalladium (II), dichloromethane complex (1:1) (91 mg, 0.111 mmol), 1,1'-bis(diphenylphosphino)ferrocene (62 mg, 0.111 mmol), potassium acetate (326 mg, 3.318 mmol) and bis(pinacolato)diboron (421 mg, 1.658 mmol) were added to a solution of trifluoromethanesulfonic acid 4-{1-ethyl-1-[4-(4-hydroxy-tetrahydro-pyran-4-ylethynyl)-3-methyl-phenyl]-propyl}-2-methyl-phenyl ester (Example 130-(2); 0.58 g, 1.106 mmol) in anhydrous dioxane (12 mL). After replacement with nitrogen, the mixture was stirred at 100° C. for four hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50, 40 minutes) to give the target compound as a colorless oil (0.55 g, 99%).

¹H-NMR (chloroform-d): 0.59 (6H, t, J=7.25 Hz), 1.33 (12H, s), 1.84-1.96 (2H, m), 1.99-2.11 (6H, m), 2.36 (3H, s), 2.47 (3H, s), 3.69-3.78 (2H, m), 3.92-3.98 (2H, m), 6.92-6.99 (4H, m), 7.27 (1H, d, J=8.08 Hz), 7.63 (1H, d, J=7.75 Hz).

(4) Synthesis of 4-(4-{1-ethyl-1-[3-methyl-4-(4,4,5,5-tetramethyl-[1,3,2]dioxaborolan-2-yl)-phenyl]-propyl}-2-methyl-phenylethynyl)-4-trimethylsilanyloxy-tetrahydro-pyran

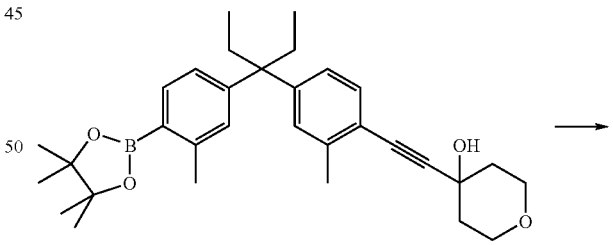

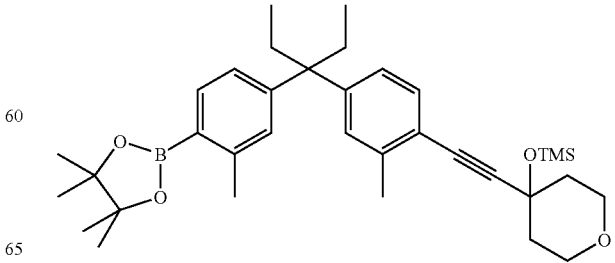

Pyridine (0.353 mL, 4.380 mmol) and trimethylsilyl triflate (0.396 mL, 2.189 mmol) were added to a solution of 4-(4-{1-ethyl-1-[3-methyl-4-(4,4,5,5-tetramethyl-[1,3,2]dioxaborolan-2-yl)-phenyl]-propyl}-2-methyl-phenylethynyl)-tetrahydro-pyran-4-ol (Example 130-(3); 0.55 g, 1.095 mmol) in dichloromethane (10 mL) at 0° C., and the mixture was stirred for 30 minutes. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50) to give the target compound as a colorless oil (548 mg, 87%).

$^1$H-NMR (chloroform-d): 0.24 (9H, s), 0.60 (6H, t, J=7.25 Hz), 1.33 (12H, s), 1.85-2.12 (8H, m), 2.37 (3H, s), 2.48 (3H, s), 3.70-3.77 (2H, m), 3.87-3.91 (2H, m), 6.92-6.99 (4H, m), 7.26 (1H, d, J=8.08 Hz), 7.63 (1H, d, J=7.92 Hz).

(5) Synthesis of (4'-{1-ethyl-1-[3-methyl-4-(4-trimethylsilanyloxy-tetrahydro-pyran-4-ylethynyl)-phenyl]-propyl}-2'-methyl-biphenyl-4-yl)-acetic Acid Methyl Ester

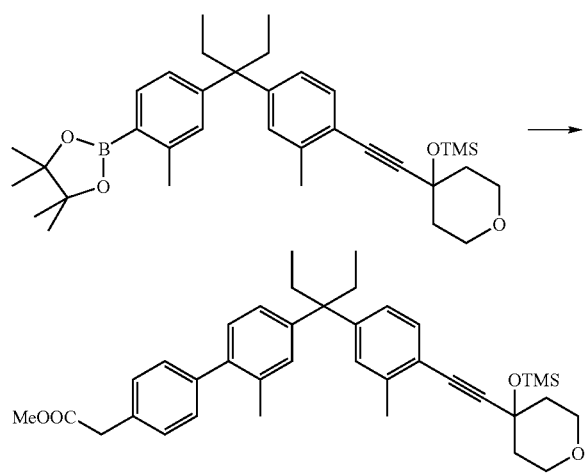

(4-Bromo-phenyl)acetic acid methyl ester (Tetrahedron Letters 44 (2003) 331-334; 34 mg, 0.146 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (62 mg, 0.294 mmol) and water (0.2 mL) were added to a solution of 4-(4-{1-ethyl-1-[3-methyl-4-(4,4,5,5-tetramethyl-[1,3,2]dioxaborolan-2-yl)-phenyl]-propyl}-2-methyl-phenylethynyl)-4-trimethylsilanyloxy-tetrahydro-pyran (Example 130-(4); 56.1 mg, 0.098 mmol) in toluene (2 mL). After replacement with nitrogen, the mixture was stirred at 100° C. for one hour. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (43.5 mg, 74%).

$^1$H-NMR (chloroform-d): 0.25 (9H, s), 0.65 (6H, t, J=7.25 Hz), 1.83-2.04 (4H, m), 2.11 (4H, q, J=7.42 Hz), 2.23 (3H, s), 2.41 (3H, s), 3.68 (2H, s), 3.69-3.78 (2H, m), 3.72 (3H, s), 3.85-3.91 (2H, m), 6.98-7.10 (5H, m), 7.26-7.32 (5H, m).

(6) Synthesis of (4'-{1-ethyl-1-[4-(4-hydroxy-tetrahydro-pyran-4-ylethynyl)-3-methyl-phenyl]-propyl}-2'-methyl-biphenyl-4-yl)-acetic Acid Methyl Ester

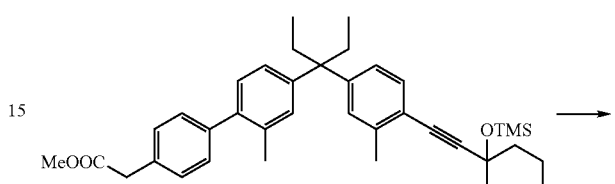

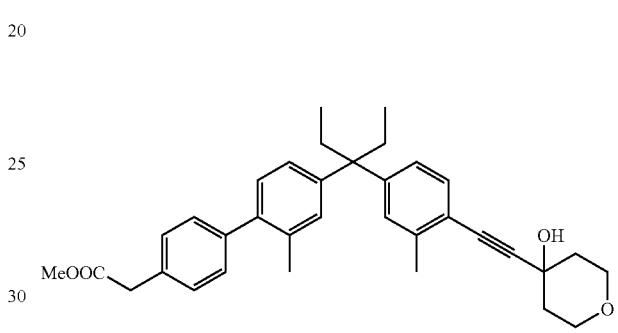

Tetrabutylammonium fluoride (1 M solution in tetrahydrofuran, 0.364 mL, 0.364 mmol) was added to a solution of (4'-{1-ethyl-1-[3-methyl-4-(4-trimethylsilanyloxytetrahydro-pyran-4-ylethynyl)-phenyl]-propyl}-2'-methyl-biphenyl-4-yl)-acetic acid methyl ester (Example 130-(5); 43.5 mg, 0.073 mmol) in tetrahydrofuran (3 mL), and the mixture was stirred at room temperature for 15 minutes. Then, the reaction mixture was diluted with ethyl acetate and was washed with brine. The organic layer was dried over anhydrous magnesium sulfate, filtered and concentrated under reduced pressure. The resulting residue was purified by silica gel chromatography (hexane:ethyl acetate=1:1) to give the target compound as a colorless oil (34.4 mg, 90%).

$^1$H-NMR (chloroform-d): 0.64 (6H, t, J=7.25 Hz), 1.85-1.95 (2H, m), 2.01-2.15 (6H, m), 2.22 (3H, s), 2.41 (3H, s), 3.67 (2H, s), 3.70-3.78 (2H, m), 3.72 (3H, s), 3.90-3.99 (2H, m), 6.96-7.09 (5H, m), 7.29-7.32 (5H, m).

(7) Synthesis of (4'-{1-ethyl-1-[4-(4-hydroxy-tetrahydro-pyran-4-ylethynyl)-3-methyl-phenyl]-propyl}-2'-methyl-biphenyl-4-yl)-acetic Acid

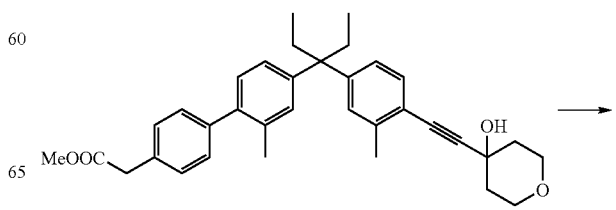

-continued

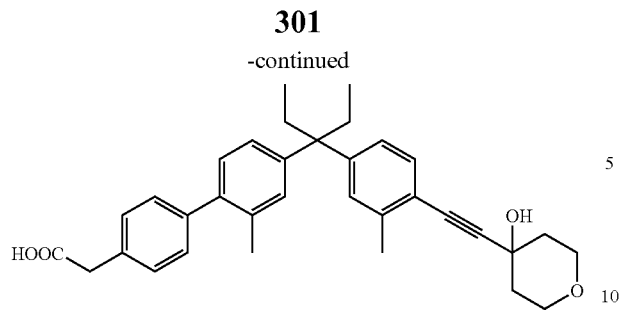

A 1 N sodium hydroxide aqueous solution (0.197 mL, 0.197 mmol) was added to a solution of (4'-{1-ethyl-1-[4-(4-hydroxy-tetrahydro-pyran-4-ylethynyl)-3-methyl-phenyl]-propyl}-2'-methyl-biphenyl-4-yl)-acetic acid methyl ester (Example 130-(6); 34.4 mg, 0.066 mmol) in methanol-tetrahydrofuran (1:1, 2 mL), and the mixture was stirred at room temperature overnight. Then, the reaction mixture was concentrated under reduced pressure. The resulting residue was purified by silica gel chromatography (ethyl acetate:methanol:water=4:1:0.3) to give the target compound as a colorless oil (32.1 mg, 95%).

$^1$H-NMR (chloroform-d): 0.64 (6H, t, J=7.26 Hz), 1.85-1.95 (2H, m), 2.01-2.14 (6H, m), 2.21 (3H, s), 2.40 (3H, s), 3.70 (2H, s), 3.74-3.78 (2H, m), 3.92-3.98 (2H, m), 6.96-7.01 (3H, m), 7.06-7.09 (2H, m), 7.26-7.32 (5H, m); MS (ESI+): 493 ([M−H$_2$O+H]$^+$).

Example 131

Synthesis of [4'-(1-ethyl-1-{4-[(E)-2-(4-hydroxy-tetrahydro-pyran-4-yl)-vinyl]-3-methyl-phenyl}-propyl)-2'-methyl-biphenyl-4-yl]-acetic Acid

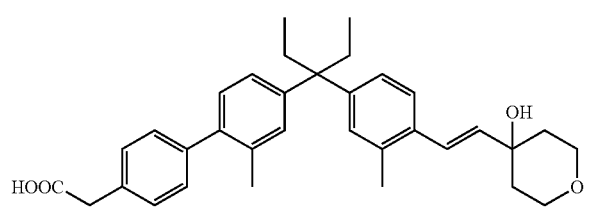

(1) Synthesis of 4-((E)-2-{4-[1-ethyl-1-(4-hydroxy-3-methyl-phenyl)-propyl]-2-methyl-phenyl}-vinyl)-tetrahydro-pyran-4-ol

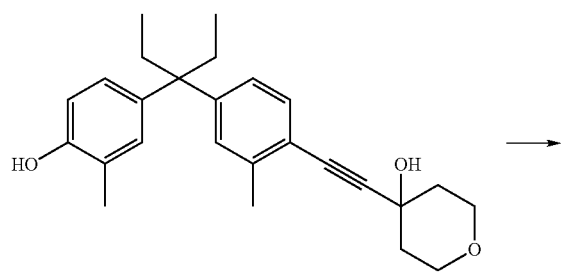

-continued

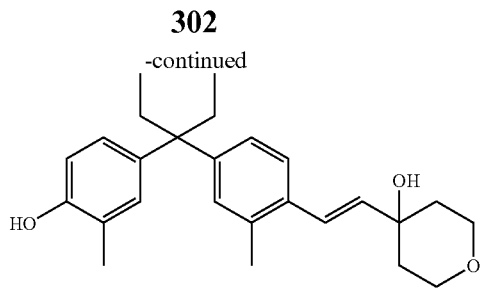

Sodium bis(2-methoxyethoxy)aluminum hydride (65 wt % solution in toluene, 1.06 mL, 3.516 mmol) was added to a solution of 4-{4-[1-ethyl-1-(4-hydroxy-3-methyl-phenyl)-propyl]-2-methyl-phenylethynyl}-tetrahydro-pyran-4-ol (Example 130-(1); 0.46 g, 1.172 mmol) in tetrahydrofuran (5 mL) in a nitrogen atmosphere at 0° C., and the mixture was stirred at 0° C. for three hours. Then, ethyl acetate and brine were added to the reaction mixture, which was further diluted with ethyl acetate. Thereafter, celite was added and the mixture was stirred at room temperature for three hours. The reaction mixture was filtered through celite, and the filtrate was concentrated under reduced pressure. The resulting residue was purified by silica gel chromatography (hexane:ethyl acetate=100:0 to 30:70, 40 minutes) to give the target compound as a colorless oil (0.46 g, 99%).

$^1$H-NMR (chloroform-d): 0.60 (6H, t, J=7.42 Hz), 1.58-1.65 (2H, m), 1.88-1.94 (2H, m), 2.04 (4H, q, J=7.25 Hz), 2.19 (3H, s), 2.30 (3H, s), 3.75-3.91 (4H, m), 4.65 (1H, brs), 6.18 (1H, d, J=15.99 Hz), 6.64 (1H, d, J=8.08 Hz), 6.80-6.97 (5H, m), 7.32 (1H, d, J=8.74 Hz).

(2) Synthesis of Trifluoromethanesulfonic Acid 4-(1-ethyl-1-{4-[(E)-2-(4-hydroxy-tetrahydro-pyran-4-yl)-vinyl]-3-methyl-phenyl}-propyl)-2-methyl-phenyl Ester

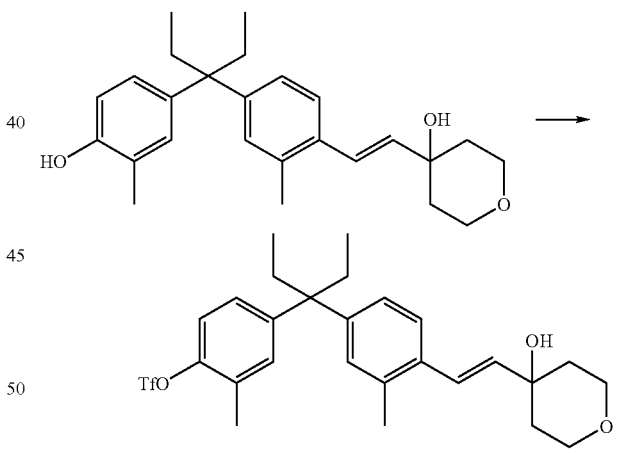

N-Phenylbis(trifluoromethanesulfonimide) (628 mg, 1.758 mmol) and triethylamine (0.325 mL, 2.344 mmol) were added to a solution of 4-((E)-2-{4-[1-ethyl-1-(4-hydroxy-3-methyl-phenyl)-propyl]-2-methyl-phenyl}-vinyl)-tetrahydro-pyran-4-ol (Example 131-(1); 0.46 g, 1.160 mmol) in dichloromethane (5 mL) at room temperature, and the mixture was stirred for six hours. Then, the reaction mixture was concentrated under reduced pressure. The resulting residue was purified by silica gel chromatography (hexane:ethyl acetate=100:0 to 50:50) to give the target compound as a colorless oil (0.53 g, 87%).

$^1$H-NMR (chloroform-d): 0.61 (6H, t, J=7.26 Hz), 1.58-1.65 (2H, m), 1.88-1.99 (2H, m), 2.07 (4H, q, J=7.42 Hz), 2.31 (6H, s), 3.80-3.91 (4H, m), 6.19 (1H, d, J=16.00 Hz), 6.83 (1H, d, J=15.99 Hz), 6.92-6.94 (2H, m), 7.02-7.11 (3H, m), 7.34 (1H, d, J=8.74 Hz).

(3) Synthesis of 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydro-pyran-4-ol

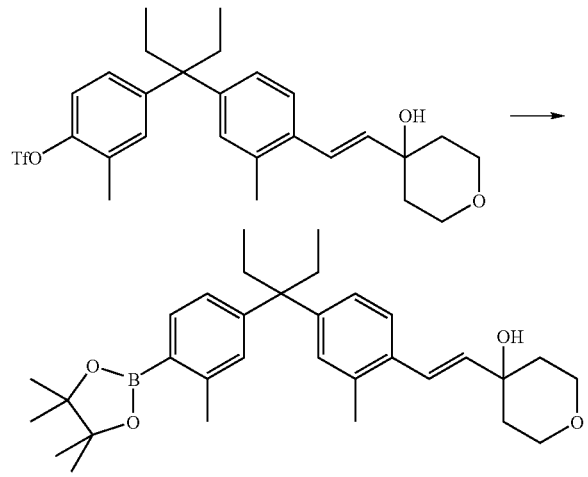

A [1,1'-bis(diphenylphosphino)ferrocene]dichloropalladium (II), dichloromethane complex (1:1) (82 mg, 0.101 mmol), 1,1'-bis(diphenylphosphino)ferrocene (56 mg, 0.101 mmol), potassium acetate (296 mg, 3.018 mmol) and bis(pinacolato)diboron (383 mg, 1.510 mmol) were added to a solution of trifluoromethanesulfonic acid 4-(1-ethyl-1-{4-[(E)-2-(4-hydroxy-tetrahydro-pyran-4-yl)-vinyl]-3-methyl-phenyl}-propyl)-2-methyl-phenyl ester (Example 131-(2); 0.53 g, 1.006 mmol) in anhydrous dioxane (10 mL). After replacement with nitrogen, the mixture was stirred at 100° C. for four hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50, 30 minutes) to give the target compound as a colorless oil (402 mg, 79%).

$^{1}$H-NMR (chloroform-d): 0.60 (6H, t, J=7.42 Hz), 1.33 (12H, s), 1.60-1.65 (2H, m), 1.87-1.99 (2H, m), 2.07 (4H, q, J=7.42 Hz), 2.29 (3H, s), 2.47 (3H, s), 3.76-3.91 (4H, m), 6.17 (1H, d, J=15.99 Hz), 6.83 (1H, d, J=15.99 Hz), 6.93-6.99 (4H, m), 7.30 (1H, d, J=8.08 Hz), 7.63 (1H, d, J=7.58 Hz).

(4) Synthesis of [4'-(1-ethyl-1-{4-[(E)-2-(4-hydroxy-tetrahydro-pyran-4-yl)-vinyl]-3-methyl-phenyl}-propyl)-2'-methyl-biphenyl-4-yl]-acetic Acid Methyl Ester

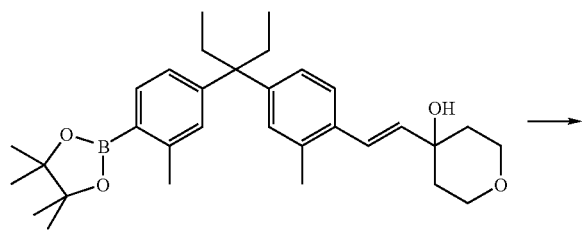

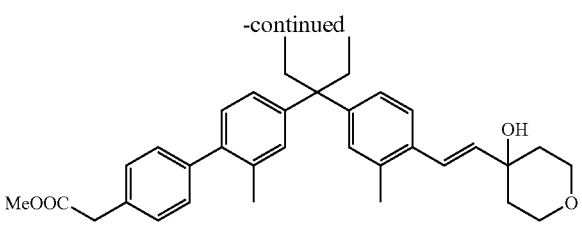

(4-Bromo-phenyl)acetic acid methyl ester (Tetrahedron Letters 44 (2003) 331-334; 37 mg, 0.162 mmol), palladium acetate (2.5 mg, 0.011 mmol), 2-dicyclohexylphosphino-2',6'-dimethoxy-1,1'-biphenyl (9.0 mg, 0.022 mmol), potassium phosphate (69 mg, 0.324 mmol) and water (0.2 mL) were added to a solution of 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydro-pyran-4-ol (Example 131-(3); 54.6 mg, 0.108 mmol) in toluene (2 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (27.6 mg, 49%).

$^{1}$H-NMR (chloroform-d): 0.65 (6H, t, J=7.26 Hz), 1.60-1.70 (2H, m), 1.88-1.99 (2H, m), 2.12 (4H, q, J=7.42 Hz), 2.22 (3H, s), 2.33 (3H, s), 3.67 (2H, s), 3.72 (3H, s), 3.80-3.91 (4H, m), 6.20 (1H, d, J=15.99 Hz), 6.85 (1H, d, J=15.82 Hz), 6.98-7.09 (5H, m), 7.29 (4H, m), 7.35 (1H, d, J=8.74 Hz).

(5) Synthesis of [4'-(1-ethyl-1-{4-[(E)-2-(4-hydroxy-tetrahydro-pyran-4-yl)-vinyl]-3-methyl-phenyl}-propyl)-2'-methyl-biphenyl-4-yl]-acetic Acid

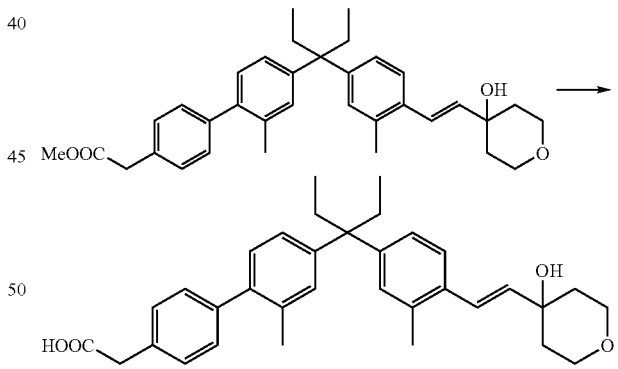

A 1 N sodium hydroxide aqueous solution (0.157 mL, 0.157 mmol) was added to a solution of [4'-(1-ethyl-1-{4-[(E)-2-(4-hydroxy-tetrahydro-pyran-4-yl)-vinyl]-3-methyl-phenyl}-propyl)-2'-methyl-biphenyl-4-yl]-acetic acid methyl ester (Example 131-(4); 27.6 mg, 0.052 mmol) in methanol-tetrahydrofuran (1:1, 2 mL), and the mixture was stirred at room temperature overnight. Then, the reaction mixture was concentrated under reduced pressure. The resulting residue was purified by silica gel chromatography (ethyl acetate:methanol=5:1) to give the target compound as a colorless oil (24.4 mg, 92%).

$^{1}$H-NMR (chloroform-d): 0.65 (6H, t, J=7.26 Hz), 1.60-1.65 (2H, m), 1.88-1.99 (2H, m), 2.11 (4H, q, J=7.42 Hz), 2.22 (3H, s), 2.33 (3H, s), 3.69 (2H, s), 3.77-3.91 (4H, m), 6.19 (1H, d, J=16.00 Hz), 6.84 (1H, d, J=16.16 Hz), 6.99-7.09 (5H, m), 7.30 (4H, m), 7.35 (1H, d, J=8.74 Hz); MS (ESI+): 495 ([M−H$_2$O+H]$^+$).

Example 132

Synthesis of [5-(4-{1-ethyl-1-[4-(4-hydroxy-tetrahydro-pyran-4-ylethynyl)-3-methyl-phenyl]-propyl}-2-methyl-phenyl)-pyridin-3-yl]-acetic Acid (1) Synthesis of [5-(4-{1-ethyl-1-[3-methyl-4-(4-trimethylsilanyloxy-tetrahydro-pyran-4-ylethynyl)-phenyl]-propyl}-2-methyl-phenyl)-pyridin-3-yl]-acetic Acid Methyl Ester

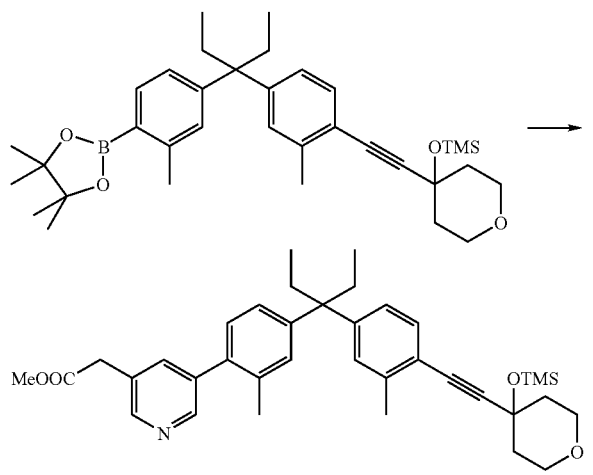

(5-Bromo-pyridin-3-yl)acetic acid methyl ester (Example 24-(2); 40 mg, 0.173 mmol), palladium acetate (2.7 mg, 0.012 mmol), 2-dicyclohexylphosphino-2',6'-dimethoxy-1,1'-biphenyl (9.9 mg, 0.024 mmol), potassium phosphate (74 mg, 0.348 mmol) and water (0.2 mL) were added to a solution of 4-(4-{1-ethyl-1-[3-methyl-4-(4,4,5,5-tetramethyl-[1,3,2]dioxaborolan-2-yl)-phenyl]-propyl}-2-methyl-phenylethynyl)-4-trimethylsilanyloxy-tetrahydro-pyran (Example 130-(4); 66.4 mg, 0.116 mmol) in toluene (3 mL). After replacement with nitrogen, the mixture was stirred at 100° C. for 3.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (62.9 mg, 91%).

$^1$H-NMR (chloroform-d): 0.25 (9H, s), 0.65 (6H, t, J=7.25 Hz), 1.88-2.01 (4H, m), 2.12 (4H, q, J=7.42 Hz), 2.24 (3H, s), 2.42 (3H, s), 3.63 (2H, s), 3.70-3.78 (2H, m), 3.73 (3H, s), 3.85-3.92 (2H, m), 6.98-7.11 (5H, m), 7.31 (1H, d, J=8.08 Hz), 7.62 (1H, s), 8.47 (1H, d, J=2.14 Hz), 8.51 (1H, d, J=1.97 Hz).

(2) Synthesis of [5-(4-{1-ethyl-1-[4-(4-hydroxy-tetrahydro-pyran-4-ylethynyl)-3-methyl-phenyl]-propyl}-2-methyl-phenyl)-pyridin-3-yl]-acetic Acid Methyl Ester

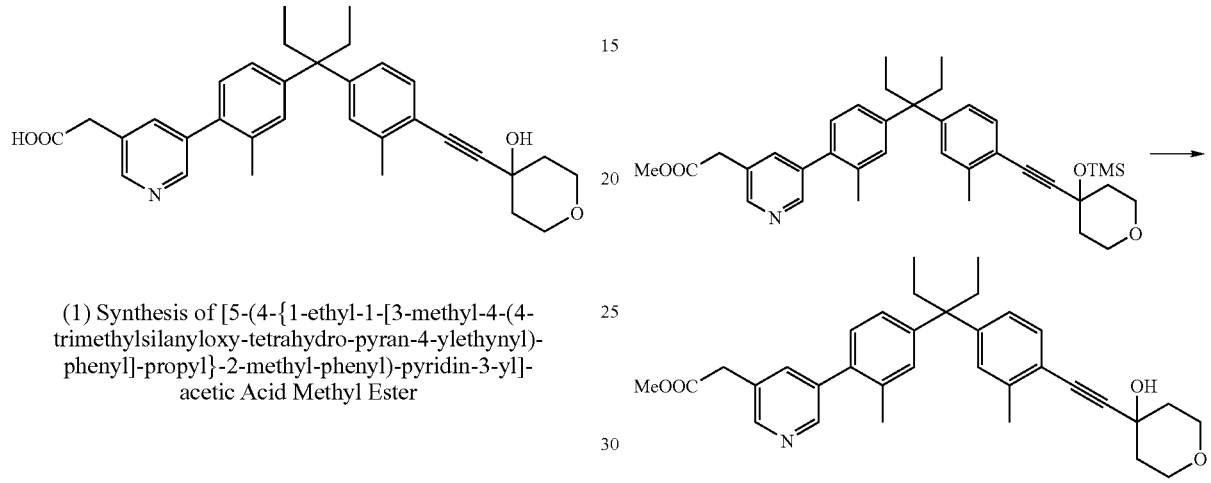

Tetrabutylammonium fluoride (1 M solution in tetrahydrofuran, 0.316 mL, 0.316 mmol) was added to a solution of [5-(4-{1-ethyl-1-[3-methyl-4-(4-trimethylsilanyloxy-tetrahydro-pyran-4-ylethynyl)-phenyl]-propyl}-2-methyl-phenyl)-pyridin-3-yl]-acetic acid methyl ester (Example 132-(1); 62.9 mg, 0.105 mmol) in tetrahydrofuran (3 mL), and the mixture was stirred at 0° C. for 10 minutes. Then, the reaction mixture was diluted with ethyl acetate and was washed with brine. The organic layer was dried over anhydrous magnesium sulfate, filtered and concentrated under reduced pressure. The resulting residue was purified by silica gel chromatography (chloroform:methanol=10:1) to give the target compound as a colorless oil (44.0 mg, 80%).

$^1$H-NMR (chloroform-d): 0.65 (6H, t, J=7.26 Hz), 1.86-1.96 (2H, m), 2.01-2.16 (6H, m), 2.22 (3H, s), 2.41 (3H, s), 3.68 (2H, s), 3.69-3.78 (2H, m), 3.72 (3H, s), 3.92-3.98 (2H, m), 6.98-7.11 (5H, m), 7.31 (1H, d, J=8.08 Hz), 7.62 (1H, m), 8.47 (1H, d, J=1.98 Hz), 8.51 (1H, d, J=1.98 Hz).

(3) Synthesis of [5-(4-{1-ethyl-1-[4-(4-hydroxy-tetrahydro-pyran-4-ylethynyl)-3-methyl-phenyl]-propyl}-2-methyl-phenyl)-pyridin-3-yl]-acetic Acid

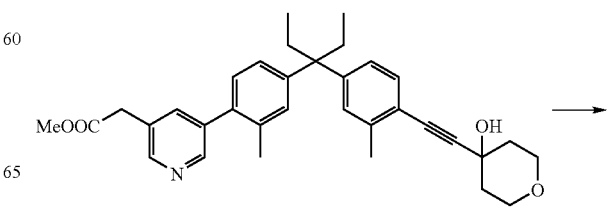

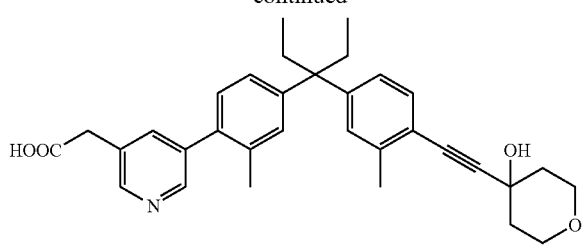
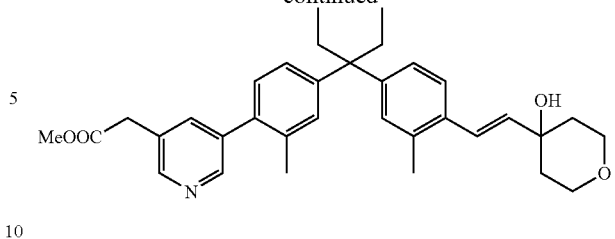

A 1 N sodium hydroxide aqueous solution (0.251 mL, 0.251 mmol) was added to a solution of [5-(4-{1-ethyl-1-[4-(4-hydroxy-tetrahydro-pyran-4-ylethynyl)-3-methyl-phenyl]-propyl}-2-methyl-phenyl)-pyridin-3-yl]-acetic acid methyl ester (Example 132-(2); 44.0 mg, 0.084 mmol) in methanol-tetrahydrofuran (1:1, 4 mL), and the mixture was stirred at room temperature for two hours. Then, the reaction mixture was concentrated under reduced pressure. The resulting residue was purified by silica gel chromatography (ethyl acetate:methanol:water=4:1:0.3) to give the target compound as a colorless oil (40.2 mg, 94%).

$^1$H-NMR (chloroform-d): 0.64 (6H, t, J=7.09 Hz), 1.86-1.95 (2H, m), 2.00-2.12 (6H, m), 2.20 (3H, s), 2.39 (3H, s), 3.70-3.77 (4H, m), 3.94-3.98 (2H, m), 6.95-7.08 (5H, m), 7.29 (1H, d, J=8.24 Hz), 7.68 (1H, s), 8.51 (2H, s); MS (ESI+): 512 ([M+H]$^+$).

Example 133

Synthesis of {5-[4-(1-ethyl-1-{4-[(E)-2-(4-hydroxy-tetrahydro-pyran-4-yl)-vinyl]-3-methyl-phenyl}-propyl)-2-methyl-phenyl]-pyridin-3-yl}-acetic Acid

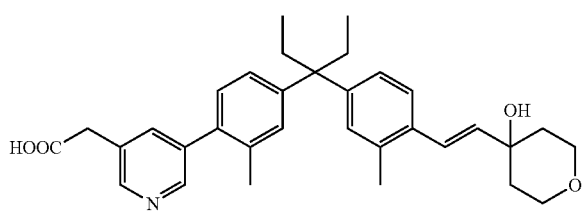

(1) Synthesis of {5-[4-(1-ethyl-1-{4-[(E)-2-(4-hydroxy-tetrahydro-pyran-4-yl)-vinyl]-3-methyl-phenyl}-propyl)-2-methyl-phenyl]-pyridin-3-yl}-acetic Acid Methyl Ester

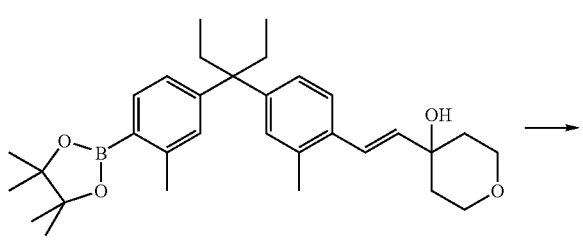

(5-Bromo-pyridin-3-yl)acetic acid methyl ester (Example 24-(2); 39 mg, 0.171 mmol), palladium acetate (2.5 mg, 0.011 mmol), 2-dicyclohexylphosphino-2',6'-dimethoxy-1,1'-biphenyl (9.0 mg, 0.022 mmol), potassium phosphate (73 mg, 0.342 mmol) and water (0.2 mL) were added to a solution of 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydro-pyran-4-ol (Example 131-(3); 57.4 mg, 0.114 mmol) in toluene (2 mL). After replacement with nitrogen, the mixture was stirred at 100° C. for three hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (29.1 mg, 48%).

$^1$H-NMR (chloroform-d): 0.66 (6H, t, J=7.26 Hz), 1.63 (2H, m), 1.85-1.97 (2H, m), 2.10 (4H, q, J=7.25 Hz), 2.23 (3H, s), 2.33 (3H, s), 3.68 (2H, s), 3.72 (3H, s), 3.80-3.87 (4H, m), 6.20 (1H, d, J=15.99 Hz), 6.85 (1H, d, J=16.16 Hz), 6.96-7.08 (5H, m), 7.35 (1H, d, J=8.57 Hz), 7.62 (1H, m), 8.46 (1H, d, J=2.14 Hz), 8.51 (1H, d, J=1.98 Hz).

(2) Synthesis of {5-[4-(1-ethyl-1-{4-[(E)-2-(4-hydroxy-tetrahydro-pyran-4-yl)-vinyl]-3-methyl-phenyl}-propyl)-2-methyl-phenyl]-pyridin-3-yl}-acetic Acid

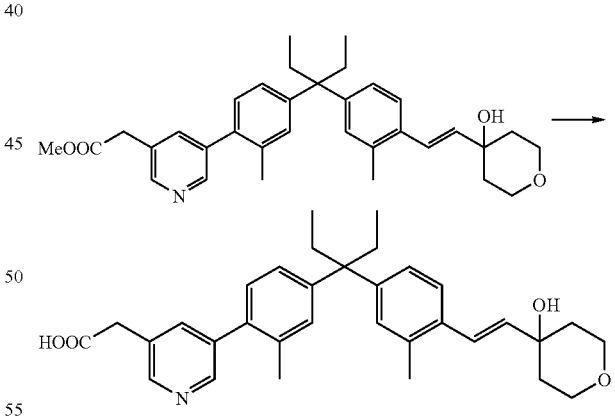

A 1 N sodium hydroxide aqueous solution (0.165 mL, 0.165 mmol) was added to a solution of {5-[4-(1-ethyl-1-{4-[(E)-2-(4-hydroxy-tetrahydro-pyran-4-yl)-vinyl]-3-methyl-phenyl}-propyl)-2-methyl-phenyl]-pyridin-3-yl}-acetic acid methyl ester (Example 133-(1); 29.1 mg, 0.055 mmol) in methanol-tetrahydrofuran (1:1, 2 mL), and the mixture was stirred at room temperature overnight. Then, the reaction mixture was concentrated under reduced pressure. The resulting residue was purified by silica gel chromatography (ethyl acetate:methanol=10:4) to give the target compound as a colorless oil (15.7 mg, 56%).

¹H-NMR (chloroform-d): 0.64 (6H, t, J=7.25 Hz), 1.58-1.66 (2H, m), 1.87-1.98 (2H, m), 2.10 (4H, q, J=7.25 Hz), 2.19 (3H, s), 2.30 (3H, s), 3.68 (2H, s), 3.80-3.91 (4H, m), 6.18 (1H, d, J=16.15 Hz), 6.83 (1H, d, J=15.99 Hz), 6.95-7.07 (5H, m), 7.33 (1H, d, J=8.57 Hz), 7.69 (1H, s), 8.49 (2H, m); MS (ESI+): 514 ([M+H]⁺).

Example 134

Synthesis of (4'-{1-ethyl-1-[4-(4-hydroxy-tetrahydro-pyran-4-ylethynyl)-3-methyl-phenyl]-propyl}-3-fluoro-2'-methyl-biphenyl-4-yl)-acetic Acid

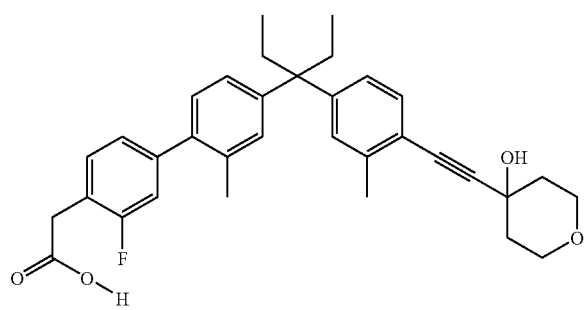

(1) Synthesis of (4'-{1-ethyl-1-[3-methyl-4-(4-trimethylsilanyloxy-tetrahydro-pyran-4-ylethynyl)-phenyl]-propyl}-3-fluoro-2'-methyl-biphenyl-4-yl)-acetic Acid Methyl Ester

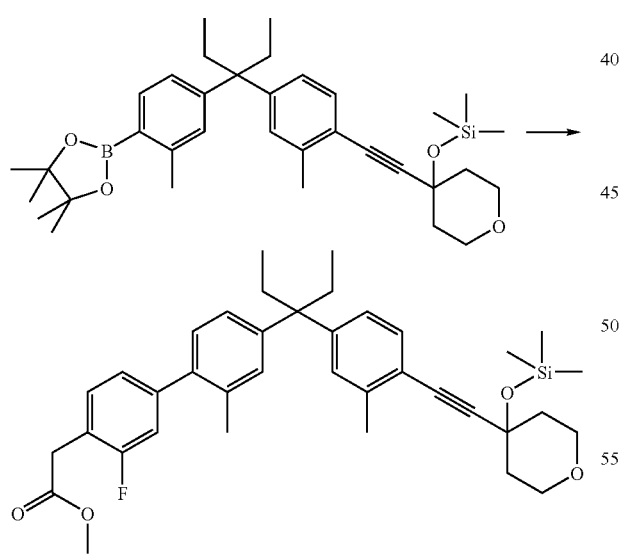

The title compound (44%) was obtained by the same method as in Example 46-(1) using 4-(4-{1-ethyl-1-[3-methyl-4-(4,4,5,5-tetramethyl-[1,3,2]dioxaborolan-2-yl)-phenyl]-propyl}-2-methyl-phenylethynyl)-4-trimethylsilanyloxy-tetrahydropyran (Example 130-(4)) and (4-chloro-2-fluoro-phenyl)-acetic acid methyl ester (Example 40) as starting materials.

¹H-NMR (chloroform-d): 0.25 (s, 9H), 0.65 (6H, t, J=7.3 Hz), 1.82-2.02 (m, 4H), 2.11 (q, 4H, J=7.3 Hz), 2.23 (s, 3H), 2.41 (s, 3H), 3.68-3.77 (m, 4H), 3.76 (s, 3H), 3.85-3.92 (m, 2H), 6.93-7.32 (m, 9H).

(2) Synthesis of (4'-{1-ethyl-1-[4-(4-hydroxy-tetrahydro-pyran-4-ylethynyl)-3-methyl-phenyl]-propyl}-3-fluoro-2'-methyl-biphenyl-4-yl)-acetic Acid Methyl Ester

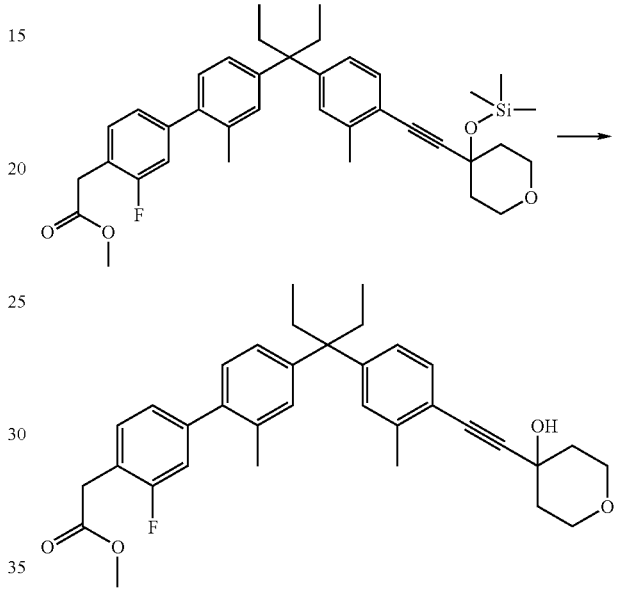

The title compound (18%) was obtained by the same method as in Example 94-(2) using (4'-{1-ethyl-1-[3-methyl-4-(4-trimethylsilanyloxy-tetrahydropyran-4-ylethynyl)-phenyl]-propyl}-3-fluoro-2'-methyl-biphenyl-4-yl)-acetic acid methyl ester as a starting material.

¹H-NMR (chloroform-d): 0.64 (6H, t, J=7.3 Hz), 1.85-2.17 (m, 4H), 2.11 (q, 4H, J=7.3 Hz), 2.23 (s, 3H), 2.41 (s, 3H), 3.68-3.77 (m, 2H), 3.69 (s, 2H), 3.75 (s, 3H), 3.90-4.00 (m, 2H), 6.93-7.32 (m, 9H).

(3) Synthesis of (4'-{1-ethyl-1-[4-(4-hydroxy-tetrahydro-pyran-4-ylethynyl)-3-methyl-phenyl]-propyl}-3-fluoro-2'-methyl-biphenyl-4-yl)-acetic Acid

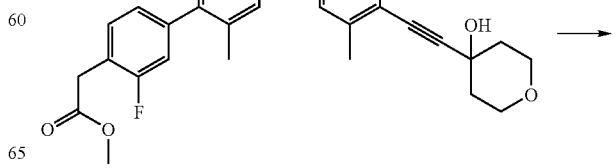

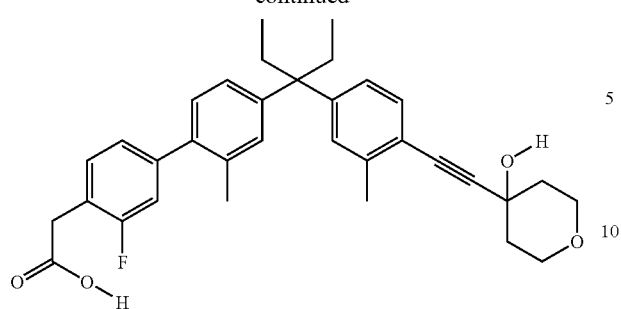

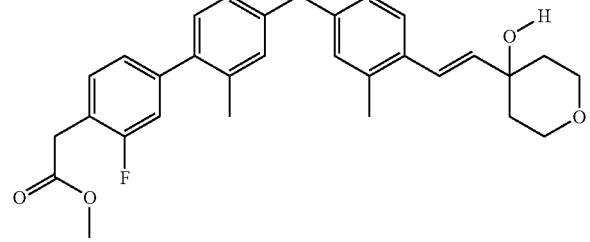

The title compound (60%) was obtained by the same method as in Example 46-(2) using (4'-{1-ethyl-1-[4-(4-hydroxy-tetrahydropyran-4-ylethynyl)-3-methyl-phenyl]-propyl}-3-fluoro-2'-methyl-biphenyl-4-yl)-acetic acid methyl ester as a starting material.

¹H-NMR (chloroform-d): 0.64 (6H, t, J=7.3 Hz), 1.85-2.17 (m, 4H), 2.11 (q, 4H, J=7.3 Hz), 2.23 (s, 3H), 2.40 (s, 3H), 3.69-3.78 (m, 4H), 3.92-4.00 (m, 2H), 6.93-7.32 (m, 9H); MS (ESI+): 511 ([M−H₂O+H]⁺).

The title compound (48%) was obtained by the same method as in Example 46-(1) using 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydropyran-4-ol (Example 131-(3)) and 4-chloro-2-fluoro-phenyl)-acetic acid methyl ester (Example 40) as starting materials.

¹H-NMR (chloroform-d): 0.65 (6H, t, J=7.3 Hz), 1.58-1.66 (m, 2H), 1.87-1.99 (m, 2H), 2.12 (q, 4H, J=7.3 Hz), 2.23 (s, 3H), 2.37 (s, 3H), 3.70-3.93 (m, 9H), 6.18 (d, 1H, J=16.0 Hz), 6.83 (d, 1H, J=16.0 Hz), 6.98-7.38 (m, 9H).

Example 135

Synthesis of [4'-(1-ethyl-1-{4-[(E)-2-(4-hydroxy-tetrahydro-pyran-4-yl)-vinyl]-3-methyl-phenyl}-propyl)-3-fluoro-2'-methyl-biphenyl-4-yl]-acetic Acid (2) Synthesis of [4'-(1-ethyl-1-{4-[(E)-2-(4-hydroxy-tetrahydro-pyran-4-yl)-vinyl]-3-methyl-phenyl}-propyl)-3-fluoro-2'-methyl-biphenyl-4-yl]-acetic Acid

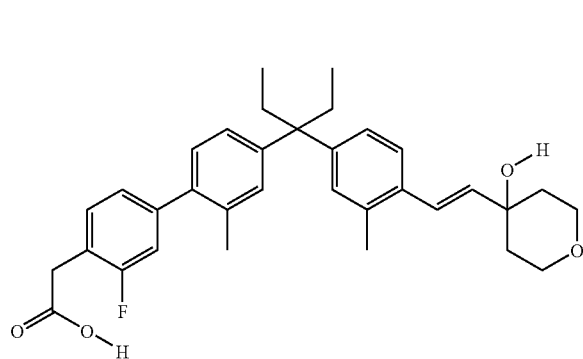

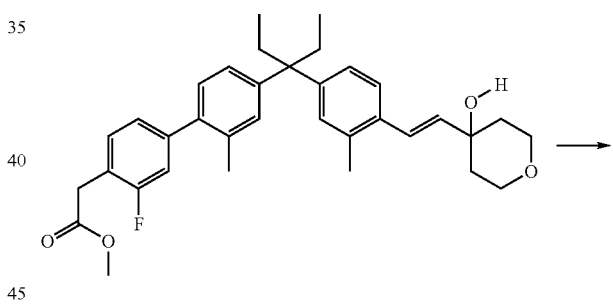

(1) Synthesis of [4'-(1-ethyl-1-{4-[(E)-2-(4-hydroxy-tetrahydro-pyran-4-yl)-vinyl]-3-methyl-phenyl}-propyl)-3-fluoro-2'-methyl-biphenyl-4-yl]-acetic Acid Methyl Ester

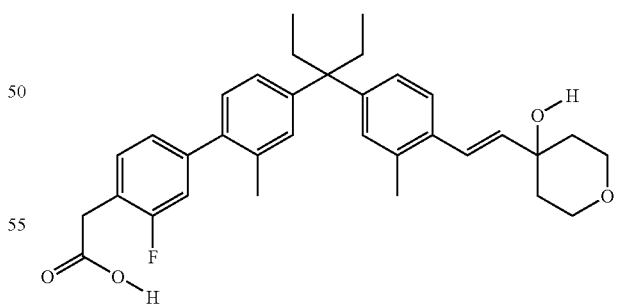

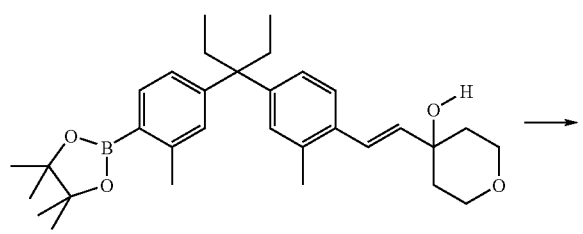

The title compound (42%) was obtained by the same method as in Example 46-(2) using [4'-(1-ethyl-1-{4-[(E)-2-(4-hydroxy-tetrahydropyran-4-yl)-vinyl]-3-methyl-phenyl}-propyl)-3-fluoro-2'-methyl-biphenyl-4-yl]-acetic acid methyl ester as a starting material.

¹H-NMR (chloroform-d): 0.65 (6H, t, J=7.3 Hz), 1.58-1.64 (m, 2H), 1.85-1.99 (m, 2H), 2.10 (q, 4H, J=7.3 Hz), 2.22 (s, 3H), 2.32 (s, 3H), 3.74-3.95 (m, 6H), 6.18 (d, 1H, J=16.0 Hz), 6.83 (d, 1H, J=16.0 Hz), 6.97-7.38 (m, 9H); MS (ESI+): 513 ([M−H₂O+H]⁺).

Example 136

Synthesis of (4'-{1-ethyl-1-[4-(4-hydroxy-tetrahydro-thiopyran-4-ylethynyl)-3-methyl-phenyl]-propyl}-2'-methyl-biphenyl-4-yl)-acetic Acid

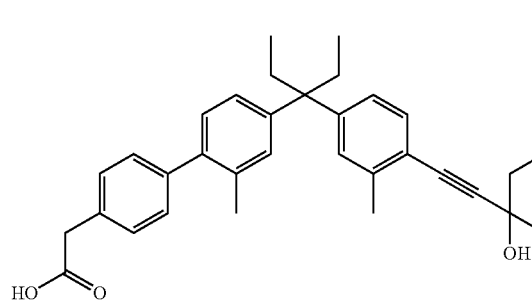

(1) Synthesis of 4-{4-[1-ethyl-1-(4-hydroxy-3-methyl-phenyl)-propyl]-2-methyl-phenylethynyl}-tetrahydro-thiopyran-4-ol

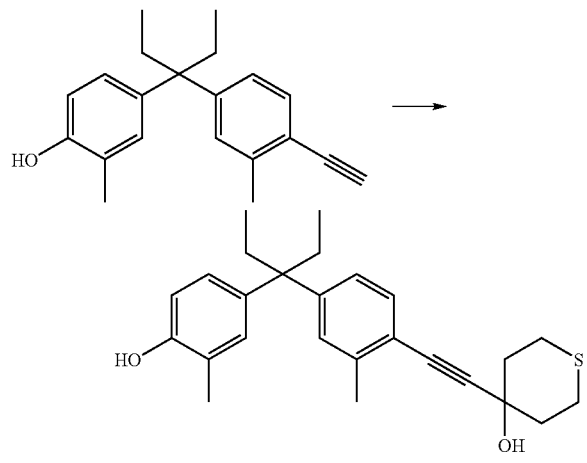

n-Butyllithium (2.71 M solution in hexane, 2.8 mL, 7.6 mmol) was added to a solution of 4-[1-ethyl-1-(4-ethynyl-3-methyl-phenyl)-propyl]-2-methyl-phenol (Example 1-(3); 1 g, 3.4 mmol) in tetrahydrofuran (17 mL) in a nitrogen atmosphere at 0° C. Then, a solution of 4-oxothiane (0.4 g, 3.4 mmol) in tetrahydrofuran (2 mL) was added to the reaction mixture, which was further stirred at 0° C. for 30 minutes. The reaction mixture was then poured into a saturated aqueous ammonium chloride solution, followed by extraction with ethyl acetate. The organic layer was dried over anhydrous magnesium sulfate, filtered and concentrated under reduced pressure. The resulting residue was purified by silica gel chromatography (hexane:ethyl acetate=2:1) to give the target compound (1.04 g, 74%).

¹H-NMR (chloroform-d): 0.59 (t, 6H, J=7.3 Hz), 1.8-2.1 (m, 6H), 2.18 (s, 3H), 2.3-2.4 (m, 2H), 2.37 (s, 3H), 2.7-2.8 (m, 2H), 2.85-3.00 (m, 2H), 6.64 (d, 1H, J=8.0 Hz), 6.8-6.9 (m, 2H), 6.95 (dd, 1H, J=1.5, 8.0 Hz), 7.01 (s, 1H), 7.2-7.3 (m, 1H).

(2) Synthesis of Trifluoromethanesulfonic Acid 4-{1-ethyl-1-[4-(4-hydroxy-tetrahydro-thiopyran-4-ylethynyl)-3-methyl-phenyl]-propyl}-2-methyl-phenyl Ester

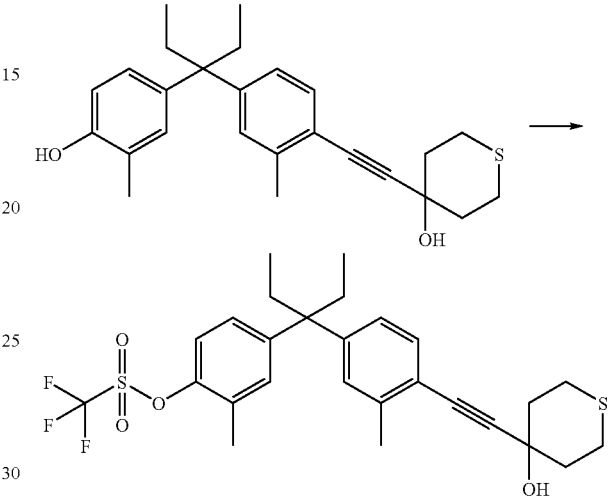

Triethylamine (0.34 mL, 2.4 mmol) and N-phenylbis(trifluoromethanesulfonimide) (0.66 g, 1.8 mmol) were added to a solution of 4-{4-[1-ethyl-1-(4-hydroxy-3-methyl-phenyl)-propyl]-2-methyl-phenylethynyl}-tetrahydro-thiopyran-4-ol (Example 136-(1); 0.5 g, 1.2 mmol) in dichloromethane (6 mL) at room temperature, and the mixture was stirred for five hours. Water was added to the reaction mixture, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 25:75) to give the target compound (0.66 g, 99%).

¹H-NMR (chloroform-d): 0.60 (t, 6H, J=7.3 Hz), 1.9-2.1 (m, 6H), 2.31 (s, 3H), 2.2-2.35 (m, 2H), 2.39 (s, 3H), 2.7-2.8 (m, 2H), 2.85-3.00 (m, 2H), 6.92 (d, 1H, J=8.1 Hz), 6.95-7.05 (m, 3H), 7.11 (dd, 1H, J=8.4 Hz), 7.31 (d, 1H, J=8.1 Hz).

(3) Synthesis of 4-(4-{1-ethyl-1-[3-methyl-4-(4,4,5,5-tetramethyl-[1,3,2]dioxaborolan-2-yl)-phenyl]-propyl}-2-methyl-phenylethynyl)-tetrahydro-thiopyran-4-ol

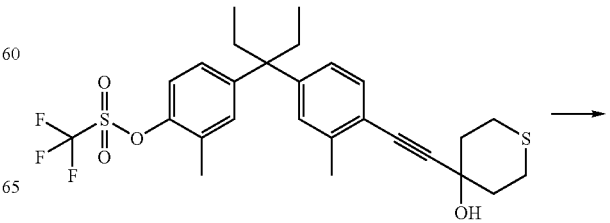

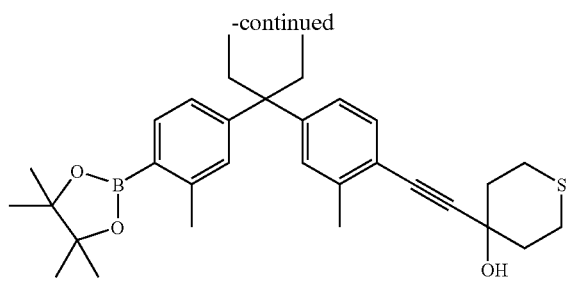

A solution of trifluoromethanesulfonic acid 4-{1-ethyl-1-[4-(4-hydroxy-tetrahydro-thiopyran-4-ylethynyl)-3-methyl-phenyl]-propyl}-2-methyl-phenyl ester (Example 136-(2); 0.66 g, 1.2 mmol), diphenylphosphinoferrocene (41 mg, 0.07 mmol), a [1,1'-bis(diphenylphosphino)ferrocene]dichloropalladium (II), dichloromethane complex (1:1) (60 mg, 0.07 mmol), potassium acetate (0.36 g, 3.6 mmol) and bis(pinacolato)diboron (0.4 g, 1.6 mmol) in dioxane (3.6 mL) was stirred in a nitrogen atmosphere at 110° C. for five hours. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=100:0 to 25:75) to give the title compound (0.54 g, 85%).

$^1$H-NMR (chloroform-d): 0.58 (t, 6H, J=7.4 Hz), 1.32 (s, 12H), 1.9-2.1 (m, 6H), 2.25-2.35 (m, 2H), 2.37 (s, 3H), 2.47 (s, 3H), 2.7-2.8 (m, 2H), 2.85-3.00 (m, 2H), 6.9-7.0 (m, 4H), 7.25-7.3 (m, 1H), 7.63 (d, 1H, J=7.7 Hz).

(4) Synthesis of 2-(4-{1-ethyl-1-[3-methyl-4-(4-trimethylsilanyloxy-tetrahydro-thiopyran-4-ylethynyl)-phenyl]-propyl}-2-methyl-phenyl)-4,4,5,5-tetramethyl-[1,3,2]dioxaborolane

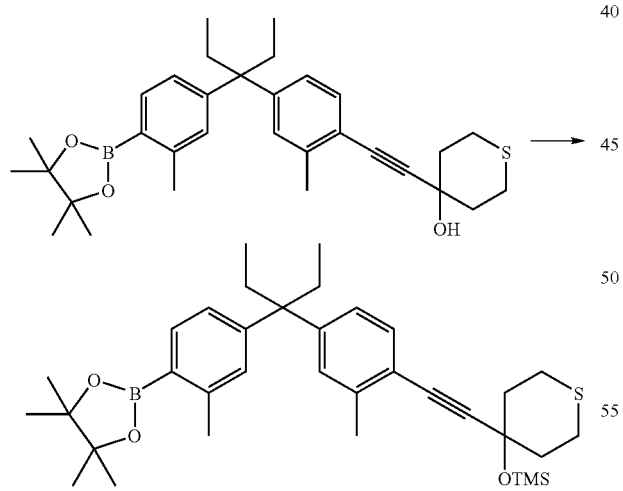

2,6-Lutidine (0.76 mL, 5 mmol) was added to a solution of 4-(4-{1-ethyl-1-[3-methyl-4-(4,4,5,5-tetramethyl-[1,3,2]dioxaborolan-2-yl)-phenyl]-propyl}-2-methyl-phenylethynyl)-tetrahydro-thiopyran-4-ol (Example 136-(3); 0.53 g, 1 mmol) in dichloromethane (5 mL). Trimethylsilyl triflate (0.32 mL, 2.5 mmol) was added at 0° C., and the mixture was stirred at the same temperature for four hours. Water was added to the reaction mixture, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the title compound (0.51 g, 84%).

$^1$H-NMR (chloroform-d): 0.001 (s, 9H), 0.60 (t, 6H, J=7.0 Hz), 1.33 (s, 12H), 1.95-2.15 (m, 6H), 2.25-2.35 (m, 2H), 2.37 (s, 3H), 2.48 (s, 3H), 2.7-2.8 (m, 2H), 2.8-2.9 (m, 2H), 6.9-7.0 (m, 4H), 7.24-7.28 (m, 1H), 7.64 (d, 2H, J=7.7 Hz).

(5) Synthesis of (4'-{1-ethyl-1-[3-methyl-4-(4-trimethylsilanyloxy-tetrahydro-thiopyran-4-ylethynyl)-phenyl]-propyl}-2'-methyl-biphenyl-4-yl)-acetic Acid Methyl Ester

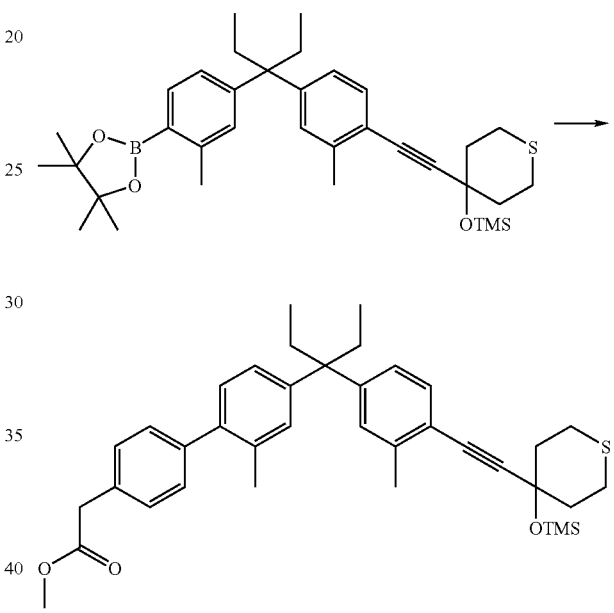

(4-Bromo-phenyl)acetic acid methyl ester (35 mg, 0.15 mmol), palladium acetate (2.3 mg, 0.01 mmol), 2-dicyclohexylphosphino-2',6'-dimethoxy-1,1'-biphenyl (8.3 mg, 0.02 mmol), potassium phosphate (65 mg, 0.3 mmol) and water (0.2 mL) were added to a solution of 2-(4-{1-ethyl-1-[3-methyl-4-(4-trimethylsilanyloxy-tetrahydro-thiopyran-4-ylethynyl)-phenyl]-propyl}-2-methyl-phenyl)-4,4,5,5-tetramethyl-[1,3,2]dioxaborolane (Example 136-(4); 60 mg, 0.1 mmol) in toluene (2 mL). The mixture was stirred in a nitrogen atmosphere at 110° C. for two hours. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=1:1) to give the target compound as a colorless oil (55 mg, 88%).

$^1$H-NMR (chloroform-d): 0.23 (s, 9H), 0.65 (t, 6H, J=7.5 Hz), 1.96-2.06 (m, 2H), 2.11 (q, 4H, J=7.5 Hz) 2.16-2.22 (m, 2H), 2.23 (s, 3H), 2.41 (s, 3H), 2.7-2.8 (m, 2H), 2.8-2.9 (2H, m), 3.67 (s, 2H), 3.72 (s, 3H), 6.95-7.04 (m, 3H), 7.06-7.12 (m, 2H), 7.28-7.34 (m, 5H).

(6) Synthesis of (4'-{1-ethyl-1-[4-(4-hydroxy-tetrahydro-thiopyran-4-ylethynyl)-3-methyl-phenyl]-propyl}-2'-methyl-biphenyl-4-yl)-acetic Acid Methyl Ester

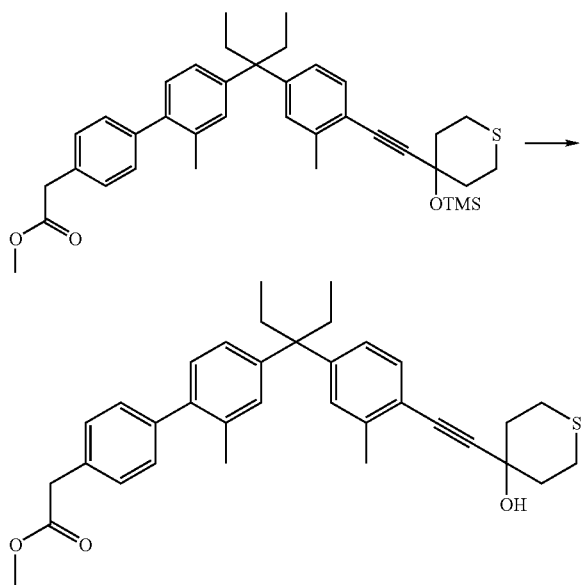

Tetrabutylammonium fluoride (1 M solution in tetrahydrofuran, 0.13 mL, 0.13 mmol) was added to a solution of (4'-{1-ethyl-1-[3-methyl-4-(4-trimethylsilanyloxy-tetrahydro-thiopyran-4-ylethynyl)-phenyl]-propyl}-2'-methyl-biphenyl-4-yl)-acetic acid methyl ester (Example 136-(5); 53 mg, 0.09 mmol) in tetrahydrofuran (1 mL) at 0° C., and the mixture was stirred at the same temperature for 30 minutes. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=1:1) to give the target compound as a colorless oil (35 mg, 78%).

¹H-NMR (chloroform-d): 0.64 (t, 6H, J=7.3 Hz), 1.96-2.06 (m, 2H), 2.11 (q, 4H, J=7.5 Hz) 2.22 (s, 3H), 2.24-2.34 (m, 2H), 2.41 (s, 3H), 2.7-2.8 (m, 2H), 2.9-3.0 (m, 2H), 3.67 (s, 2H), 3.73 (s, 3H), 6.96-7.02 (m, 3H), 7.06-7.1 (m, 2H), 7.26-7.32 (m, 5H).

(7) Synthesis of (4'-{1-ethyl-1-[4-(4-hydroxy-tetrahydro-thiopyran-4-ylethynyl)-3-methyl-phenyl]-propyl}-2'-methyl-biphenyl-4-yl)-acetic Acid

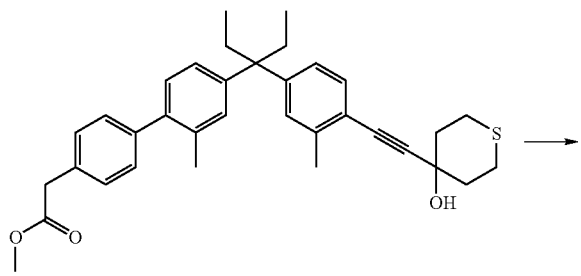

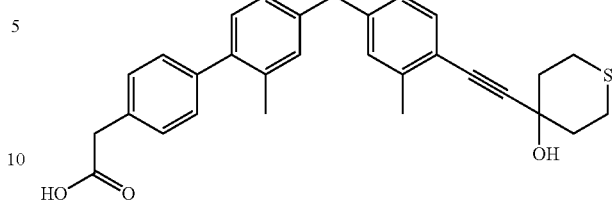

A 1 N sodium hydroxide aqueous solution (0.1 mL, 0.1 mmol) was added to a solution of (4'-{1-ethyl-1-[4-(4-hydroxy-tetrahydro-thiopyran-4-ylethynyl)-3-methyl-phenyl]-propyl}-2'-methyl-biphenyl-4-yl)-acetic acid methyl ester (Example 136-(6); 35 mg, 0.065 mmol) in methanol-tetrahydrofuran (1:1, 2 mL), and the mixture was stirred at room temperature for 13 hours. A 30% sodium dihydrogenphosphate aqueous solution was added to the reaction mixture, followed by extraction with ethyl acetate. The organic layer was dried over anhydrous magnesium sulfate, filtered and concentrated under reduced pressure. The resulting residue was purified by silica gel chromatography (dichloromethane:methanol=20:1) to give the target compound as a colorless oil (30 mg, 88%).

¹H-NMR (chloroform-d): 0.63 (t, 6H, J=7.3 Hz), 1.96-2.06 (m, 2H), 2.11 (q, 4H, J=7.3 Hz) 2.22 (s, 3H), 2.24-2.34 (m, 2H), 2.41 (s, 3H), 2.7-2.8 (m, 2H), 2.9-3.0 (m, 2H), 3.71 (s, 2H), 6.96-7.02 (m, 3H), 7.06-7.1 (m, 2H), 7.26-7.36 (m, 5H); MS (ESI-): 525 ([M-H]⁻).

Example 137

Synthesis of [5-(4-{1-ethyl-1-[4-(4-hydroxy-tetrahydro-thiopyran-4-ylethynyl)-3-methyl-phenyl]-propyl}-2-methyl-phenyl)-pyridin-3-yl]-acetic Acid

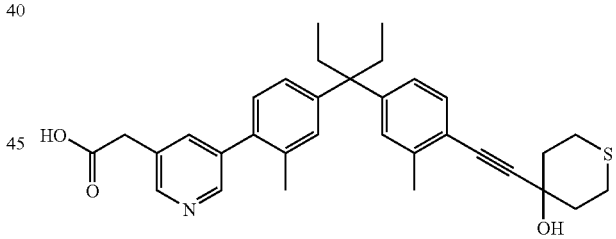

(1) Synthesis of [5-(4-{1-ethyl-1-[3-methyl-4-(4-trimethylsilanyloxy-tetrahydro-thiopyran-4-ylethynyl)-phenyl]-propyl}-2-methyl-phenyl)-pyridin-3-yl]-acetic Acid Methyl Ester

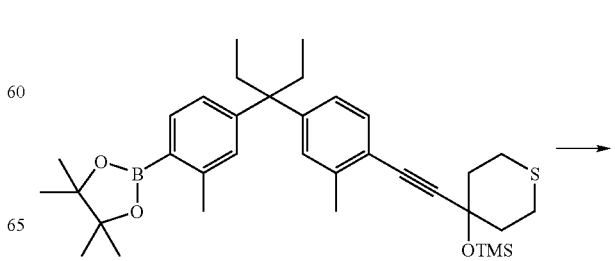

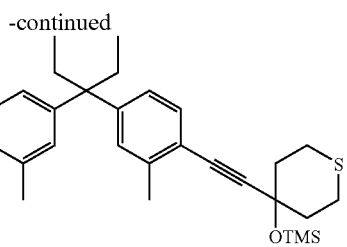

(5-Bromo-pyridin-3-yl)acetic acid methyl ester (Example 24-(2); 58 mg, 0.25 mmol), palladium acetate (3.8 mg, 0.017 mmol), 2-dicyclohexylphosphino-2',6'-dimethoxybiphenyl (14 mg, 0.034 mmol), potassium phosphate (108 mg, 0.51 mmol) and water (0.4 mL) were added to a solution of 2-(4-{1-ethyl-1-[3-methyl-4-(4-trimethylsilanyloxy-tetrahydro-thiopyran-4-ylethynyl)-phenyl]-propyl}-2-methyl-phenyl)-4,4,5,5-tetramethyl-[1,3,2]dioxaborolane (Example 136-(4); 100 mg, 0.17 mmol) in toluene (4 mL). The mixture was stirred in a nitrogen atmosphere at 110° C. for two hours. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=1:3) to give the title compound (82 mg, 79%).

$^1$H-NMR (chloroform-d): 0.23 (s, 9H), 0.65 (t, 6H, J=7.3 Hz), 1.96-2.06 (m, 2H), 2.12 (q, 4H, J=7.3 Hz) 2.16-2.24 (m, 2H), 2.24 (s, 3H), 2.41 (s, 3H), 2.7-2.8 (m, 2H), 2.8-2.9 (m, 2H), 3.67 (s, 2H), 3.72 (s, 3H), 6.96-7.12 (m, 5H), 7.30 (d, 1H, J=8.0 Hz), 7.60-7.64 (m, 1H), 8.47 (d, 1H, J=1.8 Hz), 8.52 (d, 1H, J=1.8 Hz).

(2) Synthesis of [5-(4-{1-ethyl-1-[4-(4-hydroxy-tetrahydro-thiopyran-4-ylethynyl)-3-methyl-phenyl]-propyl}-2-methyl-phenyl)-pyridin-3-yl]-acetic Acid Methyl Ester

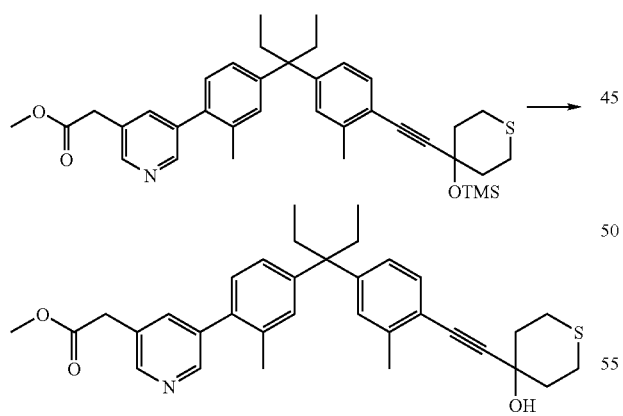

Tetrabutylammonium fluoride (1 M solution in tetrahydrofuran, 0.2 mL, 0.2 mmol) was added to a solution of [5-(4-{1-ethyl-1-[3-methyl-4-(4-trimethylsilanyloxy-tetrahydro-thiopyran-4-ylethynyl)-phenyl]-propyl}-2-methyl-phenyl)-pyridin-3-yl]-acetic acid methyl ester (Example 137-(1); 82 mg, 0.13 mmol) in tetrahydrofuran (1 mL) at 0° C., and the mixture was stirred at the same temperature for 30 minutes. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=1:3) to give the target compound as a colorless oil (50 mg, 69%).

$^1$H-NMR (chloroform-d): 0.65 (t, 6H, J=7.3 Hz), 1.96-2.06 (m, 2H), 2.12 (q, 4H, J=7.3 Hz) 2.23 (s, 3H), 2.25-2.33 (m, 2H), 2.41 (s, 3H), 2.7-2.8 (m, 2H), 2.88-2.99 (m, 2H), 3.68 (s, 2H), 3.73 (s, 3H), 6.97-7.12 (m, 5H), 7.31 (d, 1H, J=8.1 Hz), 7.26-7.32 (m, 5H), 7.61-7.64 (m, 1H), 8.47 (d, 1H, J=2.2 Hz), 8.52 (d, 1H, J=2.2 Hz).

(3) Synthesis of [5-(4-{1-ethyl-1-[4-(4-hydroxy-tetrahydro-thiopyran-4-ylethynyl)-3-methyl-phenyl]-propyl}-2-methyl-phenyl)-pyridin-3-yl]-acetic Acid

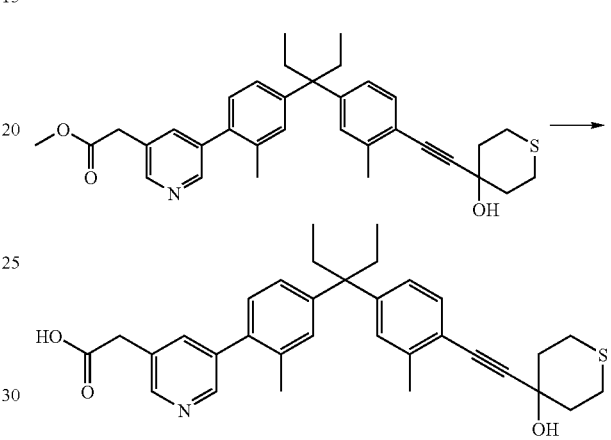

A 1 N sodium hydroxide aqueous solution (0.28 mL, 0.28 mmol) was added to a solution of [5-(4-{1-ethyl-1-[4-(4-hydroxy-tetrahydro-thiopyran-4-ylethynyl)-3-methyl-phenyl]-propyl}-2-methyl-phenyl)-pyridin-3-yl]-acetic acid methyl ester (Example 137-(2); 50 mg, 0.09 mmol) in methanol-tetrahydrofuran (1:1, 2 mL), and the mixture was stirred at room temperature for five hours. The reaction mixture was concentrated under reduced pressure. The resulting residue was purified by silica gel chromatography (ethyl acetate:methanol=5:2) to give the target compound as a colorless oil (22 mg, 45%).

$^1$H-NMR (chloroform-d): 0.61 (t, 6H, J=7.0 Hz), 1.96-2.12 (m, 6H), 2.09 (s, 3H), 2.22-2.32 (m, 2H), 2.34 (s, 3H), 2.66-2.76 (m, 2H), 2.86-2.96 (m, 2H), 3.47 (s, 2H), 6.86-7.03 (m, 5H), 7.20 (d, 1H, J=8.0 Hz), 7.51 (brs, 1H), 8.38 (brs, 1H), 8.39 (brs, 1H); MS (ESI−): 526 ([M−H]$^−$).

Example 138

Synthesis of [4'-(1-ethyl-1-{4-[(E)-2-(4-hydroxy-tetrahydro-thiopyran-4-yl)-vinyl]-3-methyl-phenyl}-propyl)-2'-methyl-biphenyl-4-yl]-acetic Acid

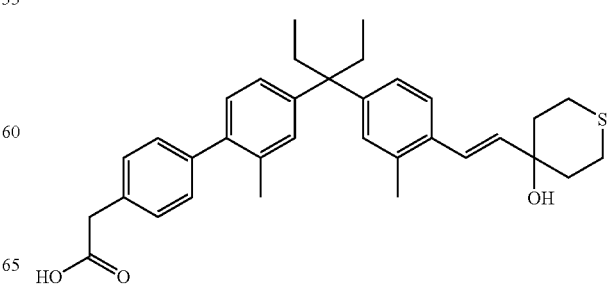

(1) Synthesis of 4-((E)-2-{4-[1-ethyl-1-(4-hydroxy-3-methyl-phenyl)-propyl]-2-methyl-phenyl}-vinyl)-tetrahydro-thiopyran-4-ol

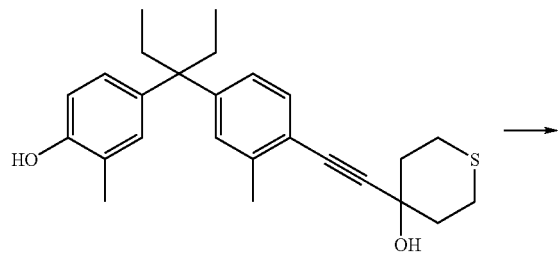

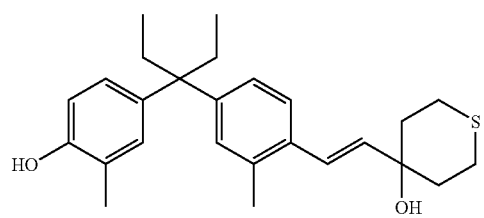

Sodium bis(2-methoxyethoxy)aluminum hydride (65 wt % solution in toluene, 1.2 mL, 4 mmol) was added to a solution of 4-{4-[1-ethyl-1-(4-hydroxy-3-methyl-phenyl)-propyl]-2-methyl-phenylethynyl}-tetrahydro-thiopyran-4-ol (Example 136-(1); 0.54 g, 1.3 mmol) in tetrahydrofuran (6 mL) in a nitrogen atmosphere at 0° C., and the mixture was stirred at 0° C. for five hours. Then, ethyl acetate and brine were added to the reaction mixture, which was further diluted with ethyl acetate. Thereafter, celite was added and the mixture was stirred at room temperature for 30 minutes. The reaction mixture was filtered through celite, and the filtrate was concentrated under reduced pressure. The resulting residue was purified by silica gel chromatography (hexane:ethyl acetate=100:0 to 25:75) to give the target compound as a colorless oil (0.5 g, 92%).

$^1$H-NMR (chloroform-d): 0.60 (t, 6H, J=7.3 Hz), 1.94-2.0 (m, 4H), 2.04 (q, 4H, J=7.3 Hz), 2.19 (s, 3H), 2.30 (s, 3H), 2.46-2.54 (m, 2H), 3.0-3.14 (m, 2H), 4.53 (s, 1H), 6.16 (d, 1H, J=16.0 Hz), 6.65 (d, 1H, J=8.4 Hz), 6.81 (d, 1H, J=16.0 Hz), 6.86 (dd, 1H, J=2.2, 8.4 Hz), 6.89 (brs, 1H), 6.94-7.0 (m, 2H), 7.30 (d, 1H, J=8.8 Hz).

(2) Synthesis of Trifluoromethanesulfonic Acid 4-(1-ethyl-1-{4-[(E)-2-(4-hydroxy-tetrahydro-thiopyran-4-yl)-vinyl]-3-methyl-phenyl}-propyl)-2-methyl-phenyl Ester

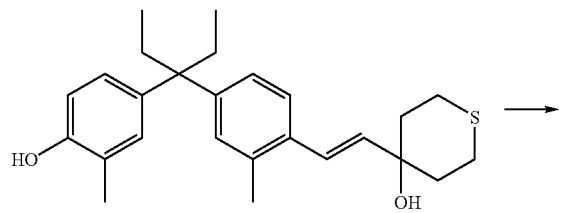

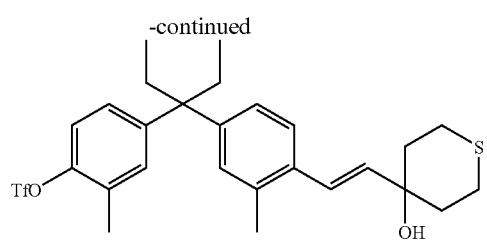

Triethylamine (0.34 mL, 2.4 mmol) and N-phenylbis(trifluoromethanesulfonimide) (0.65 g, 1.8 mmol) were added to a solution of 4-((E)-2-{4-[1-ethyl-1-(4-hydroxy-3-methyl-phenyl)-propyl]-2-methyl-phenyl}-vinyl)-tetrahydro-thiopyran-4-ol (Example 138-(1); 0.5 g, 1.2 mmol) in dichloromethane (6 mL) at room temperature, and the mixture was stirred for five hours. Water was added to the reaction mixture, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 25:75) to give the target compound (0.65 g, 98%).

$^1$H-NMR (chloroform-d): 0.61 (t, 6H, J=7.3 Hz), 1.94-2.0 (m, 4H), 2.07 (4H, q, J=7.3 Hz), 2.31 (s, 3H), 2.32 (s, 3H), 2.46-2.54 (m, 2H), 3.0-3.12 (m, 2H), 6.17 (d, 1H, J=16.1 Hz), 6.81 (d, 1H, J=16.1 Hz), 6.9-6.96 (m, 2H), 7.0-7.12 (m, 3H), 7.32 (d, 1H, J=8.8 Hz).

(3) Synthesis of 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydro-thiopyran-4-ol

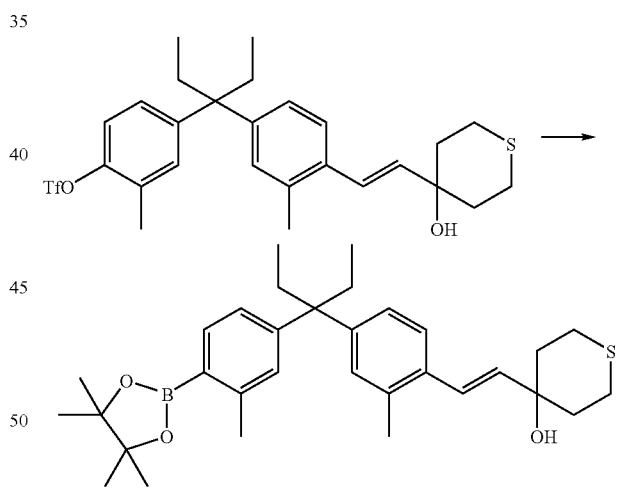

A solution of trifluoromethanesulfonic acid 4-(1-ethyl-1-{4-[(E)-2-(4-hydroxy-tetrahydro-thiopyran-4-yl)-vinyl]-3-methyl-phenyl}-propyl)-2-methyl-phenyl ester (Example 138-(2); 0.65 g, 1.2 mmol), diphenylphosphinoferrocene (41 mg, 0.07 mmol), a [1,1'-bis(diphenylphosphino)ferrocene]dichloropalladium (II), dichloromethane complex (1:1) (60 mg, 0.07 mmol), potassium acetate (0.36 g, 3.6 mmol) and bis(pinacolato)diboron (0.4 g, 1.6 mmol) in dioxane (3.6 mL) was stirred in a nitrogen atmosphere at 110° C. for five hours. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=100:0 to 25:75) to give the title compound (0.3 g, 49%).

¹H-NMR (chloroform-d): 0.59 (t, 6H, J=7.3 Hz), 1.32 (s, 12H), 1.9-2.0 (m, 4H), 2.06 (q, 4H, J=7.3 Hz), 2.27 (s, 3H), 2.4-2.45 (m, 2H), 2.46 (s, 3H), 3.0-3.1 (m, 2H), 6.14 (d, 1H, J=16.0 Hz), 6.81 (d, 1H, J=16.0 Hz), 6.9-7.0 (m, 4H), 7.25-7.3 (m, 1H), 7.62 (d, 1H, J=7.7 Hz).

(4) Synthesis of [4'-(1-ethyl-1-{4-[(E)-2-(4-hydroxy-tetrahydro-thiopyran-4-yl)-vinyl]-3-methyl-phenyl}-propyl)-2'-methyl-biphenyl-4-yl]-acetic Acid Methyl Ester

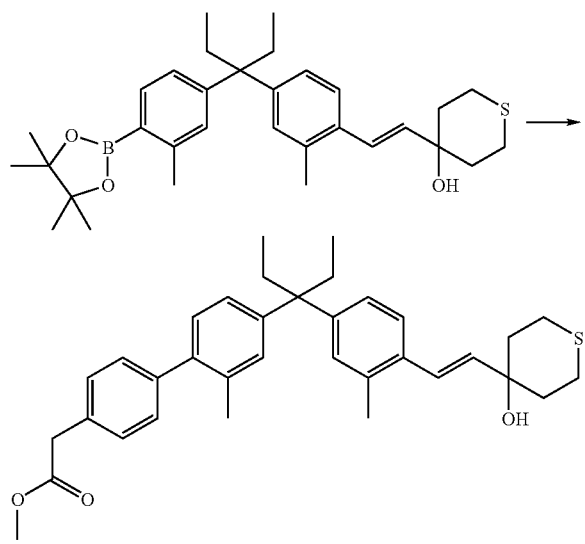

(4-Bromo-phenyl)acetic acid methyl ester (33 mg, 0.11 mmol), palladium acetate (2.2 mg, 0.0096 mmol), 2-dicyclohexylphosphino-2',6'-dimethoxy-1,1'-biphenyl (7.9 mg, 0.019 mmol), potassium phosphate (61 mg, 0.29 mmol) and water (0.2 mL) were added to a solution of 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydro-thiopyran-4-ol (Example 138-(3); 50 mg, 0.096 mmol) in toluene (2 mL). The mixture was stirred in a nitrogen atmosphere at 110° C. for two hours. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=1:1) to give the target compound as a colorless oil (20 mg, 38%).

¹H-NMR (chloroform-d): 0.65 (t, 6H, J=7.3 Hz), 1.9-2.0 (m, 4H), 2.11 (q, 4H, J=7.3 Hz) 2.22 (s, 3H), 2.33 (s, 3H), 2.4-2.5 (m, 2H), 3.0-3.1 (2H, m), 3.67 (s, 2H), 3.72 (s, 3H), 6.17 (d, 1H, J=16.0 Hz), 6.83 (d, 1H, J=16.0 Hz), 6.95-7.15 (m, 5H), 7.2-7.4 (m, 5H).

(5) Synthesis of [4'-(1-ethyl-1-{4-[(E)-2-(4-hydroxy-tetrahydro-thiopyran-4-yl)-vinyl]-3-methyl-phenyl}-propyl)-2'-methyl-biphenyl-4-yl]-acetic Acid

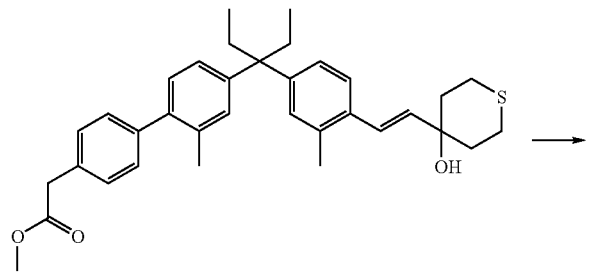

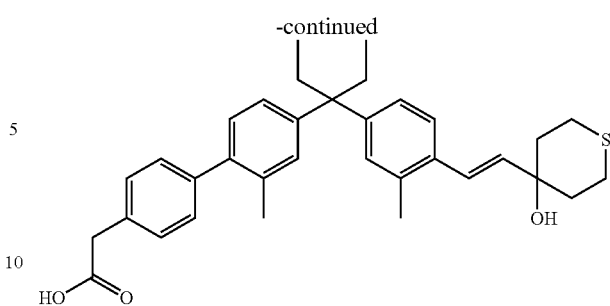

A 1 N sodium hydroxide aqueous solution (0.11 mL, 0.11 mmol) was added to a solution of [4'-(1-ethyl-1-{4-[(E)-2-(4-hydroxy-tetrahydro-thiopyran-4-yl)-vinyl]-3-methyl-phenyl}-propyl)-2'-methyl-biphenyl-4-yl]-acetic acid methyl ester (Example 138-(4); 20 mg, 0.037 mmol) in methanol-tetrahydrofuran (1:1, 2 mL), and the mixture was stirred at room temperature for 14 hours. The reaction mixture was concentrated under reduced pressure. The resulting residue was purified by silica gel chromatography (dichloromethane:methanol=10:1) to give the target compound as a colorless oil (15 mg, 77%).

¹H-NMR (chloroform-d): 0.65 (t, 6H, J=7.3 Hz), 1.9-2.0 (m, 4H), 2.11 (q, 4H, J=7.3 Hz) 2.22 (s, 3H), 2.32 (s, 3H), 2.4-2.55 (m, 2H), 3.0-3.1 (m, 2H), 3.69 (s, 2H), 6.17 (d, 1H, J=16.1 Hz), 6.82 (d, 1H, J=16.1 Hz), 6.95-7.1 (m, 5H), 7.2-7.4 (m, 5H); MS (ESI−): 527 ([M−H]⁻).

Example 139

Synthesis of {5-[4-(1-ethyl-1-{4-[(E)-2-(4-hydroxy-tetrahydro-thiopyran-4-yl)-vinyl]-3-methyl-phenyl}-propyl)-2-methyl-phenyl]-pyridin-3-yl}-acetic Acid

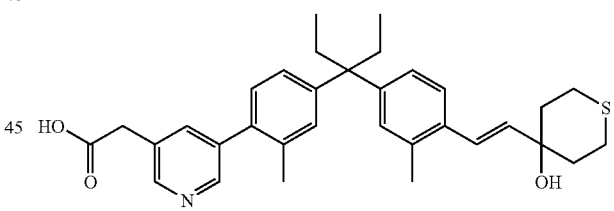

(1) Synthesis of {5-[4-(1-ethyl-1-{4-[(E)-2-(4-hydroxy-tetrahydro-thiopyran-4-yl)-vinyl]-3-methyl-phenyl}-propyl)-2-methyl-phenyl]-pyridin-3-yl}-acetic Acid Methyl Ester

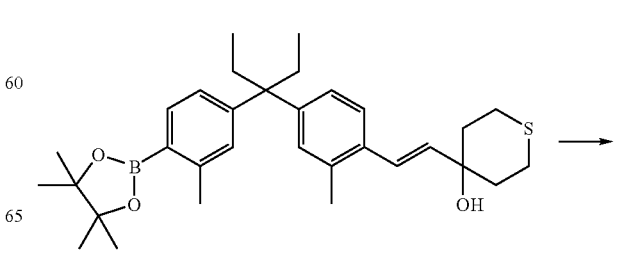

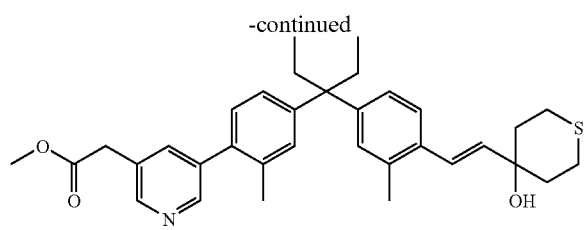

(5-Bromo-pyridin-3-yl)acetic acid methyl ester (Example 24-(2); 35 mg, 0.14 mmol), palladium acetate (2.2 mg, 0.01 mmol), 2-dicyclohexylphosphino-2',6'-dimethoxybiphenyl (7.9 mg, 0.019 mmol), potassium phosphate (61 mg, 0.29 mmol) and water (0.2 mL) were added to a solution of 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydro-thiopyran-4-ol (Example 138-(3); 50 mg, 0.096 mmol) in toluene (2 mL). The mixture was stirred in a nitrogen atmosphere at 110° C. for two hours. Water was added to the reaction mixture, followed by extraction with ethyl acetate. The organic layer was dried over anhydrous magnesium sulfate, filtered and concentrated under reduced pressure. The resulting residue was purified by silica gel chromatography (hexane:ethyl acetate=1:2) to give the title compound (20 mg, 38%).

¹H-NMR (chloroform-d): 0.65 (t, 6H, J=7.0 Hz), 1.9-2.0 (m, 4H), 2.12 (q, 4H, J=7.0 Hz) 2.24 (s, 3H), 2.33 (s, 3H), 2.46-2.54 (m, 2H), 3.0-3.12 (m, 2H), 3.68 (s, 2H), 3.73 (s, 3H), 6.18 (d, 1H, J=15.8 Hz), 6.83 (d, 1H, J=15.8 Hz), 6.98-7.12 (m, 5H), 7.34 (d, 1H, J=8.8 Hz), 7.62 (brs, 1H), 8.47 (brs, 1H), 8.52 (brs, 1H).

(2) Synthesis of {5-[4-(1-ethyl-1-{4-[(E)-2-(4-hydroxy-tetrahydro-thiopyran-4-yl)-vinyl]-3-methyl-phenyl}-propyl)-2-methyl-phenyl]-pyridin-3-yl}-acetic Acid

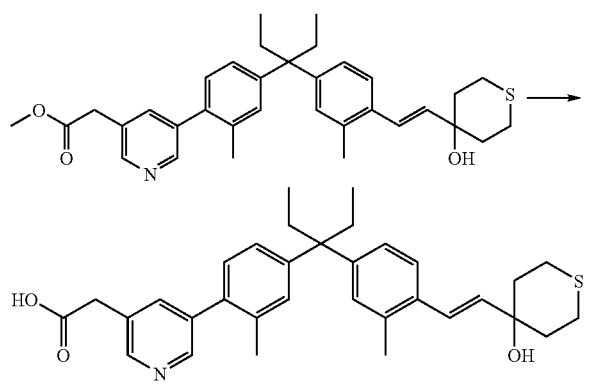

A 1 N sodium hydroxide aqueous solution (0.28 mL, 0.28 mmol) was added to a solution of {5-[4-(1-ethyl-1-{4-[(E)-2-(4-hydroxy-tetrahydro-thiopyran-4-yl)-vinyl]-3-methyl-phenyl}-propyl)-2-methyl-phenyl]-pyridin-3-yl}-acetic acid methyl ester (Example 139-(1); 50 mg, 0.09 mmol) in methanol-tetrahydrofuran (1:1, 2 mL), and the mixture was stirred at room temperature for five hours. The reaction mixture was concentrated under reduced pressure. The resulting residue was purified by silica gel chromatography (ethyl acetate: methanol=5:2) to give the target compound as a colorless oil (22 mg, 45%).

¹H-NMR (chloroform-d): 0.61 (t, 6H, J=7.0 Hz), 1.85-2.0 (m, 4H), 2.0-2.15 (m, 7H), 2.24 (s, 3H), 2.4-2.5 (m, 2H), 3.0-3.1 (m, 2H), 3.43 (s, 2H), 6.13 (d, 1H, J=16.0 Hz), 6.77 (d, 1H, J=16.0 Hz), 6.86-7.02 (m, 5H), 7.22-7.28 (m, 1H), 7.46 (brs, 1H), 8.31 (brs, 1H), 8.35 (brs, 1H); MS (ESI–): 528 ([M–H]⁻).

Example 140

Synthesis of {5-[4-(1-ethyl-1-{4-[2-(4-hydroxy-tetrahydro-thiopyran-4-yl)-ethyl]-3-methyl-phenyl}-propyl)-2-methyl-phenyl]-pyridin-3-yl}-acetic Acid Ammonium formate (100 mg, 1.6 mmol) and Pd/C (30 mg) were added to a solution of [5-(4-{1-ethyl-1-[4-(4-hydroxy-tetrahydrothiopyran-4-ylethynyl)-3-methyl-phenyl]-propyl}-2-methyl-phenyl)-pyridin-3-yl]-acetic acid (Example 137-(3); 5 mg, 0.01 mmol) in ethanol, and the mixture was stirred with microwave heating at 130° C. for 10 minutes. The reaction mixture was filtered through celite, and the filtrate was concentrated under reduced pressure. The residue was purified by thin layer silica gel chromatography (dichloromethane/methanol=10/1) to give the title compound (3.5 mg, 70%).

¹H-NMR (chloroform-d): 0.64 (6H, t, J=7.2 Hz), 1.82-2.16 (m, 8H), 2.22 (s, 3H), 2.40 (s, 3H), 3.70-3.80 (m, 4H), 3.90-4.00 (m, 2H), 6.97-7.38 (m, 9H); MS (ESI+): 532 ([M+H]⁺).

Example 141

Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid

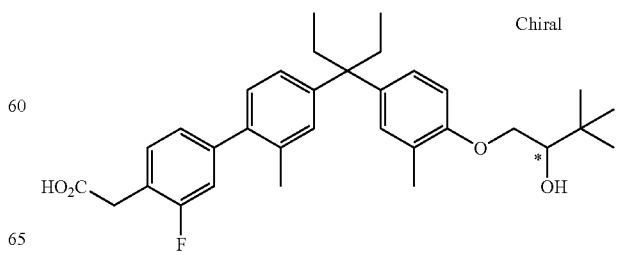

(1) Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid Methyl Ester

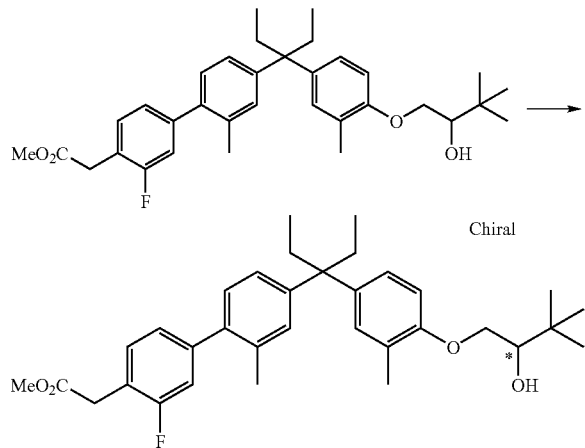

Racemic (4'-{1-ethyl-1-[4-(2-hydroxy-3,3-dimethyl-butoxy)-3-methyl-phenyl]-propyl}-3-fluoro-2'-methyl-biphenyl-4-yl)acetic acid methyl ester (Example 100-(1); 86.8 mg, 0.162 mmol) was optically resolved by high performance liquid chromatography (Daicel Chemical Industries CHIRALPAK AD, 20 mm I.D.×250 mm, hexane:isopropanol=85:15, 20 mL/min) to give the target compound as a colorless oil which is an eluate with a retention time of 5.6 minutes (33.0 mg, 38%, >99.8% e.e.).

$^1$H-NMR (chloroform-d): 0.64 (t, 6H, J=7.2 Hz), 1.01 (s, 9H), 2.09 (q, 4H, J=7.2 Hz), 2.20 (s, 3H), 2.23 (s, 3H), 2.46 (s, 1H), 3.69-3.73 (m, 3H), 3.74 (s, 3H), 3.87 (t, 1H, J=9.0 Hz), 4.10 (dd, 1H, J=9.0, 2.6 Hz), 6.73 (d, 1H, J=8.4 Hz), 6.95-7.10 (m, 7H), 7.28-7.30 (m, 1H); MS (ESI+): 552.3 ([M+NH$_4$]$^+$); MS (ESI−): 533.4 ([M−H]$^-$).

(2) Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid A 2 N sodium hydroxide aqueous solution (0.20 mL) was added to a solution of optically active (4'-{1-ethyl-1-[4-(2-hydroxy-3,3-dimethyl-butoxy)-3-methyl-phenyl]-propyl}-3-fluoro-2'-methyl-biphenyl-4-yl)-acetic acid methyl ester (Example 141-(1); 33.0 mg, 38%, >99.8% e.e.) in methanol (1.0 mL), and the mixture was stirred with microwave heating at 100° C. for five minutes. A 2 N hydrochloric acid aqueous solution (0.30 mL) was added to the reaction mixture, followed by extraction with ethyl acetate and washing with brine. The organic layer was dried over anhydrous magnesium sulfate, filtered and concentrated under reduced pressure. The resulting residue was purified by silica gel chromatography (dichloromethane:methanol=100:0 to 90:10) to give the target compound as a colorless oil (33.2 mg, 100%).

$^1$H-NMR (methanol-d): 0.63 (t, 6H, J=7.2 Hz), 1.00 (s, 9H), 2.11 (q, 4H, J=7.2 Hz), 2.17 (s, 3H), 2.20 (s, 3H), 3.62 (dd, 1H, J=7.7, 3.0 Hz), 3.67 (s, 2H), 3.87 (dd, 1H, J=10.0, 7.7 Hz), 4.11 (dd, 1H, J=10.0, 2.9 Hz), 6.77 (d, 1H, J=8.5 Hz), 6.88-6.91 (m, 1H), 6.96-7.09 (m, 6H), 7.32 (t, 1H, J=8.0 Hz); MS (ESI+): 538.2 ([M+NH$_4$]$^+$); MS (ESI−): 519.4 ([M−H]$^-$).

Example 142

Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid

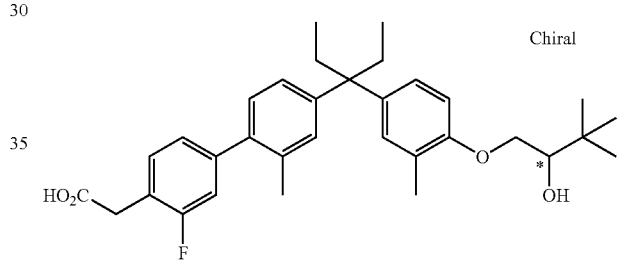

(1) Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid Methyl Ester

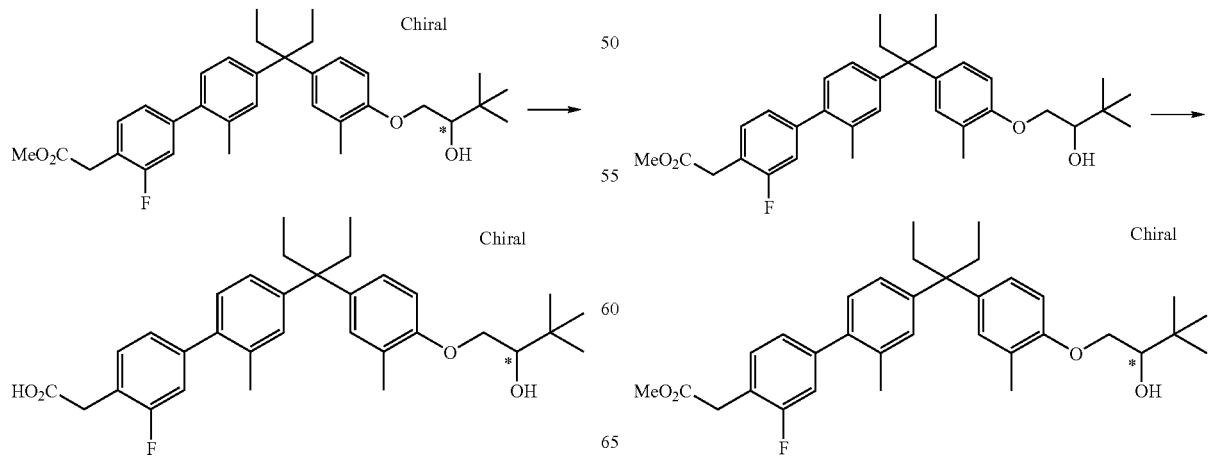

Racemic (4'-{1-ethyl-1-[4-(2-hydroxy-3,3-dimethyl-butoxy)-3-methyl-phenyl]-propyl}-3-fluoro-2'-methyl-biphenyl-4-yl)acetic acid methyl ester (Example 100-(1); 86.8 mg, 0.162 mmol) was optically resolved by high performance liquid chromatography (Daicel Chemical Industries CHIRALPAK AD, 20 mm I.D.×250 mm, hexane:isopropanol=85:15, 20 mL/min: Example 141-(1)) to give the target compound as a colorless oil which is an eluate with a retention time of 7.3 minutes (32.8 mg, 38%, >99.7% e.e.).

¹H-NMR (chloroform-d): 0.64 (t, 6H, J=7.2 Hz), 1.01 (s, 9H), 2.09 (q, 4H, J=7.2 Hz), 2.20 (s, 3H), 2.23 (s, 3H), 2.46 (s, 1H), 3.68-3.73 (m, 3H), 3.74 (s, 3H), 3.87 (t, 1H, J=9.1 Hz), 4.10 (dd, 1H, J=9.1, 2.6 Hz), 6.73 (d, 1H, J=8.4 Hz), 6.95-7.10 (m, 7H), 7.28-7.30 (m, 1H); MS (ESI+): 552.3 ([M+NH₄]⁺); MS (ESI−): 533.4 ([M−H]⁻).

(2) Synthesis of (4'-{1-ethyl-1-[4-(2-hydroxy-3,3-dimethyl-butoxy)-3-methyl-phenyl]-propyl}-3-fluoro-2'-methyl-biphenyl-4-yl)-acetic Acid

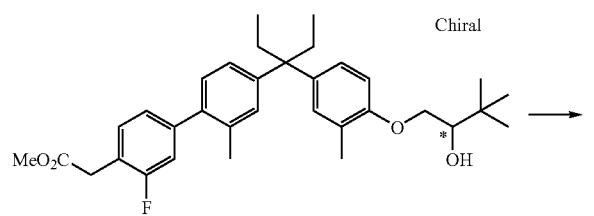

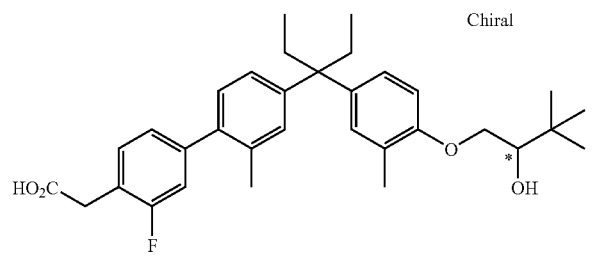

A 2 N sodium hydroxide aqueous solution (0.20 mL) was added to a solution of optically active (4'-{1-ethyl-1-[4-(2-hydroxy-3,3-dimethyl-butoxy)-3-methyl-phenyl]-propyl}-3-fluoro-2'-methyl-biphenyl-4-yl)-acetic acid methyl ester (Example 142-(1); 32.8 mg, 38%, >99.7% e.e.) in methanol (1.0 mL), and the mixture was stirred with microwave heating at 100° C. for five minutes. A 2 N hydrochloric acid aqueous solution (0.30 mL) was added to the reaction mixture, followed by extraction with ethyl acetate and washing with brine. The organic layer was dried over anhydrous magnesium sulfate, filtered and concentrated under reduced pressure. The resulting residue was purified by silica gel chromatography (dichloromethane:methanol=99:1 to 90:10) to give the target compound as a colorless oil (32.4 mg, 100%).

¹H-NMR (methanol-d): 0.63 (t, 6H, J=7.3 Hz), 1.00 (s, 9H), 2.11 (q, 4H, J=7.3 Hz), 2.17 (s, 3H), 2.20 (s, 3H), 3.62 (dd, 1H, J=7.7, 3.0 Hz), 3.68 (s, 2H), 3.87 (dd, 1H, J=10.0, 7.7 Hz), 4.11 (dd, 1H, J=10.0, 2.9 Hz), 6.77 (d, 1H, J=8.8 Hz), 6.88-6.92 (m, 1H), 6.96-7.09 (m, 6H), 7.32 (t, 1H, J=8.0 Hz); MS (ESI+): 538.3 ([M+NH₄]⁺); MS (ESI−): 519.4 ([M−H]⁻).

Example 143

Synthesis of [5-(4-{1-[4-(3,3-dimethyl-2-oxo-butoxy)-3-methyl-phenyl]-1-ethyl-propyl}-phenyl)-pyridin-3-yl]-acetic Acid

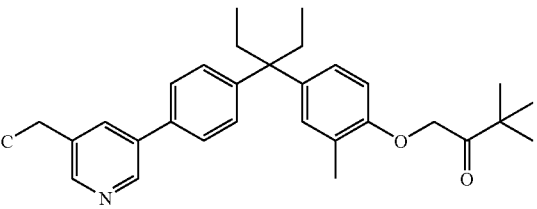

(1) Synthesis of 3-(4-bromo-phenyl)-pentan-3-ol

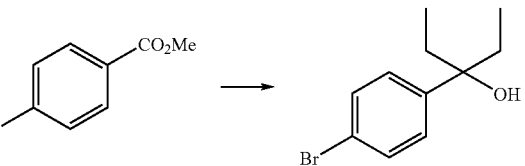

Ethylmagnesium bromide (3 M solution in diethyl ether, 77.5 mL, 233 mmol) was added to a solution of 4-bromobenzoic acid methyl ester (20 g, 93 mmol) in tetrahydrofuran (220 mL) in a nitrogen atmosphere at 0° C., and the mixture was stirred at 0° C. for 30 minutes. The reaction mixture was then poured into a saturated aqueous ammonium chloride solution, followed by extraction with ethyl acetate. The organic layer was dried over anhydrous magnesium sulfate, filtered and concentrated under reduced pressure to give the target compound as a colorless oil (22.1 g, 98%).

¹H-NMR (chloroform-d): 0.75 (6H, t, J=7.26 Hz), 1.74-1.88 (4H, m), 7.24 (2H, d, J=8.58 Hz), 7.45 (2H, d, J=8.74 Hz).

(2) Synthesis of 4-[1-(4-bromo-phenyl)-1-ethyl-propyl]-2-methyl-phenol

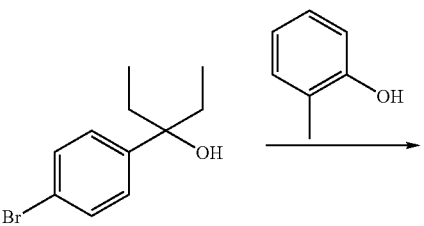

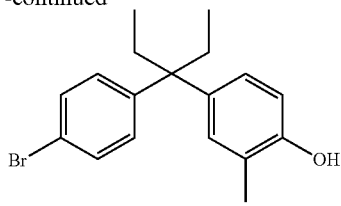

o-Cresol (890 mg, 8.23 mmol) was added to a solution of 3-(4-bromo-phenyl)-pentan-3-ol (Example 143-(1); 2.0 g, 8.23 mmol) in trifluoroacetic acid (20 mL), and the mixture was stirred at room temperature for five hours. Then, the reaction mixture was concentrated under reduced pressure. The resulting residue was purified by silica gel chromatography (hexane:ethyl acetate=100:0 to 30:70) to give the target compound as a colorless oil (2.59 g, 94%).

$^1$H-NMR (chloroform-d): 0.60 (6H, t, J=7.42 Hz), 2.02 (4H, q, J=7.42 Hz), 2.19 (3H, s), 4.61 (1H, brs), 6.65 (1H, d, J=8.90 Hz), 6.81-6.85 (2H, m), 7.04 (2H, d, J=8.74 Hz), 7.35 (2H, d, J=8.74 Hz).

(3) Synthesis of 4-{1-ethyl-1-[4-(4,4,5,5-tetramethyl-[1,3,2]dioxaborolan-2-yl)-phenyl]-propyl}-2-methyl-phenol

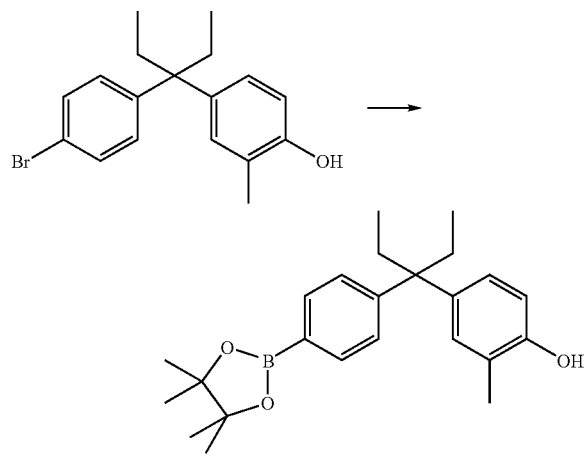

A [1,1'-bis(diphenylphosphino)ferrocene]dichloropalladium (II), dichloromethane complex (1:1) (635 mg, 0.777 mmol), 1,1'-bis(diphenylphosphino)ferrocene (431 mg, 0.777 mmol), potassium acetate (2.29 g, 23.31 mmol) and bis(pinacolato)diboron (2.57 g, 10.10 mmol) were added to a solution of 4-[1-(4-bromo-phenyl)-1-ethylpropyl]-2-methyl-phenol (Example 143-(2); 2.59 g, 7.77 mmol) in anhydrous dioxane (30 mL). After replacement with nitrogen, the mixture was stirred at 100° C. overnight. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50, 40 minutes) to give the target compound as a colorless oil (2.77 g, 94%).

$^1$H-NMR (chloroform-d): 0.60 (6H, t, J=7.26 Hz), 1.33 (12H, s), 2.06 (4H, q, J=7.26 Hz), 2.18 (3H, s), 4.60 (1H, brs), 6.64 (1H, d, J=8.08 Hz), 6.84-6.86 (2H, m), 7.18 (2H, d, J=8.24 Hz), 7.68 (2H, d, J=8.25 Hz).

(4) Synthesis of 1-(4-{1-ethyl-1-[4-(4,4,5,5-tetramethyl-[1,3,2]dioxaborolan-2-yl)-phenyl]-propyl}-2-methyl-phenoxy)-3,3-dimethyl-butan-2-one

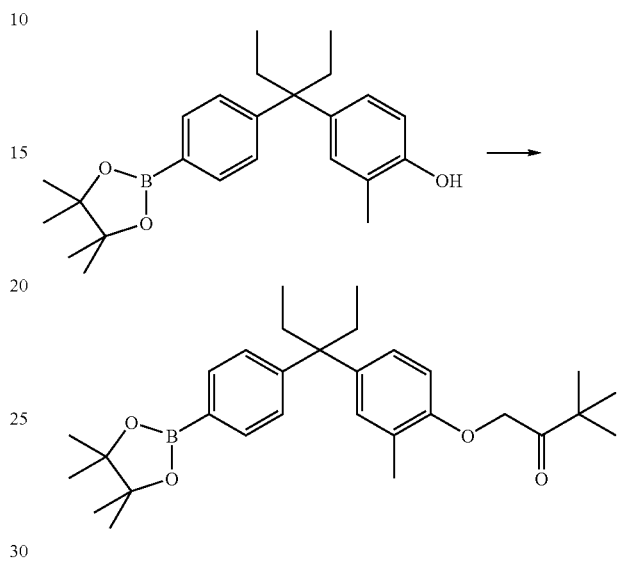

Potassium carbonate (54.5 mg, 0.395 mmol) and 1-chloropinacolin (71 mg, 0.526 mmol) were added to a solution of 4-{1-ethyl-1-[4-(4,4,5,5-tetramethyl-[1,3,2]dioxaborolan-2-yl)-phenyl]-propyl}-2-methyl-phenol (Example 143-(3); 100 mg, 0.263 mmol) in N,N-dimethylformamide (2 mL), and the mixture was stirred with microwave heating at 140° C. for 15 minutes. The reaction mixture was then poured into a saturated aqueous sodium bicarbonate solution, followed by extraction with ethyl acetate. The organic layer was washed with water and brine, dried over anhydrous magnesium sulfate, filtered and concentrated under reduced pressure. The resulting residue was purified by silica gel chromatography (hexane:ethyl acetate=100:0 to 50:50, 40 minutes) to give the target compound as a colorless oil (39.7 mg, 32%).

$^1$H-NMR (chloroform-d): 0.59 (6H, t, J=7.42 Hz), 1.25 (9H, s), 1.33 (12H, s), 2.06 (4H, q, J=7.42 Hz), 2.22 (3H, s), 4.82 (2H, s), 6.49 (1H, d, J=8.41 Hz), 6.86-6.90 (2H, m), 7.17 (2H, d, J=8.41 Hz), 7.68 (2H, d, J=8.41 Hz).

(5) Synthesis of [5-(4-{1-[4-(3,3-dimethyl-2-oxo-butoxy)-3-methyl-phenyl]-1-ethyl-propyl}-phenyl)-pyridin-3-yl]-acetic Acid Methyl Ester

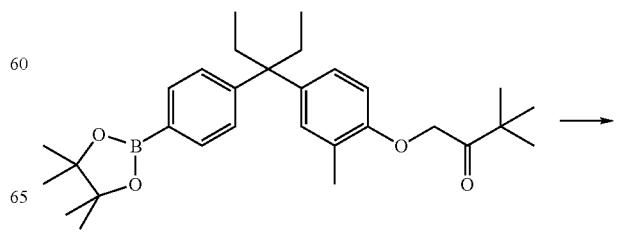

-continued

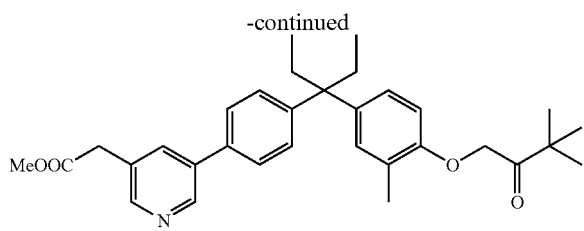

(5-Bromo-pyridin-3-yl)acetic acid methyl ester (Example 24-(2); 28.6 mg, 0.124 mmol), palladium acetate (1.8 mg, 0.008 mmol), 2-dicyclohexylphosphino-2',6'-dimethoxy-1,1'-biphenyl (7.0 mg, 0.017 mmol), potassium phosphate (53 mg, 0.249 mmol) and water (0.2 mL) were added to a solution of 1-(4-{1-ethyl-1-[4-(4,4,5,5-tetramethyl-[1,3,2]dioxaborolan-2-yl)-phenyl]-propyl}-2-methyl-phenoxy)-3,3-dimethyl-butan-2-one (Example 143-(4); 39.7 mg, 0.083 mmol) in toluene (2 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (30.4 mg, 73%).

$^1$H-NMR (chloroform-d): 0.64 (6H, t, J=7.26 Hz), 1.25 (9H, s), 2.10 (4H, q, J=7.25 Hz), 2.25 (3H, s), 3.69 (2H, s), 3.72 (3H, s), 4.84 (2H, s), 6.52 (1H, d, J=8.57 Hz), 6.90-6.94 (2H, m), 7.26 (2H, d, J=8.24 Hz), 7.47 (2H, d, J=8.24 Hz), 7.81 (1H, m), 8.46 (1H, d, J=1.82 Hz), 8.75 (1H, d, J=1.98 Hz).

(6) Synthesis of [5-(4-{1-[4-(3,3-dimethyl-2-oxo-butoxy)-3-methyl-phenyl]-1-ethyl-propyl}-phenyl)-pyridin-3-yl]-acetic Acid

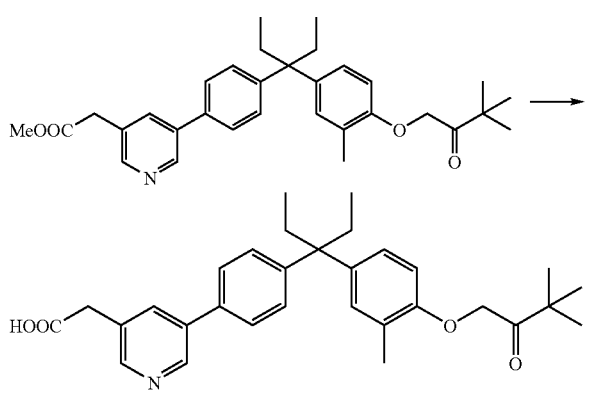

A 1 N sodium hydroxide aqueous solution (0.182 mL, 0.182 mmol) was added to a solution of [5-(4-{1-[4-(3,3-dimethyl-2-oxo-butoxy)-3-methyl-phenyl]-1-ethylpropyl}-phenyl)-pyridin-3-yl]-acetic acid methyl ester (Example 143-(5); 30.4 mg, 0.061 mmol) in methanol-tetrahydrofuran (1:1, 4 mL), and the mixture was stirred at room temperature for three days. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (19.8 mg, 67%).

$^1$H-NMR (chloroform-d): 0.63 (6H, t, J=7.25 Hz), 1.25 (9H, s), 2.09 (4H, q, J=7.25 Hz), 2.24 (3H, s), 3.73 (2H, s), 4.84 (2H, s), 6.51 (1H, d, J=9.39 Hz), 6.90-6.94 (2H, m), 7.25 (2H, d, J=8.57 Hz), 7.46 (2H, d, J=8.58 Hz), 7.88 (1H, s), 8.51 (1H, s), 8.75 (1H, s); MS (ESI+): 488 ([M+H]$^+$).

Example 144

Synthesis of [5-(4-{1-ethyl-1-[4-(3-ethyl-3-hydroxy-1-pentynyl)-3-methyl-phenyl]-propyl}-phenyl)-pyridin-3-yl]-acetic Acid

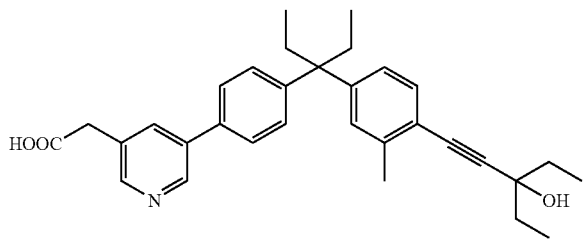

(1) Synthesis of (5-{4-[1-ethyl-1-(4-hydroxy-3-methyl-phenyl)-propyl]-phenyl}-pyridin-3-yl)-acetic Acid Methyl Ester

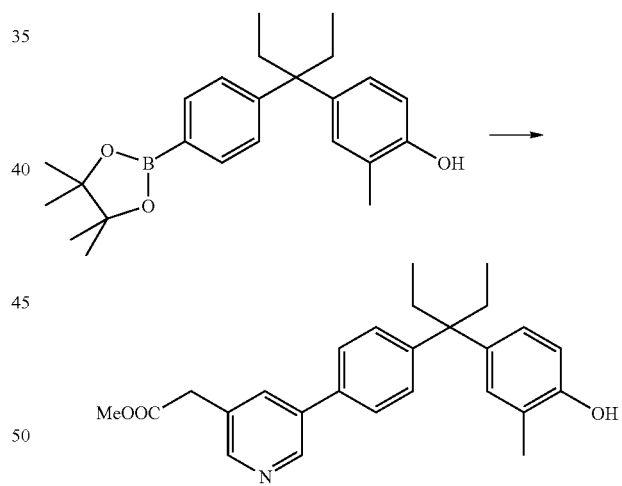

(5-Bromo-pyridin-3-yl)acetic acid methyl ester (Example 24-(2); 181 mg, 0.789 mmol), palladium acetate (12 mg, 0.053 mmol), 2-dicyclohexylphosphino-2',6'-dimethoxy-1,1'-biphenyl (22 mg, 0.053 mmol), potassium phosphate (335 mg, 1.578 mmol) and water (0.6 mL) were added to a solution of 4-{1-ethyl-1-[4-(4,4,5,5-tetramethyl-[1,3,2]dioxaborolan-2-yl)-phenyl]-propyl}-2-methyl-phenol (Example 143-(3); 200 mg, 0.526 mmol) in toluene (6 mL). After replacement with nitrogen, the mixture was stirred at 100° C. for two hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50) to give the target compound as a colorless oil (130.0 mg, 61%).

¹H-NMR (chloroform-d): 0.64 (6H, t, J=7.26 Hz), 2.10 (4H, q, J=7.25 Hz), 2.22 (3H, s), 3.69 (2H, s), 3.72 (3H, s), 6.68 (1H, d, J=8.41 Hz), 6.84 (1H, d, J=8.40 Hz), 6.94 (1H, d, J=1.81 Hz), 7.27 (2H, d, J=8.74 Hz), 7.46 (2H, d, J=8.24 Hz), 7.83 (1H, m), 8.46 (1H, d, J=2.15 Hz), 8.74 (1H, d, J=2.14 Hz).

(2) Synthesis of (5-{4-[1-ethyl-1-(3-methyl-4-trifluoromethanesulfonyloxy-phenyl)-propyl]-phenyl}-pyridin-3-yl)-acetic Acid Methyl Ester

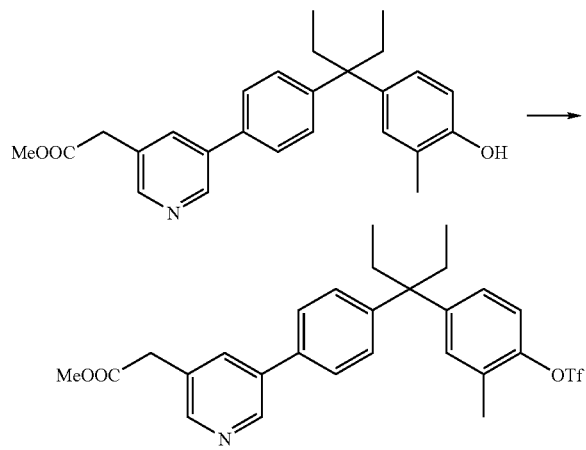

N-Phenylbis(trifluoromethanesulfonimide) (74 mg, 0.208 mmol) and triethylamine (0.036 mL, 0.260 mmol) were added to a solution of (5-{4-[1-ethyl-1-(4-hydroxy-3-methyl-phenyl)-propyl]-phenyl}-pyridin-3-yl)-acetic acid methyl ester (Example 144-(1); 70 mg, 0.173 mmol) in dichloromethane (2 mL) at 0° C., and the mixture was stirred at room temperature overnight. Then, the reaction mixture was concentrated under reduced pressure. The resulting residue was purified by silica gel chromatography (hexane:ethyl acetate=4:1) to give the target compound as a colorless oil (62 mg, 67%).

¹H-NMR (chloroform-d): 0.65 (6H, t, J=7.25 Hz), 2.13 (4H, q, J=7.25 Hz), 2.33 (3H, s), 3.70 (2H, s), 3.73 (3H, s), 7.05-7.10 (3H, m), 7.24 (2H, d, J=8.41 Hz), 7.49 (2H, d, J=8.25 Hz), 7.83 (1H, s), 8.47 (1H, s), 8.76 (1H, s).

(3) Synthesis of [5-(4-{1-ethyl-1-[4-(3-ethyl-3-hydroxy-1-pentynyl)-3-methyl-phenyl]-propyl}-phenyl)-pyridin-3-yl]-acetic Acid Methyl Ester

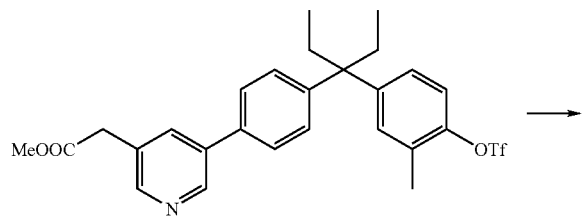

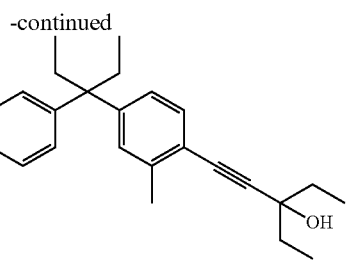

3-Ethyl-1-pentyn-3-ol (0.024 mL, 0.188 mmol), a [1,1'-bis(diphenylphosphino)ferrocene]dichloropalladium (II), dichloromethane complex (1:1) (10.6 mg, 0.013 mmol) and copper (I) iodide (2.5 mg, 0.013 mmol) were added to a solution of (5-{4-[1-ethyl-1-(3-methyl-4-trifluoromethanesulfonyloxy-phenyl)-propyl]-phenyl}-pyridin-3-yl)-acetic acid methyl ester (Example 144-(2); 67 mg, 0.125 mmol) in triethylamine (2 mL), and the mixture was stirred with microwave heating at 160° C. for three minutes. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound (48.7 mg, 78%).

¹H-NMR (chloroform-d): 0.64 (6H, t, J=7.26 Hz), 1.11 (6H, t, J=7.42 Hz), 1.73-1.84 (4H, m), 2.12 (4H, q, J=7.42 Hz), 2.39 (3H, s), 3.69 (2H, s), 3.72 (3H, s), 6.96 (1H, d, J=8.08 Hz), 7.02 (1H, s), 7.23-7.32 (3H, m), 7.47 (2H, d, J=8.07 Hz), 7.81 (1H, s), 8.46 (1H, d, J=1.65 Hz), 8.75 (1H, d, J=2.14 Hz).

(4) Synthesis of [5-(4-{1-ethyl-1-[4-(3-ethyl-3-hydroxy-1-pentynyl)-3-methyl-phenyl]-propyl}-phenyl)-pyridin-3-yl]-acetic Acid

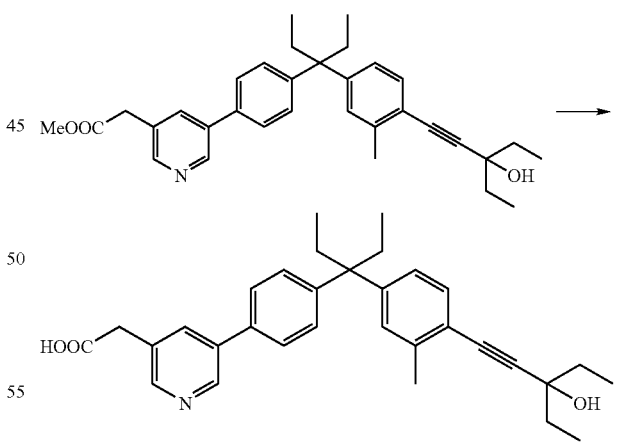

A 1 N sodium hydroxide aqueous solution (0.293 mL, 0.293 mmol) was added to a solution of [5-(4-{1-ethyl-1-[4-(3-ethyl-3-hydroxy-1-pentynyl)-3-methyl-phenyl]-propyl}-phenyl)-pyridin-3-yl]-acetic acid methyl ester (Example 144-(3); 48.7 mg, 0.098 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (37.6 mg, 79%).

$^1$H-NMR (chloroform-d): 0.63 (6H, t, J=7.09 Hz), 1.10 (6H, t, J=7.42 Hz), 1.72-1.78 (4H, m), 2.11 (4H, q, J=7.42 Hz), 2.37 (3H, s), 3.72 (2H, s), 6.94 (1H, d, J=8.74 Hz), 7.00 (1H, s), 7.20-7.30 (3H, m), 7.44 (2H, d, J=7.74 Hz), 7.89 (1H, s), 8.51 (1H, s), 8.73 (1H, s); MS (ESI+): 484 ([M+H]$^+$).

Example 145

Synthesis of [5-(4-{1-ethyl-1-[4-(3-ethyl-3-hydroxy-pentyl)-3-methyl-phenyl]-propyl}-phenyl)-pyridin-3-yl]-acetic Acid

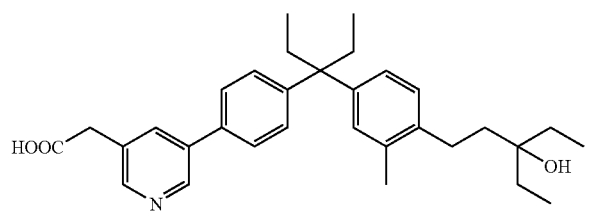

(1) Synthesis of 3-ethyl-1-(4-{1-ethyl-1-[4-(4,4,5,5-tetramethyl-[1,3,2]dioxaborolan-2-yl)-phenyl]-propyl}-2-methyl-phenyl)-pentan-3-ol

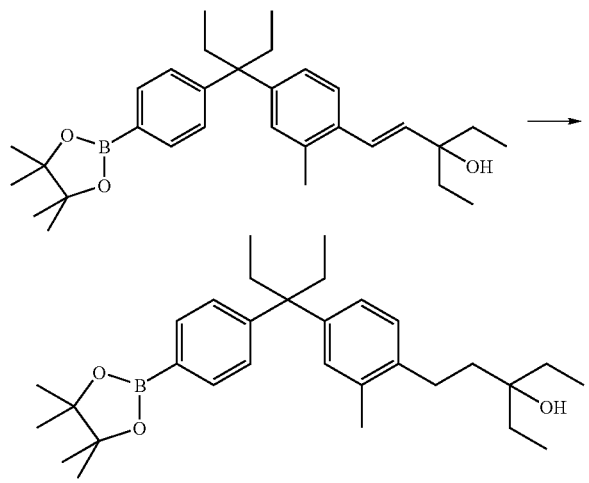

10% palladium carbon (20 mg) was added to a solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 50.5 mg, 0.106 mmol) in methanol (4 mL), and the mixture was stirred in a hydrogen atmosphere at room temperature for four hours. Then, the reaction mixture was filtered through celite, and the filtrate was concentrated under reduced pressure to give the target compound (48.8 mg, 96%).

$^1$H-NMR (chloroform-d): 0.60 (6H, t, J=7.26 Hz), 0.90 (6H, t, J=7.58 Hz), 1.33 (12H, s), 1.55 (4H, q, J=7.59 Hz), 1.61-1.68 (2H, m), 2.08 (4H, q, J=7.42 Hz), 2.24 (3H, s), 2.53-2.59 (2H, m), 6.88-6.91 (2H, m), 6.99 (1H, d, J=8.57 Hz), 7.19 (2H, d, J=7.91 Hz), 7.69 (2H, d, J=7.92 Hz).

(2) Synthesis of [5-(4-{1-ethyl-1-[4-(3-ethyl-3-hydroxy-pentyl)-3-methyl-phenyl]-propyl}-phenyl)-pyridin-3-yl]-acetic Acid Methyl Ester

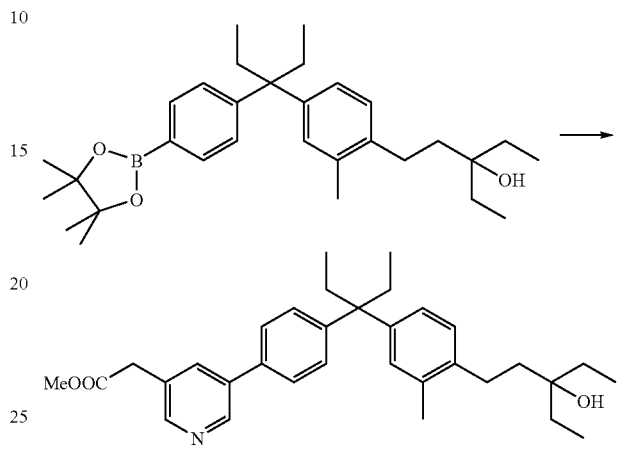

(5-Bromo-pyridin-3-yl)acetic acid methyl ester (Example 24-(2); 35.2 mg, 0.153 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (65 mg, 0.306 mmol) and water (0.2 mL) were added to a solution of 3-ethyl-1-(4-{1-ethyl-1-[4-(4,4,5,5-tetramethyl-[1,3,2]dioxaborolan-2-yl)-phenyl]-propyl}-2-methyl-phenyl)-pentan-3-ol (Example 145-(1); 48.8 mg, 0.102 mmol) in toluene (2 mL). After replacement with nitrogen, the mixture was stirred at 100° C. for 1.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (39.3 mg, 77%).

$^1$H-NMR (chloroform-d): 0.65 (6H, t, J=7.42 Hz), 0.91 (6H, t, J=7.58 Hz), 1.52-1.70 (6H, m), 2.12 (4H, q, J=7.42 Hz), 2.27 (3H, s), 2.55-2.61 (2H, m), 3.69 (2H, s), 3.72 (3H, s), 6.92-6.95 (2H, m), 7.03 (1H, d, J=8.58 Hz), 7.28 (2H, d, J=8.41 Hz), 7.47 (2H, d, J=8.41 Hz), 7.81 (1H, s), 7.46 (1H, d, J=2.15 Hz), 8.75 (1H, d, J=1.98 Hz).

(3) Synthesis of [5-(4-{1-ethyl-1-[4-(3-ethyl-3-hydroxy-pentyl)-3-methyl-phenyl]-propyl}-phenyl)-pyridin-3-yl]-acetic Acid

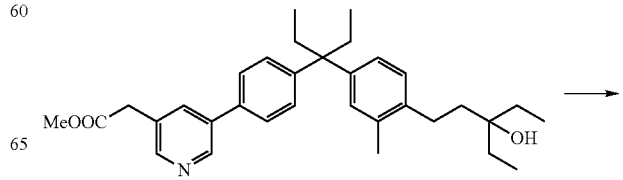

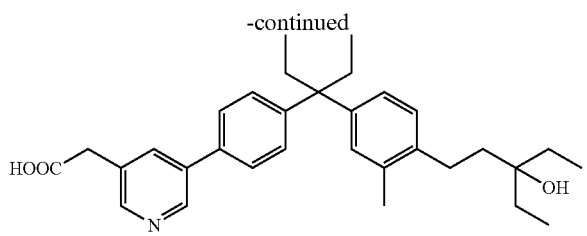

A 1 N sodium hydroxide aqueous solution (0.235 mL, 0.235 mmol) was added to a solution of [5-(4-{1-ethyl-1-[4-(3-ethyl-3-hydroxy-pentyl)-3-methyl-phenyl]-propyl}-phenyl)-pyridin-3-yl]-acetic acid methyl ester (Example 145-(2); 39.3 mg, 0.078 mmol) in methanol-tetrahydrofuran (1:1, 4 mL), and the mixture was stirred at room temperature for three days. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (26.8 mg, 70%).

$^1$H-NMR (chloroform-d): 0.63 (6H, t, J=7.26 Hz), 0.90 (6H, t, J=7.58 Hz), 1.55 (4H, q, J=7.25 Hz), 1.60-1.69 (2H, m), 2.11 (4H, q, J=7.25 Hz), 2.25 (3H, s), 2.50-2.60 (2H, m), 3.71 (2H, s), 6.90-6.93 (2H, m), 7.01 (2H, d, J=8.25 Hz), 7.26 (2H, d, J=7.91 Hz), 7.44 (2H, d, J=8.07 Hz), 7.89 (1H, s), 8.50 (1H, s), 8.73 (1H, s); MS (ESI+): 488 ([M+H]$^+$).

Example 146

Synthesis of [5-(4-{1-ethyl-1-[4-(2-hydroxy-3,3-dimethyl-butoxy)-3-methyl-phenyl]-propyl}-phenyl)-pyridin-3-yl]-acetic Acid

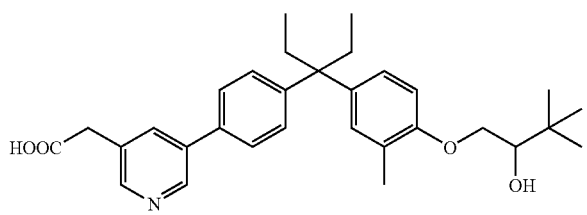

(1) Synthesis of 1-(4-{1-ethyl-1-[4-(4,4,5,5-tetramethyl-[1,3,2]dioxaborolan-2-yl)-phenyl]-propyl}-2-methyl-phenoxy)-3,3-dimethyl-butan-2-ol

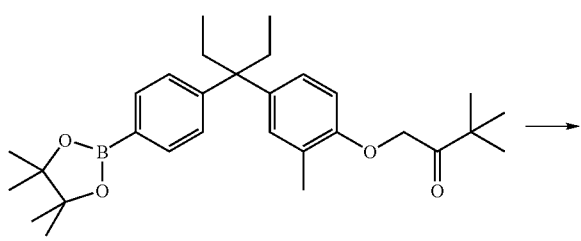

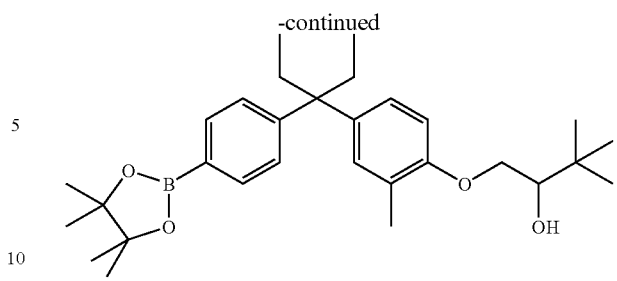

A solution of lithium tri-sec-butylborohydride in tetrahydrofuran (1.06 M, 0.178 mL, 0.189 mmol) was added to a solution of 1-(4-{1-ethyl-1-[4-(4,4,5,5-tetramethyl-[1,3,2]dioxaborolan-2-yl)-phenyl]-propyl}-2-methyl-phenoxy)-3,3-dimethyl-butan-2-one (Example 143-(4); 75.2 mg, 0.157 mmol) in tetrahydrofuran (3 mL) at −78° C., and the mixture was stirred for 30 minutes. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (46.6 mg, 62%).

$^1$H-NMR (chloroform-d): 0.60 (6H, t, J=7.25 Hz), 1.01 (9H, s), 1.33 (12H, s), 2.07 (4H, q, J=7.25 Hz), 2.16 (3H, s), 3.68-3.75 (1H, m), 3.81-3.92 (1H, m), 4.06-4.14 (1H, m), 6.69 (1H, d, J=8.58 Hz), 6.88-6.95 (2H, m), 7.18 (2H, d, J=8.24 Hz), 7.69 (2H, d, J=8.25 Hz).

(2) Synthesis of [5-(4-{1-ethyl-1-[4-(2-hydroxy-3,3-dimethyl-butoxy)-3-methyl-phenyl]-propyl}-phenyl)-pyridin-3-yl]-acetic Acid Methyl Ester

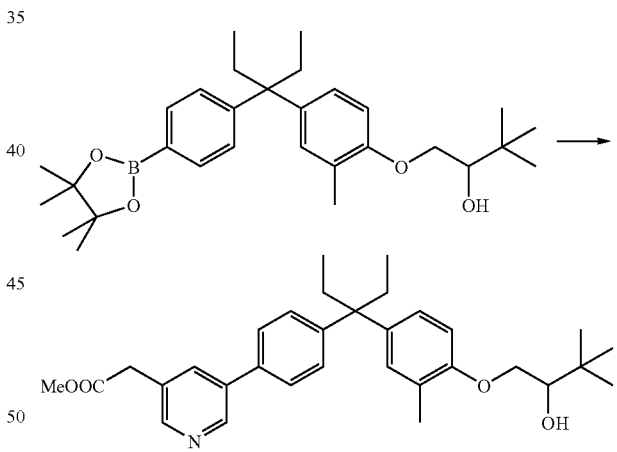

(5-Bromo-pyridin-3-yl)acetic acid methyl ester (Example 24-(2); 33.5 mg, 0.145 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (62 mg, 0.291 mmol) and water (0.2 mL) were added to a solution of 1-(4-{1-ethyl-1-[4-(4,4,5,5-tetramethyl-[1,3,2]dioxaborolan-2-yl)-phenyl]-propyl}-2-methyl-phenoxy)-3,3-dimethyl-butan-2-ol (Example 146-(1); 46.6 mg, 0.097 mmol) in toluene (2 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (30.8 mg, 63%).

$^1$H-NMR (chloroform-d): 0.65 (6H, t, J=7.42 Hz), 1.01 (9H, s), 2.11 (4H, q, J=7.42 Hz), 2.19 (3H, s), 3.69 (2H, s), 3.72 (3H, s), 3.68-3.73 (1H, m), 3.83-3.90 (1H, m), 4.08-4.13 (1H, m), 6.72 (1H, d, J=8.73 Hz), 6.92-6.99 (2H, m), 7.27 (2H, d, J=7.42 Hz), 7.47 (2H, d, J=8.40 Hz), 7.81 (1H, m), 7.46 (1H, d, J=1.98 Hz), 8.75 (1H, d, J=2.14 Hz).

(3) Synthesis of [5-(4-{1-ethyl-1-[4-(2-hydroxy-3,3-dimethyl-butoxy)-3-methyl-phenyl]-propyl}-phenyl)-pyridin-3-yl]-acetic Acid

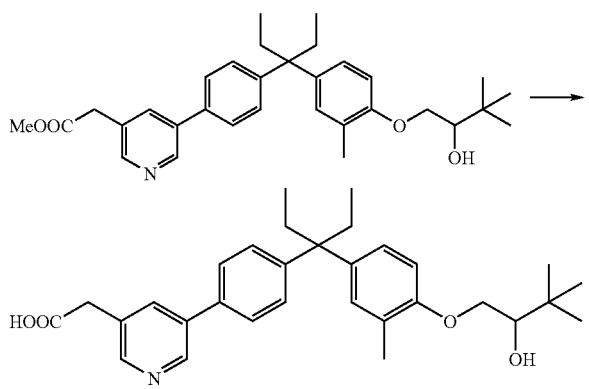

A 1 N sodium hydroxide aqueous solution (0.183 mL, 0.183 mmol) was added to a solution of [5-(4-{1-ethyl-1-[4-(2-hydroxy-3,3-dimethyl-butoxy)-3-methyl-phenyl]-propyl}-phenyl)-pyridin-3-yl]-acetic acid methyl ester (Example 146-(2); 30.8 mg, 0.061 mmol) in methanol-tetrahydrofuran (1:1, 4 mL), and the mixture was stirred at 60° C. for one hour. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (20.5 mg, 69%).

$^1$H-NMR (chloroform-d): 0.64 (6H, t, J=7.59 Hz), 1.01 (9H, s), 2.10 (4H, q, J=7.42 Hz), 2.17 (3H, s), 3.68-3.72 (3H, m), 3.83-3.89 (1H, m), 4.07-4.11 (1H, m), 6.71 (1H, d, J=8.57 Hz), 6.91-6.98 (2H, m), 7.25 (2H, d, J=8.41 Hz), 7.45 (2H, d, J=8.41 Hz), 7.88 (1H, s), 8.50 (1H, s), 8.74 (1H, d, J=1.98 Hz); MS (ESI+): 490 ([M+H]$^+$).

Example 147

Synthesis of [5-(4-{1-ethyl-1-[4-(1-hydroxy-cyclohexylethynyl)-3-methyl-phenyl]-propyl}-phenyl)-pyridin-3-yl]-acetic Acid

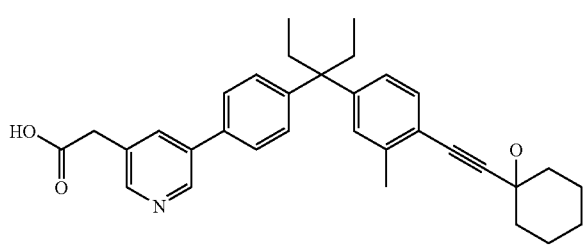

(1) Synthesis of [5-(4-{1-ethyl-1-[4-(1-hydroxy-cyclohexylethynyl)-3-methyl-phenyl]-propyl}-phenyl)-pyridin-3-yl]-acetic Acid Methyl Ester

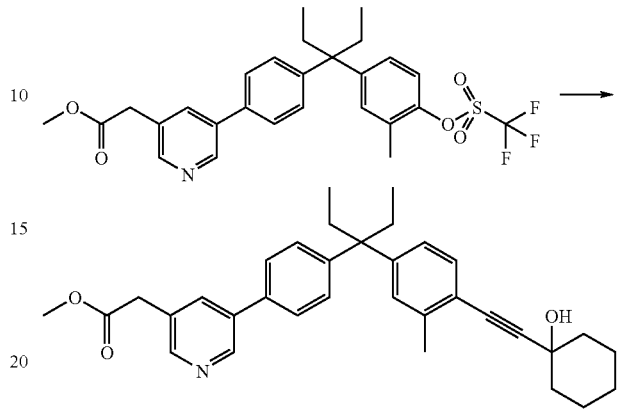

Triethylamine (0.156 mL, 1.12 mmol), tetrakistriphenylphosphine palladium (43.0 mg, 0.036 mmol) and copper (I) iodide (7.0 mg, 0.037 mmol) were added to a solution of (5-{4-[1-ethyl-1-(3-methyl-4-trifluoromethanesulfonyloxy-phenyl)-propyl]-phenyl}-pyridin-3-yl)-acetic acid methyl ester (Example 144-(2); 0.1 g, 0.186 mmol) and 1-ethynyl-cyclohexanol (69.6 mg, 0.56 mmol) in acetonitrile (0.9 mL), and the mixture was stirred with microwave heating at 160° C. for five minutes. The reaction solution was purified by silica gel chromatography (hexane:ethyl acetate=1:1) to give the title compound (63.6 mg, 66%).

$^1$H-NMR (chloroform-d)δ: 0.64 (6H, t, J=7.1 Hz), 1.54-1.75 (8H, m), 2.00-2.05 (2H, m), 2.12 (4H, q, J=7.2 Hz), 2.39 (3H, s), 3.69 (2H, s), 3.72 (3H, s), 6.97 (1H, d, J=8.4 Hz), 7.02 (1H, s), 7.25 (2H, d, J=8.4 Hz), 7.31 (1H, d, J=8.1 Hz), 7.47 (2H, d, J=8.4 Hz), 7.81 (1H, s), 8.47 (1H, d, J=2.0 Hz), 8.75 (1H, d, J=2.0 Hz).

(2) Synthesis of [5-(4-{1-ethyl-1-[4-(1-hydroxy-cyclohexylethynyl)-3-methyl-phenyl]-propyl}-phenyl)-pyridin-3-yl]-acetic Acid

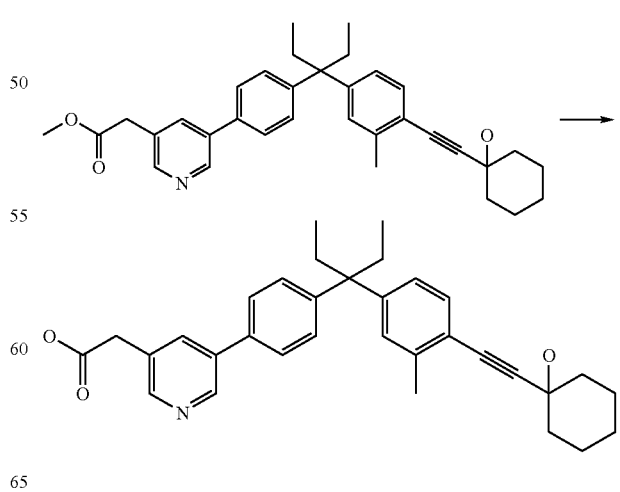

A 2 N sodium hydroxide aqueous solution (0.2 mL, 0.39 mmol) was added to a solution of [5-(4-{1-ethyl-1-[4-(1- hydroxy-cyclohexylethynyl)-3-methyl-phenyl]-propyl}-phenyl)-pyridin-3-yl]-acetic acid methyl ester (Example 147-(1); 33.9 mg, 0.066 mmol) in methanol (0.6 mL), and the mixture was stirred at room temperature for 2.5 hours. A saturated aqueous ammonium chloride solution was added to the reaction mixture, followed by extraction with ethyl acetate. The organic layer was dried over anhydrous sodium sulfate, filtered and concentrated under reduced pressure. The resulting residue was purified by thin layer silica gel chromatography (dichloromethane:methanol=9:1) to give the title compound (26.5 mg, 80%).

$^1$H-NMR (chloroform-d)δ: 0.64 (6H, t, J=7.2 Hz), 1.57-1.76 (8H, m), 2.00-2.05 (2H, m), 2.12 (4H, q, J=7.2 Hz), 2.38 (3H, s), 3.72 (2H, s), 4.60-5.32 (1H, brs), 6.94 (1H, d, J=7.8 Hz), 7.00 (1H, s), 7.22 (2H, d, J=8.4 Hz), 7.29 (1H, d, J=8.1 Hz), 7.44 (2H, d, J=8.4 Hz), 7.89 (1H, s), 8.51 (1H, d, J=1.8 Hz), 8.73 (1H, d, J=1.8 Hz); MS (ESI+): 496 ([M+H]$^+$).

Example 148

Synthesis of [5-(4-{1-ethyl-1-[4-(1-hydroxy-cyclopentylethynyl)-3-methyl-phenyl]-propyl}-phenyl)-pyridin-3-yl]-acetic Acid

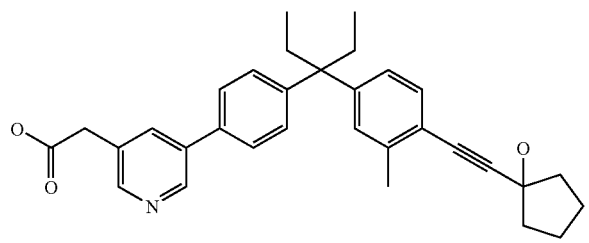

(1) Synthesis of [5-(4-{1-ethyl-1-[4-(1-hydroxy-cyclopentylethynyl)-3-methyl-phenyl]-propyl}-phenyl)-pyridin-3-yl]-acetic Acid Methyl Ester

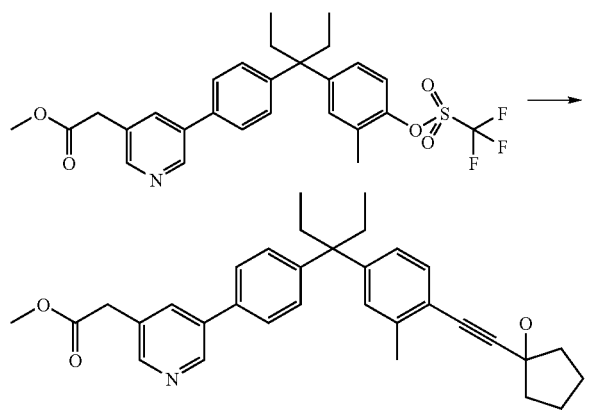

Triethylamine (0.078 mL, 0.560 mmol), tetrakistriphenylphosphine palladium (43.0 mg, 0.036 mmol) and copper (I) iodide (7.0 mg, 0.037 mmol) were added to a solution of (5-{4-[1-ethyl-1-(3-methyl-4-trifluoromethanesulfonyloxy-phenyl)-propyl]-phenyl}-pyridin-3-yl)-acetic acid methyl ester (Example 144-(2); 0.1 g, 0.186 mmol) and 1-ethynyl-cyclopentanol (61.6 mg, 0.56 mmol) in acetonitrile (0.9 mL), and the mixture was stirred with microwave heating at 160° C. for three minutes. The reaction solution was purified by silica gel chromatography (hexane:ethyl acetate=1:1) to give the title compound (31.0 mg, 33%).

$^1$H-NMR (chloroform-d)δ: 0.64 (6H, t, J=7.3 Hz), 1.78-1.90 (6H, m), 2.05-2.08 (2H, m), 2.12 (4H, q, J=7.1 Hz), 2.38 (3H, s), 3.69 (2H, s), 3.73 (3H, s), 6.97 (2H, d, J=8.1 Hz), 7.02 (1H, s), 7.30 (2H, d, J=8.4 Hz), 7.47 (2H, d, J=8.4 Hz), 7.81 (1H, s), 8.47 (1H, d, J=1.8 Hz), 8.76 (1H, d, J=1.8 Hz).

(2) Synthesis of [5-(4-{1-ethyl-1-[4-(1-hydroxy-cyclopentylethynyl)-3-methyl-phenyl]-propyl}-phenyl)-pyridin-3-yl]-acetic Acid

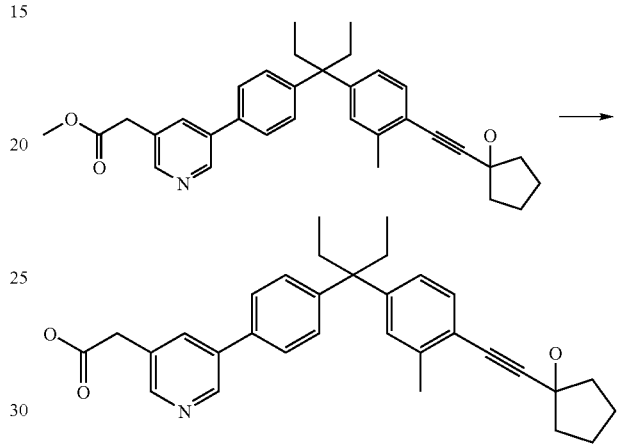

A 2 N sodium hydroxide aqueous solution (0.1 mL, 0.176 mmol) was added to a solution of [5-(4-{1-ethyl-1-[4-(1-hydroxy-cyclopentylethynyl)-3-methyl-phenyl]-propyl}-phenyl)-pyridin-3-yl]-acetic acid methyl ester (Example 148-(1); 14.6 mg, 29.4 mmol) in methanol (0.3 mL), and the mixture was stirred at room temperature for 2.5 hours. A saturated aqueous ammonium chloride solution was added to the reaction mixture, followed by extraction with ethyl acetate. The organic layer was dried over anhydrous sodium sulfate, filtered and concentrated under reduced pressure. The resulting residue was purified by thin layer silica gel chromatography (dichloromethane:methanol=9:1) to give the title compound (11.5 mg, 80%).

$^1$H-NMR (chloroform-d)δ: 0.63 (6H, t, J=7.2 Hz), 1.76-1.92 (4H, m), 1.98-2.10 (4H, m), 2.11 (4H, q, J=7.2 Hz), 2.36 (3H, s), 3.72 (2H, s), 4.60-5.43 (1H, brs), 6.94 (1H, d, J=8.1 Hz), 7.00 (1H, s), 7.22 (2H, d, J=7.8 Hz), 7.27 (1H, d, J=7.5 Hz), 7.44 (2H, d, J=7.8 Hz), 7.89 (1H, s), 8.51 (1H, d, J=1.8 Hz), 8.72 (1H, s); MS (ESI+): 482 ([M+H]$^+$).

Example 149

Synthesis of {5-[4-(1-ethyl-1-{4-[2-(1-hydroxy-cyclohexyl)-ethyl]-3-methyl-phenyl}-propyl)-phenyl]-pyridin-3-yl}-acetic Acid

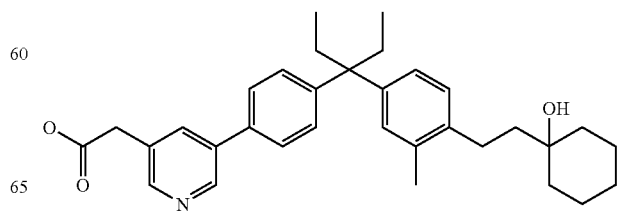

(1) Synthesis of {5-[4-(1-ethyl-1-{4-[2-(1-hydroxy-cyclohexyl)-ethyl]-3-methyl-phenyl}-propyl)-phenyl]-pyridin-3-yl}-acetic Acid Methyl Ester

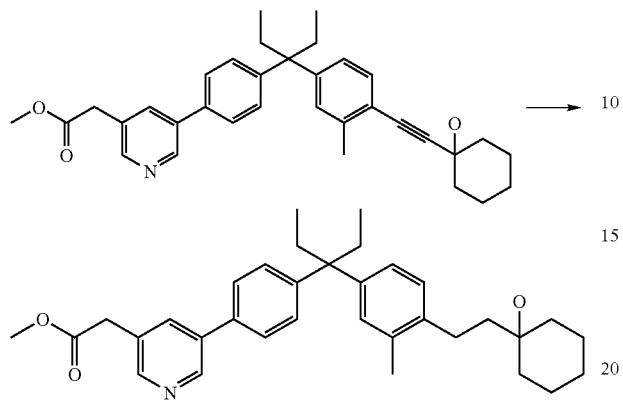

10% palladium carbon (13.0 mg) was added to a solution of [5-(4-{1-ethyl-1-[4-(1-hydroxy-cyclohexylethynyl)-3-methyl-phenyl]-propyl}-phenyl)-pyridin-3-yl]-acetic acid methyl ester (Example 147-(1); 29.7 mg, 0.058 mmol) in methanol (0.3 mL), and the mixture was stirred in a hydrogen atmosphere for 19 hours. The reaction solution was filtered and concentrated under reduced pressure to give the title compound (19.9 mg, 66%).

$^1$H-NMR (chloroform-d)δ: 0.66 (6H, t, J=7.5 Hz), 1.51-1.64 (10H, m), 1.63-1.73 (2H, m), 2.13 (4H, q, J=7.2 Hz), 2.27 (3H, s), 2.63-2.68 (2H, m), 3.69 (2H, s), 3.73 (3H, s), 6.93-6.96 (2H, m), 7.03 (1H, d, J=8.7 Hz), 7.29 (2H, dd, J=2.1, 8.7 Hz), 7.47 (2H, d, J=10.5 Hz), 7.81 (1H, t, J=2.1 Hz), 8.46 (1H, s), 8.75 (1H, d, J=2.1 Hz).

(2) Synthesis of {5-[4-(1-ethyl-1-{4-[2-(1-hydroxy-cyclohexyl)-ethyl]-3-methyl-phenyl}-propyl)-phenyl]-pyridin-3-yl}-acetic Acid

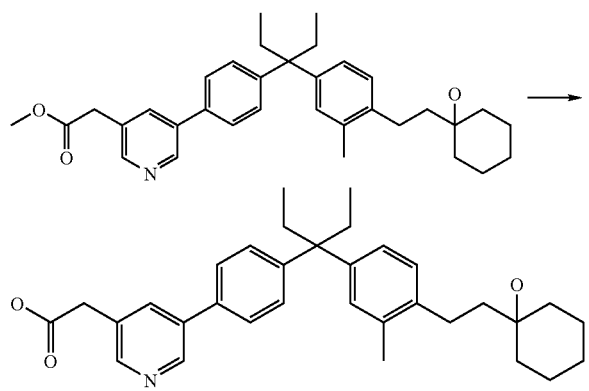

A 2 N sodium hydroxide aqueous solution (0.12 mL, 0.23 mmol) was added to a solution of {5-[4-(1-ethyl-1-{4-[2-(1-hydroxy-cyclohexyl)-ethyl]-3-methyl-phenyl}-propyl)-phenyl]-pyridin-3-yl}-acetic acid methyl ester (Example 149-(1); 19.9 mg, 0.038 mmol) in methanol (0.4 mL), and the mixture was stirred at room temperature for two hours. A saturated aqueous ammonium chloride solution was added to the reaction mixture, followed by extraction with ethyl acetate. The organic layer was dried over anhydrous sodium sulfate, filtered and concentrated under reduced pressure. The resulting residue was purified by thin layer silica gel chromatography (dichloromethane:methanol=9:1) to give the title compound (12.5 mg, 64%).

$^1$H-NMR (chloroform-d)δ: 0.64 (6H, t, J=7.2 Hz), 1.46-1.68 (10H, m), 1.66-1.72 (2H, m), 2.11 (4H, q, J=7.2 Hz), 2.25 (3H, s), 2.61-2.67 (2H, m), 3.71 (2H, s), 4.89-5.46 (1H, brs), 6.91 (1H, s), 6.92 (1H, d, J=8.4 Hz), 7.01 (1H, d, J=8.4 Hz), 7.25 (2H, d, J=8.4 Hz), 7.44 (2H, d, J=8.4 Hz), 7.90 (1H, t, J=2.1 Hz), 8.49 (1H, d, J=2.1 Hz), 8.72 (1H, d, J=2.1 Hz); MS (ESI+): 500 ([M+H]$^+$).

Example 150

Synthesis of {5-[4-(1-ethyl-1-{4-[2-(1-hydroxy-cyclopentyl)-ethyl]-3-methyl-phenyl}-propyl)-phenyl]-pyridin-3-yl}-acetic Acid

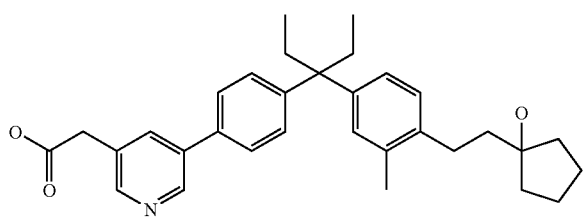

(1) Synthesis of {5-[4-(1-ethyl-1-{4-[2-(1-hydroxy-cyclopentyl)-ethyl]-3-methyl-phenyl}-propyl)-phenyl]-pyridin-3-yl}-acetic Acid Methyl Ester

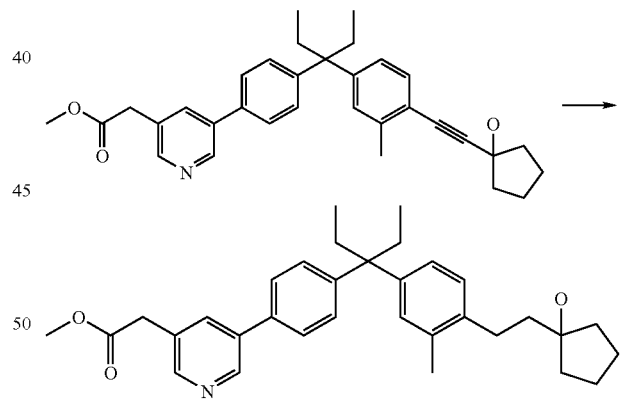

10% palladium carbon (16 mg) was added to a solution of [5-(4-{1-ethyl-1-[4-(1-hydroxy-cyclopentylethynyl)-3-methyl-phenyl]-propyl}-phenyl)-pyridin-3-yl]-acetic acid methyl ester (Example 148-(1); 16.4 mg, 0.033 mmol) in methanol (0.2 mL), and the mixture was stirred in a hydrogen atmosphere for 19 hours. The reaction solution was filtered and concentrated under reduced pressure. The residue was purified by silica gel chromatography (hexane:ethyl acetate=3:1) to give the title compound (13.1 mg, 79%).

$^1$H-NMR (chloroform-d)δ: 0.66 (6H, t, J=7.5 Hz), 1.64-1.75 (6H, m), 1.77-1.85 (2H, m), 1.82-1.88 (2H, m), 2.13 (4H, q, J=7.5 Hz), 2.28 (3H, s), 2.69-2.75 (2H, m), 3.69 (2H, s), 3.73 (3H, s), 6.93-6.96 (2H, m), 7.05 (1H, d, J=8.7 Hz), 7.28

(2H, d, J=8.4 Hz), 7.47 (2H, d, J=8.4 Hz), 7.81 (1H, t, J=2.1 Hz), 8.46 (1H, d, J=2.1 Hz), 8.76 (1H, d, J=2.1 Hz).

(2) Synthesis of {5-[4-(1-ethyl-1-{4-[2-(1-hydroxy-cyclopentyl)-ethyl]-3-methyl-phenyl}-propyl)-phenyl]-pyridin-3-yl}-acetic Acid (1) Synthesis of [5-(4-{1-ethyl-1-[4-(3-ethyl-3-trimethylsilanyloxy-1-pentynyl)-3-methyl-phenyl]-propyl}-2-methyl-phenyl)-pyridin-3-yl]-acetic Acid Methyl Ester

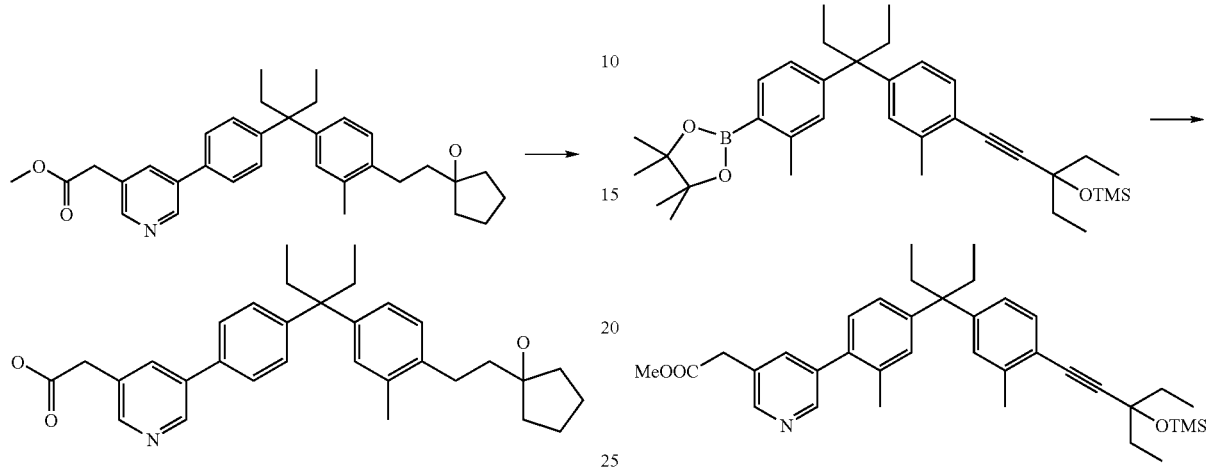

A 2 N sodium hydroxide aqueous solution (0.08 mL, 0.157 mmol) was added to a solution of {5-[4-(1-ethyl-1-{4-[2-(1-hydroxy-cyclopentyl)-ethyl]-3-methyl-phenyl}-propyl)-phenyl]-pyridin-3-yl}-acetic acid methyl ester (Example 150-(1); 13.1 mg, 0.026 mmol) in methanol (0.26 mL), and the mixture was stirred at room temperature for two hours. A saturated aqueous ammonium chloride solution was added to the reaction mixture, followed by extraction with ethyl acetate. The organic layer was dried over anhydrous sodium sulfate, filtered and concentrated under reduced pressure. The resulting residue was purified by thin layer silica gel chromatography (dichloromethane:methanol=9:1) to give the title compound (7.6 mg, 59%).

$^1$H-NMR (chloroform-d)δ: 0.65 (6H, t, J=7.2 Hz), 1.64-1.75 (6H, m), 1.80-1.85 (2H, m), 1.81-1.87 (2H, m), 2.12 (4H, q, J=7.2 Hz), 2.26 (3H, s), 2.68-2.73 (2H, m), 3.73 (2H, s), 6.92 (1H, s), 6.93 (1H, d, J=6.9 Hz), 7.03 (1H, d, J=8.7 Hz), 7.26 (2H, d, J=7.2 Hz), 7.45 (2H, d, J=8.7 Hz), 7.89 (1H, s), 8.50 (1H, s), 8.74 (1H, s); MS (ESI+): 486 ([M+H]$^+$).

Example 151

Synthesis of [5-(4-{1-ethyl-1-[4-(3-ethyl-3-hydroxy-1-pentynyl)-3-methyl-phenyl]-propyl}-2-methyl-phenyl)-pyridin-3-yl]-acetic Acid (5-Bromo-pyridin-3-yl)acetic acid methyl ester (Example 24-(2); 27 mg, 0.118 mmol), palladium acetate (1.8 mg, 0.008 mmol), 2-dicyclohexylphosphino-2',6'-dimethoxy-1,1'-biphenyl (6.6 mg, 0.016 mmol), potassium phosphate (50 mg, 0.234 mmol) and water (0.2 mL) were added to a solution of 2-(4-{1-ethyl-1-[4-(3-ethyl-3-trimethylsilanyloxy-1-pentynyl)-3-methyl-phenyl]-propyl}-2-methyl-phenyl)-4,4,5,5-tetramethyl-[1,3,2]dioxaborolane (Example 124-(3); 44 mg, 0.078 mmol) in toluene (2 mL). After replacement with nitrogen, the mixture was stirred at 100° C. for one hour. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=1:1) to give the target compound as a colorless oil (36.9 mg, 81%).

$^1$H-NMR (chloroform-d): 0.22 (9H, s), 0.65 (6H, t, J=7.25 Hz), 1.03 (6H, t, J=7.58 Hz), 1.73 (4H, q, J=7.42 Hz), 2.11 (4H, q, J=7.42 Hz), 2.34 (3H, s), 2.40 (3H, s), 3.68 (2H, s), 3.72 (3H, s), 6.97 (1H, d, J=8.41 Hz), 7.05-7.11 (4H, m), 7.30 (1H, d, J=8.08 Hz), 7.62 (1H, m), 8.46 (1H, d, J=2.15 Hz), 8.51 (1H, d, J=1.81 Hz).

(2) Synthesis of [5-(4-{1-ethyl-1-[4-(3-ethyl-3-hydroxy-1-pentynyl)-3-methyl-phenyl]-propyl}-2-methyl-phenyl)-pyridin-3-yl]-acetic Acid Methyl Ester

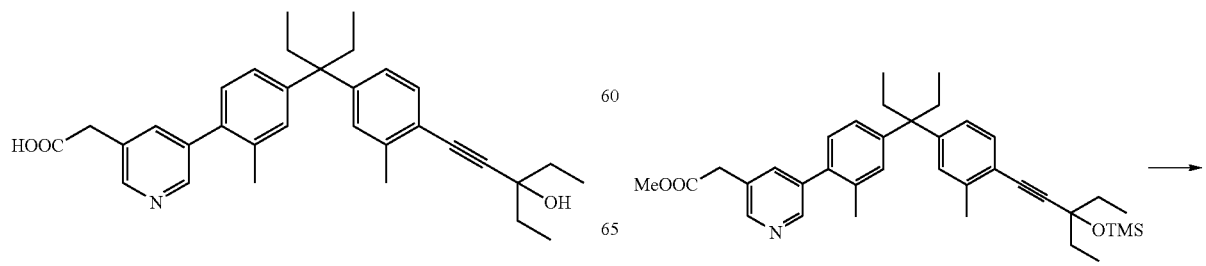

-continued

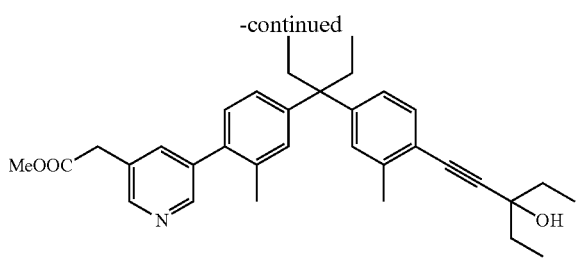

Tetrabutylammonium fluoride (1 M solution in tetrahydrofuran, 0.316 mL, 0.316 mmol) was added to a solution of [5-(4-{1-ethyl-1-[4-(3-ethyl-3-trimethylsilanyloxy-1-pentynyl)-3-methyl-phenyl]-propyl}-2-methyl-phenyl)-pyridin-3-yl]-acetic acid methyl ester (Example 151-(1); 36.9 mg, 0.063 mmol) in tetrahydrofuran (3 mL), and the mixture was stirred at room temperature for 30 minutes. Then, the reaction mixture was diluted with ethyl acetate and was washed with brine. The organic layer was dried over anhydrous magnesium sulfate, filtered and concentrated under reduced pressure. The resulting residue was purified by silica gel chromatography (hexane:ethyl acetate=1:1) to give the target compound as a colorless oil (16.7 mg, 52%).

$^1$H-NMR (chloroform-d): 0.64 (6H, t, J=7.26 Hz), 1.11 (6H, t, J=7.58 Hz), 1.70-1.84 (4H, m), 2.11 (4H, q, J=7.59 Hz), 2.23 (3H, s), 2.40 (3H, s), 3.68 (2H, s), 3.72 (3H, s), 6.96-7.11 (5H, m), 7.30 (1H, d, J=8.07 Hz), 7.62 (1H, m), 8.46 (1H, d, J=2.14 Hz), 8.51 (1H, d, J=2.14 Hz).

(3) Synthesis of [5-(4-{1-ethyl-1-[4-(3-ethyl-3-hydroxy-1-pentynyl)-3-methyl-phenyl]-propyl}-2-methyl-phenyl)-pyridin-3-yl]-acetic Acid

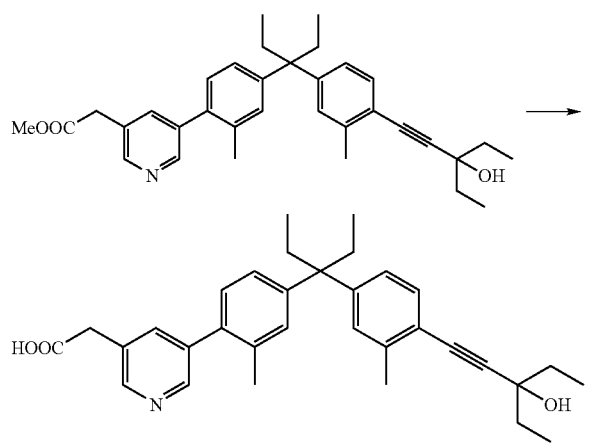

A 1 N sodium hydroxide aqueous solution (0.098 mL, 0.098 mmol) was added to a solution of [5-(4-{1-ethyl-1-[4-(3-ethyl-3-hydroxy-1-pentynyl)-3-methyl-phenyl]-propyl}-2-methyl-phenyl)-pyridin-3-yl]-acetic acid methyl ester (Example 151-(2); 16.7 mg, 0.033 mmol) in methanol-tetrahydrofuran (1:1, 2 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (7.8 mg, 47%).

$^1$H-NMR (chloroform-d): 0.63 (6H, t, J=7.42 Hz), 1.11 (6H, t, J=7.42 Hz), 1.72-1.82 (4H, m), 2.10 (4H, q, J=7.09 Hz), 2.20 (3H, s), 2.39 (3H, s), 3.71 (2H, s), 6.94-7.09 (5H, m), 7.29 (1H, d, J=8.08 Hz), 7.69 (1H, s), 8.51 (2H, m); MS (ESI+): 498 ([M+H]$^+$).

Example 152

Synthesis of [5-(4-{1-ethyl-1-[4-(1-hydroxy-cycloheptylethynyl)-3-methyl-phenyl]-propyl}-2-methyl-phenyl)-pyridin-3-yl]-acetic Acid

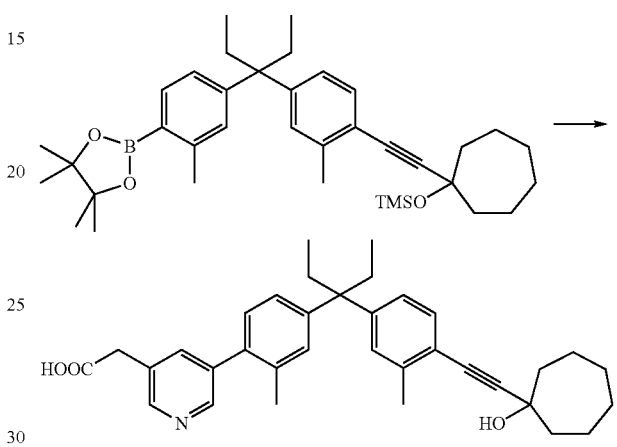

N,N-Dimethylformamide (1.0 mL) was added to 2-(4-{1-ethyl-1-[3-methyl-4-(1-trimethylsilanyloxy-cycloheptylethynyl)-phenyl]-propyl}-2-methyl-phenyl)-4,4,5,5-tetramethyl-[1,3,2]dioxaborolane (Example 128-(2); 51.4 mg, 0.0876 mmol), (5-bromo-pyridin-3-yl)-acetic acid methyl ester (Example 24-(2); 24.2 mg, 0.105 mmol), tetrakis(triphenylphosphine)palladium (0) (10.0 mg, 0.00865 mmol) and potassium phosphate (28.0 mg, 0.132 mmol), and the mixture was stirred with microwave heating at 140° C. for 10 minutes in a nitrogen atmosphere. Water was added to the reaction mixture, followed by extraction with ethyl acetate. The organic layer was concentrated under reduced pressure. The residue was purified by silica gel chromatography (dichloromethane:methanol=100:0 to 90:10) to give a mixture containing [5-(4-{1-ethyl-1-[4-(1-hydroxy-cycloheptylethynyl)-3-methyl-phenyl]-propyl}-2-methyl-phenyl)-pyridin-3-yl]-acetic acid methyl ester (32.0 mg). The mixture was used in the following reaction without further purification.

A 1 M solution of tetrabutylammonium fluoride in tetrahydrofuran (1.0 mL, 1.0 mmol) was added to the mixture containing [5-(4-{1-ethyl-1-[4-(1-hydroxy-cycloheptylethynyl)-3-methyl-phenyl]-propyl}-2-methyl-phenyl)-pyridin-3-yl]-acetic acid methyl ester (32.0 mg), and the mixture was stirred at room temperature for 15 minutes. The mixture was further stirred with microwave heating at 100° C. for five minutes. A sodium bicarbonate solution was added to the reaction mixture, followed by extraction with ethyl acetate. The organic layer was concentrated under reduced pressure. The residue was purified by high performance liquid chromatography (Shiseido CAPCELL PAK C$_{18}$ MGII, 20 mm I.D.× 50 mm, methanol:20 mM ammonium acetate solution=55:45 to 100:0, mL/min). A sodium bicarbonate solution was added to the eluate, followed by extraction with ethyl acetate. The organic layer was concentrated under reduced pressure to give the target compound as a colorless oil (10.1 mg, 22% in two steps).

¹H-NMR (methanol-d): 0.65 (t, 6H, J=7.3 Hz), 1.57-1.76 (m, 8H), 1.83-1.93 (m, 2H), 2.05-2.23 (m, 6H), 2.22 (s, 3H), 2.37 (s, 3H), 3.73 (s, 2H), 6.96-7.19 (m, 6H), 7.25 (d, 1H, J=8.0 Hz), 7.76 (brs, 1H), 8.40 (d, 1H, J=9.9 Hz); MS (ESI+): 524.3 ([M+H]⁺).

Example 153

Synthesis of {5-[4-(1-ethyl-1-{4-[2-(1-hydroxy-cycloheptyl)-(E)-vinyl]-3-methyl-phenyl}-propyl)-2-methyl-phenyl]-pyridin-3-yl}-acetic Acid

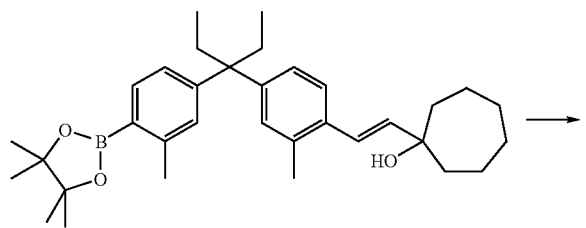

N,N-Dimethylformamide (1.0 mL) was added to 1-[2-(4-{1-ethyl-1-[3-methyl-4-(4,4,5,5-tetramethyl-[1,3,2]dioxaborolan-2-yl)-phenyl]-propyl}-2-methyl-phenyl)-(E)-vinyl]-cycloheptanol (Example 129-(3); 52.0 mg, 0.101 mmol), (5-bromo-pyridin-3-yl)-acetic acid methyl ester (Example 24-(2); 30.0 mg, 0.130 mmol), tetrakis(triphenylphosphine)palladium (0) (11.7 mg, 0.0101 mmol) and potassium phosphate (32.2 mg, 0.152 mmol), and the mixture was stirred with microwave heating at 140° C. for 10 minutes in a nitrogen atmosphere. Water was added to the reaction mixture, followed by extraction with ethyl acetate. The organic layer was washed with brine and concentrated under reduced pressure. The residue was purified by silica gel chromatography (dichloromethane:methanol=100:0 to 90:10) to give a mixture containing {5-[4-(1-ethyl-1-{4-[2-(1-hydroxy-cycloheptyl)-(E)-vinyl]-3-methyl-phenyl}-propyl)-2-methyl-phenyl]-pyridin-3-yl}-acetic acid methyl ester as a yellow oil (65.3 mg).

A 2 N sodium hydroxide aqueous solution (0.50 mL, 1.0 mmol) was added to a solution of the mixture containing {5-[4-(1-ethyl-1-{4-[2-(1-hydroxy-cycloheptyl)-(E)-vinyl]-3-methyl-phenyl}-propyl)-2-methyl-phenyl]-pyridin-3-yl}-acetic acid methyl ester (65.3 mg) in methanol (1.0 mL), and the mixture was stirred with microwave heating at 100° C. for five minutes. A sodium bicarbonate solution was added to the reaction mixture, followed by extraction with ethyl acetate and washing with brine. The organic layer was dried over anhydrous magnesium sulfate, filtered and concentrated under reduced pressure. The residue was purified by high performance liquid chromatography (Shiseido CAPCELL PAK C₁₈ MGII, 20 mm I.D.×50 mm, methanol:20 mM ammonium acetate solution=55:45 to 100:0, 20 mL/min). A sodium bicarbonate solution was added to the eluate, followed by extraction with ethyl acetate and washing with brine. The organic layer was dried over anhydrous magnesium sulfate, filtered and concentrated under reduced pressure to give the target compound as a colorless oil (16.0 mg, 30% in two steps).

¹H-NMR (methanol-d): 0.64 (t, 6H, J=7.3 Hz), 1.43-1.90 (m, 12H), 2.15 (q, 4H, J=7.3 Hz), 2.20 (s, 3H), 2.28 (s, 3H), 3.66 (s, 2H), 6.21 (d, 1H, J=15.9 Hz), 6.77 (d, 1H, J=15.9 Hz), 6.94-6.99 (m, 2H), 7.08-7.11 (m, 3H), 7.31 (d, 1H, J=8.5 Hz), 7.73 (brs, 1H), 8.37 (d, 2H, J=17.8 Hz); MS (ESI+): 526.2 ([M+H]⁺); MS (ESI−): 524.4 ([M−H]⁻).

Example 154

Synthesis of (4'-{1-ethyl-1-[4-(3-hydroxy-4,4-dimethyl-pentyl)-3-methyl-phenyl]-propyl}-2'-methyl-biphenyl-4-yl)-hydroxy-acetic Acid

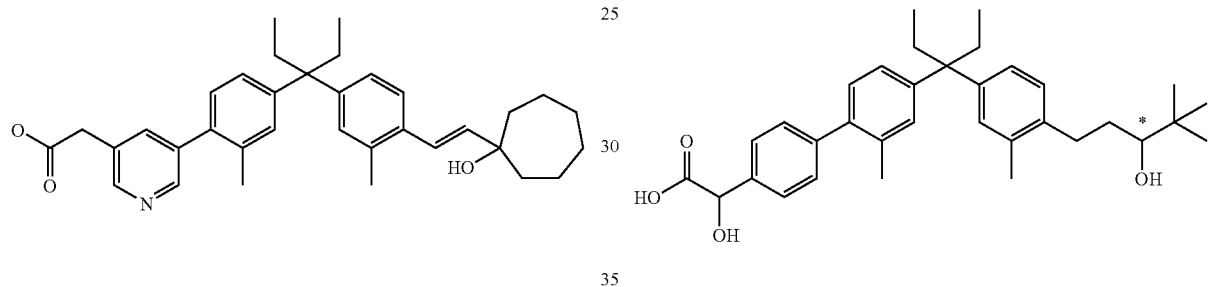

(1) Synthesis of (4-bromo-phenyl)-hydroxy-acetic Acid Methyl Ester

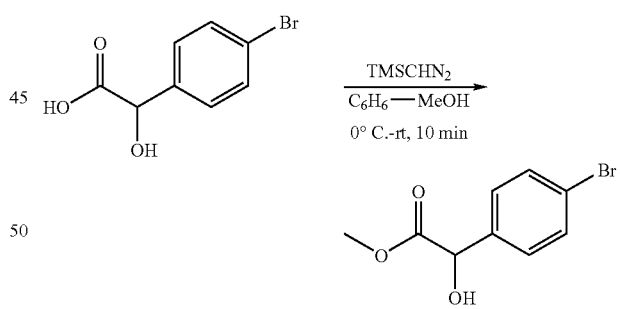

A solution of trimethylsilyldiazomethane in hexane (2 M, 1.4 mL, 2.8 mmol) was added to a solution of 4-bromo-phenyl-hydroxy-acetic acid (506 mg, 2.19 mmol) in benzene (2.1 mL)-methanol (1.0 mL) under cooling with ice, and the mixture was stirred at room temperature for five minutes. The reaction mixture was concentrated under reduced pressure. The residue was purified by silica gel chromatography (hexane/ethyl acetate=3/1) to give the title compound (500 mg, 93%).

¹H-NMR (chloroform-d): 3.43 (d, 1H, J=5.1 Hz), 3.78 (s, 3H), 5.15 (d, 1H, J=5.1 Hz), 7.31 (d, 2H, J=8.0 Hz), 7.50 (d, 2H, J=8.0 Hz); MS (ESI+): 267 ([M+Na]⁺).

(2) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-hydroxy-acetic Acid Methyl Ester

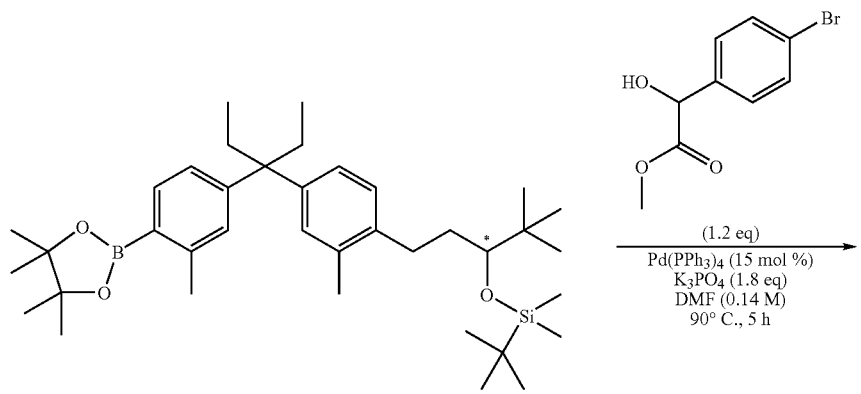

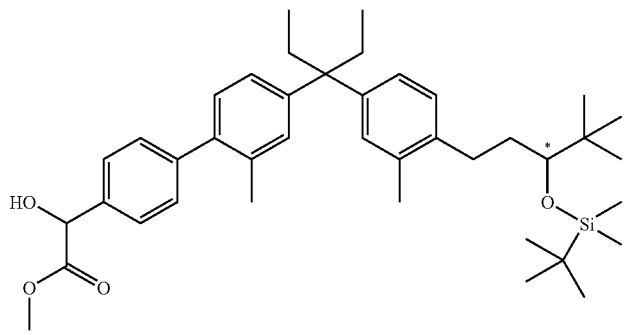

Degassed N,N-dimethylformamide (0.26 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 22.4 mg, 0.0343 mmol), 4-bromo-phenyl-hydroxy-acetic acid methyl ester (Example 154-(1); 10.5 mg, 0.0428 mmol), tetrakis(triphenylphosphine)palladium (0) (6.2 mg, 0.0054 mmol) and potassium phosphate (14.1 mg, 0.0664 mmol). After replacement with nitrogen, the mixture was heated while stirring at an external temperature of 86 to 96° C. for five hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=7/1) to give the title compound (7.0 mg, 32%).

$^1$H-NMR (chloroform-d): 0.08 (s, 3H), 0.12 (s, 3H), 0.66 (t, 6H, J=7.2 Hz), 0.90 (s, 9H), 0.95 (s, 9H), 1.60 (m, 1H), 1.79 (m, 1H), 2.11 (q, 4H, J=7.2 Hz), 2.24 (s, 3H), 2.27 (s, 3H), 2.43 (m, 1H), 2.78 (m, 1H), 3.36 (dd, 1H, J=7.0, 3.0 Hz), 3.42 (d, 1H, J=5.5 Hz), 3.81 (s, 3H), 5.23 (d, 1H, J=5.5 Hz), 6.94-7.10 (m, 6H), 7.33 (d, 2H, J=8.5 Hz), 7.43 (d, 2H, J=8.5 Hz).

(3) Synthesis of (4'-{1-ethyl-1-[4-(3-hydroxy-4,4-dimethyl-pentyl)-3-methyl-phenyl]-propyl}-2'-methyl-biphenyl-4-yl)-hydroxy-acetic Acid Methyl Ester

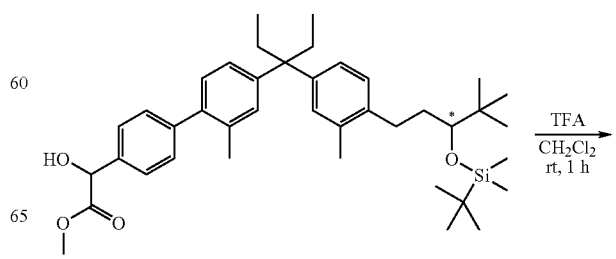

-continued

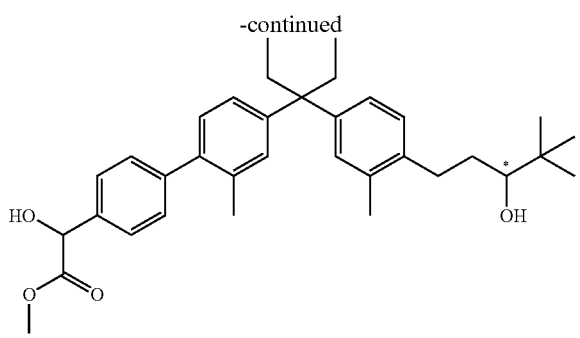

Trifluoroacetic acid (0.05 mL) was added to a solution of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-hydroxy-acetic acid methyl ester (Example 154-(2); 7.0 mg, 0.011 mmol) in dichloromethane (0.28 mL) at room temperature, and the mixture was stirred at room temperature for one hour. The solvent in the reaction solution was distilled off under reduced pressure, and the residue was diluted with diethyl ether. The mixture was adjusted to pH 7 to 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=3/1) to give the title compound (5.0 mg, 86%).

$^1$H-NMR (chloroform-d): 0.66 (t, 6H, J=7.2 Hz), 0.91 (s, 9H), 1.54 (m, 1H), 1.82 (m, 1H), 2.11 (q, 4H, J=7.2 Hz), 2.23 (s, 3H), 2.29 (s, 3H), 2.58 (m, 1H), 2.89 (m, 1H), 3.26 (d, 1H, J=10.0 Hz), 3.43 (d, 1H, J=5.7 Hz), 3.81 (s, 3H), 5.23 (d, 1H, J=5.7 Hz), 6.95-7.10 (m, 6H), 7.34 (d, 2H, J=8.4 Hz), 7.43 (d, 2H, J=8.4 Hz).

(4) Synthesis of (4'-{1-ethyl-1-[4-(3-hydroxy-4,4-dimethyl-pentyl)-3-methyl-phenyl]-propyl}-2'-methyl-biphenyl-4-yl)-hydroxy-acetic Acid A 2 N sodium hydroxide aqueous solution (0.022 mL) was added to a solution of (4'-{1-ethyl-1-[4-(3-hydroxy-4,4-dimethyl-pentyl)-3-methyl-phenyl]-propyl}-2'-methyl-biphenyl-4-yl)hydroxy-acetic acid methyl ester (Example 154-(3); 5.0 mg, 0.0094 mmol) in methanol (0.15 mL) at room temperature, and the mixture was stirred at room temperature for four hours. The mixture was acidified with dilute hydrochloric acid aqueous solution, followed by extraction with ethyl acetate. The extract was dried over anhydrous magnesium sulfate and then concentrated under reduced pressure to give the title compound (4.8 mg, 99%).

$^1$H-NMR (chloroform-d): 0.65 (t, 6H, J=7.2 Hz), 0.90 (s, 9H), 1.54 (m, 1H), 1.82 (m, 1H), 2.11 (q, 4H, J=7.2 Hz), 2.22 (s, 3H), 2.28 (s, 3H), 2.57 (m, 1H), 2.89 (m, 1H), 3.27 (dd, 1H, J=10.5, 1.8 Hz), 5.31 (s, 1H), 6.93-7.09 (m, 6H), 7.35 (d, 2H, J=8.1 Hz), 7.47 (d, 2H, J=8.1 Hz); MS (ESI−): 515 ([M−H]$^-$).

Example 155

Synthesis of (4'-{1-ethyl-1-[4-(3-hydroxy-4,4-dimethyl-pentyl)-3-methyl-phenyl]-propyl}-2'-methyl-biphenyl-4-yl)-hydroxy-acetic Acid

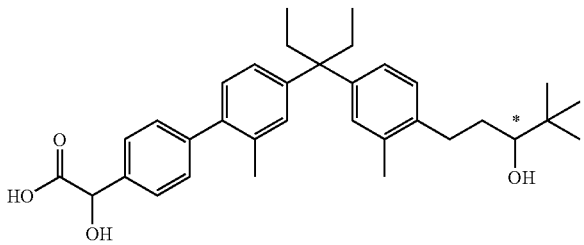

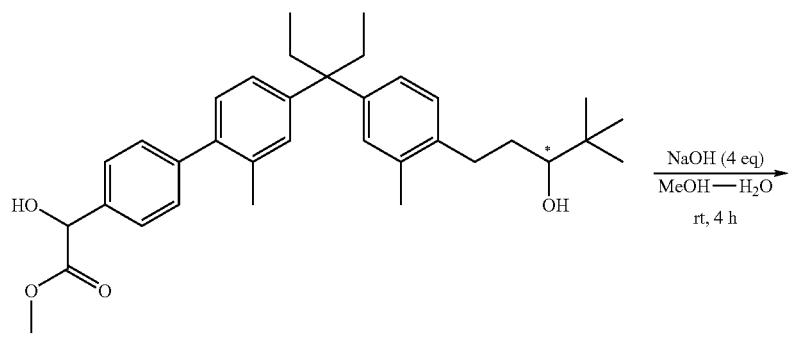

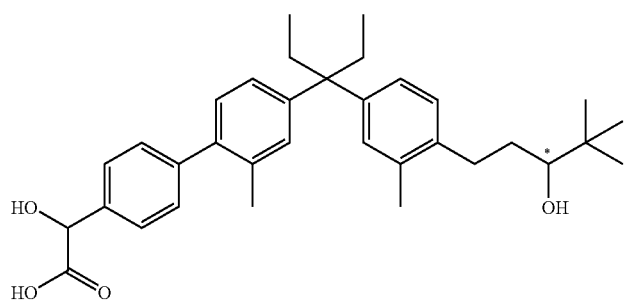

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-hydroxy-acetic Acid Methyl Ester

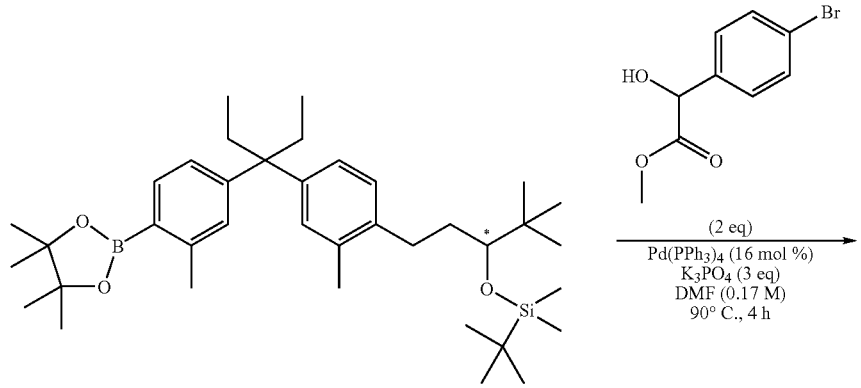

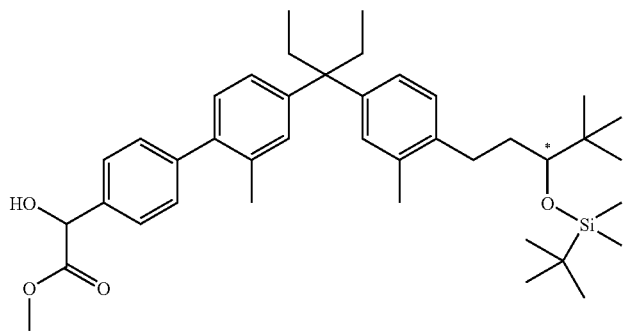

Degassed N,N-dimethylformamide (0.60 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 61.4 mg, 0.101 mmol), 4-bromo-phenyl-hydroxy-acetic acid methyl ester (Example 154-(1); 49.8 mg, 0.203 mmol), tetrakis(triphenylphosphine)palladium (0) (19 mg, 0.016 mmol) and potassium phosphate (65 mg, 0.31 mmol). After replacement with nitrogen, the mixture was heated while stirring at an external temperature of 86 to 95° C. for four hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=7/1) to give the title compound (24.4 mg, 37%).

$^1$H-NMR (chloroform-d): 0.08 (s, 3H), 0.12 (s, 3H), 0.66 (t, 6H, J=7.2 Hz), 0.89 (s, 9H), 0.95 (s, 9H), 1.60 (m, 1H), 1.80 (m, 1H), 2.11 (q, 4H, J=7.2 Hz), 2.24 (s, 3H), 2.27 (s, 3H), 2.43 (m, 1H), 2.78 (m, 1H), 3.36 (dd, 1H, J=7.0, 3.0 Hz), 3.42 (d 1H, J=5.5 Hz), 3.81 (s, 3H), 5.23 (d, 1H, J=5.5 Hz), 6.93-7.10 (m, 6H), 7.34 (d, 2H, J=8.5 Hz), 7.43 (d, 2H, J=8.5 Hz).

(2) Synthesis of (4'-{1-ethyl-1-[4-(3-hydroxy-4,4-dimethyl-pentyl)-3-methyl-phenyl]-propyl}-2'-methyl-biphenyl-4-yl)-hydroxy-acetic Acid Methyl Ester

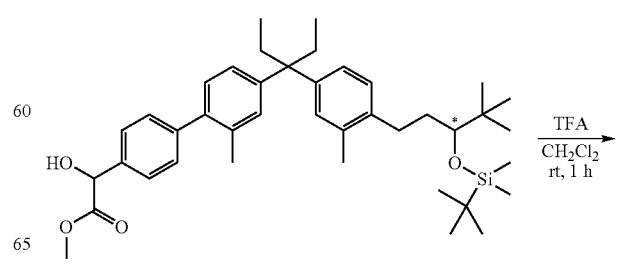

-continued

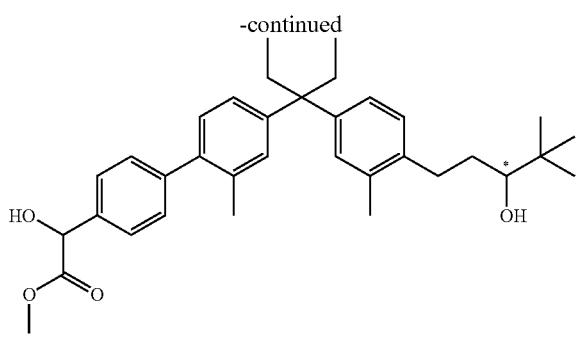

Trifluoroacetic acid (0.18 mL) was added to a solution of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-hydroxy-acetic acid methyl ester (Example 155-(1); 24.4 mg, 0.0378 mmol) in dichloromethane (0.90 mL) at room temperature, and the mixture was stirred at room temperature for one hour. The solvent in the reaction solution was distilled off under reduced pressure, and the residue was diluted with diethyl ether. The mixture was adjusted to pH 7 to 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=3/1) to give the title compound (17.5 mg, 87%).

$^1$H-NMR (chloroform-d): 0.66 (t, 6H, J=7.2 Hz), 0.91 (s, 9H), 1.54 (m, 1H), 1.82 (m, 1H), 2.11 (q, 4H, J=7.2 Hz), 2.23 (s, 3H), 2.29 (s, 3H), 2.58 (m, 1H), 2.89 (m, 1H), 3.26 (d, 1H, J=10 Hz), 3.43 (d, 1H, J=5.7 Hz), 3.81 (s, 3H), 5.23 (d, 1H, J=5.7 Hz), 6.95-7.10 (m, 6H), 7.31 (d, 2H, J=8.4 Hz), 7.43 (d, 2H, J=8.4 Hz).

(3) Synthesis of (4'-{1-ethyl-1-[4-(3-hydroxy-4,4-dimethyl-pentyl)-3-methyl-phenyl]-propyl}-2'-methyl-biphenyl-4-yl)-hydroxy-acetic Acid A 2 N sodium hydroxide aqueous solution (0.070 mL) was added to a solution of (4'-{1-ethyl-1-[4-(3-hydroxy-4,4-dimethyl-pentyl)-3-methyl-phenyl]-propyl}-2'-methyl-biphenyl-4-yl)hydroxy-acetic acid methyl ester (Example 155-(2); 17.5 mg, 0.0330 mmol) in methanol (0.47 mL) at room temperature, and the mixture was stirred at room temperature for 5.5 hours. The mixture was acidified with dilute hydrochloric acid aqueous solution, followed by extraction with ethyl acetate. The extract was dried over anhydrous magnesium sulfate and then concentrated under reduced pressure to give the title compound (17.0 mg, 100%).

$^1$H-NMR (chloroform-d): 0.65 (t, 6H, J=7.2 Hz), 0.90 (s, 9H), 1.52 (m, 1H), 1.82 (m, 1H), 2.11 (q, 4H, J=7.2 Hz), 2.22 (s, 3H), 2.28 (s, 3H), 2.57 (m, 1H), 2.88 (m, 1H), 3.27 (dd, 1H, J=10.5, 1.8 Hz), 5.30 (s, 1H), 6.93-7.09 (m, 6H), 7.35 (d, 2H, J=8.4 Hz), 7.47 (d, 2H, J=8.4 Hz); MS (ESI−): 515 ([M−H]−).

Example 156

Synthesis of (R)-(4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

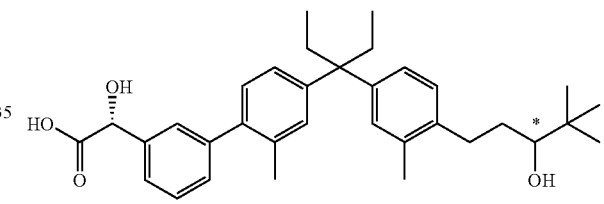

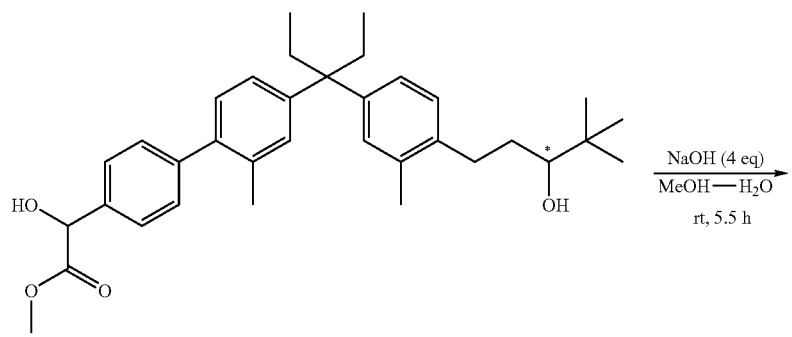

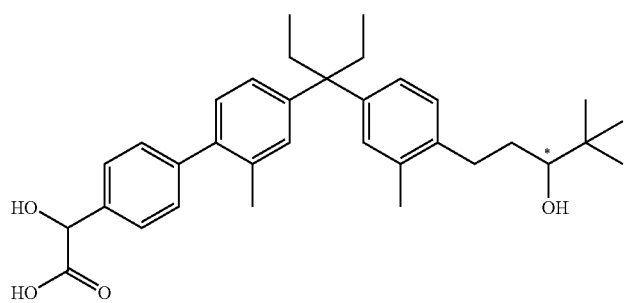

(1) Synthesis of (R)-(3-chloro-phenyl)-hydroxy-acetic Acid Methyl Ester

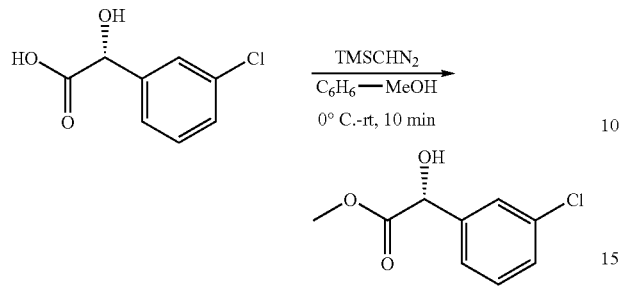

A solution of trimethylsilyldiazomethane in hexane (2 M, 1.5 mL, 3.0 mmol) was added to a solution of (R)-(3-chloro-phenyl)hydroxy-acetic acid (497 mg, 2.66 mmol) in benzene (2.6 mL)-methanol (1.3 mL) under cooling with ice. Then, the ice bath was removed and the mixture was stirred at room temperature for five minutes. The reaction mixture was concentrated under reduced pressure. The residue was purified by silica gel chromatography (hexane/ethyl acetate=3/1) to give the title compound (533 mg, 100%).

1H-NMR (chloroform-d): 3.46 (d, 1H, J=5.5 Hz), 3.79 (s, 3H), 5.16 (d, 1H, J=5.5 Hz), 7.31 (m, 3H), 7.44 (m, 1H).

(2) Synthesis of (R)-[4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic Acid Methyl Ester

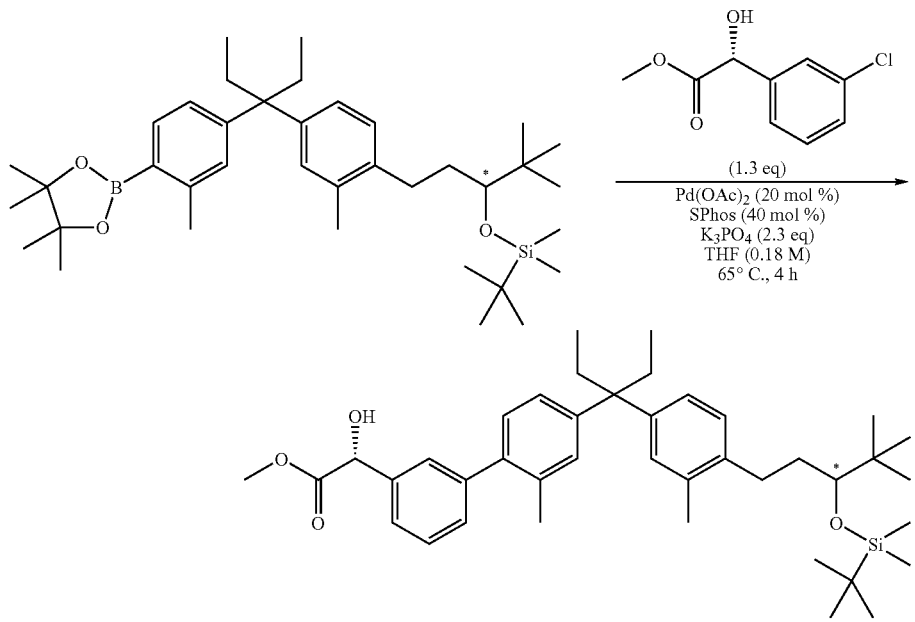

Degassed tetrahydrofuran (0.14 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 14.4 mg, 0.0237 mmol), palladium (II) acetate (1.2 mg, 0.0053 mmol), 2-dicyclohexylphosphino-2',6'-dimethoxy-1,1'-biphenyl (4.5 mg, 0.011 mmol) and potassium phosphate (13.0 mg, 0.0612 mmol). The mixture was stirred in a nitrogen atmosphere for three minutes, followed by addition of (R)-(3-chloro-phenyl)-hydroxy-acetic acid methyl ester (Example 156-(1); 0.006 mL, 6.5 mg, 0.032 mmol). After replacement with nitrogen, the mixture was heated while stirring at an external temperature of 60 to 70° C. for four hours. The reaction mixture was diluted with diethyl ether and filtered through cotton plug, and the filtrate was concentrated under reduced pressure. The residue was purified by silica gel chromatography (hexane/ethyl acetate=7/1) to give the title compound (3.6 mg, 24%).

1H-NMR (chloroform-d): 0.08 (s, 3H), 0.12 (s, 3H), 0.66 (t, 6H, J=7.3 Hz), 0.90 (s, 9H), 0.95 (s, 9H), 1.62 (m, 1H), 1.80 (m, 1H), 2.12 (q, 4H, J=7.3 Hz), 2.23 (s, 3H), 2.27 (s, 3H), 2.44 (m, 1H), 2.78 (m, 1H), 3.36 (dd, 1H, J=7.0, 4.0 Hz), 3.42 (d, 1H, J=5.5 Hz), 3.78 (s, 3H), 5.21 (d, 1H, J=5.5 Hz), 7.93-7.12 (m, 6H), 7.26-7.41 (m, 4H).

(3) Synthesis of (R)-(4'-{1-ethyl-1-[4-(3-hydroxy-4,4-dimethyl-pentyl)-3-methyl-phenyl]-propyl}-2'-methyl-biphenyl-3-yl)-hydroxy-acetic Acid Methyl Ester

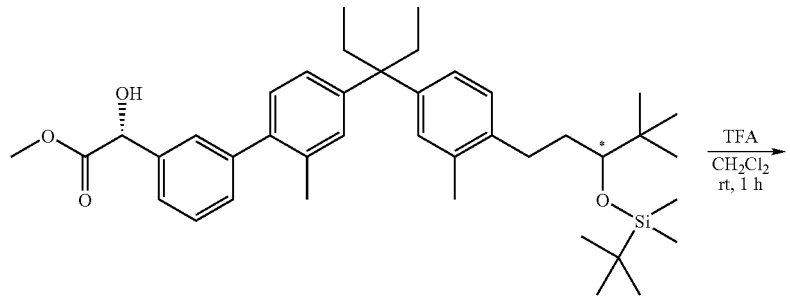

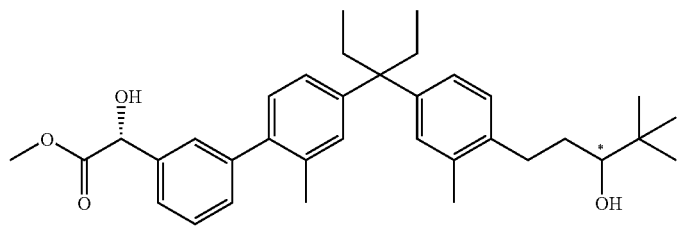

Trifluoroacetic acid (0.04 mL) was added to a solution of (R)-[4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic acid methyl ester (Example 156-(2); 3.6 mg, 0.0056 mmol) in dichloromethane (0.20 mL) at room temperature, and the mixture was stirred at room temperature for one hour. The solvent in the reaction solution was distilled off under reduced pressure, and the residue was diluted with diethyl ether. The mixture was adjusted to pH 7 to 8 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=3/1) to give the title compound (2.6 mg, 87%).

$^{1}$H-NMR (chloroform-d): 0.66 (t, 6H, J=7.3 Hz), 0.91 (s, 9H), 1.54 (m, 1H), 1.82 (m, 1H), 2.12 (q, 4H, J=7.3 Hz), 2.23 (s, 3H), 2.29 (s, 3H), 2.57 (m, 1H), 2.89 (m, 1H), 3.26 (dd, 1H, J=10.5, 1.5 Hz), 3.43 (br, 1H), 3.78 (s, 3H), 5.21 (s, 1H), 6.95-7.11 (m, 6H), 7.26-7.41 (m, 4H).

(4) Synthesis of (R)-(4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

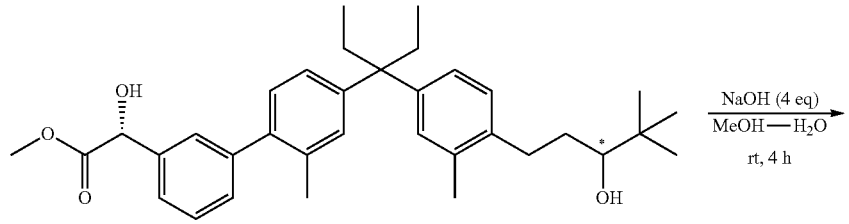

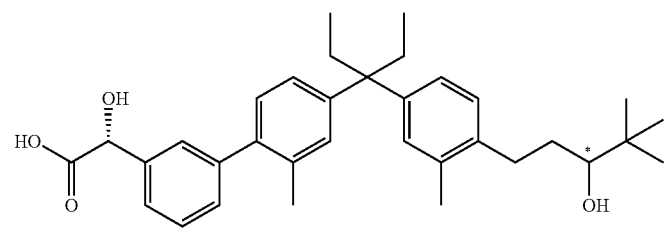

A 2 N sodium hydroxide aqueous solution (0.010 mL) was added to a solution of (R)-(4'-{1-ethyl-1-[4-(3-hydroxy-4,4-dimethyl-pentyl)-3-methyl-phenyl]-propyl}-2'-methyl-biphenyl-3-yl)hydroxy-acetic acid methyl ester (Example 156-(3); 2.6 mg, 0.0048 mmol) in methanol (0.10 mL) at room temperature, and the mixture was stirred at room temperature for four hours. The mixture was acidified with dilute hydrochloric acid aqueous solution, followed by extraction with ethyl acetate. The extract was dried over anhydrous magnesium sulfate and then concentrated under reduced pressure to give the title compound (2.5 mg, 100%).

$^1$H-NMR (chloroform-d): 0.65 (t, 6H, J=7.3 Hz), 0.90 (s, 9H), 1.52 (m, 1H), 1.82 (m, 1H), 2.11 (q, 4H, J=7.3 Hz), 2.21 (s, 3H), 2.28 (s, 3H), 2.57 (m, 1H), 2.87 (m, 1H), 3.27 (dd, 1H, J=10.5, 1.8 Hz), 5.28 (s, 1H), 6.93-7.11 (m, 6H), 7.30-7.45 (m, 4H); MS (ESI−): 515 ([M−H]−).

Example 157

Synthesis of (R)-(4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

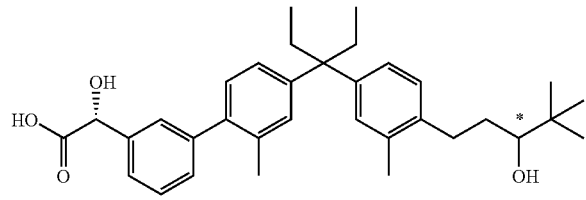

(1) Synthesis of (R)-[4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic Acid Methyl Ester Degassed toluene (0.17 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 46.5 mg, 0.0766 mmol), palladium (II) acetate (2.8 mg, 0.013 mmol), 2-dicyclohexylphosphino-2',6'-dimethoxy-1,1'-biphenyl (10.5 mg, 0.0256 mmol) and potassium phosphate (39.8 mg, 0.187 mmol), and the mixture was stirred in a nitrogen atmosphere for three minutes. Then, a solution of (R)-(3-chloro-phenyl)hydroxy-acetic acid methyl ester (Example 156-(1); 18.8 mg, 0.0937 mmol) in toluene (0.17 mL) and water (0.033 mL) were added, and the mixture was heated while stirring at an external temperature of 95 to 105° C. for one hour. The reaction mixture was diluted with diethyl ether and filtered through cotton plug, and the filtrate was concentrated under reduced pressure. The residue was purified by silica gel chromatography (hexane/ethyl acetate=8/1) to give the title compound (35 mg, 71%).

$^1$H-NMR (chloroform-d): 0.08 (s, 3H), 0.12 (s, 3H), 0.66 (t, 6H, J=7.4 Hz), 0.90 (s, 9H), 0.95 (s, 9H), 1.60 (m, 1H), 1.80 (m, 1H), 2.12 (q, 4H, J=7.4 Hz), 2.23 (s, 3H), 2.27 (s, 3H), 2.43 (m, 1H), 2.78 (m, 1H), 3.36 (dd, 1H, J=7.0, 4.0 Hz), 3.43 (d, 1H, J=5.7 Hz), 3.78 (s, 3H), 5.21 (d, 1H, J=5.5 Hz), 6.94-7.11 (m, 6H), 7.26-7.40 (m, 4H).

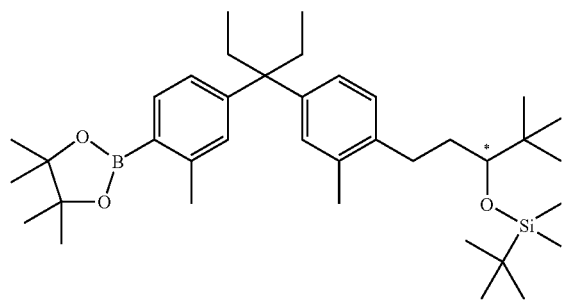 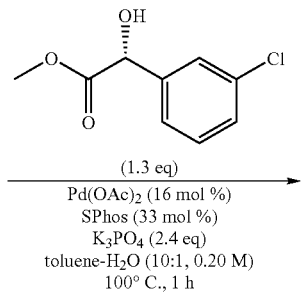

(1.3 eq)
Pd(OAc)$_2$ (16 mol %)
SPhos (33 mol %)
K$_3$PO$_4$ (2.4 eq)
toluene-H$_2$O (10:1, 0.20 M)
100° C., 1 h

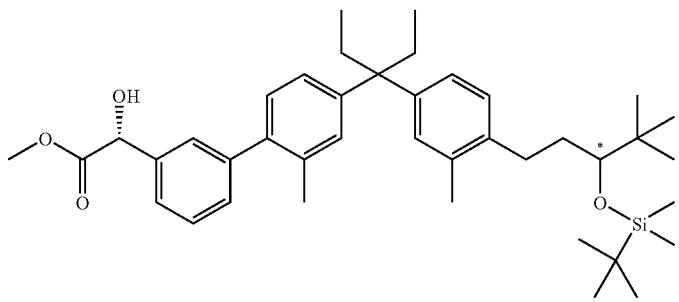

(2) Synthesis of (R)-(4'-{1-ethyl-1-[4-(3-hydroxy-4,4-dimethyl-pentyl)-3-methyl-phenyl]-propyl}-2'-methyl-biphenyl-3-yl)-hydroxy-acetic Acid Methyl Ester

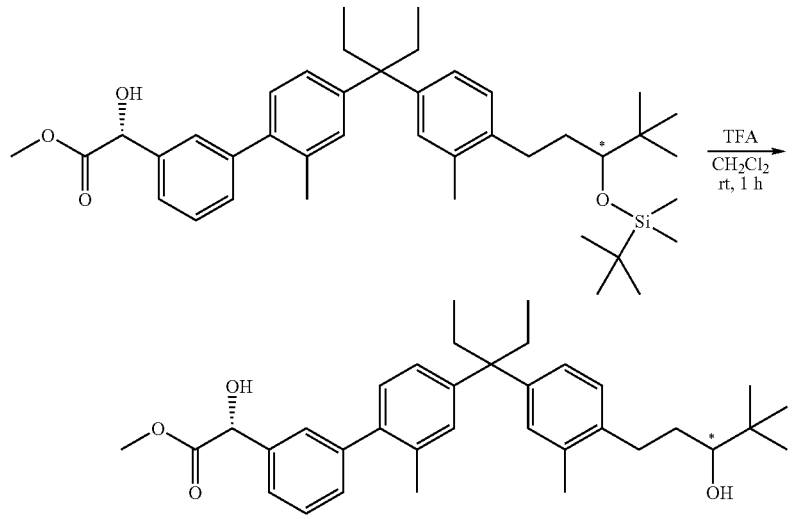

Trifluoroacetic acid (0.25 mL) was added to a solution of (R)-[4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic acid methyl ester (Example 157-(1); 34 mg, 0.053 mmol) in dichloromethane (1.25 mL) at room temperature, and the mixture was stirred at room temperature for one hour. The solvent in the reaction solution was distilled off under reduced pressure, and the residue was diluted with diethyl ether. The mixture was adjusted to pH 7 to 8 with aqueous sodium bicarbonate, followed by extraction with diethyl ether. The extract was dried over anhydrous magnesium sulfate and then concentrated under reduced pressure. The residue was purified by silica gel chromatography (hexane/ethyl acetate=3/1) to give the title compound (24 mg, 86%).

$^1$H-NMR (chloroform-d): 0.66 (t, 6H, J=7.3 Hz), 0.91 (s, 9H), 1.40 (d, 1H, J=5.6 Hz), 1.54 (m, 1H), 1.82 (m, 1H), 2.12 (q, 4H, J=7.3 Hz), 2.23 (s, 3H), 2.29 (s, 3H), 2.58 (m, 1H), 2.89 (m, 1H), 3.26 (m, 1H), 3.43 (d, 1H, J=5.5 Hz), 3.78 (s, 3H), 5.21 (d, 1H, J=5.5 Hz), 6.94-7.12 (m, 6H), 7.26-7.41 (m, 4H).

(3) Synthesis of (R)-(4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

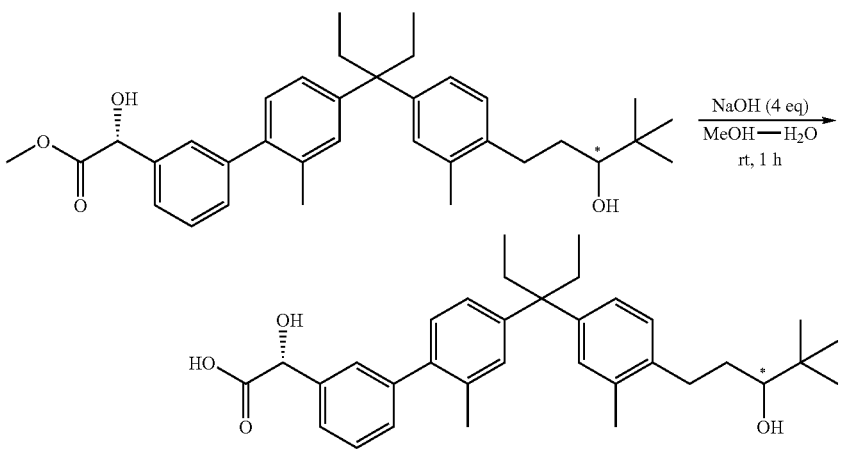

A 2 N sodium hydroxide aqueous solution (0.095 mL) was added to a solution of (R)-(4'-{1-ethyl-1-[4-(3-hydroxy-4,4-dimethyl-pentyl)-3-methyl-phenyl]-propyl}-2'-methyl-biphenyl-3-yl)hydroxy-acetic acid methyl ester (Example 157-(2); 24.2 mg, 0.0456 mmol) in methanol (0.65 mL) at room temperature, and the mixture was stirred at room temperature for four hours. The mixture was acidified with dilute hydrochloric acid aqueous solution, followed by extraction with ethyl acetate. The extract was dried over anhydrous magnesium sulfate and then concentrated under reduced pressure to give the title compound (24 mg, 100%).

¹H-NMR (chloroform-d): 0.65 (t, 6H, J=7.3 Hz), 0.90 (s, 9H), 1.52 (m, 1H), 1.82 (m, 1H), 2.11 (q, 4H, J=7.3 Hz), 2.21 (s, 3H), 2.27 (s, 3H), 2.57 (m, 1H), 2.87 (m, 1H), 3.27 (dd, 1H, J=10.5, 1.8 Hz), 5.28 (s, 1H), 6.93-7.10 (m, 6H), 7.28-7.44 (m, 4H); MS (ESI–): 515 ([M–H]⁻).

Example 158

Synthesis of (4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

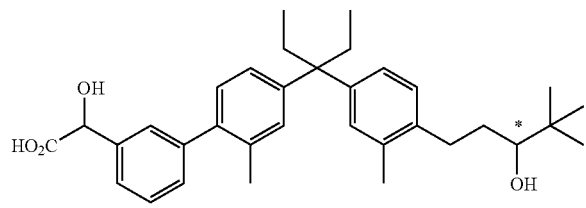

(1) Synthesis of (3-bromo-phenyl)-hydroxy-acetic Acid Methyl Ester

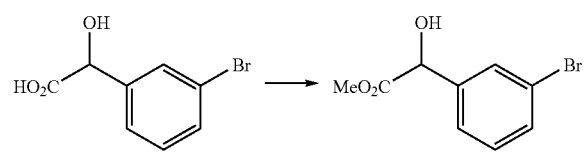

The title compound (95%) was obtained by the same method as in Example 154-(1) using (3-bromo-phenyl)-hydroxy-acetic acid as a starting material.

¹H-NMR (chloroform-d): 3.46 (d, 1H, J=5.3 Hz), 3.79 (s, 3H), 5.15 (d, 1H, J=5.3 Hz), 7.21-7.26 (m, 1H), 7.35-7.38 (m, 1H), 7.45-7.48 (m, 1H), 7.59 (m, 1H).

(2) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic Acid Methyl Ester

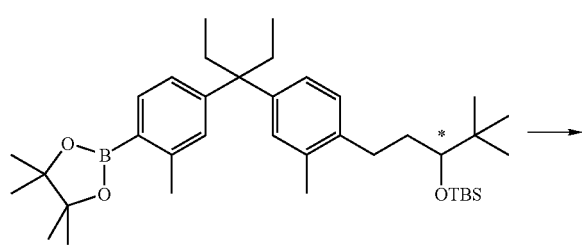

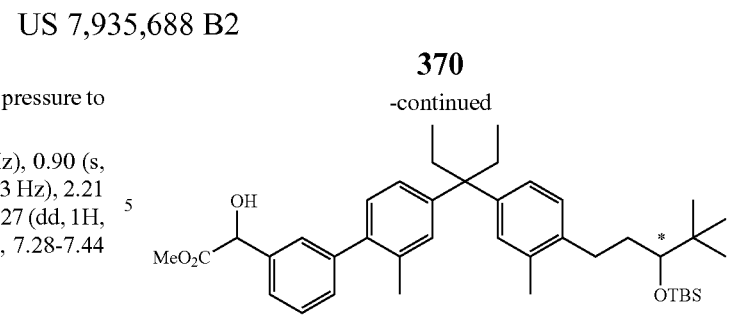

The title compound (21%) was obtained by the same method as in Example 66-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1)) and (3-bromo-phenyl)-hydroxy-acetic acid methyl ester (Example 158-(1)) as starting materials.

¹H-NMR (chloroform-d): 0.07 (s, 3H), 0.11 (s, 3H), 0.65 (t, 6H, J=7.3 Hz), 0.88 (s, 9H), 0.94 (s, 9H), 1.51-1.65 (m, 1H), 1.74-1.85 (m, 1H), 2.11 (q, 4H, J=7.3 Hz), 2.22 (s, 3H), 2.26 (s, 3H), 2.37-2.48 (m, 1H), 2.72-2.83 (m, 1H), 3.35 (dd, 1H, J=3.1, 7.1 Hz), 3.42 (d, 1H, J=5.8 Hz), 3.77 (s, 3H), 5.21 (d, 1H, J=5.8 Hz), 6.94-7.10 (m, 6H), 7.28-7.42 (m, 4H).

(3) Synthesis of (4'-{1-ethyl-1-[4-(3-hydroxy-4,4-dimethyl-pentyl)-3-methyl-phenyl]-propyl}-2'-methyl-biphenyl-3-yl)-hydroxy-acetic Acid Methyl Ester

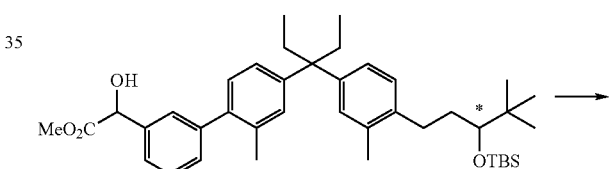

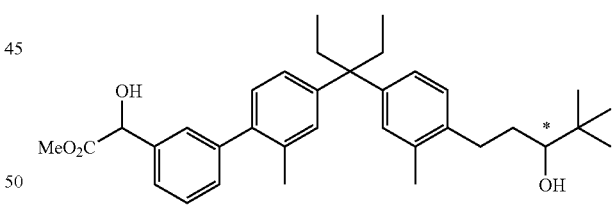

The title compound (58%) was obtained by the same method as in Example 154-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic acid methyl ester (Example 158-(2)) as a starting material.

¹H-NMR (chloroform-d): 0.65 (t, 6H, J=7.3 Hz), 0.90 (s, 9H), 1.44-1.59 (m, 1H), 1.76-1.86 (m, 1H), 2.11 (q, 4H, J=7.3 Hz), 2.22 (s, 3H), 2.28 (s, 3H), 2.51-2.63 (m, 1H), 2.82-2.93 (m, 1H), 3.26 (dd, 1H, J=1.7, 10.4 Hz), 3.44 (brs, 1H), 3.77 (s, 3H), 5.21 (brs, 1H), 6.95-7.10 (m, 6H), 7.28-7.42 (m, 4H).

(4) Synthesis of (4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

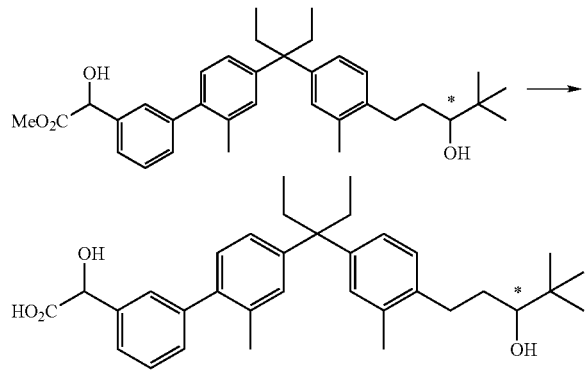

The title compound (48%) was obtained by the same method as in Example 154-(4) using (4'-{1-ethyl-1-[4-(3-hydroxy-4,4-dimethyl-pentyl)-3-methyl-phenyl]-propyl}-2'-methyl-biphenyl-3-yl)-hydroxy-acetic acid methyl ester (Example 158-(3)) as a starting material.

$^1$H-NMR (methanol-d4): 0.64 (t, 6H, J=7.3 Hz), 0.88 (s, 9H), 1.48-1.57 (m, 1H), 1.72-1.83 (m, 1H), 2.14 (q, 4H, J=7.3 Hz), 2.19 (s, 3H), 2.27 (s, 3H), 2.50-2.61 (m, 1H), 2.83-2.94 (m, 1H), 3.15-3.18 (m, 1H), 4.88 (brs, 1H), 6.95-6.97 (m, 2H), 7.01-7.10 (m, 4H), 7.19 (d, 1H, J=7.3 Hz), 7.33-7.43 (m, 3H); MS (ESI+): 534 ([M+NH$_4$]$^+$).

Example 159

Synthesis of (4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

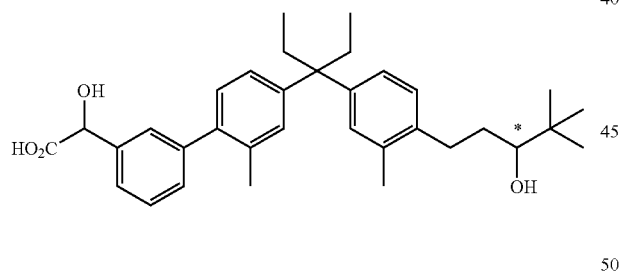

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic Acid Methyl Ester

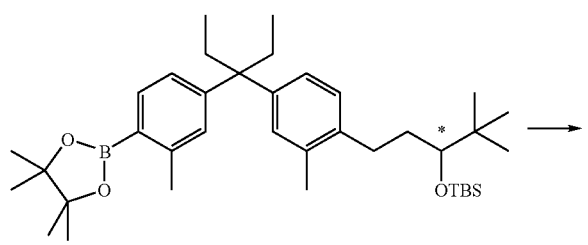

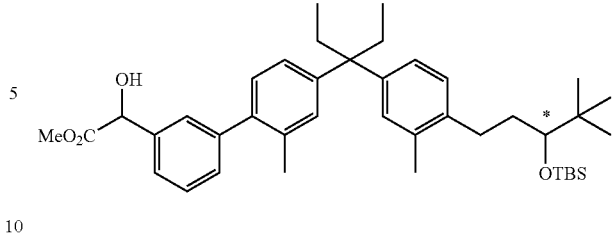

The title compound (21%) was obtained by the same method as in Example 66-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 24-(1)) and (3-bromo-phenyl)-hydroxy-acetic acid methyl ester (Example 158-(1)) as starting materials.

$^1$H-NMR (chloroform-d): 0.07 (s, 3H), 0.11 (s, 3H), 0.65 (t, 6H, J=7.3 Hz), 0.88 (s, 9H), 0.94 (s, 9H), 1.55-1.65 (m, 1H), 1.74-1.85 (m, 1H), 2.11 (q, 4H, J=7.3 Hz), 2.22 (s, 3H), 2.26 (s, 3H), 2.34-2.48 (m, 1H), 2.72-2.83 (m, 1H), 3.35 (dd, 1H, J=3.3, 7.1 Hz), 3.43 (brs, 1H), 3.77 (s, 3H), 5.21 (d, 1H, J=4.5 Hz), 6.94-7.10 (m, 6H), 7.28-7.42 (m, 4H).

(2) Synthesis of (4'-{1-ethyl-1-[4-(3-hydroxy-4,4-dimethyl-pentyl)-3-methyl-phenyl]-propyl}-2'-methyl-biphenyl-3-yl)-hydroxy-acetic Acid Methyl Ester

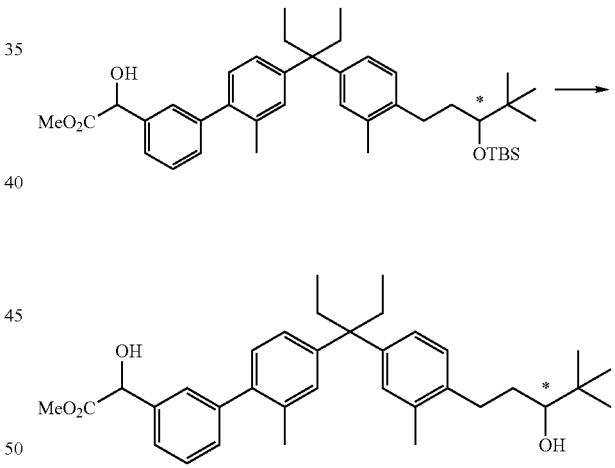

The title compound (68%) was obtained by the same method as in Example 154-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-hydroxy-acetic acid methyl ester (Example 159-(1)) as a starting material.

$^1$H-NMR (chloroform-d): 0.65 (t, 6H, J=7.3 Hz), 0.90 (s, 9H), 1.44-1.56 (m, 1H), 1.75-1.86 (m, 1H), 2.11 (q, 4H, J=7.3 Hz), 2.22 (s, 3H), 2.28 (s, 3H), 2.51-2.63 (m, 1H), 2.82-2.94 (m, 1H), 3.23-3.27 (m, 1H), 3.43 (d, 1H, J=5.3 Hz), 3.77 (s, 3H), 5.21 (d, 1H, J=5.3 Hz), 6.95-7.10 (m, 6H), 7.29-7.42 (m, 4H).

(3) Synthesis of (4'-{1-ethyl-1-[4-(3-hydroxy-4,4-dimethyl-pentyl)-3-methyl-phenyl]-propyl}-2'-methyl-biphenyl-3-yl)-hydroxy-acetic Acid

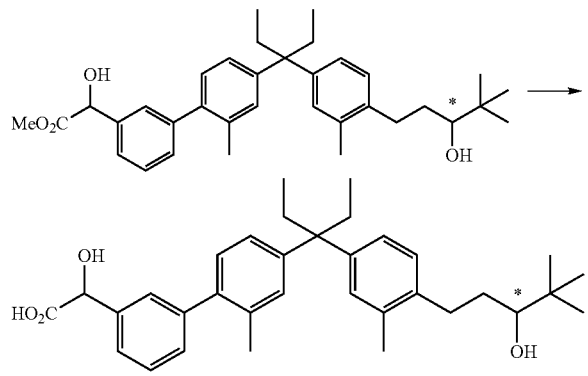

The title compound (63%) was obtained by the same method as in Example 154-(4) using (4'-{1-ethyl-1-[4-(3-hydroxy-4,4-dimethyl-pentyl)-3-methyl-phenyl]-propyl}-2'-methyl-biphenyl-3-yl)-hydroxy-acetic acid methyl ester (Example 159-(2)) as a starting material.

$^1$H-NMR (methanol-d4): 0.64 (t, 6H, J=7.4 Hz), 0.88 (s, 9H), 1.48-1.52 (m, 1H), 1.76 (m, 1H), 2.13 (q, 4H, J=7.4 Hz), 2.19 (s, 3H), 2.27 (s, 3H), 2.50-2.61 (m, 1H), 2.83-2.92 (m, 1H), 3.14-3.18 (m, 1H), 4.95 (brs, 1H), 6.95-7.10 (m, 6H), 7.20 (d, 1H, J=7.4 Hz), 7.33-7.42 (m, 3H); MS (ESI+): 534 ([M+NH$_4$]$^+$).

Example 160

Synthesis of (4'-{1-ethyl-1-[4-(3-hydroxy-4,4-dimethyl-pentyl)-3-methyl-phenyl]-propyl}-2'-methyl-biphenyl-4-yl)-oxo-acetic Acid

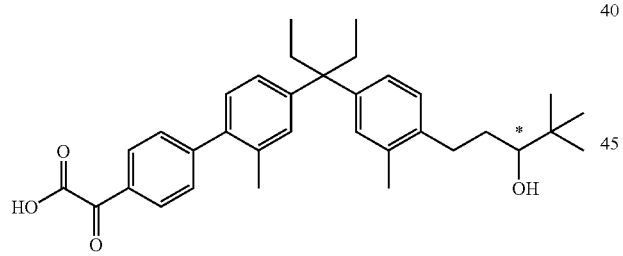

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-oxo-acetic Acid Ethyl Ester

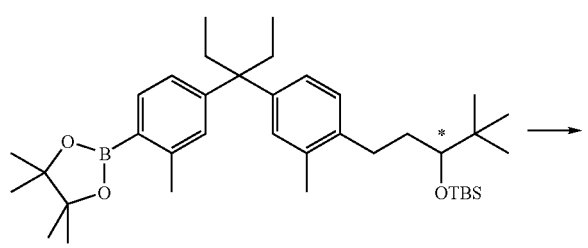

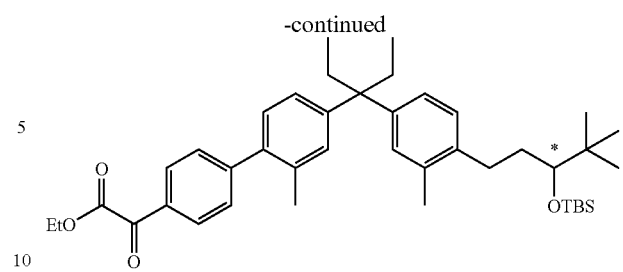

The title compound (32%) was obtained by the same method as in Example 157-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1)) and (4-chloro-phenyl)-oxo-acetic acid ethyl ester as starting materials.

$^1$H-NMR (chloroform-d): 0.07 (s, 3H), 0.11 (s, 3H), 0.65 (t, 6H, J=7.3 Hz), 0.88 (s, 9H), 0.93 (s, 9H), 1.44 (t, 3H, J=7.1 Hz), 1.55-1.65 (m, 1H), 1.74-1.83 (m, 1H), 2.11 (q, 4H, J=7.3 Hz), 2.24 (s, 3H), 2.26 (s, 3H), 2.37-2.48 (m, 1H), 2.72-2.83 (m, 1H), 3.35 (dd, 1H, J=3.1, 7.1 Hz), 4.47 (q, 2H, J=7.1 Hz), 6.93-7.11 (m, 6H), 7.48 (d, 2H, J=8.6 Hz), 8.04 (d, 2H, J=8.6 Hz).

(2) Synthesis of (4'-{1-ethyl-1-[4-(3-hydroxy-4,4-dimethyl-pentyl)-3-methyl-phenyl]-propyl}-2'-methyl-biphenyl-4-yl)-oxo-acetic Acid Ethyl Ester

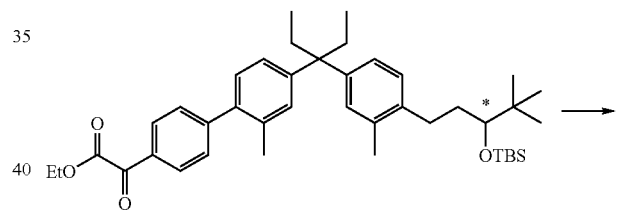

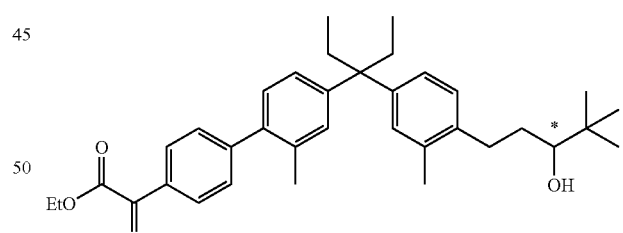

The title compound (81%) was obtained by the same method as in Example 154-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-oxo-acetic acid ethyl ester (Example 160-(1)) as a starting material.

$^1$H-NMR (chloroform-d): 0.65 (t, 6H, J=7.3 Hz), 0.90 (s, 9H), 1.44 (t, 3H, J=7.1 Hz), 1.42-1.59 (m, 1H), 1.75-1.86 (m, 1H), 2.11 (q, 4H, J=7.3 Hz), 2.24 (s, 3H), 2.28 (s, 3H), 2.52-2.63 (m, 1H), 2.83-2.94 (m, 1H), 3.23-3.27 (m, 1H), 4.47 (q, 2H, J=7.1 Hz), 6.94-6.97 (m, 2H), 7.04-7.10 (m, 4H), 7.49 (d, 2H, J=8.4 Hz), 8.04 (d, 2H, J=8.4 Hz).

(3) Synthesis of (4'-{1-ethyl-1-[4-(3-hydroxy-4,4-dimethyl-pentyl)-3-methyl-phenyl]-propyl}-2'-methyl-biphenyl-4-yl)-oxo-acetic Acid

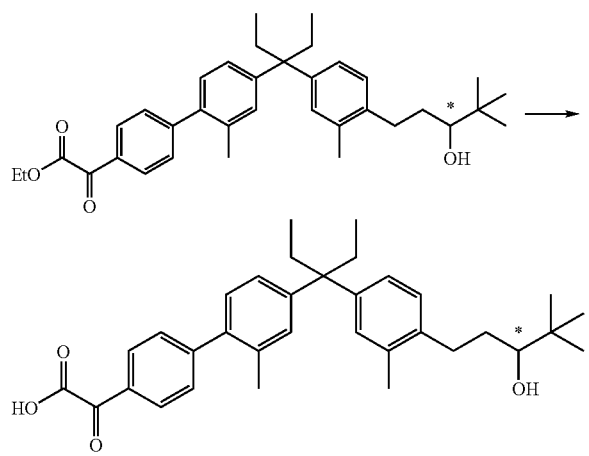

The title compound (94%) was obtained by the same method as in Example 154-(4) using (4'-{1-ethyl-1-[4-(3-hydroxy-4,4-dimethyl-pentyl)-3-methyl-phenyl]-propyl}-2'-methyl-biphenyl-4-yl)-oxo-acetic acid ethyl ester (Example 160-(2)) as a starting material.

$^1$H-NMR (methanol-d4): 0.64 (t, 6H, J=7.3 Hz), 0.88 (s, 9H), 1.44-1.57 (m, 1H), 1.72-1.82 (m, 1H), 2.15 (q, 4H, J=7.3 Hz), 2.21 (s, 3H), 2.27 (s, 3H), 2.50-2.61 (m, 1H), 2.83-2.94 (m, 1H), 3.17 (dd, 1H, J=1.5, 10.4 Hz), 6.95-6.97 (m, 2H), 7.04-7.13 (m, 4H), 7.47 (d, 2H, J=8.2 Hz), 8.02 (d, 2H, J=8.2 Hz); MS (ESI+): 532 ([M+NH$_4$]$^+$).

Example 161

Synthesis of (4'-{1-ethyl-1-[4-(3-hydroxy-4,4-dimethyl-pentyl)-3-methyl-phenyl]-propyl}-2'-methyl-biphenyl-4-yl)-oxo-acetic Acid

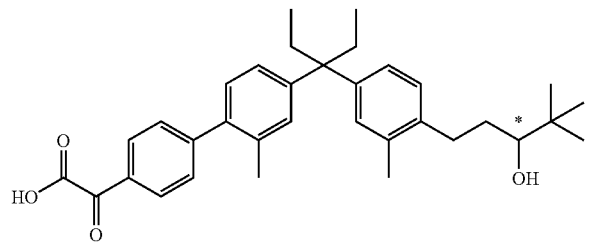

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-oxo-acetic Acid Ethyl Ester

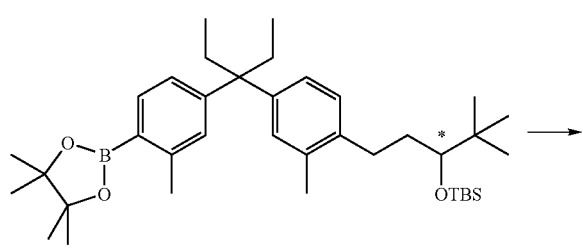

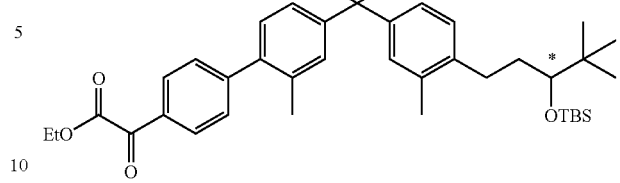

The title compound (24%) was obtained by the same method as in Example 157-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 24-(1)) and (4-chloro-phenyl)-oxo-acetic acid ethyl ester as starting materials.

$^1$H-NMR (chloroform-d): 0.07 (s, 3H), 0.11 (s, 3H), 0.65 (t, 6H, J=7.3 Hz), 0.88 (s, 9H), 0.94 (s, 9H), 1.44 (t, 3H, J=7.1 Hz), 1.55-1.65 (m, 1H), 1.74-1.84 (m, 1H), 2.11 (q, 4H, J=7.3 Hz), 2.24 (s, 3H), 2.26 (s, 3H), 2.37-2.48 (m, 1H), 2.72-2.83 (m, 1H), 3.35 (dd, 1H, J=3.1, 7.1 Hz), 4.47 (q, 2H, J=7.1 Hz), 6.93-7.11 (m, 6H), 7.48 (d, 2H, J=8.6 Hz), 8.04 (d, 2H, J=8.6 Hz).

(2) Synthesis of (4'-{1-ethyl-1-[4-(3-hydroxy-4,4-dimethyl-pentyl)-3-methyl-phenyl]-propyl}-2'-methyl-biphenyl-4-yl)-oxo-acetic Acid Ethyl Ester

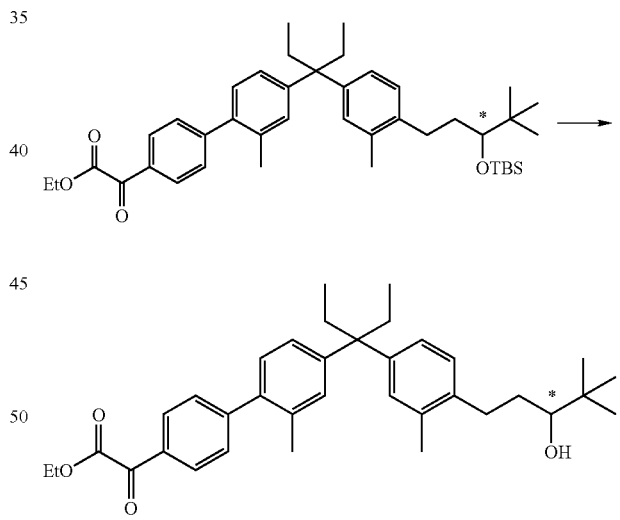

The title compound (73%) was obtained by the same method as in Example 154-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-oxo-acetic acid ethyl ester (Example 161-(1)) as a starting material.

$^1$H-NMR (chloroform-d): 0.65 (t, 6H, J=7.3 Hz), 0.90 (s, 9H), 1.44 (t, 3H, J=7.1 Hz), 1.48-1.56 (m, 1H), 1.76-1.87 (m, 1H), 2.11 (q, 4H, J=7.3 Hz), 2.24 (s, 3H), 2.29 (s, 3H), 2.52-2.63 (m, 1H), 2.83-2.94 (m, 1H), 3.26 (dd, 1H, J=1.5, 10.4 Hz), 4.47 (q, 2H, J=7.1 Hz), 6.94-6.97 (m, 2H), 7.04-7.10 (m, 4H), 7.49 (d, 2H, J=8.6 Hz), 8.04 (d, 2H, J=8.6 Hz).

(3) Synthesis of (4'-{1-ethyl-1-[4-(3-hydroxy-4,4-dimethyl-pentyl)-3-methyl-phenyl]-propyl}-2'-methyl-biphenyl-4-yl)-oxo-acetic Acid

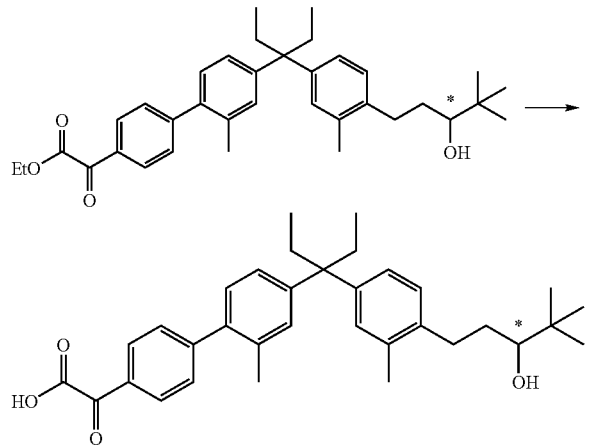

The title compound (89%) was obtained by the same method as in Example 154-(4) using (4'-{1-ethyl-1-[4-(3-hydroxy-4,4-dimethyl-pentyl)-3-methyl-phenyl]-propyl}-2'-methyl-biphenyl-4-yl)-oxo-acetic acid ethyl ester (Example 161-(2)) as a starting material.
$^1$H-NMR (methanol-d4): 0.64 (t, 6H, J=7.3 Hz), 0.87 (s, 9H), 1.42-1.57 (m, 1H), 1.71-1.82 (m, 1H), 2.14 (q, 4H, J=7.3 Hz), 2.21 (s, 3H), 2.26 (s, 3H), 2.49-2.61 (m, 1H), 2.83-2.94 (m, 1H), 3.16 (dd, 1H, J=1.5, 10.4 Hz), 6.95-6.97 (m, 2H), 7.04-7.13 (m, 4H), 7.46 (d, 2H, J=8.4 Hz), 8.02 (d, 2H, J=8.4 Hz); MS (ESI+): 532 ([M+NH$_4$]$^+$).

Example 162

Synthesis of (4'-{1-ethyl-1-[4-(3-hydroxy-4,4-dimethyl-pentyl)-3-methyl-phenyl]-propyl}-2'-methyl-biphenyl-3-yl)-oxo-acetic Acid

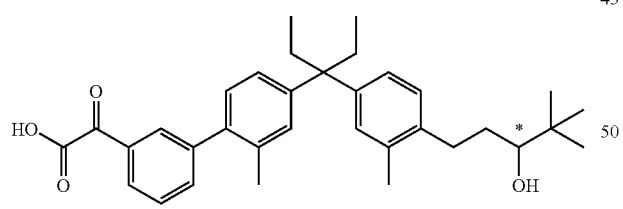

(1) Synthesis of (3-bromo-phenyl)-oxo-acetic Acid Methyl Ester

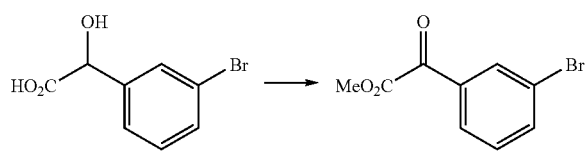

(3-Bromo-phenyl)-hydroxy-acetic acid (526.4 mg, 2.23 mmol) was dissolved in benzene (6 mL) and methanol (3 mL). Trimethylsilyldiazomethane (2 M solution in diethyl ether, 1.23 mL, 2.46 mmol) was added, and the mixture was stirred at room temperature for 10 minutes. The reaction solution was concentrated under reduced pressure, and then the residue was dissolved in dichloromethane (11.2 mL). Dess-Martin periodinane (1.95 g, 4.47 mmol) was added, and the mixture was stirred at room temperature for 10 minutes. A saturated aqueous sodium bicarbonate solution and a saturated aqueous sodium thiosulfate solution were added to the reaction solution, followed by extraction with ethyl acetate. The organic layer was washed with a saturated aqueous sodium bicarbonate solution and brine and then dried over anhydrous magnesium sulfate and concentrated under reduced pressure. The resulting residue was purified by silica gel chromatography (hexane:ethyl acetate=100:0 to 85:15) to give the title compound (502.2 mg, 95% in two steps).
$^1$H-NMR (chloroform-d): 3.99 (s, 3H), 7.40 (t, 1H, J=7.9 Hz), 7.77-7.81 (m, 1H), 7.96-7.99 (m, 1H), 8.17-8.18 (m, 1H).

(2) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-oxo-acetic Acid Methyl Ester

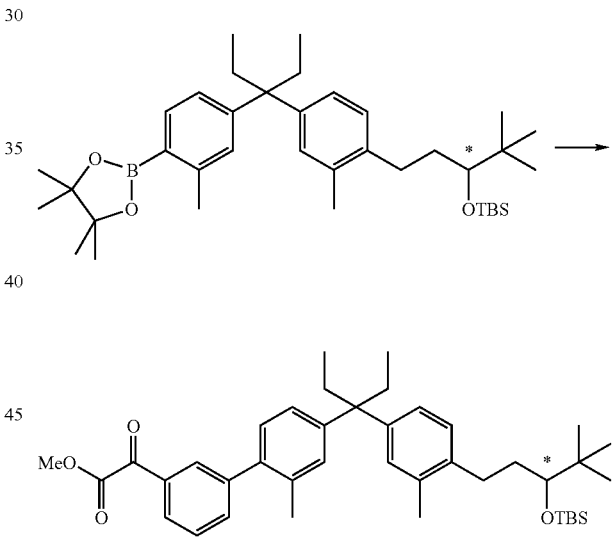

The title compound (24%) was obtained by the same method as in Example 157-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 24-(1)) and (3-bromo-phenyl)-oxo-acetic acid methyl ester (Example 162-(1)) as starting materials.
$^1$H-NMR (chloroform-d): 0.07 (s, 3H), 0.11 (s, 3H), 0.65 (t, 6H, J=7.3 Hz), 0.88 (s, 9H), 0.94 (s, 9H), 1.51-1.63 (m, 1H), 1.73-1.84 (m, 1H), 2.11 (q, 4H, J=7.3 Hz), 2.22 (s, 3H), 2.27 (s, 3H), 2.37-2.48 (m, 1H), 2.72-2.84 (m, 1H), 3.35 (dd, 1H, J=3.1, 7.1 Hz), 3.98 (s, 3H), 6.94-7.10 (m, 6H), 7.51-7.57 (m, 1H), 7.62-7.66 (m, 1H), 7.94-7.98 (m, 2H).

(3) Synthesis of (4'-{1-ethyl-1-[4-(3-hydroxy-4,4-dimethyl-pentyl)-3-methyl-phenyl]-propyl}-2'-methyl-biphenyl-3-yl)-oxo-acetic Acid Methyl Ester

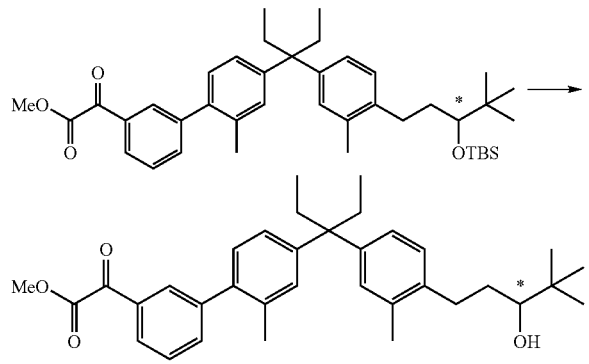

The title compound (75%) was obtained by the same method as in Example 154-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-oxo-acetic acid methyl ester (Example 162-(2)) as a starting material.

$^1$H-NMR (methanol-d4): 0.65 (t, 6H, J=7.3 Hz), 0.88 (s, 9H), 1.47-1.57 (m, 1H), 1.72-1.83 (m, 1H), 2.15 (q, 4H, J=7.3 Hz), 2.20 (s, 3H), 2.27 (s, 3H), 2.50-2.61 (m, 1H), 2.84-2.94 (m, 1H), 3.17 (dd, 1H, J=1.7, 10.6 Hz), 6.95-6.98 (m, 2H), 7.04-7.13 (m, 4H), 7.52-7.60 (m, 2H), 7.92-7.96 (m, 2H).

(4) Synthesis of (4'-{1-ethyl-1-[4-(3-hydroxy-4,4-dimethyl-pentyl)-3-methyl-phenyl]-propyl}-2'-methyl-biphenyl-3-yl)-oxo-acetic Acid

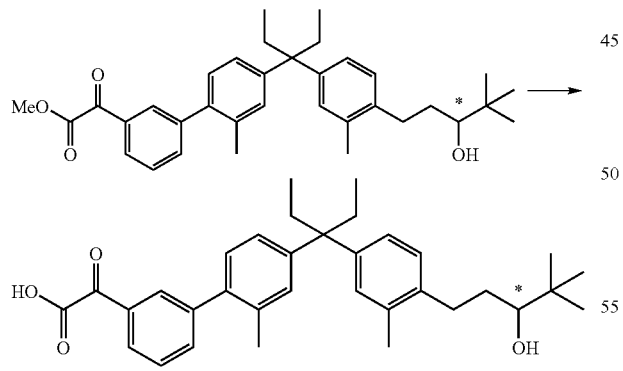

The title compound (64%) was obtained by the same method as in Example 154-(4) using (4'-{1-ethyl-1-[4-(3-hydroxy-4,4-dimethyl-pentyl)-3-methyl-phenyl]-propyl}-2'-methyl-biphenyl-3-yl)-oxo-acetic acid methyl ester (Example 162-(3)) as a starting material.

$^1$H-NMR (methanol-d4): 0.65 (t, 6H, J=7.3 Hz), 0.88 (s, 9H), 1.47-1.57 (m, 1H), 1.72-1.83 (m, 1H), 2.15 (q, 4H, J=7.3 Hz), 2.20 (s, 3H), 2.27 (s, 3H), 2.50-2.61 (m, 1H), 2.84-2.94 (m, 1H), 3.17 (dd, 1H, J=1.7, 10.6 Hz), 6.95-6.98 (m, 2H), 7.04-7.13 (m, 4H), 7.52-7.60 (m, 2H), 7.92-7.96 (m, 2H); MS (ESI+): 532 ([M+NH$_4$]$^+$).

Example 163

Synthesis of (4'-{1-ethyl-1-[4-(3-hydroxy-4,4-dimethyl-pentyl)-3-methyl-phenyl]-propyl}-2'-methyl-biphenyl-3-yl)-oxo-acetic Acid

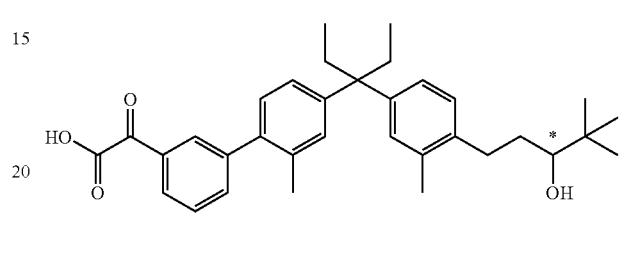

(1) Synthesis of [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-oxo-acetic Acid Methyl Ester

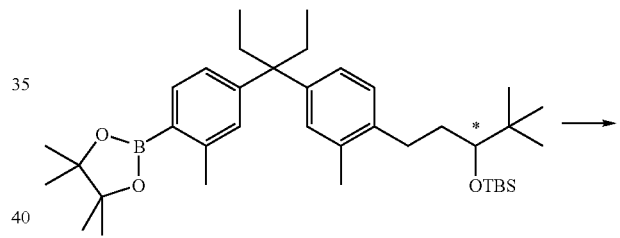

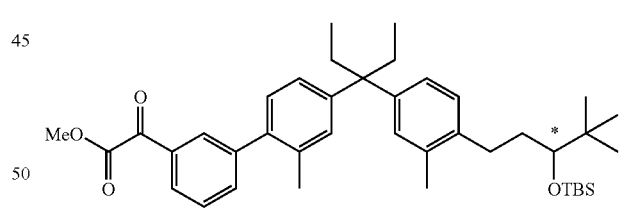

The title compound (30%) was obtained by the same method as in Example 157-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1)) and (3-bromo-phenyl)-oxo-acetic acid methyl ester (Example 162-(1)) as starting materials.

$^1$H-NMR (chloroform-d): 0.07 (s, 3H), 0.11 (s, 3H), 0.65 (t, 6H, J=7.3 Hz), 0.88 (s, 9H), 0.94 (s, 9H), 1.55-1.65 (m, 1H), 1.74-1.84 (m, 1H), 2.11 (q, 4H, J=7.3 Hz), 2.22 (s, 3H), 2.27 (s, 3H), 2.37-2.48 (m, 1H), 2.72-2.84 (m, 1H), 3.35 (dd, 1H, J=3.1, 7.1 Hz), 3.98 (s, 3H), 6.94-7.10 (m, 6H), 7.51-7.57 (m, 1H), 7.62-7.66 (m, 1H), 7.94-7.98 (m, 2H).

(2) Synthesis of (4'-{1-ethyl-1-[4-(3-hydroxy-4,4-dimethyl-pentyl)-3-methyl-phenyl]-propyl}-2'-methyl-biphenyl-3-yl)-oxo-acetic Acid Methyl Ester

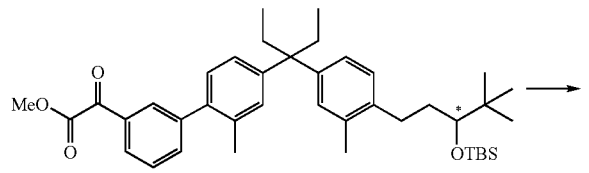

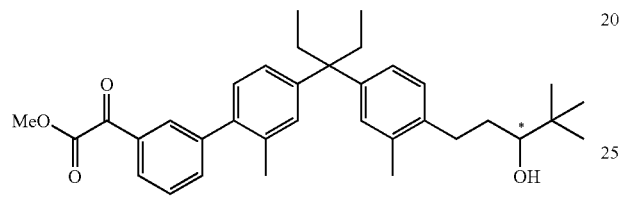

The title compound (82%) was obtained by the same method as in Example 154-(3) using [4'-(1-{4-[3-(t-butyl-dimethyl-silanyloxy)-4,4-dimethyl-pentyl]-3-methyl-phenyl}-1-ethyl-propyl)-2'-methyl-biphenyl-3-yl]-oxo-acetic acid methyl ester (Example 163-(1)) as a starting material.

$^1$H-NMR (methanol-d4): 0.65 (t, 6H, J=7.3 Hz), 0.88 (s, 9H), 1.43-1.57 (m, 1H), 1.72-1.83 (m, 1H), 2.15 (q, 4H, J=7.3 Hz), 2.20 (s, 3H), 2.27 (s, 3H), 2.50-2.61 (m, 1H), 2.83-2.94 (m, 1H), 3.17 (dd, 1H, J=1.7, 10.6 Hz), 6.95-6.98 (m, 2H), 7.04-7.13 (m, 4H), 7.52-7.60 (m, 2H), 7.92-7.97 (m, 2H).

(3) Synthesis of (4'-{1-ethyl-1-[4-(3-hydroxy-4,4-dimethyl-pentyl)-3-methyl-phenyl]-propyl}-2'-methyl-biphenyl-3-yl)-oxo-acetic Acid

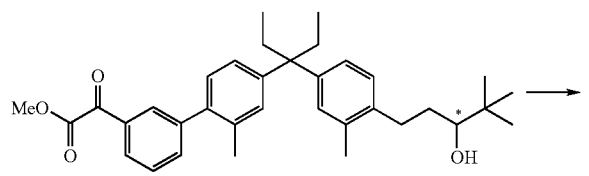

The title compound (59%) was obtained by the same method as in Example 154-(4) using (4'-{1-ethyl-1-[4-(3-hydroxy-4,4-dimethyl-pentyl)-3-methyl-phenyl]-propyl}-2'-methyl-biphenyl-3-yl)-oxo-acetic acid methyl ester (Example 163-(2)) as a starting material.

$^1$H-NMR (methanol-d4): 0.65 (t, 6H, J=7.3 Hz), 0.88 (s, 9H), 1.43-1.57 (m, 1H), 1.72-1.83 (m, 1H), 2.15 (q, 4H, J=7.3 Hz), 2.20 (s, 3H), 2.27 (s, 3H), 2.50-2.61 (m, 1H), 2.83-2.94 (m, 1H), 3.17 (dd, 1H, J=1.7, 10.6 Hz), 6.95-6.98 (m, 2H), 7.04-7.13 (m, 4H), 7.52-7.60 (m, 2H), 7.92-7.97 (m, 2H); MS (ESI+): 532 ([M+NH$_4$]$^+$).

Example 164

Synthesis of (4'-{1-ethyl-1-[4-(3-hydroxy-4,4-dimethyl-pentyl)-3-methyl-phenyl]-propyl}-5-hydroxy-2'-methyl-biphenyl-3-yl)-acetic Acid

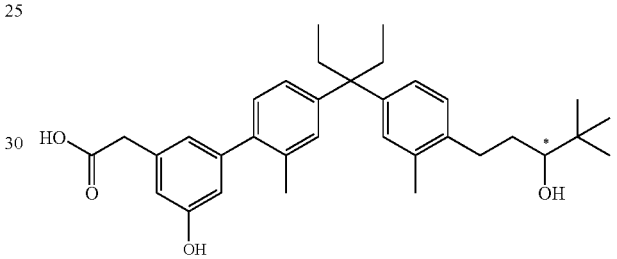

(1) Synthesis of [3-(t-butyl-diphenyl-silanyloxy)-5-hydroxy-phenyl]-acetic Acid Methyl Ester

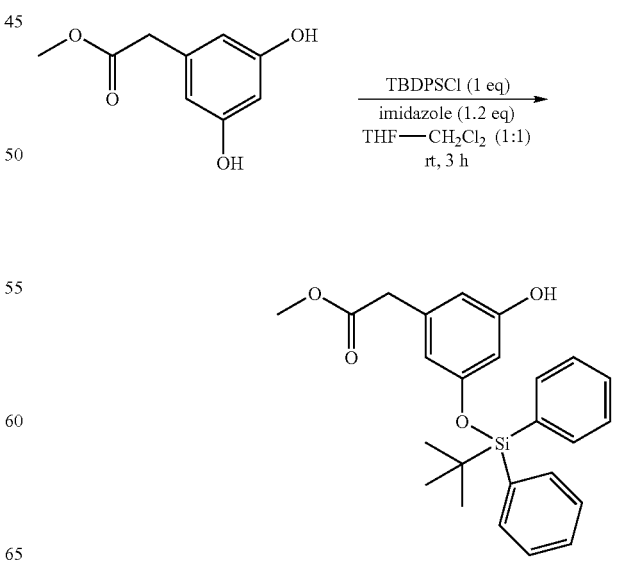

383

Imidazole (230 mg, 3.38 mmol) was added to a solution of 3,5-dihydroxyphenylacetic acid methyl ester (530 mg, 2.91 mmol) in tetrahydrofuran (6.7 mL)-dichloromethane (6.7 mL) at room temperature. t-Butylchlorodiphenylsilane (0.75 mL, 2.9 mmol) was added under cooling with ice. Then, the ice bath was removed, and the mixture was stirred at room temperature for three hours. The reaction mixture was diluted with diethyl ether. 50% saturated aqueous ammonium chloride was added, followed by extraction with diethyl ether. The extract was dried over anhydrous magnesium sulfate and concentrated under reduced pressure. The residue was purified by silica gel chromatography (hexane/ethyl acetate=3/1) to give the title compound (470 mg, 33%).

$^1$H-NMR (chloroform-d): 1.09 (s, 9H), 3.39 (s, 2H), 3.62 (s, 3H), 4.50 (s, 1H), 6.12 (t, 1H, J=2.0 Hz), 6.30 (t, 1H, J=2.0 Hz), 6.32 (t, 1H, J=2.0 Hz), 7.33-7.46 (m, 6H), 7.67-7.74 (m, 4H).

(2) Synthesis of [3-(t-butyl-diphenyl-silanyloxy)-5-trifluoromethanesulfonyloxy-phenyl]-acetic Acid Methyl Ester

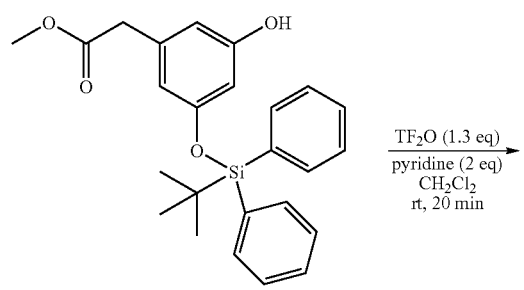

TF$_2$O (1.3 eq)
pyridine (2 eq)
CH$_2$Cl$_2$
rt, 20 min

-continued

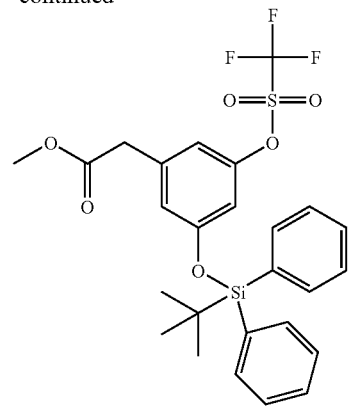

Pyridine (15 μl, 0.19 mmol) was added to a solution of [3-(t-butyl-diphenyl-silanyloxy)-5-hydroxy-phenyl]acetic acid methyl ester (Example 164-(1); 40 mg, 0.095 mmol) in dichloromethane (1 mL) at room temperature. Trifluoromethanesulfonic anhydride (0.02 mL, 0.12 mmol) was added under cooling with ice. Then, the ice bath was removed, and the mixture was stirred at room temperature for 20 minutes. The reaction mixture was diluted with diethyl ether. 50% saturated aqueous ammonium chloride was added, followed by extraction with diethyl ether. The extract was dried over anhydrous magnesium sulfate and concentrated under reduced pressure. The residue was purified by silica gel chromatography (hexane/ethyl acetate=5/1) to give the title compound (43.5 mg, 83%).

$^1$H-NMR (chloroform-d): 1.12 (s, 9H), 3.46 (s, 2H), 3.64 (s, 3H), 6.51 (t, 1H, J=2.0 Hz), 6.72 (dd, 1H, J=2.4, 2.0 Hz), 6.75 (dd, 1H, J=2.4, 2.0 Hz), 7.35-7.49 (m, 6H), 7.65-7.71 (m, 4H).

(3) Synthesis of [4'-(1-{4-[3-(t-butyl-dimethyl-silanyloxy)-4,4-dimethyl-pentyl]-3-methyl-phenyl}-1-ethyl-propyl)-5-hydroxy-2'-methyl-biphenyl-3-yl]-acetic Acid Methyl Ester

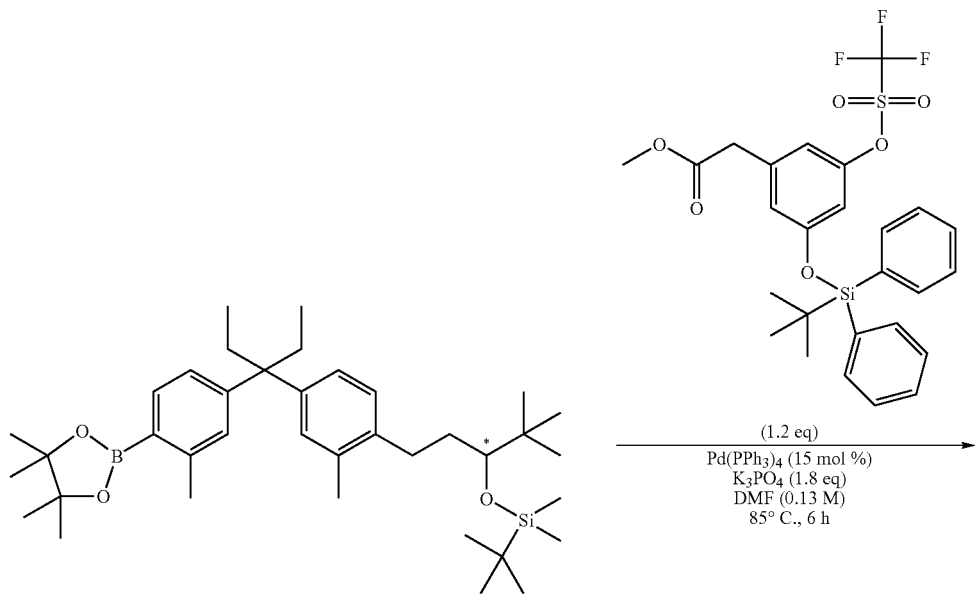

(1.2 eq)
Pd(PPh$_3$)$_4$ (15 mol %)
K$_3$PO$_4$ (1.8 eq)
DMF (0.13 M)
85° C., 6 h

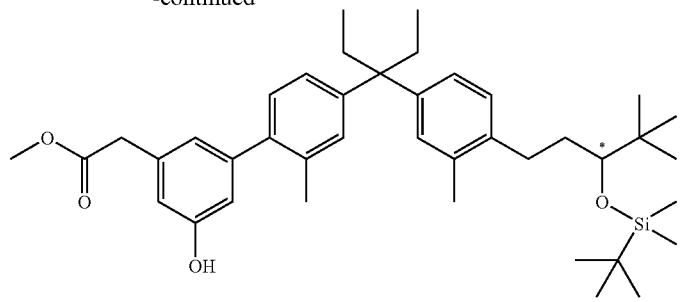

Degassed N,N-dimethylformamide (0.30 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 23.0 mg, 0.0379 mmol), [3-(t-butyl-diphenyl-silanyloxy)-5-trifluoromethanesulfonyloxy-phenyl]acetic acid methyl ester (Example 164-(2); 26.0 mg, 0.0470 mmol), tetrakis(triphenylphosphine)palladium (0) (6.6 mg, 0.0057 mmol) and potassium phosphate (14.5 mg, 0.0683 mmol). After replacement with nitrogen, the mixture was heated while stirring at an external temperature of 81 to 91° C. for five hours. 50% saturated aqueous ammonium chloride was added to the reaction mixture, followed by extraction with diethyl ether. The extract was dried over anhydrous magnesium sulfate and then concentrated under reduced pressure. The residue was purified by silica gel chromatography (hexane/ethyl acetate=5/1) to give the title compound (23.6 mg, 97%).

$^1$H-NMR (chloroform-d): 0.08 (s, 3H), 0.12 (s, 3H), 0.65 (t, 6H, J=7.4 Hz), 0.90 (s, 9H), 0.95 (s, 9H), 1.58 (m, 1H), 1.80 (m, 1H), 2.11 (q, 4H, J=7.4 Hz), 2.24 (s, 3H), 2.27 (s, 3H), 2.43 (m, 1H), 2.78 (m, 1H), 3.36 (dd, 1H, J=7.2, 3.3 Hz), 3.61 (s, 2H), 3.71 (s, 3H), 4.71 (s, 1H), 6.72 (m, 2H), 6.82 (s, 1H), 6.93-7.09 (m, 6H).

(4) Synthesis of (4'-{1-ethyl-1-[4-(3-hydroxy-4,4-dimethyl-pentyl)-3-methyl-phenyl]-propyl}-5-hydroxy-2'-methyl-biphenyl-3-yl)-acetic Acid Methyl Ester Trifluoroacetic acid (0.17 mL) was added to a solution of [4'-(1-{4-[3-(t-butyl-dimethyl-silanyloxy)-4,4-dimethyl-pentyl]-3-methyl-phenyl}-1-ethyl-propyl)-5-hydroxy-2'-methyl-biphenyl-3-yl]-acetic acid methyl ester (Example 164-(3); 23.1 mg, 0.0358 mmol) in dichloromethane (0.85 mL) at room temperature, and the mixture was stirred at room temperature for one hour. The solvent in the reaction solution was distilled off under reduced pressure, and the residue was diluted with diethyl ether. The mixture was adjusted to pH 7 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=2/1) to give the title compound (17.5 mg, 92%).

$^1$H-NMR (chloroform-d): 0.65 (t, 6H, J=7.4 Hz), 0.91 (s, 9H), 1.40 (d, 1H, J=5.0 Hz), 1.53 (m, 1H), 1.82 (m, 1H), 2.11 (q, 4H, J=7.4 Hz), 2.24 (s, 3H), 2.29 (s, 3H), 2.58 (m, 1H), 2.89 (m, 1H), 3.26 (dd, 1H, J=11.0, 5.4 Hz), 3.61 (s, 2H), 3.71 (s, 3H), 4.78 (s, 1H), 6.72 (m, 2H), 6.82 (s, 1H), 6.93-7.10 (m, 6H).

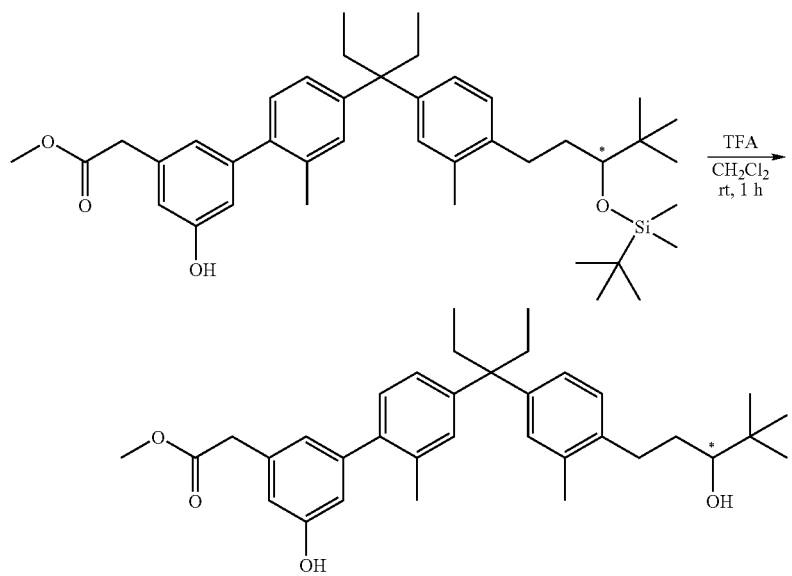

(5) Synthesis of (4'-{1-ethyl-1-[4-(3-hydroxy-4,4-dimethyl-pentyl)-3-methyl-phenyl]-propyl}-5-hydroxy-2'-methyl-biphenyl-3-yl)-acetic Acid

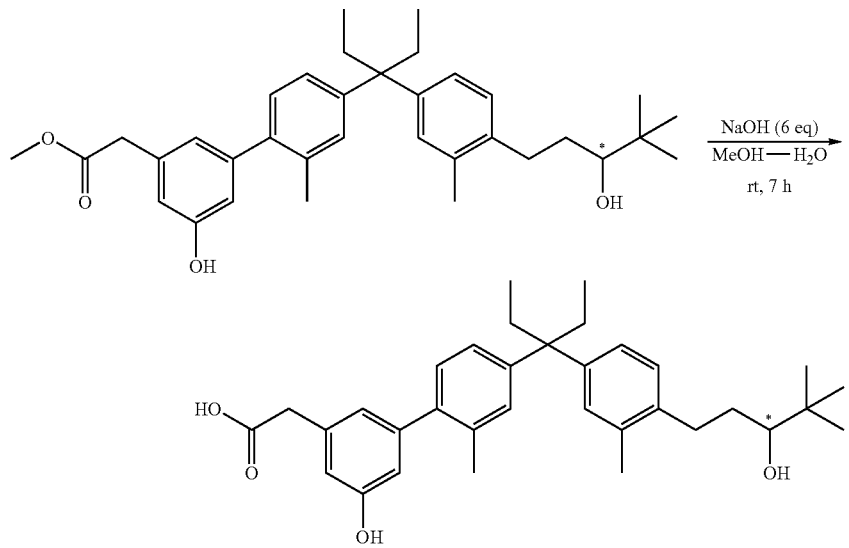

A 2 N sodium hydroxide aqueous solution (0.10 mL) was added to a solution of (4'-{1-ethyl-1-[4-(3-hydroxy-4,4-dimethyl-pentyl)-3-methyl-phenyl]-propyl}-5-hydroxy-2'-methyl-biphenyl-3-yl)acetic acid methyl ester (Example 164-(4); 17.5 mg, 0.0330 mmol) in methanol (0.40 mL) at room temperature, and the mixture was stirred at room temperature for seven hours. The mixture was acidified with dilute hydrochloric acid aqueous solution, followed by extraction with ethyl acetate. The extract was dried over anhydrous magnesium sulfate and then concentrated under reduced pressure to give the title compound (17 mg, 100%).

$^1$H-NMR (chloroform-d): 0.65 (t, 6H, J=7.4 Hz), 0.90 (s, 9H), 1.52 (m, 1H), 1.82 (m, 1H), 2.10 (q, 4H, J=7.4 Hz), 2.22 (s, 3H), 2.27 (s, 3H), 2.57 (m, 1H), 2.88 (m, 1H), 3.28 (dd, 1H, J=10.5, 1.5 Hz), 3.62 (s, 1H), 6.73 (m, 2H), 6.82 (s, 1H), 6.92-7.08 (m, 6H); MS (ESI−): 515 ([M−H]$^-$).

Example 165

Synthesis of (4'-{1-ethyl-1-[4-(3-hydroxy-4,4-dimethyl-pentyl)-3-methyl-phenyl]-propyl}-5-hydroxy-2'-methyl-biphenyl-3-yl)-acetic Acid

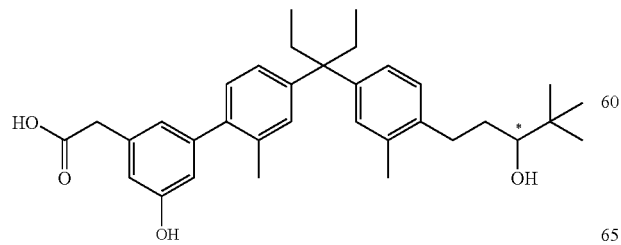

(1) Synthesis of [4'-(1-{4-[3-(t-butyl-dimethyl-silanyloxy)-4,4-dimethyl-pentyl]-3-methyl-phenyl}-1-ethyl-propyl)-5-hydroxy-2'-methyl-biphenyl-3-yl]-acetic Acid Methyl Ester

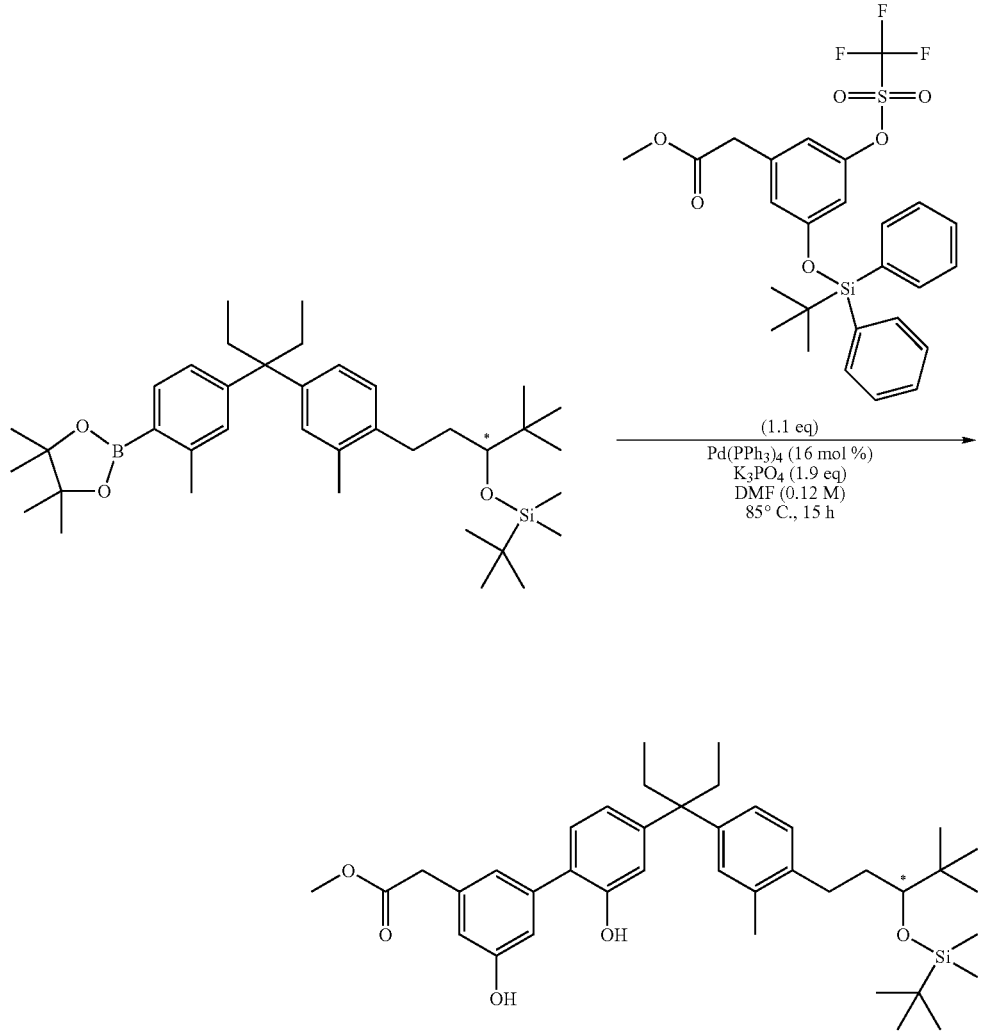

Degassed N,N-dimethylformamide (0.24 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 17.4 mg, 0.0287 mmol), [3-(t-butyl-diphenyl-silanyloxy)-5-trifluoromethanesulfonyloxy-phenyl]acetic acid methyl ester (Example 164-(2); 17.1 mg, 0.0309 mmol), tetrakis(triphenylphosphine)palladium (0) (5.4 mg, 0.0047 mmol) and potassium phosphate (11.5 mg, 0.0542 mmol). After replacement with nitrogen, the mixture was heated while stirring at an external temperature of 80 to 90° C. for 15 hours. 50% saturated aqueous ammonium chloride was added to the reaction mixture, followed by extraction with diethyl ether. The extract was dried over anhydrous magnesium sulfate and then concentrated under reduced pressure. The residue was purified by silica gel chromatography (hexane/ethyl acetate=5/1) to give the title compound (15.9 mg, 86%).

$^1$H-NMR (chloroform-d): 0.08 (s, 3H), 0.12 (s, 3H), 0.65 (t, 6H, J=7.3 Hz), 0.90 (s, 9H), 0.95 (s, 9H), 1.58 (m, 1H), 1.79 (m, 1H), 2.11 (q, 4H, J=7.3 Hz), 2.24 (s, 3H), 2.27 (s, 3H), 2.43 (m, 1H), 2.78 (m, 1H), 3.36 (dd, 1H, J=7.2, 3.3 Hz), 3.61 (s, 2H), 3.71 (s, 3H), 4.73 (s, 1H), 6.72 (m, 2H), 6.82 (s, 1H), 6.93-7.09 (m, 6H).

(2) Synthesis of (4'-{1-ethyl-1-[4-(3-hydroxy-4,4-dimethyl-pentyl)-3-methyl-phenyl]-propyl}-5-hydroxy-2'-methyl-biphenyl-3-yl)-acetic Acid Methyl Ester

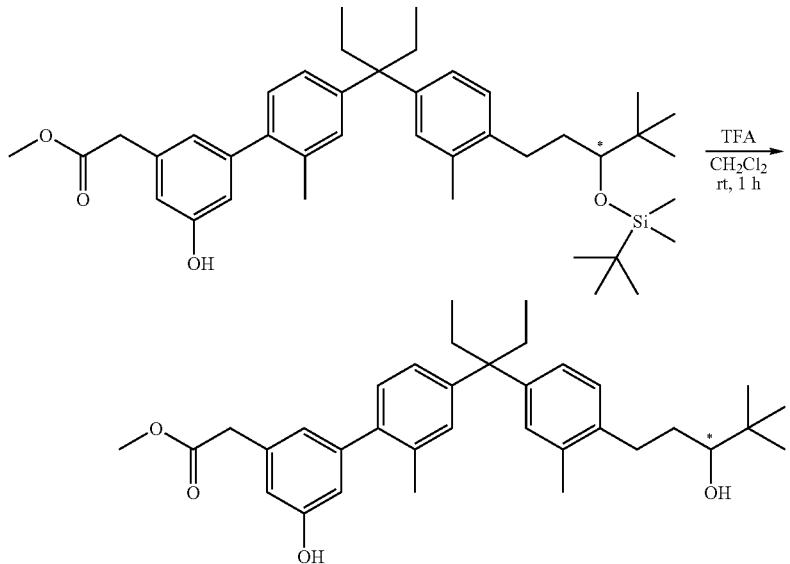

Trifluoroacetic acid (0.12 mL) was added to a solution of [4'-(1-{4-[3-(t-butyl-dimethyl-silanyloxy)-4,4-dimethyl-pentyl]-3-methyl-phenyl}-1-ethyl-propyl)-5-hydroxy-2'-methyl-biphenyl-3-yl]-acetic acid methyl ester (Example 165-(2); 15.9 mg, 0.0247 mmol) in dichloromethane (0.60 mL) at room temperature, and the mixture was stirred at room temperature for one hour. The solvent in the reaction solution was distilled off under reduced pressure, and the residue was diluted with diethyl ether. The mixture was adjusted to pH 7 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=2/1) to give the title compound (11.5 mg, 88%).

$^1$H-NMR (chloroform-d): 0.65 (t, 6H, J=7.3 Hz), 0.91 (s, 9H), 1.53 (m, 1H), 1.82 (m, 1H), 2.11 (q, 4H, J=7.4 Hz), 2.24 (s, 3H), 2.29 (s, 3H), 2.58 (m, 1H), 2.89 (m, 1H), 3.26 (dd, 1H, J=11.0, 1.5 Hz), 3.61 (s, 2H), 3.71 (s, 3H), 4.79 (s, 1H), 6.72 (m, 2H), 6.82 (s, 1H), 6.93-7.10 (m, 6H).

(3) Synthesis of (4'-{1-ethyl-1-[4-(3-hydroxy-4,4-dimethyl-pentyl)-3-methyl-phenyl]-propyl}-5-hydroxy-2'-methyl-biphenyl-3-yl)-acetic Acid A 2 N sodium hydroxide aqueous solution (0.06 mL) was added to a solution of (4'-{1-ethyl-1-[4-(3-hydroxy-4,4-dimethyl-pentyl)-3-methyl-phenyl]-propyl}-5-hydroxy-2'-methyl-biphenyl-3-yl)acetic acid methyl ester (Example 164-(4); 11.5 mg, 0.0202 mmol) in methanol (0.30 mL) at room temperature, and the mixture was stirred at room temperature for nine hours. The mixture was acidified with dilute hydrochloric acid aqueous solution, followed by extraction with ethyl acetate. The extract was dried over anhydrous magnesium sulfate and then concentrated under reduced pressure to give the title compound (10.5 mg, 100%).

$^1$H-NMR (chloroform-d): 0.65 (t, 6H, J=7.3 Hz), 0.91 (s, 9H), 1.52 (m, 1H), 1.82 (m, 1H), 2.11 (q, 4H, J=7.3 Hz), 2.23 (s, 3H), 2.28 (s, 3H), 2.58 (m, 1H), 2.88 (m, 1H), 3.27 (dd, 1H, J=10.5, 1.8 Hz), 3.64 (s, 1H), 6.73 (m, 2H), 6.83 (s, 1H), 6.93-7.09 (m, 6H); MS (ESI-): 515 ([M-H]$^-$).

Example 166

Synthesis of Sodium (S)-amino-(4'-{1-ethyl-1-[4-(3-hydroxy-4,4-dimethyl-pentyl)-3-methyl-phenyl]-propyl}-2'-methyl-biphenyl-4-yl)-acetate

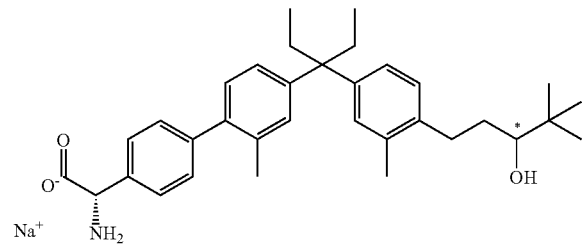

(1) Synthesis of (S)-t-butoxycarbonylamino-(4-chloro-phenyl)-acetic Acid Methyl Ester

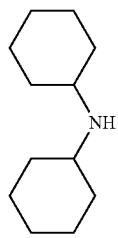

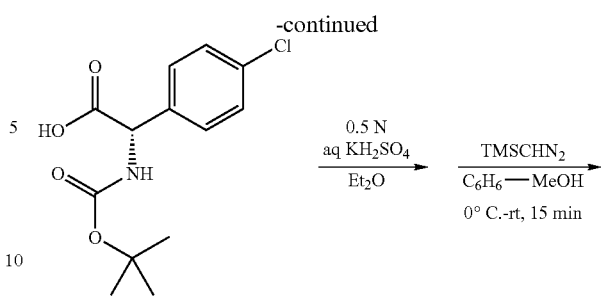

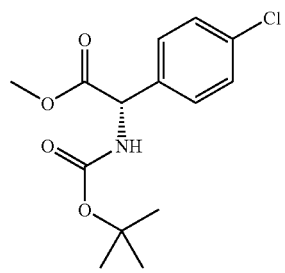

A 0.5 N potassium bisulfate aqueous solution (4.0 mL) was added to a suspension of dicyclohexylammonium (S)-t-butoxycarbonylamino-(4-chloro-phenyl)acetate (307 mg, 0.657 mmol) in ether (8.0 mL) at room temperature, and the mixture was stirred for 10 minutes. Then, the ether layer was separated, and the aqueous layer was extracted with ether (2×8 mL) and combined with the organic layer. The ether layer was washed with water (12 mL), dried over anhydrous magnesium sulfate and then concentrated under reduced pressure. The resulting residue was dissolved in benzene (1.8 mL) and methanol (0.9 mL). A solution of trimethylsilyldiazomethane in hexane (2 M, 0.36 mL, 0.72 mmol) was added dropwise under cooling with ice over five minutes, and then the mixture was stirred under cooling with ice for 10 minutes. The reaction mixture was concentrated under reduced pressure. The residue was purified by silica gel chromatography (hexane/ethyl acetate=5/1) to give the title compound (190 mg, 96%).

1H-NMR (chloroform-d): 1.44 (s, 9H), 3.73 (s, 3H), 5.30 (d, 1H, J=6.0 Hz), 5.59 (d, 1H, J=6.0 Hz), 7.27-7.36 (m, 4H).

(2) Synthesis of (S)-t-butoxycarbonylamino-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic Acid Methyl Ester

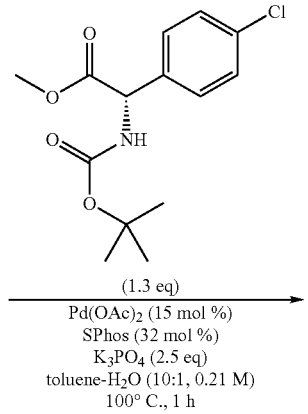

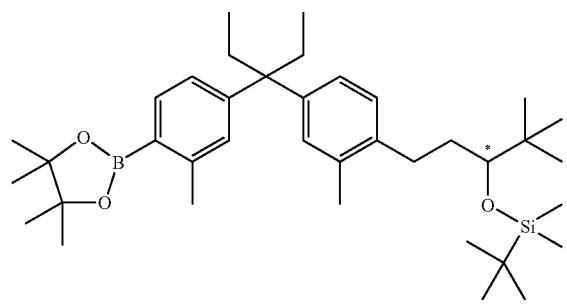

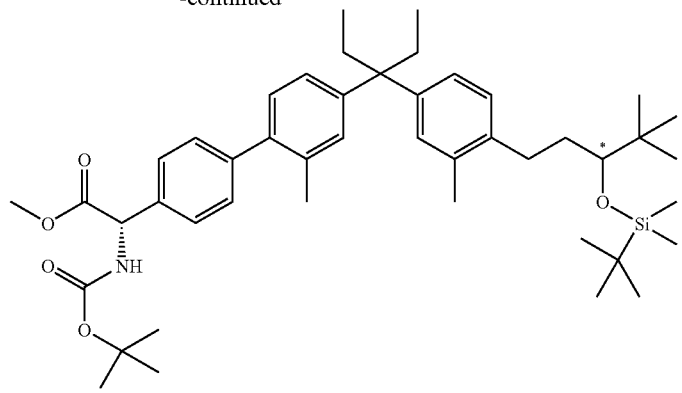

Degassed toluene (0.10 mL) was added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 25.2 mg, 0.0415 mmol), palladium (II) acetate (1.6 mg, 0.071 mmol), 2-dicyclohexylphosphino-2',6'-dimethoxy-1,1'-biphenyl (6.0 mg, 0.015 mmol) and potassium phosphate (24.5 mg, 0.115 mmol), and the mixture was stirred in a nitrogen atmosphere for three minutes. Then, a solution of (S)-t-butoxycarbonylamino-(4-chloro-phenyl)acetic acid methyl ester (Example 166-(1); 17.9 mg, 0.0597 mmol) in toluene (0.10 mL) and water (20 μL) were added, and the mixture was heated while stirring at an external temperature of 95 to 104° C. for one hour. The reaction mixture was diluted with diethyl ether and filtered through cotton plug, and the filtrate was concentrated under reduced pressure. The residue was purified by silica gel chromatography (hexane/ethyl acetate=10/1) to give the title compound (20.8 mg, 67%).

$^1$H-NMR (chloroform-d): 0.08 (s, 3H), 0.12 (s, 3H), 0.66 (t, 6H, J=7.3 Hz), 0.90 (s, 9H), 0.95 (s, 9H), 1.46 (s, 9H), 1.60 (m, 1H), 1.80 (m, 1H), 2.11 (q, 4H, J=7.3 Hz), 2.23 (s, 3H), 2.27 (s, 3H), 2.43 (m, 1H), 2.78 (m, 1H), 3.36 (dd, 1H, J=7.5, 3.3 Hz), 3.77 (s, 3H), 5.37 (d, 1H, J=8.0 Hz), 5.54 (d, 1H, J=8.0 Hz), 6.93-7.09 (m, 6H), 7.26-7.40 (m, 4H).

(3) Synthesis of (S)-amino-(4'-{1-ethyl-1-[4-(3-hydroxy-4,4-dimethyl-pentyl)-3-methyl-phenyl]-propyl}-2'-methyl-biphenyl-4-yl)-acetic Acid Methyl Ester

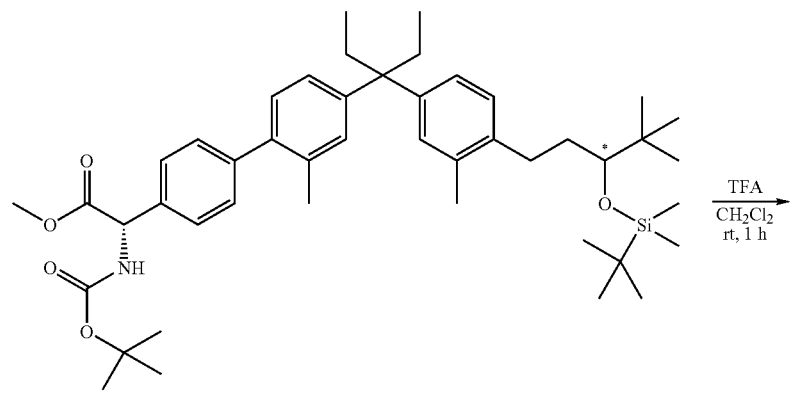

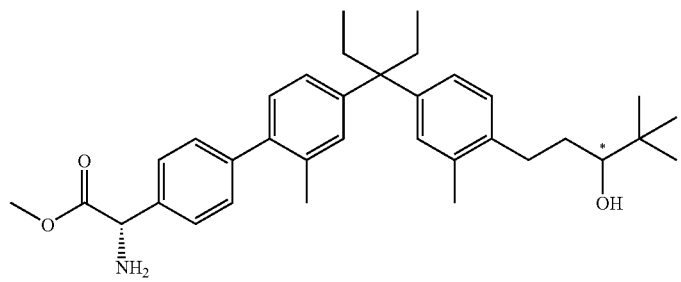

397

Trifluoroacetic acid (0.25 mL) was added to a solution of (S)-t-butoxycarbonylamino-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]acetic acid methyl ester (Example 166-(2); 20.3 mg, 0.0273 mmol) in dichloromethane (1.3 mL) at room temperature, and the mixture was stirred at room temperature for 30 minutes. The solvent in the reaction solution was distilled off under reduced pressure, and the residue was diluted with diethyl ether. The mixture was adjusted to pH 7 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=2/1) to give the title compound (12.0 mg, 83%).

$^1$H-NMR (chloroform-d): 0.66 (t, 6H, J=7.2 Hz), 0.91 (s, 9H), 1.53 (m, 1H), 1.82 (m, 1H), 2.11 (q, 4H, J=7.2 Hz), 2.23 (s, 3H), 2.29 (s, 3H), 2.58 (m, 1H), 2.89 (m, 1H), 3.26 (dd, 1H, J=10.0, 2.0 Hz), 3.75 (s, 3H), 4.66 (s, 1H), 6.90-7.10 (m, 6H), 7.32 (d, 2H, J=8.1 Hz), 7.39 (d, 2H, J=8.1 Hz).

(4) Synthesis of Sodium (S)-amino-(4'-{1-ethyl-1-[4-(3-hydroxy-4,4-dimethyl-pentyl)-3-methyl-phenyl]-propyl}-2'-methyl-biphenyl-4-yl)-acetate

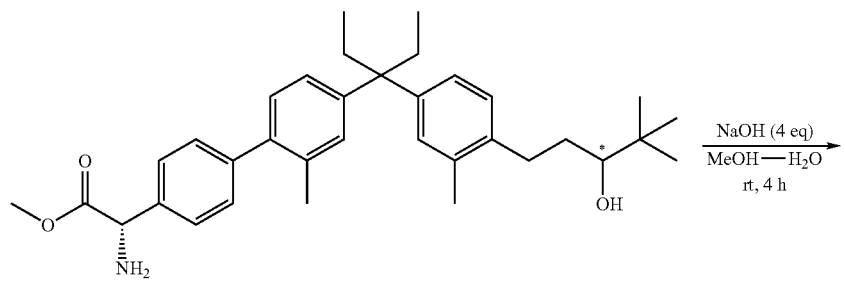

A 0.5 N sodium hydroxide aqueous solution (0.064 mL) was added to a solution of (S)-amino-(4'-{1-ethyl-1-[4-(3-hydroxy-4,4-dimethyl-pentyl)-3-methyl-phenyl]-propyl}-2'-methyl-biphenyl-4-yl)acetic acid methyl ester (Example 166-(3); 12.0 mg, 0.0226 mmol) in methanol (0.50 mL) at room temperature, and the mixture was stirred at room temperature for 10 hours. The reaction mixture was concentrated under reduced pressure to give the title compound (12.5 mg, 100%).

$^1$H-NMR (methanol-d4): 0.63 (t, 6H, J=7.4 Hz), 0.87 (s, 9H), 1.51 (m, 1H), 1.76 (m, 1H), 2.12 (q, 4H, J=7.4 Hz), 2.16 (s, 3H), 2.26 (s, 3H), 2.54 (m, 1H), 2.86 (m, 1H), 3.15 (dd, 1H, J=10.5, 1.8 Hz), 4.34 (s, 1H), 6.94 (m, 2H), 7.00-7.06 (m, 4H), 7.23 (d, 2H, J=8.2 Hz), 7.46 (d, 2H, J=8.2 Hz); MS (ESI-): 514 ([M-H]$^-$).

398

Example 167

Synthesis of (R)-amino-(4'-{1-ethyl-1-[4-(3-hydroxy-4,4-dimethyl-pentyl)-3-methyl-phenyl]-propyl}-2'-methyl-biphenyl-4-yl)-acetic Acid

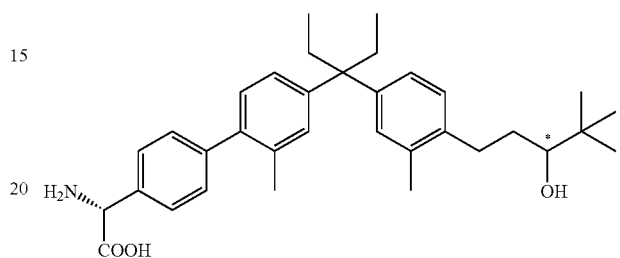

(1) Synthesis of (R)-t-butoxycarbonylamino-(4-chloro-phenyl)-acetic Acid Methyl Ester

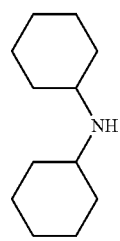

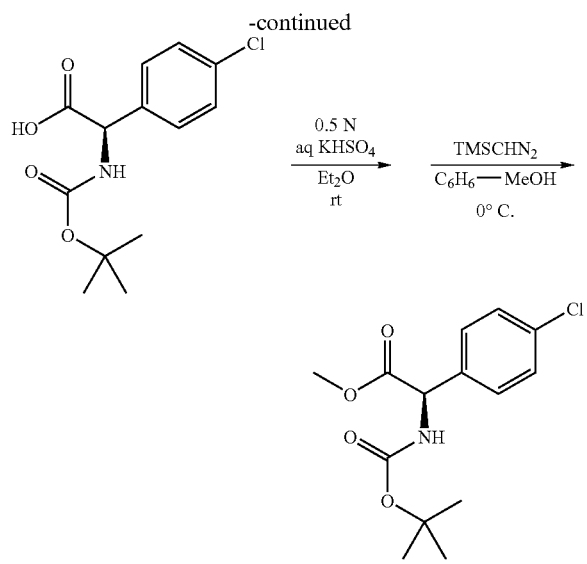

A 0.5 N potassium bisulfate aqueous solution (7.9 mL) was added to a suspension of dicyclohexylammonium (R)-t-butoxycarbonylamino-(4-chloro-phenyl)acetate (605.6 mg, 1.30 mmol) in ether (16 mL), and the mixture was stirred for 10 minutes. Then, the aqueous layer was extracted with ether. The organic layer was washed with water and then brine, dried over anhydrous magnesium sulfate and then concentrated under reduced pressure. The resulting residue was dissolved in benzene (3.6 mL) and methanol (1.8 mL). A solution of trimethylsilyldiazomethane in ether (2 M, 0.71 mL, 1.43 mmol) was added dropwise under cooling with ice, and then the mixture was stirred for 10 minutes. The reaction mixture was concentrated under reduced pressure. The residue was purified by silica gel chromatography (hexane/ethyl acetate=4/1) to give the title compound (378.9 mg, 97%).

$^1$H-NMR (chloroform-d): 1.43 (s, 9H), 3.72 (s, 3H), 5.29 (d, 1H, J=6.9 Hz), 5.59 (brs, 1H), 7.28-7.35 (m, 4H).

(2) Synthesis of (R)-t-butoxycarbonylamino-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic Acid Methyl Ester

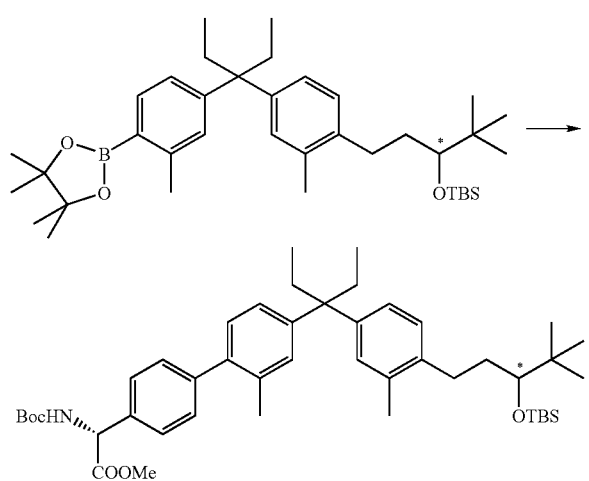

(R)-t-Butoxycarbonylamino-(4-chloro-phenyl)-acetic acid methyl ester (Example 167-(1); 37 mg, 0.124 mmol), palladium acetate (1.8 mg, 0.008 mmol), 2-dicyclohexylphosphino-2',6'-dimethoxy-1,1'-biphenyl (6.6 mg, 0.016 mmol), potassium phosphate (52 mg, 0.246 mmol) and water (0.2 mL) were added to a solution of 2-[4-(1-{4-[3-(t-butyldimethyl-silanyloxy)-4,4-dimethyl-pentyl]-3-methyl-phenyl}-1-ethyl-propyl)-2-methyl-phenyl]-4,4,5,5-tetramethyl-[1,3,2]dioxaborolane (Example 24-(1); 50 mg, 0.082 mmol) in toluene (3 mL). After replacement with nitrogen, the mixture was stirred at 100° C. for three hours. Then, the reaction mixture was dried with anhydrous magnesium sulfate and concentrated under reduced pressure. The resulting residue was purified by silica gel chromatography (hexane:ethyl acetate=4:1) to give the target compound as a colorless oil (28.5 mg, 47%).

$^1$H-NMR (chloroform-d): 0.07 (3H, s), 0.11 (3H, s), 0.64 (6H, t, J=7.26 Hz), 0.88 (9H, s), 0.93 (9H, s), 1.45 (9H, s), 1.50-1.65 (1H, m), 1.70-1.90 (1H, m), 2.10 (4H, q, J=7.26 Hz), 2.22 (3H, s), 2.26 (3H, s), 2.36-2.47 (1H, m), 2.71-2.83 (1H, m), 3.33-3.36 (1H, m), 3.76 (3H, s), 5.38 (1H, s), 6.93-7.07 (6H, m), 7.31 (2H, d, J=8.58 Hz), 7.37 (2H, d, J=8.41 Hz).

(3) Synthesis of (R)-amino-(4'-{1-ethyl-1-[4-(3-hydroxy-4,4-dimethyl-pentyl)-3-methyl-phenyl]-propyl}-2'-methyl-biphenyl-4-yl)-acetic Acid Methyl Ester

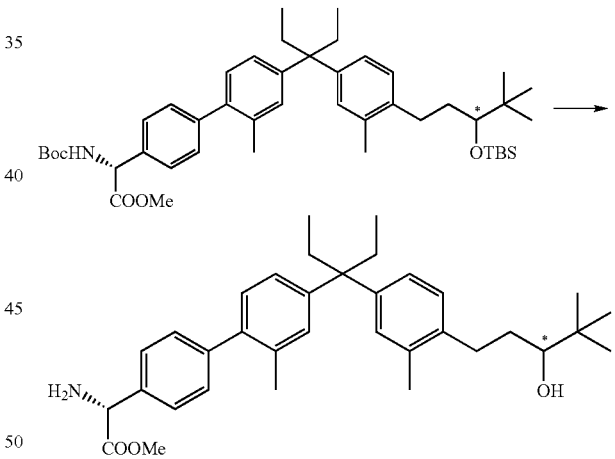

Trifluoroacetic acid (0.3 mL) was added to a solution of (R)-t-butoxycarbonylamino-[4'-(1-{4-[3-(t-butyldimethyl-silanyloxy)-4,4-dimethyl-pentyl]-3-methyl-phenyl}-1-ethyl-propyl)-2'-methyl-biphenyl-4-yl]-acetic acid methyl ester (Example 167-(2); 28.5 mg, 0.038 mmol) in dichloromethane (3 mL) at 0° C., and the mixture was stirred at room temperature for one hour. Then, the reaction mixture was concentrated under reduced pressure. The resulting residue was purified by silica gel chromatography (chloroform:methanol=10:1) to give the target compound as a colorless oil (16.6 mg, 83%).

$^1$H-NMR (chloroform-d): 0.64 (6H, t, J=7.09 Hz), 0.89 (9H, s), 1.45-1.90 (2H, m), 2.10 (4H, q, J=7.42 Hz), 2.22 (3H, s), 2.28 (3H, s), 2.50-2.66 (1H, m), 2.82-2.95 (1H, m), 3.23-

3.27 (1H, m), 3.74 (3H, s), 4.66 (1H, s), 6.95-7.08 (6H, m), 7.31 (2H, d, J=8.25 Hz), 7.39 (2H, d, J=8.08 Hz).

(4) Synthesis of (R)-amino-(4'-{1-ethyl-1-[4-(3-hydroxy-4,4-dimethyl-pentyl)-3-methyl-phenyl]-propyl}-2'-methyl-biphenyl-4-yl)-acetic Acid

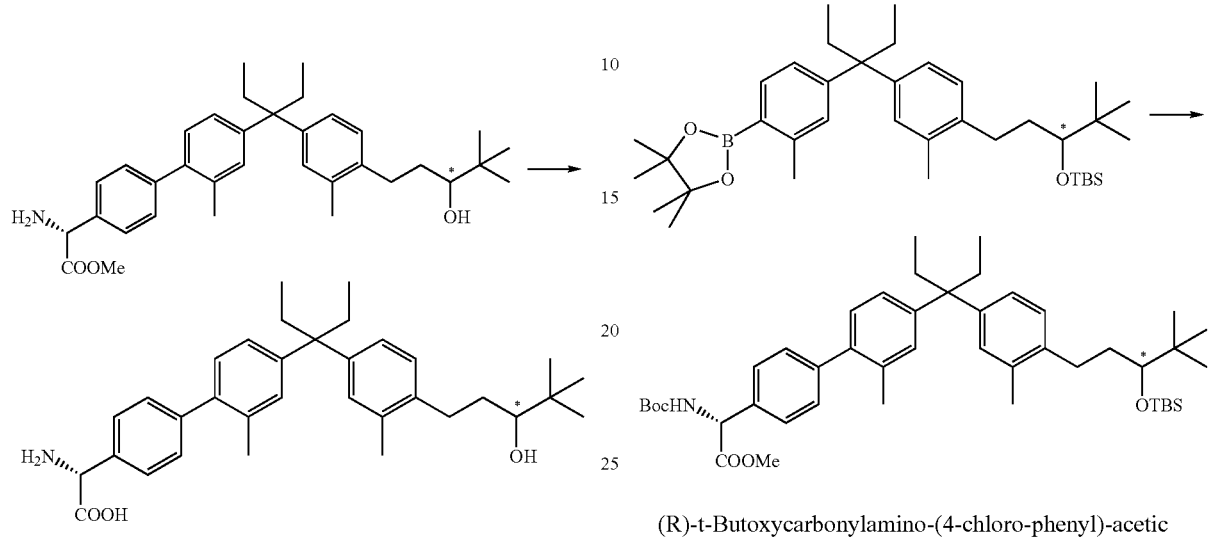

A 1 N sodium hydroxide aqueous solution (0.094 mL, 0.094 mmol) was added to a solution of (R)-amino-(4'-{1-ethyl-1-[4-(3-hydroxy-4,4-dimethyl-pentyl)-3-methyl-phenyl]-propyl}-2'-methyl-biphenyl-4-yl)-acetic acid methyl ester (Example 167-(3); 16.6 mg, 0.031 mmol) in methanol-tetrahydrofuran (1:1, 2 mL), and the mixture was stirred at room temperature for two days. Then, the reaction mixture was concentrated under reduced pressure. The resulting residue was purified by silica gel chromatography (ethyl acetate:methanol:water=4:2:0.6) to give the target compound as a colorless oil (15.2 mg, 95%).

$^1$H-NMR (methanol-d): 0.83 (6H, t, J=7.42 Hz), 1.06 (9H, s), 1.60-1.70 (1H, m), 1.86-2.02 (1H, m), 2.25-2.35 (7H, m), 2.44 (3H, s), 2.65-2.80 (1H, m), 3.03-3.12 (1H, m), 3.33-3.36 (1H, m), 4.79 (1H, s), 7.13 (2H, m), 7.23 (4H, m), 7.54 (2H, d, J=8.08 Hz), 7.40 (2H, d, J=7.92 Hz); MS (ESI+): 516 ([M+H]$^+$).

Example 168

Synthesis of (R)-amino-(4'-{1-ethyl-1-[4-(3-hydroxy-4,4-dimethyl-pentyl)-3-methyl-phenyl]-propyl}-2'-methyl-biphenyl-4-yl)-acetic Acid (1) Synthesis of (R)-t-butoxycarbonylamino-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic Acid Methyl Ester

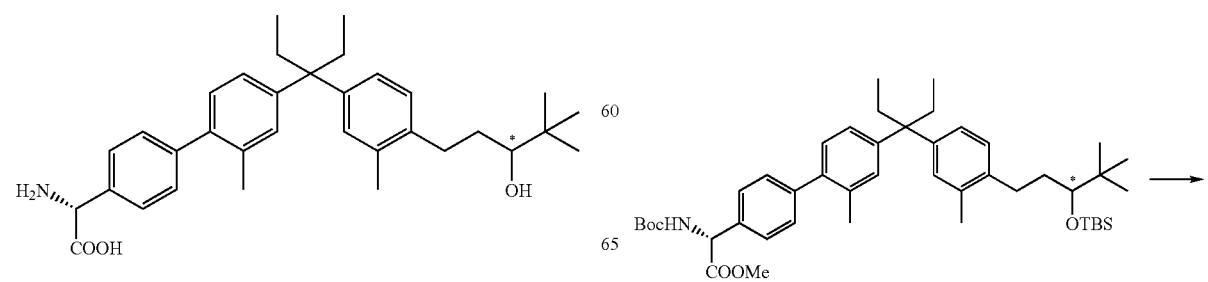

(R)-t-Butoxycarbonylamino-(4-chloro-phenyl)-acetic acid methyl ester (Example 167-(1); 37 mg, 0.124 mmol), palladium acetate (1.8 mg, 0.008 mmol), 2-dicyclohexylphosphino-2',6'-dimethoxy-1,1'-biphenyl (6.6 mg, 0.016 mmol), potassium phosphate (52 mg, 0.246 mmol) and water (0.2 mL) were added to a solution of 2-[4-(1-{4-[3-(t-butyldimethyl-silanyloxy)-4,4-dimethyl-pentyl]-3-methyl-phenyl}-1-ethyl-propyl)-2-methyl-phenyl]-4,4,5,5-tetramethyl-[1,3,2]dioxaborolane (Example 23-(1); 50 mg, 0.082 mmol) in toluene (3 mL). After replacement with nitrogen, the mixture was stirred at 100° C. for three hours. Then, the reaction mixture was dried with anhydrous magnesium sulfate and concentrated under reduced pressure. The resulting residue was purified by silica gel chromatography (hexane:ethyl acetate=4:1) to give the target compound as a colorless oil (43.1 mg, 71%).

$^1$H-NMR (chloroform-d): 0.07 (3H, s), 0.11 (3H, s), 0.64 (6H, t, J=7.26 Hz), 0.88 (9H, s), 0.93 (9H, s), 1.45 (9H, s), 1.55-1.65 (1H, m), 1.70-1.85 (1H, m), 2.10 (4H, q, J=7.42 Hz), 2.22 (3H, s), 2.26 (3H, s), 2.35-2.47 (1H, m), 2.72-2.82 (1H, m), 3.33-3.36 (1H, m), 3.76 (3H, s), 5.38 (1H, s), 6.94-7.07 (6H, m), 7.31 (2H, d, J=8.41 Hz), 7.37 (2H, d, J=8.25 Hz).

(2) Synthesis of (R)-amino-(4'-{1-ethyl-1-[4-(3-hydroxy-4,4-dimethyl-pentyl)-3-methyl-phenyl]-propyl}-2'-methyl-biphenyl-4-yl)-acetic Acid Methyl Ester

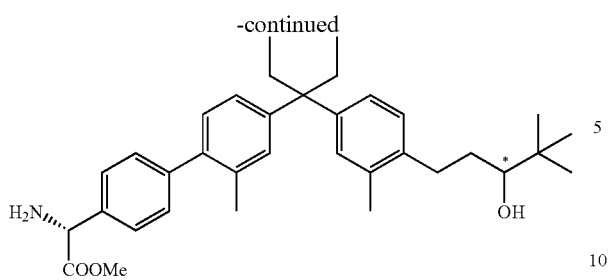

Trifluoroacetic acid (0.1 mL) was added to a solution of (R)-t-butoxycarbonylamino-[4'-(1-{4-[3-(t-butyldimethyl-silanyloxy)-4,4-dimethyl-pentyl]-3-methyl-phenyl}-1-ethyl-propyl)-2'-methyl-biphenyl-4-yl]-acetic acid methyl ester (Example 168-(1); 43.1 mg, 0.058 mmol) in dichloromethane (3 mL) at 0° C., and the mixture was stirred at room temperature for one hour. Then, the reaction mixture was concentrated under reduced pressure. The resulting residue was purified by silica gel chromatography (chloroform:methanol=10:1) to give the target compound as a colorless oil (20.0 mg, 65%).

$^1$H-NMR (chloroform-d): 0.64 (6H, t, J=7.26 Hz), 0.89 (9H, s), 1.48-1.90 (2H, m), 2.10 (4H, q, J=7.25 Hz), 2.22 (3H, s), 2.28 (3H, s), 2.50-2.63 (1H, m), 2.80-2.95 (1H, m), 3.74 (3H, s), 4.66 (1H, s), 6.95-7.08 (6H, m), 7.31 (2H, d, J=8.41 Hz), 7.39 (2H, d, J=8.24 Hz).

(3) Synthesis of (R)-amino-(4'-{1-ethyl-1-[4-(3-hydroxy-4,4-dimethyl-pentyl)-3-methyl-phenyl]-propyl}-2'-methyl-biphenyl-4-yl)-acetic Acid

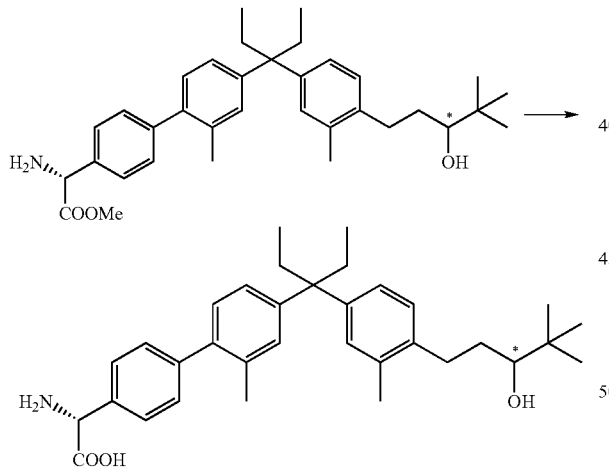

A 1 N sodium hydroxide aqueous solution (0.113 mL, 0.113 mmol) was added to a solution of (R)-amino-(4'-{1-ethyl-1-[4-(3-hydroxy-4,4-dimethyl-pentyl)-3-methyl-phenyl]-propyl}-2'-methyl-biphenyl-4-yl)-acetic acid methyl ester (Example 168-(2); 20.0 mg, 0.038 mmol) in methanol-tetrahydrofuran (1:1, 2 mL), and the mixture was stirred at room temperature for three hours. Then, the reaction mixture was concentrated under reduced pressure. The resulting residue was purified by silica gel chromatography (ethyl acetate:methanol:water=4:2:0.6) to give the target compound as a colorless oil (18.5 mg, 94%).

$^1$H-NMR (methanol-d): 0.82 (6H, t, J=7.25 Hz), 1.06 (9H, s), 1.60-1.80 (1H, m), 1.85-2.02 (1H, m), 2.28-2.35 (7H, m), 2.44 (3H, s), 2.65-2.80 (1H, m), 3.00-3.04 (1H, m), 3.33-3.36 (1H, m), 4.78 (1H, s), 7.13 (2H, m), 7.23 (4H, m), 7.53 (2H, d, J=8.08 Hz), 7.70 (2H, d, J=8.25 Hz); MS (ESI+): 515 ([M+H]$^+$).

Example 169

Synthesis of (S)-amino-(4'-{1-ethyl-1-[4-(3-hydroxy-4,4-dimethyl-pentyl)-3-methyl-phenyl]-propyl}-2'-methyl-biphenyl-4-yl)-acetic Acid

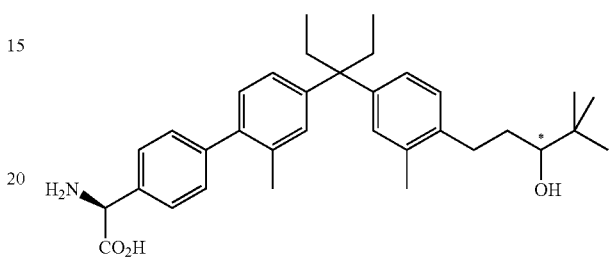

(1) Synthesis of (S)-t-butoxycarbonylamino-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic Acid Methyl Ester

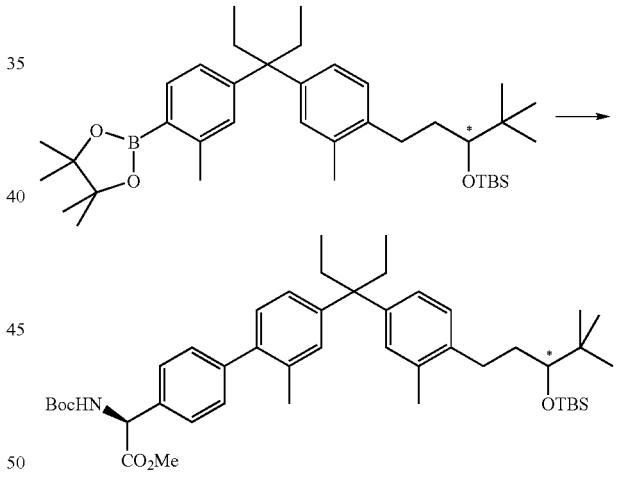

Toluene (2.0 mL) and water (0.20 mL) were added to t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1); 50.0 mg, 0.0824 mmol), (S)-t-butoxycarbonylamino-(4-chloro-phenyl)-acetic acid methyl ester (Example 166-(1); 37.0 mg, 0.123 mmol), palladium (II) acetate (1.9 mg, 0.00846 mmol), 2-dicyclohexylphosphino-2',6'-dimethoxy-1,1'-biphenyl (6.8 mg, 0.0166 mmol) and potassium phosphate (52.0 mg, 0.245 mmol). After replacement with nitrogen, the mixture was stirred with microwave heating at 150° C. for five minutes. The reaction mixture was purified by silica gel chromatography (hexane:ethyl acetate=100:0 to 70:30) to give the target compound as a colorless oil (56.4 mg, 92%).

¹H-NMR (chloroform-d): 0.07 (s, 3H), 0.11 (s, 3H), 0.64 (t, 6H, J=5.3 Hz), 0.85 (brs, 9H), 0.93 (brs, 9H), 1.45 (s, 9H), 1.75-2.15 (m, 6H), 2.22 (s, 3H), 2.26 (s, 3H), 2.37-2.47 (m, 1H), 2.71-2.82 (m, 1H), 3.32-3.37 (m, 1H), 3.76 (s, 3H), 5.31-5.40 (m, 1H), 5.51-5.60 (m, 1H), 6.92-7.09 (m, 6H), 7.30-7.40 (m, 4H); MS (ESI+): 688.4 ([M-tBu+2H]+); MS (ESI–): 742.7 ([M–H]⁻).

(2) Synthesis of (S)-amino-(4'-{1-ethyl-1-[4-(3-hydroxy-4,4-dimethyl-pentyl)-3-methyl-phenyl]-propyl}-2'-methyl-biphenyl-4-yl)-acetic Acid

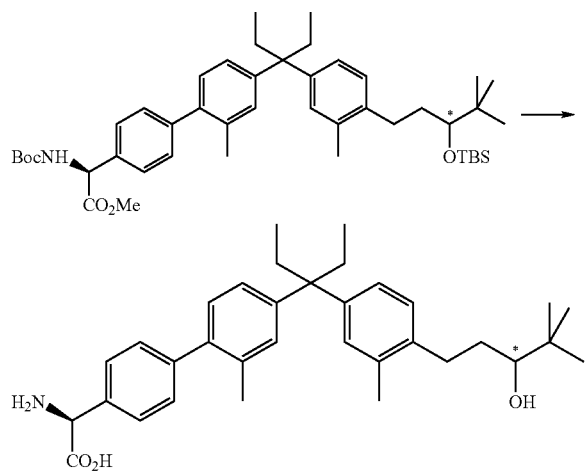

Water (0.2 mL) and trifluoroacetic acid (1.0 mL) were added to a solution of (S)-t-butoxycarbonylamino-[4'-(1-{4-[3-(t-butyl-dimethyl-silanyloxy)-4,4-dimethyl-pentyl]-3-methyl-phenyl}-1-ethyl-propyl)-2'-methyl-biphenyl-4-yl]-acetic acid methyl ester (Example 169-(1); 56.4 mg, 0.0758 mmol) in dichloromethane (2.0 mL), and the mixture was stirred at room temperature for 45 minutes. Sodium bicarbonate was added to the reaction mixture, which was crudely purified by silica gel chromatography (dichloromethane:methanol=97:3 to 90:10). The mixture was further purified by silica gel chromatography (hexane:ethyl acetate=70:30 to 0:100) to give a mixture containing (S)-amino-(4'-{1-ethyl-1-[4-(3-hydroxy-4,4-dimethyl-pentyl)-3-methyl-phenyl]-propyl}-2'-methyl-biphenyl-4-yl)-acetic acid methyl ester as a pink solid (235 mg). The mixture was used in the following reaction without further purification.

A 4 N hydrochloric acid aqueous solution (0.80 mL) was added to a solution of the mixture containing (S)-amino-(4'-{1-ethyl-1-[4-(3-hydroxy-4,4-dimethyl-pentyl)-3-methyl-phenyl]-propyl}-2'-methyl-biphenyl-4-yl)-acetic acid methyl ester (220 mg) in acetone (0.60 mL), and the mixture was stirred with microwave heating at 140° C. for 10 minutes. The reaction mixture was purified by high performance liquid chromatography (GL Sciences Inertsil ODS-3, 20 mm I.D.× 150 mm, methanol:water=20:80 to 100:0, 20 mL/min) and concentrated under reduced pressure to give the target compound as a white solid (14.0 mg, 36% in two steps).

¹H-NMR (methanol-d): 0.63 (t, 6H, J=7.4 Hz), 0.87 (s, 9H), 1.40-1.56 (m, 1H), 1.70-1.83 (m, 1H), 2.13 (q, 4H, J=7.4 Hz), 2.17 (s, 3H), 2.26 (s, 3H), 2.49-2.63 (m, 1H), 2.76-2.94 (m, 1H), 3.12-3.20 (m, 1H), 4.62 (s, 1H), 6.90-6.99 (m, 2H), 7.01-7.08 (m, 4H), 7.32-7.40 (m, 2H), 7.47-7.55 (m, 2H); MS (ESI+): 516.2 ([M+H]+); MS (ESI–): 514.4 ([M–H]⁻).

Example 170

Synthesis of 4'-{1-ethyl-1-[4-(3-hydroxy-4,4-dimethyl-pentyl)-3-methyl-phenyl]-propyl}-2'-methyl-biphenyl-4-carboxylic Acid Hydroxyamide

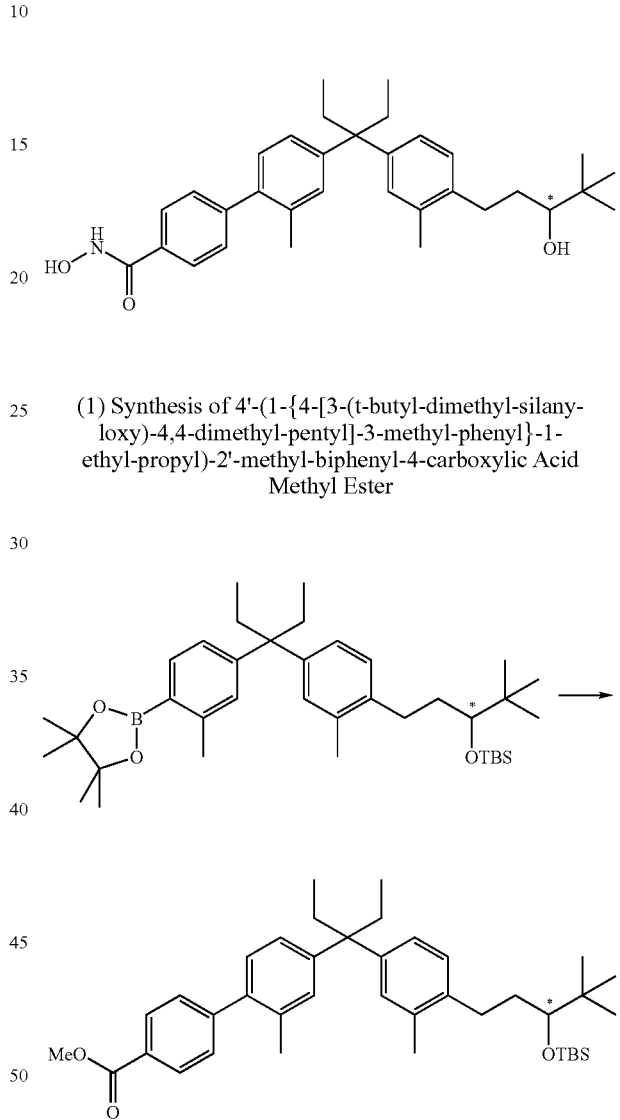

(1) Synthesis of 4'-(1-{4-[3-(t-butyl-dimethyl-silanyloxy)-4,4-dimethyl-pentyl]-3-methyl-phenyl}-1-ethyl-propyl)-2'-methyl-biphenyl-4-carboxylic Acid Methyl Ester The title compound (94%) was obtained by the same method as in Example 66-(1) using t-butyl-(1-{2-[4-(1-ethyl-1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1)) and 4-bromo-benzoic acid methyl ester as starting materials.

¹H-NMR (chloroform-d): 0.07 (s, 3H), 0.11 (s, 3H), 0.65 (t, 6H, J=7.3 Hz), 0.88 (s, 9H), 0.93 (s, 9H), 1.51-1.65 (m, 1H), 1.74-1.83 (m, 1H), 2.11 (q, 4H, J=7.3 Hz), 2.23 (s, 3H), 2.26 (s, 3H), 2.36-2.48 (m, 1H), 2.72-2.83 (m, 1H), 3.35 (dd, 1H, J=3.1, 7.1 Hz), 3.93 (s, 3H), 6.94-7.11 (m, 6H), 7.41 (d, 2H, J=8.4 Hz), 8.06 (d, 2H, J=8.4 Hz).

(2) Synthesis of 4'-{1-ethyl-1-[4-(3-hydroxy-4,4-dimethyl-pentyl)-3-methyl-phenyl]-propyl}-2'-methyl-biphenyl-4-carboxylic Acid Methyl Ester

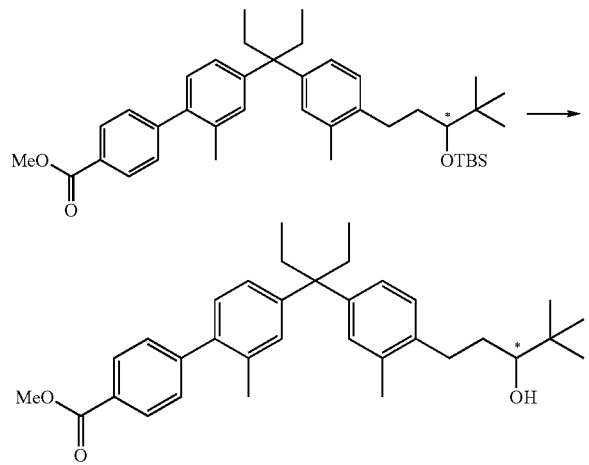

The title compound (68%) was obtained by the same method as in Example 154-(3) using 4'-(1-{4-[3-(t-butyl-dimethyl-silanyloxy)-4,4-dimethyl-pentyl]-3-methyl-phenyl}-1-ethyl-propyl)-2'-methyl-biphenyl-4-carboxylic acid methyl ester (Example 170-(1)) as a starting material.

$^1$H-NMR (chloroform-d): 0.65 (t, 6H, J=7.4 Hz), 0.90 (s, 9H), 1.44-1.53 (m, 1H), 1.75-1.86 (m, 1H), 2.11 (q, 4H, J=7.4 Hz), 2.23 (s, 3H), 2.28 (s, 3H), 2.51-2.63 (m, 1H), 2.82-2.93 (m, 1H), 3.25 (dd, 1H, J=1.7, 10.6 Hz), 3.93 (s, 3H), 6.94-7.11 (m, 6H), 7.41 (d, 2H, J=8.1 Hz), 8.06 (d, 2H, J=8.1 Hz).

(3) Synthesis of 4'-{1-ethyl-1-[4-(3-hydroxy-4,4-dimethyl-pentyl)-3-methyl-phenyl]-propyl}-2'-methyl-biphenyl-4-carboxylic Acid

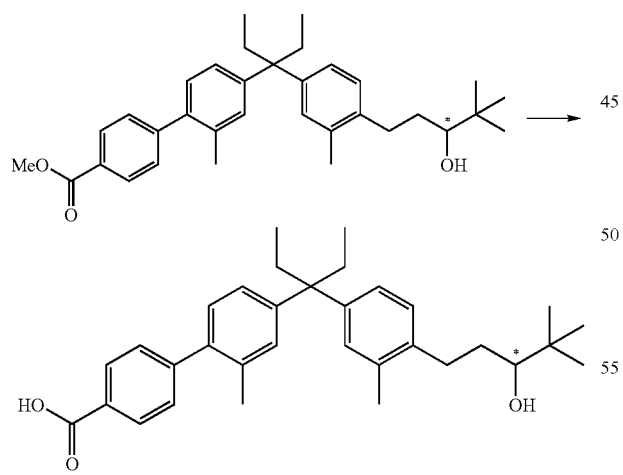

The title compound (100%) was obtained by the same method as in Example 154-(4) using 4'-{1-ethyl-1-[4-(3-hydroxy-4,4-dimethyl-pentyl)-3-methyl-phenyl]-propyl}-2'-methyl-biphenyl-4-carboxylic acid methyl ester (Example 170-(2)) as a starting material.

$^1$H-NMR (methanol-d4): 0.62 (t, 6H, J=7.3 Hz), 0.86 (s, 9H), 1.47-1.52 (m, 1H), 1.76 (m, 1H), 2.12 (q, 4H, J=7.3 Hz), 2.17 (s, 3H), 2.24 (s, 3H), 2.48-2.59 (m, 1H), 2.82-2.93 (m, 1H), 3.14-3.18 (m, 1H), 6.95-7.07 (m, 6H), 7.36 (d, 2H, J=8.3 Hz), 8.03 (d, 2H, J=8.3 Hz).

(4) Synthesis of 4'-{1-ethyl-1-[4-(3-hydroxy-4,4-dimethyl-pentyl)-3-methyl-phenyl]-propyl}-2'-methyl-biphenyl-4-carboxylic Acid Hydroxyamide

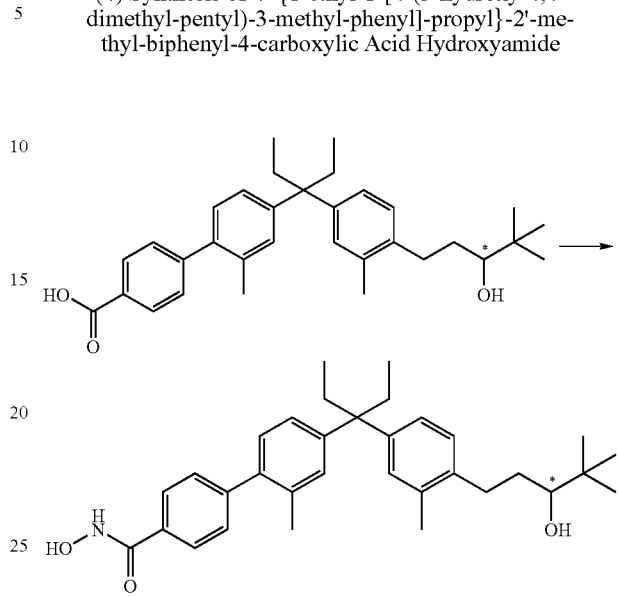

4'-{1-Ethyl-1-[4-(3-hydroxy-4,4-dimethyl-pentyl)-3-methyl-phenyl]-propyl}-2'-methyl-biphenyl-4-carboxylic acid (Example 170-(3); 25.7 mg, 0.053 mmol), hydroxylamine hydrochloride (7.4 mg, 0.106 mmol) and dichloromethane (0.5 mL) were placed in a reaction vessel. 1-Ethyl-3-(3-dimethylaminopropyl)carbodiimide hydrochloride (13.2 mg, 0.069 mmol) was added at 0° C., and then the mixture was stirred for 30 minutes. Subsequently, diisopropylethylamine (0.0184 mL, 0.106 mmol) and 4-dimethylaminopyridine (1.94 mg, 0.016 mmol) were added and the mixture was stirred at room temperature overnight. 1 N hydrochloric acid aqueous solution was added to the reaction solution, followed by extraction with ethyl acetate. The organic layer was washed with brine and then dried over anhydrous magnesium sulfate and concentrated under reduced pressure. The resulting residue was purified by thin layer silica gel chromatography (chloroform:methanol=10:1) to give the title compound (1.2 mg, 5%).

$^1$H-NMR (methanol-d4): 0.64 (t, 6H, J=7.1 Hz), 0.88 (s, 9H), 1.48-1.53 (m, 1H), 1.75 (m, 1H), 2.15 (q, 4H, J=7.1 Hz), 2.20 (s, 3H), 2.27 (s, 3H), 2.50-2.61 (m, 1H), 2.83-2.92 (m, 1H), 3.15-3.18 (m, 1H), 6.95-6.97 (m, 2H), 7.04-7.08 (m, 4H), 7.42 (d, 2H, J=8.4 Hz), 7.79 (d, 2H, J=8.4 Hz); MS (ESI+): 502 ([M+H]$^+$).

Example 171

Synthesis of 2-(4'-{1-ethyl-1-[4-(3-hydroxy-4,4-dimethyl-pentyl)-3-methyl-phenyl]-propyl}-2'-methyl-biphenyl-3-yl)-N-hydroxy-acetamide

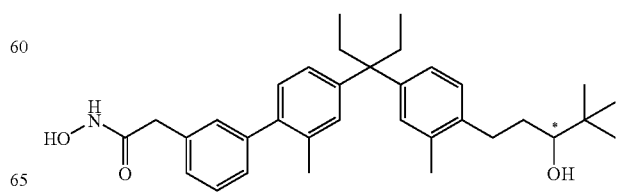

(1) Synthesis of 2-(4'-{1-ethyl-1-[4-(3-hydroxy-4,4-dimethyl-pentyl)-3-methyl-phenyl]-propyl}-2'-methyl-biphenyl-3-yl)-N-hydroxy-acetamide

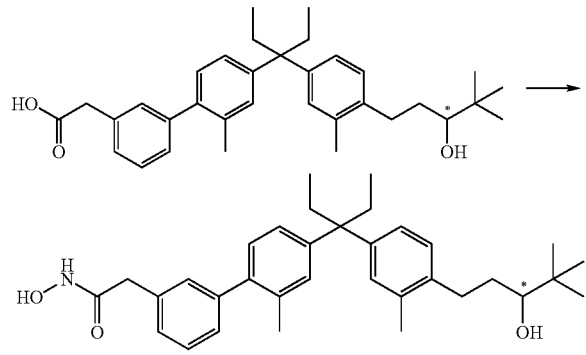

The title compound (37%) was obtained by the same method as in Example 170-(4) using (4'-{1-ethyl-1-[4-(3-hydroxy-4,4-dimethyl-pentyl)-3-methyl-phenyl]-propyl}-2'-methyl-biphenyl-3-yl)-acetic acid (Example 14-(2)) as a starting material.

$^1$H-NMR (methanol-d4): 0.64 (t, 6H, J=7.3 Hz), 0.88 (s, 9H), 1.46-1.57 (m, 1H), 1.72-1.82 (m, 1H), 2.14 (q, 4H, J=7.3 Hz), 2.18 (s, 3H), 2.27 (s, 3H), 2.50-2.61 (m, 1H), 2.83-2.94 (m, 1H), 3.17 (dd, 1H, J=1.7, 10.6 Hz), 3.44 (s, 2H), 6.95-6.97 (m, 2H), 7.03-7.09 (m, 4H), 7.18-7.37 (m, 4H); MS (ESI+): 533 ([M+NH$_4$]$^+$).

Example 172

Synthesis of 2-(4'-{1-ethyl-1-[4-(3-hydroxy-4,4-dimethyl-pentyl)-3-methyl-phenyl]-propyl}-2'-methyl-biphenyl-4-yl)-N-hydroxy-acetamide

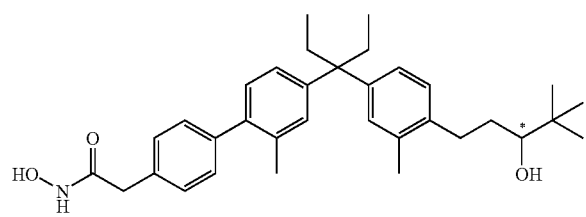

(1) Synthesis of 2-(4'-{1-ethyl-1-[4-(3-hydroxy-4,4-dimethyl-pentyl)-3-methyl-phenyl]-propyl}-2'-methyl-biphenyl-4-yl)-N-hydroxy-acetamide

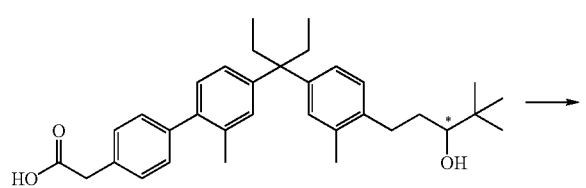

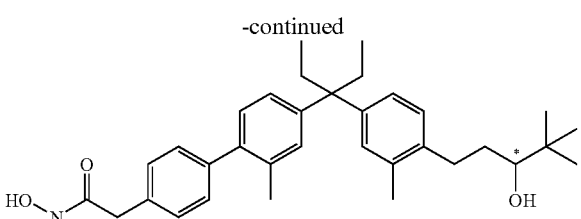

The title compound (33%) was obtained by the same method as in Example 170-(4) using (4'-{1-ethyl-1-[4-(3-hydroxy-4,4-dimethyl-pentyl)-3-methyl-phenyl]-propyl}-2'-methyl-biphenyl-4-yl)-acetic acid (Example 13-(2)) as a starting material.

$^1$H-NMR (methanol-d4): 0.64 (t, 6H, J=7.1 Hz), 0.88 (s, 9H), 1.48-1.57 (m, 1H), 1.72-1.75 (m, 1H), 2.13 (q, 4H, J=7.1 Hz), 2.18 (s, 3H), 2.27 (s, 3H), 2.49-2.61 (m, 1H), 2.83-2.92 (m, 1H), 3.16 (dd, 1H, J=1.7, 10.6 Hz), 3.44 (s, 2H), 6.95-6.97 (m, 2H), 7.04-7.06 (m, 4H), 7.25 (d, 2H, J=8.3 Hz), 7.33 (d, 2H, J=8.3 Hz); MS (ESI+): 533 ([M+NH$_4$]$^+$).

Example 173

Synthesis of 4'-{1-ethyl-1-[4-(3-hydroxy-4,4-dimethyl-pentyl)-3-methyl-phenyl]-propyl}-2'-methyl-biphenyl-3-carboxylic Acid Hydroxyamide

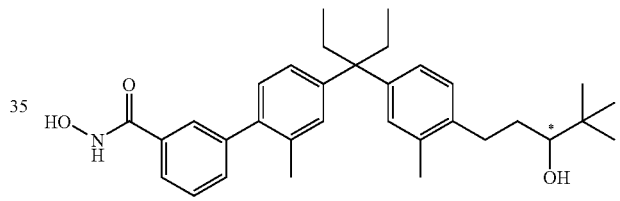

(1) Synthesis of 4'-(1-{4-[3-(t-butyl-dimethyl-silanyloxy)-4,4-dimethyl-pentyl]-3-methyl-phenyl}-1-ethyl-propyl)-2'-methyl-biphenyl-3-carboxylic Acid Methyl Ester

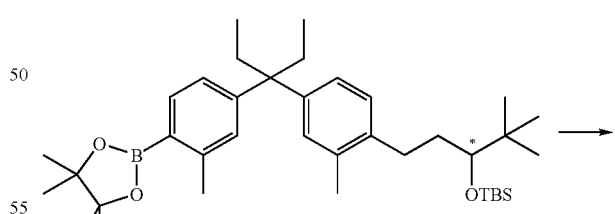

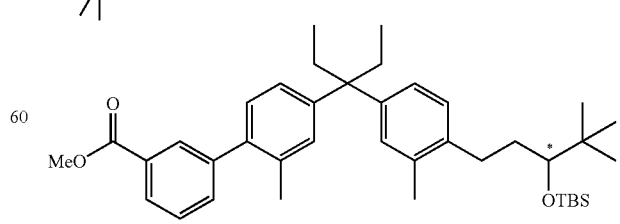

The title compound (74%) was obtained by the same method as in Example 66-(1) using t-butyl-(1-{2-[4-(1-ethyl- 1-{4-[4,4,5,5-tetramethyl-1,3,2-dioxaborolan-2-yl]-3-methyl-phenyl}-propyl)-2-methyl-phenyl]-ethyl}-2,2-dimethyl-propoxy)dimethylsilane (Example 23-(1)) and 3-bromo-benzoic acid methyl ester as starting materials.

$^1$H-NMR (chloroform-d): 0.65 (t, 6H, J=7.1 Hz), 0.88 (s, 9H), 0.94 (s, 9H), 1.53-1.65 (m, 1H), 1.74-1.84 (m, 1H), 2.11 (q, 4H, J=7.1 Hz), 2.22 (s, 3H), 2.27 (s, 3H), 2.37-2.48 (m, 1H), 2.72-2.84 (m, 1H), 3.35 (dd, 1H, J=3.1, 7.1 Hz), 3.92 (s, 3H), 6.94-7.11 (m, 6H), 7.43-7.55 (m, 2H), 7.97-8.02 (m, 2H).

(2) Synthesis of 4'-{1-ethyl-1-[4-(3-hydroxy-4,4-dimethyl-pentyl)-3-methyl-phenyl]-propyl}-2'-methyl-biphenyl-3-carboxylic Acid Methyl Ester

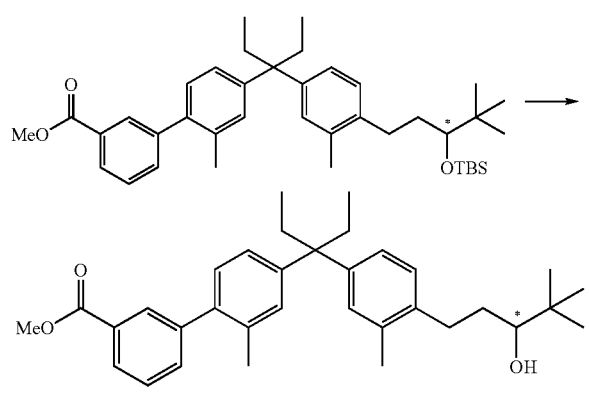

The title compound (66%) was obtained by the same method as in Example 154-(3) using 4'-(1-{4-[3-(t-butyl-dimethyl-silanyloxy)-4,4-dimethyl-pentyl]-3-methyl-phenyl}-1-ethyl-propyl)-2'-methyl-biphenyl-3-carboxylic acid methyl ester (Example 173-(1)) as a starting material.

$^1$H-NMR (chloroform-d): 0.65 (t, 6H, J=7.3 Hz), 0.90 (s, 9H), 1.45-1.59 (m, 1H), 1.76-1.87 (m, 1H), 2.11 (q, 4H, J=7.3 Hz), 2.22 (s, 3H), 2.29 (s, 3H), 2.52-2.63 (m, 1H), 2.83-2.94 (m, 1H), 3.24-3.28 (m, 1H), 3.92 (s, 3H), 6.95-7.11 (m, 6H), 7.43-7.55 (m, 2H), 7.97-8.02 (m, 2H).

(3) Synthesis of 4'-{1-ethyl-1-[4-(3-hydroxy-4,4-dimethyl-pentyl)-3-methyl-phenyl]-propyl}-2'-methyl-biphenyl-3-carboxylic Acid

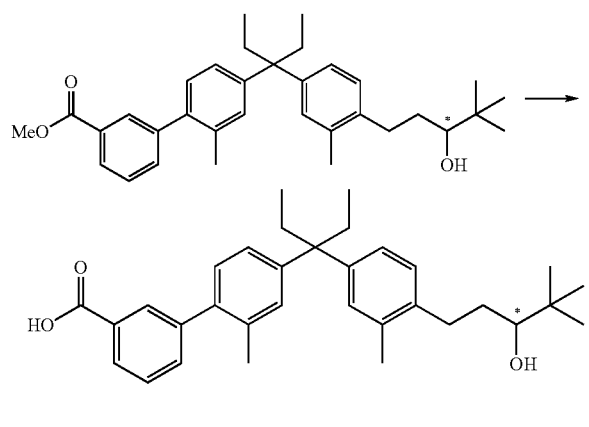

The title compound (92%) was obtained by the same method as in Example 154-(4) using 4'-{1-ethyl-1-[4-(3-hydroxy-4,4-dimethyl-pentyl)-3-methyl-phenyl]-propyl}-2'-methyl-biphenyl-3-carboxylic acid methyl ester (Example 173-(2)) as a starting material.

$^1$H-NMR (chloroform-d): 0.65 (t, 6H, J=7.1 Hz), 0.90 (s, 9H), 1.45-1.60 (m, 1H), 1.76-1.87 (m, 1H), 2.12 (q, 4H, J=7.1 Hz), 2.24 (s, 3H), 2.29 (s, 3H), 2.52-2.63 (m, 1H), 2.83-2.94 (m, 1H), 3.25-3.28 (m, 1H), 6.95-7.12 (m, 6H), 7.47-7.60 (m, 2H), 8.04-8.09 (m, 2H).

(4) Synthesis of 4'-{1-ethyl-1-[4-(3-hydroxy-4,4-dimethyl-pentyl)-3-methyl-phenyl]-propyl}-2'-methyl-biphenyl-3-carboxylic Acid Hydroxyamide

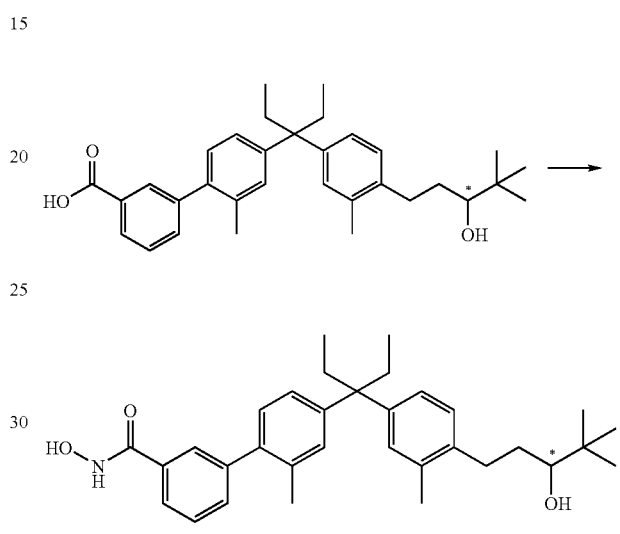

The title compound (18%) was obtained by the same method as in Example 170-(4) using 4'-{1-ethyl-1-[4-(3-hydroxy-4,4-dimethyl-pentyl)-3-methyl-phenyl]-propyl}-2'-methyl-biphenyl-3-carboxylic acid (Example 173-(3)) as a starting material.

$^1$H-NMR (methanol-d4): 0.64 (t, 6H, J=7.1 Hz), 0.88 (s, 9H), 1.48-1.53 (m, 1H), 1.77 (m, 1H), 2.15 (q, 4H, J=7.1 Hz), 2.20 (s, 3H), 2.27 (s, 3H), 2.50-2.61 (m, 1H), 2.83-2.92 (m, 1H), 3.15-3.18 (m, 1H), 6.95-6.97 (m, 2H), 7.04-7.09 (m, 4H), 7.48-7.50 (m, 2H), 7.69-7.72 (m, 2H); MS (ESI−): 500 ([M−H]−).

Example 174

Synthesis of {5-[4-(1-ethyl-1-{4-[2-(4-hydroxy-tetrahydro-pyran-4-yl)-ethyl]-3-methyl-phenyl}-propyl)-2-methyl-phenyl]-pyridin-3-yl}-acetic Acid

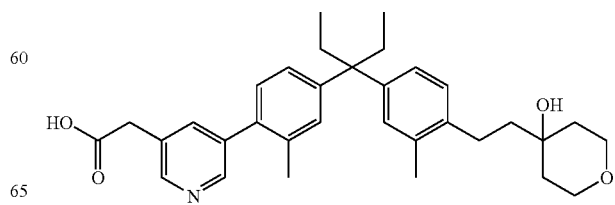

(1) Synthesis of 4-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-tetrahydro-pyran-4-ol

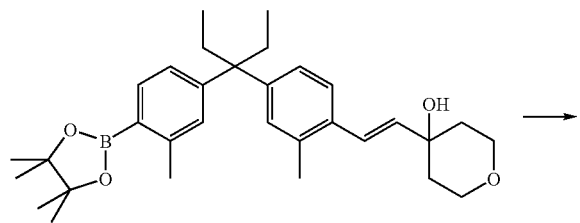

The title compound (100%) was obtained by the same method as in Example 27-(2) using 4-[(E)-2-(4-{1-ethyl-1-[3-methyl-4-(4,4,5,5-tetramethyl-[1,3,2]dioxaborolan-2-yl)-phenyl]-propyl}-2-methyl-phenyl)-vinyl]-tetrahydropyran-4-ol (Example 131-(3)) as a starting material.

¹H-NMR (chloroform-d): 0.59 (6H, t, J=7.2 Hz), 1.32 (s, 12H), 1.53-1.90 (m, 4H), 2.06 (q, 4H, J=7.2 Hz), 2.22 (s, 3H), 2.48 (s, 3H), 2.60-2.70 (m, 2H), 3.73-3.82 (m, 4H), 6.88-7.01 (m, 5H), 7.62 (d, 1H, J=8.4 Hz).

(2) Synthesis of {5-[4-(1-ethyl-1-{4-[2-(4-hydroxy-tetrahydro-pyran-4-yl)-ethyl]-3-methyl-phenyl}-propyl)-2-methyl-phenyl]-pyridin-3-yl}-acetic Acid Methyl Ester

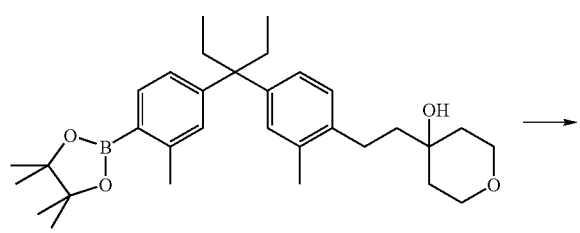

The title compound (49%) was obtained by the same method as in Example 66-(1) using 4-[2-(4-{1-ethyl-1-[3-methyl-4-(4,4,5,5-tetramethyl-[1,3,2]dioxaborolan-2-yl)-phenyl]-propyl}-2-methyl-phenyl)-ethyl]-tetrahydropyran-4-ol and (5-bromo-pyridin-3-yl)-acetic acid methyl ester (Example 24-(2)) as starting materials.

¹H-NMR (chloroform-d): 0.64 (6H, t, J=7.2 Hz), 1.53-1.80 (m, 4H), 2.11 (q, 4H, J=7.2 Hz), 2.24 (s, 3H), 2.28 (s, 3H), 2.63-2.70 (m, 2H), 3.68-3.81 (m, 9H), 6.94-7.09 (m, 6H), 7.62-7.64 (m, 1H), 8.45-8.52 (m, 2H): MS (ESI+): 530 ([M+H]+).

(3) Synthesis of {5-[4-(1-ethyl-1-{4-[2-(4-hydroxy-tetrahydro-pyran-4-yl)-ethyl]-3-methyl-phenyl}-propyl)-2-methyl-phenyl]-pyridin-3-yl}-acetic Acid

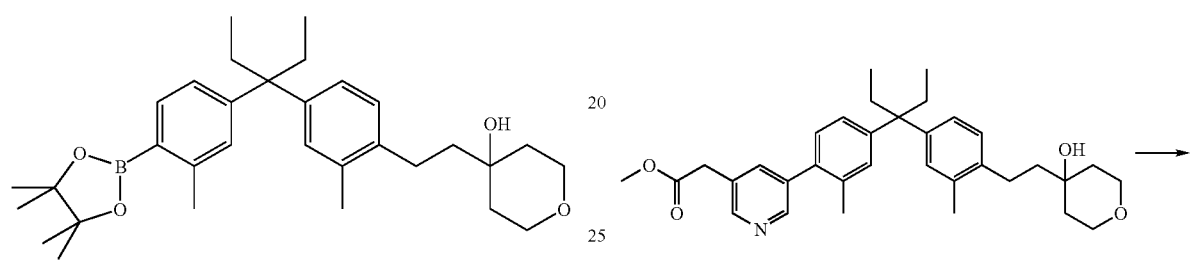

The title compound (27%) was obtained by the same method as in Example 46-(2) using {5-[4-(1-ethyl-1-{4-[2-(4-hydroxy-tetrahydropyran-4-yl)-ethyl]-3-methyl-phenyl}-propyl)-2-methyl-phenyl]-pyridin-3-yl}-acetic acid methyl ester as a starting material.

¹H-NMR (chloroform-d): 0.63 (6H, t, J=7.2 Hz), 1.55-1.81 (m, 4H), 2.09 (q, 4H, J=7.2 Hz), 2.19 (s, 3H), 2.24 (s, 3H), 2.63-2.69 (m, 2H), 3.65-3.82 (m, 6H), 6.90-7.09 (m, 6H), 6.91-7.09 (m, 6H), 7.72 (s, 1H), 8.47-8.49 (m, 2H); MS (ESI+): 516 ([M+H]⁺).

Example 175

Synthesis of (4'-{1-ethyl-1-[4-((E)-3-ethyl-3-hydroxy-1-pentenyl)-3-methyl-phenyl]-propyl}-6-methoxy-biphenyl-3-yl)-acetic Acid

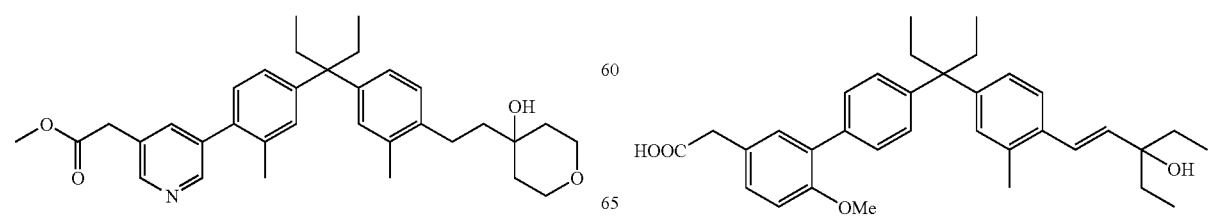

(1) Synthesis of (3-bromo-4-methoxy-phenyl)-acetic Acid Methyl Ester

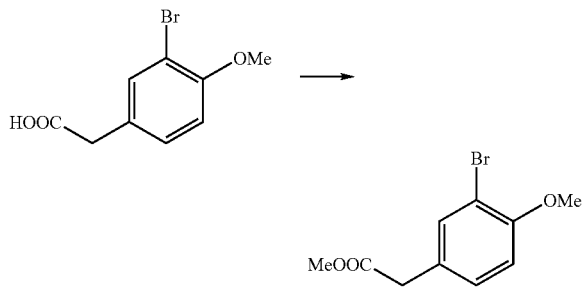

Trimethylsilyldiazomethane (2 M solution in diethyl ether, 0.306 mL, 0.612 mmol) was added to a solution of (3-bromo-4-methoxy-phenyl)-acetic acid (100 mg, 0.408 mmol) in methanol (1 mL) and toluene (4 mL), and the mixture was stirred at room temperature for 10 minutes. Acetic acid was added to the reaction mixture to terminate the reaction, and then the mixture was concentrated under reduced pressure to give the target compound as a colorless oil (100 mg, 95%).

$^1$H-NMR (chloroform-d): 3.54 (2H, s), 3.70 (3H, s), 3.88 (3H, s), 6.85 (1H, d, J=8.25 Hz), 7.18 (1H, dd, J=8.25, 2.15 Hz), 7.47 (1H, d, J=2.14 Hz).

(2) Synthesis of (4'-{1-ethyl-1-[4-((E)-3-ethyl-3-hydroxy-1-pentenyl)-3-methyl-phenyl]-propyl}-6-methoxy-biphenyl-3-yl)-acetic Acid Methyl Ester

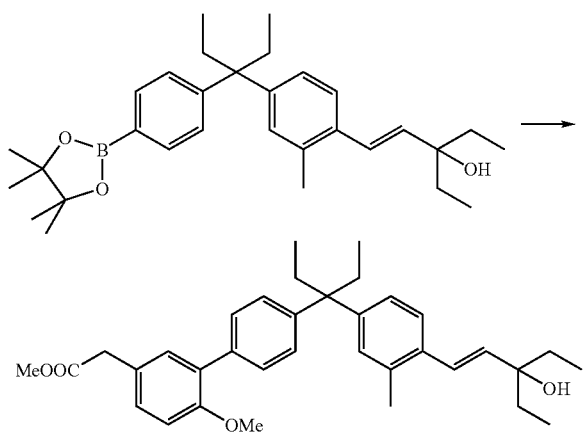

(3-Bromo-4-methoxy-phenyl)-acetic acid methyl ester (Example 175-(1); 39 mg, 0.151 mmol), palladium acetate (2.2 mg, 0.010 mmol), 2-dicyclohexylphosphino-2',6'-dimethoxy-1,1'-biphenyl (8.2 mg, 0.020 mmol), potassium phosphate (64 mg, 0.303 mmol) and water (0.2 mL) were added to a solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 48 mg, 0.101 mmol) in toluene (2 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (26.2 mg, 49%).

$^1$H-NMR (chloroform-d): 0.66 (6H, t, J=7.42 Hz), 0.92 (6H, t, J=7.42 Hz), 1.64 (4H, q, J=7.58 Hz), 2.12 (4H, q, J=7.25 Hz), 2.33 (3H, s), 3.59 (2H, s), 3.69 (3H, s), 3.79 (3H, s), 6.02 (1H, d, J=15.99 Hz), 6.75 (1H, d, J=15.99 Hz), 6.91 (1H, d, J=8.24 Hz), 6.99-7.02 (2H, m), 7.18-7.24 (4H, m), 7.32 (1H, d, J=8.74 Hz), 7.41 (2H, d, J=8.41 Hz).

(3) Synthesis of (4'-{1-ethyl-1-[4-((E)-3-ethyl-3-hydroxy-1-pentenyl)-3-methyl-phenyl]-propyl}-6-methoxy-biphenyl-3-yl)-acetic Acid

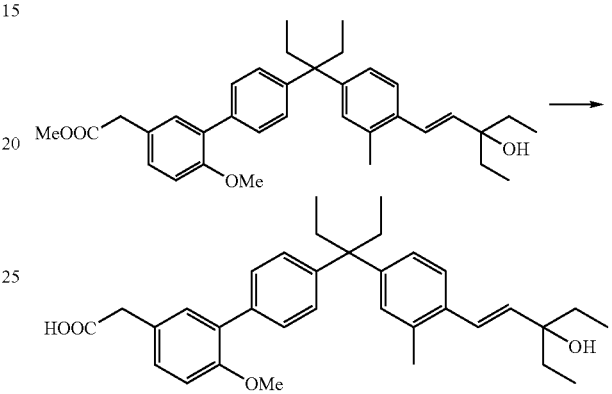

A 1 N sodium hydroxide aqueous solution (0.150 mL, 0.150 mmol) was added to a solution of (4'-{1-ethyl-1-[4-((E)-3-ethyl-3-hydroxy-1-pentenyl)-3-methyl-phenyl]-propyl}-6-methoxy-biphenyl-3-yl)-acetic acid methyl ester (Example 175-(2); 26.2 mg, 0.050 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (24.1 mg, 94%).

$^1$H-NMR (chloroform-d): 0.66 (6H, t, J=7.26 Hz), 0.92 (6H, t, J=7.42 Hz), 1.64 (4H, q, J=7.58 Hz), 2.12 (4H, q, J=7.42 Hz), 2.32 (3H, s), 3.62 (2H, s), 3.79 (3H, s), 6.01 (1H, d, J=15.99 Hz), 6.75 (1H, d, J=15.99 Hz), 6.92 (1H, d, J=8.24 Hz), 6.98-7.03 (2H, m), 7.17-7.24 (4H, m), 7.32 (1H, d, J=8.74 Hz), 7.40 (2H, d, J=8.41 Hz); MS (ESI+): 497 ([M−H$_2$O+H]$^+$).

Example 176

Synthesis of (4'-{1-ethyl-1-[4-(3-hydroxy-4,4-dimethyl-pentyl)-3-methyl-phenyl]-propyl}-2'-hydroxy-biphenyl-4-yl)-acetic Acid

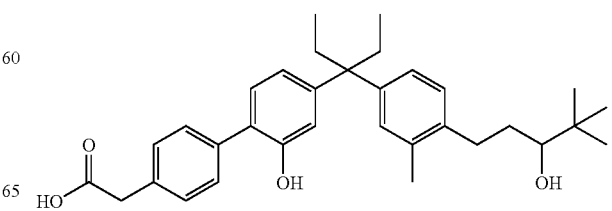

(1) Synthesis of 4-(t-butyl-dimethyl-silanyloxy)-3-methoxy-benzoic Acid Methyl Ester

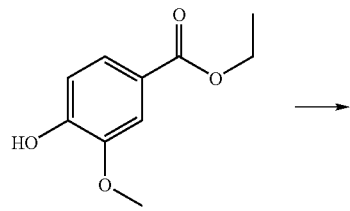

Imidazole (3.47 g, 51.0 mmol) and t-butyldimethylsilyl chloride (3.84 g, 25.5 mmol) were added to a solution of ethyl vanillate (5.0 g, 25.5 mmol) in N,N-dimethylformamide (50 mL) at room temperature, and the mixture was stirred at room temperature for three hours. The reaction solution was extracted with ethyl acetate. The organic layer was washed with a saturated aqueous sodium bicarbonate solution and water, dried over anhydrous magnesium sulfate, filtered and concentrated under reduced pressure. The resulting residue was purified by silica gel chromatography (hexane only to hexane:ethyl acetate=10:1) to give the title compound (7.90 g, 100%).

$^1$H-NMR (chloroform-d): 0.18 (s, 6H), 1.00 (s, 9H), 1.38 (t, 3H, J=7.1 Hz), 3.86 (s, 3H), 4.34 (q, 2H, J=7.1 Hz), 6.85 (d, 1H, J=7.9 Hz), 7.52-7.60 (m, 2H).

(2) Synthesis of 3-[4-(t-butyl-dimethyl-silanyloxy)-3-methoxy-phenyl]-pentan-3-ol

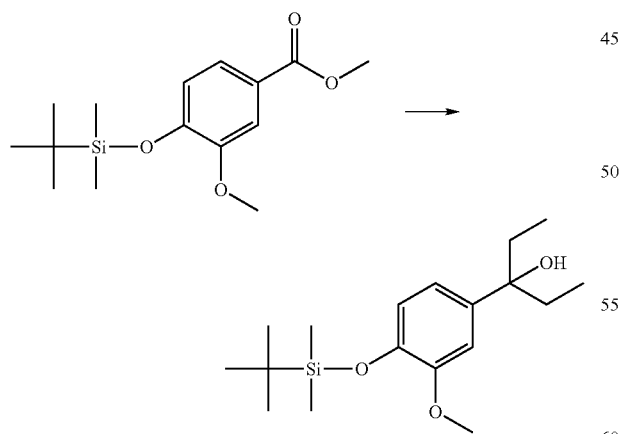

Ethylmagnesium bromide (solution in diethyl ether, 25.5 mL, 77.4 mmol) was added to a solution of 4-(t-butyl-dimethyl-silanyloxy)-3-methoxy-benzoic acid methyl ester (Example 176-(1); 7.9 g, 25.5 mmol) in tetrahydrofuran (50 mL) at room temperature, and the mixture was stirred at room temperature for 16 hours. The reaction mixture was poured into a saturated aqueous ammonium chloride solution, followed by extraction with ethyl acetate. The organic layer was dried over anhydrous magnesium sulfate, filtered and concentrated under reduced pressure. The residue was purified by silica gel chromatography (hexane only to hexane:ethyl acetate=10:1) to give the title compound (8.05 g, 98%).

$^1$H-NMR (chloroform-d): 0.15 (s, 6H), 0.76 (t, 6H, J=7.4 Hz), 1.75-1.85 (m, 4H), 3.81 (s, 3H), 6.72-6.93 (m, 3H).

(3) Synthesis of 4-(1-ethyl-1-hydroxy-propyl)-2-methoxy-phenol

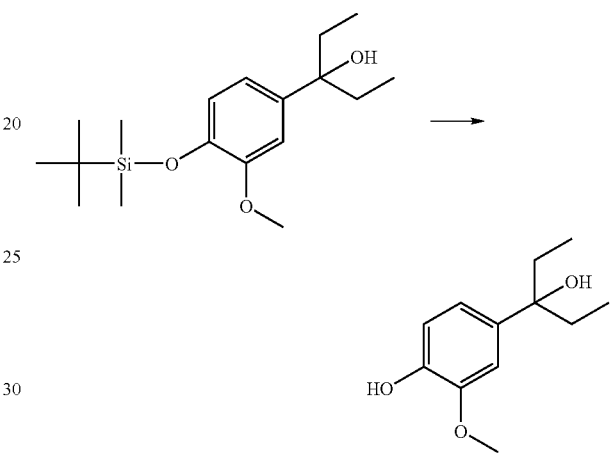

A 1 M solution of tetrabutylammonium fluoride in tetrahydrofuran (24.7 mL, 24.7 mmol) was added to a solution of 3-[4-(t-butyl-dimethyl-silanyloxy)-3-methoxy-phenyl]-pentan-3-ol (Example 176-(2); 8.0 g, 24.7 mmol) in tetrahydrofuran (30 mL) at room temperature, and the mixture was stirred at room temperature for 30 minutes. The reaction solution was diluted with ethyl acetate. The organic layer was washed with a saturated aqueous sodium bicarbonate solution and water, dried over anhydrous magnesium sulfate, filtered and concentrated under reduced pressure. The resulting residue was purified by silica gel chromatography (hexane only to hexane:ethyl acetate=1:1) to give the title compound (4.25 g, 83%).

$^1$H-NMR (chloroform-d): 0.77 (t, 6H, J=7.4 Hz), 1.73-1.88 (m, 4H), 3.90 (s, 3H), 5.52 (s, 1H), 6.79-6.98 (m, 3H).

(4) Synthesis of Trifluoromethanesulfonic Acid 4-[1-ethyl-1-(4-hydroxy-3-methyl-phenyl)-propyl]-2-methoxy-phenyl Ester

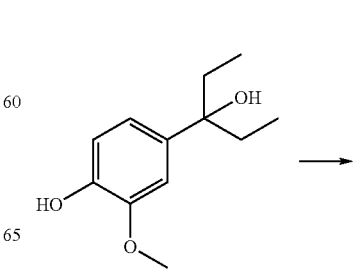

-continued

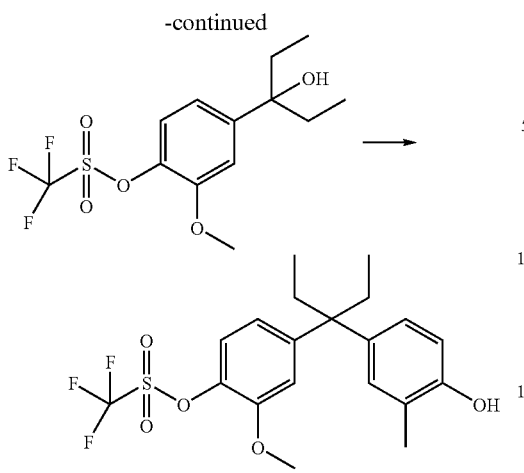

Trifluoromethanesulfonic anhydride (0.8 mL, 4.76 mmol) was added to a solution of 4-(1-ethyl-1-hydroxy-propyl)-2-methoxy-phenol (Example 176-(3); 1.0 g, 4.76 mmol) in pyridine (4 mL) at room temperature, and the mixture was stirred at room temperature for one hour. The reaction solution was extracted with ethyl acetate. The organic layer was washed with 1 N hydrochloric acid aqueous solution and brine, dried over anhydrous magnesium sulfate, filtered and concentrated under reduced pressure. The resulting residue was purified by silica gel chromatography (hexane only to hexane:ethyl acetate=1:1) to give trifluoromethanesulfonic acid 4-(1-ethyl-1-hydroxy-propyl)-2-methoxy-phenyl ester (1.51 g, 93%). Trifluoroacetic acid (0.1 mL) was added to a mixture of trifluoromethanesulfonic acid 4-(1-ethyl-1-hydroxy-propyl)-2-methoxy-phenyl ester (100 mg, 0.292 mmol) with o-cresol (68.2 mg, 585 mmol) at room temperature, and the mixture was stirred at room temperature for 16 hours. The mixture was concentrated under reduced pressure. Then, the resulting residue was purified by silica gel chromatography (hexane only to hexane:ethyl acetate=4:1) to give the title compound (0.12 g, 95%).

$^1$H-NMR (chloroform-d): 0.61 (t, 6H, J=7.2 Hz), 2.04 (q, 4H, J=7.2 Hz), 2.20 (s, 3H), 3.79 (s, 3H), 6.50-7.09 (m, 6H).

(5) Synthesis of 4-{1-ethyl-1-[3-methoxy-4-(4,4,5,5-tetramethyl-[1,3,2]dioxaborolan-2-yl)-phenyl]-propyl}-2-methyl-phenol

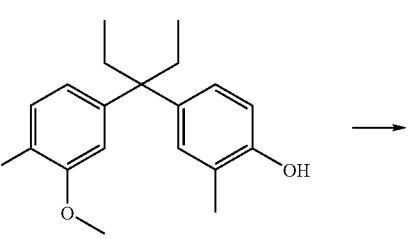

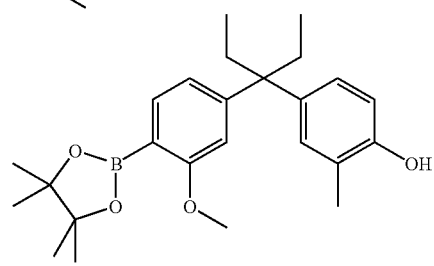

The title compound (39%) was obtained by the same method as in Example 28-(1) using trifluoro-methanesulfonic acid 4-[1-ethyl-1-(4-hydroxy-3-methyl-phenyl)-propyl]-2-methoxy-phenyl ester (Example 176-(4)) as a starting material.

$^1$H-NMR (chloroform-d): 0.60 (t, 6H, J=7.3 Hz), 1.36 (s, 12H), 2.03 (q, 4H, J=7.3 Hz), 2.20 (s, 3H), 3.64 (s, 3H), 5.23 (s, 1H), 6.58-6.88 (m, 5H), 7.56 (d, 1H, J=7.8 Hz).

(6) Synthesis of {4'-[1-ethyl-1-(4-hydroxy-3-methyl-phenyl)-propyl]-2'-methoxy-biphenyl-4-yl}-acetic Acid Methyl Ester

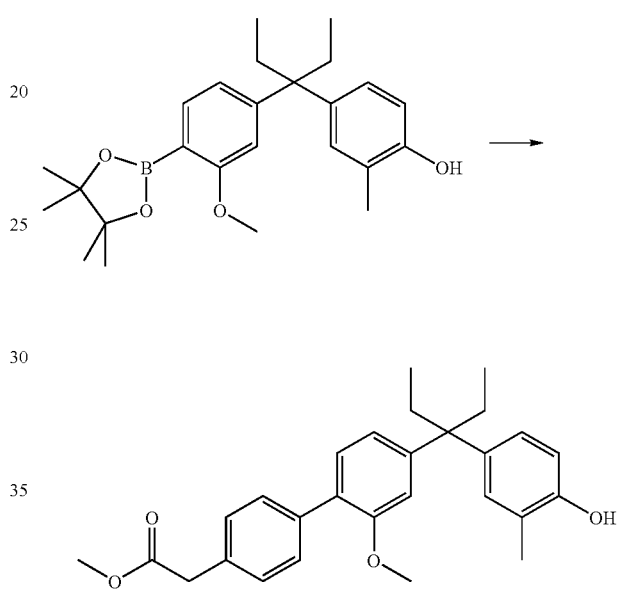

The title compound (79%) was obtained by the same method as in Example 66-(1) using 4-{1-ethyl-1-[3-methoxy-4-(4,4,5,5-tetramethyl-[1,3,2]dioxaborolan-2-yl)-phenyl]-propyl}-2-methyl-phenol (Example 176-(5)) and (4-bromo-phenyl)-acetic acid methyl ester (Tetrahedron Letters, 44 (2003), 331-334) as starting materials.

$^1$H-NMR (chloroform-d): 0.65 (t, 6H, J=7.2 Hz), 2.03-2.10 (m, 4H), 2.20 (s, 3H), 3.61-3.72 (m, 8H), 4.86 (s, 1H), 6.61-6.98 (m, 6H), 7.13-7.30 (m, 3H), 7.47-7.51 (m, 1H).

(7) Synthesis of {4'-[1-ethyl-1-(3-methyl-4-trifluoromethanesulfonyloxy-phenyl)-propyl]-2'-methoxy-biphenyl-4-yl}-acetic Acid Methyl Ester

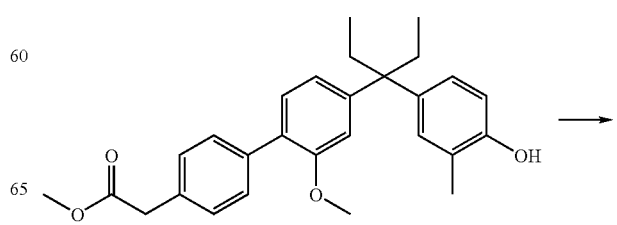

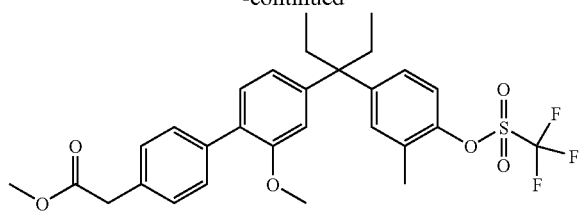

The title compound (79%) was obtained by the same method as in Example 26-(3) using {4'-[1-ethyl-1-(4-hydroxy-3-methyl-phenyl)-propyl]-2'-methoxy-biphenyl-4-yl}-acetic acid methyl ester (Example 176-(6)) as a starting material.

$^1$H-NMR (chloroform-d): 0.66 (t, 6H, J=7.2 Hz), 2.09 (q, 4H, J=7.2 Hz), 2.34 (s, 3H), 3.65 (s, 2H), 3.68 (s, 3H), 3.71 (s, 3H), 6.67-6.68 (m, 1H), 6.78-6.85 (m, 1H), 7.10-7.50 (m, 8H).

(8) Synthesis of {4'-[1-ethyl-1-(3-methyl-4-trifluoromethanesulfonyloxy-phenyl)-propyl]-2'-hydroxy-biphenyl-4-yl}-acetic Acid Methyl Ester

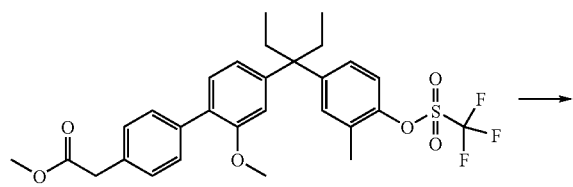

A 1 M solution of boron tribromide in dichloromethane (0.15 mL, 0.15 mmol) was added to a solution of {4'-[1-ethyl-1-(3-methyl-4-trifluoromethanesulfonyloxy-phenyl)-propyl]-2'-methoxy-biphenyl-4-yl}-acetic acid methyl ester (Example 176-(7); 20 mg, 0.0366 mmol) in dichloromethane (0.2 mL) at −78° C., and the mixture was stirred at −78° C. for 30 minutes. The reaction mixture was poured into a saturated aqueous sodium bicarbonate solution, followed by extraction with ethyl acetate. The organic layer was dried over anhydrous magnesium sulfate, filtered and concentrated under reduced pressure. The residue was purified by silica gel chromatography (hexane only to hexane:ethyl acetate=3:1) to give the title compound (10.8 mg, 55%).

$^1$H-NMR (chloroform-d): 0.64 (t, 6H, J=7.2 Hz), 2.09 (q, 4H, J=7.2 Hz), 2.34 (s, 3H), 3.67 (s, 2H), 3.71 (s, 3H), 5.14 (brs, 1H), 6.70-6.80 (m, 2H), 7.08-7.14 (m, 4H), 7.38-7.43 (m, 4H); MS (ESI+): 568 ([M+NH$_4$]$^+$).

(9) Synthesis of (4'-{1-ethyl-1-[4-(3-hydroxy-4,4-dimethyl-1-pentynyl)-3-methyl-phenyl]-propyl}-2'-hydroxy-biphenyl-4-yl)-acetic Acid Methyl Ester

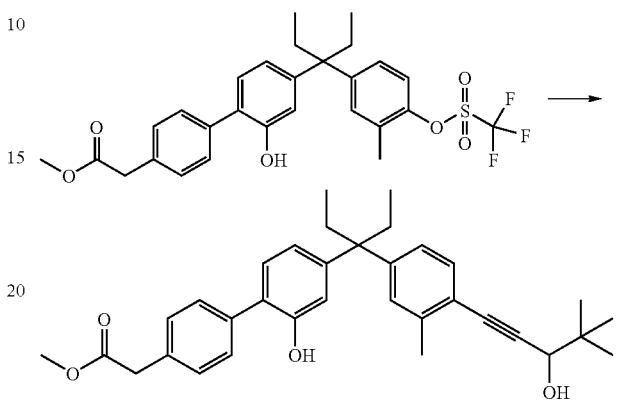

The title compound (60%) was obtained by the same method as in Example 35-(1) using {4'-[1-ethyl-1-(3-methyl-4-trifluoromethanesulfonyloxy-phenyl)-propyl]-2'-hydroxy-biphenyl-4-yl}-acetic acid methyl ester (Example 176-(8)) and 4,4-dimethyl-pent-1-yn-3-ol as starting materials.

$^1$H-NMR (chloroform-d): 0.65 (t, 6H, J=7.2 Hz), 1.01 (s, 9H), 2.09 (q, 4H, J=7.2 Hz), 2.40 (s, 3H), 3.67 (s, 2H), 3.72 (s, 3H), 5.10 (s, 1H), 6.70-6.80 (m, 2H), 6.95-7.13 (m, 3H), 7.25-7.45 (m, 5H); MS (ESI+): 530 ([M+NH$_4$]$^+$).

(10) Synthesis of (4'-{1-ethyl-1-[4-(3-hydroxy-4,4-dimethyl-pentyl)-3-methyl-phenyl]-propyl}-2'-hydroxy-biphenyl-4-yl)-acetic Acid Methyl Ester

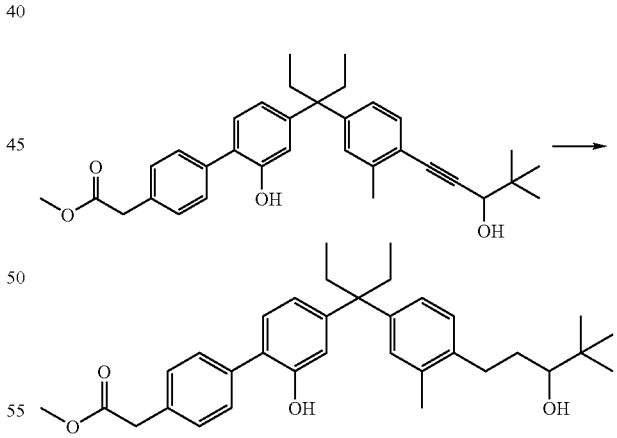

The title compound (60%) was obtained by the same method as in Example 27-(2) using (4'-{1-ethyl-1-[4-(3-hydroxy-4,4-dimethyl-1-pentynyl)-3-methyl-phenyl]-propyl}-2'-hydroxy-biphenyl-4-yl)-acetic acid methyl ester (Example 176-(9)) as a starting material.

$^1$H-NMR (chloroform-d): 0.65 (t, 6H, J=7.2 Hz), 0.90 (s, 9H), 2.08 (q, 4H, J=7.2 Hz), 2.27 (s, 3H), 2.48-2.60 (m, 1H), 2.80-2.90 (m, 1H), 3.22-3.30 (m, 1H), 3.67 (s, 2H), 3.72 (s, 3H), 5.12 (brs, 1H), 6.77-7.46 (m, 10H); MS (ESI+): 534 ([M+NH$_4$]$^+$).

(11) Synthesis of (4'-{1-ethyl-1-[4-(3-hydroxy-4,4-dimethyl-pentyl)-3-methyl-phenyl]-propyl}-2'-hydroxy-biphenyl-4-yl)-acetic Acid

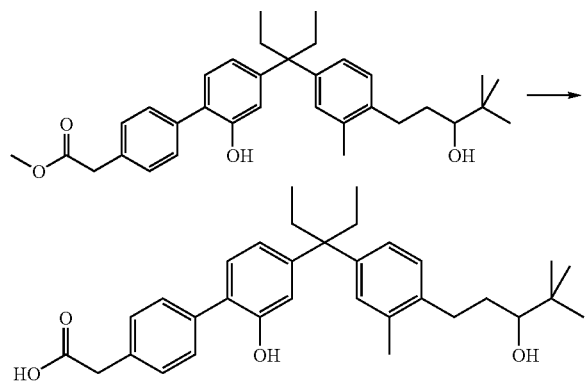

The title compound (71%) was obtained by the same method as in Example 46-(2) using (4'-{1-ethyl-1-[4-(3-hydroxy-4,4-dimethyl-pentyl)-3-methyl-phenyl]-propyl}-2'-hydroxy-biphenyl-4-yl)-acetic acid methyl ester (Example 176-(10)) as a starting material.

$^1$H-NMR (chloroform-d): 0.65 (t, 6H, J=7.2 Hz), 0.89 (s, 9H), 1.43-1.60 (m, 1H), 1.67-1.86 (m, 1H), 2.09 (q, 4H, J=7.2 Hz), 2.27 (s, 3H), 2.50-2.63 (m, 1H), 2.80-2.90 (m, 1H), 3.22-3.29 (m, 1H), 3.69 (s, 2H), 6.78-7.48 (m, 10H);

MS (ESI+): 520 ([M+NH$_4$]$^+$).

Example 177

Synthesis of (4'-{1-ethyl-1-[4-((E)-3-ethyl-3-hydroxy-1-pentenyl)-3-methyl-phenyl]-propyl}-6-methoxy-2'-methyl-biphenyl-3-yl)-acetic Acid

(1) Synthesis of (4'-{1-ethyl-1-[4-((E)-3-ethyl-3-hydroxy-1-pentenyl)-3-methyl-phenyl]-propyl}-6-methoxy-2'-methyl-biphenyl-3-yl)-acetic Acid Methyl Ester

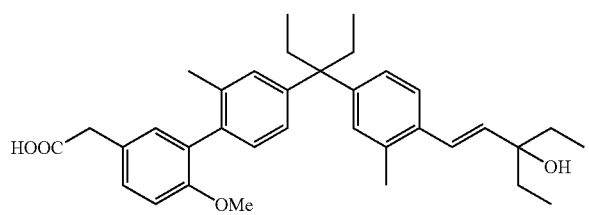

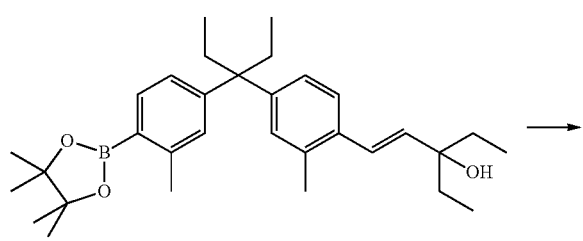

-continued

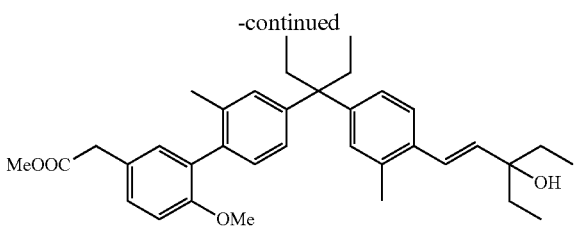

(3-Bromo-4-methoxy-phenyl)-acetic acid methyl ester (Example 175-(1); 42 mg, 0.162 mmol), palladium acetate (2.5 mg, 0.011 mmol), 2-dicyclohexylphosphino-2',6'-dimethoxy-1,1'-biphenyl (9.0 mg, 0.022 mmol), potassium phosphate (69 mg, 0.324 mmol) and water (0.2 mL) were added to a solution of (E)-3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-penten-3-ol (Example 28; 53 mg, 0.108 mmol) in toluene (2 mL). After replacement with nitrogen, the mixture was stirred at 100° C. for two hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (35.0 mg, 60%).

$^1$H-NMR (chloroform-d): 0.66 (6H, t, J=7.25 Hz), 0.92 (6H, t, J=7.42 Hz), 1.64 (4H, q, J=7.42 Hz), 2.08 (3H, s), 2.11 (4H, q, J=7.25 Hz), 2.34 (3H, s), 3.58 (2H, s), 3.69 (3H, s), 3.73 (3H, s), 6.02 (1H, d, J=15.99 Hz), 6.76 (1H, d, J=15.99 Hz), 6.89 (1H, d, J=8.40 Hz), 7.00-7.06 (6H, m), 7.21 (1H, dd, J=8.40, 2.30 Hz), 7.32 (1H, d, J=8.08 Hz).

(2) Synthesis of (4'-{1-ethyl-1-[4-((E)-3-ethyl-3-hydroxy-1-pentenyl)-3-methyl-phenyl]-propyl}-6-methoxy-2'-methyl-biphenyl-3-yl)-acetic Acid

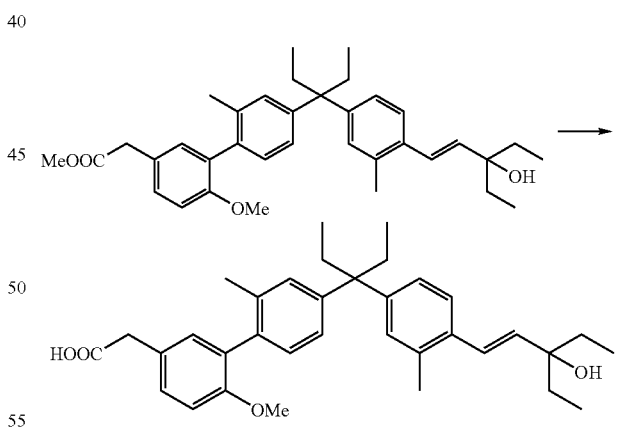

A 1 N sodium hydroxide aqueous solution (0.193 mL, 0.193 mmol) was added to a solution of (4'-{1-ethyl-1-[4-((E)-3-ethyl-3-hydroxy-1-pentenyl)-3-methyl-phenyl]-propyl}-6-methoxy-2'-methyl-biphenyl-3-yl)-acetic acid methyl ester (Example 177-(1); 35.0 mg, 0.064 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (31.0 mg, 92%).

$^1$H-NMR (chloroform-d): 0.66 (6H, t, J=7.25 Hz), 0.92 (6H, t, J=7.59 Hz), 1.64 (4H, q, J=7.59 Hz), 2.07 (3H, s), 2.11 (4H, q, J=7.42 Hz), 2.33 (3H, s), 3.60 (2H, s), 3.73 (3H, s), 6.02 (1H, d, J=15.99 Hz), 6.75 (1H, d, J=15.99 Hz), 6.89 (1H, d, J=8.41 Hz), 6.99-7.06 (6H, m), 7.22 (1H, dd, J=8.41, 2.31 Hz), 7.32 (1H, d, J=8.25 Hz); MS (ESI+): 511 ([M–H$_2$O+H]$^+$).

Example 178

Synthesis of (4'-{1-ethyl-1-[4-((E)-3-ethyl-3-hydroxy-1-pentenyl)-3-methyl-phenyl]-propyl}-6-hydroxy-5-methoxy-biphenyl-3-yl)-acetic Acid

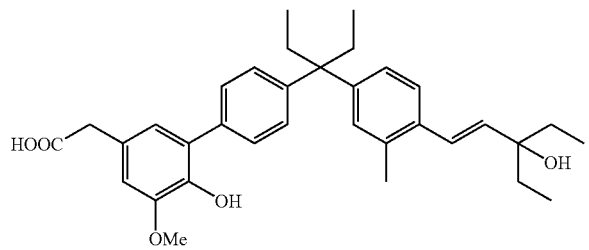

(1) Synthesis of (3-bromo-4-hydroxy-5-methoxy-phenyl)-acetic Acid Methyl Ester

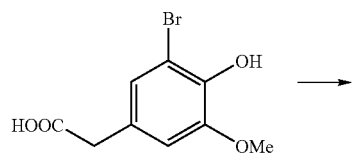

Trimethylsilyldiazomethane (2 M solution in diethyl ether, 0.409 mL, 0.818 mmol) was added to a solution of (3-bromo-4-hydroxy-5-methoxy-phenyl)-acetic acid (150 mg, 0.575 mmol) in methanol (1 mL) and toluene (4 mL), and the mixture was stirred at room temperature for 30 minutes. Acetic acid was added to the reaction mixture to terminate the reaction, and then the mixture was concentrated under reduced pressure to give the target compound as a colorless oil (158 mg, 99%).

$^1$H-NMR (chloroform-d): 3.52 (2H, s), 3.70 (3H, s), 3.89 (3H, s), 6.75 (1H, d, J=1.82 Hz), 7.01 (1H, d, J=1.81 Hz).

(2) Synthesis of [3-bromo-4-(t-butyl-dimethyl-silanyloxy)-5-methoxy-phenyl]-acetic Acid Methyl Ester

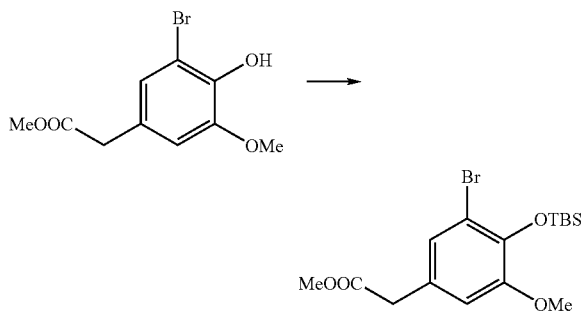

Trifluoromethanesulfonic acid t-butyldimethylsilyl ester (0.159 mL, 0.690 mmol) and triethylamine (0.120 mL, 0.863 mmol) were added to a solution of (3-bromo-4-hydroxy-5-methoxy-phenyl)-acetic acid methyl ester (158 mg, 0.574 mmol) in dichloromethane (4 mL), and the mixture was stirred at room temperature for one hour. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=100:0 to 50:50) to give the target compound as a colorless oil (203 mg, 91%).

$^1$H-NMR (chloroform-d): 0.20 (6H, s), 1.03 (9H, s), 3.51 (2H, s), 3.70 (3H, s), 3.78 (3H, s), 6.71 (1H, d, J=1.98 Hz), 7.02 (1H, d, J=1.98 Hz).

(3) Synthesis of (4'-{1-ethyl-1-[4-((E)-3-ethyl-3-hydroxy-1-pentenyl)-3-methyl-phenyl]-propyl}-6-hydroxy-5-methoxy-biphenyl-3-yl)-acetic Acid Methyl Ester

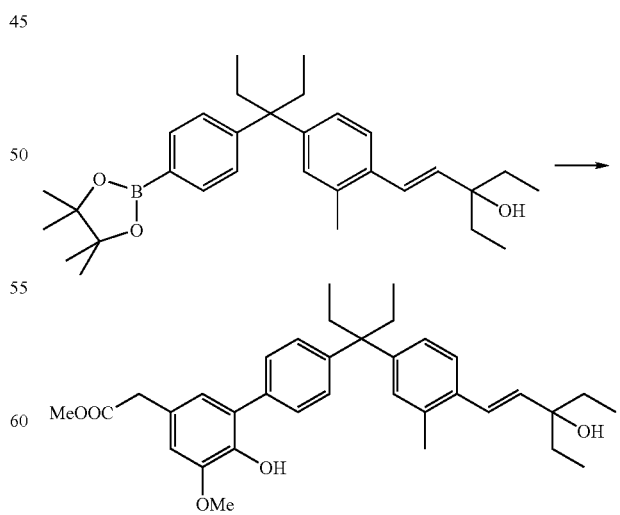

[3-Bromo-4-(t-butyldimethyl-silanyloxy)-5-methoxy-phenyl]-acetic acid methyl ester (Example 178-(2); 61 mg, 0.156 mmol), palladium acetate (2.2 mg, 0.010 mmol), 2-dicyclohexylphosphino-2',6'-dimethoxy-1,1'-biphenyl (8.6 mg, 0.021 mmol), potassium phosphate (66 mg, 0.312 mmol) and water (0.2 mL) were added to a solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 49.7 mg, 0.104 mmol) in toluene (2 mL). After replacement with nitrogen, the mixture was stirred at 100° C. for 1.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (22.1 mg, 39%).

¹H-NMR (chloroform-d): 0.66 (6H, t, J=7.42 Hz), 0.92 (6H, t, J=7.42 Hz), 1.64 (4H, q, J=7.42 Hz), 2.10 (4H, q, J=7.25 Hz), 2.31 (3H, s), 3.57 (2H, s), 3.69 (3H, s), 3.82 (3H, s), 6.01 (1H, d, J=15.99 Hz), 6.65-6.79 (3H, m), 6.95-7.00 (2H, m), 7.16 (2H, d, J=8.24 Hz), 7.31 (1H, d, J=8.08 Hz), 7.35 (2H, d, J=8.25 Hz).

(4) Synthesis of (4'-{1-ethyl-1-[4-((E)-3-ethyl-3-hydroxy-1-pentenyl)-3-methyl-phenyl]-propyl}-6-hydroxy-5-methoxy-biphenyl-3-yl)-acetic Acid

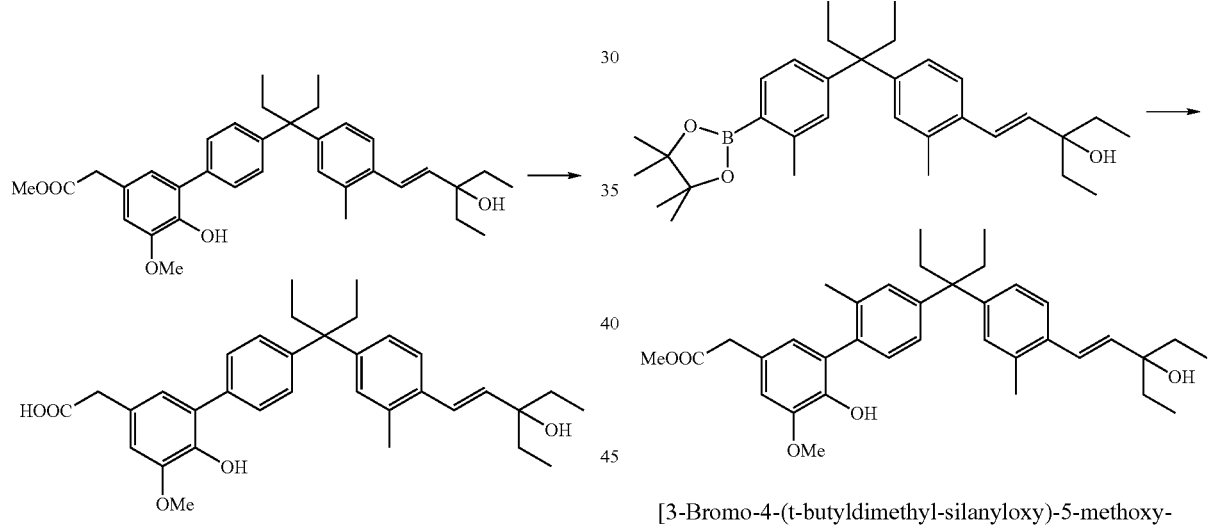

A 1 N sodium hydroxide aqueous solution (0.203 mL, 0.203 mmol) was added to a solution of (4'-{1-ethyl-1-[4-((E)-3-ethyl-3-hydroxy-1-pentenyl)-3-methyl-phenyl]-propyl}-6-hydroxy-5-methoxy-biphenyl-3-yl)-acetic acid methyl ester (Example 178-(3); 22.1 mg, 0.041 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (1.3 mg, 6%).

¹H-NMR (chloroform-d): 0.65 (6H, t, J=7.42 Hz), 0.92 (6H, t, J=7.58 Hz), 1.64 (4H, q, J=7.64 Hz), 2.12 (4H, q, J=7.26 Hz), 2.32 (3H, s), 3.61 (2H, s), 3.93 (3H, s), 6.01 (1H, d, J=16.00 Hz), 6.72-6.78 (2H, m), 6.89 (1H, d, J=1.98 Hz), 6.97-7.03 (2H, m), 7.22 (2H, d, J=8.41 Hz), 7.31 (1H, d, J=8.74 Hz), 7.49 (2H, d, J=8.57 Hz); MS (ESI+): 513 ([M−H₂O+H]⁺).

Example 179

Synthesis of (4'-{1-ethyl-1-[4-((E)-3-ethyl-3-hydroxy-1-pentenyl)-3-methyl-phenyl]-propyl}-6-hydroxy-5-methoxy-2'-methyl-biphenyl-3-yl)-acetic Acid

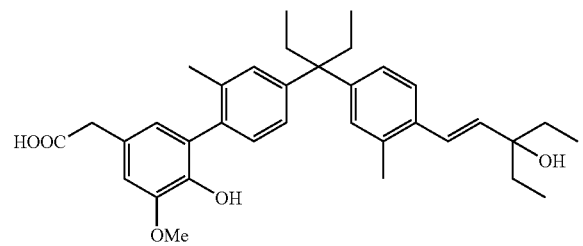

(1) Synthesis of (4'-{1-ethyl-1-[4-(3-ethyl-3-hydroxy-1-pentenyl)-3-methyl-phenyl]-propyl}-6-hydroxy-5-methoxy-2'-methyl-biphenyl-3-yl)-acetic Acid Methyl Ester

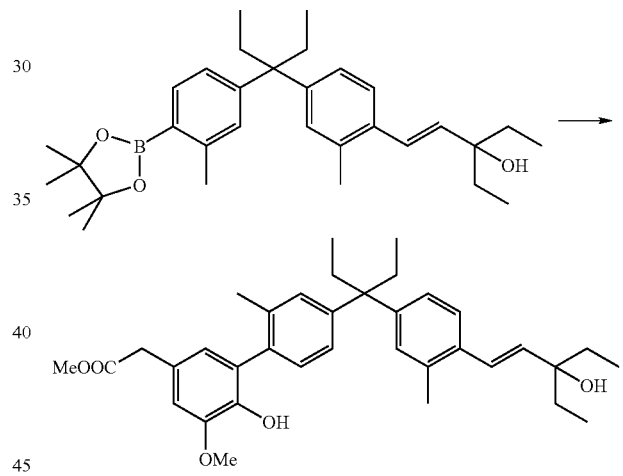

[3-Bromo-4-(t-butyldimethyl-silanyloxy)-5-methoxyphenyl]-acetic acid methyl ester (Example 178-(2); 68 mg, 0.176 mmol), palladium acetate (2.7 mg, 0.012 mmol), 2-dicyclohexylphosphino-2',6'-dimethoxy-1,1'-biphenyl (9.9 mg, 0.024 mmol), potassium phosphate (75 mg, 0.351 mmol) and water (0.2 mL) were added to a solution of (E)-3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-penten-3-ol (Example 28; 57.2 mg, 0.117 mmol) in toluene (2 mL). After replacement with nitrogen, the mixture was stirred at 100° C. for 1.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=4:1) to give the target compound as a colorless oil (33.6 mg, 51%).

¹H-NMR (chloroform-d): 0.65 (6H, t, J=7.25 Hz), 0.92 (6H, t, J=7.42 Hz), 1.64 (4H, q, J=7.58 Hz), 2.05-2.11 (7H, m), 2.32 (3H, s), 3.55 (2H, s), 3.69 (3H, s), 3.81 (3H, s), 6.02 (1H, d, J=15.99 Hz), 6.64-6.78 (3H, m), 6.94-7.05 (5H, m), 7.30 (1H, d, J=8.08 Hz).

(2) Synthesis of (4'-{1-ethyl-1-[4-((E)-3-ethyl-3-hydroxy-1-pentenyl)-3-methyl-phenyl]-propyl}-6-hydroxy-5-methoxy-2'-methyl-biphenyl-3-yl)-acetic Acid

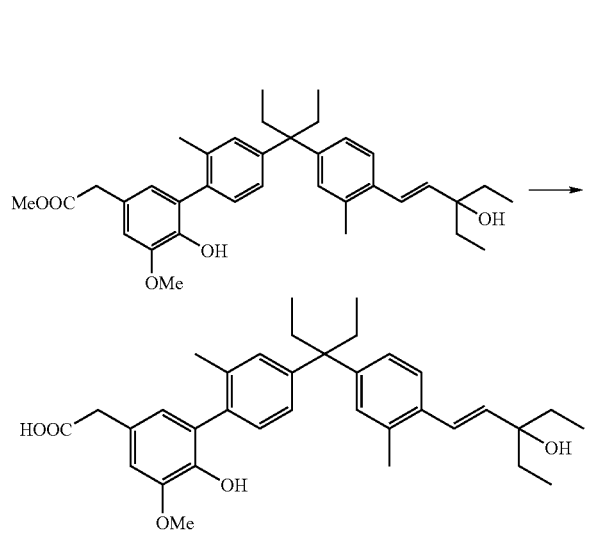

A 1 N sodium hydroxide aqueous solution (0.301 mL, 0.301 mmol) was added to a solution of (4'-{1-ethyl-1-[4-((E)-3-ethyl-3-hydroxy-1-pentenyl)-3-methyl-phenyl]-propyl}-6-hydroxy-5-methoxy-2'-methyl-biphenyl-3-yl)-acetic acid methyl ester (Example 179-(1); 33.6 mg, 0.050 mmol) in methanol-tetrahydrofuran (1:1, 4 mL), and the mixture was stirred at room temperature overnight. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (3.4 mg, 10%).

$^1$H-NMR (chloroform-d): 0.65 (6H, t, J=7.25 Hz), 0.92 (6H, t, J=7.25 Hz), 1.64 (4H, q, J=7.58 Hz), 2.07-2.15 (7H, m), 2.33 (3H, s), 3.59 (2H, s), 3.92 (3H, s), 6.02 (1H, d, J=15.99 Hz), 6.69 (1H, d, J=1.98 Hz), 6.75 (1H, d, J=15.99 Hz), 6.81 (1H, d, J=1.98 Hz), 6.97-7.10 (5H, m), 7.31 (1H, d, J=8.08 Hz); MS (ESI+): 527 ([M–H$_2$O+H]$^+$).

Example 180

Synthesis of (4'-{1-ethyl-1-[4-((E)-3-ethyl-3-hydroxy-1-pentenyl)-3-methyl-phenyl]-propyl}-4-methoxy-biphenyl-3-yl)-acetic Acid

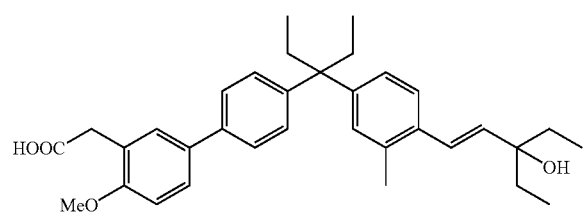

(1) Synthesis of (5-bromo-2-methoxy-phenyl)-acetic Acid Methyl Ester

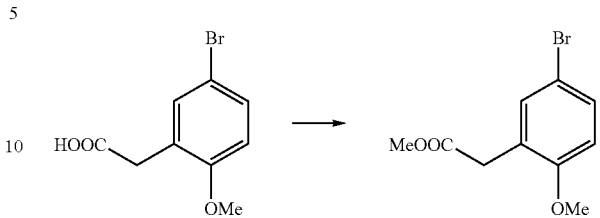

Trimethylsilyldiazomethane (2 M solution in diethyl ether, 0.306 mL, 0.612 mmol) was added to a solution of (5-bromo-2-methoxy-phenyl)-acetic acid (100 mg, 0408 mmol) in methanol (1 mL) and toluene (4 mL), and the mixture was stirred at room temperature for 30 minutes. Acetic acid was added to the reaction mixture to terminate the reaction, and then the mixture was concentrated under reduced pressure to give the target compound as a colorless oil (103.7 mg, 98%).

$^1$H-NMR (chloroform-d): 3.59 (2H, s), 3.69 (3H, s), 3.80 (3H, s), 6.74 (1H, d, J=8.73 Hz), 7.29 (1H, d, J=2.47 Hz), 7.35 (1H, dd, J=8.57, 2.48 Hz).

(2) Synthesis of (4'-{1-ethyl-1-[4-((E)-3-ethyl-3-hydroxy-1-pentenyl)-3-methyl-phenyl]-propyl}-4-methoxy-biphenyl-3-yl)-acetic Acid Methyl Ester

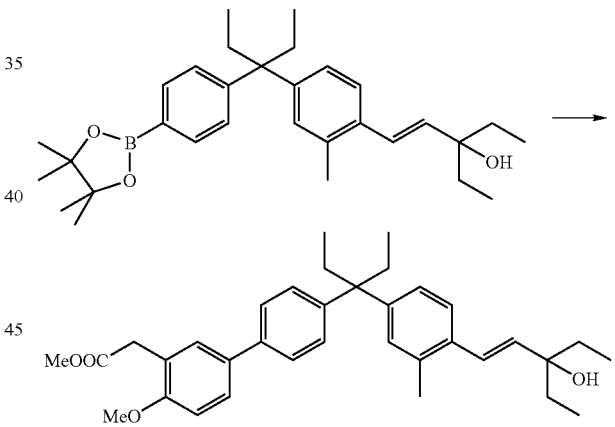

(5-Bromo-2-methoxy-phenyl)-acetic acid methyl ester (Example 180-(1); 40.5 mg, 0.156 mmol), palladium acetate (2.2 mg, 0.010 mmol), 2-dicyclohexylphosphino-2',6'-dimethoxy-1,1'-biphenyl (8.6 mg, 0.021 mmol), potassium phosphate (66 mg, 0.312 mmol) and water (0.2 mL) were added to a solution of (E)-3-ethyl-1-(4-{1-ethyl-1-[4-(4,4,5,5-tetramethyl-[1,3,2]dioxaborolan-2-yl)-phenyl]-propyl}-2-methyl-phenyl)-1-penten-3-ol (Example 39-(5); 49.7 mg, 0.104 mmol) in toluene (2 mL). After replacement with nitrogen, the mixture was stirred at 100° C. for 1.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (35.2 mg, 64%).

¹H-NMR (chloroform-d): 0.65 (6H, t, J=7.26 Hz), 0.92 (6H, t, J=7.42 Hz), 1.64 (4H, q, J=7.58 Hz), 2.12 (4H, q, J=7.25 Hz), 2.32 (3H, s), 3.68 (2H, s), 3.69 (3H, s), 3.85 (3H, s), 6.01 (1H, d, J=15.99 Hz), 6.75 (1H, d, J=15.99 Hz), 6.90-7.00 (3H, m), 7.20 (2H, d, J=8.25 Hz), 7.31 (1H, d, J=8.58 Hz), 7.41-7.49 (4H, m).

(3) Synthesis of (4'-{1-ethyl-1-[4-((E)-3-ethyl-3-hydroxy-1-pentenyl)-3-methyl-phenyl]-propyl}-4-methoxy-biphenyl-3-yl)-acetic Acid

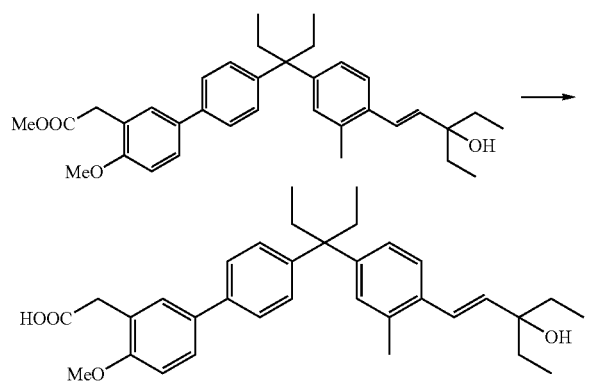

A 1 N sodium hydroxide aqueous solution (0.200 mL, 0.200 mmol) was added to a solution of (4'-{1-ethyl-1-[4-((E)-3-ethyl-3-hydroxy-1-pentenyl)-3-methyl-phenyl]-propyl}-4-methoxy-biphenyl-3-yl)-acetic acid methyl ester (Example 180-(2); 35.2 mg, 0.067 mmol) in methanol-tetrahydrofuran (1:1, 4 mL), and the mixture was stirred at 60° C. for two hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (30.1 mg, 87%).

¹H-NMR (chloroform-d): 0.65 (6H, t, J=7.41 Hz), 0.92 (6H, t, J=7.42 Hz), 1.64 (4H, q, J=7.42 Hz), 2.12 (4H, q, J=7.41 Hz), 2.32 (3H, s), 3.72 (2H, s), 3.87 (3H, s), 6.01 (1H, d, J=15.83 Hz), 6.75 (1H, d, J=16.00 Hz), 6.92-6.99 (3H, m), 7.20 (2H, d, J=8.41 Hz), 7.31 (1H, d, J=8.74 Hz), 7.40-7.43 (3H, m), 7.49 (1H, dd, J=8.41, 2.31 Hz); MS (ESI+): 497 ([M−H₂O+H]⁺).

Example 181

Synthesis of (4'-{1-ethyl-1-[4-((E)-3-ethyl-3-hydroxy-1-pentenyl)-3-methyl-phenyl]-propyl}-4-methoxy-2'-methyl-biphenyl-3-yl)-acetic Acid

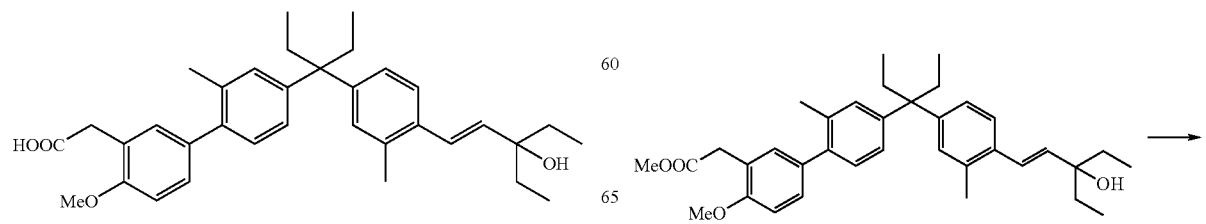

(1) Synthesis of (4'-{1-ethyl-1-[4-((E)-3-ethyl-3-hydroxy-1-pentenyl)-3-methyl-phenyl]-propyl}-4-methoxy-2'-methyl-biphenyl-3-yl)-acetic Acid Methyl Ester

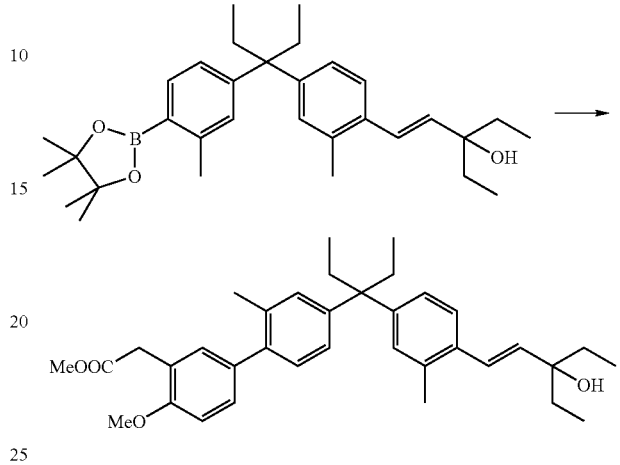

(5-Bromo-2-methoxy-phenyl)-acetic acid methyl ester (Example 180-(1); 45.1 mg, 0.174 mmol), palladium acetate (2.7 mg, 0.012 mmol), 2-dicyclohexylphosphino-2',6'-dimethoxy-1,1'-biphenyl (9.5 mg, 0.023 mmol), potassium phosphate (74 mg, 0.348 mmol) and water (0.2 mL) were added to a solution of (E)-3-ethyl-1-(4-{1-ethyl-1-[3-methyl-4-(4,4,5,5-tetramethyl-[1,3,2]dioxaborolan-2-yl)-phenyl]-propyl}-2-methyl-phenyl)-1-penten-3-ol (Example 28; 56.7 mg, 0.116 mmol) in toluene (2 mL). After replacement with nitrogen, the mixture was stirred at 100° C. for 1.5 hours. The reaction mixture was then poured into a saturated aqueous sodium bicarbonate solution, followed by extraction with dichloromethane. The organic layer was dried over anhydrous magnesium sulfate, filtered and concentrated under reduced pressure. The resulting residue was purified by silica gel chromatography (hexane:ethyl acetate=2:1) to give the target compound as a colorless oil (54.7 mg, 87%).

¹H-NMR (chloroform-d): 0.65 (6H, t, J=7.42 Hz), 0.92 (6H, t, J=7.42 Hz), 1.64 (4H, q, J=7.42 Hz), 2.11 (4H, q, J=7.42 Hz), 2.23 (3H, s), 2.33 (3H, s), 3.66 (2H, s), 3.69 (3H, s), 3.85 (3H, s), 6.02 (1H, d, J=15.99 Hz), 6.76 (1H, d, J=16.16 Hz), 6.89 (1H, d, J=8.41 Hz), 6.99-7.10 (5H, m), 7.16 (1H, d, J=2.15 Hz), 7.22 (1H, dd, J=8.25, 2.15 Hz), 7.32 (1H, d, J=8.74 Hz).

(2) Synthesis of (4'-{1-ethyl-1-[4-((E)-3-ethyl-3-hydroxy-1-pentenyl)-3-methyl-phenyl]-propyl}-4-methoxy-2'-methyl-biphenyl-3-yl)-acetic Acid

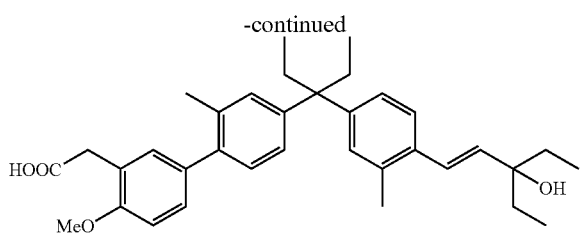

A 1 N sodium hydroxide aqueous solution (0.303 mL, 0.303 mmol) was added to a solution of (4'-{1-ethyl-1-[4-((E)-3-ethyl-3-hydroxy-1-pentenyl)-3-methyl-phenyl]-propyl}-4-methoxy-2'-methyl-biphenyl-3-yl)-acetic acid methyl ester (Example 181-(1); 54.7 mg, 0.101 mmol) in methanol-tetrahydrofuran (1:1, 4 mL), and the mixture was stirred at 60° C. for two hours. The reaction mixture was then poured into a saturated aqueous ammonium chloride solution, followed by extraction with dichloromethane. The organic layer was dried over anhydrous magnesium sulfate, filtered and concentrated under reduced pressure. The resulting residue was purified by silica gel chromatography (chloroform:methanol=10:1) to give the target compound as a colorless oil (41.9 mg, 78%).

$^1$H-NMR (chloroform-d): 0.65 (6H, t, J=7.25 Hz), 0.92 (6H, t, J=7.59 Hz), 1.64 (4H, q, J=7.64 Hz), 2.11 (4H, q, J=7.42 Hz), 2.22 (3H, s), 2.33 (3H, s), 3.69 (2H, s), 3.86 (3H, s), 6.02 (1H, d, J=15.99 Hz), 6.75 (1H, d, J=15.99 Hz), 6.91 (1H, d, J=8.57 Hz), 6.97-7.09 (5H, m), 7.17 (1H, d, J=2.14 Hz), 7.23 (1H, dd, J=8.41, 2.14 Hz), 7.31 (1H, d, J=8.74 Hz); MS (ESI+): 511 ([M–H$_2$O+H]$^+$).

Example 182

Synthesis of [6-(4-{1-ethyl-1-[4-(3-hydroxy-4,4-dimethyl-pentyl)-3-methyl-phenyl]-propyl}-2-methyl-phenyl)-pyridazin-4-yl]-acetic Acid Ethyl Ester

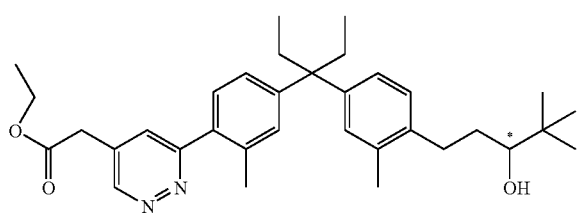

(1) Synthesis of (6-hydroxy-3-oxo-2,3-dihydro-pyridazin-4-yl)-acetic Acid

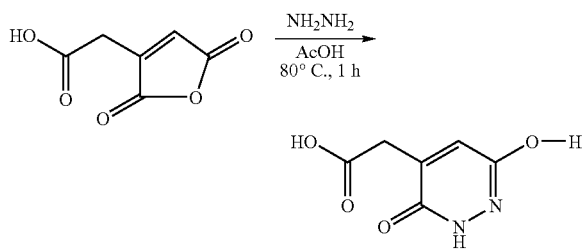

A solution of hydrazine (103 mg, 3.21 mmol) in acetic acid (16 mL) was added to (2,5-dioxo-2,5-dihydro-furan-3-yl)acetic acid (500 mg, 3.04 mmol) under cooling with ice, and the mixture was heated with stirring at an external temperature of 76 to 84° C. for one hour. The reaction mixture was concentrated under reduced pressure. The resulting solid was sequentially washed with water, ethanol and ether to give the title compound (414 mg, 80%).

$^1$H-NMR (methanol-d4): 3.55 (d, 2H, J=0.9 Hz), 7.01 (s, 1H); MS (ESI–): 169 ([M–H]$^-$); MS (ESI+): 171 ([M+H]$^+$).

(2) Synthesis of (6-hydroxy-3-oxo-2,3-dihydro-pyridazin-4-yl)-acetic Acid Ethyl Ester

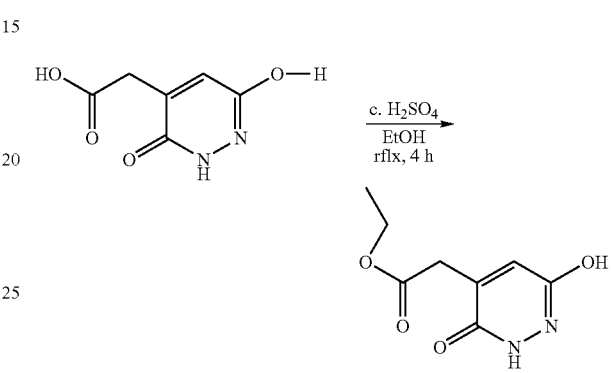

Concentrated sulfuric acid (0.04 mL, 0.75 mmol) was added to a solution of (6-hydroxy-3-oxo-2,3-dihydro-pyridazin-4-yl)-acetic acid (Example 182-(1); 259 mg, 1.52 mmol) in ethanol (3.2 mL), and the mixture was heated while stirring at an external temperature of 84 to 92° C. for four hours. The mixture was left to stand at room temperature overnight. Then, the resulting solid was collected by filtration and sequentially washed with water and ether to give the title compound (246 mg, 82%).

$^1$H-NMR (methanol-d4): 1.25 (t, 3H, J=7.1 Hz), 3.56 (d, 2H, J=0.9 Hz), 4.16 (q, 2H, J=7.1 Hz), 7.01 (s, 1H).

(3) Synthesis of (3,6-dichloro-pyridazin-4-yl)-acetic Acid Ethyl Ester

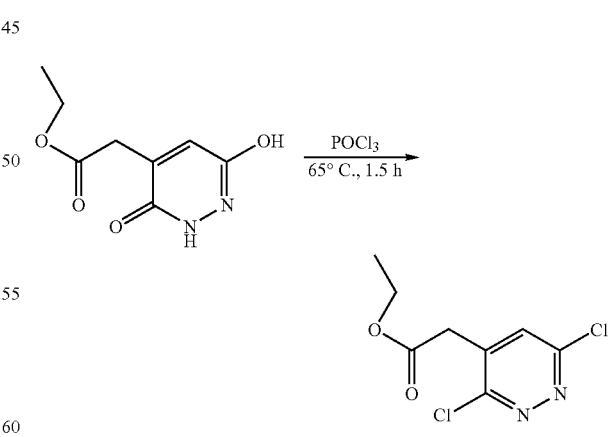

Phosphoryl chloride (0.80 mL, 8.6 mmol) was added to (6-hydroxy-3-oxo-2,3-dihydro-pyridazin-4-yl)acetic acid ethyl ester (Example 182-(2); 59.6 mg, 0.301 mmol), and the mixture was heated while stirring at an external temperature of 60 to 70° C. for 1.5 hours. The reaction mixture was concentrated under reduced pressure. Ice water (2.7 mL) was added to the resulting residue, followed by extraction with chloroform. The extract was dried over anhydrous magnesium sulfate and then concentrated under reduced pressure. The residue was purified by silica gel chromatography (hexane/ethyl acetate=2/1) to give the title compound (51.0 mg, 72%).

$^1$H-NMR (chloroform-d): 1.30 (t, 3H, J=7.2 Hz), 3.77 (d, 2H, J=0.9 Hz), 4.24 (q, 2H, J=7.1 Hz), 7.56 (t, 1H, J=0.9 Hz).

(4) Synthesis of 2-[4-(1-{4-[3-(t-butyl-dimethylsilanyloxy)-4,4-dimethyl-pentyl]-3-methyl-phenyl}-1-ethyl-propyl)-2-methyl-phenyl]-boronic Acid

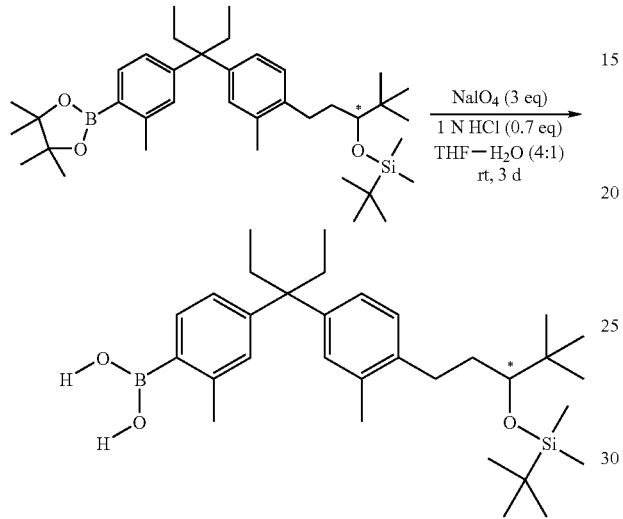

Tetrahydrofuran (5.0 mL) and water (1.1 mL) were added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 23-(1); 202 mg, 0.333 mmol) and sodium periodate (213 mg, 0.996 mmol) at room temperature, and the mixture was stirred for 2.5 hours. Then, 1 N hydrochloric acid aqueous solution (224 µl) was added, and the mixture was stirred at room temperature for 71 hours. The reaction mixture was adjusted to pH 7 with saturated aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=5/1) to give the title compound (126 mg, 72%).

$^1$H-NMR (chloroform-d): 0.08 (s, 3H), 0.12 (s, 3H), 0.65 (t, 6H, J=7.3 Hz), 0.89 (s, 9H), 0.95 (s, 9H), 1.58 (m, 1H), 1.79 (m, 1H), 2.16 (q, 4H, J=7.3 Hz), 2.26 (s, 3H), 2.44 (m, 1H), 2.76 (s, 3H), 2.78 (m, 1H), 3.35 (dd, 1H, J=6.9, 3.0 Hz), 6.90-7.13 (m, 5H), 8.08 (d, 1H, J=8.7 Hz).

(5) Synthesis of {6-[4-(1-{4-[3-(t-butyl-dimethyl-silanyloxy)-4,4-dimethyl-pentyl]-3-methyl-phenyl}-1-ethyl-propyl)-2-methyl-phenyl]-3-chloro-pyridazin-4-yl}-acetic Acid Ethyl Ester

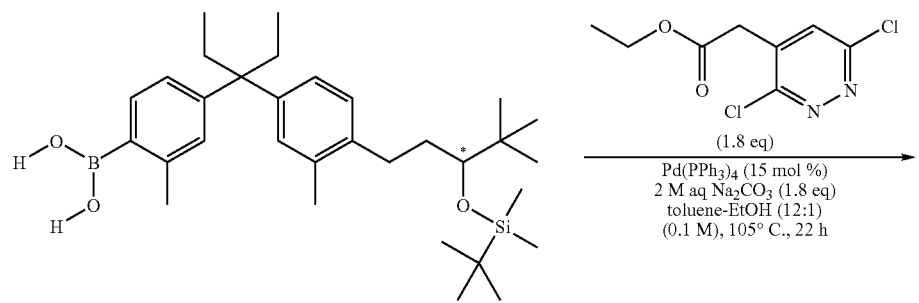

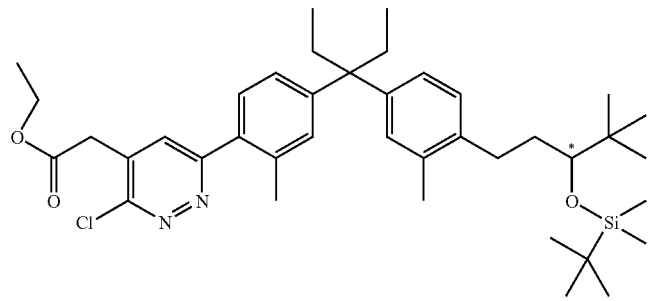

Degassed toluene (1.0 mL), ethanol (0.081 mL) and a 2 M sodium carbonate solution (0.081 mL, 0.162 mmol) were added to 2-[4-(1-{4-[3-(t-butyl-dimethylsilanyloxy)-4,4-dimethyl-pentyl]-3-methyl-phenyl}-1-ethyl-propyl)-2-methyl-phenyl]boronic acid (Example 182-(4); 49.4 mg, 0.0941 mmol), (3,6-dichloro-pyridazin-4-yl)acetic acid ethyl ester (Example 182-(3); 39.8 mg, 0.169 mmol) and tetrakis(triphenylphosphine)palladium (0) (16.0 mg, 0.0138 mmol). After replacement with nitrogen, the mixture was heated while stirring at an external temperature of 101 to 110° C. for 22 hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=15/1) to give the title compound (22.0 mg, 31%).

$^1$H-NMR (chloroform-d): 0.08 (s, 3H), 0.12 (s, 3H), 0.66 (t, 6H, J=7.2 Hz), 0.89 (s, 9H), 0.95 (s, 9H), 1.30 (t, 3H, J=7.0 Hz), 1.61 (m, 1H), 1.79 (m, 1H), 2.12 (q, 4H, J=7.2 Hz), 2.26 (s, 3H), 2.38 (s, 3H), 2.43 (m, 1H), 2.78 (m, 1H), 3.35 (dd, 1H, J=10.1, 2.7 Hz), 3.82 (s, 2H), 4.23 (q, 2H, J=7.0 Hz), 6.90-7.18 (m, 5H), 7.32 (d, 1H, J=7.8 Hz), 7.59 (s, 1H).

(6) Synthesis of {6-[4-(1-{4-[3-(t-butyl-dimethyl-silanyloxy)-4,4-dimethyl-pentyl]-3-methyl-phenyl}-1-ethyl-propyl)-2-methyl-phenyl]-pyridazin-4-yl}-acetic Acid Ethyl Ester

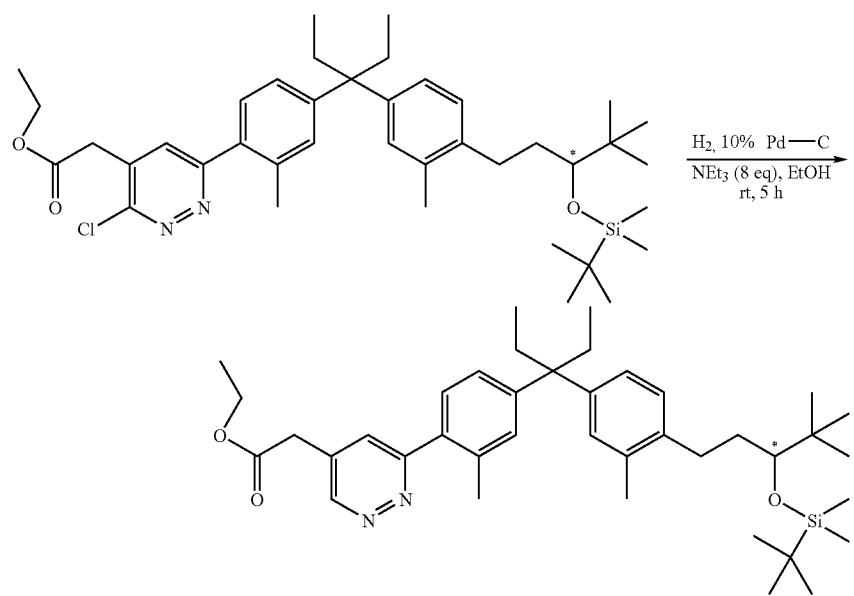

10% Pd-C (4.2 mg) and triethylamine (0.033 mL, 0.24 mmol) were added to a solution of {6-[4-(1-{4-[3-(t-butyl-dimethyl-silanyloxy)-4,4-dimethyl-pentyl]-3-methyl-phenyl}-1-ethyl-propyl)-2-methyl-phenyl]-3-chloro-pyridazin-4-yl}acetic acid ethyl ester (Example 182-(5); 10.8 mg, 0.0159 mmol) in ethanol (1.6 mL) at room temperature. After replacement with hydrogen, the mixture was stirred in a hydrogen atmosphere at room temperature for five hours. The reaction mixture was diluted with diethyl ether and filtered. The filtrate was washed with water, dried over anhydrous magnesium sulfate and then concentrated under reduced pressure. The residue was purified by silica gel chromatography (hexane/ethyl acetate=3/1) to give the title compound (10 mg, 98%).

$^1$H-NMR (chloroform-d): 0.08 (s, 3H), 0.12 (s, 3H), 0.66 (t, 6H, J=7.4 Hz), 0.89 (s, 9H), 0.95 (s, 9H), 1.29 (t, 3H, J=7.2 Hz), 1.61 (m, 1H), 1.79 (m, 1H), 2.13 (q, 4H, J=7.4 Hz), 2.26 (s, 3H), 2.37 (s, 3H), 2.43 (m, 1H), 2.78 (m, 1H), 3.35 (dd, 1H, J=8.6, 4.3 Hz), 3.69 (s, 2H), 4.22 (q, 2H, J=7.0 Hz), 6.90-7.18 (m, 5H), 7.33 (d, 1H, J=8.1 Hz), 7.56 (d, 1H, J=2.1 Hz), 9.08 (d, 1H, J=2.1 Hz).

(7) Synthesis of [6-(4-{1-ethyl-1-[4-(3-hydroxy-4,4-dimethyl-pentyl)-3-methyl-phenyl]-propyl}-2-methyl-phenyl)-pyridazin-4-yl]-acetic Acid Ethyl Ester

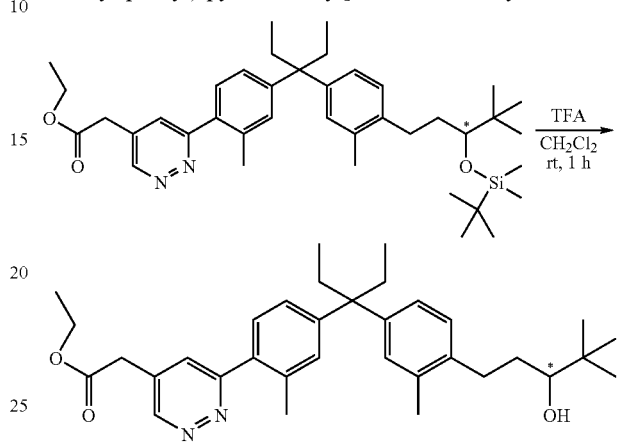

Trifluoroacetic acid (0.07 mL) was added to a solution of {6-[4-(1-{4-[3-(t-butyl-dimethyl-silanyloxy)-4,4-dimethyl-pentyl]-3-methyl-phenyl}-1-ethyl-propyl)-2-methyl-phenyl]pyridazin-4-yl}acetic acid ethyl ester (Example 182-(6); 10.0 mg, 0.0155 mmol) in dichloromethane (0.40 mL) at room temperature, and the mixture was stirred at room temperature for one hour. The solvent in the reaction solution was distilled off under reduced pressure, and the residue was diluted with diethyl ether. The mixture was adjusted to pH 7 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=2/1) to give the title compound (7.0 mg, 85%).

¹H-NMR (chloroform-d): 0.66 (t, 6H, J=7.4 Hz), 0.91 (s, 9H), 1.30 (t, 3H, J=7.2 Hz), 1.52 (m, 1H), 1.82 (m, 1H), 2.13 (q, 4H, J=7.4 Hz), 2.28 (s, 3H), 2.36 (s, 3H), 2.58 (m, 1H), 2.88 (m, 1H), 3.26 (d, 1H, J=10.5 Hz), 3.69 (s, 2H), 4.22 (q 2H, J=7.2 Hz), 6.92-7.17 (m, 5H), 7.33 (d, 1H, J=7.8 Hz), 7.56 (d, 1H, J=2.1 Hz), 9.09 (d, 1H, J=2.1 Hz); MS (ESI-): 529 ([M−H]⁻).

Example 183

Synthesis of 1-(4-{1-ethyl-1-[3-methyl-4-(5-methyl-pyridazin-3-yl)-phenyl]-propyl}-2-methyl-phenyl)-4,4-dimethyl-pentan-3-ol

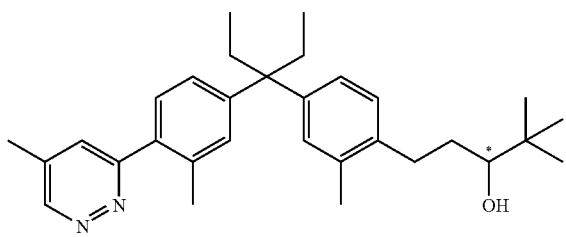

(1) Synthesis of 2-[4-(1-{4-[3-(t-butyl-dimethylsilanyloxy)-4,4-dimethyl-pentyl]-3-methyl-phenyl}-1-ethyl-propyl)-2-methyl-phenyl]-boronic Acid

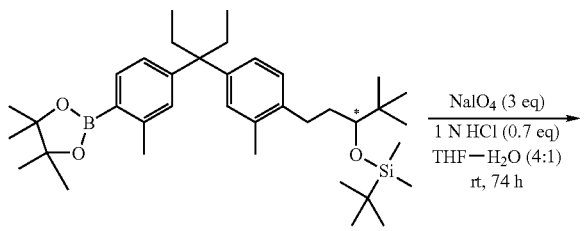

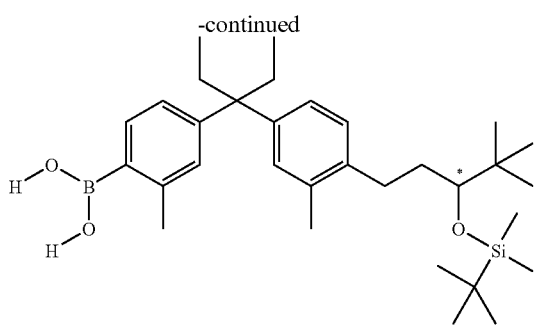

Tetrahydrofuran (2.0 mL) and water (0.45 mL) were added to t-butyl-(1-{2-[4-(1-ethyl-1-{4-[4,4,5,5-tetramethyl-[1,3,2]dioxaborolan-2-yl]-3-methyl-phenyl}-propyl)-2-methyl-phenyl]-ethyl}-2,2-dimethyl-propoxy)dimethylsilane (Example 24-(1); 79.0 mg, 0.130 mmol) and sodium periodate (90.7 mg, 0.424 mmol) at room temperature, and the mixture was stirred for 2.5 hours. Then, 1 N hydrochloric acid aqueous solution (0.094 mL) was added, and the mixture was stirred at room temperature for 74 hours. The reaction mixture was adjusted to pH 7 with saturated aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=5/1) to give the title compound (43 mg, 63%).

¹H-NMR (chloroform-d): 0.08 (s, 3H), 0.12 (s, 3H), 0.65 (t, 6H, J=7.3 Hz), 0.90 (s, 9H), 0.95 (s, 9H), 1.58 (m, 1H), 1.79 (m, 1H), 2.16 (q, 4H, J=7.3 Hz), 2.26 (s, 3H), 2.43 (m, 1H), 2.76 (s, 3H), 2.78 (m, 1H), 3.35 (dd, 1H, J=6.9, 3.0 Hz), 6.90-7.13 (m, 5H), 8.08 (d, 1H, J=8.7 Hz).

(2) Synthesis of {6-[4-(1-{4-[3-(t-butyl-dimethyl-silanyloxy)-4,4-dimethyl-pentyl]-3-methyl-phenyl}-1-ethyl-propyl)-2-methyl-phenyl]-3-chloro-pyridazin-4-yl}-acetic Acid Ethyl Ester

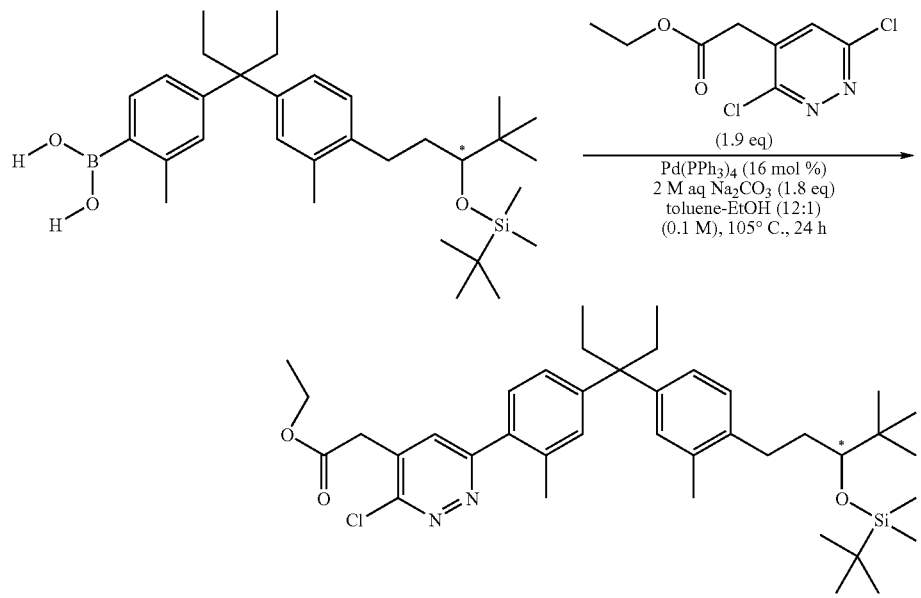

Degassed toluene (0.59 mL), ethanol (0.048 mL) and a 2 M sodium carbonate solution (0.048 mL, 0.096 mmol) were added to 2-[4-(1-{4-[3-(t-butyl-dimethylsilanyloxy)-4,4-dimethyl-pentyl]-3-methyl-phenyl}-1-ethyl-propyl)-2-methyl-phenyl]boronic acid (Example 183-(1); 27.5 mg, 0.0524 mmol), (3,6-dichloro-pyridazin-4-yl)acetic acid ethyl ester (Example 182-(3); 23.4 mg, 0.0995 mmol) and tetrakis(triphenylphosphine)palladium (0) (9.8 mg, 0.0085 mmol). After replacement with nitrogen, the mixture was heated while stirring at an external temperature of 101 to 110° C. for 24 hours. Water was added to the reaction mixture, followed by extraction with diethyl ether. The extract was dried over anhydrous magnesium sulfate and then concentrated under reduced pressure. The residue was purified by silica gel chromatography (hexane/ethyl acetate=15/1) to give the title compound (14.9 mg, 43%).

$^1$H-NMR (chloroform-d): 0.08 (s, 3H), 0.12 (s, 3H), 0.66 (t, 6H, J=7.3 Hz), 0.89 (s, 9H), 0.95 (s, 9H), 1.30 (t, 3H, J=7.1 Hz), 1.61 (m, 1H), 1.79 (m, 1H), 2.12 (q, 4H, J=7.3 Hz), 2.26 (s, 3H), 2.38 (s, 3H), 2.43 (m, 1H), 2.78 (m, 1H), 3.35 (dd, 1H, J=10.1, 2.7 Hz), 3.81 (s, 2H), 4.23 (q, 2H, J=7.1 Hz), 6.90-7.18 (m, 5H), 7.32 (d, 1H, J=8.1 Hz), 7.58 (s, 1H).

(3) Synthesis of {6-[4-(1-{4-[3-(t-butyl-dimethyl-silanyloxy)-4,4-dimethyl-pentyl]-3-methyl-phenyl}-1-ethyl-propyl)-2-methyl-phenyl]-pyridazin-4-yl}-acetic Acid Ethyl Ester $^1$H-NMR (chloroform-d): 0.08 (s, 3H), 0.12 (s, 3H), 0.66 (t, 6H, J=7.2 Hz), 0.89 (s, 9H), 0.95 (s, 9H), 1.30 (t, 3H, J=7.2 Hz), 1.61 (m, 1H), 1.79 (m, 1H), 2.13 (q, 4H, J=7.2 Hz), 2.26 (s, 3H), 2.37 (s, 3H), 2.43 (m, 1H), 2.78 (m, 1H), 3.35 (dd, 1H, J=8.6, 4.3 Hz), 3.69 (s, 2H), 4.22 (q, 2H, J=7.2 Hz), 6.90-7.18 (m, 5H), 7.33 (d, 1H, J=8.1 Hz), 7.56 (d, 1H, J=2.1 Hz), 9.09 (d, 1H, J=2.1 Hz).

(4) Synthesis of [6-(4-{1-ethyl-1-[4-(3-hydroxy-4,4-dimethyl-pentyl)-3-methyl-phenyl]-propyl}-2-methyl-phenyl)-pyridazin-4-yl]-acetic Acid Ethyl Ester

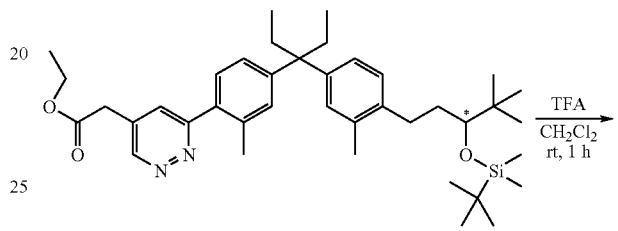

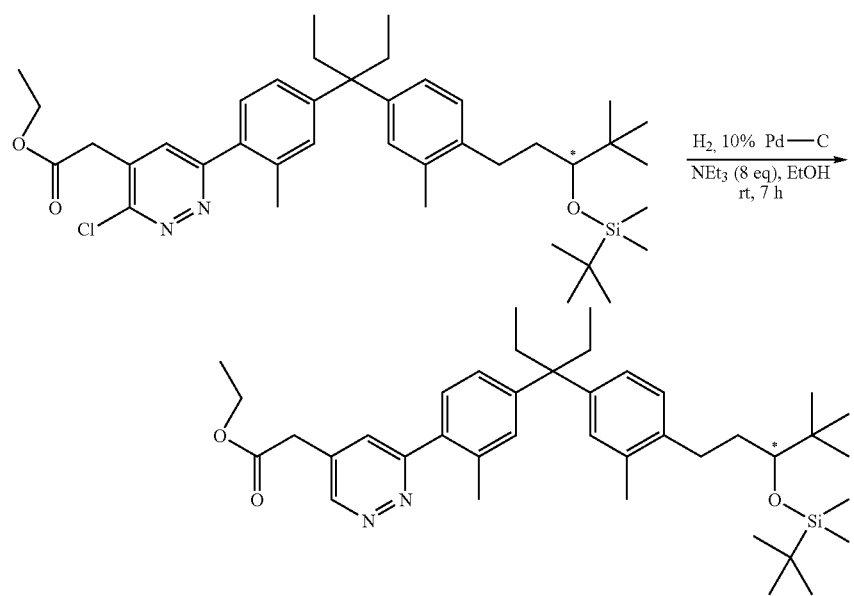

10% Pd-C (2 mg) and triethylamine (0.011 mL, 0.079 mmol) were added to a solution of {6-[4-(1-{4-[3-(t-butyl-dimethyl-silanyloxy)-4,4-dimethyl-pentyl]-3-methyl-phenyl}-1-ethyl-propyl)-2-methyl-phenyl]-3-chloro-pyridazin-4-yl}acetic acid ethyl ester (Example 183-(2); 4.8 mg, 0.007 mmol) in ethanol (0.6 mL) at room temperature. After replacement with hydrogen, the mixture was stirred in a hydrogen atmosphere at room temperature for seven hours. The reaction mixture was diluted with diethyl ether and filtered. The filtrate was washed with water, dried over anhydrous magnesium sulfate and then concentrated under reduced pressure. The residue was purified by silica gel chromatography (hexane/ethyl acetate=3/1) to give the title compound (3.7 mg, 82%).

Trifluoroacetic acid (0.063 mL) was added to a solution of {6-[4-(1-{4-[3-(t-butyl-dimethyl-silanyloxy)-4,4-dimethyl-pentyl]-3-methyl-phenyl}-1-ethyl-propyl)-2-methyl-phenyl]pyridazin-4-yl}acetic acid ethyl ester (Example 183-(3);

9.0 mg, 0.014 mmol) in dichloromethane (0.36 mL) at room temperature, and the mixture was stirred at room temperature for one hour. The solvent in the reaction solution was distilled off under reduced pressure, and the residue was diluted with diethyl ether. The mixture was adjusted to pH 7 with aqueous sodium bicarbonate solution, followed by extraction with diethyl ether. The extract was dried over anhydrous magnesium sulfate and then concentrated under reduced pressure. The residue was purified by silica gel chromatography (hexane/ethyl acetate=2/1) to give the title compound (6.5 mg, 87%).

$^1$H-NMR (chloroform-d): 0.66 (t, 6H, J=7.3 Hz), 0.91 (s, 9H), 1.30 (t, 3H, J=7.2 Hz), 1.52 (m, 1H), 1.82 (m, 1H), 2.13 (q, 4H, J=7.3 Hz), 2.28 (s, 3H), 2.36 (s, 3H), 2.58 (m, 1H), 2.88 (m, 1H), 3.26 (d, 1H, J=10.5 Hz), 3.69 (s, 2H), 4.22 (q, 2H, J=7.2 Hz), 6.92-7.17 (m, 5H), 7.33 (d, 1H, J=7.8 Hz), 7.56 (d, 1H, J=2.1 Hz), 9.09 (d, 1H, J=2.1 Hz).

(5) Synthesis of 1-(4-{1-ethyl-1-[3-methyl-4-(5-methyl-pyridazin-3-yl)-phenyl]-propyl}-2-methyl-phenyl)-4,4-dimethyl-pentan-3-ol

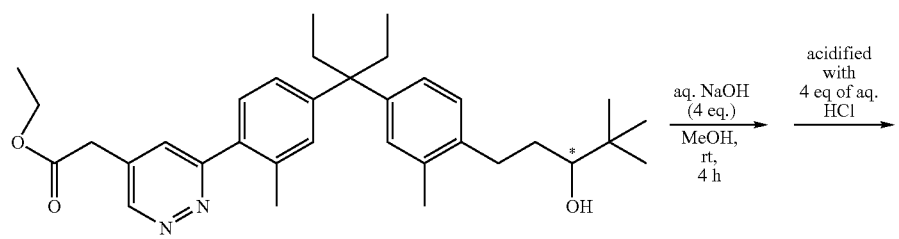

A 2 N sodium hydroxide aqueous solution (0.010 mL) was added to a solution of [6-(4-{1-ethyl-1-[4-(3-hydroxy-4,4-dimethyl-pentyl)-3-methyl-phenyl]-propyl}-2-methyl-phenyl)-pyridazin-4-yl]acetic acid ethyl ester (Example 183-(4); 2.5 mg, 0.0047 mmol) in methanol (0.10 mL) at room temperature, and the mixture was stirred at room temperature for four hours. The mixture was acidified with dilute hydrochloric acid aqueous solution, followed by extraction with ethyl acetate. The extract was dried over anhydrous magnesium sulfate and then concentrated under reduced pressure. The residue was purified by silica gel chromatography (hexane/ethyl acetate=1/2) to give the title compound (1.8 mg, 83%).

$^1$H-NMR (chloroform-d): 0.66 (t, 6H, J=7.4 Hz), 0.91 (s, 9H), 1.51 (m, 1H), 1.81 (m, 1H), 2.13 (q, 4H, J=7.4 Hz), 2.28 (s, 3H), 2.35 (s, 3H), 2.42 (s, 3H), 2.58 (m, 1H), 2.88 (m, 1H), 3.26 (d, 1H, J=9.6 Hz), 6.92-7.16 (m, 5H), 7.29 (d, 1H, J=8.1 Hz), 7.40 (d, 1H, J=2.1, 0.9 Hz), 9.00 (d, 1H, J=2.1, 0.9 Hz); MS (ESI+): 459 ([M+H]$^+$).

Example 184

Synthesis of Sodium [6-(4-{1-ethyl-1-[4-(3-hydroxy-4,4-dimethyl-pentyl)-3-methyl-phenyl]-propyl}-2-methyl-phenyl)-pyridazin-4-yl]-acetate

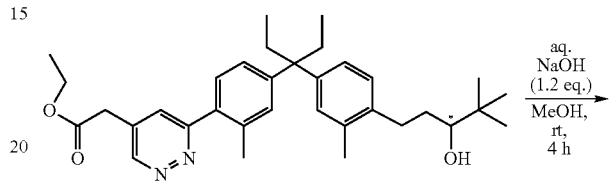

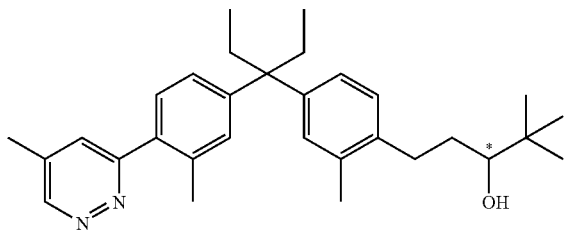

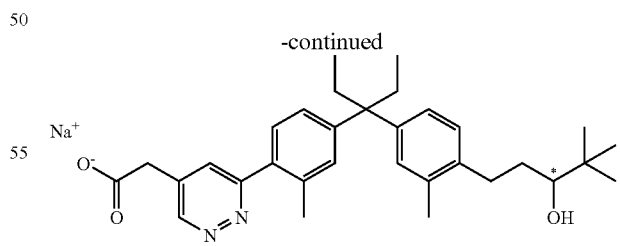

A 0.25 N sodium hydroxide aqueous solution (0.024 mL) was added to a solution of [6-(4-{1-ethyl-1-[4-(3-hydroxy-4,4-dimethyl-pentyl)-3-methyl-phenyl]-propyl}-2-methyl-phenyl)-pyridazin-4-yl]acetic acid ethyl ester (Example 182-(7); 2.5 mg, 0.0047 mmol) in methanol (0.10 mL) at room temperature, and the mixture was stirred at room temperature for four hours. The reaction mixture was concentrated under reduced pressure to give the title compound (2.5 mg, 100%).

¹H-NMR (methanol-d4): 0.65 (t, 6H, J=7.3 Hz), 0.87 (s, 9H), 1.50 (m, 1H), 1.75 (m, 1H), 2.16 (q, 4H, J=7.3 Hz), 2.25 (s, 3H), 2.27 (s, 3H), 2.55 (m, 1H), 2.88 (m, 1H), 3.15 (dd, 1H, J=10.0, 2.0 Hz), 3.59 (m, 2H), 6.90-7.18 (m, 5H), 7.31 (d, 1H, J=8.4 Hz), 7.73 (dd, 1H, J=2.1, 0.6 Hz), 9.07 (d, 1H, J=2.1 Hz); MS (ESI+): 503 ([M-Na+2H]⁺).

Example 185

Synthesis of Sodium [6-(4-{1-ethyl-1-[4-(3-hydroxy-4,4-dimethyl-pentyl)-3-methyl-phenyl]-propyl}-2-methyl-phenyl)-pyridazin-4-yl]-acetate

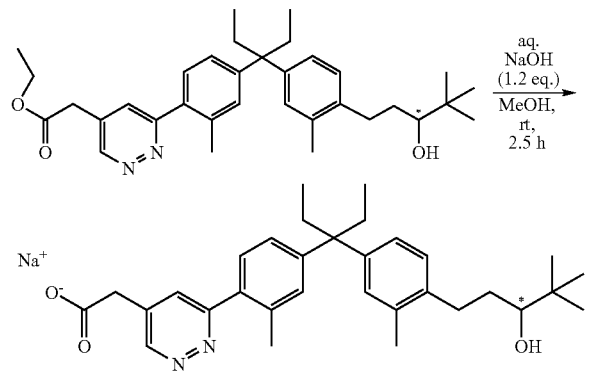

A 0.25 N sodium hydroxide aqueous solution (0.060 mL) was added to a solution of [6-(4-{1-ethyl-1-[4-(3-hydroxy-4,4-dimethyl-pentyl)-3-methyl-phenyl]-propyl}-2-methyl-phenyl)-pyridazin-4-yl]acetic acid ethyl ester (Example 183-(4); 6.5 mg, 0.012 mmol) in methanol (0.20 mL) at room temperature, and the mixture was stirred at room temperature for four hours. The reaction mixture was concentrated under reduced pressure to give the title compound (6.5 mg, 100%).

¹H-NMR (methanol-d4): 0.65 (t, 6H, J=7.3 Hz), 0.87 (s, 9H), 1.50 (m, 1H), 1.75 (m, 1H), 2.16 (q, 4H, J=7.3 Hz), 2.25 (s, 3H), 2.27 (s, 3H), 2.55 (m, 1H), 2.87 (m, 1H), 3.15 (dd, 1H, J=10.0, 2.0 Hz), 3.59 (m, 2H), 6.90-7.18 (m, 5H), 7.31 (d, 1H, J=8.4 Hz), 7.73 (dd, 1H, J=2.1, 0.9 Hz), 9.07 (d, 1H, J=2.1 Hz); MS (ESI+): 503 ([M-Na+2H]⁺).

Evaluation of Activity

Some of the aforementioned compounds of the present invention were compared with the following comparative compounds in terms of (1) ECAC2 mRNA expression in Caco-2 cells and (2) osteocalcin production in MG-63 cells.

(Comparative Compounds)

1,25-Dihydroxyvitamin D₃ (1,25(OH)₂D₃) was purchased from Solvay Pharmaceuticals (Netherlands). LG190178 had the following structure and was synthesized by the method described in Example 10 of WO 00/10958.

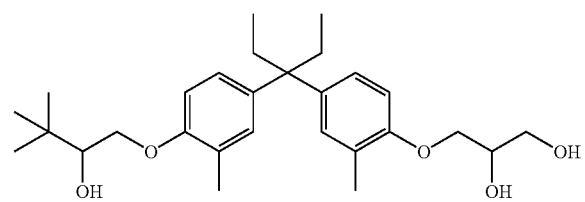

Compounds A, B, C and D had the following structures and were synthesized by the method described in "Example 110 and its diastereomers" of WO 03/101978 A1.

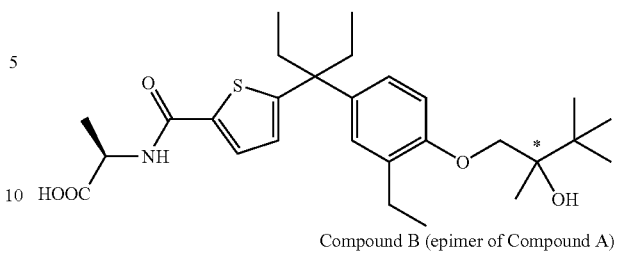

Compound A

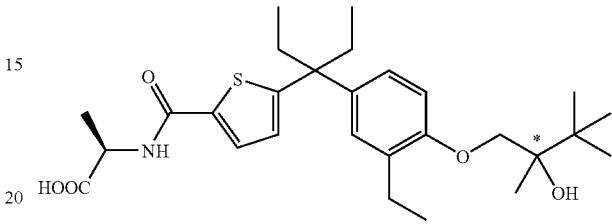

Compound B (epimer of Compound A)

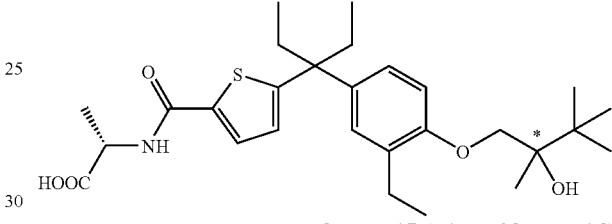

Compound C

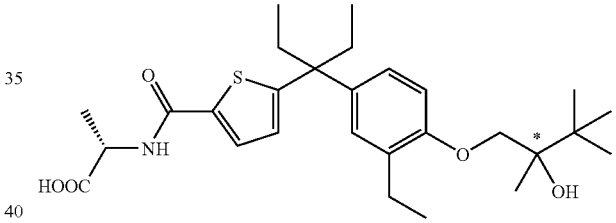

Compound D (epimer of Compound C)

1. Screening by ECAC2 mRNA Expression Level in Caco-2 Cells (1) Cell Culture

Caco-2 cells were plated in a 48-well plate at $6.3 \times 10^4$ cells/well and cultured at 37° C. for four days. After culturing for four days, the medium was replaced with a medium containing a predetermined concentration of a test substance (Dulbecco's Modified Eagle Medium (D-MEM) without NaHCO₃ with 44 mM NaHCO₃, 1 mM non-essential amino acids and 2 mM L-glutamine, 90%; fetal bovine serum, 10%), and the cells were exposed to the medium for 24 hours. During the exposure period, the medium was replaced with such a fresh medium containing the test substance.

(2) Extraction of Total RNA from Caco-2 Cells

Total RNA was collected in accordance with the ABI PRISM™ 6100 Nucleic Acid PrepStation protocol.

(3) Measurement Method for ECAC2 mRNA Using Real-Time RT-PCR

ECAC2 mRNA was measured by PRISM 7000 systems using the TaqMan One-step RT-PCR Master Mix Reagents Kit. The ECAC2 mRNA expression was corrected by calculating the ratio of the ECAC2 mRNA expression to the GAPDH mRNA expression.

The primer and PCR conditions were as follows.
1) ECAC2, (SEQ ID: 1)
(a) forward 5'-CCTTCACCATCATGATTCAGAAG-3'

(SEQ ID: 2)
(b) reverse 5'-GTCCTCTGTCTGGAAGATGA-3'

(SEQ ID: 3)
(c) Taqman probe 5'-TTCTGCTGGCTGATGGCTGTGGTC-3'

(d) 55 cycles, annealing temperature (Ta) = 60° C.

2) GAPDH, (SEQ ID: 4)
(a) forward 5'-GAAGGTGAAGGTCGGAGTC-3'

(SEQ ID: 5)
(b) reverse 5'-GAAGATGGTGATGGGATTTC-3'

(SEQ ID: 6)
(c) Taqman probe 5'-CAAGCTTCCCGTTCTCAGCC-3'

(d) 55 cycles, Ta = 60 ° C.

(4) Comparison of ECAC2 mRNA Expression Levels $EC_{50}$ values of ECAC2 mRNA expression were calculated by application to the Emax model. The ECAC2 mRNA expression level was calculated as a ratio of an $EC_{50}$ value of LG190178 to an $EC_{50}$ value of the compound. The results are shown in Table 1.

ECAC2 is a transporter similar to a channel affecting Ca absorption in the intestinal tract, as shown in J. Biol. Chem. 1999 Aug. 6; 274 (32): 22739-46.

2. Measurement of Osteocalcin Production in MG-63 Cells
(Materials and Method)
(1) Culture and Drug Treatment mg-63 was obtained from Institute for Fermentation, Osaka as a human osteoblast-like cell line. MG-63 cells were maintained and cultured in a MEM medium (Minimum essential medium; pH 7.0; Invitrogen Corporation, Carlsbad, Calif., USA) containing 5% fetal bovine serum (FBS; HyClone, Logan, Utah, USA).

MG-63 cells were adjusted to a density of $4.0 \times 10^4$ cells/mL, plated in a 96-well plate at 200 μL per well, and cultured under conditions of 37° C. and 5% carbon dioxide for 24 hours.

After removing the medium, MEM containing 5% charcoal/dextran treated FBS (DCC-FBS; Hyclone, Logan, Utah, USA) was added at 180 μL/well. The test substance ($1.0 \times 10^{-3}$ mol/L) was diluted with dimethyl sulfoxide (DMSO) to $1.0 \times 10^{-4}$ mol/L, $1.0 \times 10^{-5}$ mol/L, $1.0 \times 10^{-6}$ mol/L, $1.0 \times 10^{-7}$ mol/L and $1.0 \times 10^{-8}$ mol/L. $1,25(OH)_2D_3$ was used as a positive control. Like the test substance, $1,25(OH)_2D_3$ was diluted with DMSO. 0.02 mL of the positive control and the test substance diluted 100-fold with MEM containing 5% DCC-FCS was added to each well of the 96-well plate, so that the final drug concentration was $1.0 \times 10^{-6}$ mol/L to $1.0 \times 10^{-11}$ mol/L. Thereafter, the cells were cultured under conditions of 37° C. and 5% carbon dioxide for eight hours.

After culturing for eight hours, the medium was removed, and MEM containing 5% DCC-FBS was added at 0.2 mL per well. The cells were cultured under conditions of 37° C. and 5% carbon dioxide for four days, and the medium was recovered. The medium was stored at −80° C. until osteocalcin measurement.

(2) Measurement Method for Osteocalcin

The Gla-type Osteocalcin EIA kit (Takara Bio Inc., Tokyo, Japan) was used for measurement of osteocalcin. Measurement was carried out using a microplate reader (Model 3550, Bio-Rad Laboratories, Inc., Hercules, Calif., USA) at a wavelength of 450 nm, and the results were analyzed by Microplate Manager III (Bio-Rad Laboratories, Inc., ver. 1.57).

(3) Comparison for Potency of Induction of Osteocalcin Production Using MG-63

The median effective concentration ($EC_{50}$) was calculated from the osteocalcin concentration. Potency of induction of each compound was calculated as a ratio of $EC_{50}$ of $1,25(OH)_2D_3$ to $EC_{50}$ of the compound. The relation between diseases and induction of osteocalcin production is described in Lancet (1984 May 19), 1 (8386), 1091-3; Steroids 66, 159-170 (2001); and Journal of Steroid Biochemistry & Molecular Biology 89-90, 269-271 (2004), for example.

TABLE 1

| | ECAC2 mRNA expression level in Caco-2 cells (%) | Osteocalcin production level in MG-63 cells (%) |
|---|---|---|
| $1,25(OH)_2D_3$ | 556 | 100 |
| LG190178 | 100 | 185 |
| Compound A | 123 | 67 |
| Compound B | 15 | 3 |
| Compound C | 34 | 43 |
| Compound D | 14 | 4 |
| Compound of Example 13 | <10 | 401 |
| Compound of Example 14 | 52 | 161 |
| Compound of Example 22 | 353 | 1044 |
| Compound of Example 23 | 88 | 3264 |
| Compound of Example 24 | 129 | 660 |
| Compound of Example 45 | 344 | 546 |
| Compound of Example 46 | 916 | 2233 |
| Compound of Example 48 | 1356 | 508 |
| Compound of Example 51 | 183 | 650 |
| Compound of Example 53 | 778 | 772 |
| Compound of Example 56 | 199 | 1379 |
| Compound of Example 60 | 831 | 3798 |
| Compound of Example 61 | 143 | 956 |
| Compound of Example 71 | 467 | 746 |
| Compound of Example 72 | 664 | 1624 |
| Compound of Example 73 | 441 | 1595 |
| Compound of Example 74 | 1616 | 1848 |
| Compound of Example 75 | 806 | 1283 |
| Compound of Example 76 | 366 | 407 |
| Compound of Example 78 | 491 | 617 |
| Compound of Example 81 | 680 | 652 |
| Compound of Example 84 | 1006 | 739 |
| Compound of Example 85 | 778 | 765 |
| Compound of Example 88 | 784 | 4562 |

TABLE 1-continued

| | ECAC2 mRNA expression level in Caco-2 cells (%) | Osteocalcin production level in MG-63 cells (%) |
|---|---|---|
| Compound of Example 90 | 66 | 1604 |
| Compound of Example 91 | 455 | 1074 |
| Compound of Example 93 | 579 | 487 |
| Compound of Example 97 | 522 | 533 |
| Compound of Example 100 | 696 | 878 |
| Compound of Example 101 | 175 | 508 |
| Compound of Example 146 | 5499 | 3721 |
| Compound of Example 147 | 3554 | 1228 |
| Compound of Example 148 | 2698 | 1022 |
| Compound of Example 149 | 301 | 1305 |
| Compound of Example 150 | 1129 | 645 |

The ECAC2 mRNA expression level in Caco-2 cells (%) was calculated by the formula: ($EC_{50}$ value of LG190178/$EC_{50}$ value of each compound)×100.

The osteocalcin production level in MG-63 cells (%) was calculated by the formula: ($EC_{50}$ value of 1,25(OH)$_2$D$_3$/$EC_{50}$ value of each compound)×100.

The experimental results shown in Table 1 demonstrate the following facts.
(1) A compound having a small ECAC2 mRNA expression level in Caco-2 cells (%) and a large osteocalcin production level in MG-63 cells (%) is a compound having a small potency of increasing the blood calcium level and high potency of induction of osteocalcin production.
(2) A compound having a large ECAC2 mRNA expression level in Caco-2 cells (%) and a small osteocalcin production level in MG-63 cells (%) is a compound having a large potency of increasing the blood calcium level and low potency of induction of osteocalcin production.
(3) A compound having a large ECAC2 mRNA expression level in Caco-2 cells (%) and a large osteocalcin production level in MG-63 cells (%) is a compound having a large potency of increasing the blood calcium level and high potency of induction of osteocalcin production.

The compounds of the present invention had potency of induction of osteocalcin production considerably higher than those of the comparative compounds (such as 1,25(OH)$_2$D$_3$ and LG190178 having a similar basic structure).

Further, all the compounds of the present invention had a ratio of osteocalcin production level to ECAC2 mRNA expression level higher than that of 1,25(OH)$_2$D$_3$. That is, all the compounds of the present invention were compounds in which induction of osteocalcin production as a main effect can be separated from the effect of increasing the blood calcium level as a side effect.

3. Measurement of Effect of Increasing Bone Density in Rats
(1) Materials and Method
Reagent The compound of the present invention was adjusted to each concentration using middle chain triglyceride (MCT) as a base. The adjusted solution was stored under shading at 4° C. until use.

Animals

Seven-week-old Sprague-Dawley (Crj:CD(SD)) female rats (Charles River Laboratories Japan, Inc.) were preliminarily bred for one week in an environment at a room temperature of 20 to 26° C., at a humidity of 35 to 75% and with an air change of 10 times or more per hour. The rats were allowed to freely take tap water and CE-2 (CLEA Japan, Inc.) as a feed.

Animal Treatment and Sample Collection

After preliminary breeding, the animals were subjected to ovariectomy (OVX) and divided into groups (eight animals per group) on the day after the operation. Only MCT as a base was forcibly orally administered to the sham operation group (sham) and the pathological control group (OVX-vehicle) at a dose of 1 mL/kg (five times per week). The compound of the present invention was also forcibly orally administered at the same dose five times per week.

The animals were bred in a metabolic cage and urine was collected for 24 hours after the final administration. Blood was collected from the abdominal aorta under ether anesthesia for 24 hours after the final administration. The blood was allowed to stand at room temperature for 30 minutes and then centrifuged to provide serum. The femur and lumbar spine were collected and stored in 70% ethanol until bone density measurement.

The Ca, phosphorus or creatinine concentration in the serum and urine was measured by an autoanalyzer (Hitachi 7170). Serum osteocalcin was measured by a rat Elisa system (Amersham), and urine deoxypyridinoline was measured by Osteolinks DPD (Sumitomo Seiyaku Biomedical Co., Ltd.).

Bone Density Measurement

The bone density of the femur and the second to fifth lumbar spines of the isolated lumbar spines was measured by the dual X-ray bone densitometry system DCS-600-EX (ALOKA). The distal femur bone density was measured for three proximal regions out of 10 regions of the femur equally divided in length. The bone density in each site was described based on the bone density of the pathological control group (vehicle group) in each experiment as 100%.

(2) Results

The effects of the compounds of the present invention on the lumbar spine bone density are shown in Table 2 as an example of the obtained results. Table 2 shows that all the compounds of the present invention had an excellent effect of improving the bone density.

TABLE 2

| | Serum calcium concentration (mg/dl) | Lumbar spine bone density (%) |
|---|---|---|
| Sham operation group | 10.39 | 109.8 |
| Pathological control group | 10.23 | 100.0 |
| Compound of Example 71 0.025 μg/kg | 10.12 | 110.58 |
| Compound of Example 71 0.05 μg/kg | 11.13 | 115.09 |
| Compound of Example 76 0.015 μg/kg | 9.97 | 110.22 |
| Compound of Example 76 0.03 μg/kg | 10.45 | 111.00 |

TABLE 2-continued

| | Serum calcium concentration (mg/dl) | Lumbar spine bone density (%) |
|---|---|---|
| Compound of Example 80 0.05 µg/kg | 10.08 | 110.75 |
| Compound of Example 80 0.1 µg/kg | 10.15 | 116.68 |
| Compound of Example 81 0.01 µg/kg | 9.97 | 115.66 |
| Compound of Example 81 0.02 µg/kg | 10.50 | 115.66 |
| Compound of Example 89 1.25 µg/kg | 10.37 | 109.24 |
| Compound of Example 89 2.5 µg/kg | 10.90 | 121.37 |
| Compound of Example 149 0.075 µg/kg | 10.23 | 111.40 |
| Compound of Example 149 0.15 µg/kg | 10.65 | 116.00 |

INDUSTRIAL APPLICABILITY

The compound of the present invention has activity to modulate the effect of a vitamin D receptor (in particular, agonist activity to a vitamin D3 receptor). Therefore, the compound and the composition of the present invention are useful as a medicine for therapy of conditions and diseases such as abscess, acne, adhesion, alopecia, Alzheimer's disease, benign prostatic hyperplasia, fracture healing, cancer, autoimmune induced diabetes, host-graft rejection, insufficient sebum secretion, insufficient dermal firmness, humoral hypercalcemia, insufficient dermal hydration, leukemia, lupus, multiple sclerosis, osteomalacia, osteoporosis, psoriatic arthritis, psoriasis, renal failure, renal osteodystrophy, chronic rheumatoid arthritis, scleroderma, secondary hyperparathyroidism, systemic lupus erythematosus, wrinkle, corneal wound, corneal healing, retinopathy, sway, muscle weakness, fall, chronic glomerulonephritis, lupus nephritis, diabetic nephropathy, hypocalcemia, hypoparathyroidism, rachitis and osteoarthritis.

In particular, the compound and the composition of the present invention are useful as a medicine for therapy of benign prostatic hyperplasia, cancer, osteoporosis, psoriasis, secondary hyperparathyroidism, chronic glomerulonephritis, lupus nephritis, diabetic nephropathy, sway, muscle weakness, fall, chronic rheumatoid arthritis and/or osteoarthritis, for example.

Typical diseases to be cured with the compound and the composition of the present invention among the above diseases are benign prostatic hyperplasia, cancer, osteoporosis, psoriasis, secondary hyperparathyroidism, chronic glomerulonephritis, lupus nephritis and/or diabetic nephropathy.

Some of the compounds of the formula (I) of the present invention (for example, a compound having a protected hydroxyl group such as a compound having —OR' shown in the "General synthesis method" and a compound having an alkoxycarbonyl group such as a compound having —COOR" shown in the "General synthesis method") are also useful as synthetic intermediates for other compounds of the present invention (for example, a compound having a hydroxyl group corresponding to the protected hydroxyl group of the aforementioned compound and a compound having a carboxyl group corresponding to the alkoxycarbonyl group of the aforementioned compound). Further, the compound of the formula (II) of the present invention is useful as a synthetic intermediate for the compound of the formula (I) of the present invention.

The invention claimed is:

1. A compound represented by the following general formula (I):

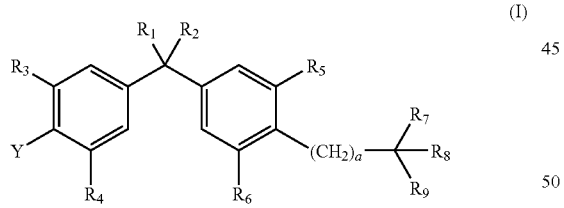

wherein

R$_1$ and R$_2$ independently represent an optionally substituted C$_{1-6}$ alkyl group, a C$_{1-6}$ haloalkyl group, an optionally substituted C$_{2-6}$ alkenyl group, an optionally substituted C$_{2-6}$ alkynyl group or an optionally substituted C$_{1-6}$ alkoxy group, or R$_1$ and R$_2$ are taken together to form an optionally substituted C$_{3-8}$ cycloalkyl group;

R$_3$, R$_4$, R$_5$ and R$_6$ independently represent a hydrogen atom, a halogen atom, an optionally substituted C$_{1-6}$ alkyl group, a C$_{1-6}$ haloalkyl group, an optionally substituted C$_{2-6}$ alkenyl group, an optionally substituted C$_{2-6}$ alkynyl group or an optionally substituted C$_{1-6}$ alkoxy group;

R$_7$, R$_8$ and R$_9$ independently represent a hydrogen atom, an optionally protected hydroxyl group, an optionally substituted amino group, an optionally substituted carboxyl group, an optionally substituted C$_{1-10}$ alkyl group or a C$_{1-6}$ haloalkyl group, or any one pair of (R$_7$ and R$_8$), (R$_7$ and R$_9$) and (R$_8$ and R$_9$) are taken together to form an optionally substituted C$_{3-10}$ cycloalkyl group, a carbonyl group, an optionally substituted 3- to 12-membered heterocycle or a C$_{3-7}$ lactone;

X is a direct bond, methylene, ethylene, vinylene, ethynylene, —O—, —S—, —NH—, carbonyl;

Y represents a phenyl group having one or two substituent or a nitrogen containing 3- to 12-membered heterocycle having one or two substituent; and the heterocycle is selected from pyrrole, oxazole, isoxazole, thiazole, isothiazole, furazan, imidazole, pyrazole, piperidine, piperazine, morpholine, thiomorpholine, pyridine, pyrazine, pyrimidine, pyridazine, indole, isoindole, indolizine, quinoline, isoquinoline, quinolizine, naphthyridine, benzimidazole, indazole, quinoxaline, quinazoline, cinnoline, phthalazine, purine, pteridine, benzoxazole and benzothiazole, wherein substituents each selected from a C$_{1-6}$ alkyl group optionally substituted with one or two hydroxyl groups, amino groups, C$_{1-6}$ alkoxycarbonyl groups and/or carboxyl groups; a C$_{1-6}$ haloalkyl group optionally substituted with one or two hydroxyl groups, amino groups, C$_{1-6}$ alkoxycarbonyl groups and/or carboxyl groups; a C$_{2-6}$ alkenyl group optionally substituted with one or two halogen atoms, amino groups, C$_{1-6}$ alkoxycarbonyl groups and/or carboxyl groups; a C$_{2-6}$ alkynyl group optionally substituted with one or two halogen atoms, amino groups, $C_{1-6}$ alkoxycarbonyl groups and/or carboxyl groups; a $C_{1-6}$ alkoxycarbonyl group; a carboxyl group; a $C_{1-6}$ alkoxy group; a cyano group; a halogen atom; a hydroxyl group; and/or a hydroxamic acid group, at least one of the substituents of Y is a $C_{1-6}$ alkyl group substituted with a carboxyl group; and a represents an integer of 0 to 3, or a pharmaceutically acceptable salt thereof.

2. The compound according to claim 1, wherein $R_1$ and $R_2$ are independently an optionally substituted $C_{1-6}$ alkyl group or a $C_{1-6}$ haloalkyl group, or a pharmaceutically acceptable salt thereof.

3. The compound according to claim 2, wherein $R_1$ and $R_2$ are independently a $C_{1-6}$ alkyl group, or a pharmaceutically acceptable salt thereof.

4. The compound according to claim 3, wherein $R_1$ and $R_2$ are independently an ethyl group, or a pharmaceutically acceptable salt thereof.

5. The compound according to claim 1, wherein $R_3$, $R_4$, $R_5$ and $R_6$ are independently a hydrogen atom, a halogen atom, a $C_{1-6}$ alkyl group or a $C_{1-6}$ haloalkyl group, or a pharmaceutically acceptable salt thereof.

6. The compound according to claim 5, wherein $R_3$, $R_4$, $R_5$ and $R_6$ are independently a hydrogen atom, a halogen atom or a $C_{1-6}$ alkyl group, or a pharmaceutically acceptable salt thereof.

7. The compound according to claim 6, wherein $R_3$, $R_4$, $R_5$ and $R_6$ are independently a hydrogen atom, a halogen atom or a methyl group, or a pharmaceutically acceptable salt thereof.

8. The compound according to claim 7, wherein $R_3$ and $R_4$ are independently a hydrogen atom or a methyl group; $R_5$ is a hydrogen atom; and $R_6$ is a methyl group, or a pharmaceutically acceptable salt thereof.

9. The compound according to claim 8, wherein $R_3$ is a hydrogen atom, or a pharmaceutically acceptable salt thereof.

10. The compound according to claim 8, wherein $R_3$ is a methyl group, or a pharmaceutically acceptable salt thereof.

11. The compound according to claim 8, wherein $R_4$ is a hydrogen atom, or a pharmaceutically acceptable salt thereof.

12. The compound according to claim 8, wherein $R_4$ is a methyl group, or a pharmaceutically acceptable salt thereof.

13. The compound according to claim 1, wherein $R_7$, $R_8$ and $R_9$ independently represent a hydrogen atom, a hydroxyl group, a $C_{1-6}$ alkyl group or a $C_{1-6}$ haloalkyl group, or any one pair of ($R_7$ and $R_8$), ($R_7$ and $R_9$) and ($R_8$ and $R_9$) are taken together to form an optionally substituted $C_{3-10}$ cycloalkyl group, or a pharmaceutically acceptable salt thereof.

14. The compound according to claim 13, wherein any one of $R_7$, $R_8$ and $R_9$ is a hydroxyl group; and the remaining two are independently a hydrogen atom, a $C_{1-6}$ alkyl group or a $C_{1-6}$ haloalkyl group, or the remaining two are taken together to form a $C_{3-10}$ cycloalkyl group optionally substituted with one or two halogen atoms, hydroxyl groups and/or $C_{1-4}$ alkyl groups, or a pharmaceutically acceptable salt thereof.

15. The compound according to claim 14, wherein any one of $R_7$, $R_8$ and $R_9$ is a hydroxyl group and the remaining two are the same and are each a $C_{1-6}$ alkyl group or a $C_{1-6}$ haloalkyl group, or a pharmaceutically acceptable salt thereof.

16. The compound according to claim 15, wherein any one of $R_7$, $R_8$ and $R_9$ is a hydroxyl group and the remaining two are the same and are each an ethyl group or a trifluoromethyl group, or a pharmaceutically acceptable salt thereof.

17. The compound according to claim 1, wherein the substituents of Y are each selected from a $C_{1-6}$ alkyl group optionally substituted with a carboxyl group; a $C_{2-6}$ alkenyl group optionally substituted with a carboxyl group; a $C_{2-6}$ alkynyl group optionally substituted with a carboxyl group; a carboxyl group; and/or a halogen atom, or a pharmaceutically acceptable salt thereof.

18. The compound according to claim 17, wherein the substituents of Y are each selected from a $C_{1-6}$ alkyl group optionally substituted with a carboxyl group; and/or a halogen atom, or a pharmaceutically acceptable salt thereof.

19. The compound according to claim 1, which is selected from (4'-{1-ethyl-1-[4-(-3-hydroxy-4,4-dimethyl-pentyl)-3-methyl-phenyl]-propyl}-2'-methyl-biphenyl-4-yl)-acetic acid;

(4'-{1-ethyl-1-[4-(3-hydroxy-4,4-dimethyl-pentyl)-3-methyl-phenyl]-propyl}-2'-methyl-biphenyl-3-yl)-acetic acid;

(E)-(4'-{1-ethyl-1-[4-(3-ethyl-3-hydroxy-1-pentenyl)-3-methyl-phenyl]-propyl}-2'-methyl-biphenyl-4-yl)-acetic acid;

[6-(4-{1-ethyl-1-[4-(3-hydroxy-4,4-dimethyl-pentyl)-3-methyl-phenyl]-propyl}-2-methyl-phenyl)-pyridin-3-yl]-acetic acid;

[5-(4-{1-ethyl-1-[4-(3-hydroxy-4,4-dimethyl-pentyl)-3-methyl-phenyl]-propyl}-2-methyl-phenyl)-pyridin-3-yl]-acetic acid;

(4'-{1-ethyl-1-[3-methyl-4-(4,4,4-trifluoro-3-hydroxy-3-trifluoromethyl-1-butynyl)-phenyl]-propyl}-2'-methyl-biphenyl-4-yl)acetic acid;

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid;

sodium (4'-{1-ethyl-1-[4-((E)-3-ethyl-3-hydroxy-1-pentenyl)-3-methyl-phenyl]-propyl}-3-fluoro-2'-methyl-biphenyl-4-yl)acetate; (4'-{1-ethyl-1-[4-(2-hydroxy-3,3-dimethyl-butoxy)-3-methyl-phenyl]-propyl}-2'-methyl-biphenyl-4-yl)acetic acid;

(E)-[4'-(1-ethyl-1-{4-[2-(1-hydroxy-cyclopentyl)-vinyl]-3-methyl-phenyl}-propyl)-2'-methyl-biphenyl-4-yl]-acetic acid;

(E)-[4'-(1-ethyl-1-{4-[2-(1-hydroxycyclohexyl)-vinyl]-3-methylphenyl}-propyl)-2'-methylbiphenyl-4-yl]-acetic acid; (4'-{1-ethyl-1-[4-(3-hydroxy-4,4-dimethyl-pentyl)-3-methyl-phenyl]-propyl}-3-fluoro-2'-methyl-biphenyl-4-yl)acetic acid;

(4'-{1-ethyl-1-[4-(3-hydroxy-4,4-dimethyl-pentyl)-3-methyl-phenyl]-propyl}-3-chloro-2'-methyl-biphenyl-4-yl)acetic acid;

(4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid;

sodium (4-{1-ethyl-1-[4-((E)-3-ethyl-3-hydroxy-1-pentenyl)-3-methyl-phenyl]-propyl}-3- fluoro-2'-methyl-biphenyl-4-yl)acetate;(4'-{1-ethyl-1-[4'(2-hydroxy-3,3-dimethyl-butoxy)-3- methyl-phenyl]-propyl}-2'-methyl-biphenyl-4-yl)acetic acid;

(E)-[4'-(1-ethyl]-1-{4[2-(1-hydroxy-cyclopentyl)-vinyl]-3 -methyl-phenyl}-propyl)-2'-methyl- biphenyl-4-yl]-acetic acid;

(E)-{4'-(1-ethyl-1-(4-[2(1-hydroxycyclohexyl)-vinyl]-3-methlphenyl}-propyl)-2'- methylbiphenyl-4-yl]-acetic acid;(4'-{1-ethyl-1-[4-(3-hydroxy-4,4-dimethyl-pentyl)3-methyl- phenyl]-propyl}-3-fluoro-2'-methyl-biphenyl-4-yl)acetic acid;

(4'-{1-ethyl-1-[4-(3-hydroxy-4,4-dimetyl-pentyl)-3-methyl-phenyl-propyl-3-chloro-2'- methyl-biphenyl-4-yl) acetic acid;

(4'-{1-ethyl-1-[3-methyl-4-((E)-4,4,4-trifluoro-3-hydroxy-3-trifluoromethyl-1-butenyl)-phenyl]-propyl}-3-fluoro-2'-methyl-biphenyl-4-yl)acetic acid;

(3-chloro-4'-{1-ethyl-1-[3-methyl-4-((E)-4,4,4-trifluoro-3-hydroxy-3-trifluoromethyl-1-butenyl)-phenyl]-propyl}-2'-methyl-biphenyl-4-yl)acetic acid;

[6-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid;

[5-(4-{1-ethyl-1-[3-methyl-4-((E)-4,4,4-trifluoro-3-hydroxy-3-trifluoromethyl-1-butenyl)-phenyl]-propyl}-2-methyl-phenyl)-pyridin-3-yl]-acetic acid;

[2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid;

(4'-{1-ethyl-1-[3-methyl-4-(4,4,4-trifluoro-3-hydroxy-3-trifluoromethyl-1-butynyl)-phenyl]-propyl}-3-fluoro-2'-methyl-biphenyl-4-yl)acetic acid;

[5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid;

[6-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid;

sodium [4'-(1-ethyl-1-{4-[(E)-2-(1-hydroxy-cyclopentyl)-vinyl]-3-methyl-phenyl}-propyl)-3-fluoro-2'-methyl-biphenyl-4-yl]-acetate;

{6-[4-(1-ethyl-1-{4-[(E)-2-(1-hydroxy-cyclopentyl)-vinyl]-3-methyl-phenyl}-propyl)-2-methyl-phenyl]-pyridin-3-yl}-acetic acid;

[4'-(1-ethyl-1-{4-[(E)-2-(1-hydroxycyclohexyl)-vinyl]-3-methylphenyl}-propyl)-3-fluoro-2'-methylbiphenyl-4-yl]-acetic acid;

[5-chloro-4'-(1-ethyl-1-{4-[(E)-2-(1-hydroxycyclohexyl)-vinyl]-3-methylphenyl}-propyl)-2'-methylbiphenyl-2-yl]-acetic acid;

[3-chloro-4'-(1-ethyl-1-{4-[(E)-2-(1-hydroxycyclohexyl)-vinyl]-3-methylphenyl}-propyl)-2'-methylbiphenyl-4-yl]-acetic acid;

{6-[4-(1-ethyl-1-{4-[(E)-2-(1-hydroxy-cyclohexyl)-vinyl]-3-methyl-phenyl}-propyl)-2-methyl-phenyl]-pyridin-3-yl}-acetic acid;

(4'-{1-ethyl-1-[4-(1-hydroxy-cyclopentylethynyl)-3-methyl-phenyl]-propyl}-3-fluoro-2'-methyl-biphenyl-4-yl)acetic acid;

(4'-{1-ethyl-1-[4-(1-hydroxy-cyclohexylethynyl)-3-methyl-phenyl]-propyl}-3-fluoro-2'-methyl-biphenyl-4-yl)acetic acid;

(4'-{1-ethyl-1-[4-(2-hydroxy-3,3-dimethyl-butoxy)-3-methyl-phenyl]-propyl}-3-fluoro-2'-methyl-biphenyl-4-yl)acetic acid;

[6-(4-{1-ethyl-1-[4-(2-hydroxy-3,3-dimethyl-butoxy)-3-methyl-phenyl]-[propyl}-2-methyl-phenyl)-pyridin-3-yl]-acetic acid;

[5-(4-{1-ethyl-1-[4-(2-hydroxy-3,3-dimethyl-butoxy)-3-methyl-phenyl]-propyl}-phenyl)-pyridin-3-yl]-acetic acid;

[5-(4-{1-ethyl-1-[4-(1-hydroxy-cyclohexylethynyl)-3-methyl-phenyl]-propyl}-phenyl)-pyridin-3-yl]-acetic acid;

[5-(4-{1-ethyl-1-[4-(1-hydroxy-cyclopentylethynyl)-3-methyl-phenyl]-propyl}-phenyl)-pyridin-3-yl]-acetic acid;

{5-[4-(1-ethyl-1-{4-[2-(1-hydroxy-cyclohexyl)-ethyl]-3-methyl-phenyl}-propyl)-phenyl]-pyridin-3-yl}-acetic acid;

{5-[4-(1-ethyl-1-{4-[2-(1-hydroxy-cyclopentyl)-ethyl]-3-methyl-phenyl}-propyl)-phenyl]-pyridin-3-yl}-acetic acid; and pharmaceutically acceptable salts thereof.

20. The compound according to claim 1, which is selected from (4'-{1-ethyl-1-[3-methyl-4-((E)-4,4,4-trifluoro-3-hydroxy-3-trifluoromethyl-1-butenyl)-phenyl]-propyl}-2'-methyl-biphenyl-3-yl)acetic acid;

[2-(4-{1-ethyl-1-[3-methyl-4-((E)-4,4,4-trifluoro-3-hydroxy-3-trifluoromethyl-1-butenyl)-phenyl]-propyl}-2-methyl-phenyl)-thiazol-4-yl]-acetic acid;

[5-(4-{1-ethyl-1-[3-methyl-4-(4,4,4-trifluoro-3-hydroxy-3-trifluoromethyl-1-butynyl)-phenyl]-propyl}-2-methyl-phenyl)-pyridin-3-yl]-acetic acid;

[6-(4-{1-ethyl-1-[4-((E)-3-ethyl-3-hydroxy-1-pentenyl)-3-methyl-phenyl]-propyl}-2-methyl-phenyl)-pyridin-3-yl]-acetic acid;

[5-chloro-4'-(1-ethyl-1-{4-[(E)-2-(1-hydroxycyclohexyl)-vinyl]-3-methylphenyl}-propyl)-2'-methylbiphenyl-2-yl]-acetic acid;

{5-[4-(1-ethyl-1-{4-[2-(1-hydroxy-cyclohexyl)-ethyl]-3-methyl-phenyl}-propyl)-phenyl]-pyridin-3-yl}-acetic acid; and pharmaceutically acceptable salts thereof.

21. A pharmaceutical composition comprising the compound according to claim 1 and a pharmaceutically acceptable carrier.

\* \* \* \* \*

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial
<220> FEATURE:
<223> OTHER INFORMATION: Forward Primer for amplifying ECAC2

<400> SEQUENCE: 1
ccttcaccat catgattcag aag                                           23

<210> SEQ ID NO 2
<211> LENGTH: 20
<212> TYPE: DNA
<213> ORGANISM: Artificial
<220> FEATURE:
<223> OTHER INFORMATION: Reverse Primer for amplifying ECAC2

<400> SEQUENCE: 2
gtcctctgtc tggaagatga                                               20

<210> SEQ ID NO 3
<211> LENGTH: 24
<212> TYPE: DNA
<213> ORGANISM: Artificial
```

```
<220> FEATURE:
<223> OTHER INFORMATION: Probe for RT-PCR

<400> SEQUENCE: 3
ttctgctggc tgatggctgt ggtc                                  24

<210> SEQ ID NO 4
<211> LENGTH: 19
<212> TYPE: DNA
<213> ORGANISM: Artificial
<220> FEATURE:
<223> OTHER INFORMATION: Forward Primer for amplifying GAPDH

<400> SEQUENCE: 4
gaaggtgaag gtcggagtc                                        19

<210> SEQ ID NO 5
<211> LENGTH: 20
<212> TYPE: DNA
<213> ORGANISM: Artificial
<220> FEATURE:
<223> OTHER INFORMATION: Reverse Primer for amplifying GAPDH

<400> SEQUENCE: 5
gaagatggtg atgggatttc                                       20

<210> SEQ ID NO 6
<211> LENGTH: 20
<212> TYPE: DNA
<213> ORGANISM: Artificial
<220> FEATURE:
<223> OTHER INFORMATION: Probe for RT-PCR

<400> SEQUENCE: 6
caagcttccc gttctcagcc                                       20
```